(12) United States Patent
Bisaha et al.

(10) Patent No.: US 8,586,611 B2
(45) Date of Patent: Nov. 19, 2013

(54) FUNGICIDAL CARBOXAMIDES

(75) Inventors: John Joseph Bisaha, Hockessin, DE (US); Patrick Ryan Kovacs, New Castle, DE (US); Renee Marie Lett, Newark, DE (US); Jeffrey Keith Long, Wilmington, DE (US); Robert James Pasteris, Newark, DE (US); Boris Abramovich Klyashchitsky, Wilmington, DE (US); Bruce Lawrence Finkelstein, Newark, DE (US); Brenton Todd Smith, Southlake, TX (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 987 days.

(21) Appl. No.: 11/988,359

(22) PCT Filed: Jul. 26, 2006

(86) PCT No.: PCT/US2006/029175
§ 371 (c)(1),
(2), (4) Date: Dec. 6, 2010

(87) PCT Pub. No.: WO2007/014290
PCT Pub. Date: Feb. 1, 2007

(65) Prior Publication Data
US 2011/0269712 A1  Nov. 3, 2011

Related U.S. Application Data

(60) Provisional application No. 60/702,579, filed on Jul. 26, 2005.

(51) Int. Cl.
*A01N 43/72* (2006.01)
*C07D 417/04* (2006.01)

(52) U.S. Cl.
USPC ........... 514/326; 514/325; 546/203; 546/205; 546/207; 546/208; 546/209; 546/210; 546/211

(58) Field of Classification Search
USPC .......... 514/325, 326; 546/203, 205, 207, 208, 546/209, 210, 211
See application file for complete search history.

(56) References Cited

U.S. PATENT DOCUMENTS

| | | | |
|---|---|---|---|
| 5,354,747 A | 10/1994 | Hansen, Jr. et al. | |
| 5,817,677 A | 10/1998 | Linz et al. | |
| 5,908,843 A | 6/1999 | Gante et al. | |
| 7,601,745 B2* | 10/2009 | Leban et al. | 514/367 |
| 7,812,041 B2* | 10/2010 | Leban et al. | 514/365 |
| 2004/0106655 A1 | 6/2004 | Kitajima et al. | |
| 2006/0069102 A1 | 3/2006 | Leban et al. | |
| 2010/0004288 A1* | 1/2010 | Pasteris et al. | 514/326 |
| 2010/0267717 A1* | 10/2010 | Leban et al. | 514/234.5 |

FOREIGN PATENT DOCUMENTS

| | | |
|---|---|---|
| JP | 61137869 A | 6/1986 |
| JP | 4235183 A | 8/1992 |
| JP | 6271549 A | 9/1994 |
| JP | 9500107 T | 1/1997 |
| JP | 2000505795 T | 8/1997 |
| JP | 11199572 A | 7/1999 |
| JP | 11209284 A | 8/1999 |
| JP | 2000086641 A | 3/2000 |
| JP | 2004/519464 A | 8/2002 |
| JP | 2005/060255 A | 3/2005 |
| WO | 97/15567 A1 | 5/1997 |
| WO | 01/74788 A1 | 10/2001 |
| WO | 02/14271 A1 | 2/2002 |
| WO | 02/059086 A1 | 8/2002 |
| WO | 02/064558 A2 | 8/2002 |
| WO | 03/007990 A1 | 1/2003 |
| WO | 2004/000821 A1 | 12/2003 |
| WO | 2004/004657 A2 | 1/2004 |
| WO | 2004/018453 A1 | 3/2004 |
| WO | 2004/058750 A1 | 7/2004 |
| WO | 2004/058751 A1 | 7/2004 |

(Continued)

OTHER PUBLICATIONS

Arrang et al. "Imidazolyl . . . " CA106:84602 (1987).*

(Continued)

*Primary Examiner* — Celia Chang
(74) *Attorney, Agent, or Firm* — Jane O. Hamby; Renee M. Lett

(57) ABSTRACT

This invention is directed to compounds of Formula (1) including all geometric and stereoisomers, N oxides, and agriculturally suitable salts thereof, agricultural compositions containing them and their use as fungicides, (1) provided that the compound of Formula 1 is other than 2-[1-[(2-chlorophenyl)acetyl]-4-piperidinyl]-N-methyl-N-[(1R)-1-phenylethyl]-4-thiazolecarboxamide and $R^1$ is other than 4-fluorophenyl; wherein $R^1$, $R^2$, A, G, Q, $W^1$, $W^2$, X and n are otherwise as defined in the disclosure, Also disclosed are compositions containing the a compound having a formula corresponding to Formula (1) where the provisos are both omitted; and methods for controlling plant diseases caused by fungal plant pathogens which involves applying an effective amount of a compound having a formula corresponding to Formula (1) where the provisos are both omitted.

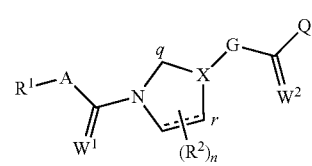

(1)

4 Claims, No Drawings

(56) References Cited

FOREIGN PATENT DOCUMENTS

| WO | 2004/092124 | A2 | | 10/2004 |
|---|---|---|---|---|
| WO | 2005/003128 | A1 | | 1/2005 |
| WO | 2005/040161 | A1 | | 5/2005 |
| WO | 2005/116653 | A2 | | 12/2005 |
| WO | 2008/091594 | | * | 7/2008 |

OTHER PUBLICATIONS

Leban et al. "Thiazoles, oxazoles . . . " CA144:350663 (2006).*
Leban et al. "Novel 1-piperidine- . . . " CA153:55147 (2010).*
Leriche et. al. "Novel NIP theazole . . . " CA151:515291 (2009).*
Otte "Preparation of . . . " CA147:344079 (2007).*
Dorwald "Side reactions . . . " p .ix (2005).*
Improper Markush training slides 1, 64-67 (2011).*
Mikaberidze et al. "Can high risk fungicides . . . " Inst. Integrat. Bio. p. 1-2 (2013).*
Johnson et al. "Acaridide, . . . " PLOS ONE v.8, p. 1-10 (2013).*
Xing et al., Evaluation and Application of Multiple Scoring Functions are a Virtual Screening Experiment, Journal of Computer-Aided Molecular Design, 18(5), pp. 333-344, 2004.

* cited by examiner

FUNGICIDAL CARBOXAMIDES

FIELD OF THE INVENTION

This invention relates to certain carboxamides, their N-oxides, agriculturally suitable salts and compositions, and methods of their use as fungicides.

BACKGROUND OF THE INVENTION

The control of plant diseases caused by fungal plant pathogens is extremely important in achieving high crop efficiency. Plant disease damage to ornamental, vegetable, field, cereal, and fruit crops can cause significant reduction in productivity and thereby result in increased costs to the consumer. Many products are commercially available for these purposes, but the need continues for new compounds which are more effective, less costly, less toxic, environmentally safer or have different sites of action.

World Patent Publication WO 05/003128 discloses thiazolylpiperidine derivatives of Formula i as MTP (Microsomal Triglyceride transfer Protein) inhibitors.

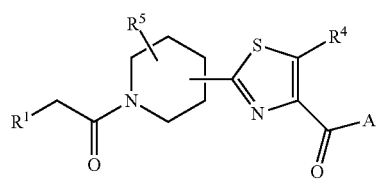

i wherein
A is a radical selected from the radicals a1 and a2 below

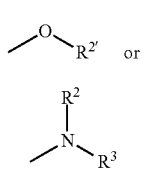

a1
a2 and $R^1$, $R^2$, $R^{2'}$, $R^3$, $R^4$ and $R^5$ are as defined in the disclosure.

World Patent Publication WO 04/058751 discloses piperidinyl-thiazole carboxamide derivatives for altering vascular tone.

SUMMARY OF THE INVENTION

This invention is directed to compounds of Formula 1 including all geometric and stereoisomers, N-oxides, and agriculturally suitable salts thereof, agricultural compositions containing them and their use as fungicides:

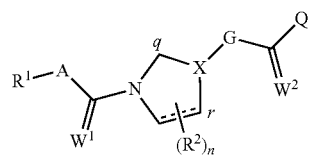

1 wherein
$R^1$ is an optionally substituted phenyl or 5- or 6-membered heteroaromatic ring;
A is $CH_2$ or NH;
$W^1$ is O or S;
X is a radical selected from

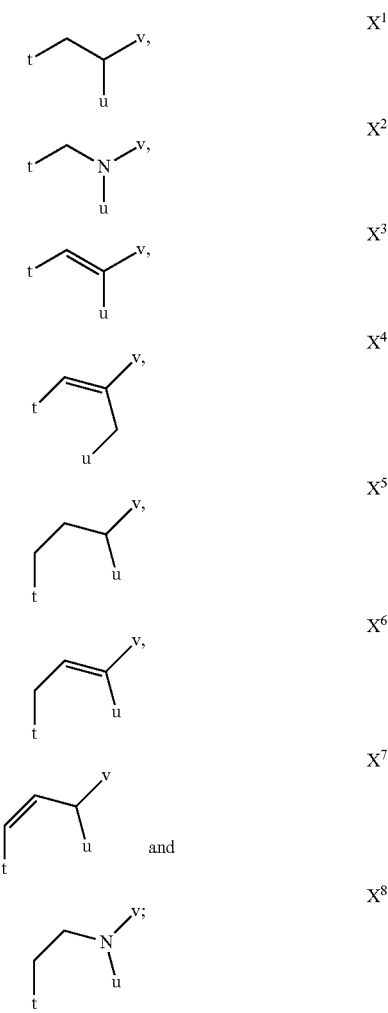

$X^1$
$X^2$
$X^3$
$X^4$
$X^5$
$X^6$
$X^7$ and
$X^8$;

wherein the bond of X which is identified with "t" is connected to the carbon atom identified with "q" of Formula 1, the bond which is identified with "u" is connected to the carbon atom identified with "r" of Formula 1, and the bond which is identified with "v" is connected to G;
each $R^2$ is independently $C_1$-$C_4$ alkyl, $C_1$-$C_4$ alkenyl, $C_1$-$C_4$ haloalkyl, $C_1$-$C_4$ alkoxy, halogen, cyano or hydroxy;
n is 0, 1 or 2; or
two $R^2$ are taken together as $C_1$-$C_3$ alkylene or $C_2$-$C_3$ alkenylene to form a bridged bicyclic ring system; or
two $R^2$ attached to adjacent ring carbon atoms joined by a double bond are taken together as —CH=CH—CH=CH= optionally substituted with 1-3 substituents selected from $C_1$-$C_4$ alkyl, $C_1$-$C_4$ haloalkyl, $C_1$-$C_4$ alkoxy, $C_1$-$C_4$ haloalkoxy, halogen, hydroxy, amino, cyano and nitro;
G is an optionally substituted 5-membered heteroaromatic ring or 5-membered saturated or partially saturated heterocyclic ring;

W² is O or S;

Q is —NQᵃQᵇ;

Qᵃ is H, $C_1$-$C_3$ alkyl, $C_2$-$C_3$ alkenyl, $C_2$-$C_3$ alkynyl, $C_4$-$C_{10}$ cycloalkylalkyl, $C_4$-$C_{10}$ alkylcycloalkyl, $C_5$-$C_{10}$ alkylcycloalkylalkyl, $C_1$-$C_3$ haloalkyl, $C_2$-$C_3$ haloalkenyl, cyano, hydroxy, $C_1$-$C_3$ alkoxy, $C_2$-$C_3$ alkoxyalkyl, $C_1$-$C_3$ hydroxyalkyl, $C_2$-$C_3$ alkylcarbonyl, $C_2$-$C_3$ alkoxycarbonyl, $C_2$-$C_3$ alkylaminocarbonyl or $C_3$-$C_5$ dialkylaminocarbonyl;

Qᵇ is an optionally substituted 8- to 11-membered saturated or partially saturated bicyclic ring system or an optionally substituted 10- to 15-membered partially saturated tricyclic ring system, each ring system optionally containing 1 to 3 heteroatoms selected from up to 1 O, up to 1 S and up to 3 N, and optionally including 1-3 ring members selected from the group consisting of C(=O), C(=S), S(O), or S(O)$_2$; or Qᵇ is CR⁵R⁶R¹⁵; or Qᵃ and Qᵇ are taken together with the nitrogen atom to which they are bonded to form an optionally substituted 5- or 6-membered saturated or partially saturated heterocyclic ring;

R⁵ is H, $C_1$-$C_6$ alkyl, $C_2$-$C_6$ alkenyl, $C_2$-$C_6$ alkynyl, $C_3$-$C_6$ cycloalkyl, $C_4$-$C_{10}$ cycloalkylalkyl, $C_4$-$C_{10}$ alkylcycloalkyl, $C_5$-$C_{10}$ alkylcycloalkylalkyl, $C_1$-$C_6$ haloalkyl, $C_2$-$C_6$ haloalkenyl, $C_2$-$C_6$ haloalkynyl, $C_3$-$C_6$ halocycloalkyl, cyano, nitro, $C_2$-$C_4$ alkoxyalkyl, $C_1$-$C_4$ hydroxyalkyl, $C_2$-$C_4$ alkylcarbonyl, $C_2$-$C_6$ alkoxycarbonyl, $C_2$-$C_6$ alkylaminocarbonyl, $C_3$-$C_8$ dialkylaminocarbonyl or $C_3$-$C_6$ trialkylsilyl;

R⁶ is an optionally substituted phenyl, benzyl, naphthalenyl, $C_3$-$C_6$ cycloalkyl, $C_3$-$C_6$ cycloalkenyl or 5- or 6-membered heteroaromatic ring; and R¹⁵ is H, $C_1$-$C_4$ alkyl, $C_2$-$C_4$ alkenyl, $C_2$-$C_4$ alkynyl, $C_3$-$C_4$ cycloalkyl, $C_4$-$C_{10}$ cycloalkylalkyl, $C_4$-$C_{10}$ alkylcycloalkyl, $C_5$-$C_{10}$ alkylcycloalkylalkyl, $C_1$-$C_4$ haloalkyl, $C_2$-$C_4$ haloalkenyl, $C_2$-$C_4$ haloalkynyl, $C_3$-$C_4$ halocycloalkyl or $C_2$-$C_4$ alkoxyalkyl; or Qᵃ and R⁵ are taken together with the atoms connecting them to form an optionally substituted 5- to 7-membered ring containing as ring members 2 to 7 carbon atoms and optionally 1 to 3 heteroatoms selected from up to 1 O, up to 1 S and up to 2 N; or Qᵃ and R⁶ are taken together with the atoms connecting them to form an optionally substituted 5- to 7-membered ring containing as ring members 2 to 7 carbon atoms and optionally 1 to 3 heteroatoms selected from up to 1 O, up to 1 S and up to 2 N; or R⁵ and R¹⁵ are taken together with the carbon atom to which they are bonded to form an optionally substituted 5- to 7-membered ring containing as ring members 2 to 7 carbon atoms and, optionally 1 to 3 heteroatoms selected from up to 1 O, up to 1 S and up to 1 N; or R⁵ and R⁶ are taken together with the carbon atom to which they are bonded to form an optionally substituted 5- to 7-membered ring containing as ring members 2 to 7 carbon atoms and, optionally 1 to 3 heteroatoms selected from up to 1 O, up to 1 S and up to 1 N;

provided that:
(a) the compound of Formula 1 is other than 2-[1-[(2-chlorophenyl)acetyl]-4-piperidinyl]-N-methyl-N-[(1R)-1-phenylethyl]-4-thiazolecarboxamide;
(b) when X is X², X³, X⁴, X⁶ or X⁸, then G is not linked to X via a heteroatom of the G ring; and
(c) R¹ is other than 4-fluorophenyl.

More particularly, this invention pertains to a compound of Formula 1, including all geometric and stereoisomers, an N-oxide or an agriculturally suitable salt thereof.

This invention also relates to a fungicidal composition comprising a fungicidally effective amount of a compound of Formula 1 and at least one additional component selected from the group consisting of surfactants, solid diluents or liquid diluents.

This invention also relates to a fungicidal composition comprising a mixture of a compound of Formula 1 and at least one other fungicide, particularly at least one other fungicide having a different mode of action.

This invention further relates to a method for controlling plant diseases caused by fungal plant pathogens comprising applying to the plant or portion thereof, or to the plant seed or seedling, a fungicidally effective amount of a compound of the invention (i.e. as a composition described herein).

This invention also provides a fungicidal composition comprising a fungicidally effective amount of a compound having a formula corresponding to Formula 1 except that R¹ is 4-fluorophenyl and at least one additional component selected from the group consisting of surfactants, solid diluents or liquid diluents.

This invention also relates to a fungicidal composition comprising a fungicidally effective amount of a compound having a formula corresponding to Formula 1 except that R¹ is 4-fluorophenyl and at least one other fungicide.

This invention further relates to a method for controlling plant diseases caused by fungal plant pathogens comprising applying to the plant or portion thereof, or to the plant seed or seedling, a fungicidally effective amount of the compound having a formula corresponding to Formula 1 except that R¹ is 4-fluorophenyl (i.e. as a composition described herein).

This invention also provides a fungicidal composition comprising a fungicidally effective amount of the compound of 2-[1-[(2-chlorophenyl)acetyl]-4-piperidinyl]-N-methyl-N-[(1R)-1-phenylethyl]-4-thiazolecarboxamide and at least one additional component selected from the group consisting of surfactants, solid diluents or liquid diluents.

This invention also relates to a fungicidal composition comprising a mixture of the compound of 2-[1-[(2-chlorophenyl)acetyl]-4-piperidinyl]-N-methyl-N-[(1R)-1-phenylethyl]-4-thiazolecarboxamide and at least one other fungicide.

This invention further relates to a method for controlling plant diseases caused by fungal plant pathogens comprising applying to the plant or portion thereof, or to the plant seed or seedling, a fungicidally effective amount of the compound of 2-[1-[(2-chlorophenyl)acetyl]-4-piperidinyl]-N-methyl-N-[(1R)-1-phenylethyl]-4-thiazole-carboxamide (i.e. as a composition described herein).

DETAILS OF THE INVENTION

As used herein, the terms "comprises," "comprising," "includes," "including," "has," "having" or any other variation thereof, are intended to cover a non-exclusive inclusion. For example, a composition, process, method, article, or apparatus that comprises a list of elements is not necessarily limited to only those elements but may include other elements not expressly listed or inherent to such composition, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and Both A and B are true (or present).

Also, use of "a" or "an" are employed to describe elements and components of the invention. This is done merely for convenience and to give a general sense of the invention. This description should be read to include one or at least one and the singular also includes the plural unless it is obvious that it is meant otherwise.

In the above recitations, the term "alkyl", used either alone or in compound words such as "alkylthio" or "haloalkyl" includes straight-chain or branched alkyl, such as, methyl, ethyl, n-propyl, i-propyl, or the different butyl, pentyl or hexyl isomers. The term "1-2 alkyl" indicates that one or two of the available positions for that substituent may be alkyl which are independently selected: "Alkenyl" includes straight-chain or branched alkenes such as ethenyl, 1-propenyl, 2-propenyl, and the different butenyl, pentenyl and hexenyl isomers. "Alkenyl" also includes polyenes such as 1,2-propadienyl and 2,4-hexadienyl. "Alkynyl" includes straight-chain or branched alkynes such as ethynyl, 1-propynyl, 2-propynyl and the different butynyl, pentynyl and hexynyl isomers. "Alcynyl" can also include moieties comprised of multiple triple bonds such as 2,5-hexadiynyl. "Alkylene" denotes a straight-chain or branched alkanediyl. Examples of "alkylene" include $CH_2$, $CH_2CH_2$, $CH(CH_3)$, $CH_2CH_2CH_2$, $CH_2CH(CH_3)$ and the different butylene isomers. "Alkenylene" denotes a straight-chain or branched alkenediyl containing one olefinic bond. Examples of "alkenylene" include $CH=CH$, $CH_2CH=CH$, $CH=C(CH_3)$ and the different butenylene isomers. "Alkynylene" denotes a straight-chain or branched alkynediyl containing one triple bond. Examples of "alkynylene" include $C\equiv C$, $CH_2C\equiv C$, $C\equiv CCH_2$ and the different butynylene isomers. "Alkoxy" includes, for example, methoxy, ethoxy, n-propyloxy, isopropyloxy and the different butoxy, pentoxy and hexyloxy isomers. "Alkoxyalkyl" denotes alkoxy substitution on alkyl. Examples of "alkoxyalkyl" include $CH_3OCH_2$, $CH_3OCH_2CH_2$, $CH_3CH_2OCH_2$, $CH_3CH_2CH_2CH_2OCH_2$ and $CH_3CH_2OCH_2CH_2$. "Alkoxyalkoxy" denotes alkoxy substitution on alkoxy. "Alkenyloxy" includes straight-chain or branched alkenyloxy moieties. Examples of "alkenyloxy" include $H_2C=CHCH_2O$, $(CH_3)_2C=CHCH_2O$, $(CH_3)CH=CHCH_2O$, $(CH_3)CH=C(CH_3)CH_2O$ and $CH_2=CHCH_2CH_2O$. "Alkynyloxy" includes straight-chain or branched alkynyloxy moieties. Examples of "alkynyloxy" include $HC\equiv CCH_2O$, $CH_3C\equiv CCH_2O$ and $CH_3C\equiv CCH_2CH_2O$. "Alkylthio" includes branched or straight-chain alkylthio moieties such as methylthio, ethylthio, and the different propylthio, butylthio, pentylthio and hexylthio isomers. "Alkylsulfinyl" includes both enantiomers of an alkylsulfinyl group. Examples of "alkylsulfinyl" include $CH_3S(O)$, $CH_3CH_2S(O)$, $CH_3CH_2CH_2S(O)$, $(CH_3)_2CHS(O)$ and the different butylsulfinyl, pentylsulfinyl and hexylsulfinyl isomers. Examples of "alkylsulfonyl" include $CH_3S(O)_2$, $CH_3CH_2S(O)_2$, $CH_3CH_2CH_2S(O)_2$, $(CH_3)_2CHS(O)_2$ and the different butylsulfonyl, pentylsulfonyl and hexylsulfonyl isomers. "Alkylamino", "dialkylamino", "alkenylthio", "alkenylsulfinyl", "alkenylsulfonyl", "alkynylthio", "alkynylsulfonyl", and the like, are defined analogously to the above examples. "Cycloalkyl" includes, for example, cyclopropyl, cyclobutyl, cyclopentyl, and cyclohexyl. The term "carbocyclic ring" denotes a ring wherein the atoms forming the ring backbone and selected only from carbon. The term "aromatic ring system" denotes fully unsaturated carbocycles and heterocycles in which the polycyclic ring system is aromatic. Aromatic indicates that each of ring atoms is essentially in the same plane and has a p-orbital perpendicular to the ring plane, and in which (4n+2) π electrons, when n is 0 or a positive integer, are associated with the ring to comply with Hückel's rule. The term "aromatic carbocyclic ring system" includes fully aromatic carbocycles and carbocycles in which at least one ring of a polycyclic ring system is aromatic. The terms "aromatic heterocyclic ring system" and "heteroaromatic ring" include fully aromatic heterocycles and heterocycles in which at least one ring of a polycyclic ring system is aromatic. The term "saturated heterocyclic ring system" denotes fully saturated heterocycles wherein none of the rings in the ring system are aromatic. The term "partially saturated heterocyclic ring system" denotes partially unsaturated heterocycles wherein part of the rings in the ring system can be aromatic. The heterocyclic ring systems can be attached through any available carbon or nitrogen by replacement of a hydrogen on said carbon or nitrogen. One skilled in the art will appreciate that not all nitrogen containing heterocycles can form N-oxides since the nitrogen requires an available lone pair of electrons for oxidation to the oxide; one skilled in the art will recognize those nitrogen containing heterocycles which can form N-oxides. One skilled in the art will also recognize that tertiary amines can form N-oxides. Synthetic methods for the preparation of N-oxides of heterocycles and tertiary amines are very well known by one skilled in the art including the oxidation of heterocycles and tertiary amines with peroxy acids such as peracetic and m-chloroperbenzoic acid (MCPBA), hydrogen peroxide, alkyl hydroperoxides such as t-butyl hydroperoxide, sodium perborate, and dioxiranes such as dimethydroxirane. These methods for the preparation of N-oxides have been extensively described and reviewed in the literature, see for example: T. L. Gilchrist in *Comprehensive Organic Synthesis*, vol. 7, pp 748-750, S. V. Ley, Ed., Pergamon Press; M. Tisler and B. Stanovnik in *Comprehensive Heterocyclic Chemistry*, vol. 3, pp 18-20, A. J. Boulton and A. McKillop, Eds., Pergamon Press; M. R. Grimmett and B. R. T. Keene in *Advances in Heterocyclic Chemistry*, vol. 43, pp 149-161, A. R. Katritzky, Ed., Academic Press; M. Tisler and B. Stanovnik in *Advances in Heterocyclic Chemistry*, vol. 9, pp 285-291, A. R. Katritzky and A. J. Boulton, Eds., Academic Press; and G. W. H. Cheeseman and E. S. G. Werstiuk in *Advances in Heterocyclic Chemistry*, vol. 22, pp 390-392, A. R. Katritzky and A. J. Boulton, Eds., Academic Press.

The term "halogen", either alone or in compound words such as "haloalkyl", includes fluorine, chlorine, bromine or iodine. The term "1-2 halogen" indicates that one or two of the available positions for that substituent may be halogen which are independently selected. Further, when used in compound words such as "haloalkyl", said alkyl may be partially or fully substituted with halogen atoms which may be the same or different. Examples of "haloalkyl" include $F_3C$, $ClCH_2$, $CF_3CH_2$ and $CF_3CCl_2$. The terms "haloalkenyl", "haloalkynyl", "halocycloalkyl", "haloalkoxy", "haloalkylthio", and the like, are defined analogously to the term "haloalkyl". Examples of "haloalkenyl" include $(Cl)_2C=CHCH_2$ and $CF_3CH_2CH=CHCH_2$. Examples of "haloalkynyl" include $HC\equiv CCHCl$, $CF_3C\equiv C$, $CCl_3C\equiv C$ and $FCH_2C\equiv CCH_2$. Examples of "haloalkoxy" include CF$_3$O, CCl$_3$CH$_2$O, HCF$_2$CH$_2$CH$_2$O and CF$_3$CH$_2$O. Examples of "haloalkylthio" include CCl$_3$S, CF$_3$S, CCl$_3$CH$_2$S and ClCH$_2$CH$_2$CH$_2$S. Examples of "haloalkylsulfinyl" include CF$_3$S(O), CCl$_3$S(O), CF$_3$CH$_2$S(O) and CF$_3$CF$_2$S(O). Examples of "haloalkylsulfonyl" include CF$_3$S(O)$_2$, CCl$_3$S(O)$_2$, CF$_3$CH$_2$S(O)$_2$ and CF$_3$CF$_2$S(O)$_2$. Examples of "partially saturated bicyclic ring system" include tetrahydronaphthalene, tetrahydroquinoline, tetrahydroisoquinoline. "Trialkylsilyl" includes 3 branched and/or straight-chain alkyl radicals attached to and linked through a silicon atom such as trimethylsilyl, triethylsilyl and t-butyldimethylsilyl. The total number of carbon atoms in a substituent group is indicated by the "C$_i$-C$_j$" prefix where i and j are numbers from 1 to 10. For example, C$_1$-C$_4$ alkylsulfonyl designates methylsulfonyl through butylsulfonyl; C$_2$ alkoxyalkyl designates CH$_3$OCH$_2$; C$_3$ alkoxyalkyl designates, for example, CH$_3$CH(OCH$_3$), CH$_3$OCH$_2$CH$_2$ or CH$_3$CH$_2$OCH$_2$; and C$_4$ alkoxyalkyl designates the various isomers of an alkyl group substituted with an alkoxy group containing a total of four carbon atoms, examples including CH$_3$CH$_2$CH$_2$OCH$_2$ and CH$_3$CH$_2$OCH$_2$CH$_2$. C$_2$ alkylaminoalkyl designates CH$_3$NHCH$_2$—; C$_3$ alkylaminoalkyl designates, for example, CH$_3$(CH$_3$NH)CH—, CH$_3$NHCH$_2$CH$_2$— or CH$_3$CH$_2$NHCH$_2$—; and Examples of "alkylcarbonyl" include C(O)CH$_3$, C(O)CH$_2$CH$_3$ and C(O)CH(CH$_3$)$_2$. Examples of "alkoxycarbonyl" include CH$_3$C(=O), CH$_3$CH$_2$OC(=O), CH$_3$CH$_2$CH$_2$OC(=O), (CH$_3$)$_2$CHOC(=O) and the different butoxy- or pentoxycarbonyl isomers. Examples of "alkylaminocarbonyl" include CH$_3$NHC(=O)—, CH$_3$CH$_2$NHC(=O)—, CH$_3$CH$_2$CH$_2$NHC(=O)—, (CH$_3$)$_2$CHNHC(=O)— and the different butylamino- or pentylaminocarbonyl isomers. Examples of "dialkylaminocarbonyl" include (CH$_3$)$_2$NC(=O)—, (CH$_3$CH$_2$)$_2$NC(=O)—, CH$_3$CH$_2$(CH$_3$)NC(=O)—, (CH$_3$)$_2$CHN(CH$_3$)C(=O)— and CH$_3$CH$_2$CH$_2$(CH$_3$)NC(=O)—. In the above recitations, when a compound of Formula 1 is comprised of one or more heterocyclic rings, all substituents are attached to these rings through any available carbon or nitrogen by replacement of a hydrogen on said carbon or nitrogen.

The dotted line in Formula 1 represents that the bond indicated can be a single bond or double bond.

When X is a radical selected from X$^1$, X$^2$, X$^3$, X$^4$, X$^5$, X$^6$, X$^7$ and X$^8$, the left-hand bond of X which is identified with "t" is connected to the carbon atom next to the nitrogen identified with "q" of Formula 1, and the right-bottom bond of X which is identified with "u" is connected to the carbon atom identified with "r" of Formula 1 and the right upper-hand bond of X which is identified with "v" is connected to the G ring of Formula 1.

When a compound is substituted with a substituent bearing a subscript that indicates the number of said substituents can vary, when the number of said substituents is greater than 1, said substituents are independently selected from the group of defined substituents. Further, when the subscript indicates a range, e.g. (R)$_{i-j}$, then the number of substituents may be selected from the integers between i and j inclusive. Also, one skilled in the art recognizes that the number of available points of attachment places a limit on the number of substituents possible that may be lower than the broad definition; for example, the subscript "k" in U-16, U-17, U-18, U-19, U-32, U-33 and U-35 shown in Embodiment 14 cannot be greater than 1.

When a group contains a substituent which can be hydrogen, for example Q$^a$, R$^5$ or R$^{15}$, then, when this substituent is taken as hydrogen, it is recognized that this is equivalent to said group being unsubstituted. When a variable group is shown to be optionally attached to a position, for example (R$^2$)$_n$ wherein n may be 0, then hydrogen may be at the position even if not recited in the variable group definition. When a position on a group is said to be "not substituted" or "unsubstituted", then hydrogen atoms are attached to take up any free valency. The term "optionally substituted" in connection with groups listed for R$^1$, R$^2$, R$^5$, R$^6$, R$^{15}$, R$^{16}$, R$^{16a}$, G, Q$^a$ and Q$^b$ refers to groups that are unsubstituted or have at least 1 non-hydrogen substituent. These groups may be substituted with as many optional substituents as can be accommodated by replacing a hydrogen atom with a non-hydrogen substituent on any available carbon or nitrogen atom. Commonly, the number of optional substituents (when present) ranges from 1 to 3.

As noted above, R$^1$ is an optionally substituted phenyl or 5- or 6-membered heteroaromatic ring; G is an optionally substituted 5-membered heteroaromatic ring or 5-membered saturated or partially saturated heterocyclic ring; Q$^a$ and Q$^b$ are taken together with the nitrogen atom to which they are bonded to form an optionally substituted 5- or 6-membered saturated or partially saturated heterocyclic ring; and R$^6$ is an optionally substituted phenyl, benzyl, naphthalenyl, C$_3$-C$_6$ cycloalkyl, C$_3$-C$_6$ cycloalkenyl or 5- or 6-membered heteroaromatic ring; and Q-2 through Q-85 are optionally substituted. The term "substituted" in connection with these R$^1$, G, R$^6$, Q$^a$ and Q$^b$ groups refers to groups that have at least one non-hydrogen substituent that does not extinguish the fungicidal activity. Since these groups are optionally substituted, they need not have any non-hydrogen substituents.

Naming of substituents in the present disclosure uses recognized terminology providing conciseness in precisely conveying to those skilled in the art the chemical structure. For example, as is used in nomenclature, the prefix "per" indicates "completely", and "perhydro" means that the referenced heteroaromatic ring or ring system (e.g., quinoline, isoquinoline) has been completely hydrogenated, so that it is fully saturated. Also, ending a heterocyclic substituent name with the letter "o" (e.g., "piperidino", "pyrrolidino", "isoquinolino", "isoindolo") means that the heterocyclic substituent is bonded to the remainder of the molecule through the nitrogen atom of the heterocycle. For sake of conciseness, locant descriptors may be omitted; "pyrazol-1-yl" means "1H-pyrazol-1-yl" according to the Chemical Abstracts system of nomenclature. The term "pyridyl" is synonymous with "pyridinyl". The order of listing substituents may be different from the Chemical Abstracts system if the difference does not affect the meaning.

A. Examples of compounds of Formula 1 include compounds wherein
R$^1$ is a phenyl or 5- or 6-membered heteroaromatic ring, optionally substituted with 1 to 2 substituents independently selected from R$^4$;
each R$^4$ is independently C$_1$-C$_6$ alkyl, C$_2$-C$_6$ alkenyl, C$_2$-C$_6$ alkynyl, C$_3$-C$_6$ cycloalkyl, C$_4$-C$_{10}$ cycloalkylalkyl, C$_4$-C$_{10}$ alkylcycloalkyl, C$_5$-C$_{10}$ alkylcycloalkylalkyl, C$_1$-C$_6$ haloalkyl, C$_2$-C$_6$ haloalkenyl, C$_2$-C$_6$ haloalkynyl, C$_3$-C$_6$ halocycloalkyl, halogen, hydroxy, amino, cyano, nitro, C$_1$-C$_4$ alkoxy, C$_1$-C$_4$ haloalkoxy, C$_1$-C$_4$ alkylthio, C$_1$-C$_4$ alkylsulfinyl, C$_1$-C$_4$ alkylsulfonyl, C$_1$-C$_4$ haloalkylthio, C$_1$-C$_4$ haloalkylsulfinyl, C$_1$-C$_4$ haloalkylsulfonyl, C$_1$-C$_4$ alkylamino, C$_2$-C$_8$ dialkylamino, C$_3$-C$_6$ cycloalkylamino, C$_2$-C$_4$ alkoxyalkyl, C$_1$-C$_4$ hydroxyalkyl, C$_2$-C$_4$ alkylcarbonyl, C$_2$-C$_6$ alkoxycarbonyl, C$_2$-C$_6$ alkylcarbonyloxy, C$_2$-C$_6$ alkylcarbonylthio, C$_2$-C$_6$ alkylaminocarbonyl, C$_3$-C$_8$ dialkylaminocarbonyl or C$_3$-C$_6$ trialkylsilyl;

G is a 5-membered heteroaromatic ring or 5-membered saturated or partially saturated heterocyclic ring, each ring optionally substituted with up to 2 substituents selected from $R^3$ on carbon ring members and selected from $R^{11}$ on nitrogen ring members;

each $R^3$ is independently $C_1$-$C_3$ alkyl, $C_1$-$C_3$ haloalkyl or halogen;

$R^{11}$ is $C_1$-$C_3$ alkyl; and

Q is a radical selected from Q-1 through Q-85 as described in connection with Embodiment 50 described hereinafter.

B. Of note are compounds of Paragraph A above wherein $R^1$ is one of U-1 through U-50 as described in connection with Embodiment 14 described hereinafter; G is one of G-1 through G-55 as described in connection with Embodiment 36 described hereinafter; each $R^{3a}$ is independently H, $C_1$-$C_3$ alkyl, $C_1$-$C_3$ haloalkyl or halogen (more particularly H, $C_1$-$C_3$ alkyl or halogen, and most particularly H or $C_1$-$C_3$ alkyl); $R^{11a}$ is H or $C_1$-$C_3$ alkyl; $R^6$ is one of H-1 through H-46 as described in connection with Embodiment 65 described hereinafter; and $R^{12}$ is H or $C_1$-$C_3$ alkyl. Of particular note among these compounds are compounds wherein each $R^4$ is independently $C_1$-$C_3$ alkyl, $C_2$-$C_3$ alkenyl, $C_2$-$C_3$ alkynyl, cyclopropyl, $C_1$-$C_3$ haloalkyl, $C_2$-$C_3$ haloalkenyl, $C_2$-$C_3$ haloalkynyl, halocyclopropyl, halogen, cyano, nitro, $C_1$-$C_2$ alkoxy or $C_1$-$C_2$ haloalkoxy; $R^5$ is $C_1$-$C_4$ alkyl, $C_2$-$C_4$ alkenyl, $C_2$-$C_4$ alkynyl, $C_3$-$C_4$ cycloalkyl, $C_1$-$C_4$ haloalkyl, $C_2$-$C_4$ haloalkenyl, $C_2$-$C_4$ haloalkynyl, $C_3$-$C_4$ halocycloalkyl, cyano or $C_2$-$C_4$ alkoxyalkyl; and each $R^7$ is independently $C_1$-$C_3$ alkyl, $C_2$-$C_3$ alkenyl, $C_2$-$C_3$ alkynyl, cyclopropyl, $C_1$-$C_3$ haloalkyl, $C_2$-$C_3$ haloalkenyl, $C_2$-$C_3$ haloalkynyl, halocyclopropyl, halogen, cyano, nitro, $C_1$-$C_2$ alkoxy or $C_1$-$C_2$ haloalkoxy; each $R^8$ is independently H, $C_1$-$C_4$ alkyl, $C_2$-$C_4$ alkenyl, $C_3$-$C_4$ alkynyl, $C_3$-$C_6$ cycloalkyl, $C_1$-$C_4$ haloalkyl, $C_2$-$C_4$ haloalkenyl, $C_2$-$C_4$ haloalkynyl, $C_3$-$C_6$ halocycloalkyl, halogen, hydroxy, amino, cyano, nitro, $C_1$-$C_4$ alkoxy or $C_2$-$C_4$ alkylcarbonyloxy; each $R^9$ is independently $C_1$-$C_3$ alkyl, cyclopropyl, $C_1$-$C_3$ haloalkyl, halocyclopropyl, halogen, hydroxy, $C_2$-$C_3$ alkylcarbonyloxy, $C_1$-$C_2$ alkoxy or $C_1$-$C_2$ haloalkoxy; $R^{10}$ is H or methyl; each $R^{16}$ is independently $C_1$-$C_3$ alkyl, $C_2$-$C_3$ alkenyl, $C_2$-$C_3$ alkynyl, cyclopropyl, $C_1$-$C_3$ haloalkyl, $C_2$-$C_3$ haloalkenyl, $C_2$-$C_3$ haloalkynyl, halocyclopropyl, halogen, cyano, nitro, $C_1$-$C_2$ alkoxy or $C_1$-$C_2$ haloalkoxy; or a phenyl or benzyl ring, optionally substituted with up to 3 substituents selected from $R^{13}$; $R^{16a}$ is H, $C_1$-$C_3$ alkyl, allyl, propargyl, cyclopropyl or $C_1$-$C_3$ haloalkyl; or a phenyl or benzyl ring, optionally substituted with up to 3 substituents selected from $R^{13}$; and each $R^{13}$ is independently $C_1$-$C_3$ alkyl, $C_2$-$C_3$ alkenyl, $C_2$-$C_3$ alkynyl, cyclopropyl, $C_1$-$C_3$ haloalkyl, $C_2$-$C_3$ haloalkenyl, $C_2$-$C_3$ haloalkynyl, halocyclopropyl, halogen, cyano, nitro, $C_1$-$C_2$ alkoxy or $C_1$-$C_2$ haloalkoxy.

C. Examples of the compounds of the Paragraph B above include compounds wherein X is one of $X^1$, $X^2$ and $X^3$; and each $R^2$ is independently $C_1$-$C_2$ alkyl, $C_1$-$C_2$ haloalkyl, $C_1$-$C_2$ alkoxy, halogen, cyano or hydroxy; $Q^a$ is H or $CH_3$; and $R^{15}$ is H or $CH_3$.

D. Examples of the compounds of the Paragraph C above include compounds wherein $R^1$ is one of U-1 through U-3, U-11, U-13, U-20, U-22, U-23, U-36, U-37 through U-39 and U-50; and each $R^4$ is independently halogen, $C_1$-$C_3$ alkyl, $C_1$-$C_3$ haloalkyl, $C_1$-$C_2$ alkoxy or $C_1$-$C_2$ haloalkoxy. Also included are compounds wherein G is G-1, G-2, G-3, G-7, G-8, G-10, G-11, G-14, G-15, G-23, G-24, G-26, G-27, G-28, G-30, G-36, G-37, G-38 or G-49 through G-55; $R^{1a}$ is H, $CH_3$, Cl or Br; and $R^{11}$ is H or $CH_3$. Of note are compounds wherein G is G-1, G-2, G-7, G-8, G-14, G-15, G-23, G-24, G-26, G-27, G-36, G-37, G-38, G-49 or G-50 (including e.g., where G is unsubstituted).

E. Further examples of the compounds of Paragraph C include compounds wherein Q is Q-1, Q-2, Q-3, Q-4, Q-8, Q-9, Q-10, Q-12, Q-14, Q-22, Q-23, Q-24, Q-40, Q-41, Q-59, Q-62, Q-74 or Q-84; $R^5$ is $C_1$-$C_4$ alkyl, $C_2$-$C_4$ alkenyl, $C_2$-$C_4$ alkynyl, $C_3$-$C_4$ cycloalkyl, $C_1$-$C_4$ haloalkyl, $C_2$-$C_4$ haloalkenyl, $C_2$-$C_4$ haloalkynyl, $C_3$-$C_4$ halocycloalkyl, cyano or $C_2$-$C_4$ alkoxyalkyl; $R^6$ is H-1, H-20, H-32, H-45 or H-46; each $R^7$ is independently halogen, $C_1$-$C_3$ alkyl, $C_1$-$C_3$ haloalkyl, $C_1$-$C_2$ alkoxy or $C_1$-$C_2$ haloalkoxy; each $R^8$ is independently $C_1$-$C_2$ alkyl, $C_1$-$C_2$ haloalkyl, $C_1$-$C_2$ alkoxy, $C_1$-$C_2$ haloalkoxy, $C_2$-$C_4$ alkylcarbonyloxy or hydroxy; and each $R^9$ is independently halogen, hydroxy, $OCH_3$ or $CH_3$. Included are compounds wherein Q is Q-1, Q-2, Q-8, Q-14, Q-23, Q-41, Q-59 or Q-62; $Q^a$ is methyl; $R^5$ is $C_1$-$C_4$ alkyl, $C_1$-$C_4$ haloalkyl, $C_2$-$C_4$ alkenyl, $C_2$-$C_4$ haloalkenyl or cyano; $R^6$ is H-1 or H-45; $R^{12}$ is H or $CH_3$; each $R^7$ is independently F, Cl, Br, $OCH_3$ or methyl; $R^{15}$ is H; $R^8$ is $CH_3$, $OCH_3$ or OH; and $R^{10}$ is H or $CH_3$.

F. Additional examples of the compounds of Paragraph C include compounds wherein $W^1$ and $W^2$ are independently 0; $Q^a$ is $CH_3$; m, j, n and p are all independently 0 or 1; $R^{1a}$ is H; each $R^7$ is independently F, Cl, Br, $OCH_3$ or methyl; each $R^8$ is independently $C_1$-$C_2$ alkyl, $C_1$-$C_2$ alkoxy or hydroxy; and each $R^9$ is independently F, Cl, Br, hydroxy, $OCH_3$ or $CH_3$. Included are compounds wherein $R^1$ is U-1 or U-50; each $R^4$ is independently halogen, $C_1$-$C_3$ alkyl, $C_1$-$C_3$ haloalkyl or $C_1$-$C_2$ alkoxy; G is G-1, G-2, G-15, G-26, G-27, G-36, G-37 or G-38; Q is Q-1, Q-2, Q-8, Q-23 or Q-41; $R^5$ is $C_1$-$C_4$ alkyl, $C_2$-$C_4$ alkenyl or cyano; $R^6$ is H-45; and each $R^4$ is independently connected to the 3- or 5-position of U-1, each $R^4$ is independently connected to the 3- and 5-position of U-1, each $R^4$ is independently connected to the 2- or 3-position of U-50, or each $R^4$ is independently connected to the 2- and 5-position of U-50 (e.g., compounds where X is $X^1$ and G is G-1; X is $X^1$ and G is G-2; X is $X^1$ and G is G-15; X is $X^1$ and G is G-26; X is $X^1$ and G is G-36; X is $X^2$ and G is G-1; or X is $X^2$ and G is G-2). In the foregoing, "each $R^4$ is independently connected to the 3- or 5-position of U-1" means k is 1 and $R^4$ is connected to the 3- or 5-position of U-1, "each $R^4$ is independently connected to the 3- and 5-position of U-1" means k is 2 and an independently selected $R^4$ is connected to each of the 3- and 5-positions of U-1, "each $R^4$ is independently connected to the 2- or 3-position of U-50" means k is 1 and $R^4$ is connected to the 3- or 5-position of U-50, and "each $R^4$ is independently connected to the 2- and 5-position of U-50" means k is 2 and an independently selected $R^4$ is connected to each of the 2- and 5-positions of U-50.

Compounds of this invention can exist as one or more stereoisomers. The various stereoisomers include enantiomers, diastereomers, atropisomers and geometric isomers. One skilled in the art will appreciate that one stereoisomer may be more active and/or may exhibit beneficial effects when enriched relative to the other stereoisomer(s) or when separated from the other stereoisomer(s). Additionally, the skilled artisan knows how to separate, enrich, and/or to selectively prepare said stereoisomers. Accordingly, the present invention comprises compounds selected from Formula 1, N-oxides and agriculturally suitable salts thereof. The compounds of the invention may be present as a mixture of stereoisomers, individual stereoisomers, or as an optically active form. For example, when Q is Q-1, and $R^5$, $R^6$ and $R^{15}$ of Q-1 in Formula 1 are different, then Formula 1 possesses a chiral center at the carbon atom to which they are commonly bonded. This invention comprises racemic mixtures. In addition, this invention includes compounds that are enriched compared to the racemic mixture in an enantiomer of Formula 1.

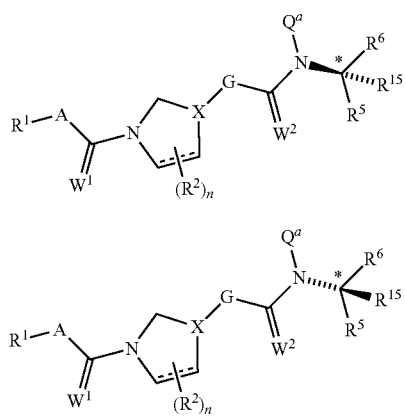

Included are the essentially pure enantiomers of compounds of Formula 1, for example, Formula 1' and Formula 1" wherein Q is Q-1.

When enantiomerically enriched, one enantiomer is present in greater amounts than the other, and the extent of enrichment can be defined by an expression of enantiomeric excess ("ee"), which is defined as $(2x-1)\cdot 100\%$, where x is the mole fraction of the dominant enantiomer in the mixture (e.g., an ee of 20% corresponds to a 60:40 ratio of enantiomers).

For the compounds of Formula 1 where Q is Q-1 through Q-74, the more fungicidally active enantiomer is believed to be that wherein $R^{15}$ is a hydrogen, the hydrogen atom attached to the carbon atom identified with an asterisk (*) is below the plane defined by the 3-non-hydrogen atoms attached to the carbon atom identified with the asterisk (*) as in Formula 1' (with the aromatic ring of Q-2 through Q-74 positioned with respect to the carbon atom identified with an asterisk (*) in a manner analogous to $R^6$ in Q-1 in Formula 1'). For example when $R^5$ is $CH_3$, $R^6$ is phenyl and $R^{15}$ is H, Formula 1' has the R configuration at the carbon atom to which $R^5$, $R^6$ and $R^{15}$ are commonly bonded.

Preferably the compositions of this invention have at least a 50% enantiomeric excess; more preferably at least a 75 enantiomeric excess; still more preferably at least a 90% enantiomeric excess; and the most preferably at least a 94% enantiomeric excess of the more active isomer. Of particular note are enantiomerically pure embodiments of the more active isomer.

Compounds of Formula 1 can comprise additional chiral centers. For example, the substituents $R^4$, $R^5$, $R^7$, $R^8$, $R^9$, $R^{13}$, $R^{15}$, $R^{16}$, $R^{16a}$, $Q^a$, $Q^b$ and $X^1$ through $X^8$ may themselves contain chiral centers. This invention comprises racemic mixtures as well as enriched and essentially pure stereoconfigurations at these additional chiral centers.

Compounds of this invention can exist as one or more conformational isomers due to the amide bonds in the compounds of Formula 1 as known by one skilled in the art. This invention comprises mixtures of conformational isomers. In addition, this invention includes compounds that are enriched compared to the mixture of a conformer of Formula 1.

The agriculturally suitable salts of the compounds of the invention include acid-addition salts with inorganic or organic acids such as hydrobromic, hydrochloric, nitric, phosphoric, sulfuric, acetic, butyric, fumaric, lactic, maleic, malonic, oxalic, propionic, salicylic, tartaric, 4-toluenesulfonic or valeric acids. The agriculturally suitable salts of the compounds of the invention also include those formed with organic bases (e.g., pyridine, ammonia, or triethylamine) or inorganic bases (e.g., hydrides, hydroxides, or carbonates of sodium, potassium, lithium, calcium, magnesium or barium) when the compound contains an acidic group such as a carboxylic acid or phenol. One skilled in the art recognizes that because in the environment and under physiological conditions salts of the compounds of the invention are in equilibrium with their corresponding nonsalt forms, agriculturally suitable salts share the biological utility of the nonsalt forms.

Embodiments of the present invention include:
Embodiment 1. A compound of Formula 1 wherein A is $CH_2$.
Embodiment 2. A compound of Formula 1 wherein A is NH.
Embodiment 3. A compound of Formula 1 wherein $W^1$ is O.
Embodiment 4. A compound of Formula 1 wherein $W^1$ is S.
Embodiment 5. A compound of Formula 1 wherein $W^2$ is O.
Embodiment 6. A compound of Formula 1 wherein $W^2$ is S.
Embodiment 7. A compound of Formula 1 wherein $R^2$ is methyl.
Embodiment 8. A compound of Formula 1 wherein n is 0 or 1.
Embodiment 9. A compound of Embodiment 8 wherein n is 0.
Embodiment 10. A compound of Formula 1 wherein X is $X^1$, $X^2$ or $X^3$.
Embodiment 11. A compound of Embodiment 10 wherein X is $X^1$ or $X^2$ and each ring is saturated.
Embodiment 12. A compound of Embodiment 10 wherein X is $X^1$.
Embodiment 13. A compound of Embodiment 12 wherein X is $X^1$ and the ring is saturated.
Embodiment 14. A compound of Formula 1 wherein $R^1$ is one of U-1 through U-50;

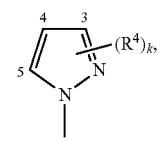

U-1

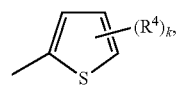

U-2

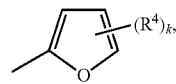

U-3

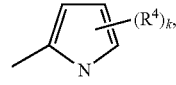

U-4

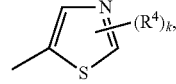

U-5

-continued

| | |
|---|---|
| (structure) | U-6 |
| (structure) | U-7 |
| (structure) | U-8 |
| (structure) | U-9 |
| (structure) | U-10 |
| (structure) | U-11 |
| (structure) | U-12 |
| (structure) | U-13 |
| (structure) | U-14 |
| (structure) | U-15 |
| (structure) | U-16 |
| (structure) | U-17 |
| (structure) | U-18 |
| (structure) | U-19 |
| (structure) | U-20 |

-continued

| | |
|---|---|
| (structure) | U-21 |
| (structure) | U-22 |
| (structure) | U-23 |
| (structure) | U-24 |
| (structure) | U-25 |
| (structure) | U-26 |
| (structure) | U-27 |
| (structure) | U-28 |
| (structure) | U-29 |
| (structure) | U-30 |
| (structure) | U-31 |
| (structure) | U-32 |

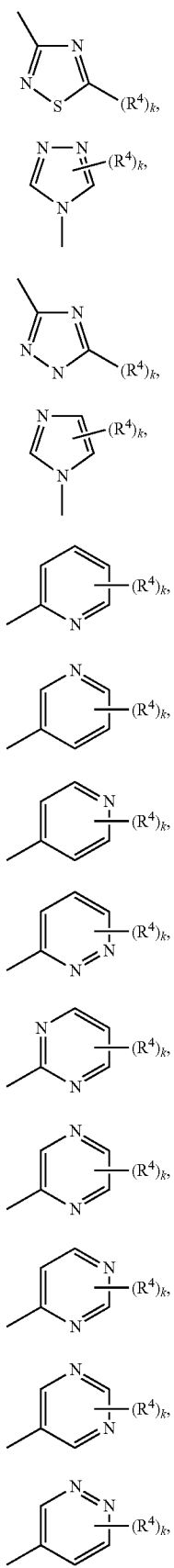

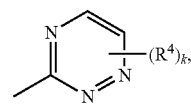

U-46

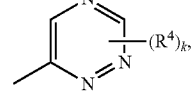

U-47

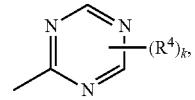

U-48

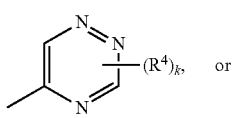

U-49

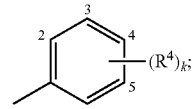

U-50 wherein k is 0, 1 or 2;

provided that when U is U-4, U-11 through U-15, U-24 through U-26, U-31 and U-35, and an $R^4$ radical is attached to a nitrogen atom of the ring, said $R^4$ radical is $C_1$-$C_6$ alkyl, $C_2$-$C_6$ alkenyl, $C_2$-$C_6$ alkynyl, $C_3$-$C_6$ cycloalkyl, $C_1$-$C_6$ haloalkyl, $C_2$-$C_6$ haloalkenyl, $C_2$-$C_6$ haloalkynyl, $C_3$-$C_6$ halocycloalkyl or $C_2$-$C_4$ alkoxyalkyl.

Embodiment 15. A compound of Embodiment 14 wherein $R^1$ is selected from U-1 through U-5, U-8, U-11, U-13, U-15, U-20 through U-28, U-31, U-36, U-37, U-38, U-39 and U-50.

Embodiment 16. A compound of Embodiment 15 wherein $R^1$ is selected from U-1 through U-3, U-5, U-8, U-13, U-20, U-22, U-23, U-25 through U-28, U-36 through U-39 and U-50.

Embodiment 17. A compound of Embodiment 16 wherein $R^1$ is selected from U-1 through U-3, U-13, U-20, U-22, U-23, U-36 through U-39 and U-50.

Embodiment 18. A compound of Embodiment 17 wherein $R^1$ is U-1 or U-50.

Embodiment 19. A compound of Embodiment 18 wherein $R^1$ is U-1.

Embodiment 19a. A compound of any one of Formula 1 and Embodiments 18 and 19 where X is $X^1$, $X^2$ or $X^3$, each $R^2$ is independently $C_1$-$C_3$ alkyl, G is an optionally substituted 5-membered heteroaromatic ring containing 1 to 3 heteroatoms selected from 0 to 1 O, 0 to 1 S and 0 to 3 N, $Q^a$ is $CH_3$, $Q^b$ is radical selected from

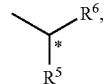

$Q^b$-1

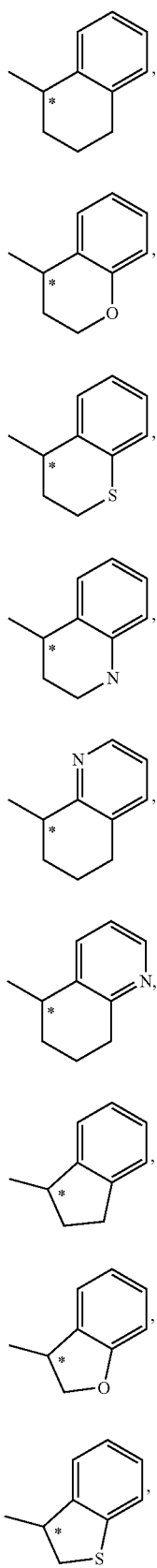

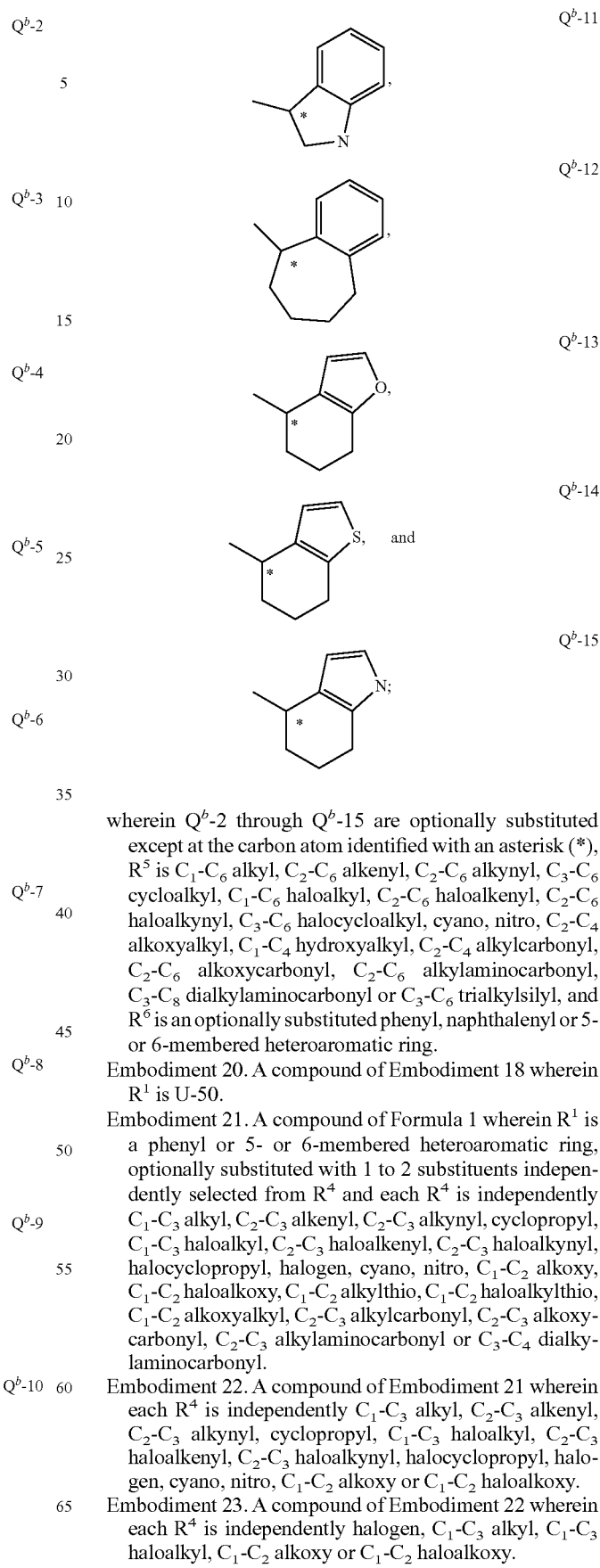

wherein $Q^b$-2 through $Q^b$-15 are optionally substituted except at the carbon atom identified with an asterisk (*), $R^5$ is $C_1$-$C_6$ alkyl, $C_2$-$C_6$ alkenyl, $C_2$-$C_6$ alkynyl, $C_3$-$C_6$ cycloalkyl, $C_1$-$C_6$ haloalkyl, $C_2$-$C_6$ haloalkenyl, $C_2$-$C_6$ haloalkynyl, $C_3$-$C_6$ halocycloalkyl, cyano, nitro, $C_2$-$C_4$ alkoxyalkyl, $C_1$-$C_4$ hydroxyalkyl, $C_2$-$C_4$ alkylcarbonyl, $C_2$-$C_6$ alkoxycarbonyl, $C_2$-$C_6$ alkylaminocarbonyl, $C_3$-$C_8$ dialkylaminocarbonyl or $C_3$-$C_6$ trialkylsilyl, and $R^6$ is an optionally substituted phenyl, naphthalenyl or 5- or 6-membered heteroaromatic ring.

Embodiment 20. A compound of Embodiment 18 wherein $R^1$ is U-50.

Embodiment 21. A compound of Formula 1 wherein $R^1$ is a phenyl or 5- or 6-membered heteroaromatic ring, optionally substituted with 1 to 2 substituents independently selected from $R^4$ and each $R^4$ is independently $C_1$-$C_3$ alkyl, $C_2$-$C_3$ alkenyl, $C_2$-$C_3$ alkynyl, cyclopropyl, $C_1$-$C_3$ haloalkyl, $C_2$-$C_3$ haloalkenyl, $C_2$-$C_3$ haloalkynyl, halocyclopropyl, halogen, cyano, nitro, $C_1$-$C_2$ alkoxy, $C_1$-$C_2$ haloalkoxy, $C_1$-$C_2$ alkylthio, $C_1$-$C_2$ haloalkylthio, $C_1$-$C_2$ alkoxyalkyl, $C_2$-$C_3$ alkylcarbonyl, $C_2$-$C_3$ alkoxycarbonyl, $C_2$-$C_3$ alkylaminocarbonyl or $C_3$-$C_4$ dialkylaminocarbonyl.

Embodiment 22. A compound of Embodiment 21 wherein each $R^4$ is independently $C_1$-$C_3$ alkyl, $C_2$-$C_3$ alkenyl, $C_2$-$C_3$ alkynyl, cyclopropyl, $C_1$-$C_3$ haloalkyl, $C_2$-$C_3$ haloalkenyl, $C_2$-$C_3$ haloalkynyl, halocyclopropyl, halogen, cyano, nitro, $C_1$-$C_2$ alkoxy or $C_1$-$C_2$ haloalkoxy.

Embodiment 23. A compound of Embodiment 22 wherein each $R^4$ is independently halogen, $C_1$-$C_3$ alkyl, $C_1$-$C_3$ haloalkyl, $C_1$-$C_2$ alkoxy or $C_1$-$C_2$ haloalkoxy.

Embodiment 24. A compound of Embodiment 23 wherein each $R^4$ is independently halogen, $C_1$-$C_2$ alkyl, $C_1$-$C_2$ haloalkyl or $C_1$-$C_2$ alkoxy.

Embodiment 25. A compound of Embodiment 24 wherein each $R^4$ is independently Cl, Br, I, methyl, ethyl, trifluoromethyl or methoxy.

Embodiment 26. A compound of Embodiment 25 wherein at least one $R^4$ is Cl.

Embodiment 27. A compound of Embodiment 25 wherein at least one $R^4$ is Br.

Embodiment 28. A compound of Embodiment 25 wherein at least one $R^4$ is methyl.

Embodiment 29. A compound of Embodiment 25 wherein at least one $R^4$ is ethyl.

Embodiment 30. A compound of Embodiment 25 wherein at least one $R^4$ is trifluoromethyl.

Embodiment 31. A compound of Embodiment 25 wherein at least one $R^4$ is methoxy.

Embodiment 32. A compound of Embodiment 19 wherein each $R^4$ is independently connected to the 3- or 5-position of U-1 (i.e. k is 1, and $R^4$ is connected to the 3- or 5-position of U-1).

Embodiment 32a. A compound of Embodiment 19a wherein each $R^4$ is independently connected to the 3- or 5-position of U-1 (i.e. k is 1, and $R^4$ is connected to the 3- or 5-position of U-1); and each $R^4$ is independently $C_1$-$C_6$ alkyl, $C_2$-$C_6$ alkenyl, $C_2$-$C_6$ alkynyl, $C_3$-$C_6$ cycloalkyl, $C_1$-$C_6$ haloalkyl, $C_2$-$C_6$ haloalkenyl, $C_2$-$C_6$ haloalkynyl, $C_3$-$C_6$ halocycloalkyl, halogen, hydroxy, amino, cyano, nitro, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ haloalkylthio, $C_1$-$C_4$ haloalkylsulfinyl, $C_1$-$C_4$ haloalkylsulfonyl, $C_1$-$C_4$ alkylamino, $C_2$-$C_8$ dialkylamino, $C_3$-$C_6$ cycloalkylamino, $C_2$-$C_4$ alkoxyalkyl, $C_1$-$C_4$ hydroxyalkyl, $C_2$-$C_4$ alkylcarbonyl, $C_2$-$C_6$ alkoxycarbonyl, $C_2$-$C_6$ alkylcarbonyloxy, $C_2$-$C_6$ alkylcarbonylthio, $C_2$-$C_6$ alkylaminocarbonyl, $C_3$-$C_8$ dialkylaminocarbonyl or $C_3$-$C_6$ trialkylsilyl.

Embodiment 33. A compound of Embodiment 19 wherein each $R^4$ is independently connected to the 3- and 5-position of U-1 (i.e. k is 2, and an independently selected $R^4$ is connected to the 3- and 5-positions of U-1). Of note are compounds of Embodiment 33 which correspond to compounds of note for Embodiment 19 above where each $R^4$ is independently $C_1$-$C_6$ alkyl, $C_2$-$C_6$ alkenyl, $C_2$-$C_6$ alkynyl, $C_3$-$C_6$ cycloalkyl, $C_1$-$C_6$ haloalkyl, $C_2$-$C_6$ haloalkenyl, $C_2$-$C_6$ haloalkynyl, $C_3$-$C_6$ halocycloalkyl, halogen, hydroxy, amino, cyano, nitro, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ haloalkylthio, $C_1$-$C_4$ haloalkylsulfinyl, $C_1$-$C_4$ haloalkylsulfonyl, $C_1$-$C_4$ alkylamino, $C_2$-$C_8$ dialkylamino, $C_3$-$C_6$ cycloalkylamino, $C_2$-$C_4$ alkoxyalkyl, $C_1$-$C_4$ hydroxyalkyl, $C_2$-$C_4$ alkylcarbonyl, $C_2$-$C_6$ alkoxycarbonyl, $C_2$-$C_6$ alkylcarbonyloxy, $C_2$-$C_6$ alkylcarbonylthio, $C_2$-$C_6$ alkylaminocarbonyl, $C_3$-$C_8$ dialkylaminocarbonyl or $C_3$-$C_6$ trialkylsilyl.

Embodiment 34. A compound of Embodiment 20 wherein each $R^4$ is independently connected to the 2- or 3-position of U-50 (i.e. k is 1, and $R^4$ is connected to the 2- or 3-position of U-50).

Embodiment 35. A compound of Embodiment 20 wherein each $R^4$ is independently connected to the 2- and 5-position of U-50 (i.e. k is 2, and an independently selected $R^4$ is connected to each of 2- and 5-positions of U-50).

Embodiment 36. A compound of Formula 1 wherein G is one of G-1 through G-55;

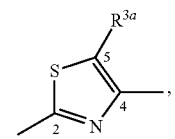 G-1

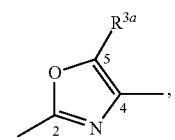 G-2

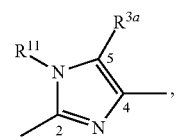 G-3

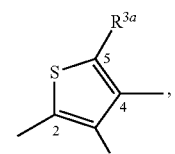 G-4

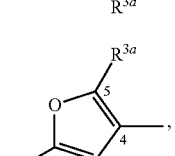 G-5

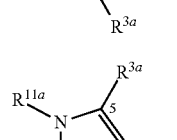 G-6

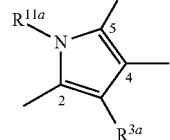 G-7

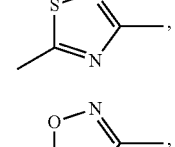 G-8

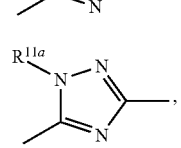 G-9

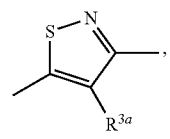 G-10

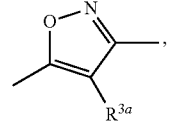 G-11

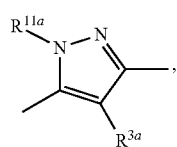 G-12
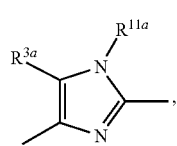 G-13
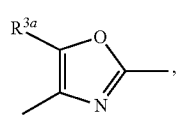 G-14
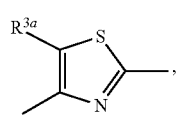 G-15
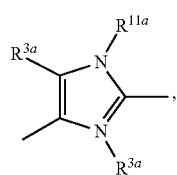 G-16
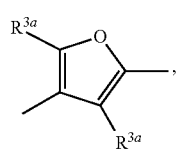 G-17
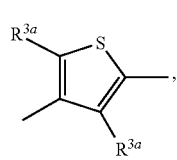 G-18
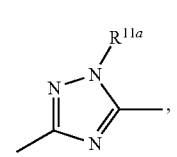 G-19
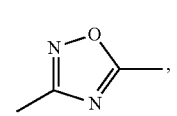 G-20
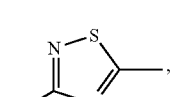 G-21
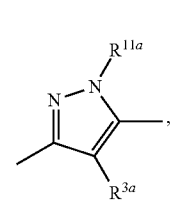 G-22
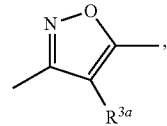 G-23
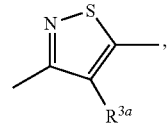 G-24
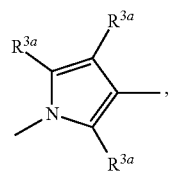 G-25
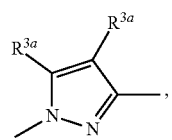 G-26
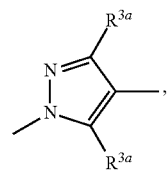 G-27
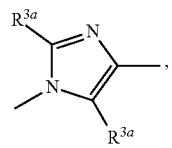 G-28
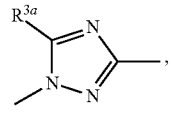 G-29
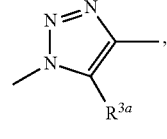 G-30
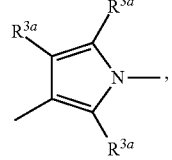 G-31
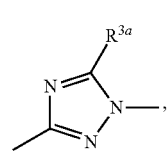 G-32

G-33 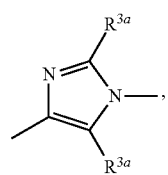
G-34 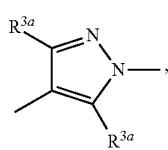
G-35 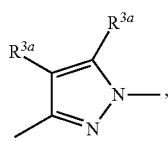
G-36 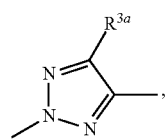
G-37 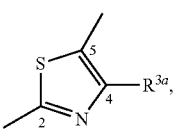
G-38 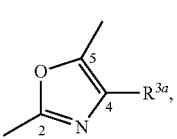
G-39 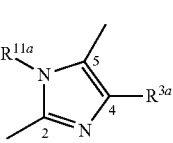
G-40 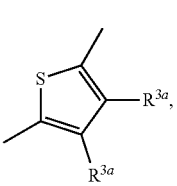
G-41 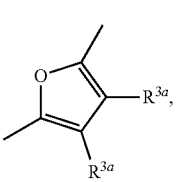
G-42 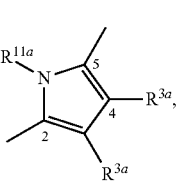
G-43 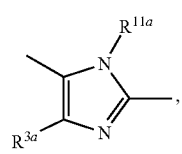
G-44 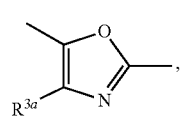
G-45 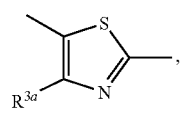
G-46 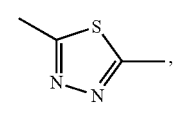
G-47 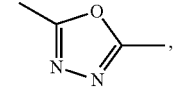
G-48 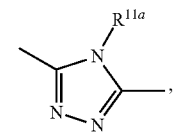
G-49 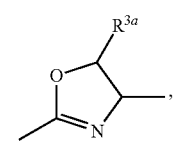
G-50 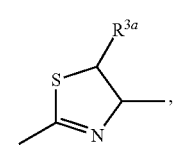
G-51 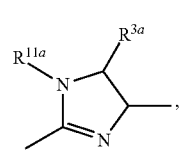
G-52 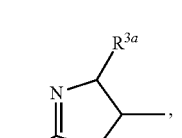
G-53 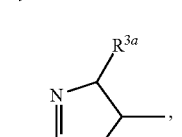

-continued

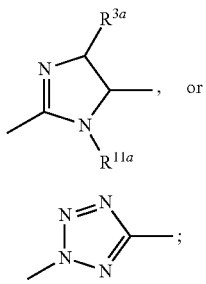
G-54

G-55 wherein each $R^3$ is independently $C_1$-$C_3$ alkyl, $C_1$-$C_3$ haloalkyl or halogen; each $R^{1a}$ is independently selected from H or $R^3$; $R^{11}$ is $C_1$-$C_3$ alkyl; $R^{11a}$ is selected from H or $R^{11}$; and the bond projecting to the left is bonded to X, and bond projecting to the right is bonded to C(=$W^2$).

Embodiment 37. A compound of Embodiment 36 wherein G is selected from G-1 through G-3, G-7, G-8, G-10, G-11, G-14, G-15, G-23, G-24, G-26 through G-28, G-30, G-36 through G-38 and G-49 through G-55.

Embodiment 38. A compound of Embodiment 37 wherein G is selected from G-1, G-2, G-7, G-8, G-14, G-15, G-23, G-24, G-26, G-27, G-36, G-37, G-38, G-49, G-50 and G-55.

Embodiment 39. A compound of Embodiment 38 wherein G is selected from G-1, G-2, G-15, G-26, G-27, G-36, G-37 and G-38.

Embodiment 40. A compound of Embodiment 39 wherein G is selected from G-1, G-2, G-15, G-26 and G-36.

Embodiment 41. A compound of Embodiment 40 wherein G is G-1. Of note are embodiments of these compounds within Embodiments 1 through 35, Embodiments 46 through 96, Embodiments A1 through A4, and Embodiments A6 through A13.

Embodiment 42. A compound of Embodiment 39 wherein G is G-2. Of note are embodiments of these compounds within Embodiments 1 through 35, Embodiments 46 through 96, Embodiments A1 through A4, and Embodiments A6 through A13.

Embodiment 43. A compound of Embodiment 36 wherein G is G-15. Of note are embodiments of these compounds within Embodiments 1 through 35, Embodiments 46 through 96, Embodiments A1 through A4, and Embodiments A6 through A13.

Embodiment 44. A compound of Embodiment 36 wherein G is G-26. Of note are embodiments of these compounds within Embodiments 1 through 35, Embodiments 46 through 96, Embodiments A1 through A4, and Embodiments A6 through A13.

Embodiment 45. A compound of Embodiment 36 wherein G is G-36. Of note are embodiments of these compounds within Embodiments 1 through 35, Embodiments 46 through 96, Embodiments A1 through A4, and Embodiments A6 through A13.

Embodiment 46. A compound of Formula 1 wherein G is a 5-membered heteroaromatic ring or 5-membered saturated or partially saturated heterocyclic ring, each ring optionally substituted with up to 2 substituents selected from $R^3$ on carbon ring members and selected from $R^{11}$ on nitrogen ring members; each $R^{11}$ is independently $C_1$-$C_3$ alkyl; each $R^3$ is independently $C_1$-$C_3$ alkyl or halogen.

Embodiment 47. A compound of Embodiment 46 wherein $R^3$ is methyl.

Embodiment 48. A compound of any one of Embodiments 36 through 45 wherein G is unsubstituted.

Embodiment 49. A compound of Embodiment 36 wherein $R^{1a}$ is H and $R^{11}$ is H or methyl.

Embodiment 50. A compound of Formula 1 wherein Q is selected from Q-1 through Q-85;

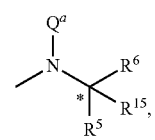
Q-1

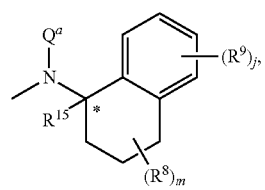
Q-2

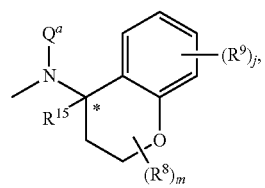
Q-3

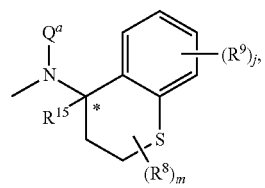
Q-4

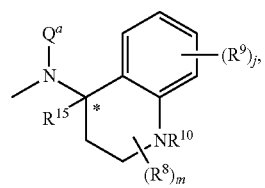
Q-5

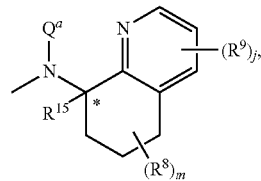
Q-6

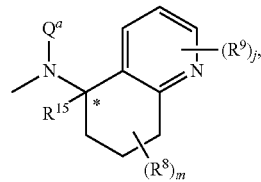
Q-7

-continued
Q-8
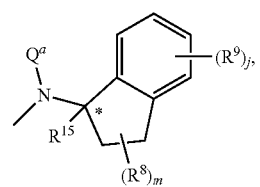
Q-9
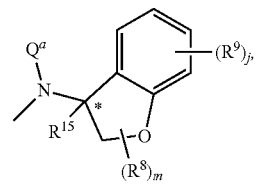
Q-10
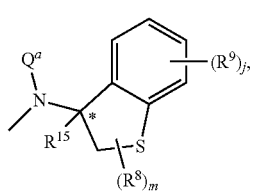
Q-11
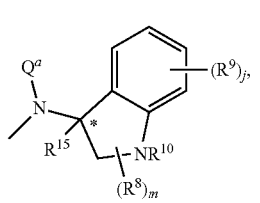
Q-12
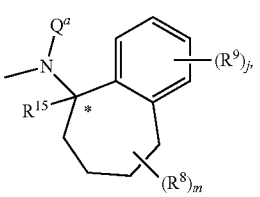
Q-13
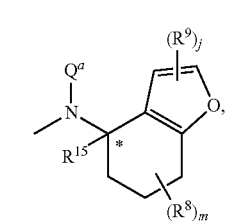
Q-14
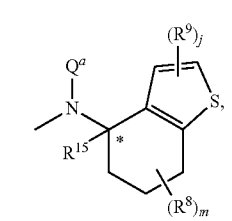
Q-15
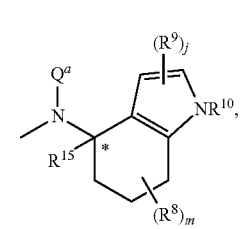
-continued
Q-16
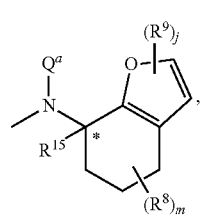
Q-17
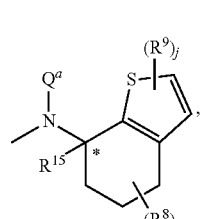
Q-18
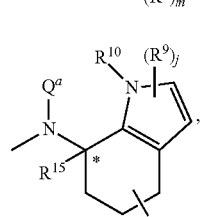
Q-19
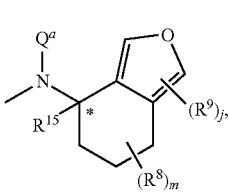
Q-20
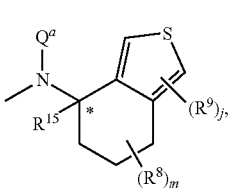
Q-21
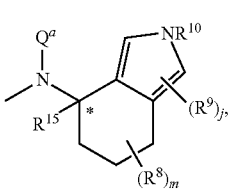
Q-22
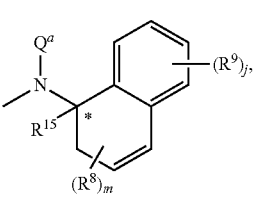
Q-23
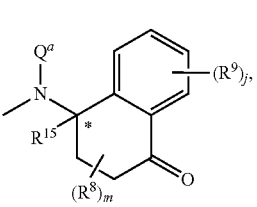

-continued
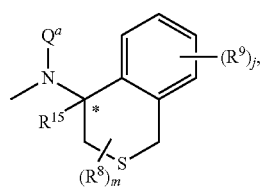 Q-24
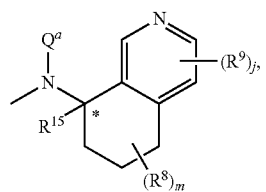 Q-25
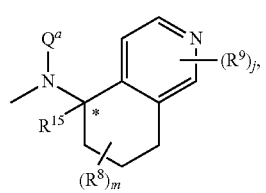 Q-26
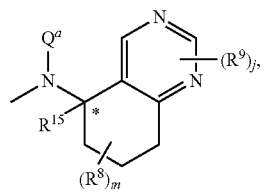 Q-27
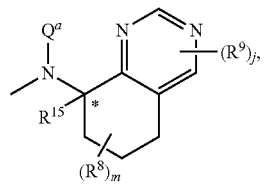 Q-28
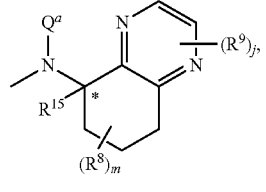 Q-29
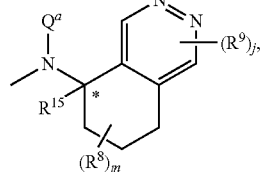 Q-30
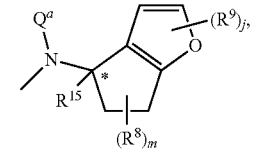 Q-31
-continued
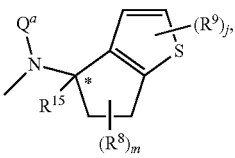 Q-32
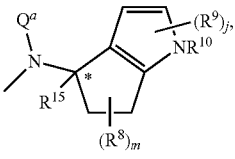 Q-33
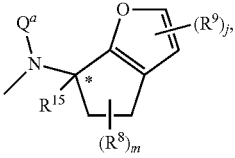 Q-34
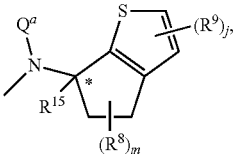 Q-35
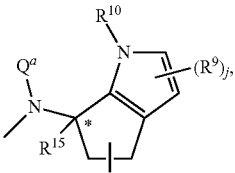 Q-36
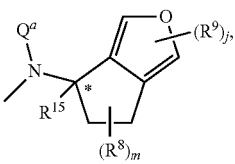 Q-37
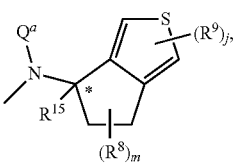 Q-38
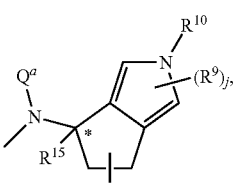 Q-39
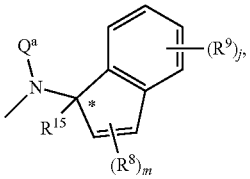 Q-40

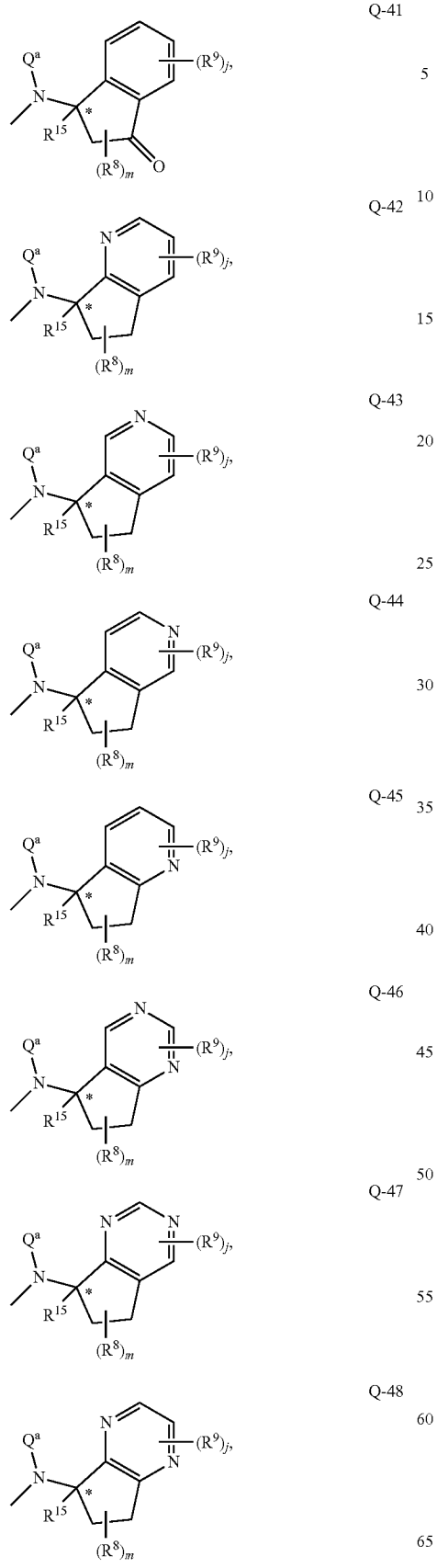
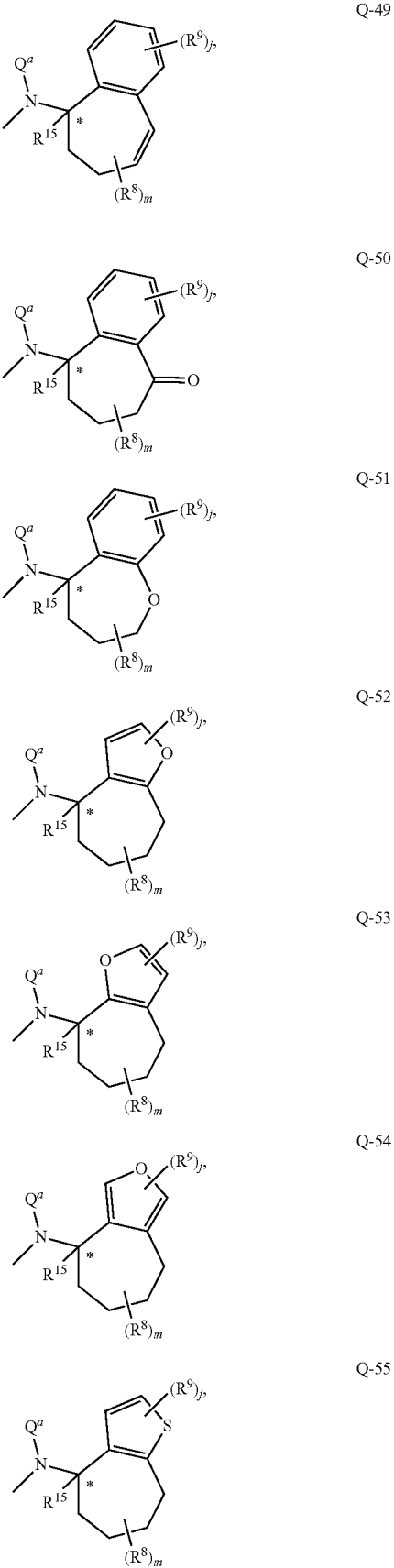

Q-56 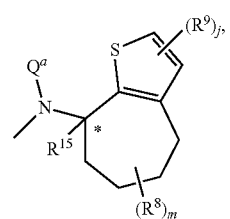
Q-57 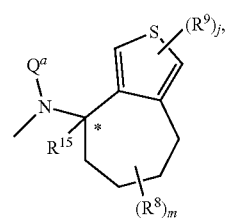
Q-58 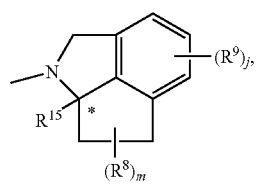
Q-59 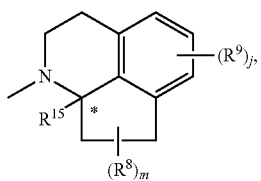
Q-60 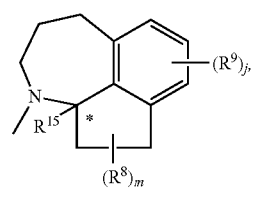
Q-61 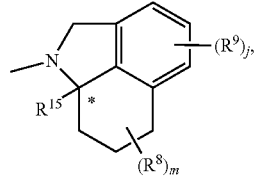
Q-62 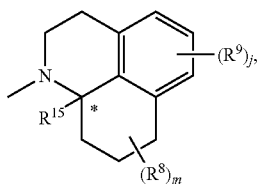
Q-63 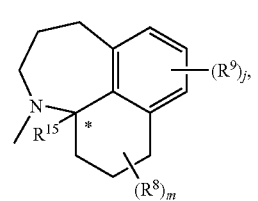
Q-64 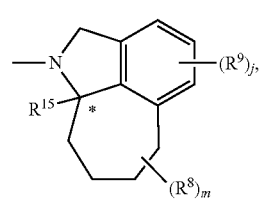
Q-65 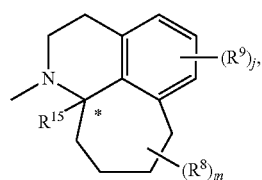
Q-66 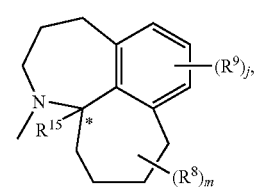
Q-67 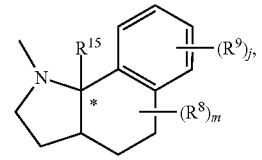
Q-68 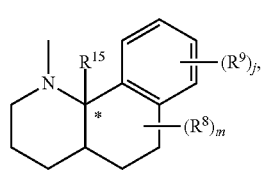
Q-69 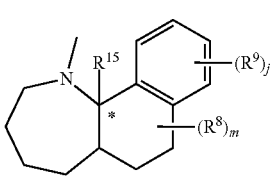
Q-70 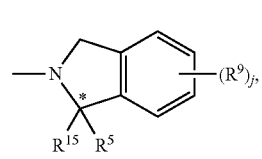
Q-71 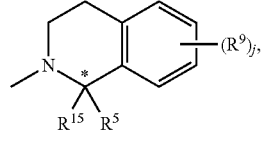
Q-72 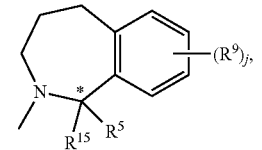

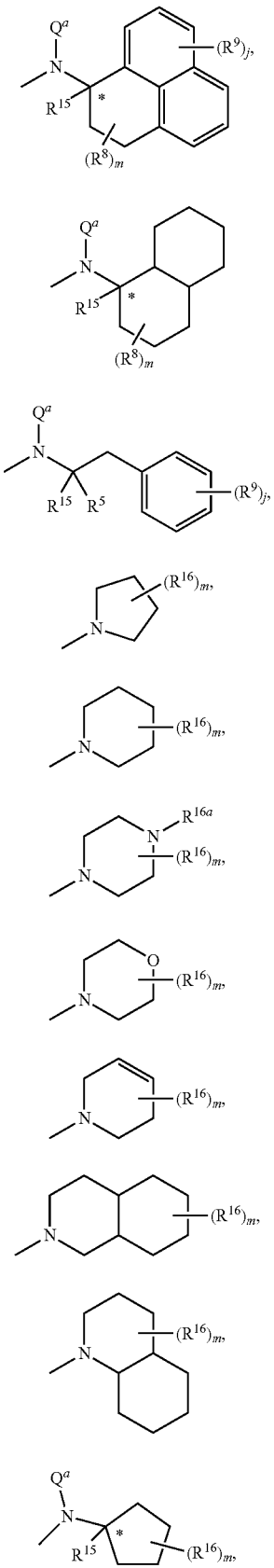
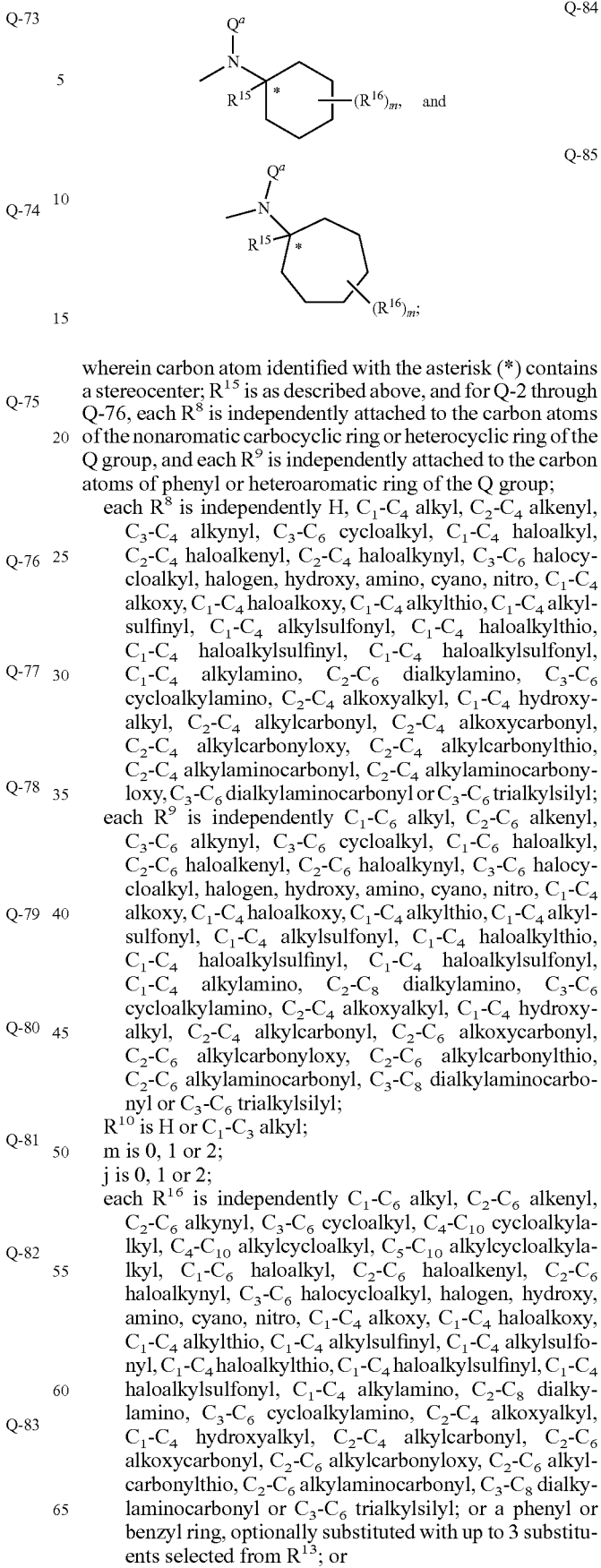

wherein carbon atom identified with the asterisk (*) contains a stereocenter; $R^{15}$ is as described above, and for Q-2 through Q-76, each $R^8$ is independently attached to the carbon atoms of the nonaromatic carbocyclic ring or heterocyclic ring of the Q group, and each $R^9$ is independently attached to the carbon atoms of phenyl or heteroaromatic ring of the Q group;

each $R^8$ is independently H, $C_1$-$C_4$ alkyl, $C_2$-$C_4$ alkenyl, $C_3$-$C_4$ alkynyl, $C_3$-$C_6$ cycloalkyl, $C_1$-$C_4$ haloalkyl, $C_2$-$C_4$ haloalkenyl, $C_2$-$C_4$ haloalkynyl, $C_3$-$C_6$ halocycloalkyl, halogen, hydroxy, amino, cyano, nitro, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ haloalkylthio, $C_1$-$C_4$ haloalkylsulfinyl, $C_1$-$C_4$ haloalkylsulfonyl, $C_1$-$C_4$ alkylamino, $C_2$-$C_6$ dialkylamino, $C_3$-$C_6$ cycloalkylamino, $C_2$-$C_4$ alkoxyalkyl, $C_1$-$C_4$ hydroxyalkyl, $C_2$-$C_4$ alkylcarbonyl, $C_2$-$C_4$ alkoxycarbonyl, $C_2$-$C_4$ alkylcarbonyloxy, $C_2$-$C_4$ alkylcarbonylthio, $C_2$-$C_4$ alkylaminocarbonyl, $C_2$-$C_4$ alkylaminocarbonyloxy, $C_3$-$C_6$ dialkylaminocarbonyl or $C_3$-$C_6$ trialkylsilyl;

each $R^9$ is independently $C_1$-$C_6$ alkyl, $C_2$-$C_6$ alkenyl, $C_3$-$C_6$ alkynyl, $C_3$-$C_6$ cycloalkyl, $C_1$-$C_6$ haloalkyl, $C_2$-$C_6$ haloalkenyl, $C_2$-$C_6$ haloalkynyl, $C_3$-$C_6$ halocycloalkyl, halogen, hydroxy, amino, cyano, nitro, $C_1$-$C_4$ alkoxy, $C_1$-$C_4$ haloalkoxy, $C_1$-$C_4$ alkylthio, $C_1$-$C_4$ alkylsulfonyl, $C_1$-$C_4$ alkylsulfonyl, $C_1$-$C_4$ haloalkylthio, $C_1$-$C_4$ haloalkylsulfinyl, $C_1$-$C_4$ haloalkylsulfonyl, $C_1$-$C_4$ alkylamino, $C_2$-$C_8$ dialkylamino, $C_3$-$C_6$ cycloalkylamino, $C_2$-$C_4$ alkoxyalkyl, $C_1$-$C_4$ hydroxyalkyl, $C_2$-$C_4$ alkylcarbonyl, $C_2$-$C_6$ alkoxycarbonyl, $C_2$-$C_6$ alkylcarbonyloxy, $C_2$-$C_6$ alkylcarbonylthio, $C_2$-$C_6$ alkylaminocarbonyl, $C_3$-$C_8$ dialkylaminocarbonyl or $C_3$-$C_6$ trialkylsilyl;

$R^{10}$ is H or $C_1$-$C_3$ alkyl;

m is 0, 1 or 2;

j is 0, 1 or 2;

each $R^{16}$ is independently $C_1$-$C_6$ alkyl, $C_2$-$C_6$ alkenyl, $C_2$-$C_6$ alkynyl, $C_3$-$C_6$ cycloalkyl, $C_4$-$C_{10}$ cycloalkylalkyl, $C_4$-$C_{10}$ alkylcycloalkyl, $C_5$-$C_{10}$ alkylcycloalkylalkyl, $C_1$-$C_6$ haloalkyl, $C_2$-$C_6$ haloalkenyl, $C_2$-$C_6$ haloalkynyl, $C_3$-$C_6$ halocycloalkyl, halogen, hydroxy, amino, cyano, nitro, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ haloalkylthio, $C_1$-$C_4$ haloalkylsulfinyl, $C_1$-$C_4$ haloalkylsulfonyl, $C_1$-$C_4$ alkylamino, $C_2$-$C_8$ dialkylamino, $C_3$-$C_6$ cycloalkylamino, $C_2$-$C_4$ alkoxyalkyl, $C_1$-$C_4$ hydroxyalkyl, $C_2$-$C_4$ alkylcarbonyl, $C_2$-$C_6$ alkoxycarbonyl, $C_2$-$C_6$ alkylcarbonyloxy, $C_2$-$C_6$ alkylcarbonylthio, $C_2$-$C_6$ alkylaminocarbonyl, $C_3$-$C_8$ dialkylaminocarbonyl or $C_3$-$C_6$ trialkylsilyl; or a phenyl or benzyl ring, optionally substituted with up to 3 substituents selected from $R^{13}$; or two R$^{16}$ attached to adjacent ring carbon atoms are taken together as —(CH$_2$)$_3$— or —(CH$_2$)$_4$— optionally substituted with 1-3 substituents selected from C$_1$-C$_4$ alkyl, C$_1$-C$_4$ haloalkyl, C$_1$-C$_4$ alkoxy, C$_1$-C$_4$ haloalkoxy, halogen, hydroxy, amino, cyano and nitro;

R$^{16a}$ is H, C$_1$-C$_6$ alkyl, C$_3$-C$_6$ alkenyl, C$_3$-C$_6$ alkynyl, C$_3$-C$_6$ cycloalkyl, C$_4$-C$_{10}$ cycloalkylalkyl, C$_4$-C$_{10}$ alkylcycloalkyl, C$_5$-C$_{10}$ alkylcycloalkylalkyl, C$_1$-C$_6$ haloalkyl, C$_3$-C$_6$ haloalkenyl, C$_3$-C$_6$ haloalkynyl, C$_3$-C$_6$ halocycloalkyl, C$_1$-C$_4$ alkoxy, C$_1$-C$_4$ haloalkoxy, C$_1$-C$_4$ alkylsulfonyl, C$_1$-C$_4$ haloalkylsulfonyl, amino, C$_1$-C$_4$ alkylamino, C$_2$-C$_8$ dialkylamino, C$_3$-C$_6$ cycloalkylamino, C$_2$-C$_4$ alkoxyalkyl, C$_1$-C$_4$ hydroxyalkyl, C$_2$-C$_4$ alkylcarbonyl, C$_2$-C$_6$ alkoxycarbonyl, C$_2$-C$_6$ alkylaminocarbonyl or C$_3$-C$_8$ dialkylaminocarbonyl; or a phenyl or benzyl ring, optionally substituted with up to 3 substituents selected from R$^{13}$ each R$^{13}$ is independently C$_1$-C$_6$ alkyl, C$_2$-C$_6$ alkenyl, C$_2$-C$_6$ alkynyl, C$_3$-C$_6$ cycloalkyl, C$_4$-C$_{10}$ cycloalkylalkyl, C$_4$-C$_{10}$ alkylcycloalkyl, C$_5$-C$_{10}$ alkylcycloalkylalkyl, C$_1$-C$_6$ haloalkyl, C$_2$-C$_6$ haloalkenyl, C$_2$-C$_6$ haloalkynyl, C$_3$-C$_6$ halocycloalkyl, halogen, hydroxy, amino, cyano, nitro, C$_1$-C$_4$ alkoxy, C$_1$-C$_4$ haloalkoxy, C$_1$-C$_4$ alkylthio, C$_1$-C$_4$ alkylsulfinyl, C$_1$-C$_4$ alkylsulfonyl, C$_1$-C$_4$ haloalkylthio, C$_1$-C$_4$ haloalkylsulfinyl, C$_1$-C$_4$ haloalkylsulfonyl, C$_1$-C$_4$ alkylamino, C$_2$-C$_8$ dialkylamino, C$_3$-C$_6$ cycloalkylamino, C$_2$-C$_4$ alkoxyalkyl, C$_1$-C$_4$ hydroxyalkyl, C$_2$-C$_4$ alkylcarbonyl, C$_2$-C$_6$ alkoxycarbonyl, C$_2$-C$_6$ alkylcarbonyloxy, C$_2$-C$_6$ alkylcarbonylthio, C$_2$-C$_6$ alkylaminocarbonyl, C$_3$-C$_8$ dialkylaminocarbonyl or C$_3$-C$_6$ trialkylsilyl;

R$^6$ is a phenyl, benzyl, naphthalenyl, C$_3$-C$_6$ cycloalkyl, C$_3$-C$_6$ cycloalkenyl or 5- or 6-membered heteroaromatic ring, each optionally substituted with 1 to 3 substituents selected from R$^7$ on carbon ring members and R$^{12}$ on nitrogen ring members;

each R$^7$ is independently C$_1$-C$_6$ alkyl, C$_2$-C$_6$ alkenyl, C$_2$-C$_6$ alkynyl, C$_3$-C$_6$ cycloalkyl, C$_4$-C$_{10}$ cycloalkylalkyl, C$_4$-C$_{10}$ alkylcycloalkyl, C$_5$-C$_{10}$ alkylcycloalkylalkyl, C$_1$-C$_6$ haloalkyl, C$_2$-C$_6$ haloalkenyl, C$_2$-C$_6$ haloalkynyl, C$_3$-C$_6$ halocycloalkyl, halogen, hydroxy, amino, cyano, nitro, C$_1$-C$_4$ alkoxy, C$_1$-C$_4$ haloalkoxy, C$_1$-C$_4$ alkylthio, C$_1$-C$_4$ alkylsulfinyl, C$_1$-C$_4$ alkylsulfonyl, C$_1$-C$_4$ haloalkylthio, C$_1$-C$_4$ haloalkylsulfinyl, C$_1$-C$_4$ haloalkylsulfonyl, C$_1$-C$_4$ alkylamino, C$_2$-C$_8$ dialkylamino, C$_3$-C$_6$ cycloalkylamino, C$_2$-C$_4$ alkoxyalkyl, C$_1$-C$_4$ hydroxyalkyl, C$_2$-C$_4$ alkylcarbonyl, C$_2$-C$_6$ alkoxycarbonyl, C$_2$-C$_6$ alkylcarbonyloxy, C$_2$-C$_6$ alkylcarbonylthio, C$_2$-C$_6$ alkylaminocarbonyl, C$_3$-C$_8$ dialkylaminocarbonyl or C$_3$-C$_6$ trialkylsilyl; and R$^{12}$ is H or C$_1$-C$_3$ alkyl.

Embodiment 51. A compound of Formula 1 wherein Q is selected from Q-1 through Q-4, Q-8 through Q-10, Q-12, Q-14, Q-22 through Q-24, Q-40, Q-41, Q-59, Q-62, Q-74 and Q-84.

Embodiment 52. A compound of Embodiment 51 wherein Q is Q-1, Q-2, Q-8, Q-14, Q-23, Q-41, Q-59 and Q-62.

Embodiment 53. A compound of Embodiment 52 wherein Q is Q-1, Q-2, Q-8, Q-23 and Q-41.

Embodiment 54. A compound of Embodiment 53 wherein Q is Q-1.

Embodiment 55. A compound of Embodiment 53 wherein Q is Q-2.

Embodiment 56. A compound of Embodiment 53 wherein Q is Q-8.

Embodiment 57. A compound of Embodiment 53 wherein Q is Q-23.

Embodiment 58. A compound of Embodiment 53 wherein Q is Q-41.

Embodiment 59. A compound of Formula 1 wherein R$^5$ is C$_1$-C$_4$ alkyl, C$_2$-C$_4$ alkenyl, C$_2$-C$_4$ alkynyl, C$_3$-C$_4$ cycloalkyl, C$_1$-C$_4$ haloalkyl, C$_2$-C$_4$ haloalkenyl, C$_2$-C$_4$ haloalkynyl, C$_3$-C$_4$ halocycloalkyl, cyano, nitro, C$_2$-C$_4$ alkoxyalkyl, C$_2$-C$_6$ alkoxycarbonyl, C$_2$-C$_6$ alkylaminocarbonyl or C$_3$-C$_8$ dialkylaminocarbonyl.

Embodiment 60. A compound of Embodiment 59 wherein R$^5$ is C$_1$-C$_4$ alkyl, C$_2$-C$_4$ alkenyl, C$_2$-C$_4$ alkynyl, C$_3$-C$_4$ cycloalkyl, C$_1$-C$_4$ haloalkyl, C$_2$-C$_4$ haloalkenyl, C$_2$-C$_4$ haloalkynyl, C$_3$-C$_4$ halocycloalkyl, cyano or C$_2$-C$_4$ alkoxyalkyl.

Embodiment 61. A compound of Embodiment 60 wherein R$^5$ is C$_1$-C$_4$ alkyl, C$_1$-C$_4$ haloalkyl, C$_2$-C$_4$ alkenyl, C$_2$-C$_4$ haloalkenyl or cyano.

Embodiment 62. A compound of Embodiment 61 wherein R$^5$ is C$_1$-C$_4$ alkyl, C$_2$-C$_4$ alkenyl or cyano.

Embodiment 63. A compound of Embodiment 62 wherein R$^5$ is C$_1$-C$_3$ alkyl.

Embodiment 64. A compound of Embodiment 63 wherein R$^5$ is ethyl.

Embodiment 65. A compound of Embodiment 50 wherein R$^6$ is one of H-1 through H-46;

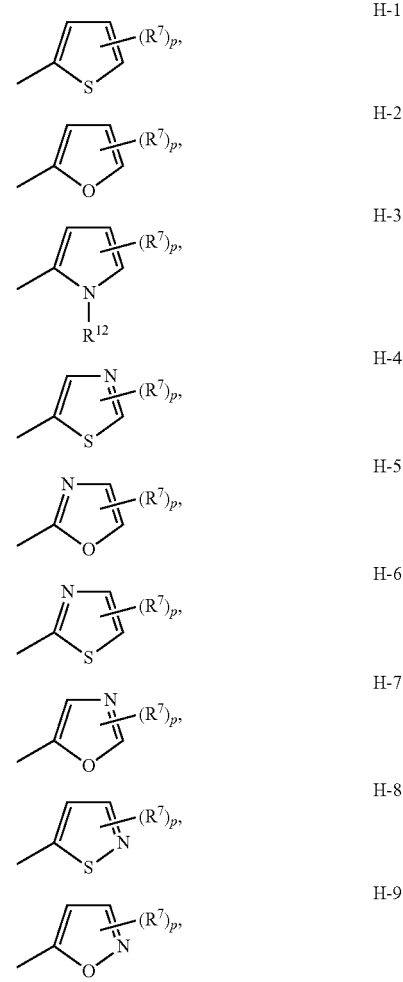

-continued
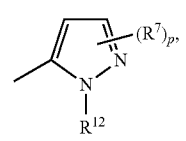 H-10
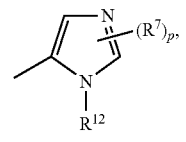 H-11
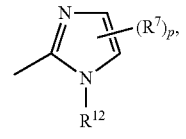 H-12
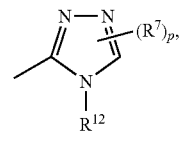 H-13
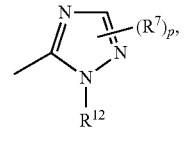 H-14
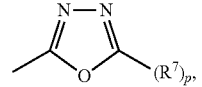 H-15
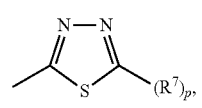 H-16
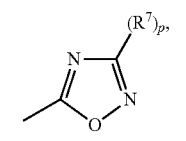 H-17
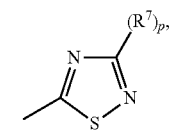 H-18
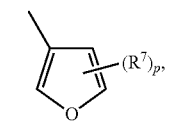 H-19
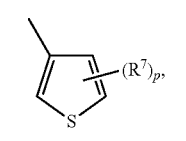 H-20
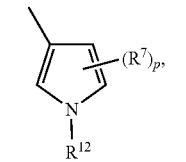 H-21
-continued
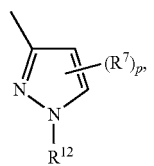 H-22
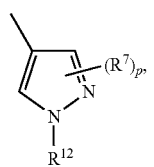 H-23
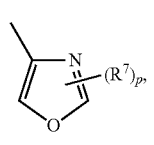 H-24
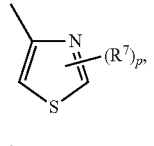 H-25
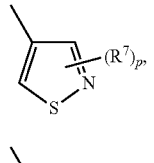 H-26
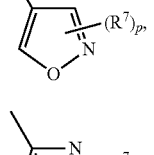 H-27
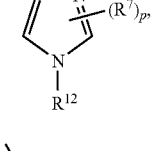 H-28
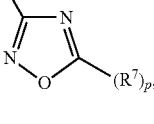 H-29
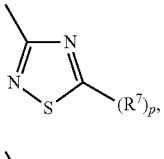 H-30
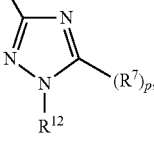 H-31
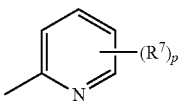 H-32

H-33 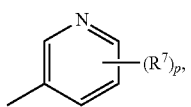

H-34 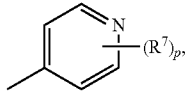

H-35 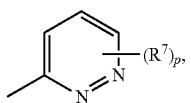

H-36 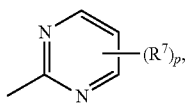

H-37 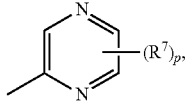

H-38 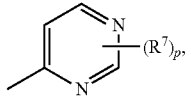

H-39 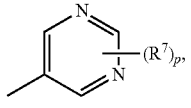

H-40 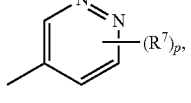

H-41 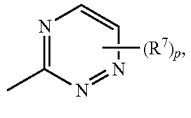

H-42 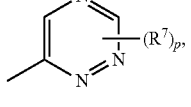

H-43 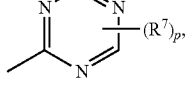

H-44 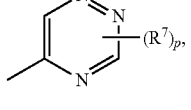

H-45 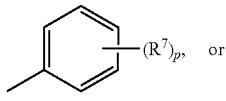, or

H-46 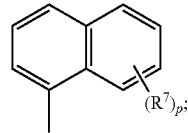

wherein each $R^7$ is independently $C_1$-$C_6$ alkyl, $C_2$-$C_6$ alkenyl, $C_2$-$C_6$ alkynyl, $C_3$-$C_6$ cycloalkyl, $C_4$-$C_{10}$ cycloalkylalkyl, $C_4$-$C_{10}$ alkylcycloalkyl, $C_5$-$C_{10}$ alkylcycloalkylalkyl, $C_1$-$C_6$ haloalkyl, $C_2$-$C_6$ haloalkenyl, $C_2$-$C_6$ haloalkynyl, $C_3$-$C_6$ halocycloalkyl, halogen, hydroxy, amino, cyano, nitro, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ haloalkylthio, $C_1$-$C_4$ haloalkylsulfinyl, $C_1$-$C_4$ haloalkylsulfonyl, $C_1$-$C_4$ alkylamino, $C_2$-$C_8$ dialkylamino, $C_3$-$C_6$ cycloalkylamino, $C_2$-$C_4$ alkoxyalkyl, $C_1$-$C_4$ hydroxyalkyl, $C_2$-$C_4$ alkylcarbonyl, $C_2$-$C_6$ alkoxycarbonyl, $C_2$-$C_6$ alkylcarbonyloxy, $C_2$-$C_6$ alkylcarbonylthio, $C_2$-$C_6$ alkylaminocarbonyl, $C_3$-$C_8$ dialkylaminocarbonyl or $C_3$-$C_6$ trialkylsilyl; and p is 0, 1 or 2.

Embodiment 66. A compound of Embodiment 65 wherein $R^6$ is H-1, H-20, H-32, H-45 or H-46.

Embodiment 67. A compound of Embodiment 66 wherein $R^6$ is H-1 or H-45.

Embodiment 68. A compound of Embodiment 67 wherein $R^6$ is H-45.

Embodiment 69. A compound of Formula 1 wherein $Q^b$ is $CR^5R^6R^{15}$; $R^6$ is a phenyl, benzyl, naphthalenyl, $C_3$-$C_6$ cycloalkyl, $C_3$-$C_6$ cycloalkenyl or 5- or 6-membered heteroaromatic ring, each optionally substituted with 1 to 3 substituents selected from $R^7$ on carbon ring members and $R^{12}$ on nitrogen ring members; each $R^7$ is independently $C_1$-$C_3$ alkyl, $C_2$-$C_3$ alkenyl, $C_2$-$C_3$ alkynyl, cyclopropyl, $C_1$-$C_3$ haloalkyl, $C_2$-$C_3$ haloalkenyl, $C_2$-$C_3$ haloalkynyl, halocyclopropyl, halogen, cyano, nitro, hydroxy, $C_1$-$C_2$ alkoxy, $C_1$-$C_2$ haloalkoxy, $C_1$-$C_2$ alkylthio, $C_1$-$C_2$ haloalkylthio, $C_2$-$C_3$ alkoxyalkyl, $C_2$-$C_3$ alkylcarbonyl, $C_2$-$C_3$ alkylcarbonyloxy, $C_2$-$C_3$ alkoxycarbonyl, $C_2$-$C_3$ alkylaminocarbonyl or $C_3$-$C_4$ dialkylaminocarbonyl; and $R^{12}$ is $C_1$-$C_3$ alkyl.

Embodiment 70. A compound of Embodiment 69 wherein each $R^7$ is independently $C_1$-$C_3$ alkyl, $C_2$-$C_3$ alkenyl, $C_2$-$C_3$ alkynyl, cyclopropyl, $C_1$-$C_3$ haloalkyl, $C_2$-$C_3$ haloalkenyl, $C_2$-$C_3$ haloalkynyl, halocyclopropyl, halogen, cyano, nitro, hydroxy, $C_1$-$C_2$ alkoxy or $C_1$-$C_2$ haloalkoxy.

Embodiment 71. A compound of Embodiment 70 wherein each $R^7$ is independently halogen, $C_1$-$C_3$ alkyl, $C_1$-$C_3$ haloalkyl, hydroxy, $C_1$-$C_2$ alkoxy or $C_1$-$C_2$ haloalkoxy.

Embodiment 72. A compound of Embodiment 71 wherein each $R^7$ is independently halogen, hydroxy, $C_1$-$C_2$ alkoxy or $C_1$-$C_3$ alkyl.

Embodiment 73. A compound of Embodiment 72 wherein each $R^7$ is independently F, Cl, Br, hydroxy, methoxy or methyl.

Embodiment 74. A compound of Embodiment 65 wherein p is 0.

Embodiment 75. A compound of Embodiment 65 wherein $R^{12}$ is H or $C_1$-$C_2$ alkyl.

Embodiment 76. A compound of Embodiment 75 wherein $R^{12}$ is methyl.

Embodiment 77. A compound of Formula 1 wherein $R^{15}$ is H, $C_1$-$C_4$ alkyl, $C_2$-$C_4$ alkenyl, $C_2$-$C_8$ alkynyl, $C_3$-$C_4$ cycloalkyl or $C_1$-$C_4$ haloalkyl.

Embodiment 78. A compound of Embodiment 77 wherein $R^{15}$ is H or $C_1$-$C_3$ alkyl.

Embodiment 79. A compound of Embodiment 78 wherein $R^{15}$ is H.

Embodiment 80. A compound of Formula 1 wherein $Q^a$ is H or $C_1$-$C_3$ alkyl.

Embodiment 81. A compound of Embodiment 80 wherein $Q^a$ is H or methyl.

Embodiment 82. A compound of Embodiment 81 wherein $Q^a$ is methyl.

Embodiment 83. A compound of Embodiment 50 wherein each $R^8$ is independently H, $C_1$-$C_4$ alkyl, $C_2$-$C_4$ alkenyl, $C_3$-$C_4$ alkynyl, $C_3$-$C_6$ cycloalkyl, $C_1$-$C_4$ haloalkyl, $C_2$-$C_4$ haloalkenyl, $C_2$-$C_4$ haloalkynyl, $C_3$-$C_6$ halocycloalkyl, halogen, hydroxy, amino, cyano, nitro, $C_1$-$C_4$ alkoxy or $C_2$-$C_4$ alkylcarbonyloxy.

Embodiment 84. A compound of Embodiment 83 wherein each $R^8$ is independently H, $C_1$-$C_4$ alkyl, $C_2$-$C_4$ alkenyl, $C_3$-$C_4$ alkynyl, $C_3$-$C_6$ cycloalkyl, $C_1$-$C_4$ haloalkyl, $C_3$-$C_6$ halocycloalkyl, halogen, hydroxy, amino, cyano, nitro, $C_1$-$C_4$ alkoxy or $C_2$-$C_4$ alkylcarbonyloxy.

Embodiment 85. A compound of Embodiment 84 wherein each $R^8$ is independently H, $C_1$-$C_3$ alkyl, hydroxy, $C_1$-$C_3$ alkoxy or $C_2$-$C_3$ alkylcarbonyloxy.

Embodiment 86. A compound of Embodiment 85 wherein $R^8$ is H, methyl, methoxy or hydroxy.

Embodiment 87. A compound of Embodiment 50 wherein m is 0 or 1.

Embodiment 88. A compound of Embodiment 87 wherein m is 0.

Embodiment 89. A compound of Embodiment 50 wherein each $R^9$ is independently $C_1$-$C_3$ alkyl, $C_2$-$C_3$ alkenyl, $C_2$-$C_3$ alkynyl, cyclopropyl, $C_1$-$C_3$ haloalkyl, $C_2$-$C_3$ haloalkenyl, $C_2$-$C_3$ haloalkynyl, halocyclopropyl, halogen, cyano, nitro, hydroxy, $C_2$-$C_3$ alkylcarbonyloxy, $C_1$-$C_2$ alkoxy, $C_1$-$C_2$ haloalkoxy, $C_1$-$C_2$ alkylthio, $C_1$-$C_2$ haloalkylthio, $C_2$-$C_3$ alkoxyalkyl, $C_2$-$C_3$ alkylcarbonyl, $C_2$-$C_3$ alkoxycarbonyl, $C_2$-$C_3$ alkylaminocarbonyl or $C_3$-$C_4$ dialkylaminocarbonyl.

Embodiment 90. A compound of Embodiment 89 wherein each $R^9$ is independently $C_1$-$C_3$ alkyl, cyclopropyl, $C_1$-$C_3$ haloalkyl, halocyclopropyl, halogen, hydroxy, $C_2$-$C_3$ alkylcarbonyloxy, $C_1$-$C_2$ alkoxy or $C_1$-$C_2$ haloalkoxy.

Embodiment 91. A compound of Embodiment 90 wherein each $R^9$ is independently $C_1$-$C_3$ alkyl, hydroxy, $C_1$-$C_2$ alkoxy or halogen.

Embodiment 92. A compound of Embodiment 91 wherein each $R^9$ is independently methyl, F, Cl, Br, hydroxy or methoxy.

Embodiment 93. A compound of Embodiment 50 wherein j is 0 or 1.

Embodiment 94. A compound of Embodiment 93 wherein j is 0.

Embodiment 95. A compound of Embodiment 50 wherein each $R^{10}$ is H or methyl.

Embodiment 96. A compound of Formula 1 wherein Q is Q-1 through Q-75 and Q-83 through Q-85 and Q has the orientation depicted above in Embodiment 50, and wherein $R^{15}$ has an orientation below the plane defined by the 3 non-hydrogen atoms attached to the carbon atom identified with the asterisk (*) (e.g., for Q-1, Formula 1').

Embodiment 97. A compound of Embodiment 50 wherein each $R^{16}$ is independently $C_1$-$C_3$ alkyl, $C_2$-$C_3$ alkenyl, $C_2$-$C_3$ alkynyl, cyclopropyl, $C_1$-$C_3$ haloalkyl, $C_2$-$C_3$ haloalkenyl, $C_2$-$C_3$ haloalkynyl, halocyclopropyl, halogen, cyano, nitro, $C_1$-$C_2$ alkoxy or $C_1$-$C_2$ haloalkoxy; or a phenyl or benzyl ring, optionally substituted with up to 3 substituents selected from $R^{13}$.

Embodiment 98. A compound of Embodiment 50 wherein $R^{16a}$ is H, $C_1$-$C_3$ alkyl, propargyl, cyclopropyl or $C_1$-$C_3$ haloalkyl; or a phenyl or benzyl ring, optionally substituted with up to 3 substituents selected from $R^{13}$.

Embodiment 99. A compound of Embodiment 50 wherein when Q is Q-76, Q-77, Q-79, Q-80, Q-81, Q-82, Q-83, Q-84 or Q-85, then m is 0 or 1.

Embodiment 100. A compound of Embodiment 99 wherein m is 1.

Embodiment 101. A compound of Embodiment 50 wherein when Q is Q-78 and $R^{16a}$ is other than H, then m is 0.

Embodiment 102. A compound of Embodiment 50 wherein when Q is Q-78 and $R^{16a}$ is H, then m is 1.

Embodiment 103. A compound of Embodiment 50 wherein when Q is Q-78, then $R^{16a}$ is other than H and m is 0.

Combinations of Embodiments 1-103 are illustrated by:

Embodiment A1. A compound of Formula 1 wherein n is 0; $R^1$ is a phenyl or 5- or 6-membered heteroaromatic ring, optionally substituted with 1 to 2 substituents independently selected from $R^4$; and each $R^4$ is independently $C_1$-$C_6$ alkyl, $C_2$-$C_6$ alkenyl, $C_2$-$C_6$ alkynyl, $C_3$-$C_6$ cycloalkyl, $C_1$-$C_6$ haloalkyl, $C_2$-$C_6$ haloalkenyl, $C_2$-$C_6$ haloalkynyl, $C_3$-$C_6$ halocycloalkyl, halogen, hydroxy, amino, cyano, nitro, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ haloalkylthio, $C_1$-$C_4$ haloalkylsulfinyl, $C_1$-$C_4$ haloalkylsulfonyl, $C_1$-$C_4$ alkylamino, $C_2$-$C_8$ dialkylamino, $C_3$-$C_6$ cycloalkylamino, $C_2$-$C_4$ alkoxyalkyl, $C_1$-$C_4$ hydroxyalkyl, $C_2$-$C_4$ alkylcarbonyl, $C_2$-$C_6$ alkoxycarbonyl, $C_2$-$C_6$ alkylcarbonyloxy, $C_2$-$C_6$ alkylcarbonylthio, $C_2$-$C_6$ alkylaminocarbonyl, $C_3$-$C_8$ dialkylaminocarbonyl or $C_3$-$C_6$ trialkylsilyl.

Embodiment A2. A compound of Embodiment A1 wherein $W^1$ is O and $W^2$ is O.

Embodiment A3. A compound of Embodiment A2 wherein A is $CH_2$.

Embodiment A4. A compound of Embodiment A3 wherein X is $X^1$ and $X^2$.

Embodiment A5. A compound of Embodiment A4 wherein G is G-1, G-2, G-15, G-26 or G-36.

Embodiment A6. A compound of Embodiment A5 wherein G is unsubstituted.

Embodiment A7. A compound of Embodiment A6 wherein Q is Q-1, Q-2, Q-8, Q-23 or Q-41 and $Q^a$ is H or $C_1$-$C_3$ alkyl.

Embodiment A8. A compound of Embodiment A7 wherein $R^5$ is $C_1$-$C_3$ alkyl, $R^6$ is H-45, $R^{15}$ is H, and p is 0.

Embodiment A9. A compound of Embodiment A7 wherein j is 0, m is 0 or 1, and $R^8$ is H, methyl, methoxy or hydroxy.

Embodiment A10. A compound of any one of Embodiments A8 and A9 wherein $R^1$ is U-1 or U-50.

Embodiment A11. A compound of Embodiment A10 wherein each $R^4$ is independently Cl, Br, methyl, ethyl, trifluoromethyl or methoxy.

Embodiment A12. A compound of Embodiment A11 wherein Q is Q-1, $Q^a$ is methyl, $R^5$ is $C_1$-$C_2$ alkyl, $R^{15}$ is H, and the carbon atom to which $R^5$ and $R^6$ are attached is a stereocenter with the R configuration.

Embodiment A13. A compound of Embodiment A11 wherein Q is Q-2, Q-8, Q-23 or Q-41, $Q^a$ is methyl, $R^{15}$ is H, and the carbon atom identified with the asterisk (*) is a stereocenter having a configuration described as R, provided that when m is 1, $R^8$ is hydroxy or methoxy and the $R^8$ group is attached to the carbon adjacent to the carbon atom identified with an asterisk (*), then the carbon atom identified with the asterisk (*) is a stereocenter having a configuration described as S.

Specific embodiments include compounds of Formula 1 selected from the group consisting of:

2-[1-[(2,5-dimethylphenyl)acetyl]-4-piperidinyl]-N-methyl-N-[(1R)-1,2,3,4-tetrahydro-1-naphthalenyl]-4-thiazolecarboxamide, 2-[1-[(2,5-dichlorophenyl)acetyl]-4-piperidinyl]-N-methyl-N-[(1R)-1,2,3,4-tetrahydro-1-naphthalenyl]-4-thiazolecarboxamide, N-methyl-2-[1-[[5-methyl-3-(trifluoromethyl)-1H-pyrazol-1-yl]acetyl]-4-piperidinyl]-N-[(1R)-1,2,3,4-tetrahydro-1-naphthalenyl]-4-thiazolecarboxamide, N-[(1R)-2,3-dihydro-1H-inden-1-yl]-N-methyl-2-[1-[[5-methyl-3-(trifluoromethyl)-1H-pyrazol-1-yl]acetyl]-4-piperidinyl]-4-thiazolecarboxamide, N-methyl-2-[1-[[5-methyl-3-(trifluoromethyl)-1H-pyrazol-1-yl]acetyl]-4-piperidinyl]-N-[(1R)-1,2,3,4-tetrahydro-1-naphthalenyl]-4-thiazolecarbothioamide, N-methyl-2-[1-[[5-methyl-3-(trifluoromethyl)-1H-pyrazol-1-yl]acetyl]-4-piperidinyl]-N-[(1R,4S)-1,2,3,4-tetrahydro-4-hydroxy-1-naphthalenyl]-4-thiazolecarboxamide and its enantiomer, N-methyl-2-[1-[[5-methyl-3-(trifluoromethyl)-1H-pyrazol-1-yl]acetyl]-4-piperidinyl]-N-(1,2,3,4-tetrahydro-2-methyl-1-naphthalenyl)-4-thiazolecarboxamide, N-methyl-2-[1-[[5-methyl-3-(trifluoromethyl)-1H-pyrazol-1-yl]acetyl]-4-piperidinyl]-N-[(1R,4R)-1,2,3,4-tetrahydro-4-hydroxy-1-naphthalenyl]-4-thiazolecarboxamide and its enantiomer, 2-[1-[[5-ethyl-3-(trifluoromethyl)-1H-pyrazol-1-yl]acetyl]-4-piperidinyl]-N-methyl-N-[(1R)-1,2,3,4-tetrahydro-1-naphthalenyl]-4-thiazolecarboxamide, 2-[1-[[3,5-bis(trifluoromethyl)-1H-pyrazol-1-yl]acetyl]-4-piperidinyl]-N-methyl-N-[(1R)-1,2,3,4-tetrahydro-1-naphthalenyl]-4-thiazolecarboxamide, N-methyl-2-[1-[[5-methyl-3-(trifluoromethyl)-1H-pyrazol-1-yl]acetyl]-4-piperidinyl]-N-(1,2,3,4-tetrahydro-4-oxo-1-naphthalenyl)-4-thiazolecarboxamide, N-methyl-2-[4-[[5-methyl-3-(trifluoromethyl)-1H-pyrazol-1-yl]acetyl]-1-piperazinyl]-N-[(1R)-1,2,3,4-tetrahydro-1-naphthalenyl]-4-thiazolecarboxamide, N-(2,3-dihydro-2,2-dimethyl-1H-inden-1-yl)-N-methyl-2-[1-[[5-methyl-3-(trifluoromethyl)-1H-pyrazol-1-yl]acetyl]-4-piperidinyl]-4-thiazolecarboxamide, N-(2,3-dihydro-2-methyl-1H-inden-1-yl)-N-methyl-2-[1-[[5-methyl-3-(trifluoromethyl)-1H-pyrazol-1-yl]acetyl]-4-piperidinyl]-4-thiazolecarboxamide, N-methyl-1-[1-[[5-methyl-3-(trifluoromethyl)-1H-pyrazol-1-yl]acetyl]-4-piperidinyl]-N-[(1R)-1,2,3,4-tetrahydro-1-naphthalenyl]-1H-pyrazole-3-carboxamide, N-methyl-2-[1-[[5-methyl-3-(trifluoromethyl)-1H-pyrazol-1-yl]acetyl]-4-piperidinyl]-N-[(1R)-1,2,3,4-tetrahydro-1-naphthalenyl]-2H-1,2,3-triazole-4-carboxamide, N-methyl-1-[1-[[5-methyl-3-(trifluoromethyl)-1H-pyrazol-1-yl]acetyl]-4-piperidinyl]-N-[(1R)-1,2,3,4-tetrahydro-1-naphthalenyl]-1H-pyrazole-4-carboxamide, N-methyl-2-[1-[[5-methyl-3-(trifluoromethyl)-1H-pyrazol-1-yl]acetyl]-4-piperidinyl]-N-[(1R,2S)-1,2,3,4-tetrahydro-2-methyl-1-naphthalenyl]-4-thiazolecarboxamide and its enantiomer, N-methyl-2-[1-[[5-methyl-3-(trifluoromethyl)-1H-pyrazol-1-yl]acetyl]-4-piperidinyl]-N-(1,2,3,4-tetrahydro-2,2-dimethyl-1-naphthalenyl)-4-thiazolecarboxamide, 2-[1-[(3,5-dichloro-1H-pyrazol-1-yl)acetyl]-4-piperidinyl]-N-methyl-N-[(1R)-1,2,3,4-tetrahydro-1-naphthalenyl]-4-thiazolecarboxamide, 2-[1-[[5-chloro-3-(trifluoromethyl)-1H-pyrazol-1-yl]acetyl]-4-piperidinyl]-N-methyl-N-[(1R)-1,2,3,4-tetrahydro-1-naphthalenyl]-4-thiazolecarboxamide, N-methyl-2-[1-[[5-methyl-3-(trifluoromethyl)-1H-pyrazol-1-yl]acetyl]-4-piperidinyl]-N-[(1R)-1,2,3,4-tetrahydro-1-naphthalenyl]-4-oxazolecarboxamide, and N-methyl-2-[1-[[5-methyl-3-(trifluoromethyl)-1H-pyrazol-1-yl]acetyl]-4-piperidinyl]-N-(1,2,3,4-tetrahydro-1-naphthalenyl)-4-thiazolecarboxamide.

Of note are compounds of Formula 1 where G is the thiazole ring, Q is Q-1 and X is $X^1$ and X is linked to the G thiazole ring at the 2 position of said thiazole ring. Of particular note are embodiments of these compounds within Embodiments 1 through 35, Embodiment 41, Embodiments 59 through 82, Embodiment 96, Embodiments A1 through A4, Embodiment A6, Embodiment A8 and Embodiments A10 through A12.

Of note are compounds of Formula 1 where G is the oxazole ring, Q is Q-1 and X is $X^1$ and X is linked to the G oxazole ring at the 2 position of said oxazole ring. Of particular note are embodiments of these compounds within Embodiments 1 through 35, Embodiment 42, Embodiments 59 through 82, Embodiment 96, Embodiments A1 through A4, Embodiment A6, Embodiment A8 and Embodiments A10 through A12.

Of note are compounds of Formula 1 where G is the thiazole ring, Q is Q-1 and X is $X^2$ and X is linked to the G thiazole ring at the 2 position of said thiazole ring. Of particular note are embodiments of these compounds within Embodiments 1 through 11, Embodiments 14 through 35, Embodiment 41, Embodiments 59 through 82, Embodiment 96, Embodiments A1 through A4, Embodiment A6, Embodiment A8 and Embodiments A10 through A12.

Of note are compounds of Formula 1 where G is the oxazole ring, Q is Q-1 and X is $X^2$ and X is linked to the G oxazole ring at the 2 position of said oxazole ring. Of particular note are embodiments of these compounds within Embodiments 1 through 11, Embodiments 14 through 35, Embodiment 41, Embodiments 59 through 82, Embodiment 96, Embodiments A1 through A4, Embodiment A6, Embodiment A8 and Embodiments A10 through A12.

Of note are compounds of Formula 1 where G is the thiazole ring, Q is Q-2 and X is $X^1$ and X is linked to the G thiazole ring at the 2 position of said thiazole ring. Of particular note are embodiments of these compounds within Embodiments 1 through 35, Embodiment 41, Embodiments 59 through 82, Embodiment 96, Embodiments A1 through A4, Embodiment A6, Embodiment A8 and Embodiments A10 through A12.

Of note are compounds of Formula 1 where G is the oxazole ring, Q is Q-2 and X is $X^1$ and X is linked to the G oxazole ring at the 2 position of said oxazole ring. Of particular note are embodiments of these compounds within Embodiments 1 through 35, Embodiment 42, Embodiments 59 through 82, Embodiment 96, Embodiments A1 through A4, Embodiment A6, Embodiment A8 and Embodiments A10 through A12.

Of note are compounds of Formula 1 where G is the thiazole ring, Q is Q-2 and X is $X^2$ and X is linked to the G thiazole ring at the 2 position of said thiazole ring. Of particular note are embodiments of these compounds within Embodiments 1 through 11, Embodiments 14 through 35, Embodiment 41, Embodiments 59 through 82, Embodiment 96, Embodiments A1 through A4, Embodiment A6, Embodiment A8 and Embodiments A10 through A12.

Of note are compounds of Formula 1 where G is the oxazole ring, Q is Q-2 and X is $X^2$ and X is linked to the G oxazole ring at the 2 position of said oxazole ring. Of particular note are embodiments of these compounds within Embodiments 1 through 11, Embodiments 14 through 35, Embodiment 41, Embodiments 59 through 82, Embodiment 96, Embodiments A1 through A4, Embodiment A6, Embodiment A8 and Embodiments A10 through A12.

Of note are compounds of Formula 1 where G is the thiazole ring, Q is Q-8 and X is $X^1$ and X is linked to the G thiazole ring at the 2 position of said thiazole ring. Of particular note are embodiments of these compounds within Embodiments 1 through 35, Embodiment 41, Embodiments 59 through 82, Embodiment 96, Embodiments A1 through A4, Embodiment A6, Embodiment A8 and Embodiments A10 through A12.

Of note are compounds of Formula 1 where G is the oxazole ring, Q is Q-8 and X is $X^1$ and X is linked to the G oxazole ring at the 2 position of said oxazole ring. Of particular note are embodiments of these compounds within Embodiments 1 through 35, Embodiment 42, Embodiments 59 through 82, Embodiment 96, Embodiments A1 through A4, Embodiment A6, Embodiment A8 and Embodiments A10 through A12.

Of note are compounds of Formula 1 where G is the thiazole ring, Q is Q-8 and X is $X^2$ and X is linked to the G thiazole ring at the 2 position of said thiazole ring. Of particular note are embodiments of these compounds within Embodiments 1 through 11, Embodiments 14 through 35, Embodiment 41, Embodiments 59 through 82, Embodiment 96, Embodiments A1 through A4, Embodiment A6, Embodiment A8 and Embodiments A10 through A12.

Of note are compounds of Formula 1 where G is the oxazole ring, Q is Q-8 and X is $X^2$ and X is linked to the G oxazole ring at the 2 position of said oxazole ring. Of particular note are embodiments of these compounds within Embodiments 1 through 11, Embodiments 14 through 35, Embodiment 41, Embodiments 59 through 82, Embodiment 96, Embodiments A1 through A4, Embodiment A6, Embodiment A8 and Embodiments A10 through A12.

This invention provides a fungicidal composition comprising a compound of Formula 1 (including all geometric and stereoisomers, N-oxides, and agriculturally suitable salts thereof), and at least one other fungicide. Of note as embodiment of such compositions are compositions comprising a compound corresponding to any of the compound embodiments describe above.

This invention provides a fungicidal composition comprising a fungicidally effective amount of a compound of Formula 1 (including all geometric and stereoisomers, N-oxides, and agriculturally suitable salts thereof), and at least one additional component selected from the group consisting of surfactants, solid diluents and liquid diluents. Of note as embodiment of such compositions are compositions comprising a compound corresponding to any of the compound embodiments describe above.

This invention provides a method for controlling plant diseases caused by fungal plant pathogens comprising applying to the plant or portion thereof, or to the plant seed or seedling, a fungicidally effective amount of a compound of Formula 1 (including all geometric and stereoisomers, N-oxides, and agriculturally suitable salts thereof). Of note as embodiment of such methods are methods comprising applying a fungicidally effective amount of a compound corresponding to any of the compound embodiments describe above. Of particular notes are embodiment where the compounds are applied as compositions of this invention.

The compounds of Formula 1 can be prepared by one or more of the following methods and variations as described in Schemes 1-22. The definitions of $R^1$, $R^2$, A, $W^1$, $W^2$, X, G, $Q^a$, $Q^b$ and n in the compounds of Formulae 1-46 below are as defined above in the Summary of the Invention unless otherwise noted. Compounds of Formulae 1a-1k are various subsets of the compounds of Formula 1. Compounds of Formulae 19a-19b are various subsets of the compounds of Formula 19. Compounds of Formulae 23a, 26a and 27a are various subsets of the compounds of Formula 23, 26 and 27 respectively.

As shown in Scheme 1, compounds of Formula 1 can be prepared by coupling of an acid chloride of Formula 2 with an amine of Formula 3 in the presence of an acid scavenger to provide the compound of Formula 1a. Typical acid scavengers include amine bases such as triethylamine, diisopropylethylamine and pyridine. Other scavengers include hydroxides such as sodium and potassium hydroxide and carbonates such as sodium carbonate and potassium carbonate. In certain instances it is useful to use polymer-supported acid scavengers such as polymer-bound diisopropylethylamine and polymer-bound N,N-dimethylaminopyridine. In a subsequent step, amides of Formula 1a can be converted to thioamides of Formula 1b using a variety of standard thiating reagents such as phosphorus pentasulfide or 2,4-bis(4-methoxyphenyl)-1,3-dithia-2,4-diphosphetane-2,4-disulfide (Lawesson's reagent). One skilled in the art will recognize that when $W^1$ is O, the conversion of $W^2$ from O to S may be accompanied by conversion of $W^1$ from O to S. The amines of Formula 3 are known or can be prepared by methods known to one skilled in the art. The amines of Formula 3 wherein $Q^a$ is an alkyl group can be prepared by either first heating a primary amine $Q^a$-$NH_2$ with alkyl formate followed by lithium aluminum hydride reduction or by a sodium borohydride reduction of N-alkyl imines prepared by treating $Q^a(=O)$ with an alkylamine.

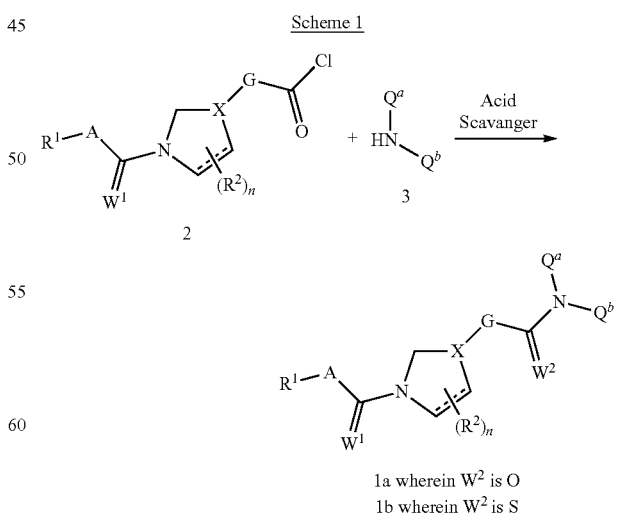

Scheme 1

1a wherein $W^2$ is O
1b wherein $W^2$ is S

An alternate procedure for the preparation of compounds of Formula 1a is depicted in Scheme 2 and involves coupling of an acid of Formula 4 with an amine of Formula 3 in the presence of a dehydrative coupling reagent such as dicyclohexylcarbocliimide (DCC), 1-(3-dimethylaminopropyl)-3-ethylcarbodiimide hydrochloride (EDC) or O-benzotriazol-1-yl-N,N,N',N'-tetramethyluronium hexafluorophosphate (HBTU). Polymer supported reagents are again useful here, such as polymer-bound cyclohexylcarbodiimide. These reactions are typically run at 0-40° C. in a solvent such as dichloromethane or acetonitrile in the presence of a base such as triethylamine or diisopropylethylamine.

Scheme 2

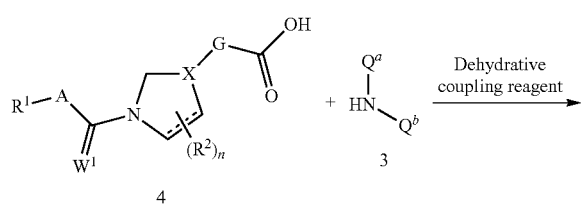

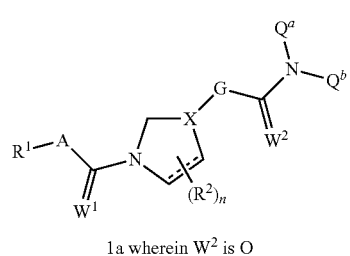

1a wherein $W^2$ is O

As shown in Scheme 3, compounds of Formula 1c wherein A is methylene can be prepared by coupling of an acid chloride of Formula 5 with an amine of Formula 6 in the presence of an acid scavenger, as described for Scheme 1 above. Acid salts of the Formula 6 amines can also be used in this reaction, provided at least 2 equivalents of the acid scavenger is present, as known to one skilled in the art. Typical acids used to form salts with amines include hydrochloric acid, oxalic acid and trifluoroacetic acid. In a subsequent step, amides of Formula 1c can be converted to thioamides of Formula 1d using a variety of standard dilating reagents such as phosphorus pentasulfide or 2,4-bis(4-methoxyphenyl)-1,3-dithia-2,4-diphosphetane-2,4-disulfide (Lawesson's reagent). One skilled in the art will recognize that when $W^2$ is O, that the conversion of $W^1$ from O to S may not be selective.

Scheme 3

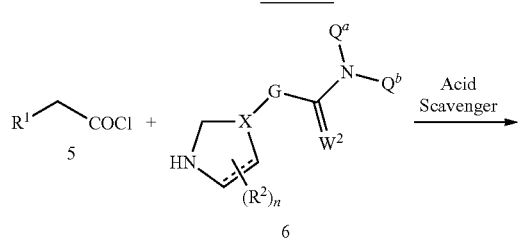

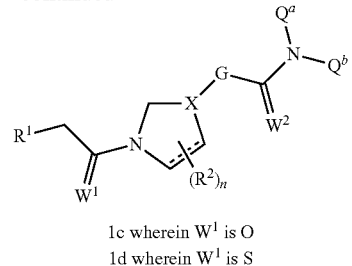

1c wherein $W^1$ is O
1d wherein $W^1$ is S

As shown in Scheme 4, compounds of Formula 1e can also be prepared by coupling of an acid of Formula 7 with an amine of Formula 6 (or its acid salt) in the presence of a dehydrative coupling reagent, analogous to the procedure described in Scheme 2 above. The acids of Formula 7 are known or can be prepared by methods known to one skilled in the art. For example, $R^1CH_2COOH$ where $R^1$ is a heteroaromatic ring linked through nitrogen can be prepared by reacting the corresponding $R^1H$ compound with a haloacetic acid or ester in the presence of base; see, for example, U.S. Pat. No. 4,084,955. $R^1CH_2COOH$ where $R^1$ is a phenyl or a heteroaromatic ring linked through carbon can be prepared from the corresponding $R^1CH_2$-halogen compounds by displacement of the halogen with cyanide followed by hydrolysis; see, for example, K. Adachi, *Yuki Gosei Kagaku Kyokaishi* 1969, 27, 875-876; from $R^1C(\!=\!O)CH_3$ by the Willgerodt-Kindler reaction; see, for example, H. R. Darabi, et. al., *Tetrahedron Letters* 1999, 40, 7549-7552 and M. M. Alam and S. R. Adapa, *Synthetic Communications* 2003, 33, 59-63 and references sited therein; or from $R^1Br$ or $R^1I$ by palladium catalyzed coupling with t-butyl acetate or diethyl malonate followed by ester hydrolysis; see, for example, W. A. Moradi and S. L. Buchwald, *J. Am. Chem. Soc.* 2001, 123, 7996-8002 and J. F. Hartwig et al., *J. Am. Chem. Soc.* 2002, 124, 12557-12565.

Scheme 4

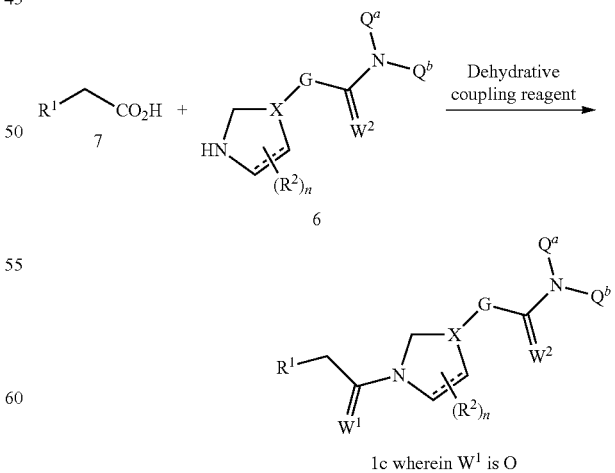

1c wherein $W^1$ is O

The synthetic procedures of Schemes 1, 2, 3 and 4 are only representative examples of useful methods for the preparation of Formula 1 compounds, as the synthetic literature is extensive for amide forming reactions. One skilled in the art will recognize that compound of Formula 1 where $Q^a$ is other than H or OH can be prepared from compounds of Formula 1 where $Q^a$ is H by standard alkylation or acylation methods. One skilled in the art will also realize that acid chlorides of Formula 2 and Formula 5 may be prepared from acids of Formula 4 and Formula 7, respectively, by numerous well-known methods.

Certain compounds of Formula 1c where $R^1$ is a 5-membered nitrogen containing heteroaromatic ring linked through the nitrogen atom can be prepared by reaction of the parent heterocycle of Formula 8 and a haloacetamide of Formula 9 as shown in Scheme 5. The reaction is carried out in the presence of a base such as sodium hydride or potassium carbonate in a solvent such as tetrahydrofuran, N,N-dimethylformamide or acetonitrile at 0 to 80° C. The haloacetamide of Formula 9 can be prepared by the reaction of an amine of Formula 6 with a haloacetyl halide or a haloacetic acid or its anhydride, analogous to the amide-forming reactions described in Schemes 3 and 4, respectively.

Scheme 5

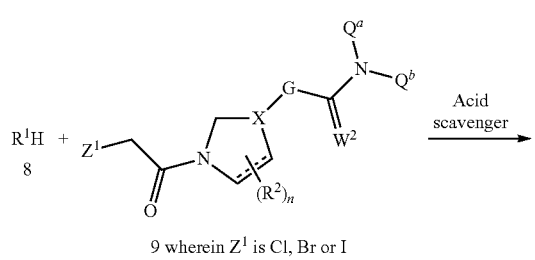

9 wherein $Z^1$ is Cl, Br or I

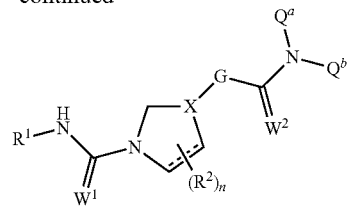

1c wherein $W^1$ is O

Compounds of Formula 1e and 1f wherein A is NH, where $R^1$ is phenyl or a 5- or 6-membered heteroaromatic ring linked via a carbon atom, can be prepared by reaction of an isocyanate or an isothiocyanate of Formula 10 with an amine of Formula 6, respectively, as depicted in Scheme 6. This reaction is typically carried out at an ambient temperature in an aprotic solvent such as dichloromethane or acetonitrile.

Scheme 6

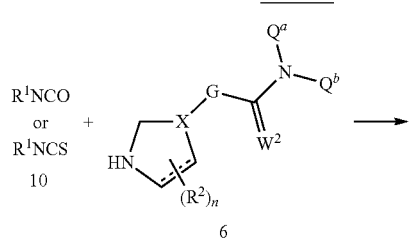

1e wherein $W^1$ is O
1f wherein $W^1$ is S

Compounds of Formula 1e and 1f can also be prepared by the reaction of an amine of Formula 11 with a carbamoyl or thiocarbamoyl chloride or imidazole of Formula 12 as shown in Scheme 7. When $Z^2$ is chlorine, the reaction is typically carried out in the presence of an acid scavenger. Typical acid scavengers include amine bases such as triethylamine, diisopropylethylamine and pyridine. Other scavengers include hydroxides such as sodium and potassium hydroxide and carbonates such as sodium carbonate and potassium carbonate. The carbamoyl or thiocarbamoyl chlorides of Formula 12 (wherein $Z^2$ is Cl) can be prepared from amines of Formula 6 by treatment with phosgene or thiophosgene, respectively, or their equivalents, while carbamoyl or thiocarbamoyl imidazoles of Formula 12 (wherein $Z^2$ is imidazol-1-yl) can be prepared from amines of Formula 6 by treatment with 1,1'-carbonyldiimidazole or 1,1'-thiocarbonyldiimidazole, respectively, according to general methods known to one skilled in the art.

Scheme 7

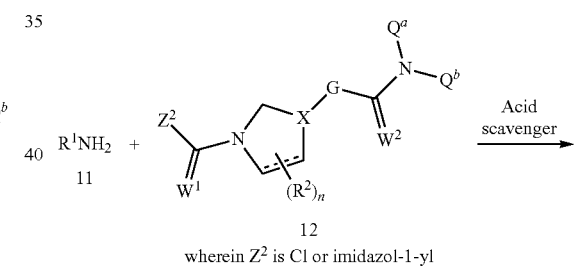

wherein $Z^2$ is Cl or imidazol-1-yl

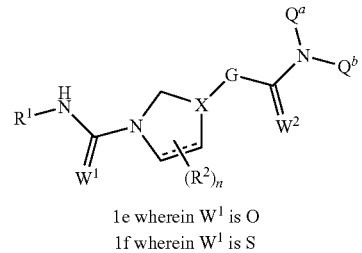

1e wherein $W^1$ is O
1f wherein $W^1$ is S

Certain compounds of Formula 1g where G is linked to the piperidine ring via a carbon atom can be prepared from compounds of Formula 1h by catalytic hydrogenation as shown in Scheme 8. Typical conditions involve exposing a compound of Formula 1h to hydrogen gas at a pressure of 14 to 100 psi (96 to 689 kPa), preferably 40 to 50 psi (276 to 345 kPa), in the presence of a metal catalyst such as palladium supported on an inert carrier such as activated carbon, in a weight ratio of 5 to 20% of metal to carrier, suspended in a solvent such as ethanol at an ambient temperature. The synthetic literature on these types of reductions is extensive; see, for example, *Catalytic Hydrogenation*, L. Cerveny, Ed., Elsevier Science, Amsterdam, 1986. One skilled in the art will recognize that certain functionalities that may be present in compounds of Formula 1h can also be reduced under catalytic hydrogenation conditions, requiring a suitable choice of catalyst and conditions.

Scheme 8

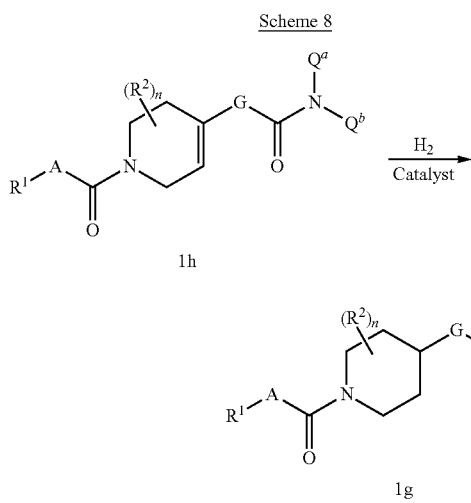

1h

1g

Certain compounds of Formula 1g where G is linked to the piperidine ring via a nitrogen atom can be prepared by displacement of an appropriate leaving group $Z^3$ on a piperidine of Formula 13 with a nitrogen-containing heterocycle of Formula 14 in the presence of a base as depicted in Scheme 9. Suitable bases include sodium hydride or potassium carbonate and the reaction is carried out in a solvent such as N,N-dimethylformamide or acetonitrile at 0 to 80° C. Suitable leaving groups in the piperidines of Formula 13 include bromine, iodine, mesylate (OMs, $OS(O)_2CH_3$), triflate ($OS(O)_2CF_3$) and the like, and can be prepared from the corresponding piperidine compounds of Formula 13 where $Z^3$ is OH, as known to one skilled in the art.

Scheme 9

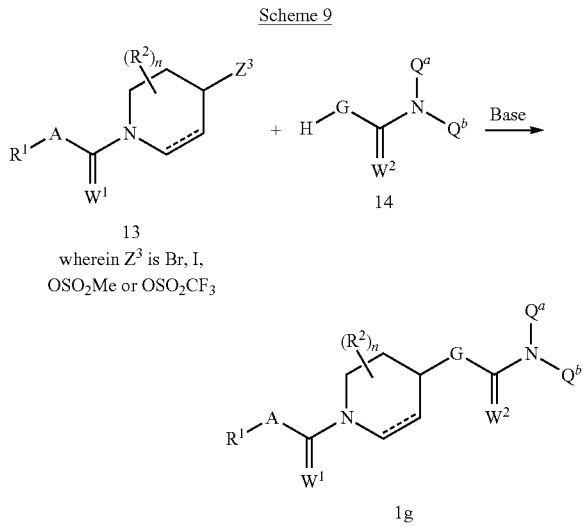

1g

Compounds of Formula 1i can be prepared by reaction of a piperazine of Formula 15 with a heterocyclic halide or triflate (OTf, $OS(O)_2CF_3$) of Formula 16 as shown is Scheme 10. The reaction is carried out in the presence of a base such as potassium carbonate in a solvent such as dimethylsulfoxide, N,N-dimethylformamide or acetonitrile at 0 to 80° C. In a subsequent step, compounds of Formula 11 can be converted to compounds of Formula 1j using a variety of standard thiating reagents such as phosphorus pentasulfide or 2,4-bis (4-methoxyphenyl)-1,3-dithia-2,4-diphosphetane-2,4-disulfide (Lawesson's reagent). One skilled in the art will recognize that when $W^2$ is O, that the conversion of $W^1$ from O to S may not be selective. The compounds of Formula 16 where $Z^4$ is triflate can be prepared from the corresponding compounds of Formula 16 where $Z^4$ is OH by methods known to one skilled in the art.

Scheme 10

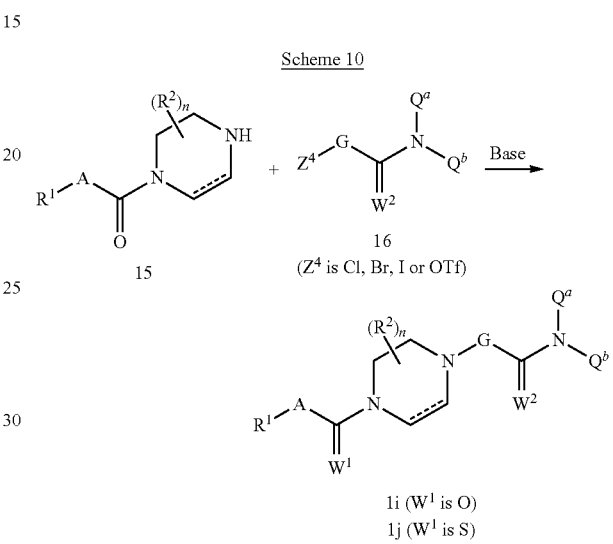

1i ($W^1$ is O)
1j ($W^1$ is S)

The acid compounds of Formula 4 can be prepared by saponification of the corresponding ester compounds of Formula 17 using an alkali metal hydroxide such as LiOH, NaOH or KOH usually in the presence of water along with a co-solvent such as tetrahydrofuran and/or methanol to aid solubility of the ester as shown in Scheme 11. The reaction is typically run at 0 to 60° C. with the resultant carboxylate salt being converted to the free acid by addition of a slight excess of a mineral acid such as hydrochloric acid or sulfuric acid.

Scheme 11

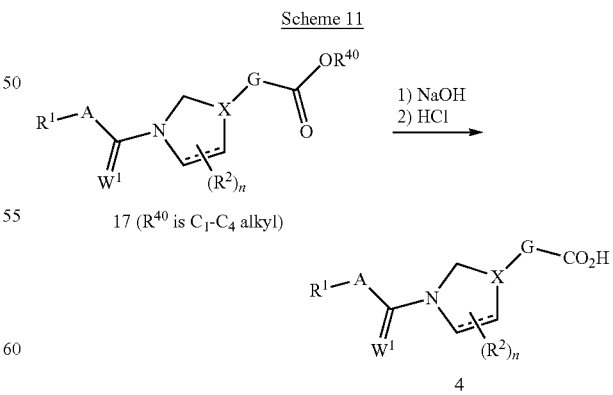

17 ($R^{40}$ is $C_1$-$C_4$ alkyl)

4

As outlined in Scheme 12, the ester compounds of Formula 17 can be prepared from the amine compounds of Formula 18 by methods analogous to those described above for the preparation of compounds of Formula 1 as outlined in Scheme 12.

One skilled in the art will recognize that analogous methods to those of Schemes 3, 4, 5, 6, 7, 8, 9 and 10, wherein the group COOR$^{40}$ where R$^{40}$ is C$_1$-C$_4$ alkyl is substituted for the group C(=W$^2$)NQ$^a$Q$^b$ can be used to provide intermediates of Formula 17 useful for the preparation of compounds of Formula 1.

Scheme 12

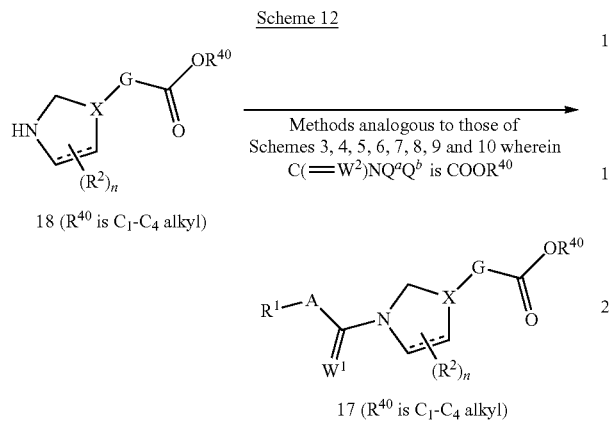

The amine compounds of Formula 18 can be prepared from the protected amine compounds of Formula 19 where PG is an acid-labile amine protecting group such as a t-butoxycarbonyl (t-Boc) or a benzyloxycarbonyl (Cbz) group as shown in Scheme 13. The protecting group is removed by treating with an acid such as trifluoroacetic acid or gaseous HCl in the presence of a solvent such as dichloromethane or dioxane. The amine can be isolated as its acid salt or converted in a subsequent step to the free amine by treatment with a base, as known to one skilled in the art.

Scheme 13

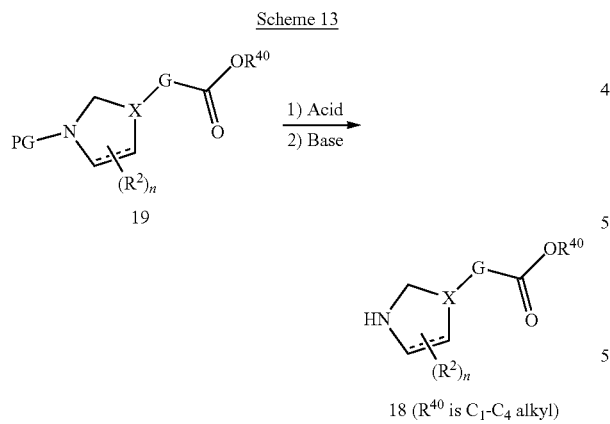

wherein R$^{40}$ is C$_1$-C$_4$ alkyl; PG is an acid-labile protecting group.

The amines of Formula 6 can be prepared from the protected amines of Formula 20 where PG is an acid-labile amine protecting group such as a t-butoxycarbonyl (t-Boc) or a benzyloxycarbonyl (Cbz) group as depicted in Scheme 14 by methods analogous to those described above for the preparation of compounds of Formula 18 as outlined in Scheme 13.

Scheme 14

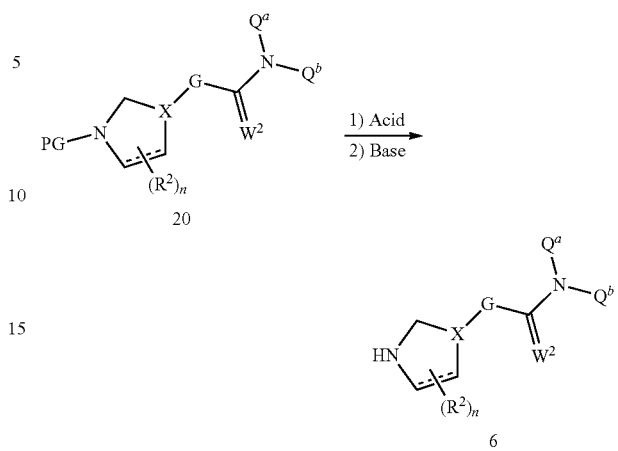

wherein PG is an acid-labile protecting group.

The protected amines of Formula 20 can be prepared from the acid or acid chloride compounds of Formula 21 by methods analogous to those described above for the preparation of compounds of Formula 1 as outlined in Scheme 15. One skilled in the art will recognize that in Schemes 1, 2, 8, 9 and 10, the group R$^1$AC(=W$^1$) can analogously be replaced by PG where PG is a standard, acid-labile amine protecting group such as a t-butoxycarbonyl (t-Boc) or a benzyloxycarbonyl (Cbz) group to give useful intermediates of Formula 20 for the preparation of compounds of Formula 1. The compounds of Formula 21 where R$^{41}$ is OH can be obtained from compounds of Formula 19 by saponification, analogous to methods described for Scheme 11.

Scheme 15

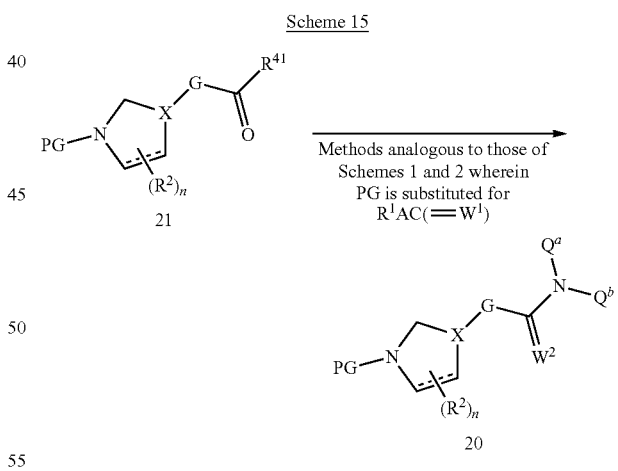

wherein R$^{41}$ is Cl or OH; PG is an acid-labile protecting group.

Many compounds of Formula 19 are known or can be prepared by methods known to one skilled in the art starting with the intermediates such as, but not limited to, those depicted in Exhibit 1. The synthetic literature is extensive for the formation of 5-membered heteroaromatic ring system or 5-membered partially saturated heterocyclic ring system (for example, G-1 through G-55); see, for example, *Comprehensive Heterocyclic Chemistry*, Vol. 4-6, A. R. Katritzky and C. W. Rees editors, Pergamon Press, New York, 1984; *Compre-* hensive Heterocyclic Chemistry II, Vol. 2-4, A. R. Katritzky, C. W. Rees, and E. F. Scriven editors, Pergamon Press, New York, 1996; and the series, The Chemistry of Heterocyclic Compounds, E. C. Taylor, editor, Wiley, New York. The use of intermediates of Formula 26 to prepare organo zinc reagents for use in cross coupling reactions with aromatic ring systems has been described, see, for example, S. Bellotte, Synlett 1998, 379-380, and M. Nakamura et al., Synlett 2005, 1794-1798.

the heteroaromatic compounds of Formula 31 where $Z^6$ is a halogen, preferably Br or I, or a triflate group as shown in Scheme 16. The reaction is carried out in the presence of a catalytic amount of palladium such as $PdCl_2dppf$ ($PdCl_2$-1, 1'-bis(diphenylphosphino)ferrocene) and a base such as potassium acetate in a solvent such as dioxane at 80 to 100° C., similar to that reported for the coupling of boronates of Formula 30 with aryl halides and triflates by P. R. Eastwood, Tetrahedron Letters 2000, 41, 3705-3708. The use of palladium in the synthesis of heterocycles is well known; see, for example, J. J. Li and G. W. Gribble, "*Palladium in Heterocyclic Chemistry*", Pergamon Press, Amsterdam, 2000. There are many variations of catalyst type, base and reaction conditions which can be used as known to one skilled in the art. Many compounds of Formula 31 where Y is halogen are known or can be prepared by methods known to one skilled in the art.

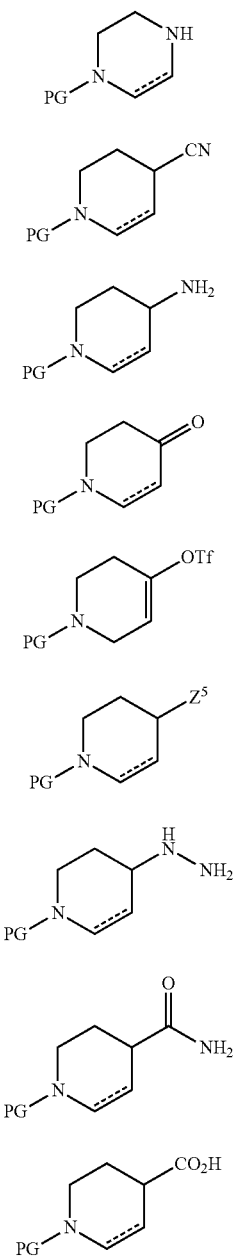

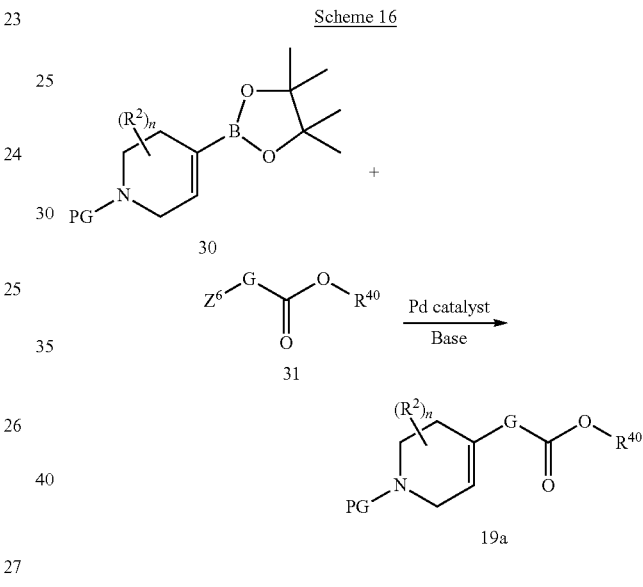

Scheme 16 wherein PG is an acid-labile protecting group; $Z^6$ is Cl, Br, I or OTf; $R^{40}$ is $C_1$-$C_4$ alkyl.

Preparation of the N-linked analogs wherein G is G-25 through G-30 may be carried out by displacement of an appropriate leaving group on the piperidine ring with the desired heterocycle ester as outlined in Scheme 17 using the procedures described in Bioorganic & Medicinal Chemistry Letters 2001, 11(18), 2475-2479; Bioorganic & Medicinal Chemistry Letters 2002, 12(12), 1683-1686; Tetrahedron 2002, 58(23), 4707-4716 and PCT Patent Application Publication WO 2004/007499. Alternatively N-linked analogs can be prepared from hydroxypiperidines and the appropriate heterocycle via a Mitsunobu reaction, for examples of reactions of this type see: J. Med. Chem. 2004, 47(27), 6921-6934. Preparation of the heterocycle esters are described in the following references: Synthesis 1990, 753-754; Synthesis 1995, 1491-1492; J. Het. Chem. 1993, 30(4), 865-872; Tetrahedron 1986, 42(8), 2351-2358; J. Het. Chem. 1988, 25(2), 651-654; and Helv. Chem. Acta 1996, 79(2), 449-453.

wherein $Z^5$ is Br, I, OH, OMs, or OTf; W is O or S; and PG is an acid-labile protecting group such as t-Boc or Cbz.

Additionally, the compounds of Formula 19a where G is linked to the tetrahydropyridine ring via a carbon atom can be prepared by reacting the cyclic boronates of Formula 30 with Scheme 17

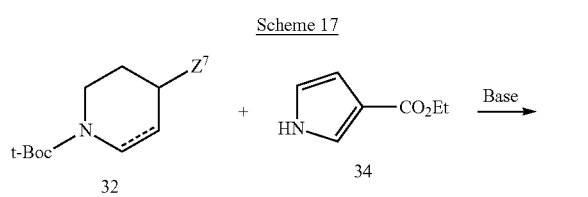

$Z^7$ is Br, I or OMs

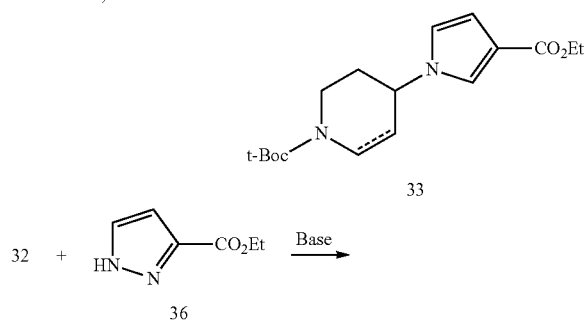

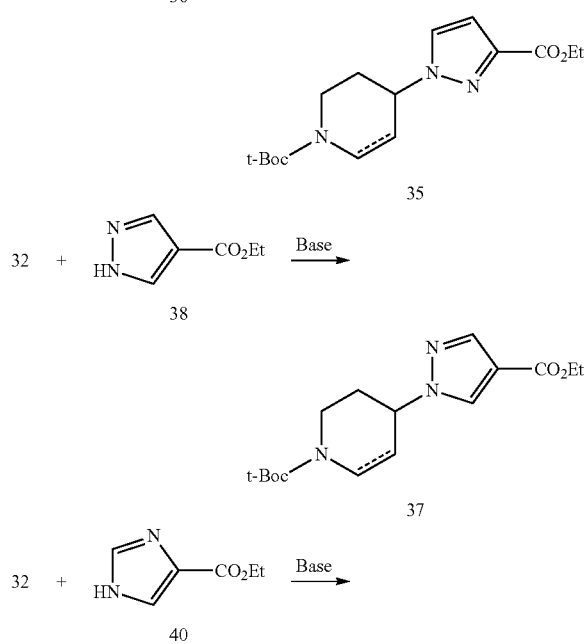

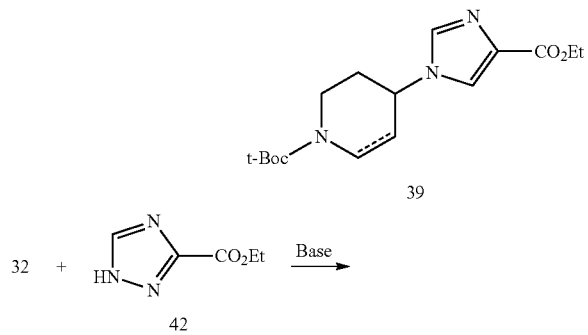

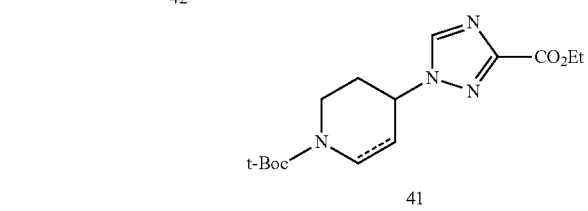

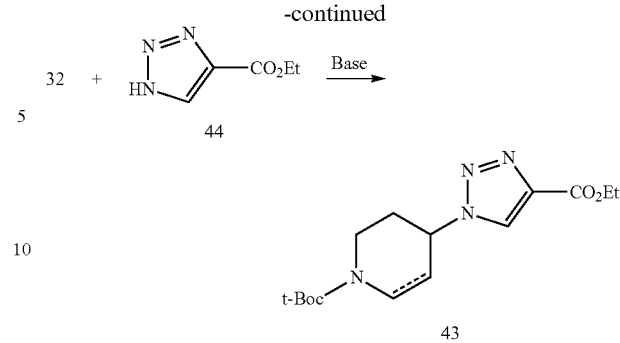

Removal of the t-BOC group of the compound of Formula 19b and saponification of the ester followed by amide formation with the appropriate acid chloride or amine under standard conditions yields the final compound of Formula 1k as shown in Scheme 18.

Scheme 18

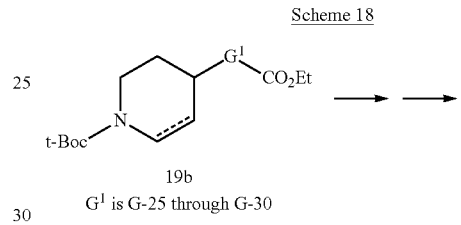

$G^1$ is G-25 through G-30

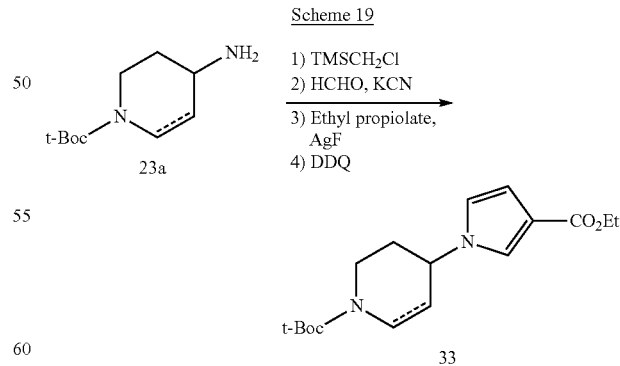

The compound of Formula 33 can be obtained by the route shown in Scheme 19 from the amino piperidine of Formula 23a; see, for example, *Bioorganic & Medicinal Chemistry Letters* 2001, 11(18), 2475-2479 and *J. Org. Chem.* 1985, 50(21), 4006-4014.

Scheme 19

The compound of Formula 46 can also be prepared from the N-benzyl hydrazino piperidine of Formula 27a as shown in Scheme 20; see, for example, *Bioorganic & Medicinal Chemistry Letters* 1999, 9(9), 1285-1290 and *J. Het. Chem.*, 1993, 30(4), 865-872.

Scheme 20

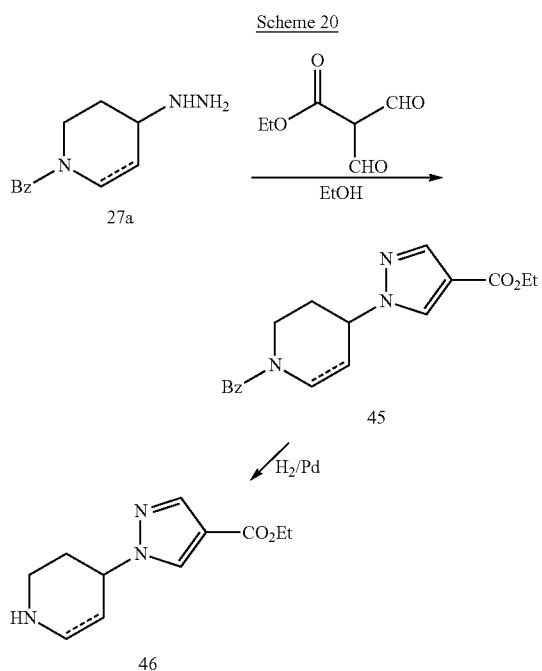

Scheme 22

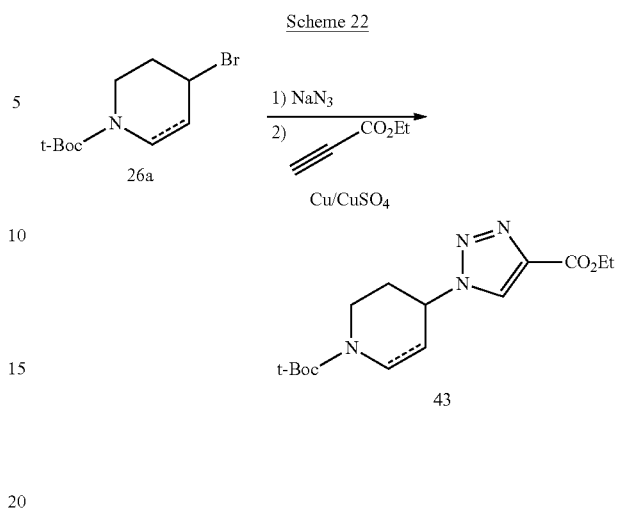

The compound of Formula 37 can also be obtained by the route shown in Scheme 21 from the amino piperidine of Formula 23a; see, for example, *Bioorganic & Medicinal Chemistry Letters* 2001, 11(18), 2475-2479 and *Organic Letters* 2002, 4(23), 4133-4134.

Scheme 21

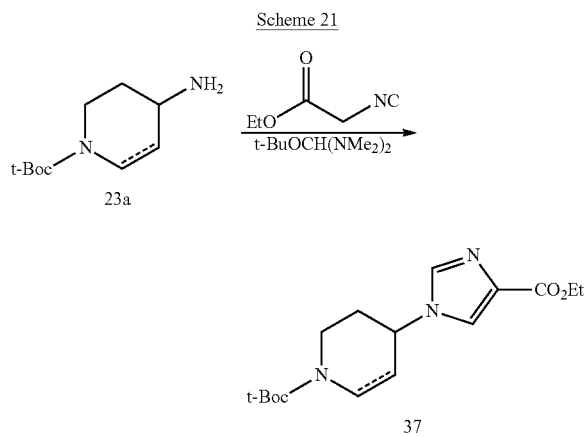

The compound of Formula 43 is also available from the 4-bromo piperidine of Formula 26a as shown in Scheme 22; see, for example, *Bioorganic & Medicinal Chemistry Letters* 1999, 9(9), 1285-1290, by initial conversion to the azide followed by cycloaddition with ethyl propiolate according to the general method of *Organic Letters* 2004, 6(23), 4223-4225.

It is recognized that some reagents and reaction conditions described above for preparing compounds of Formula 1 may not be compatible with certain functionalities present in the intermediates. In these instances, the incorporation of protection/deprotection sequences or functional group interconversions into the synthesis will aid in obtaining the desired products. The use and choice of the protecting groups will be apparent to one skilled in chemical synthesis (see, for example, Greene, T. W.; Wuts, P. G. M. *Protective Groups in Organic Synthesis*, 2nd ed.; Wiley: New York, 1991). One skilled in the art will recognize that, in some cases, after the introduction of a given reagent as it is depicted in any individual scheme, it may be necessary to perform additional routine synthetic steps not described in detail to complete the synthesis of compounds of Formula 1. One skilled in the art will also recognize that it may be necessary to perform a combination of the steps illustrated in the above schemes in an order other than that implied by the particular sequence presented to prepare the compounds of Formula 1.

One skilled in the art will also recognize that compounds of Formula 1 and the intermediates described herein can be subjected to various electrophilic, nucleophilic, radical, organometallic, oxidation, and reduction reactions to add substituents or modify existing substituents.

Without further elaboration, it is believed that one skilled in the art using the preceding description can utilize the present invention to its fullest extent. The following Examples are, therefore, to be construed as merely illustrative, and not limiting of the disclosure in any way whatsoever. Steps in the following Examples illustrate a procedure for each step in an overall synthetic transformation, and the starting material for each step may not have necessarily been prepared by a particular preparative run whose procedure is described in other Examples or Steps. Percentages are by weight except for chromatographic solvent mixtures or where otherwise indicated. Parts and percentages for chromatographic solvent mixtures are by volume unless otherwise indicated. $^1$H NMR spectra are reported in ppm downfield from tetramethylsilane; "s" means singlet, "d" means doublet, "t" means triplet, "m" means multiplet, "q" means quartet, "br s" means broad singlet, "br d" means broad doublet, "br m" means broad multiplet.

EXAMPLE 1

Preparation of 2-[1-[(2,5-dimethylphenyl)acetyl]-4-piperidinyl]-N-methyl-N-[(1R)-1-phenylpropyl]-4-thiazolecarboxamide (Compound 58)

Step A: Preparation of 1,1-dimethylethyl 4-[4-(ethoxycarbonyl)-2-thiazolyl]-1-piperidinecarboxylate To a suspension of 1,1-dimethylethyl 4-(aminothioxomethyl)-1-tetrahydropyridine-carboxylate (30 g, 123 mmol) in ethanol (180 mL), cooled to 0° C. in an ice bath, was added dropwise a solution of ethyl bromopyruvate (15.7 mL, 125 mmol) in ethanol (180 mL). The ice bath was removed, and the mixture was stirred at ambient temperature overnight. Triethylamine (30 mL) was added, and the mixture was concentrated under reduced pressure, diluted with ethyl acetate, washed with brine, dried over magnesium sulfate and concentrated under reduced pressure to give 31 g of a brown oil, which solidified on standing. A portion of this crude product (8.1 g) was heated with 200 mL of ether, and the ether was then decanted. This was repeated a second time, and the combined ether solutions were evaporated under reduced pressure to give 7.6 g of the title compound as a yellow solid.

$^1$H NMR (CDCl$_3$) δ 1.40 (t, 3H), 1.46 (s, 9H), 1.7 (m, 2H), 2.1 (m, 2H), 2.85 (m, 2H), 3.25 (m, 1H), 4.2 (m, 2H), 4.42 (q, 2H), 8.08 (s, 1H).

Step B: Preparation of 1-(1,1-dimethyl ethyl) 4-(4-carboxy-2-thiazolyl)-1-piperidine-carboxylate To a solution of 1,1-dimethylethyl 4-[4-(ethoxycarbonyl)-2-thiazolyl]-1-piperidinecarboxylate (i.e. the product of Example 1, Step A) (3.4 g, 10 mmol) in 20 mL of methanol and 20 mL of tetrahydrofuran was added 1 N aqueous NaOH solution (15 mL), and the resulting mixture was stirred at ambient temperature for 1.5 h. The reaction mixture was concentrated under reduced pressure, diluted with water and acidified with excess 20% aqueous citric acid solution to give a gummy precipitate. Ethyl acetate (30 mL) was added to dissolve the precipitate, the aqueous layer was saturated with NaCl, and the reaction mixture was extracted with ethyl acetate. The extract was dried over MgSO$_4$ and concentrated under reduced pressure to give 3.09 g of the title compound as a tan solid.

$^1$H NMR (CDCl$_3$) δ 1.47 (s, 9H), 1.75 (m, 2H), 2.13 (m, 2H), 2.88 (m, 2H), 3.2 (m, 1H), 4.22 (m, 2H), 8.19 (s, 1H).

Step C: Preparation of (α,R)-α-ethyl-N-methylbenzenemethanamine (alternatively named (α,R)-α-ethyl-N-methylbenzenemethanamine)

A solution of (R)-(+)-1-phenylpropylamine (9.19 g, 68.1 mmol) in 90 mL of dichloromethane was cooled to −30° C. and treated with triethylamine (11.4 mL, 81.7 mmol) followed by dropwise addition of ethyl chloroformate (7.8 mL, 81.7 mmol). The reaction mixture was warmed to ambient temperature, stirred for 1 h, poured into 100 mL of 1 N aqueous hydrochloric acid and extracted with dichloromethane. The extract was washed with saturated aqueous sodium bicarbonate solution, dried over MgSO$_4$ and concentrated under reduced pressure to give 14.2 g of a colorless oil. The oil was dissolved in 15 mL of tetrahydrofuran and added dropwise to a suspension of lithium aluminum hydride (7.82 g, 206 mmol) in 25 mL of tetrahydrofuran that had been cooled to 0° C. The reaction mixture was refluxed overnight, cooled to 0° C. and quenched by the sequential addition of 8 mL of water, 8 mL of 15% aqueous NaOH solution and 24 mL of water. The mixture was filtered through Celite®, diatomaceous filter aid, the resulting solid was washed with hot ethyl acetate, and the combined filtrates and washings were concentrated under reduced pressure to give 7.06 g of the title compound as a yellow oil.

$^1$H NMR (CDCl$_3$) δ 0.81 (t, 3H), 1.4 (br s, 1H), 1.55-1.85 (m, 2H), 2.28 (s, 3H), 3.37 (m, 1H), 7.2-7.4 (m, 5H).

Step D: Preparation of 1,1-dimethylethyl 4-[4-[[methyl[(1R)-1-phenylpropyl]amino]-carbonyl]-2-thiazolyl]-1-piperidinecarboxylate 1-(1,1-Dimethylethyl) 4-(4-carboxy-2-thiazolyl)-1-piperidinecarboxylate (i.e. the product of Example 1, Step B) (3.1 g, 9.9 mmol) was suspended in 10 mL of dry acetonitrile and treated with triethylamine (3.0 mL, 21 mmol) to give a homogeneous solution. To this was added O-benzotriazol-1-yl-N,N,N',N'-tetramethyluronium hexafluorophosphate (3.98 g, 10.5 mmol) followed by (α,R)-α-ethyl-N-methyl-benzenemethanamine (i.e. the product of Example 1, Step C) (10 mmol, 1.50 g). The mixture was stirred at ambient temperature for 4 days, concentrated under reduced pressure, diluted with ethyl acetate, washed with 1 N aqueous hydrochloric acid, saturated aqueous sodium bicarbonate solution and brine, dried over MgSO$_4$ and concentrated under reduced pressure to give 5.1 g of a dark oil. Purification by silica gel chromatography using 25% ethyl acetate in hexanes gave 3.6 g of the title compound as a yellow oil.

$^1$H NMR (CDCl$_3$) δ 0.9-1.1 (br m, 3H), 1.46 (s, 9H), 1.6-1.8 (m, 2H), 1.9-2.2 (m, 4H), 2.7-3.0 (m, 5H), 3.15 (m, 1H), 4.15 (m, 2H), 5.6-6.0 (m, 1H), 7.25-7.45 (m, 5H), 7.8 (s, 1H).

Step E: Preparation of N-methyl-N-[(1R)-1-phenylpropyl]-2-(4-piperidinyl)-4-thiazolecarboxamide 1,1-Dimethylethyl 4-[4-[[methyl[(1R)-1-phenylpropyl]amino]carbonyl]-2-thiazolyl]-1-piperidinecarboxylate (i.e. the product of Example 1, Step D) (3.6 g, 8.1 mmol) was dissolved in 100 mL of ether and treated with 20 mL of 4 N HCl in dioxane. The reaction mixture was stirred at ambient temperature for 4 h during which time a precipitate formed and was collected. The mother liquid was concentrated under reduced pressure, treated with 20 mL of 4 N HCl in dioxane, stirred at ambient temperature for 1 h and concentrated under reduced pressure. The residue was combined with the previously collected precipitate, dissolved in water and washed with ether. The aqueous layer was basified with 1 N aqueous NaOH solution and extracted with ethyl acetate. The extract was dried over MgSO$_4$ and concentrated under reduced pressure to give 2.33 g of the title compound as an orange oil suitable for use in subsequent reactions.

$^1$H NMR (CDCl$_3$) δ 0.9-1.1 (br m, 3H), 1.75 (m, 2H), 1.9-2.2 (m, 5H), 2.7-3.0 (m, 5H), 5.7-6.0 (m, 1H), 7.25-7.45 (m, 5H), 7.8 (s, 1H).

Step F: Preparation of 2-[1-[(2,5-dimethylphenyl)acetyl]-4-piperidinyl]-N-methyl-N-[(1R)-1-phenylpropyl]-4-thiazolecarboxamide N-Methyl-N-[(1R)-1-phenylpropyl]-2-(4-piperidinyl)-4-thiazolecarboxamide (i.e. the product of Example 1, Step E) (206 mg, 0.6 mmol) was dissolved in 4 mL of dry dichloromethane. To this reaction mixture was added triethylamine (90 μL, 0.65 mmol), 2,5-dimethylbenzeneacetic acid (98 mg, 0.6 mmol), 1-(3-dimethylaminopropyl)-3-ethylcarbodiimide hydrochloride (125 mg, 0.65 mmol) and a catalytic amount of 4-(dimethylamino)pyridine (~1 mg). The mixture was shaken overnight at ambient temperature, passed through a 5 mL capacity ChemEluten™, diatomaceous filter tube, pretreated with 3 mL of 1 N aqueous hydrochloric acid solution and eluted with 2 column volumes of dichloromethane. The dichloromethane solution was concentrated under reduced pressure, and the residue was purified by silica gel chromatography using acetone to give 276 mg of the title product, a compound of the present invention as a light yellow oil.

$^1$H NMR (CDCl$_3$) δ 0.9-1.1 (br m, 3H), 1.5-1.9 (m, 2H), 1.9-2.2 (m, 4H), 2.23 (s, 3H), 2.26 (s, 3H), 2.7-3.0 (m, 4H), 3.1-3.3 (m, 2H), 3.65 (s, 2H), 3.8 (br m, 1H), 4.7 (br m, 1H), 5.6-6.0 (m, 1H), 6.9-7.1 (m, 3H) 7.25-7.45 (m, 5H), 7.8 (s, 1H).

EXAMPLE 2

Preparation of N-methyl-2-[1-[[5-methyl-3-(trifluoromethyl)-1H-pyrazol-1-yl]acetyl]-4-piperidinyl]-N-[(1R)-1-phenylpropyl]-4-thiazolecarboxamide (Compound 117)

Step A: Preparation of 5-methyl-3-(trifluoromethyl)-1H-pyrazol-1-acetic acid

A mixture of 3-methyl-5-trifluoromethylpyrazole (10.0 g, 66.7 mmol), ethyl bromoacetate (11.1 mL, 100 mmol) and potassium carbonate (18.4 g, 133 mmol) in 80 mL of N,N-dimethylformamide was stirred at ambient temperature overnight. The orange mixture was filtered, diluted with ethyl acetate, washed with water and brine, dried over MgSO$_4$ and concentrated under reduced pressure to give 15.7 g of the pyrazole ester. The ester, in 100 mL of tetrahydrofuran, was treated with 11 mL of a 50% aqueous NaOH solution in 90 mL of water and stirred at ambient temperature overnight. The tetrahydrofuran was removed under reduced pressure and the aqueous solution was washed with ether and acidified with conc. HCl to pH 1 to give a precipitate. The precipitate was filtered, washed with water and dried to give 12.1 g of the title compound as a white solid.

$^1$H NMR (Acetone-d$_6$) δ 2.35 (s, 3H), 5.07 (s, 2H), 6.45 (s, 1H).

Step B: Preparation of N-methyl-2-[1-[[5-methyl-3-(trifluoromethyl)-1H-pyrazol-1-yl]acetyl]-4-piperidinyl]-N-[(1R)-1-phenylpropyl]-4-thiazolecarboxamide N-Methyl-N-[(1R)-1-phenylpropyl]-2-(4-piperidinyl)-4-thiazolecarboxamide (i.e. the product of Example 1, Step E) (150 mg, 0.44 mmol) was dissolved in 3 mL of dry dichloromethane. To this solution was added triethylamine (30 μL, 0.22 mmol), 5-methyl-3-(trifluoromethyl)-1H-pyrazol-1-acetic acid (83 mg, 0.4 mmol), 1-(3-dimethylaminopropyl)-3-ethylcarbodiimide hydrochloride (84 mg, 0.44 mmol) and a catalytic amount of 4-(dimethylamino)pyridine (~1 mg). The reaction mixture was shaken overnight at ambient temperature, concentrated under reduced pressure and passed through a silica gel column (2 g) using 1:1 hexanes/ethyl acetate as eluant. The dichloromethane/hexanes/ethyl acetate solution was concentrated under reduced pressure, and the residue was purified by preparative reverse phase High Pressure Liquid Chromatography (HPLC) using a solvent gradient going from 100% water to 100% acetonitrile to give 85 mg of the title product, a compound of the present invention as an oil.

$^1$H NMR (CDCl$_3$) δ 0.9-1.1 (br m, 3H), 1.7-1.9 (m, 2H), 1.9-2.2 (m, 4H), 2.31 (s, 3H), 2.7-3.0 (m, 4H), 3.2-3.4 (m, 2H), 3.9-4.6 (br m, 2H), 4.96 (br s, 2H), 5.6-6.0 (m, 1H), 6.3 (s, 1H) 7.20-7.45 (m, 5H), 7.8 (s, 1H).

EXAMPLE 3

Preparation of 2-[1-[(2,5-dichlorophenyl)acetyl]-4-piperidinyl]-N-methyl-N-[(1R)-1-phenylpropyl]-4-thiazolecarboxamide (Compound 110)

Step A: Preparation of 2,5-dichlorobenzeneacetic acid

A mixture of 2,5-dichlorobenzyl bromide (5.4 g, 22.5 mmol) in 16 mL of ethanol and potassium cyanide (1.63 g, 25 mmol) in 4 mL of water was heated at 80° C. overnight, then cooled, and the solids were filtered and washed with ethanol to give 3.5 g of 2,5-dichlorophenylacetonitrile as a white powder melting at 89-91° C. The nitrile was suspended in 20 red, of ethanol, and 20 mL of a 25% aqueous NaOH solution was added. The mixture was heated in a CEM Explore™ microwave reactor at 140° C. for 30 minutes, then cooled, poured into ice water and acidified to pH 1 with concentrated HCl to give a precipitate. The precipitate was filtered, washed with water and dried in a vacuum oven at 90° C. for 5 h to give the title compound as a white powder.

$^1$H NMR (CDCl$_3$) δ 3.79 (s, 2H), 7.2-7.4 (m, 3H).

Step B: Preparation of 2-[1-[(2,5-dichlorophenyl)acetyl]-4-piperidinyl]-N-methyl-N-[(1R)-1-phenylpropyl]-4-thiazolecarboxamide N-Methyl-N-[(1R)-1-phenylpropyl]-2-(4-piperidinyl)-4-thiazolecarboxamide (i.e. the product of Example 1, Step E) (171 mg, 0.5 mmol) was dissolved in 3 mL of dry dichloromethane. To this was added triethylamine (35 μL, 0.25 mmol), 2,5-dichlorobenzeneacetic acid (102 mg, 0.5 mmol) (i.e. the product of Example 3, Step A), 1-(3-dimethylaminopropyl)-3-ethylcarbodiimide hydrochloride (100 mg, 0.56 mmol) and a catalytic amount of 4-(dimethylamino)pyridine (~1 mg). The mixture was shaken overnight at ambient temperature, diluted with dichloromethane, washed with 1 N aqueous hydrochloric acid, saturated aqueous sodium bicarbonate solution and brine, dried over MgSO$_4$ and concentrated under reduced pressure. The residue was purified by silica gel chromatography using ethyl acetate to give 170 mg of the title product, a compound of the present invention as an oil.

$^1$H NMR (CDCl$_3$) δ 0.9-1.1 (br m, 3H), 1.65-1.9 (m, 2H), 1.9-2.2 (m, 4H), 2.7-3.0 (m, 4H), 3.25 (m, 2H), 3.8 (s, 2H), 3.9 (br m, 1H), 4.6 (br m, 1H), 5.6-6.0 (m, 1H), 7.15-7.45 (m, 8H), 7.81 (s, 1H).

EXAMPLE 4

Preparation of 2-[4-[(2,5-dimethylphenyl)acetyl]-1-piperazinyl]-N-methyl-N-[(1R)-1-phenylethyl]-5-thiazolecarboxamide (Compound 74)

Step A: Preparation of 1,1-dimethylethyl 4-[5-(methoxycarbonyl)-2-thiazolyl]-1-piperazinecarboxylate 1,1-Dimethylethyl 1-piperazinecarboxylate (1.86 g, 10 mmol), methyl 2-bromo-5-thiazolecarboxylate (2.0 g, 9.0 mmol), diazabicycloundecene (1.5 mL, 10 mmol) and a catalytic amount of potassium iodide (2 mg) were dissolved in 10 mL of dry dimethylsulfoxide and stirred at ambient temperature for 1 h to give a precipitate. An additional 10 mL of dimethylsulfoxide was added, the mixture was heated briefly to dissolve the solids, and the mixture was stirred at ambient temperature for 40 minutes and then at 50° C. for 2 h. The warm solution was added dropwise with stirring to 200 mL of cold water containing 10 mL of 1 N aqueous hydrochloric acid, and the resulting precipitate was filtered, dissolved in ether, dried over MgSO$_4$ and concentrated under reduced pressure to give 2.62 g of the title compound as a light yellow solid.

$^1$H NMR (CDCl$_3$) δ 1.48 (s, 9H), 3.56 (s, 8H), 3.83 (s, 3H), 7.88 (s, 1H).

Step B: Preparation of 1-(1,1-dimethylethyl) 4-(5-carboxy-2-thiazolyl)-1-piperazine-carboxylate 1,1-Dimethylethyl 4-[5-(methoxycarbonyl)-2-thiazolyl]-1-piperazinecarboxylate (i.e. the product of Example 4, Step A) (2.56 g, 8 mmol) in 15 mL of methanol and 15 mL of tetrahydrofuran was added 1 N aqueous NaOH solution (10 mL), and the mixture was stirred at ambient temperature overnight. The mixture was concentrated under reduced pressure, diluted with water, washed with ether, and acidified with excess 20% aqueous citric acid solution to give a precipitate. The precipitate was filtered, washed with water and dried to give 2.12 g of the title compound as a slightly pink solid.

$^1$H NMR (CDCl$_3$) δ 1.49 (s, 9H), 3.58 (br s, 8H), 7.97 (s, 1H).

Step C: Preparation of 1,1-dimethylethyl 4-[5-[[methyl[(1R)-1-phenylethyl]amino]-carbonyl]-2-thiazolyl]-1-piperazinecarboxylate 1-(1,1-Dimethylethyl) 4-(5-carboxy-2-thiazolyl)-1-piperazinecarboxylate (i.e. the product of Example 4, Step B) (1.0 g, 3.2 mmol) was suspended in 10 mL of dry acetonitrile and treated with triethylanaine (892 μL, 6.4 mmol) to give a homogeneous solution. To this was added O-benzotriazol-1-yl-N,N,N',N'-tetramethyluronium hexafluorophosphate (1.33 g, 3.5 mmol) followed by (α,R)—N,α-dimethylbenzenemethanamine (i.e. the product of Example 1, Step C) (200 μL, 1.38 mmol). The reaction mixture was stirred at ambient temperature for 3 days, concentrated under reduced pressure, diluted with ethyl acetate, washed with 1 N aqueous hydrochloric acid, saturated aqueous sodium bicarbonate solution and brine, dried over magnesium sulfate and concentrated under reduced pressure to give 1.38 g of an orange foam. Purification by silica gel chromatography using an ethyl acetate/hexanes gradient from 1:9 to 100:0 gave 0.78 g of the title compound as a yellow solid.

$^1$H NMR (CDCl$_3$) δ 1.48 (s, 9H), 1.6 (m, 3H), 2.88 (s, 3H), 3.54 (br m, 8H), 5.9 (m, 1H), 7.25-7.45 (m, 5H), 7.47 (s, 1H).

Step D: Preparation of N-methyl-N-[(1R)-1-phenylethyl]-2-(1-piperazinyl)-5-thiazole-carboxamide 1,1-Dimethylethyl 4-[5-[[methyl[(1R)-1-phenylethyl] amino]carbonyl]-2-thiazolyl]-1-piperazinecarboxylate (i.e. the product of Example 4, Step C) (0.75 g, 1.7 mmol) in 10 mL of methanol and 10 mL of dichloromethane was treated with 15 mL of 1 N HCl in ether. The reaction mixture was stirred at ambient temperature overnight, concentrated under reduced pressure, dissolved in water and brine, basified with 1. N aqueous NaOH solution and extracted with dichloromethane. The extract was dried over MgSO$_4$ and concentrated under reduced pressure to give 0.48 g of the title compound as a yellow oil.

$^1$H NMR (CDCl$_3$) δ 1.6 (d, 3H), 2.87 (s, 3H), 2.98 (m, 4H), 3.52 (m, 4H), 5.9 (m, 1H), 7.25-7.45 (m, 5H), 7.47 (s,

Step E: Preparation of 2-[4-[(2,5-dimethylphenyl) acetyl]-1-piperazinyl]-N-methyl-N-[(1R)-1-phenylethyl]-5-thiazolecarboxamide 2,5-Dimethylphenylacetic acid (1.64 g, 10 mmol) in 40 mL of dry dichloromethane was treated with oxalyl chloride (1.0 mL, 11 mmol) and a catalytic amount of N,N-dimethylformamide (1 drop) and allowed to stir at ambient temperature overnight. The reaction mixture was concentrated under reduced pressure to give 2,5-dimethylphenylacetyl chloride as an oil. The acid chloride (97 μL, 0.6 mmol) was added to a mixture of N-methyl-N-[(1R)-1-phenylethyl]-2-(1-piperazinyl)-5-thiazolecarboxamide (i.e. the product of Example 4, Step D) (165 mg, 0.5 mmol) and polymer-bound 4-(dimethylamino)pyridine (PS-DMAP, 1.4 meq (milli-equivalent)/g, 1.0 g) in 15 mL of dichloromethane, which was then shaken for 3 h, filtered and concentrated under reduced pressure to give 140 mg of the title product, a compound of the present invention as a yellow solid.

$^1$H NMR (CDCl$_3$) δ 1.6 (br d, 3H), 2.24 (s, 3H), 2.28 (s, 3H), 2.87 (s, 3H), 3.42 (m, 2H), 3.55 (m, 4H), 3.69 (s, 2H), 3.82 (m, 2H), 5.9 (m, 1H), 6.9-7.1 (m, 3H) 7.25-7.45 (m, 5H), 7.46 (s, 1H).

EXAMPLE 5

Preparation of N-methyl-2-[1-[[5-methyl-3-(trifluoromethyl)-1H-pyrazol-1-yl]acetyl]-4-piperidinyl]-N-[(1R)-1-phenylethyl]-4-thiazolecarboxamide (Compound 70)

Step A: Preparation of 1,1-dimethyl ethyl 4-[4-[[methyl[(1R)-1-phenylethyl]amino]-carbonyl]-2-thiazolyl]-1-piperidinecarboxylate 1-(1,1-Dimethylethyl) 4-(4-carboxy-2-thiazolyl)-1-piperidinecarboxylate (i.e. the product of Example 1, Step B) (6.86 g, 21.96 mmol) was suspended in 30 mL of dry acetonitrile and treated with triethylamine (6.12 mL, 43.92 mmol) to give a homogeneous solution. To this was added O-benzotriazol-1-yl-N,N,N',N'-tetramethyluronium hexafluorophosphate (9.16 g, 24.16 mmol) followed by (α,R)—N,α-dimethylbenzene-methanamine (3.19 mL, 21.96 mmol). The reaction mixture was stirred at ambient temperature for 3 days, concentrated under reduced pressure, diluted with ethyl acetate, washed with 1 N aqueous hydrochloric acid, saturated aqueous sodium bicarbonate solution and brine, dried over magnesium sulfate and concentrated under reduced pressure to give a dark oil. Purification by silica gel chromatography using 25-100% ethyl acetate in hexanes as eluant gave 9.12 g of the title compound as an oil.

$^1$H NMR (CDCl$_3$) δ 1.46 (s, 9H), 1.6-1.8 (m, 5H), 2.0-2.2 (m, 2H), (m, 5H), 3.15 (m, 1H), 4.15 (m, 2H), 5.7-6.2 (m, 1H), 7.25-7.45 (m, 5H), 7.81 (s, 1H).

Step B: Preparation of N-methyl-2-[1-[[5-methyl-3-(trifluoromethyl)-1H-pyrazol-1-yl]acetyl]-4-piperidinyl]-N-[(1R)-1-phenylethyl]-4-thiazolecarboxamide A solution of 400 mg (0.77 mmol) of 1,1-dimethylethyl 4-[4-[[methyl[(1R)-1-phenylethyl]amine]carbonyl]-2-thiazolyl]-1-piperidinecarboxylate (i.e. the product of Example 5, Step A) in 10 mL of a 1:1 mixture of methanol and dichloromethane was treated with 10 mL of 2 N hydrochloric acid in ether and stirred at room temperature for 4 h. The reaction mixture was concentrated on rotary evaporator, and the residue was three times treated with 10 mL of methanol followed by concentration to leave the crude piperidine hydrochloride. The reaction mixture was then dissolved in 10 mL of acetonitrile, and 1.0 mL of triethylamine was added. Meanwhile, a solution of 310 mg (1.49 mmol) of 5-methyl-3-(trifluoromethyl)-1H-pyrazole-1-acetic acid in 10 mL of acetonitrile was treated with 1.0 mL of a solution of 1-propanephosphonic acid cyclic anhydride (50% in ethyl acetate), stirred at room temperature for 15 minutes, then combined with the above amine solution. The reaction mixture was stirred at room temperature overnight, diluted with 50 mL of ethyl acetate, washed with 1 N aqueous hydrochloric acid, 1 N aqueous sodium hydroxide and brine, dried with MgSO$_4$, filtered and concentrated under reduced pressure. Purification by Medium Pressure Liquid Chromatography (HPLC) on silica gel using ethyl acetate/methanol as eluant provided 330 mg of the title product, a compound of the present invention as a white solid.

$^1$H NMR (CDCl$_3$) δ 1.60-1.80 (m, 5 H), 2.18 (m, 2 H), 2.30 (s, 3H), 2.80 (m, 5 H), 3.27 (m, 2 H), 4.00 (m, 1H), 4.95 (s, 2 H), 5.79 and 6.14 (m, total 1H), 6.35 (s, 1H), 7.37 (m, 5H), 7.84 (s, 1H).

EXAMPLE 6

General preparation of 2-[1-[(substituted-phenyl)acetyl]-4-piperidinyl]-N-methyl-N-[(1R)-1,2,3,4-tetrahydro-1-naphthalenyl]-4-thiazolecarboxamide (Compound 144, Compound 145, Compound 146, Compound 147, Compound 148 and Compound 132) and N-methyl-2-[1-[[substituted-1H-pyrazol-1-yl]acetyl]-4-piperidinyl]-N-[(1R)-1,2,3,4-tetrahydro-1-naphthalenyl]-4-thiazolecarboxamide (Compound 149 and Compound 150)

Step A: Preparation of (1R)-1,2,3,4-tetrahydro-N-methyl-1-naphthalenamine (1R)-1,2,3,4-Tetrahydro-1-naphthalenamine (5.0 g, 34 mmol) was heated in 15 mL of ethyl formate at 60° C. overnight, during which time a precipitate formed. The reaction mixture was added to 100 mL of hexanes with stirring, and the resulting solids were filtered, washed with hexanes and dried to give 4.63 g of the formamide as white needles. The resulting formamide (4.54 g, 26 mmol) was dissolved in 50 mL of tetrahydrofuran and added dropwise to a suspension of lithium aluminum hydride (1.1 g, 29 mmol) in 20 mL of tetrahydrofuran that had been cooled to 0° C. The reaction mixture was refluxed overnight, then cooled to 0° C. and quenched by the sequential addition of 1.1 mL of water, 1.1 mL of 15% aqueous NaOH solution and 3.3 mL of water. The mixture was stirred at ambient temperature for 30 minutes and diluted with ethyl acetate. Several grams of MgSO$_4$ were added, and the mixture was filtered through Celite® diatomaceous filter aid and concentrated under reduced pressure to give 4.0 g of the title compound as a colorless oil.

$^1$H NMR (CDCl$_3$) δ 1.17 (s, 1H), 1.65-2.0 (m, 4H), 2.47 (s, 3H), 2.65-2.85 (m, 2H), 3.63 (m, 1H), 7.0-7.35 (m, 4H).

Step B: Preparation of 1,1-dimethylethyl 4-[4-[(methyl[(1R)-1,2,3,4-tetrahydro-1-naphthalenyl]amino] carbonyl]-2-thiazolyl]-1-piperidinecarboxylate A mixture of 1-(1,1-dimethylethyl) 4-[4-carboxy-2-thiazolyl]-1-piperidinecarboxylate (i.e. the product of Example 1, Step B) (3.84 g, 12.29 mmol), 1-[3-(dimethylamino)propyl]-3-ethylcarbodiimide hydrochloride (2.36 g, 12.29 mmol) and triethylamine (2.3 mL, 16.76 mmol) in 50 mL dichloromethane was stirred for 15 minutes at room temperature. (1R)-1,2,3,4-Tetrahydro-N-methyl-1-naphthalenamine (i.e. the product of Example 6, Step A) (2.18 g, 13.5 mmol) was added and the reaction mixture was stirred for 16 h. The reaction mixture was diluted with 20 mL of dichloromethane, washed with 1 N aqueous hydrochloric acid, water, saturated aqueous sodium bicarbonate solution, water and brine, dried over MgSO$_4$ and concentrated under reduced pressure. The residue was purified by silica gel chromatography using 20% to 100% of ethyl acetate in hexanes to give 2.4 g of the title compound as an oil.

$^1$H NMR (CDCl$_3$) δ 1.46-1.48 (s, 9H), 1.62-2.35 (m, 9H), 2.7-2.93 (m, 6H), 3.08-3.10 (m, 1H), 4.06-4.10 (m, 2H), 5.68-6.04 (m, 1H), 7.1-7.2 (m, 4H), 7.82-7.83 (m, 1H).

Step C: Preparation of N-methyl-2-(4-piperidinyl)-N-[(1R)-1,2,3,4-tetrahydro-1-naphthalenyl]-4-thiazolecarboxamide monohydrochloride 1,1-Dimethylethyl 4-[4-[(methyl[(1R)-1,2,3,4-tetrahydro-1-naphthalenyl]amino]-carbonyl]-2-thiazolyl]-1-piperidinecarboxylate (i.e. the product of Example 6, Step B) (2.4 g, 5.26 mmol) was dissolved in 20 mL of a mixture of dichloromethane and methanol (1:1), and 13.15 mL (52.6 mmol) of 1 N HCl in dioxane was added. The reaction mixture was stirred at room temperature for 2 h and then concentrated under reduced pressure. The residue was dissolved in 20 mL of methanol and concentrated under reduced pressure (this procedure was repeated 3 times) resulting in 1.7 g of the title compound as a solid.

$^1$H NMR (DMSO-D$_6$) δ 1.80-2.05 (m, 3H), 2.1-2.3 (m, 2H), 2.5-2.9 (m, 8H), 2.92-3.12 (m, 2H), 3.25-3.42 (m, 3H), 4.55-4.63 (m, 2H), 5.3-5.8 (m, 1H), 7.0-7.2 (m, 4H), 8.1-8.14 (m, 1H), 8.72-8.88 (m, 1H), 9.0-9.1 (m, 1H).

Step D: General preparation of 2-[1-[(substituted-phenyl)acetyl]-4-piperidinyl]-N-methyl-N-[(1R)-1,2,3,4-tetrahydro-1-naphthalenyl]-4-thiazolecarboxamide and N-methyl-2-[1-[[substituted-1H-pyrazol-1-yl]acetyl]-4-piperidinyl]-N-[(1R)-1,2,3,4-tetrahydro-1-naphthalenyl]-4-thiazolecarboxamide A mixture of N-methyl-2-(4-piperidinyl)-N-[(1R)-1,2,3,4-tetrahydro-1-naphthalenyl]-4-thiazolecarboxamide monohydrochloride (i.e. the product of Example 6, Step C) (157 mg, 0.4 mmol), the appropriate aryl or heteroaryl acetic acid (0.44 mmol), 1-[3-(dimethylamino)propyl]-3-ethylcarbodiimide hydrochloride (92 mg, 0.48 mmol), triethylamine (100 μL) and a catalytic amount of 4-(dimethylamino)pyridine (~1 mg) in 3 mL of dichloromethane was stirred at room temperature for 16 h. The reaction mixture was diluted with 10 mL of dichloromethane, washed with 1 N aqueous hydrochloric acid, water and brine, dried over MgSO$_4$ and concentrated under reduced pressure. The products were purified by silica gel chromatography using ethyl acetate or a mixture of ethyl acetate with 20% methanol as eluant to give following title products, compounds of the present invention as oils.

2-[1-[(2,5-dichlorophenyl)acetyl]-4-piperidinyl]-N-methyl-N-[(1R)-1,2,3,4-tetrahydro-1-naphthalenyl]-4-thiazolecarboxamide (Compound 144); $^1$H NMR (CDCl$_3$) δ 1.7-2.24 (m, 8H), 2.7-3.0 (m, 6H), 3.2-3.3 (m, 2H), 3.8-4.0 (m, 3H), 4.5-4.7 (m, 1H), 5.62-6.05 (m, 1H), (m, 7H), 7.85 (d, 1H).

2-[1-[(2-methoxyphenyl)acetyl]-4-piperidinyl]-N-methyl-N-[(1R)-1,2,3,4-tetrahydro-1-naphthalenyl]-4-thiazolecarboxamide (Compound 145); $^1$H NMR (CDCl$_3$) δ 1.5-2.24 (m, 8H), 2.7-2.9 (m, 5H), 3.05-3.1 (m, 2H), 3.62-4.01 (m, 7H), 4.58-4.65 (m, 1H), 5.62-6.05 (m, 1H), 6.82-7.27 (m, 8H), 7.82 (d, 1H).

2-[1-[(2-methoxy-5-methylphenyl)acetyl]-4-piperidinyl]-N-methyl-N-[(1R)-1,2,3,4-tetrahydro-1-naphthalenyl]-4-thiazolecarboxamide (Compound 146); $^1$H NMR (CDCl$_3$) δ 1.5-2.2 (m, 11H), 2.7-2.9 (m, 6H), 3.05-3.22 (m, 2H), 3.6-4.0 (m, 6H), 4.57-4.72 (m, 1H), 5.6-6.04 (m, 1H), 6.76-7.22 (m, 7H), 7.82 (d, 1H).

2-[1-[(2-chloro-5-(trifluoromethyl)phenyl)acetyl]-4-piperidinyl]-N-methyl-N-[(1R)-1,2,3,4-tetrahydro-1-naphthalenyl]-4-thiazolecarboxamide (Compound 147); $^1$H NMR (CDCl$_3$) δ 1.6-2.0 (m, 5H), 2.1-2.2 (m, 3H), 2.7-3.0 (m, 6H), 3.22-3.35 (m, 2H), 3.85-4.0 (m, 3H), 4.5-4.7 (m, 1H), 5.6-6.05 (m, 1H), 7.05-7.6 (m, 7H), 7.83 (d, 1H).

2-[1-[(5-bromo-2-methoxyphenyl)acetyl]-4-piperidinyl]-N-methyl-N-[(1R)-1,2,3,4-tetrahydro-1-naphthalenyl]-4-thiazolecarboxamide (Compound 148); $^1$H NMR (CDCl$_3$) δ 1.6-2.25 (m, 9H), 2.7-2.9 (m, 5H), 3.15-3.28 (m, 2H), 3.6-3.7 (m, 2H), 3.8 (m, 3H), 3.9-4.0 (m, 1H), 4.5-4.7 (m, 1H), 5.62-6.07 (m, 1H), 6.7-6.72 (m, 1H), 7.1-7.35 (m, 6H), 7.82 (d, 1H).

N-methyl-2-[1-[[5-methyl-3-(trifluoromethyl)-1H-pyrazol-1-yl]acetyl]-4-piperidinyl]-N-[(1R)-1,2,3,4-tetrahydro-1-naphthalenyl]-4-thiazolecarboxamide (Compound 149); $^1$H NMR (CDCl$_3$) δ 1.6-2.1 (m, 5H), 2.1-2.3 (m, 3H), 2.32 (m, 3H), 2.7-3.0 (m, 6H), 3.2-3.35 (m, 2H), 3.95-4.1 (m, 1H), 4.35-4.6 (m, 1H), 4.96-5.02 (m, 2H), 5.6-6.1 (m, 1H), 6.32 (s, 1H), 7.05-7.25 (m, 4H), 7.85 (m, 1H).

2-[1-[(3,5-dimethyl-1H-pyrazol-1-yl)acetyl]-4-piperidinyl]-N-methyl-N-[(1R)-1,2,3,4-tetrahydro-1-naphthalenyl]-4-thiazolecarboxamide (Compound 150); $^1$H NMR (CDCl$_3$) δ 1.7-2.2 (m, 14H), 2.7-2.9 (m, 5H), 3.2-3.3 (m, 2H), 3.95-4.6 (m, 3H), 5.05 (m, 2H), 5.85 (s, 1H), 5.65-6.05 (m, 1H), 7.12-7.3 (m, 4H), 7.85 (m, 1H).

2-[1-[(2,5-dimethylphenyl)acetyl]-4-piperidinyl]-N-methyl-N-[(1R)-1,2,3,4-tetrahydro-1-naphthalenyl]-4-thiazolecarboxamide (Compound 132); $^1$H NMR (CDCl$_3$) δ 1.6-2.3 (m, 8H), 2.7-2.9 (m, 7H), 3.1-3.3 (m, 2H), 3.63-3.65 (m, 2H), 3.8-3.9 (m, 1H), 4.4.55-4.77 (m, 1H), 5.62-6.07 (m, 1H), 6.92-7.22 (m, 7H), 7.82-7.85 (m, 1H).

EXAMPLE 7

Preparation of N-methyl-2-[1-[[5-methyl-3-(trifluoromethyl)-1H-pyrazol-1-yl]acetyl]-4-piperidinyl]-N-[(1R)-1-phenylpropyl]-4-oxazolecarboxamide (Compound 152)

Step A: Preparation of 1,1-dimethylethyl 4-[[(1-(hydroxymethyl)-2-methoxy-2-oxoethyl)amino]carbonyl]-1-piperidinecarboxylate A mixture of 1-(1,1-dimethylethyl)hydrogen 1,4-piperidinedicarboxylate (5.5 g, 24 mmol), 1-[3-(dimethylamino)propyl]-3-ethylcarbodiimide hydrochloride (5.08 g, 26.5 mmol), and N-methylmorpholine (2.75 mL, 25 mmol) in 100 mL of dichloromethane was stirred at room temperature for 15 minutes. DL-Serine methyl ester hydrochloride (3.89 g, 25 mmol) was added, and the reaction mixture was stirred at room temperature for 16 h. The reaction mixture was partitioned between 1 N aqueous hydrochloric acid and dichloromethane, and the organic layer was washed with 1 N aqueous hydrochloric acid, water and brine, dried over MgSO$_4$ and concentrated under reduced pressure to give 6.58 g of the title compound.

$^1$H NMR (CDCl$_3$) δ1.45 (s, 9H), 1.62-1.75 (m, 3H), 1.9 (m, 2H), 2.38 (t, 1H), 2.7-2.8 (m, 3H), 3.8 (s, 3H), 3.9-4.0 (m, 2H), 4.08 (br s, 2H), 4.68 (m, 1H), 6.5 (m, 1H).

Step B: Preparation of 1,1-dimethylethyl 4-[4,5-dihydro-4-(methoxycarbonyl)-2-oxazolyl]-1-piperidinecarboxylate To a solution of 1,1-dimethylethyl 4-[[[1-(hydroxymethyl)-2-methoxy-2-oxoethyl]amino]carbonyl]-1-piperidinecarboxylate (i.e. the product of Example 7, Step A) (6.58 g, 19.92 mmol) in 70 mL of dry acetonitrile and 20 mL of dry dichloromethane was added triphenylphosphine (7.8 g, 29.87 mmol) and then 4.12 g (31.87 mmol) of N,N-diisopropylethylamine. The reaction mixture was stirred until homogeneous, and 4.59 g (29.87 mmol) of carbon tetrachloride was added dropwise over 5 minutes. The reaction mixture was stirred for 2.5 h at room temperature, cooled to 0° C. and diluted with 170 mL of ethyl acetate followed by 50 mL of saturated aqueous sodium bicarbonate solution. The mixture was stirred for 10 minutes, poured into 120 mL of water, and the organic layer was separated, washed with brine, dried over MgSO$_4$ and concentrated under reduced pressure to give a yellow oil. The oil was purified by silica gel chromatography using 75-100% ethyl acetate in hexanes as eluant to give 2.95 g of the title compound as an oil containing traces of triphenylphosphine.

$^1$H NMR (CDCl$_3$) δ 1.43 (s, 9H), 1.6-176 (m, 2H), 1.86-1.91 (m, 2H), 2.47-2.55 (m, 1H), 2.80-2.86 (m, 2H), 3.8 (s, 3H), 4.02 (br s, 2H), 4.38-4.50 (m, 2H), 4.71-4.75 (m, 1H).

Step C: Preparation of 1,1-dimethylethyl 4-[4-(methoxycarbonyl)-2-oxazolyl]-1-piperidinecarboxylate To a solution of 1,1-dimethylethyl 4-[4,5-dihydro-4-(methoxycarbonyl)-2-oxazolyl]-1-piperidinecarboxylate (i.e. the product of Example 7, Step B) (2.89 g, 9.26 mmol) in 100 mL of dichloromethane at 0° C. was added 1.52 mL (10.18 mmol) of 1,8-diazabicyclo[5.4.0]undec-7-ene (DBU), and the reaction mixture was stirred for 10 minutes at 0° C. Bromotrichloromethane (1 mL, 10.18 mmol) was added dropwise over 7 minutes, and the reaction mixture was stirred for 6 h at 0° C. The mixture was washed with saturated aqueous ammonium chloride (2×50 mL), the aqueous phase was extracted with ethyl acetate (2×25 mL), and the combined organic layers were dried over magnesium sulfate and concentrated under reduced pressure. The residue was purified by silica gel chromatography using 25-75% of ethyl acetate in hexanes as eluant to give 1.41 g of the title compound as white crystals.

$^1$H NMR (CDCl$_3$) δ 1.46 (s, 9H), 1.77-1.85 (m, 2H), 2.00-2.05 (m, 2H), 2.85-2.92 (m, 2H), 2.99-3.02 (m, 1H), 3.9 (s, 3H), 4.08-4.15 (m, 2H), 8.18 (s, 1H).

Step D: Preparation of 1-(1,1-dimethylethyl) 4-(4-carboxy-2-oxazolyl)-1-piperidine-carboxylate 1,1-Dimethylethyl 4-[4-(methoxycarbonyl)-2-oxazolyl]-1-piperidinecarboxylate (i.e. the product of Example 7, Step C) (1.41 g, 4.55 mmol) was dissolved in 12 mL tetrahydrofuran, and 8 mL of water was added. The reaction mixture was cooled to 0° C. with vigorous stirring. A 1 N aqueous sodium hydroxide solution (9.1 mL) was added dropwise, and the reaction mixture was stirred at room temperature for 2 h. The mixture was diluted with saturated sodium chloride solution (10 mL), 30 mL of diethyl ether was added and the aqueous phase was acidified to pH 3-4 by dropwise addition of 20% citric acid solution. The precipitated solid was filtered and dried to give 1.21 g of the title compound.

$^1$H NMR (DMSO-d$_6$) δ 1.4 (s, 9H), 1.55-1.60 (m, 2H), 1.92-2.00 (m, 2H), 2.90-2.99 (m, 2H), 3.00-3.1 (m, 1H), 3.9-4.0 (m, 2H), 8.45 (s, 1H).

Step E: Preparation of 1,1-dimethylethyl 4-[4-[[methyl[(1R)-1-phenylpropyl]amino]-carbonyl]-2-oxazolyl]-1-piperidinecarboxylate A mixture of 1-(1,1-dimethylethyl) 4-(4-carboxy-2-oxazolyl)-1-piperidinecarboxylate (i.e. the product of Example 7, Step D) (600 mg, 2.02 mmol), 1-[3-(dimethylamino)propyl]-3-ethylcarbodiimide hydrochloride (425 mg, 2.22 mmol) and N-methylmorpholine (224 mg, 2.22 mmol) in 4 mL dichloromethane was stirred for 15 minutes at room temperature. To the reaction mixture 392.5 mg (2.63 mmol) of (α,R)-α-ethyl-N-methylbenzenemethanamine was added and the reaction mixture was stirred at ambient temperature for 16 h. The reaction mixture was poured into 4 mL of 1 N aqueous hydrochloric acid, and the organic layer was washed with 1 N aqueous hydrochloric acid, water and brine, dried (MgSO$_4$) and concentrated under reduced pressure. The residue was purified by silica gel chromatography using 25-75% of ethyl acetate in hexanes as eluant to give 209 mg of the title compound as an oil. $^1$H NMR (CDCl$_3$) δ 0.95-1.02 (m, 3H), 1.42 (s, 9H), 1.72-1.86 (m, 2H), 1.90-2.11 (m, 4H), 2.9-3.0 (m, 4H), 4.0-4.1 (m, 2H), 5.9-6.2 (m, 1H), 7.2-7.4 (m, 5H), 8.1 (s, 1H).

Step F: Preparation of N-methyl-2-[1-[[5-methyl-3-(trifluoromethyl)-1H-pyrazol-1-yl]acetyl]-4-piperidinyl]-N-[(1R)-1-phenylpropyl]-4-oxazolecarboxamide 1,1-Dimethylethyl 4-[4-[[methyl[(1R)-1-phenylpropyl]amino]carbonyl]-2-oxazolyl]-1-piperidinecarboxylate (i.e. the product of Example 7, Step E) (209 mg, 0.49 mmol) was dissolved in 3 mL of a mixture of dichloromethane and methanol (1:1), and 1.23 mL (4.9 mmol) of 1 N HCl in dioxane was added. The reaction mixture was stirred at room temperature for 3 h. The solvents were evaporated under reduced pressure, and the residue was dissolved in 5 mL methanol and concentrated under reduced pressure (this procedure was repeated 3 times) to give the amine hydrochloride. To a solution of 5-methyl-3-(trifluoromethyl)-1H-pyrazole-1-acetic acid (89.5 mg, 0.43 mmol) and triethylamine (87 mg, 0.86 mmol) in 2 mL of dry acetonitrile was added a suspension of O-benzotriazol-1-yl-N,N,N',N'-tetramethyluronium hexafluorophosphate (178.25 mg. 0.47 mmol) in 2 mL acetonitrile and then a mixture of 140 mg (0.43 mmol) of the amine hydrochloride in 2 mL acetonitrile. The resulting mixture was stirred at room temperature for 3 h and concentrated under reduced pressure. The residue was purified by silica gel chromatography using 25-75% of ethyl acetate in hexanes to give 84 mg of the title product, a compound of the present invention as an oil.

$^1$H NMR (CDCl$_3$) δ 0.90-1.04 (m, 3H), 1.71-1.89 (m, 2H), 1.90-2.19 (m, 4H), 2.28-2.35 (m, 3H), 2.72 (s, 2H), 3.00-3.2 (m, 3H), 3.30-3.36 (t, 1H), 3.87-4.35 (m, 2H), 4.98 (s, 2H), 5.92-6.12 (m, 1H), 6.3 (s, 1H), 7.25-7.4 (m, 5H), 8.08-8.15 (br s, 1H).

EXAMPLE 8

Preparation of N-methyl-2-[1-[[5-methyl-3-(trifluoromethyl)-1H-pyrazol-1-yl]acetyl]-4-piperidinyl]-N-[(1R)-1,2,3,4-tetrahydro-1-naphthalenyl]-4-oxazole-carboxamide (Compound 151)

Step A: Preparation of 1,1-dimethylethyl 4-[4-[[methyl[(1R)-1,2,3,4-tetrahydro-1-naphthalenyl]amino]carbonyl]-2-oxazolyl]-1-piperidinecarboxylate A mixture of 1-(1,1-dimethylethyl) 4-(4-carboxy-2-oxazolyl)-1-piperidinecarboxylate (600 mg, 2.02 mmol), 1-[3-(dimethylamino)propyl]-3-ethylcarbodiimide hydrochloride (425.57 mg, 2.22 mmol) and N-methylmorpholine (224.55 mg, 2.22 mmol) in 4 mL dichloromethane was stirred for 15 minutes at room temperature. To the reaction mixture was added 424 mg (2.63 mmol) of (1R)-1,2,3,4-tetrahydro-N-methyl-1-naphthalenamine was added and the reaction mixture was stirred for 16 h. The reaction mixture was concentrated under reduced pressure, and the residue was purified by silica gel chromatography using 25-75% of ethyl acetate in hexanes as eluant to give 360 mg of the title compound as an oil.

$^1$H NMR (CDCl$_3$) δ 1.42 (s, 9H), 1.68-2.26 (m, 9H), 2.72-3.01 (m, 7H), 4.0-4.1 (m, 2H), 6.0-6.1 (m, 1H), 7.10-7.18 (m, 4H), 8.12-8.14 (m, 1H).

Step B: Preparation of N-methyl-2-[1-[[5-methyl-3-(trifluoromethyl)-1H-pyrazol-1-yl]acetyl]-4-piperidinyl]-N-[(1R)-1,2,3,4-tetrahydro-1-naphthalenyl]-4-oxazolecarboxamide 1,1-Dimethylethyl 4-[4-[[methyl[(1R)-1,2,3,4-tetrahydro-1-naphthalenyl]amino]-carbonyl]-2-oxazolyl]-1-piperidinecarboxylate (i.e. the product of Example 8, Step A) (317 mg, 0.72 mmol) was dissolved in 3 mL of a mixture of dichloromethane and methanol (1:1), and 1.8 mL (7.2 mmol) of 1 N HCl in dioxane was added. The reaction mixture was stirred at room temperature for 3 h. The solvents were evaporated under reduced pressure, and the residue was dissolved in 5 mL methanol and evaporated (this sequence was repeated 3 times) giving the amine hydrochloride. A mixture of 5-methyl-3-trifluoromethylpyrazol-1-ylacetic acid (179 mg, 0.86 mmol), 1-[3-(dimethylamino)propyl]-3-ethylcarbodiimide hydrochloride (191.7 mg, 1.00 mmol), and 1-methylmorpholine (354 mg, 3.5 mmol) in 3 mL of dry dichloromethane was stirred 15 minutes at room temperature, and a solution of the amine hydrochloride in 2 mL of dry dichloromethane was added. The resulting mixture was stirred at room temperature for 16 h and concentrated under reduced pressure. The residue was purified by silica gel chromatography using 75% ethyl acetate in hexanes as eluant to give 79 mg of the title product, a compound of the present invention as an oil. $^1$H NMR (CDCl$_3$) δ 1.70-2.00 (m, 5H), 2.01-2.32 (m, 6H), 2.72-3.2 (m, 7H), 3.28-3.40 (m, 1H), 3.85-4.4 (m, 2H), 4.96-5.00 (m, 2H), 5.97-6.1 (m, 1H), 6.29-6.31 (m, 1H), 7.1-7.2 (m, 4H), 8.13-8.18 (m, 1H).

EXAMPLE 9

Preparation of 2-[1-[(2,5-dimethylphenyl)acetyl]-4-piperidinyl]-N-methyl-N-[(1R)-1,2,3,4-tetrahydro-1-naphthalenyl]-4-oxazolecarboxamide (Compound 153)

Step A: Preparation of methyl 1-[(2,5-dimethylphenyl)acetyl]-4-piperidine-carboxylate A solution of 2.86 g (20 mmol) of methyl isonipecotate and 2.53 g (2.5 mmol) of triethylamine in 10 mL of dry dichloromethane was cooled to 0° C., and a solution of 4.02 g (22 mmol) of 2,5-dimethylphenylacetyl chloride in 5 mL of dichloromethane was added dropwise. The mixture was stirred at room temperature for 16 h and then poured into 20 mL of water. The organic layer was washed with water and brine, dried (MgSO$_4$) and concentrated under reduced pressure. The residue was crystallized from a mixture of ethyl acetate and hexanes to give 4.95 g (87.5% yield) of the title compound as white crystals.

$^1$H NMR (CDCl$_3$) δ 1.5-1.7 (m, 2H), 1.78-1.98 (m, 2H), 2.22 (s, 3H), 2.28 (s, 3H), 2.50-2.58 (m, 1H), 2.85-3.10 (m, 2H), 3.65 (s, 2H), 3.70 (s, 3H), 3.71-3.98 (m, 1H), 4.45-4.52 (m, 1H), 6.90-7.08 (m, 3H).

Step B: Preparation of 1-[(2,5-dimethylphenyl)acetyl]-4-piperidinecarboxylic acid Methyl 1-[(2,5-dimethylphenyl)acetyl]-4-piperidinecarboxylate (i.e. the product of Example 9, Step A) (4.95 g, 17.1 mmol) was dissolved in 20 mL of tetrahydrofuran, and 15 mL of water was added. With vigorous stirring the reaction mixture was cooled to 0° C., and 35 mL of a 1 N aqueous sodium hydroxide solution was added dropwise. The reaction mixture was stirred at room temperature for 1 h, diluted with 20 mL of brine, washed with diethyl ether (3×20 mL), and the aqueous phase was acidified with 1 N aqueous hydrochloric acid to pH 3-4. The precipitate was collected and dried to give 4.08 g of the title compound.

$^1$H NMR (CDCl$_3$) δ 1.2 (m, 2H), 1.8 (m, 2H), 2.16 (s, 3H), 2.22 (s, 3H), 2.5 (m, 1H), 2.75 (m 1H), 3.1 (m, 1H), 3.62 (m, 2H), 3.8 (m, 1H), 4.25 (m, 1H), 6.8-7.1 (m, 3H), 12.1 (s, 1H).

Step C: Preparation of N-[[1-[(2,5-dimethylphenyl)acetyl]-4-piperidinyl]carbonyl]-DL-serine methyl ester A mixture of 1-[(2,5-dimethylphenyl)acetyl]-4-piperidinecarboxylic acid (i.e. the product of Example 9, Step B) (1.44 g, 5.23 mmol), 1-[3-(dimethylamino)propyl]-3-ethylcarbodiimide hydrochloride (1.1 g, 5.75 mmol), and N-methylmorpholine (529 mg, 5.23 mmol) in 5 mL of dichloromethane was stirred at room temperature for 15 minutes. DL-Serine methyl ester hydrochloride (814 mg, 5.23 mmol) was added and the reaction mixture was stirred at room temperature for 16 h. The reaction was partitioned between 1 N aqueous hydrochloric acid (10 mL) and dichloromethane (10 mL), and the organic layer was washed with 1 N aqueous hydrochloric acid, water and brine, dried over MgSO$_4$ and concentrated under reduced pressure to give 1.61 g of the title compound.

$^1$H NMR (CDCl$_3$) δ 1.6-1.92 (m, 4H), 2.12 (s, 3H), 2.26 (s, 3H), 2.38-2.45 (m, 1H), 2.7-2.8 (m, 2H), 3.0-3.3 (m, 2H), 3.63 (s, 2H), 3.72 (s, 2H), 3.8-4.0 (m, 2H), 4.55-4.62 (m, 2H), 6.62-6.70 (m, 1H), 6.90-7.05 (m, 3H).

Step D: Preparation of methyl 2-[1-[(2,5-dimethylphenyl)acetyl]-4-piperidinyl]-4,5-dihydro-4-oxazolecarboxylate To a solution of N-[[1-[(2,5-dimethylphenyl)acetyl]-4-piperidinyl]carbonyl]-DL-serine methyl ester (i.e. the product of Example 9, Step C) (2.59 g, 6.88 mmol) in 25 mL of dry acetonitrile and 7 mL of dry dichloromethane was added triphenylphosphine (2.71 g, 10.32 mmol) and then N,N-diisopropylethylamine (1.6 g, 12.38 mmol). The reaction mixture was stirred until homogeneous, and carbon tetrachloride (1.59 g, 10.32 mmol) was added dropwise over 5 minutes. The reaction mixture was stirred for 2.5 h at room temperature, cooled to 0° C. and diluted with 50 mL of ethyl acetate followed by 15 mL of saturated aqueous sodium bicarbonate solution. The mixture was stirred for 10 minutes, poured into 40 mL of water, and the organic layer was separated, washed with brine, dried over MgSO$_4$ and concentrated under reduced pressure to give 6 g of a yellow oil. The oil was purified by flash chromatography on silica gel using 50-100% of ethyl acetate in hexanes to give 900 mg of the title compound. 360 mg of starting amide was also recovered from the reaction mixture.

$^1$H NMR (CDCl$_3$) δ 1.57-2.00 (m, 5H), 2.2 (s, 3H), 2.27 (s, 3H), 2.57-2.62 (m, 1H), 2.82-2.93 (m, 2H), 3.6 (s, 2H), 3.72-3.80 (s, 3H), 4.37-4.5 (m, 3H), 4.68-4.75 (m, 1H), 6.90-7.03 (m, 3H).

Step E: Preparation of methyl 2-[1-[(2,5-dimethylphenyl)acetyl]-4-piperidinyl]-4-oxazolecarboxylate To a solution of methyl 2-[1-[(2,5-dimethylphenyl)acetyl]-4-piperidinyl]-4,5-dihydro-4-oxazolecarboxylate (i.e. the product of Example 9, Step D) (1.09 g, 3.04 mmol) in 25 mL of dichloromethane at 0° C. was added 1,8-diazabicyclo[5.4.0]undec-7-ene (508 mg, 3.34 mmol). Bromotrichloromethane (662 mg, 3.34 mmol) was then added dropwise over 5 minutes. The reaction mixture was stirred for 6 h at 0° C. The reaction mixture was washed with saturated aqueous ammonium chloride (2×50 mL), the aqueous phase was back-extracted with ethyl acetate (2×25 mL), and the combined organic layers were dried over MgSO$_4$ and concentrated under reduced pressure. The residue was purified by silica gel chromatography using 50-100% of ethyl acetate in hexanes as eluant to give 600 mg of the title compound as an oil.

$^1$H NMR (CDCl$_3$) δ 1.70-1.86 (m, 2H), 2.00-2.25 (m, 2H), 2.21 (s, 3H), 2.28 (s, 3H), 2.90-2.98 (m, 1H), 3.05-3.20 (m, 2H), 3.64 (s, 2H), 3.80-3.85 (m, 1H), 3.9 (s, 3H), 4.60-4.77 (m, 1H), 6.91-7.06 (m, 3H), 8.18 (s, 1H).

Step F: Preparation of 2-[1-[(2,5-dimethylphenyl)acetyl]-4-piperidinyl]-4-oxazole-carboxylic acid Methyl 2-[1-[(2,5-dimethylphenyl)acetyl]-4-piperidinyl]-4-oxazolecarboxylate (i.e. the product of Example 9, Step E) (665 mg, 1.87 mmol) was dissolved in 5 mL tetrahydrofuran, and 3.3 mL of water was added. The reaction mixture was cooled to 0° C. with vigorous stirring. A 1 N aqueous sodium hydroxide solution (3.7 mL) was added dropwise, and the reaction mixture was stirred at room temperature for 2 h. The reaction mixture was diluted with saturated sodium chloride solution (4 mL), washed with diethyl ether, and the aqueous phase was acidified to pH 3-4 by dropwise addition of 20% citric acid solution. The precipitated solid was filtered and dried to give 490 mg of the title compound. $^1$H NMR (DMSO-d$_6$) δ 1.55 (m, 2H), 2.0 m, 2H), 2.14 (s, 3H), 2.23 (s, 3H), 2.85 (m, 1H), 3.1-3.3 (m, 2H), 3.65 (m, 2H), 3.9 (m, 1H), 4.35 (m, 1H), 6.8-7.1 (m, 3H), 8.66 (s, 1H), 13.0 (s, 1H).

Step G: Preparation of 2-[1-[(2,5-dimethylphenyl)acetyl]-4-piperidinyl]-N-methyl-N-[(1R)-1,2,3,4-tetrahydro-1-naphthalenyl]-4-oxazolecarboxamide A mixture of 2-[1-[(2,5-dimethylphenyl)acetyl]-4-piperidinyl]-4-oxazolecarboxylic acid (i.e. the product of Example 9, Step F) (245 mg, 0.72 mmol), 1-[3-(dimethylamino)propyl]-3-ethylcarbodiimide hydrochloride (153 mg, 80 mmol) and N-methyl morpholine (88 µL) in 3 mL of dichloromethane was stirred at room temperature for 15 minutes. (1R)-1,2,3,4-Tetrahydro-N-methyl-1-naphthalenamine (129 mg, 0.80 mmol) was added and the reaction mixture was stirred at ambient temperature overnight. The reaction mixture was diluted with dichloromethane, washed with 1 N aqueous hydrochloric acid and water, dried over MgSO$_4$ and concentrated under reduced pressure. The products were purified by silica gel chromatography using ethyl acetate as eluant to give 75 mg of the title product, a compound of the present invention as an oil.

$^1$H NMR (CDCl$_3$) δ 1.6-2.3 (m, 8H), 2.2-2.3 (m, 6H), 2.7-2.9 (m, 3H), 3.0-3.25 (m, 4H), 3.64 (m, 2H), 3.75 (m, 1H), 4.4-4.6 (m, 1H), 5.95-6.1 (m, 1H), 6.9-7.2 (m, 7H), 8.1 (m, 1H).

EXAMPLE 10

Preparation of 2-[1-[(2,5-dimethylphenyl)acetyl]-4-piperidinyl]-N-methyl-N-[(1R)-1-phenylpropyl]-4-oxazolecarboxamide (Compound 154)

A mixture of 2-[1-[(2,5-dimethylphenyl)acetyl]-4-piperidinyl]-4-oxazolecarboxylic acid (i.e. the product of Example 9, Step F) (245 mg, 0.72 mmol), 1-[3-(dimethylamino)propyl]-3-ethylcarbodiimide hydrochloride (153 mg, 80 mmol) and 4-methylmorpholine (88 µL) in 3 mL of dichloromethane were stirred at room temperature for 15 minutes. (α,R)-α-Ethyl-N-methylbenzenemethanamine (i.e. the product of Example 1, Step C) (0.80 mmol, 119 mg) was added and the reaction mixture was stirred at ambient temperature overnight. The reaction mixture was diluted with dichloromethane, washed with 1 N aqueous hydrochloric acid and water, dried over MgSO$_4$ and concentrated under reduced pressure. The products were purified by silica gel chromatography using 50-100% ethyl acetate in hexanes as eluant to give 90 mg of the title product, a compound of the present invention as an oil.

$^1$H NMR (CDCl$_3$) δ 0.9-1.1 (br m, 3H), 1.6-1.9 (m, 2H), 1.9-2.2 (m, 4H), 2.22 (s, 3H), 2.26 (s, 3H), 2.72 (br s, 2H), 2.9-3.1 (m, 4H), 3.15 (m, 1H), 3.65 (s, 2H), 3.75 (br m, 1H), 4.45 (br m, 1H), 5.85-6.2 (m, 1H), 6.9-7.1 (m, 3H) 7.25-7.40 (m, 5H), 8.1 (m, 1H).

EXAMPLE 11

Preparation of N-[(1R)-1-(3,5-dichloro-2-pyridinyl)ethyl]ethyl]-2-[1-[(2,5-dimethyl-phenyl)acetyl]-4-piperidinyl]-N-methyl-4-thiazolecarboxamide (Compound 11)

To a solution of 200 mg (0.56 mmol) of 2-[1-[(2,5-dimethylphenyl)acetyl]-4-piperidinyl]-4-thiazolecarboxylic acid (i.e. the product of Example 9, Step B) in 5 mL of acetonitrile was added 0.5 mL of a solution of 1-propanephosphonic acid cyclic anhydride (50% in ethyl acetate, 0.8 mmol) and stirred at room temperature for 15 minutes. To this mixture was added 110 mg (0.54 mmol) of (R)-[1-(3,5-dichloro-pyridin-2-yl)-ethyl]-methylamine in 5 mL of acetonitrile containing 0.5 mL of triethylamine. The reaction mixture was stirred at room temperature overnight, diluted with ethyl acetate, washed with 1 N aqueous sodium hydroxide and brine, dried (MgSO$_4$), filtered and concentrated. The crude product was purified by silica gel medium pressure liquid chromatography using ethyl acetate/methanol as eluant to provide 80 mg of the title product, a compound of the present invention as a viscous oil.

$^1$H NMR (CDCl$_3$) δ 1.50-1.80 (m, 3H), 2.04 (m, 1H), 2.17 (m, 1H), 2.23 (s, 3H), 2.26 (s, 3H), 2.80-3.30 (m, 6H), 3.68 (s, 2H), 3.82 (m, 1H), 4.71 (m, 1H), 6.16 (m, 1H), 6.96 (m, 2H), 7.08 (m, 1H), 7.78 (m, 2H), 8.51 (br s, 1H).

EXAMPLE 12

Preparation of 2-[1-[(3,5-dichloro-1H-pyrazol-1-yl)acetyl]-4-piperidinyl]-N-methyl-N-[(1R)-1,2,3,4-tetrahydro-1-naphthalenyl]-4-thiazolecarboxamide (Compound 238)

Step A: Preparation of N,N-dimethyl-1H-pyrazole-1-sulfonamide

To a solution of pyrazole (10.0 g, 147 mmol) in dichloromethane (150 mL), triethylamine (26.6 mL, 192 mmol) and N,N-dimethylsulfamoyl chloride (20.0 mL, 181 mmol) were added and the reaction mixture was heated to reflux for approximately 60 h. The reaction mixture was then cooled to ambient temperature and filtered through a pad of silica gel using dichloromethane as an eluent. The filtrate was then concentrated under reduced pressure and treated with diethyl ether (100 mL) resulting in the formation of a solid. The suspension was filtered, and the precipitate was washed with diethyl ether. The combined filtrates were combined and concentrated in vacuo to give 27.46 g of the title compound. This compound was of sufficient purity to use in subsequent reactions. $^1$H NMR (CDCl$_3$) δ 2.94 (s, 6H), 6.40 (s, 1H), 7.75 (s, 1H), 7.99 (s, 1H).

Step B: Preparation of 3-chloro-N,N-dimethyl-1H-pyrazole-1-sulfonamide

Under a nitrogen atmosphere, a solution of N,N-dimethyl-1H-pyrazole-1-sulfonamide (5.0 g, 28 mmol) (i.e. the product of Example 12, Step A) in tetrahydrofuran (50 mL) was cooled to –78° C. and then treated with n-butyllithium (2 M solution in cyclohexane, 15.0 mL, 30 mmol) dropwise. The reaction mixture formed a thick precipitate, and stirring was continued for 30 minutes after the addition. To the stirred suspension, a solution of hexachloroethane (7.1 g, 30 mmol) in tetrahydrofuran (20 mL) was added dropwise. After 30 minutes the resulting clear solution was warmed to ambient temperature and quenched with the addition of water (70 mL). The reaction mixture was extracted with dichloromethane and dried over MgSO$_4$. The reaction mixture was filtered and concentrated under reduced pressure. The crude product was purified by silica gel chromatography (50% hexanes in dichloromethane as eluant) to give 1.71 g of 5-chloro-N,N-dimethyl-1H-pyrazole-1-sulfonamide. The 5-chloro-N,N-dimethyl-1H-pyrazole-1-sulfonamide was heated to 110° C. for 12 h with a catalytic amount of pyrazole to isomerize to the title compound.

$^1$H NMR (CDCl$_3$) δ 3.07 (s, 6H), 6.33 (s, 1H), 7.60 (s, 1H).

Step C: Preparation of 3,5-dichloro-N,N-dimethyl-1H-pyrazole-1-sulfonamide

Under a nitrogen atmosphere, a solution of 3-chloro-N,N-dimethyl-1H-pyrazole-1-sulfonamide (1.68 g, 8 mmol) (i.e. the product of Example 12, Step B) in tetrahydrofuran (10 mL) was cooled to –78° C. and then treated with a solution of 2 M n-butyllithium in cyclohexane (4.5 mL, 9 mmol) dropwise. The solution formed a thick precipitate and was allowed to stir for 30 minutes after the addition. To the stirred suspension, a solution of hexachloroethane (2.0 g, 8.5 mmol) in tetrahydrofuran (10 mL) was added dropwise. After 1.5 h the resulting clear solution was warmed to ambient temperature and quenched with the addition of water (20 mL). The reaction mixture was extracted with dichloromethane and dried over $MgSO_4$. The solution was filtered and concentrated under reduced pressure to give 1.97 g of the title compound. This compound was of sufficient purity to use in subsequent reactions.

$^1H$ NMR ($CDCl_3$) δ 3.10 (s, 6H), 6.28 (s, 1H).

Step D: Preparation of 3,5-dichloro-1H-pyrazole

In a round bottom flask with magnetic stirrer, 3,5-dichloro-N,N-dimethyl-1H-pyrazole-1-sulfonamide (1.97 g, 8.0 mmol) (i.e. the product of Example 12, Step C) was cooled to 0° C. and treated with trifluoroacetic acid (1.3 mL, 17 mmol) and stirred for 1.5 h.

The solution was extracted with diethyl ether. The extract was dried over $MgSO_4$ and concentrated under reduced pressure giving 690 mg of the title compound. This compound was of sufficient purity to use in subsequent reactions.

$^1H$ NMR ($CDCl_3$) δ 2.98 (s, 1H), 6.21 (s, 1H).

Step E: Preparation of ethyl 3,5-dichloro-1H-pyrazole-1-acetate

A suspension of 3,5-dichloro-1H-pyrazole (690 mg, 5.0 mmol) (i.e. the product of Example 12, Step D), potassium carbonate (3 g, 21 mmol) in N,N-dimethylformamide (10 mL) was treated with ethyl bromoacetate (1.0 mL, 9.0 mmol) and stirred at ambient temperature for 12 h. The suspension was diluted with ethyl acetate, washed with water, and dried over $MgSO_4$. The reaction mixture was then concentrated under reduced pressure giving 1.05 g of the title compound. This compound was of sufficient purity to use in subsequent reactions.

$^1H$ NMR ($CDCl_3$) δ 1.29 (t, 3H), 4.25 (q, 2H), 4.85 (s, 2H), 6.20 (m, 1H).

Step F: Preparation of 3,5-dichloro-1H-pyrazol-1-acetic acid

A solution of ethyl 3,5-dichloro-1H-pyrazole-1-acetate (1.29 g, 5.8 mmol) (i.e. the product of Example 12, Step E) in tetrahydrofuran (10 mL) was treated with sodium hydroxide (5 mL, 15% aqueous solution) in water (3 mL), and the reaction mixture was stirred at ambient temperature for 1.5 h. The reaction mixture was then diluted with water (15 mL) and was concentrated under reduced pressure. The aqueous solution was acidified with concentrated hydrochloric acid to pH 1. The reaction mixture was then extracted with ethyl acetate and the extract was dried over $MgSO_4$. The extract was then concentrated and recrystallized from 20% ethyl acetate in hexanes to give 370 mg of the title compound.

$^1H$ NMR ($CDCl_3$) δ 4.94 (s, 2H), 6.24 (s, 1H).

Step G: Preparation of 2-[1-[(3,5-dichloro-1H-pyrazol-1-yl)acetyl]-4-piperidinyl]-N-methyl-N-[(1R)-1,2,3,4-tetrahydro-1-naphthalenyl]-4-thiazolecarboxamide A solution of 3,5-dichloro-1H-pyrazol-1-acetic acid (70 mg, 0.36 mmol) (i.e. the product of Example 12, Step F) in dichloromethane (1 mL) and a catalytic amount of N,N-dimethylformamide (1 drop) was treated with oxalyl chloride (0.1 mL, 1.1 mmol) and stirred at ambient temperature for 20 minutes. The reaction mixture was concentrated under reduced pressure and re-dissolved in dichloromethane (1 mL). The reaction mixture was added to a stirred suspension of N-methyl-2-(4-piperidinyl)-N-[(1R)-1,2,3,4-tetrahydro-1-naphthalenyl]-4-thiazolecarboxamide monohydrochloride (i.e. the product of Example 6, Step C) (100 mg, 0.26 mmol), triethylamine (0.1 mL, 0.72 mmol), and potassium carbonate (150 mg, 1 mmol) in dichloromethane (2 mL). The reaction mixture was then heated to reflux for 2 h, and then cooled to ambient temperature. The resulting suspension was diluted with dichloromethane (10 mL), filtered, and concentrated in vacuo. The crude product was purified by silica gel chromatography using 50-100% ethyl acetate in hexanes as eluant to give 80 mg of the title product, a compound of the present invention as an oil.

$^1H$ NMR ($CDCl_3$) δ 1.6-2.1 (m, 5H), 2.1-2.3 (m, 3H), 2.32 (m, 3H), 2.7-3.0 (m, 6H), 3.2-3.35 (m, 2H), 3.95-4.1 (m, 1H), 4.35-4.6 (m, 1H), 4.96-5.02 (m, 2H), 5.6-6.1 (m, 1H), 6.20 (s, 1H), 7.11-7.24 (m, 4H), 7.86 (m, 1H).

EXAMPLE 13

Preparation of 2-[1-[[5-chloro-3-(trifluoromethyl)-1H-pyrazol-1-yl]acetyl]-4-piperidinyl]-N-methyl-N-[(1R)-1,2,3,4-tetrahydro-1-naphthalenyl]-4-thiazole-carboxamide (Compound 249)

Step A: Preparation of N,N-dimethyl-3-(trifluoromethyl)-1H-pyrazole-1-sulfonamide To a solution of 3-trifluoromethylpyrazole (5.0 g, 36 mmol), triethylamine (7.0 mL, 50 mmol) in dichloromethane (40 mL) was added N,N-dimethylsulfamoyl chloride (5.5 mL, 51 mmol) and the reaction mixture was warmed to reflux for 2 days. The reaction mixture was cooled to ambient temperature and filtered through a pad of silica gel using dichloromethane as an eluent. The resulting solution was then concentrated under reduced pressure to give an amber residue. The residue was dissolved in diethyl ether and washed with water. The extract was then dried over $MgSO_4$ and concentrated under reduced pressure giving 8.71 g of the title compound. This compound was of sufficient purity to use in subsequent reactions.

$^1H$ NMR ($CDCl_3$) δ 3.01 (s, 6H), 6.65 (s, 1H), 8.03 (s, 1H).

Step B: Preparation of 5-chloro-N,N-dimethyl-3-(trifluoromethyl)-1H-pyrazole-1-sulfonamide Under a nitrogen atmosphere, N,N-dimethyl-3-(trifluoromethyl)-1H-pyrazole-1-sulfonamide (4.0 g, 16 mmol) (i.e. the product of Example 13, Step A) in tetrahydrofuran (25 mL) was cooled to −78° C. was then treated with n-butyl-lithium (2 M solution in cyclohexane, 8.6 mL, 17.2 mmol) dropwise. The reaction mixture formed a thick precipitate, and stirring was continued for 30 minutes after the addition. To the stirred suspension, a solution of hexachloroethane (4.2 g, 18 mmol) in tetrahydrofuran (15 mL) was added dropwise. After 1 h the resulting clear solution was warmed to ambient temperature and quenched with the addition of water (50 mL). The reaction mixture was extracted with dichloromethane and dried over $MgSO_4$. The reaction mixture was filtered and concentrated under reduced pressure to give 4.38 g of the title compound. This compound was of sufficient purity to use in subsequent reactions.

$^1H$ NMR ($CDCl_3$) δ 3.15 (s, 6H), 6.58 (s,

Step C: Preparation of 5-chloro-3-trifluoromethyl-1H-pyrazole

In a round bottom flask with magnetic stirrer, 5-chloro-N,N-dimethyl-3-(trifluoromethyl)-1H-pyrazole-1-sulfonamide (4.38 g, 15.8 mmol) (i.e. the product of Example 13, Step B) was cooled to 0° C. and treated with trifluoroacetic acid (2.7 mL, 35 mmol). The reaction mixture was stirred at 0° C. for 1.5 h. The resulting solution was diluted with water (15 mL) and basified with sodium carbonate to pH 12. The reaction mixture was extracted with diethyl ether. The extract was dried over $MgSO_4$ and concentrated under reduced pressure giving 2.1 g of the title compound. This compound was of sufficient purity to use in subsequent reactions.

$^1$H NMR ($CDCl_3$) δ 6.57 (m, 1H).

Step D: Preparation of ethyl 5-chloro-3-(trifluoromethyl)-1H-pyrazole-1-acetate

A suspension of 5-chloro-3-trifluoromethyl-1H-pyrazole (2.1 g, 12.3 mmol) (i.e. the product of Example 13, Step C), potassium carbonate (3.6 g, 26 mmol) in N,N-dimethylformamide (20 mL) was treated with ethyl bromoacetate (2.1 mL, 18.8 mmol) and the reaction mixture was stirred at ambient temperature for 12 h. The reaction mixture was diluted with ethyl acetate, washed with water, and dried over $MgSO_4$. The reaction mixture was filtered and concentrated under reduced pressure. The crude product was purified by silica gel chromatography using 0-50% ethyl acetate in hexanes as eluant to give 940 mg of the title compound.

$^1$H NMR ($CDCl_3$) δ 1.29 (m, 3H), 4.27 (q, 2H), 4.96 (m, 2H), 6.55 (s, 1H).

Step E: Preparation of 5-chloro-3-(trifluoromethyl)-1H-pyrazole-1-acetic acid

A solution of ethyl 5-chloro-3-(trifluoromethyl)-1H-pyrazole-1-acetate (218 mg, 0.85 mmol) in tetrahydrofuran (1 mL) was treated with sodium hydroxide (0.2 mL, 50% aqueous solution) in water (0.6 mL), and stirred at ambient temperature for 4 h. The reaction mixture was then diluted with water (15 mL) and was concentrated under reduced pressure. The reaction mixture was acidified with concentrated hydrochloric acid to pH 1. The resulting mixture was extracted with ethyl acetate, dried over $MgSO_4$, and concentrated to give 140 mg of the title compound. This compound was of sufficient purity to use in subsequent reactions.

$^1$H NMR (DMSO-$d_6$) δ 5.41 (s, 2H), 7.09 (s, 1H).

Step F: Preparation of 2-(1-[[5-chloro-3-(trifluoromethyl)-1H-pyrazol-1-yl]acetyl]-4-piperidinyl]-N-methyl-N-[(1R)-1,2,3,4-tetrahydro-1-naphthalenyl]-4-thiazolecarboxamide A solution of 5-chloro-3-(trifluoromethyl)-1H-pyrazole-1-acetic acid (140 mg, 0.61 mmol) (i.e. the product of Example 13, Step E) in dichloromethane (2 mL) and a catalytic amount of N,N-dimethylformamide (1 drop) was treated with oxalyl chloride (0.1 mL, 1.1 mmol) and stirred at ambient temperature for 20 minutes. The reaction mixture was concentrated under reduced pressure and re-dissolved in dichloromethane (1 mL). The reaction mixture was added to a stirred suspension of N-methyl-2-(4-piperidinyl)-N-[(1R)-1,2,3,4-tetrahydro-1-naphthalenyl]-4-thiazolecarboxamide monohydrochloride (i.e. the product of Example 6, Step C) (280 mg, 0.72 mmol), triethylamine (0.2 mL, 1.5 mmol), and potassium carbonate (300 mg, 2.1 mmol) in dichloromethane (2 mL). The reaction mixture was then heated to reflux for 4 h, and then cooled to ambient temperature. The resulting suspension was diluted with dichloromethane (10 mL), filtered, and concentrated in vacuo. The crude product was purified by silica gel chromatography using 50-100% ethyl acetate in hexanes as eluant to give 130 mg of the title product, a compound of the present invention as an oil.

$^1$H NMR ($CDCl_3$) δ 1.6-2.1 (m, 5H), 2.1-2.3 (m, 3H), 2.32 (m, 3H), 2.7-3.0 On, 6H), 3.2-3.35 (m, 2H), 3.95-4.1 (m, 1H), 4.35-4.6 (m, 1H), 4.96-5.02 (m, 2H), 5.6-6.1 (m, 1H), 6.59 (s, 1H); 7.05-7.25 (m, 4H), 7.96 (m, 1H).

EXAMPLE 14

Preparation of 2-[1-[[3,5-bis(trifluoromethyl)-1H-pyrazol-1-yl]acetyl]-4-piperidinyl]-N-methyl-N-[(1R)-1,2,3,4-tetrahydro-1-naphthalenyl]-4-thiazolecarboxamide (Compound 210)

Step A: Preparation of 3,5-bis-(trifluoromethyl)-1H-pyrazole-1-acetic acid

A solution of 3,5-bis-(trifluoromethyl)pyrazole (1.0 g, 4.90 mmol) in N,N-dimethyl-formamide (10 mL) at 0° C. was treated with sodium hydride (60% dispersion in oil, 215 mg, 5.37 mmol) and the reaction mixture was allowed to stir at room temperature for 1 h. A solution of ethyl iodoacetate (2.0 g, 9.30 mmol) in N,N-dimethylformamide (10 mL) was then added and the reaction mixture heated at 80° C. for 24 h. The reaction mixture was then cooled to room temperature, diluted with ethyl acetate and washed with water. The organic layer was dried with $MgSO_4$, filtered and concentrated to provide 570 mg of the crude ester. The crude ester was dissolved in tetrahydrofuran (2 mL) and treated with sodium hydroxide (150 mg) in water (1.5 mL). The reaction mixture was then stirred at room temperature overnight. The resulting mixture was diluted with water (10 mL), extracted with diethyl ether (20 mL). The organic layers were dried with $MgSO_4$, filtered and concentrated in vacuo to provide 190 mg of the title compound. This compound was of sufficient purity to use in subsequent reactions.

$^1$H NMR (DMSO-$d_6$) δ 5.29 (s, 2H), 7.65 (s, 1H).
$^{19}$F NMR (DMSO-$d_6$) δ −59.4, −61.4.

Step B: Preparation of 2-[1-[[3,5-bis(trifluoromethyl)-1H-pyrazol-1-yl]acetyl]-4-piperidinyl]-N-methyl-N-[(1R)-1,2,3,4-tetrahydro-1-naphthalenyl]-4-thiazolecarboxamide A solution of 3,5-bis-(trifluoromethyl)-1H-pyrazole-1-acetic acid (190 mg, 0.73 mmol) (i.e. the product of Example 14, Step A) in ethyl acetate (5.0 mL) was treated with 1-propanephosphonic acid cyclic anhydride (50% solution in ethyl acetate, 1.0 mL, 1.6 mmol) and the reaction mixture was stirred at room temperature for 30 minutes. The reaction mixture was added to a stirred suspension of N-methyl-2-(4-piperidinyl)-N-[(1R)-1,2,3,4-tetrahydro-1-naphthalenyl]-4-thiazolecarboxamide monohydrochloride (i.e. the product of Example 6, Step C) (210 mg, 0.53 mmol), triethylamine (0.5 mL, 3.75 mmol) in ethyl acetate (5 mL). The reaction mixture was then stirred at room temperature for 12 h. The resulting suspension was concentrated in vacuo and purified by MPLC on silica gel using ethyl acetate/hexanes as eluant to give 110 mg of the title product, a compound of the present invention as an oil.

$^1$H NMR ($CDCl_3$) δ 1.60-2.31 (m, 5H), 2.67-3.06 (m, 9H), 3.20-3.45 (m, 2H), 3.62-3.92 (m, 1H), 4.26-4.60 (m, 1H), 5.08-5.23 (m, 2H), 5.60-6.10 (m, 1H), 6.93 (s, 1H), 7.07-7.30 (m, 4H), 7.86 (m, 1H).

EXAMPLE 15

Preparation of 2-[1-[(3,5-diethyl-1H-pyrazol-1-yl)acetyl]-4-piperidinyl]-N-methyl-N-[(1R)-1,2,3,4-tetrahydro-1-naphthalenyl]-4-thiazolecarboxamide (Compound 209)

Step A: Preparation of 3,5-diethyl-1H-pyrazole

A solution of 3,5-heptanedione (2.4 g, 18.8 mmol) and hydrazine hydrate (1.0 g, 19.0 mmol) and acetic acid (1 drop) in water (10 mL) was heated to reflux for 1 h. The reaction mixture was then cooled in an ice bath to form a white precipitate. The precipitate was then filtered, dissolved in chloroform and dried over $MgSO_4$. The resulting reaction was concentrated under reduced pressure to provide 2.14 g of the title compound. This compound was of sufficient purity to use in subsequent reactions.

$^1$H NMR ($CDCl_3$) δ 1.27 (t, 6H), 2.65 (q, 4H), 5.90 (s, 1H).

Step B: Preparation of ethyl 3,5-diethyl-1H-pyrazole-1-acetate

To a solution of 3,5-diethyl-4H-pyrazole (2.14 g, 17.2 mmol) (i.e. the product of Example 15, Step A) in N,N-dimethylformamide (10 mL) was added potassium carbonate (4.7 g) and ethyl bromoacetate (2.9 mL, 26.1 mmol). The reaction mixture was stirred at room temperature overnight. The resulting solids were filtered off and the filtrate was diluted with ethyl acetate, washed with water and dried over $MgSO_4$. The reaction mixture was concentrated under reduced pressure to give 2.79 g of the title compound.

$^1$H NMR ($CDCl_3$) δ 1.27 (m, 9H), 2.57 (m, 4H), 4.22 (q, 2H), 4.78 (s, 2H), 5.93 (s, 1H).

Step C: Preparation of 3,5-diethyl-1H-pyrazole-1-acetic acid

Ethyl 3,5-diethyl-1H-pyrazole-1-acetate (2.79 g, 13.3 mmol) (i.e. the product of Example 15, Step B) in tetrahydrofuran (10 mL) was treated with sodium hydroxide (1.0 g) in water (7.5 mL) The reaction mixture was then stirred at room temperature overnight. The reaction mixture was concentrated under reduced pressure and washed with diethyl ether. The resulting aqueous layer was acidified with concentrated hydrochloric acid to give a white precipitate. The precipitate was filtered and dried in air to give 690 mg of the title compound.

$^1$H NMR (DMSO-$d_6$) δ 1.12 (m, 6H), 2.49 (m, 4H), 4.74 (s, 2H), 5.87 (s, 1H).

Step D: Preparation of 2-[1-[(3,5-diethyl-1H-pyrazol-1-yl) acetyl]-4-piperidinyl]-N-methyl-N-[(1R)-1,2,3,4-tetrahydro-1-naphthalenyl]-4-thiazolecarboxamide A solution of 3,5-diethyl-1H-pyrazol-1-acetic acid (135 mg, 0.74 mmol) (i.e. the product of Example 15, Step C) in ethyl acetate (5.0 mL) was treated with 1-propanephosphonic acid cyclic anhydride (50% solution in ethyl acetate, 1.0 mL, 1.6 mmol) and the reaction mixture was stirred at room temperature for 30 minutes. The reaction mixture was added to a stirred suspension of N-methyl-2-(4-piperidinyl)-N-[(1R)-1,2,3,4-tetrahydro-1-naphthalenyl]-4-thiazolecarboxamide monohydrochloride (i.e. the product of Example 6, Step C) (210 mg, 0.53 mmol), triethylamine (0.5 mL, 3.75 mmol) in ethyl acetate (5 mL). The reaction mixture was then stirred at room temperature for 12 h. The resulting suspension was concentrated in vacuo and purified by MPLC on silica gel using ethyl acetate/hexanes as eluant to give 60 mg of the title product, a compound of the present invention as an oil.

$^1$H NMR ($CDCl_3$) δ 1.10-1.30 (m, 6H), 1.50-2.30 (m, 8H), 2.45-2.65 (m, 4H), 2.70-2.95 (m, 5H), 3.10-3.30 (m, 2H), 3.90-4.15 (m, 2H), 4.40-4.60 (m, 1H), 4.70-5.00 (m, 2H), 5.60-6.10 (m, 2H), 7.05-7.50 (m, 4H), 7.87 (m, 1H).

EXAMPLE 16

Preparation of 2-[1-[[5-ethyl-3-(trifluoromethyl)-1H-pyrazol-1-yl]acetyl]-4-piperidinyl]-N-methyl-N-[(1R)-1,2,3,4-tetrahydro-1-naphthalenyl]-4-thiazolecarboxamide (Compound 208)

Step A: Preparation of 5-ethyl-3-(trifluoromethyl)-1H-pyrazole

A solution of 1,1,1-trifluoro-2,4-hexane-dione (2.4 g, 14.3 mmol), hydrazine hydrate (1.0 g, 19.0 mmol) and acetic acid (1 drop) in water (10 mL) was heated to reflux for 1 h. The reaction mixture was then cooled in an ice bath to form a white precipitate. The precipitate was then filtered, dissolved in chloroform and dried over $MgSO_4$. The resulting solution was concentrated under reduced pressure to provide 1.39 g of the title compound. This compound was of sufficient purity to use in subsequent reactions.

$^1$H NMR ($CDCl_3$) δ 1.26 (t, 3H), 2.70 (q, 2H), 6.34 (s, 1H).

Step B: Preparation of ethyl 5-ethyl-3-(trifluoromethyl)-1H-pyrazole-1-acetate

To a solution of 5-ethyl-3-(trifluoromethyl)-1H-pyrazole (1.39 g, 8.5 mmol) (i.e. the product of Example 16, Step A) in N,N-dimethylformamide (10 mL) was added potassium carbonate (2.3 g) and ethyl bromoacetate (1.4 mL, 12.6 mmol). The reaction mixture was stirred at room temperature overnight. The resulting solids were filtered off and the filtrate was diluted with ethyl acetate, washed with water and dried over $MgSO_4$. The resulting solution was concentrated under reduced pressure to give 1.34 g of the title compound. This compound was of sufficient purity to use in subsequent reactions.

Step C: Preparation of 5-ethyl-3-(trifluoromethyl)-1H-pyrazole-1-acetic acid

Ethyl 5-ethyl-3-(trifluoromethyl)-1H-pyrazole-1-acetate (1.34 g, 7.5 mmol) (i.e. the product of Example 16, Step B) in tetrahydrofuran (5 mL) was treated with sodium hydroxide (0.5 g) in water (3.5 mL). The reaction mixture was then stirred at room temperature overnight. The reaction mixture was concentrated under reduced pressure and washed with diethyl ether. The resulting aqueous layer was acidified with concentrated hydrochloric acid to give a white precipitate. The precipitate was filtered and dried in air to give 690 mg of the title compound.

$^1$H NMR (DMSO-$d_6$) δ 1.20 (m, 3H), 2.60 (m, 2H), 5.06 (s, 2H), 6.54 (s, 1H).

Step D: Preparation of 2-[1-[[5-ethyl-3-(trifluoromethyl)-1H-pyrazol-1-yl]acetyl]-4-piperidinyl]-N-methyl-N-[(1R)-1,2,3,4-tetrahydro-1-naphthalenyl]-4-thiazolecarboxamide A solution of 5-ethyl-3-(trifluoromethyl)-1H-pyrazole-1-acetic acid (170 mg, 0.76 mmol) (i.e. the product of Example 16, Step C) in ethyl acetate (5.0 mL) was treated with 1-propanephosphonic acid cyclic anhydride (50% solution in ethyl acetate, 1.0 mL, 1.6 mmol) and the reaction mixture was stirred at room temperature for 30 minutes. The reaction mixture was added to a stirred suspension of N-methyl-2-(4-piperidinyl)-N-[(1R)-1,2,3,4-tetrahydro-1-naphthalenyl]-4-thiazolecarboxamide monohydrochloride (i.e. the product of Example 6 Step C) (219 mg, 0.56 mmol), triethylamine (0.5 mL, 3.75 mmol) in ethyl acetate (5 mL). The reaction mixture was then stirred at room temperature for 12 h. The resulting suspension was concentrated in vacuo and purified by silica gel MPLC using ethyl acetate/hexanes as eluant to give 200 mg of the title product, a compound of the present invention as an oil.

$^1$H NMR (CDCl$_3$) δ 1.20-1.30 (m, 3H), 1.55-2.25 (m, 8 H), 2.50-2.70 (m, 2H), 2.70-3.00 (m, 6H), 3.10-3.50 (m, 2H), 3.90-4.10 (m, 1H), 4.30-4.60 (m, 1H), 4.80-5.10 (m, 2H), 5.60-6.10 (m, 1H), 6.33 (m, 1H), 7.05-7.50 (m, 4H), 7.88 (m, 1H).

EXAMPLE 17

Preparation of N-methyl-2-[1-[[5-methyl-3-(trifluoromethyl)-1H-pyrazol-1-yl]acetyl]-4-piperidinyl]-N-[(1R)-1,2,3,4-tetrahydro-1-naphthalenyl]-4-oxazolinecarboxamide (Compound 246)

Step A: Preparation of 1,1-dimethylethyl [(1S)-1-(hydroxymethyl)-2-[methyl[(1R)-1,2,3,4-tetrahydro-1-naphthalenyl]amino]-2-oxoethyl]carbamate A solution of (1R)-1,2,3,4-tetrahydro-N-methyl-1-naphthalenamine (0.887 g, 5.5 mmol) (i.e. the product of Example 6, Step A) in tetrahydrofuran (15 mL) was treated with t-Boc-L-serine (1.03 g, 5 mmol), N-hydroxybenzotriazole (0.677 g, 0.5 mmol) and N,N-diisopropylcarbodiimide (0.663 g, 5.25 mmol) at 0° C. The reaction mixture was allowed to warm to room temperature and stirred for 16 h. The precipitate formed was filtered and washed with tetrahydrofuran. The filtrate and washings were concentrated, and the residue was purified by medium-pressure liquid chromatography using a gradient of 50-100% of ethyl acetate in hexanes as eluant to give 1.11 g of the title compound.

$^1$H NMR (CDCl$_3$) δ 1.46-1.48 (m, 9H), 1.8-1.9 (m, 2H), 1.97-2.05 (m, 2H), 2.65, 2.83 (d, 3H), 2.72-2.80 (br s, 2H), 3.33-3.43 (m, 1H), 3.78-4.00 (m, 2H), 4.65-4.80 (m, 1H), 5.27-5.91 (m, 2H), 6.98-7.2 (m, 4H).

Step B: Preparation of (2S)-2-amino-3-hydroxy-N-methyl-N-[(1R)-1,2,3,4-tetrahydro-1-naphthalenyl] propanamide monohydrochloride To a solution of 1,1-dimethylethyl [(1S)-1-(hydroxymethyl)-2-[methyl[(1R)-1,2,3,4-tetrahydro-1-naphthalenyl] amino]-2-oxoethyl]carbamate (1.11 g, 3.19 mmol) (i.e. the product of Example 17, Step A) in methanol (15 mL) was added a 2 M solution of hydrogen chloride in ether (15 mL, 30 mmol), and the reaction mixture was stirred at room temperature for 3 h. The reaction mixture was concentrated in vacuo and the resulting residue was dissolved in methanol and concentrated in vacuo again. The residue was dried in high vacuum to give 750 mg of the title compound as a white solid.

$^1$H NMR (DMSO-d$_6$) δ 1.6-2.0 (m, 4H), 2.7 (s, 3H), 3.61-3.80 (m, 2H), 4.38-4.43 (d, 1H), 5.18-5.66 (m, 2H), 7.0-7.2 (m, 4H), 8.2-8.3 (br s, 3H).

Step C: Preparation of ethyl 1-[[5-methyl-3-(trifluoromethyl)-1H-pyrazol-1-yl]acetyl]-4-piperidinylcarboxylate A solution of ethyl 4-piperidinecarboxylate (1.57 g, 10 mmol) and triethylamine (2.09 mL, 15 mmol) in dichloromethane (20 mL) was cooled to 0° C. and a solution of 5-methyl-3-(trifluoromethyl)-1H-pyrazole-1-acetyl chloride (prepared as described in Example 19, step B) in 5 mL of dichloromethane was added dropwise with stirring. The reaction mixture was allowed to warm to room temperature and stirred for 16 h. The reaction mixture was poured in 50 mL of water, and the organic layer was subsequently washed with water, 1 M aqueous hydrochloric acid, water, saturated aqueous solution of sodium bicarbonate and brine. The separated organic layers were dried (MgSO$_4$) and evaporated in vacuo to give 3.2 g of the title compound.

$^1$H NMR (CDCl$_3$) δ 1.22-1.24 (t, 3H), 1.61-1.74 (m, 2H), 1.85-2.00 (m, 2H), 2.3 (s, 3H), 2.5-2.6 (m, 1H), 2.88-3.23 (m, 2H), 3.82-4.32 (m, 2H), 4.17-4.19 (q, 2H), 4.85 (s, 2H), 6.31 (s, 1H).

Step D: Preparation of 1-[[5-methyl-3-(trifluoromethyl)-1H-pyrazol-1-yl]acetyl]-4-piperidinylcarboxylic acid A solution of ethyl 1-[[5-methyl-3-(trifluoromethyl)-1H-pyrazol-1-yl]acetyl]-4-piperidinylcarboxylate (3.6 g, 10.36 mmol) (i.e. the product of Example 17, Step C) in methanol (10 mL) was treated with 1 M sodium hydroxide aqueous solution (15.54 mL, 15.54 mmol) at 0° C. The reaction mixture was stirred at room temperature for 2 h and then 1 M hydrochloric acid (15.54 mL, 15.54 mmol) was added, and most of methanol was evaporated in vacuo leaving white crystals. The crystals were filtered and dried to give 2.25 g of the title compound as a white solid.

$^1$H NMR (DMSO-d$_6$) δ 1.30-1.65 (m, 2H), 1.80-1.92 (m, 2H), 2.2 (s, 3H), 2.72-3.21 (m, 2H), 3.25-3.36 (m, 1H), 3.77-4.20 (m, 2H), 5.18-5.34 (m, 2H), 6.5 (s, 1H).

Step E: Preparation of N-[(1S)-1-(hydroxymethyl)-2-[methyl[(1R)-1,2,3,4-tetrahydro-1-naphthalenyl] amino]-2-oxoethyl]-1-[[5-methyl-3-(trifluoromethyl)-1H-pyrazol-1-yl]acetyl]-4-piperidinecarboxamide A solution of (2S)-2-amino-3-hydroxy-N-methyl-N-[(1R)-1,2,3,4-tetrahydro-1-naphthalenyl]propanamide monohydrochloride (546.33 mg, 2.2 mmol) (i.e. the product of Example 17, Step B) and N-methylmorpholine (222.53 mg, 2.2 mmol) in 8 mL of tetrahydrofuran was cooled to 0° C. and 1-[[5-methyl-3-(trifluoromethyl)-1H-pyrazol-1-yl] acetyl]-4-piperidinylcarboxylic acid (638.56 mg, 2 mmol) (i.e. the product of Example 17, Step D) was added followed by N-hydroxybenzotriazole (27 mg, 0.2 mmol) and N,N-diisopropylcarbodiimide (265 mg, 2.1 mmol). The reaction mixture was stirred for 16 h at room temperature and filtered. The precipitate was washed with tetrahydrofuran and the resulting filtrate and washings were concentrated in vacuo. The residue was dissolved in dichloromethane and the resulting solution was washed with water, 1 M aqueous hydrochloric acid, water, saturated aqueous solution of sodium bicarbonate and brine, dried over MgSO$_4$ and concentrated in vacuo. The resulting product was purified by medium-pressure liquid chromatography on silica gel using 0-20% methanol in ethyl acetate as eluant to give 600 mg of the title compound as a white solid.

¹H NMR (CDCl₃) δ1.65-2.05 (m, 8H), 2.3 (s, 3H), 2.40-3.26 (m, 2H), 2.7-2.9 (m, 6H), 3.55 (s, 1H), 3.8-3.92 (m, 2H), 3.92-4.54 (m, 2H), 5.0-5.1 (m, 2H), 5.2-5.9 (m, 1H), 6.35 (s, 1H), 6.9-7.2 (m, 5H).

Step F: Preparation of N-methyl-2-[1-[[5-methyl-3-(trifluoromethyl)-1H-pyrazol-1-yl]acetyl]-4-piperidinyl]-N-[(1R)-1,2,3,4-tetrahydro-1-naphthalenyl]-4-oxazolinecarboxamide A mixture of 207 mg (0.38 mmol) of N-[(1S)-1-(hydroxymethyl)-2-[methyl[(1R)-1,2,3,4-tetrahydro-1-naphthalenyl]amino]-2-oxoethyl]-1-[[5-methyl-3-(trifluoromethyl)-1H-pyrazol-1-yl]acetyl]-4-piperidinecarboxamide (207 mg, 0.38 mmol) (i.e. the product of Example 17, Step E) and (methoxycarbonylsulfamoyl)triethylammonium hydroxide, inner salt (Burgess reagent) (104.86 mg, 0.44 mmol) in 2 mL of tetrahydrofuran were heated at 70° C. for 2.5 h in the sealed tube. The reaction mixture was concentrated in vacuo and further purified by medium-pressure liquid chromatography using 75-100% of ethyl acetate in hexanes as eluant to give 90 mg of the title compound, a compound of the present invention as an oil.

¹H NMR (CDCl₃) δ 1.60-2.05 (m, 8H), 2.1 (s, 3H), 2.65-2.97 (m, 5H), 3.00-3.12 (m, 1H), 3.2-3.92 (m, 2H), 4.20-4.35 (m, 2H), 4.9-5.1 (m, 4H), 05.6-5.9 (m, 1H), 6.32 (s, 1H), 6.97-7.20 (m, 4H).

EXAMPLE 18

Preparation of N-methyl-1-[1-[[5-methyl-3-(trifluoromethyl)-1H-pyrazol-1-yl]acetyl]-4-piperidinyl]-N-[(1R)-1,2,3,4-tetrahydro-1-naphthalenyl]-1H-pyrazole-3-carboxamide (Compound 231)

Step A: Preparation of 1,1-dimethylethyl 4-[(methylsulfonyl)oxy]-1-piperidine-carboxylate To a solution of 1,1-dimethylethyl 4-hydroxy-1-piperidinecarboxylate (4.02 g, 20 mmol) and triethylamine (4.4 mL) in 50 mL of dichloromethane was slowly added methanesulfonylchloride (1.7 mL, 22 mmol) at 0° C. The reaction mixture was stirred for 1 h at 0° C., washed with 1 M aqueous hydrochloric acid, dried over MgSO₄ and concentrated in vacuo to give 5 g of the title compound as a white solid.

¹H NMR (CDCl₃) δ 1.44 (s, 9H), 1.74-1.86 (m, 2H), 1.9-2.1 (m, 2H), 3.02 (s, 3H), 3.27-3.35 (m, 2H), 3.66-3.75 (m, 2H), 4.84-4.92 (m, 1H).

Step B: Preparation of 1,1-dimethylethyl 4-[3-(methoxycarbonyl)-1H-pyrazol-1-yl]-1-piperidinecarboxylate A suspension of 60% dispersion of sodium hydride in mineral oil (192 mg, 4.8 mmol) in 20 mL of N,N-dimethylformamide was cooled to 0° C., and methyl 3-pyrazolecarboxylate (605.37 mg, 4.8 mmol) was gradually added with stirring in nitrogen atmosphere. The reaction mixture was stirred at room temperature for 0.5 h and cooled again to 0° C. A solution of 1,1-dimethylethyl 4-[(methylsulfonyl)oxy]-1-piperidine-carboxylate (1.18 g, 4 mmol) (i.e. the product of Example 18, Step A) in 5 mL of N,N-dimethylformamide was gradually added to the reaction mixture. The resulting mixture was stirred for 5 days at 60° C. The reaction mixture was poured in ice water and extracted with ethyl acetate. The organic layer was dried (MgSO₄), evaporated in vacuo, and purified by medium-pressure liquid chromatography on silica gel eluting with 0-10% methanol in ethyl acetate as eluant to give 290 mg of the title compound as a white solid.

¹H NMR (CDCl₃) δ 1.46 (s, 9H), 1.88-2.00 (m, 2H), 2.12-2.20 (m, 2H), 2.80-2.92 (m, 2H), 3.92 (s, 3H), 4.24-4.33 (m, 2H), 4.34-4.31 (m, 1H), 6.82 (s, 1H), 7.44 (s, 1H).

Additionally, 370 mg of 1,1-dimethylethyl 4-[5-(methoxycarbonyl)-1H-pyrazol-1-yl]-1-piperidinecarboxylate was isolated eluting before the title compound.

¹H NMR (CDCl₃) δ 1.46 (s, 9H), 1.92-2.00 (m, 2H), 2.08-2.15 (m, 2H), 2.85-2.95 (m, 2H), 3.89 (s, 3H), 4.20-4.31 (m, 2H), 5.24-5.32 (m, 1H), 6.85 (s, 1H), 7.51 (s, 1H).

Step C: Preparation of methyl 1-(4-piperidinyl)-1H-pyrazole-3-carboxylate monohydrochloride To a solution of 1,1-dimethylethyl 4-[3-(methoxycarbonyl)-1H-pyrazol-1-yl]-1-piperidinecarboxylate (300 mg, 0.97 mmol) (i.e. the product of Example 18, Step B) in 5 mL of diethyl ether was added a 2 M solution of hydrogen chloride in ether (4.85 mL, 9.7 mmol), and the reaction mixture was stirred for 5 h at room temperature. The reaction mixture was evaporated in vacuo, the resulting residue was dissolved in methanol and concentrated in vacuo. The residue was dried in high vacuum to give 200 mg of the title compound as a white solid.

¹H NMR (DMSO-d₆) δ 2.1-2.3 (m, 4H), 3.0-3.1 (m, 2H), 3.31-3.41 (m, 2H), 3.8 (s, 3H), 4.56-4.68 (m, 1H), 6.8 (s, 1H), 7.96 (s, 1H), 9.10-9.58 (br s, 2H).

Step D: Preparation of Methyl 1-[1-[[5-methyl-3-(trifluoromethyl)-1H-pyrazol-1-yl]acetyl]-4-piperidinyl]-1H-pyrazole-3-carboxylate A mixture of methyl 1-(4-piperidinyl)-1H-pyrazole-3-carboxylate monohydrochloride (220 mg, 0.9 mmol) (i.e. the product of Example 18, Step C) and triethylamine (0.42 mL, 3 mmol) in 5 mL of dichloromethane was stirred at room temperature for about 15 minutes until complete dissolution and cooled to 0° C. A solution of 5-methyl-3-(trifluoromethyl)-1H-pyrazole-1-acetyl chloride (227 mg, 1 mmol) (prepared as described in Example 19, Step B) was gradually added, and the resulting mixture was stirred at room temperature for 16 h. The reaction mixture was poured in water, the organic layer was washed with 1 M aqueous hydrochloric acid, water, saturated aqueous solution of sodium bicarbonate, brine. The filtered reaction mixture was dried over magnesium sulfate and concentrated in vacuo to give 320 mg of the title compound.

¹H NMR (CDCl₃) δ 1.90-2.07 (m, 2H), 2.2-2.3 (m, 2H), 2.34 (s, 3H), 2.79-3.36 (m, 2H), 3.93 (s, 3H), 4.10-4.71 (m, 2H), 4.25-4.52 (m, 1H), 4.94-5.04 (m, 2H), 6.35 (s, 1H), 6.85 (s, 1H), 7.22 (s, 1H).

Step E: Preparation of 1-[1-[[5-methyl-3-(trifluoromethyl)-1H-pyrazol-1-yl]acetyl]-4-piperidinyl]-1H-pyrazole-3-carboxylic acid A solution of methyl 1-[1-[[5-methyl-3-(trifluoromethyl)-1H-pyrazol-1-yl]acetyl]-4-piperidinyl]-1H-pyrazole-3-carboxylate (320 mg, 0.8 mmol) (i.e. the product of Example 18, Step D) in 8 mL of methanol was cooled to 0° C. and 1 M aqueous sodium hydroxide solution (1.6 mL, 1.6 mmol) was gradually added. The reaction mixture was stirred at 50° C. for 16 h, and 1 M aqueous hydrochloric acid (1.6 mL, 1.6 mmol) was added followed by 5 mL of saturated aqueous solution of sodium chloride. The resulting mixture was extracted with ethyl acetate, and the extract was dried over magnesium sulfate and evaporated in vacuo to give 270 mg of the title compound as a glassy solid.

$^1$H NMR (DMSO-d$_6$) δ 1.80-2.19 (m, 4H), 2.2 (s, 3H), 2.8-3.3 (m, 2H), 3.98-4.48 (m, 2H), 4.5-4.6 (m, 1H), 5.23-5.4 (m, 2H), 6.5 (s, 1H), 6.7 (s, 1H), 7.9 (s, 1H), 12.6 (s, 1H).

Step F: Preparation of N-methyl-1-[1-[[5-methyl-3-(trifluoromethyl)-1H-pyrazol-1-yl]acetyl]-4-piperidinyl]-N-[(1R)-1,2,3,4-tetrahydro-1-naphthalenyl]-1H-pyrazole-3-carboxamide A mixture of 1-[1-[[5-methyl-3-(trifluoromethyl)-1H-pyrazol-1-yl]acetyl]-4-piperidinyl]-1H-pyrazole-3-carboxylic acid (270 mg, 0.7 mmol) (i.e. the product of Example 18, Step E), N-(3-dimethylaminopropyl)-Y-ethylcarbodiimide hydrochloride (EDC) (147.61 mg, 0.77 mmol) and N-methylmorpholine (0.088 mL, 0.8 mmol) in 5 mL of dichloromethane was stirred at room temperature for 15 minutes. (1R)-1,2,3,4-tetrahydro-N-methyl-1-naphthalenamine (124.16 mg, 0.77 mmol) (i.e. the product of Example 6, Step A) was added and the reaction mixture was stirred at room temperature for 16 h. The reaction mixture was poured in water, and the organic layer was subsequently washed with water, 1 M aqueous hydrochloric acid, water, saturated aqueous solution of sodium bicarbonate, brine. The filtered reaction mixture was dried over magnesium sulfate and evaporated in vacuo. The crude product was purified by medium-pressure liquid chromatography on silica gel using 75-100 of ethyl acetate in hexanes as eluant to give 55 mg of the title compound, a compound of the present invention as an oil.

$^1$H NMR (CDCl$_3$) δ 1.68-2.10 (m, 6H), 2.11-2.27 (s, 3H), 2.33-2.35 (d, 3H), 2.74-3.00 (m, 5H), 3.22-3.4 (m, 1H), 4.00-4.18 (m, 1H), 4.30-4.66 (m, 2H), 4.93-5.07 (m, 2H), 5.88-6.12 (m, 1H), 6.29-6.38 (m, 1H), 6.74-6.81 (d, 1H), 7.1-7.3 (m, 4H), 7.40-7.42 (d, 1H).

EXAMPLE 19

N-[(1R)-2,3-dihydro-1H-inden-1-yl]-N-methyl-2-[1-[[5-methyl-3-(trifluoromethyl)-1H-pyrazol-1-yl]acetyl]-4-piperidinyl]-4-thiazolecarboxamide (Compound 178)

Step A: Preparation of ethyl 2-(4-piperidinyl)-4-thiazolecarboxylate monohydrochloride A solution of 1,1-dimethylethyl 4-[4-(ethoxycarbonyl)-2-thiazolyl]-1-piperidine-carboxylate (11.1 g, 32.7 mmol) (i.e. the product of Example 1, Step A) in 100 mL of diethyl ether was treated with a solution of 2 M hydrogen chloride in diethyl ether (166 mL, 331 mmol) at 0° C. The resulting reaction precipitate was dissolved with 100 mL of absolute ethanol and was stirred overnight at room temperature. The reaction mixture was evaporated in vacuo, re-dissolved in ethanol and evaporated again to give a solid. The resulting solid was placed under a high vacuum for several hours to give 10.38 g of the title compound as a hygroscopic white powder.

$^1$H NMR (DMSO-d$_6$) δ 1.30 (t, 3H), 1.9 (m, 2H), 2.2 (m, 2H), 3.0 (m, 2H), 3.35 (m, 2H), 3.4 (m, 1H), 4.3 (q, 2H), 8.9-9.3 (b, 2H).

Step B: Preparation of ethyl-2-[1-[[5-methyl-3-(trifluoromethyl)-1H-pyrazol-1-yl]acetyl]-4-piperidinyl]-4-thiazolecarboxylate 5-Methyl-3-(trifluoromethyl)-1H-pyrazol-1-yl]acetic acid (7.58 g, 36.4 mmol) (i.e. the product of Example 2, Step A) was dissolved in 100 mL of dichloromethane. To the reaction mixture, 1 drop of N,N-dimethylformamide was added and the reaction mixture was cooled to 0° C. The reaction mixture was treated with oxalyl chloride (3.5 mL, 40 mmol) dropwise and allowed to warm to room temperature and stirred for 3 h. The resulting mixture was evaporated in vacuo and placed under high vacuum to give 7.93 g of the corresponding acid chloride, 5-methyl-3-(trifluoromethyl)-1H-pyrazole-1-acetyl chloride, as a tan solid. The acid chloride was dissolved in 50 mL of dichloromethane and a solution of ethyl 2-(4-piperidinyl)-4-thiazolecarboxylate monohydrochloride (10.38 g, 33.1 mmol) (i.e. the product of Example 19, Step A) and triethylamine (23 mL, 165 mmol) in 200 mL of dichloromethane was added at 0° C. The reaction mixture was allowed to warm to room temperature and stirred overnight. The reaction mixture was poured into water and extracted with dichloromethane. The extract was washed with 1 M aqueous hydrochloric acid, water, saturated aqueous solution of sodium bicarbonate, and brine. The filtered mixture was dried (MgSO$_4$) and evaporated in vacuo to give 13.0 g of the title compound as an oil.

$^1$H NMR (CDCl$_3$) δ 1.4 (t, 3H), 1.78 (m, 2H), 2.2 (m, 2H), 2.32 (s, 3H), 2.80 (m, 1H), 3.25 (m, 1H), 3.36 (m, 1H), 4.07 (m, 1H), 4.42 (q, 2H), 4.62 (m, 1H), 4.98 (m, 2H), 6.34 (s, 1H), 8.09 (s, 1H).

Step C: Preparation of 2-[1-[[5-methyl-3-(trifluoromethyl)-1H-pyrazol-1-yl]acetyl]-4-piperidinyl]-4-thiazolecarboxylic acid A solution of ethyl-2-[1-[[5-methyl-3-(trifluoromethyl)-1H-pyrazol-1-yl]acetyl]-4-piperidinyl]-4-thiazolecarboxylate (13.0 g, 30.2 mmol) (i.e. the product of Example 19, Step B) in 60 mL of methanol was cooled to 0° C. and treated with a 1 N aqueous NaOH solution (36.3 mL, 36.3 mmol). The reaction mixture was allowed to warm to room temperature, and stirred for 5 h. The reaction mixture was cooled again to 0° C. and treated with 1 N aqueous hydrochloric acid (36.3 mL, 36.3 mmol). The resulting precipitate was filtered, washed with water and dried in a vacuum oven at 100° C. to give 10.95 g of the title compound as a white solid.

$^1$H NMR (DMSO-d$_6$) δ 1.55 (m, 1H), 1.80 (m, 1H), 2.1 (m, 2H), 2.21 (s, 3H), 2.82 (in; 1H), 3.30 (m, 2H), 3.98 (m, 1H), 4.38 (m, 1H), 5.28 (m, 2H), 6.50 (s, 1H), 8.36 (s, 1H), 12.9 (br s, 1H).

Step D: Preparation of 2-[1-[[5-methyl-3-(trifluoromethyl)-1H-pyrazol-1-yl]acetyl]-4-piperidinyl]-4-thiazolecarbonyl chloride A solution of 2-[1-[[5-methyl-3-(trifluoromethyl)-1H-pyrazol-1-yl]acetyl]-4-piperidinyl]-4-thiazolecarboxylic acid (2.55 g, 5.87 mmol) (i.e. the product of Example 19, Step C) in 100 mL of dichloromethane was cooled to -10° C. and added 1 drop of N,N-dimethylformamide. The reaction mixture was treated with a dropwise addition of a solution of oxalyl chloride (0.60 mL, 6.8 mmol) in 10 mL of dichloromethane. The reaction mixture was stirred at -10° C. for 30 minutes, allowed to warm to room temperature and stirred an additional 16 h. The resulting homogeneous mixture was evaporated in vacuo and the residue placed under high vacuum for several hours to give 2.46 g of the title compound as a light yellow solid.

$^1$H NMR (CDCl$_3$) δ 1.80 (m, 2H), 2.2 (m, 2H), 2.33 (s, 3H), 2.88 (m, 1H), 3.36 (m, 2H), 4.10 (m, 1H), 4.60 (m, 1H), 4.99 (m, 2H), 6.34 (s, 1H), 8.39 (s, 1H).

Step E: Preparation of N-[(1R)-2,3-dihydro-1H-inden-1-yl]-N-methyl-2-[1-[[5-methyl-3-(trifluoromethyl)-1H-pyrazol-1-yl]acetyl]-4-piperidinyl]-4-thiazolecarboxamide 2-[1-[[5-Methyl-3-(trifluoromethyl)-1H-pyrazol-1-yl]acetyl]-4-piperidinyl]-4-thiazolecarbonyl chloride (210 mg, 0.5 mmol) (i.e. the product of Example 19, Step D) was treated with a solution of (1R)-2,3-dihydro-N,2-dimethyl-1H-inden-1-amine (147 µL, 1.0 mmol) and triethylamine (139 µL, 1.0 mmol) in 5 mL of dichloromethane. The reaction mixture was stirred at room temperature for 2 h, passed through a Varian 1005 Chem Elut™ column pretreated with 3 mL of 1 N aqueous hydrochloric acid. The column was flushed with three column volumes of dichloromethane. The collected dichloromethane solution was evaporated in vacuo and purified by medium-pressure liquid chromatography on silica gel using 50-100% of ethyl acetate in 1-chlorobutane as eluant to give 214 mg of the title compound, the product of present invention as a white foam.

$^1$H NMR (CDCl$_3$) δ 178 (m, 3H), 2.18 (m, 2H), 2.39-3.31 (two s, 3H), 2.45 (m, 1 H), 2.7-3.2 (s and m, 6H), 3.28 (m, 2H), 4.00 (m, 1H), 4.50 (m, 1H), 4.97 (m, 2H), 5.9-6.4 (m, 2H), 7.2-7.3 (m, 4H), 7.83 (s, 1H).

EXAMPLE 20

Preparation of N-(2,3-dihydro-2-methyl-1H-inden-1-yl)-N-methyl-2-[1-[[5-methyl-3-(trifluoromethyl)-1H-pyrazol-1-yl]acetyl]-4-piperidinyl]-4-thiazolecarboxamide (Compound 226)

To a solution of 2,3-dihydro-N,2-dimethyl-1H-inden-1-amine (177 mg, 1.1 mmol) and triethylamine (0.22 mL, 1.6 mmol) in 5 mL of dichloromethane was gradually added 2-[1-[[5-methyl-3-(trifluoromethyl)-1H-pyrazol-1-yl]acetyl]-4-piperidinyl]-4-thiazolecarbonyl chloride (421 mg, 1 mmol) (i.e. the product of Example 19, Step D) at 0° C. The reaction mixture was stirred at room temperature for 16 h, diluted with 4 mL of dichloromethane, and washed with water, 1 N aqueous hydrochloric acid, water, saturated solution of sodium bicarbonate and brine. The filtered reaction mixture was dried over magnesium sulfate and concentrated in vacuo to give 215 mg of the title compound, the product of present invention as a white foam.

$^1$H NMR (CDCl$_3$) δ 1.56 (s, 3H), 1.70-1.86 (m, 2H), 2.11-2.27 (m, 2H), 2.3 (s, 3H), 2.62-2.75 (m, 4H), 2.87-3.00 (m, 2H), 3.09-3.18 (m, 1H), 3.2-3.4 (m, 2H), 4.00-4.55 (m, 2H), 4.90-5.05 (m, 2H), 5.93-6.20 (m, 1H), 6.30-6.35 (m, 1H), 7.20-7.33 (m, 4H). 7.8-7.9 (d, 1H).

EXAMPLE 21

Preparation of N-(2,3-dihydro-2,2-dimethyl-1H-inden-1-yl)-N-methyl-2-[1-[[5-methyl-3-(trifluoromethyl)-1H-pyrazol-1-yl]acetyl]-4-piperidinyl]-4-thiazolecarboxamide (Compound 222)

To a solution of 2,3-dihydro-N,2,2-trimethyl-1H-inden-1-amine (193 mg, 1.1 mmol) and triethylamine (0.19 mL, 1.38 mmol) in 5 mL of dichloromethane was gradually added 2-[1-[[5-methyl-3-(trifluoromethyl)-1H-pyrazol-1-yl]acetyl]-4-piperidinyl]-4-thiazolecarbonyl chloride (386 mg, 0.92 mmol) (i.e. the product of Example 19, Step D) at 0° C. The reaction mixture was stirred at room temperature for 16 h, diluted with 4 mL of dichloromethane, and washed with water, 1 N aqueous hydrochloric acid, water, saturated solution of sodium bicarbonate and brine. The filtered reaction mixture was dried over magnesium sulfate and concentrated in vacuo to give 300 mg of the title compound, the product of present invention as a white foam.

$^1$H NMR (CDCl$_3$) δ 0.98 (s, 2H), 1.18-1.28 (m, 4H), 1.70-1.82 (m, 2H), 2.12-2.29 (m, 2H), 2.3 (s, 3H), 2.61-2.75 (m, 4H), 2.82-2.98 (m, 2H), 3.22-3.37 (m, 2H), 3.98-4.60 (m, 2H), 4.92-5.08 (m, 2H), 5.52-5.81 (d, 1H), 6.3 (s, 1H), 7.20-7.32 (m, 4H), 7.80-7.83 (d, 1H).

EXAMPLE 22

Preparation of N-methyl-2-[1-[[5-methyl-3-(trifluoromethyl)-1H-pyrazol-1-yl]acetyl]-4-piperidinyl]-N-(1,2,3,4-tetrahydro-2-methyl-1-naphthalenyl)-4-thiazolecarboxamide (Compound 193)

To a solution of 1,2,3,4-tetrahydro-N,2-dimethyl-1-naphthalenamine (115 mg, 0.66 mmol) and triethylamine (0.12 mL, 0.825 mmol) in 2 mL of dichloromethane was gradually added 2-[1-[[5-methyl-3-(trifluoromethyl)-1H-pyrazol-1-yl]acetyl]-4-piperidinyl]-4-thiazolecarbonyl chloride (231 mg, 0.55 mmol) (i.e. the product of Example 19, Step D) at 0° C. The reaction mixture was stirred at room temperature for 16 h, diluted with 4 mL of dichloromethane, and washed with water, 1 N aqueous hydrochloric acid, water, saturated solution of sodium bicarbonate and brine. The filtered reaction mixture was dried over magnesium sulfate and concentrated in vacuo to give 270 mg of the title compound, the product of present invention as a white foam.

$^1$H NMR (CDCl$_3$) δ 1.06-1.10 (m, 3H), 1.61-1.83 (m, 4H), 2.08-2.24 (m, 3H), 2.32-2.35 (m, 3H), 2.72-2.82 (m, 4H), 2-86-3.00 (m, 3H), 3.20-3.38 (m, 2H), 3.93-4.08 (m, 1H), 4.47-4.59 (m, 1H), 4.91-5.06 (m, 2H), 5.82-6.15 (m, 1H), 6.32-6.35 (m, 1H), 7.10-7.54 (m, 4H), 7.79-7.90 (d, 1H).

EXAMPLE 23

Preparation of N-methyl-2-[1-[[5-methyl-3-(trifluoromethyl)-1H-pyrazol-1-yl]acetyl]-4-piperidinyl]-N-(1,2,3,4-tetrahydro-1-naphthalenyl)-4-thiazolecarboxamide (compound 188)

To a solution of 1,2,3,4-tetrahydro-N-methyl-1-naphthalenamine (145 mg, 0.9 mmol) (prepared by the method described from Example 6, Step A) and triethylamine (0.16 mL, 1.13 mmol) in 2 mL of dichloromethane was gradually added 2-[1-[[5-methyl-3-(trifluoromethyl)-1H-pyrazol-1-yl]acetyl]-4-piperidinyl]-4-thiazolecarbonyl chloride (316 mg, 0.75 mmol) (i.e. the product of Example 19, Step D) at 0° C. The reaction mixture was stirred at room temperature for 16 h, diluted with 4 mL of dichloromethane, and washed with water, 1 N aqueous hydrochloric acid, water, saturated solution of sodium bicarbonate and brine. The filtered reaction mixture was dried over magnesium sulfate and concentrated in vacuo. The crude product was purified by medium-pressure liquid chromatography on silica gel using 60-100% of ethyl acetate in hexanes as eluant to give 242 mg of the title compound, a compound of the present invention as white foam.

$^1$H NMR (CDCl$_3$) δ 1.6-2.0 (m, 4H), 2.05-2.3 (m, 6H), 2.7-3.0 (m, 6H), 3.22-3.35 (m, 2H), 3.95-4.58 (m, 3H), 4.96-5.02 (m, 2H), 5.67-6.05 (m, 1H), 6.32 (s, 1H), 7.05-7.25 (m, 4H), 7.85 (m, 1H).

EXAMPLE 24

Preparation of N-methyl-2-[1-[[5-methyl-3-(trifluoromethyl)-1H-pyrazol-1-yl]acetyl]-4-piperidinyl]-N-[(1R,2S)-1,2,3,4-tetrahydro-2-methyl-1-naphthalenyl]-4-thiazolecarboxamide and its enantiomer (Compound 234)

To a solution of (1R,2S)-1,2,3,4-tetrahydro-N,2-dimethyl-naphthalenamine and its enantiomer (0.043 g, 0.25 mmol) (prepared by the method described from Example 6, Step A) and triethylamine (0.104 mL, 0.74 mmol) in 2 mL of dichloromethane was gradually added 2-[1-[[5-methyl-3-(trifluoromethyl)-1H-pyrazol-1-yl]acetyl]-4-piperidinyl]-4-thiazolecarbonyl chloride (85 mg, 0.2 mmol) (i.e. the product of Example 19, Step D) at 0° C. The reaction mixture was stirred at room temperature for 16 h, diluted with 4 mL of dichloromethane, and washed with water, 1 N aqueous hydrochloric acid, water, saturated solution of sodium bicarbonate and brine. The filtered reaction mixture was dried over sodium sulfate and concentrated in vacuo. The crude product was purified by medium-pressure liquid chromatography on silica gel using 60-100% of ethyl acetate in hexanes as eluant to give 43 mg of the title compounds, compounds of the present invention as white foam.

Mass spectrum at 558 (M+1).

EXAMPLE 25

Preparation of N-methyl-2-1-[[5-methyl-3-(trifluoromethyl)-1H-pyrazol-1-yl]acetyl]-4-piperidinyl]-N-(1,2,3,4-tetrahydro-2,2-dimethyl-1-naphthalenyl]-4-thiazolecarboxamide (Compound 236)

To a solution of 1,2,3,4-tetrahydro-N,2,2-trimethyl-naphthalenamine (0.0423 g, 0.22 mmol) (prepared by the method described from Example 6, Step A) and triethylamine (0.036 mL, 0.26 mmol) in 1 mL of dichloromethane was gradually added 2-[1-[[5-methyl-3-(trifluoromethyl)-1H-pyrazol-1-yl]acetyl]-4-piperidinyl]-4-thiazolecarbonyl chloride (316 mg, 0.75 mmol) (i.e. the product of Example 19, Step D) at 0° C. The reaction mixture was stirred at room temperature for 16 h, diluted with 2 mL of dichloromethane, and washed with water, 1 N aqueous hydrochloric acid, water, saturated solution of sodium bicarbonate and brine. The filtered reaction mixture was dried over sodium sulfate and concentrated in vacuo. The crude product was purified by medium-pressure liquid chromatography on silica gel using 60-100% of ethyl acetate in hexanes as eluant to give 70 mg of the title compound, a compound of the present invention as white foam.

$^1$H NMR (CDCl$_3$) δ 0.85 and 1.10 (two s, total 4H), 0.94-1.65 (m, 2H), 1.02 and 1.14 (two s, total 3H), 1.77 (m, 3H), 2.17 (m, 1H), 2.29 and 2.32 (two s, total 3H), 2.77 and 2.86 (two s, total 3H), 2.82 (m, 1H), 2.90 (m, 1H), 3.29 (m, 1H), 4.00 (m, 1H), 4.37 (m, 1H), 4.50 (m, 1H), 5.00 (m, 2H), 5.69 and 5.85 (s and d, total 1H), 6.34 (m, 1H), 7.19-7.42 (m, 4H), 7.79 and 7.86 (two s, total 1H),

EXAMPLE 26

Preparation of N-methyl-2-[1-[[5-methyl-3-(trifluoromethyl)-1H-pyrazol-1-yl]acetyl]-4-piperidinyl]-N-[(1R,4S)-1,2,3,4-tetrahydro-4-hydroxy-1-naphthalenyl]-4-thiazolecarboxamide and its enantiomer (Compound 191)

Step A: Preparation of (1S,4R)-1,2,3,4-tetrahydro-4-(methylamino)-1-naphthalenol and its enantiomer To a solution of 1,2,3,4-tetrahydro-1,4-epoxynaphthalene (2.92 g, 20 mmol) and triethylamine (0.3 mL, 2 mmol) in 40 mL of dichloromethane at 0° C. was added 9-bromo-9-borabicyclo[3.3.1]nonane (1 M solution in tetrahydrofuran, 30 mL, 30 mmol). The reaction mixture was stirred at 0° C. for 20 minutes, and a 2 M solution of methylamine in tetrahydrofuran (40 mL) was then added, forming a white precipitate. The reaction mixture was stirred at room temperature for 16 h, poured into 100 mL of 1 M aqueous hydrochloric acid, and filtered. The filtered aqueous layer was washed with dichloromethane, basified with NaOH pellets to pH 13, and then extracted with dichloromethane. The extract was washed with brine, dried over magnesium sulfate and evaporated in vacuo to give a gummy yellow solid. The solid was slurried in diethyl ether, filtered, washed with diethyl ether and air dried to give 2.15 g of the title compounds as white powder.

$^1$H NMR (CDCl$_3$) δ 1.90 (m, 2H), 2.1 (m, 1H), 2.25 (m, 1H), 2.35 (s, 3H), 3.0-4.0 (br s, 2H), 3.76 (m, 1H), 4.70 (m, 1H), 7.2-7.4 (m, 4H).

Step B: Preparation of N-methyl-2-[1-[[5-methyl-3-(trifluoromethyl)-1H-pyrazol-1-yl]acetyl]-4-piperidinyl]-N-[(1R,4S)-1,2,3,4-tetrahydro-4-hydroxy-1-naphthalenyl]-4-thiazolecarboxamide and its enantiomer To a solution of (1S,4R)-1,2,3,4-tetrahydro-4-(methylamino)-1-naphthalenol and its enantiomer (283 mg, 1.6 mmol) (i.e. the product of Example 26, Step A) and triethylamine (0.5 mL, 3.6 mmol) in 5 mL of dichloromethane was gradually added 2-[1-[[5-methyl-3-(trifluoromethyl)-1H-pyrazol-1-yl]acetyl]-4-piperidinyl]-4-thiazolecarbonyl chloride (605 mg, 1.44 mmol) (i.e. the product of Example 19, Step D) at 0° C. The reaction mixture was stirred at room temperature for 1 h, diluted with dichloromethane, and washed with water, 1 N aqueous hydrochloric acid, water, saturated solution of sodium bicarbonate and brine. The filtered reaction mixture was dried over magnesium sulfate and concentrated in vacuo. The crude product was purified by medium-pressure liquid chromatography on silica gel using 0-20% of acetone in ethyl acetate as eluant to give 700 mg of the title compounds, compounds of the present invention as an off-white powder.

$^1$H NMR (CDCl$_3$) δ 1.6-1.9 (m, 3H), 2.0-2.3 (m, 6H), 2.31 and 2.33 (2s, 3H), 2.40 (m, 1 H), 2.7-3.0 (s and m, 4H), 3.2-3.4 (m, 2H), 3.9-4.1 (m, 1H), 4.3-4.6 (m, 1H), 4.80 (m, 1H), 4.97 (m, 2H), 5.6-6.0 (m, 1H), 6.35 (m, 1H), 7.2-7.4 (m, 4H), 7.88 (s, 1H).

EXAMPLE 27

Preparation of N-methyl-2-[1-[[5-methyl-3-(trifluoromethyl)-1H-pyrazol-1-yl]acetyl]-4-piperidinyl]-N-(1,2,3,4-tetrahydro-4-oxo-1-naphthalenyl)-4-thiazolecarboxamide (Compound 211)

A mixture of N-methyl-2-[1-[[5-methyl-3-(trifluoromethyl)-1H-pyrazol-1-yl]acetyl]-4-piperidinyl]-N-[(1R,4S)-1,2,3,4-tetrahydro-4-hydroxy-1-naphthalenyl]-4-thiazolecarboxamide and its enantiomer (96 mg, 0.17 mmol) (i.e. the product of Example 26, Step B) and manganese dioxide (400 mg, 4.6 mmol) in chloroform (2 mL) were swirled to form a vortex overnight at room temperature. The reaction mixture was filtered through Celite® diatomaceous filter aid, and purified by medium-pressure liquid chromatography on silica gel using 20% acetone in ethyl acetate as eluant to give 70 mg of the title compound, a compound of the present invention as a white foam.

¹H NMR (CDCl₃) δ 1.6-1.9 (m, 3H), 2.0-2.7 (m, 7H), 2.7-3.4 (s and m, 7H), 3.8-4.2 (m, 1H), 4.3-4.7 (m, 1H), 4.9-5.1 (m, 2H), 6.0-6.4 (m, 2H), 7.4 (m, 2H), 7.6 (m, 1H), 7.98 (m, 1H), 8.1 (m, 1H).

EXAMPLE 28

Preparation of N-methyl-2-[1-[[5-methyl-3-(trifluoromethyl)-1H-pyrazol-1-yl]acetyl]-4-piperidinyl]-N-[(1R,4R)-1,2,3,4-tetrahydro-4-hydroxy-1-naphthalenyl]-4-thiazolecarboxamide and its enantiomer (compound 206)

Step A: Preparation of (1R,4R)-1,2,3,4-tetrahydro-4-(methylamino)-1-naphthalenol and its enantiomer To a solution of (1S,4R)-1,2,3,4-tetrahydro-4-(methylamino)-1-naphthalenol and its enantiomer (517.6 mg, 2.92 mmol) (i.e. the product of Example 26, Step A) in tetrahydrofuran (3 mL) was added triphenylphosphine (766 mg, 2.92 mmol) and acetic acid (175 mg, 2.92 mmol). The mixture was cooled to 0° C. and diethyl azodicarboxylate (0.541 mL, 3.4 mmol) was gradually added. The reaction mixture was stirred at room temperature for 16 h, and concentrated in vacuo. The resulting residue was diluted with diethyl ether and allowed to stand at room temperature for 16 h. The precipitate formed was filtered, the filtrate was washed with saturated aqueous solution of sodium bicarbonate, dried over magnesium sulfate and concentrated under reduced pressure. The reaction residue was diluted with diethyl ether and extracted with 1 N aqueous hydrochloric acid. The aqueous extract was basified with 50% aqueous solution of sodium hydroxide to pH 9 and immediately extracted with diethyl ether. The organic extract was dried (MgSO₄) and concentrated to give 390 mg of inverted acetates, (1R,4R)-1,2,3,4-tetrahydro-4-(methylamino)-1-naphthalenyl acetate and its enantiomer. The acetate and its enantiomer were shaken for 6 h at room temperature with 2 g of Bio-Rad AG1-X2 (OH⁻) resin. The resin was filtered, the filtrate was evaporated in vacuo and the resulting residue was diluted with diethyl ether and extracted with 1 N aqueous hydrochloric acid. The acidic extract was basified with 50% aqueous solution of sodium hydroxide and extracted with dichloromethane. The organic extract was dried over magnesium sulfate and concentrated to give 70 mg of the title compounds as solid.
¹H NMR (CDCl₃) δ 1.73-1.86 (m, 2H), 2.1-2.3 (m, 2H), 3.68-3.72 (m, 1H), 4.78-4.81 (m, 1H), 7.23-7.46 (m, 4H).

Step B: Preparation of N-methyl-2-[1-[[5-methyl-3-(trifluoromethyl)-1H-pyrazol-1-yl]acetyl]-4-piperidinyl]-N-[(1R,4R)-1,2,3,4-tetrahydro-4-hydroxy-1-naphthalenyl]-4-thiazolecarboxamide and its enantiomer To a solution of (1R,4R)-1,2,3,4-tetrahydro-4-(methylamino)-1-naphthalenol and its enantiomer (70 mg, 0.39 mmol) (i.e. the product of Example 28, Step A) and triethylamine (0.082 mL, 0.59 mmol) in 2 mL of dichloromethane was gradually added 2-[1-[[5-methyl-3-(trifluoromethyl)-1H-pyrazol-1-yl]acetyl]-4-piperidinyl]-4-thiazolecarbonyl chloride (181 mg, 0.43 mmol) (i.e. the product of Example 19, Step D) at 0° C. The reaction mixture was stirred at room temperature for 3 h, diluted with 5 mL of dichloromethane, and washed with water, 1 N aqueous hydrochloric acid, saturated solution of sodium bicarbonate and brine. The filtered reaction mixture was dried over magnesium sulfate and concentrated in vacuo. The crude product was purified by medium-pressure liquid chromatography on silica gel using 0-20% of acetone in ethyl acetate as eluant to give 160 mg of the title compounds, compounds of the present invention as a white foam.
¹H NMR (CDCl₃) δ 1.6-2.3 (m, 11H), 2.78-3.03 (m, 4H), 3.20-3.36 (m, 2H), 3.88-4.61 (m, 2H), 4.80-5.05 (m, 3H), 5.78-6.12 (m, 1H), 6.32 (s, 1H), 7.18-7.36 (m, 4H), 7.60-7.66 (m, 1H), 7.91-7.95 (m, 1H).

EXAMPLE 29

Preparation of N-methyl-2-[1-[[5-methyl-3-(trifluoromethyl)-1H-pyrazol-1-yl]acetyl]-4-piperidinyl]-N-[(1R)-1,2,3,4-tetrahydro-1-naphthalenyl]-4-thiazolecarbothioamide (Compound 289)

A mixture of N-methyl-2-[1-[[5-methyl-3-(trifluoromethyl)-1H-pyrazol-1-yl]acetyl]-4-piperidinyl]-N-[(1R)-1,2,3,4-tetrahydro-1-naphthalenyl]-4-thiazolecarboxamide (Compound 149) (273 mg, 0.5 mmol) (i.e. the product of Example 6, Step D) and 2,4-bis(4-methoxyphenyl)-1,3-dithia-2,4-diphosphetane-2,4-disulfide (202 mg, 0.5 mmol) (Lawesson's reagent) in 5 mL of toluene was heated at 100° C. for 3 days. The reaction mixture was concentrated in vacuo, and the resulting residue was dissolved in 10 mL of dichloromethane and washed with 1 M aqueous solution of potassium carbonate, and dried over magnesium sulfate. The filtered residue was concentrated in vacuo and purified by medium-pressure liquid chromatography on silica gel using 50-100% of ethyl acetate in hexanes as eluant to give 70 mg of the title compound, a compound of the present invention as a white foam.
¹H NMR (CDCl₃) δ 1.54-2.40 (m, 1H), 230-2.93 (m, 4H), 3.20-3.33 (m, 4H), 3.90-4.60 (m, 2H), 4.92-5.45 (m, 3H), 6.31 (s, 1H), 7.00-7.22 (m, 4H), 7.72 (s, 1H).

EXAMPLE 30

Preparation of N-methyl-2-[4-[[5-methyl-3-(trifluoromethyl)-1H-pyrazol-1-yl]acetyl]-1-piperazinyl]-N-[(1R)-1,2,3,4-tetrahydro-1-naphthalenyl]-4-thiazolecarboxamide (Compound 220)

Step A: Preparation of 1,1-dimethylethyl 4-[4-(ethoxycarbonyl)-2-thiazolyl]-1-piperazinecarboxylate 1,1-Dimethylethyl 1-piperazinecarboxylate (1.86 g, 10 mmol), methyl 2-chloro-5-thiazolecarboxylate (1.92 g, 10.0 mmol), diazabicycloundecene (1.5 mL, 10 mmol) and a catalytic amount of potassium iodide (2 mg) were dissolved in 10 mL of dry dimethylsulfoxide and warmed to 80° C. for 16 h. The warm solution was added dropwise with stirring to 200 mL of cold water. The reaction mixture was extracted with diethyl ether. The resulting extract was washed with water and brine, dried over magnesium sulfate and concentrated under reduced pressure to give 3.23 g of a yellow oil which solidified on standing. The solid was recrystallized from diethyl ether/hexanes to give 1.0 g of the title compound as light yellow crystals. This compound was of sufficient purity to use in subsequent reactions.
¹H NMR (CDCl₃) δ1.37 (t, 3H), 1.48 (s, 9H), 3.53 (s, 8H), 4.38 (q, 2H), 7.47 (s, 1H).

Step B: Preparation of ethyl 2-(1-piperazinyl)-4-thiazolecarboxylate monohydrochloride A solution of 1,1-dimethylethyl 4-[4-(ethoxycarbonyl)-2-thiazolyl]-1-piperazinecarboxylate (1.0 g, 3.4 mmol) (i.e. the product of Example 30, Step A) in 10 mL of dichloromethane was treated with 2 M hydrogen chloride in diethyl ether (10 mL) and the reaction mixture was stirred at room temperature for 16 h. The resulting mixture was evaporated in vacuo to give 1.0 g of the title compound as a white solid. This compound was of sufficient purity to use in subsequent reactions.

$^1$H NMR (DMSO-$d_6$) δ 1.27 (t, 3H), 3.20 (br s, 4H), 3.70 (m, 4H), 4.22 (q, 2H), 7.81 (s, 1H), 9.55 (br s, 2H).

Step C: Preparation of ethyl-2-[4-[[5-methyl-3-(trifluoromethyl)-1H-pyrazol-1-yl]acetyl]-1-piperazinyl]-4-thiazolecarboxylate 5-Methyl-3-(trifluoromethyl)-1H-pyrazole-1-acetyl chloride (1.05 g, 2.5 mmol) (prepared as described in Example 19, step B) was dissolved in 10 mL of dichloromethane and added to a mixture of 2-(1-piperazinyl)-4-thiazolecarboxylate monohydrochloride (1.0 g, 3.0 mmol) (i.e. the product of Example 30, Step B) and powdered anhydrous potassium carbonate (2.2 g, 15.9 mmol) in 20 mL of dichloromethane at 0° C. The reaction mixture was allowed to warm to room temperature and stirred for 3 h. Then triethylamine (2 mL) was added to the reaction mixture, and the stirring was continued for an additional 30 minutes. The reaction mixture was diluted with dichloromethane, washed with 1 N aqueous hydrochloric acid, water, saturated aqueous solution of sodium bicarbonate and brine, and dried over magnesium sulfate. The filtered residue was evaporated in vacuo to give 1.0 g of a white foam. The resulting foam was slurried in 1-chlorobutane and filtered to give 0.83 g of the title compound as a white solid.

$^1$H NMR (CDCl$_3$) δ 1.38 (t, 3H), 2.33 (s, 3H), 3.5-3.8 (m, 8H), 4.36 (q, 2H), 5.00 (s, 2H), 6.34 (s, 1H), 7.51 (s, 1H).

Step D: Preparation of 2-[4-[[5-methyl-3-(trifluoromethyl)-1H-pyrazol-1-yl]acetyl]-1-piperazinyl]-4-thiazolecarboxylic acid A solution of ethyl-2-[4-[[5-methyl-3-(trifluoromethyl)-1H-pyrazol-1-yl]acetyl]-1-piperazinyl]-4-thiazolecarboxylate (0.83 g, 1.93 mmol) (i.e. the product of Example 30, Step C) in a mixture of methanol (10 mL) and tetrahydrofuran (10 mL) was treated with a 1 N aqueous NaOH solution (4.0 mL, 4.0 mmol). The reaction mixture was stirred at room temperature for 2 h, then treated with 1 N aqueous hydrochloric acid solution (4.5 mL, 4.5 mmol). The resulting mixture was concentrated in vacuo and the resulting suspension was diluted with dichloromethane and filtered to give solid. The resulting solid was washed with dichloromethane and diethyl ether, and air dried to give 0.64 g of the title compound as a white solid.

$^1$H NMR (DMSO-$d_6$) δ 2.21 (s, 3H), 3.4-3.7 (m, 8H), 5.32 (m, 2H), 6.51 (s, 1H), 7.69 (s, 1H), 12.7 (br s, 1H).

Step E: Preparation of N-methyl-2-[4-[[5-methyl-3-(trifluoromethyl)-1H-pyrazol-1-yl]acetyl]-1-piperazinyl]-N-[(1R)-1,2,3,4-tetrahydro-1-naphthalenyl]-4-thiazolecarboxamide 2-[4-[[5-methyl-3-(trifluoromethyl)-1H-pyrazol-1-yl]acetyl]-1-piperazin yl]-4-thiazolecarboxylic acid (200 mg, 0.5 mmol) (i.e. the product of Example 30, Step D) was suspended in 5 mL of dry dichloromethane and treated with triethylamine (150 μl, 1.08 mmol) to give a homogeneous solution. To this reaction mixture was added O-benzotriazol-1-yl-N,N,N',N'-tetramethyluronium hexafluorophosphate (HBTU, 210 mg, 0.55 mmol) followed by (1R)-1,2,3,4-tetrahydro-N-methyl-1-naphthalenamine (106 mg, 0.60 mmol) (i.e. the product of Example 6, Step A). The reaction mixture was stirred at ambient temperature for 3 h, passed through a Varian Chem Elut™ CE1010 column pretreated with 5 mL of 20% aqueous citric acid solution. The column was flushed with three column volumes of dichloromethane, concentrated and purified by silica gel chromatography eluting with ethyl acetate to give 223 mg of the title product, the compound of present invention as white foam.

$^1$H NMR (CDCl$_3$) δ 1.7-2.1 (m, 4H), 2.32 (s, 3H), 2.27 and 2.80 (two s, 3H), 3.4-3.8 (m, 8H), 4.98 (m, 2H), 5-65-6.05 (m, 1H), 6.34 (s, 1H), 7.1-7.3 (m, 5H).

EXAMPLE 31

Preparation of N-methyl-2-[1,2,3,6-tetrahydro-1-[[5-methyl-3-(trifluoromethyl)-1H-pyrazol-1-yl]acetyl]-4-pyridinyl]-N-[(1R)-1,2,3,4-tetrahydro-1-naphthalenyl]-4-thiazolecarboxamide (Compound 218) and N-methyl-2-[1,2,3,4-tetrahydro-1-[[5-methyl-3-(trifluoromethyl)-1H-pyrazol-1-yl]acetyl]-4-pyridinyl]-N-[(1R)-1,2,3,4-tetrahydro-1-naphthalenyl]-4-thiazolecarboxamide (Compound 315)

Step A: Preparation of 1,1-dimethylethyl 4-bromo-4-[4-(ethoxycarbonyl)-2-thiazolyl]-1-piperidinecarboxylate A mixture of 1,1-dimethylethyl 4-[4-(ethoxycarbonyl)-2-thiazolyl]-1-piperazinecarboxylate (3.4 g, 10 mmol) (i.e. the product of Example 30, Step A), N-bromosuccinimide (1.96 g, 11 mmol) and 2,2'-azobisisobutyronitrile (AIBN, 40 mg, 0.24 mmol) in 40 mL of carbon tetrachloride was refluxed for 1 h. The reaction mixture was then cooled, filtered, concentrated in vacuo, and purified by medium-pressure liquid chromatography on silica gel using 0-20% of ethyl acetate in 1-chlorobutane as eluant to give 1.9 g of the title compound as an oil.

$^1$H NMR (CDCl$_3$) δ 1.40 (t, 3H), 1.46 (s, 9H), 2.3-2.5 (m, 4H), 3.35 (m, 2H), 4.05 (m, 2H), 4.2 (m, 2H), 4.41 (q, 2H), 8.20 (s, 1H).

Step B: Preparation of 1,1-dimethylethyl 4-[4-(ethoxycarbonyl)-2-thiazolyl]-3,6-dihydro-1(2H)-piperidinecarboxylate A mixture of 1,1-dimethylethyl 4-bromo-4-[4-(ethoxycarbonyl)-2-thiazolyl]-1-piperidinecarboxylate (1.9 g, 4.5 mmol) (i.e. the product of Example 31, Step A) and anhydrous potassium carbonate (1.0 g, 7.2 mmol) were heated in 20 mL of acetonitrile at 80° C. overnight. The reaction mixture was cooled, filtered, concentrated in vacuo, and purified by medium-pressure liquid chromatography on silica gel using 0-20% of ethyl acetate in 1-chlorobutane as eluant to give 1.1 g of the title compound as a yellow oil.

$^1$H NMR (CDCl$_3$) δ 1.41 (t, 3H), 1.47 (s, 9H), 2.75 (m, 2H), 3.65 (m, 2H), 4.12 (m, 2H), 4.42 (q, 2H), 6.62 (m, 1H), 8.07 (s, 1H).

Step C: Preparation of ethyl 2-(1,2,3,6-tetrahydro-4-pyridinyl)-4-thiazolecarboxylate monohydrochloride A mixture of 1,1-dimethylethyl 4-[4-(ethoxycarbonyl)-2-thiazolyl]-3,6-dihydro-1(2H)-piperidinecarboxylate (1.1 g, 3.25 mmol) (i.e. the product of Example 31, Step B) in 50 mL of dichloromethane was treated with 10 mL of a 2 M solution of HCl in diethyl ether. The reaction mixture was stirred at room temperature for 16 h and concentrated in vacuo to give 1.0 g of the title compound as an orange solid.

$^1$H NMR (DMSO-d$_6$) δ 1.31 (t, 3H), 2.80 (m, 2H), 3.33 (m, 2H), 3.80 (m, 2H), 4.33 (q, 2H), 6.70 (m, 1H), 8.50 (s, 1H), 9.45 (br s, 2H).

Step D: Preparation of ethyl 2-[1,2,3,6-tetrahydro-1-[[5-methyl-3-(trifluoromethyl)-1H-pyrazol-1-yl]acetyl]-4-pyridinyl]-4-thiazolecarboxylate 5-Methyl-3-(trifluoromethyl)-1H-pyrazole-1-acetyl chloride (1.05 g, 2.5 mmol). (prepared as described in Example 19, step B) was dissolved in 10 mL of dichloromethane and added to a mixture of 2-(1,2,3,6-tetrahydro-4-pyridinyl)-4-thiazolecarboxylate monohydrochloride (1.0 g, 3.3 mmol) (i.e. the product of Example 31, Step C) and powdered anhydrous potassium carbonate (2.2 g, 15.9 mmol) in 20 mL of dichloromethane at 0° C. The reaction mixture was allowed to warm to room temperature and stirred for 3 h. Then triethylamine (2 mL) was added to the reaction mixture, and the stirring continued for an additional 20 minutes. The reaction mixture was diluted with dichloromethane, washed with 1 N aqueous hydrochloric acid, water, saturated aqueous solution of sodium bicarbonate and brine, and dried over magnesium sulfate. The filtered residue was evaporated in vacuo to give 1.0 g of a white foam. The resulting foam was purified by medium-pressure liquid chromatography on silica gel eluting with 0-50% ethyl acetate in 1-chlorobutane to give 0.67 g of the title compound as a yellow oil which solidified on standing.

$^1$H NMR (CDCl$_3$) δ 1.42 (t, 3H), 2.32 (s, 3H), 2.8 (m, 2H), 3.75-3.90 (m, 2H), 4.30 (m, 2H), 4.42 (q, 2H), 5.00 (m, 2H), 6.34 (s, 1H), 6.62 (m, 1H), 8.06 (m, 1H).

Step E: Preparation of N-methyl-2-[1,2,3,6-tetrahydro-1-[[5-methyl-3-(trifluoromethyl)-1H-pyrazol-1-yl]acetyl]-4-pyridinyl]-N-[(1R)-1,2,3,4-tetrahydro-1-naphthalenyl]-4-thiazolecarboxamide (Compound 218) and N-methyl-2-[1,2,3,4-tetrahydro-1-[[5-methyl-3-(trifluoromethyl)-1H-pyrazol-1-yl]acetyl]-4-pyridinyl]-N-[(1R)-1,2,3,4-tetrahydro-1-naphthalenyl]-4-thiazolecarboxamide (Compound 315)

Ethyl 2-[1,2,3,6-tetrahydro-1-[[5-methyl-3-(trifluoromethyl)-1H-pyrazol-1-yl]acetyl]-4-pyridinyl]-4-thiazolecarboxylate (0.67 g) (i.e. the product of Example 31, Step D) was dissolved in 10 mL of methanol and treated with 2 mL of a 1 N aqueous NaOH solution. The reaction mixture was stirred at room temperature for 1 h, and a solution of 1 N aqueous hydrochloric acid (2 mL) was added. The reaction mixture was diluted with water and the resulting aqueous layer was extracted with ethyl acetate. The extract was dried over magnesium sulfate and concentrated in vacuo to give 0.61 g of a tan solid. The resulting solid was dissolved in 25 mL of dichloromethane and treated with 0.5 mL of oxalyl chloride and 5 μL of N,N-dimethylformamide. The reaction mixture was stirred at room temperature for 3 h, and then concentrated in vacuo to give a tan foam. The resulting foam was dissolved in 3 mL of dichloromethane and the resulting mixture was added dropwise to a mixture of (1R)-1,2,3,4-tetrahydro-N-methyl-1-naphthalenamine (350 mg, 1.97 mmol) (i.e. the product of Example 6, Step A) and triethylamine (0.5 mL, 3.6 mmol) in 5 mL of dichloromethane.

The reaction mixture was then stirred at ambient temperature for 1 h and passed through a Varian Chem Elut™ CE1010 column pretreated with 7 mL of 1 N aqueous hydrochloric acid. The column was flushed with three column volumes of dichloromethane, concentrated in vacuo and purified by silica gel chromatography eluting with ethyl acetate to give two isomeric compounds:

124 mg of N-methyl-2-[1,2,3,4-tetrahydro-1-[[5-methyl-3-(trifluoromethyl)-1H-pyrazol-1-yl]acetyl]-4-pyridinyl]-N-[(1R)-1,2,3,4-tetrahydro-1-naphthalenyl]-4-thiazolecarboxamide (Compound 315) as white foam; $^1$H NMR (CDCl$_3$) δ 1.7-2.1 (m, 4H), 2.1-2.4 (m, 5H), 2.7-3.0 (m, 4H), 3.5-4.1 (m, 4H), 4.85-5.15 (m, 3H), 5.25-6.95 (m, 3H), 7.1-7.3 (m, 4H), 7.85 (m, 1H) and 114 mg of N-methyl-2-[1,2,3,6-tetrahydro-1-[[5-methyl-3-(trifluoromethyl)-1H-pyrazol-1-yl]acetyl]-4-pyridinyl]-N-[(1R)-1,2,3,4-tetrahydro-1-naphthalenyl]-4-thiazolecarboxamide (Compound 218) as a white foam; $^1$H NMR (CDCl$_3$) δ 1.7-2.1 (m, 3H), 2.1-2.4 (m, 4H), 2.6-3.0 (m, 7H), 3.7-3.9 (m, 2H), 4.25 (m, 2H), 5.02 (m, 2H), 5.7-6.6 (m, 3H), 7.1-7.3 (m, 4H), 7.88 (m, 1H).

EXAMPLE 32

Preparation of N-methyl-2-[1-[[5-methyl-3-(trifluoromethyl)-1H-pyrazol-1-yl]acetyl]-4-piperidinyl]-N-[(1R)-1,2,3,4-tetrahydro-1-naphthalenyl]-2H-1,2,3-triazole-4-carboxamide (Compound 232)

Step A: Preparation of 1,1-dimethylethyl 4-[4-(ethoxycarbonyl)-2H-1,2,3-triazol-2-yl]-1-piperidinecarboxylate To a solution of t-butyl 4-hydroxypiperidine-1-carboxylate (0.43 g, 3.3 mmol) and triphenylphosphine (1.05 g, 4.0 mmol) in tetrahydrofuran (15 mL) at 0° C. was added dropwise diethyl azodicarboxylate (0.63 mL, 4.0 mmol). After 5 minutes ethyl 1H-1,2,3-triazole-4-carboxylate (0.43 g, 3.0 mmol, prepared according to D. R. Buckle, C. J. M. Rockell, J. Chem. Soc., Perkin Transaction 1 1982, 2, 627-630) was added in tetrahydrofuran (5 mL). The reaction mixture was stirred overnight at room temperature. The reaction mixture was concentrated under reduced pressure and the residue was purified by medium pressure liquid chromatography (HPLC) using 15 to 40% ethyl acetate in hexanes as eluant to afford 0.42 g of the title compound as an oil.

$^1$H NMR (CDCl$_3$) δ 1.41 (t, 3H), 1.47 (s, 9H), 2.13 (m, 4H), 2.97 (m, 2H), 4.19 (m, 2H), 4.42 (q, 2H), 4.69 (m, 1H), 8.04 (s, 1H).

Additionally eluting before the title compound was isolated 0.35 g of 1,1-dimethyl-ethyl 4-[5-(ethoxycarbonyl)-1H-1,2,3-triazol-1-yl]-1-piperidinecarboxylate.

$^1$H NMR (CDCl$_3$) δ 1.41 (t, 3H), 1.48 (s, 9H), 2.09 (m, 2H), 2.29 (m, 2H), 2.94 (m, 2H), 4.30 (m, 2H), 4.39 (q, 2H), 5.27 (m, 1H), 8.13 (s, 1H).

Step B: Preparation of ethyl 2-[1-[[5-methyl-3-(trifluoromethyl)-1H-pyrazol-1-yl]acetyl]-4-piperidinyl]-2H-1,2,3-triazole-4-carboxylate Trifluoroacetic acid (3 mL) was added to 1,1-dimethylethyl 4-[4-(ethoxycarbonyl)-2H-1,2,3-triazol-2-yl]-1-piperidinecarboxylate (0.41 g, 1.3 mmol) (i.e. the product of Example 32, Step A). The reaction mixture was stirred for 45 minutes. The reaction mixture was then concentrated in vacuo. The resulting mixture was treated with saturated aqueous sodium bicarbonate and the aqueous layer was extracted three times with dichloromethane. The solvent was removed with a rotary evaporator to afford 0.23 g of ethyl 4-piperidinyl-2H-1,2,3-triazole-4-carboxylate as an oil. This compound was of sufficient purity to use in subsequent reactions.

To a slurry of 5-methyl-3-(trifluoromethyl)-1H-pyrazole-1-acetic acid (0.23 g, 1.1 mmol) in dichloromethane (5 mL) was added oxalyl chloride (0.20 mL, 14 mmol) and one drop of N,N-dimethylformamide. After 45 minutes the reaction mixture was concentrated in vacuo and the resulting residue was dissolved in dichloromethane (10 mL). The reaction mixture was then added to a solution of ethyl 4-piperidinyl-2H-1,2,3-triazole-4-carboxylate (0.23 g) and triethylamine (0.20 mL, 1.4 mmol) in dichloromethane (10 mL) at 0° C. The reaction mixture was stirred at room temperature overnight. The organic layer was washed with saturated aqueous sodium bicarbonate, dried ($Na_2SO_4$) and the solvent was removed with a rotary evaporator. The residue was purified by medium pressure liquid chromatography (MPLC) using 35 to 60% ethyl acetate in hexanes as eluant to afford 0.35 g of the title compound as a white solid.

$^1$H NMR ($CDCl_3$) δ 1.41 (t, 3H), 2.23 (m, 4H), 2.33 (s, 3H), 3.09 (m, 1H), 3.40 (m, 1H), 4.10 (m, 1H), 4.43 (q, 2H), 4.45 (m, 1H), 4.80 (m, 1H), 5.00 (m, 2H), 6.34 (s, 1H), 8.06 (s, 1H).

Step C: Preparation of 2-[1-[[5-methyl-3-(trifluoromethyl)-1H-pyrazol-1-yl]acetyl]-4-piperidinyl]-2H-1,2,3-triazole-4-carboxylic acid Ethyl 2-[1-[[5-methyl-3-(trifluoromethyl)-1H-pyrazol-1-yl]acetyl]-4-piperidinyl]-2H-1,2,3-triazole-4-carboxylate (0.35 g, 0.82 mmol) (i.e. the product of Example 32, Step B) was dissolved in a mixture of methanol (5 mL) and tetrahydrofuran (2 mL). A 1 N aqueous solution of sodium hydroxide (1.6 mL, 1.6 mmol) was added to the reaction mixture and the mixture was stirred overnight. The reaction mixture was concentrated in vacuo and the residue was dissolved in water. The aqueous layer was washed with diethyl ether and the aqueous layer was acidified with concentrated hydrochloric acid to pH 1, and extracted with dichloromethane and then chloroform. The combined organic layers were dried ($Na_2SO_4$) and concentrated in vacuo to afford 0.27 g of the title compound as a white solid.

$^1$H NMR ($CDCl_3$) δ 2.23 (m, 4H), 2.33 (s, 3H), 3.10 (m, 1H), 3.41 (m, 1H), 4.08 (m, 1H), 4.45 (m, 1H), 4.81 (m, 1H), 5.02 (m, 2H), 6.37 (s, 1H), 8.13 (s, 1H).

Step D: Preparation of N-methyl-2-[1-[[5-methyl-3-(trifluoromethyl)-1H-pyrazol-1-yl]acetyl]-4-piperidinyl]-N-[(1R)-1,2,3,4-tetrahydro-1-naphthalenyl]-2H-1,2,3-triazole-4-carboxamide To a slurry of 2-[1-[[5-methyl-3-(trifluoromethyl)-1H-pyrazol-1-yl]acetyl]-4-piperidinyl]-2H-1,2,3-triazole-4-carboxylic acid (0.070 g, 0.18 mmol) (i.e. the product of Example 32, Step C) in dichloromethane (2 mL) was added oxalyl chloride (0.05 mL, 0.35 mmol) and one drop of N,N-dimethylformamide. After 45 minutes the reaction mixture was concentrated in vacuo and the resulting residue was dissolved in dichloromethane (10 mL). The reaction mixture was then added to a solution of (R)—N-methyl-1,2,3,4-tetrahydronaphthalen-1-ylamine (32 mg, 0.20 mmol) and triethylamine (0.033 mL, 0.24 mmol) in dichloromethane (2 mL) at 0° C. The reaction mixture was stirred at room temperature overnight. The organic layer was washed with saturated aqueous sodium bicarbonate, dried ($Na_2SO_4$) and the solvent was removed with a rotary evaporator. The residue was purified by medium pressure liquid chromatography (MPLC) using 35-60% ethyl acetate in hexanes as eluant to afford 74 mg of the title product, a compound of the present invention as an oil.

$^1$H NMR ($CDCl_3$) δ 1.8-2.3 (m, 8H), 2.31 and 2.33 (2s, total 3H), 2.86 (m, 2H), 2.81 and 3.01 (2s, total 3H), 3.13 (m, 1H), 3.40 (m, 1H), 3.98 and 4.07 (2 m, total 1H), 4.32 and 4.42 (2 m, total 1H), 4.71 and 4.75 (2 m, total 1H), 5.02 (m, 2H), 5.83 and 6.08 (2 m, total 1H), 6.34 and 6.34 (s and d, total 1H), 7.30 (m, 4H), 8.06 and 8.11 (2s, total 1H).

EXAMPLE 33

Preparation of N-methyl-1-[1-[[5-methyl-3-(trifluoromethyl)-1H-pyrazol-1-yl]acetyl]-4-piperidinyl]-N-[(1R)-1,2,3,4-tetrahydro-1-naphthalenyl]-1H-pyrazole-4-carboxamide (Compound 233)

Step A: Preparation of 1,1-dimethylethyl 4-[4-(ethoxycarbonyl)-1H-pyrazol-1-yl]-1-piperidinecarboxylate By a procedure analogous to that of Example 32 Step A, t-butyl 4-hydroxypiperidine-1-carboxylate (0.79 g, 3.6 mmol) was reacted with triphenylphosphine (1.26 g, 4.8 mmol), diethyl azodicarboxylate (0.76 mL, 4.8 mmol) and ethyl 1H-pyrazole-4-carboxylate (0.50 g, 3.6 mmol) to afford the title compound (0.76 g) as a white solid.

$^1$H NMR (acetone-$d_6$) δ 1.29 (t, 3H), 1.46 (s, 9H), 1.93 (m, 2H), 2.07 (m, 2H), 2.95 (m, 2H), 4.20 (m, 2H), 4.25 (q, 2H), 4.46 (m, 1H), 7.82 (s, 1H), 8.19 (s, 1H).

Step B: Preparation of ethyl 141-[[5-methyl-3-(trifluoromethyl)-1H-pyrazol-1-yl]acetyl)-4-piperidinyl]-1H-pyrazole-4-carboxylate By a procedure analogous to that of Example 32 Step B, 1,1-dimethylethyl 4-[4-(ethoxycarbonyl)-1H-pyrazol-1-yl]-1-piperidinecarboxylate (0.38 g, 1.2 mmol) (i.e. the product of Example 33, Step A) was deprotected with trifluoroacetic acid (4 mL) to afford the corresponding amine (0.18 g). This amine was reacted with the acid chloride formed from 5-methyl-3-(trifluoromethyl)-1H-pyrazole-1-acetic acid (0.18 g, 0.88 mmol) and oxalyl chloride (0.10 mL, 1.15 mmol) in the presence of triethylamine (0.16 mL, 1.15 mmol) to afford 0.24 g of the title compound as a white solid.

$^1$H NMR ($CDCl_3$) δ 1.35 (t, 3H), 1.95 (m, 2H), 2.24 (m, 2H), 2.34 (s, 3H), 2.90 (m, 1H), 3.32 (m, 1H), 4.13 (m, 1H), 4.30 (q, 2H), 4.37 (m, 1H), 4.63 (m, 1H), 4.99 (s, 2H), 6.34 (s, 1H), 7.91 (s, 1H), 7.92 (s, 1H).

Step C: Preparation of 1-[1-[[5-methyl-3-(trifluoromethyl)-1H-pyrazol-1-yl]acetyl]-4-piperidinyl]-1H-pyrazole-4-carboxylic acid By a procedure analogous to that of Example 32 Step C, ethyl 2-[1-[[5-methyl-3-(trifluoromethyl)-1H-pyrazol-1-yl]acetyl]-4-piperidinyl]-2H-1,2,3-triazole-4-carboxylate (0.24 g, 0.58 mmol) (i.e. the product of Example 33, Step B) was hydrolyzed with 1 N aqueous sodium hydroxide (1.2 mL, 1.2 mmol) to afford 0.125 g of the title compound as a white solid.

$^1$H NMR (DMSO-$d_6$) δ 1.82 (m, 1H), 2.07 (m, 3H), 2.21 (s, 3H), 2.83 (m, 1H), 3.26 (m, 1H), 4.00 (d, 1H), 4.39 (d, 1H), 4.52 (m, 1H), 5.29 (m, 2H), 6.50 (s, 1H), 7.82 and 7.90 (two s, total 1H), 8.30 and 8.42 (two s, total 1H).

Step D: Preparation of N-methyl-1-[1-[[5-methyl-3-(trifluoromethyl)-1H-pyrazol-1-yl]acetyl]-4-piperidinyl]-N-[(1R)-1,2,3,4-tetrahydro-1-naphthalenyl]-1H-pyrazole-4-carboxamide By a procedure analogous to that of Example 32, Step D, 1-[1-[[5-methyl-3-(trifluoromethyl)-1H-pyrazol-1-yl]

acetyl]-4-piperidin yl]-1H-pyrazole-4-carboxylic acid (0.081 g, 0.21 mmol) (i.e. the product of Example 33, Step C) was reacted with oxalyl chloride (0.05 mL) and the resulting product was reacted with (R)—N-methyl-1,2,3,4-tetrahydronaphthalen-1-ylamine (0.038 g, 0.23 mmol) and triethylamine (0.038 mL, 0.27 mmol) to afford 0.073 g of the title compound, a compound of the present invention as an oil after purification by medium pressure liquid chromatography.

$^1$H NMR (CDCl$_3$) δ 1.8-2.3 (m, 8H), 2.33 and 2.34 (two s, total 3H), 2.82 (m, 3H), 2.78 and 2.92 (two s, total 3H), 3.31 (m, 1H), 4.00 (m, 1H), 4.37 (m, 1H), 4.64 (m, 1H), 5.00 (m, 2H), 5.36 and 6.02 (two m, total 1H), 6.34 (s, 1H), 7.19 (m, 4H), 7.68 and 7.80 (two s, total 1H), 7.80 and 7.93 (two s, total 1H).

By the procedures described herein, together with methods known in the art, the following compounds of Tables 1A to 10 can be prepared. The following abbreviations are used in the Tables which follow: t means tertiary, s means secondary, n means normal, means iso, c means cyclo, Ac means acetyl, Me means methyl, Et means ethyl, Pr means propyl, i-Pr means isopropyl, c-Pr means cyclopropyl, Bu means butyl, Pen means pentyl, Hex means hexyl, CN means cyano. A dash (-) indicates no substituents.

The invention includes but is not limited to the following exemplary species.

TABLE 1A

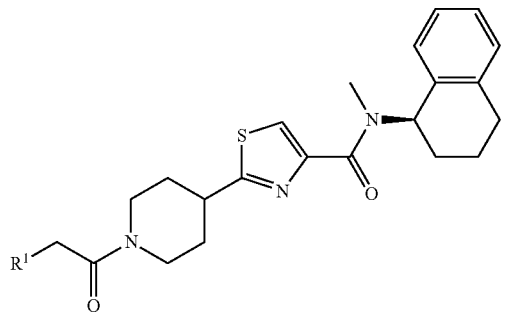

| R$^1$ |
|---|
| phenyl |
| 2-methylphenyl |
| 2-methoxyphenyl |
| 2-chlorophenyl |
| 2-bromophenyl |
| 2-ethylphenyl |
| 2-ethoxyphenyl |
| 2-(methylthio)phenyl |
| 2-(ethylthio)phenyl |
| 2-(trifluoromethoxy)phenyl |
| 3-chlorophenyl |
| 3-bromophenyl |
| 3-iodophenyl |
| 3-methylphenyl |
| 3-ethylphenyl |
| 3-propylphenyl |
| 3-isopropylphenyl |
| 3-(trifluoromethyl)phenyl |
| 3-(2,2,2-trifluoroethyl)phenyl |
| 3-(pentafluoroethyl)phenyl |
| 3-cyanophenyl |
| 3-nitrophenyl |
| 2,5-dichlorophenyl |
| 5-bromo-2-chlorophenyl |
| 2-chloro-5-iodophenyl |
| 2-chloro-5-methylphenyl |
| 2-chloro-5-ethylphenyl |
| 2-chloro-5-propylphenyl |
| 2-chloro-5-isopropylphenyl |
| 2-chloro-5-(trifluoromethyl)phenyl |

TABLE 1A-continued

| R$^1$ |
|---|
| 2-chloro-5-(2,2,2-trifluoroethyl)phenyl |
| 2-chloro-5-(pentafluoroethyl)phenyl |
| 2-chloro-5-cyanophenyl |
| 2-chloro-5-nitrophenyl |
| 2-bromo-5-chlorophenyl |
| 2,5-dibromophenyl |
| 2-bromo-5-iodophenyl |
| 2-bromo-5-methylphenyl |
| 2-bromo-5-ethylphenyl |
| 2-bromo-5-propylphenyl |
| 2-bromo-5-isopropylphenyl |
| 2-bromo-5-(trifluoromethyl)phenyl |
| 2-bromo-5-(2,2,2-trifluoroethyl)phenyl |
| 2-bromo-5-(pentafluoroethyl)phenyl |
| 2-bromo-5-cyanophenyl |
| 2-bromo-5-nitrophenyl |
| 5-chloro-2-methylphenyl |
| 5-bromo-2-methylphenyl |
| 5-iodo-2-methylphenyl |
| 2,5-dimethylphenyl |
| 5-ethyl-2-methylphenyl |
| 2-methyl-5-propylphenyl |
| 5-isopropyl-2-methylphenyl |
| 2-methyl-5-(trifluoromethyl)phenyl |
| 2-methyl-5-(2,2,2-trifluoroethyl)phenyl |
| 2-methyl-5-(pentafluoroethyl)phenyl |
| 5-cyano-2-methylphenyl |
| 2-methyl-5-nitrophenyl |
| 5-chloro-2-methoxyphenyl |
| 5-bromo-2-methoxyphenyl |
| 5-iodo-2-methoxyphenyl |
| 2-methoxy-5-methylphenyl |
| 5-ethyl-2-methoxyphenyl |
| 2-methoxy-5-propylphenyl |
| 5-isopropyl-2-methoxyphenyl |
| 2-methoxy-5-(trifluoromethyl)phenyl |
| 2-methoxy-5-(2,2,2-trifluoroethyl)phenyl |
| 2-methoxy-5-(pentafluoroethyl)phenyl |
| 5-cyano-2-methoxyphenyl |
| 2-methoxy-5-nitrophenyl |
| 5-chloro-2-ethylphenyl |
| 5-bromo-2-ethylphenyl |
| 2-ethyl-5-iodophenyl |
| 2-ethyl-5-methylphenyl |
| 2,5-diethylphenyl |
| 2-ethyl-5-propylphenyl |
| 2-ethyl-5-isopropylphenyl |
| 2-ethyl-5-(trifluoromethyl)phenyl |
| 2-ethyl-5-(2,2,2-trifluoroethyl)phenyl |
| 2-ethyl-5-(pentafluoroethyl)phenyl |
| 5-cyano-2-ethylphenyl |
| 2-ethyl-5-nitrophenyl |
| 3-methylpyrazol-1-yl |
| 3-chloropyrazol-1-yl |
| 3-bromopyrazol-1-yl |
| 3-iodopyrazol-1-yl |
| 3-ethylpyrazol-1-yl |
| 3-(trifluoromethyl)pyrazol-1-yl |
| 3-(2,2,2-trifluoroethyl)pyrazol-1-yl |
| 3-(pentafluoroethyl)pyrazol-1-yl |
| 3-cyanopyrazol-1-yl |
| 3-nitropyrazol-1-yl |

TABLE 1A-continued

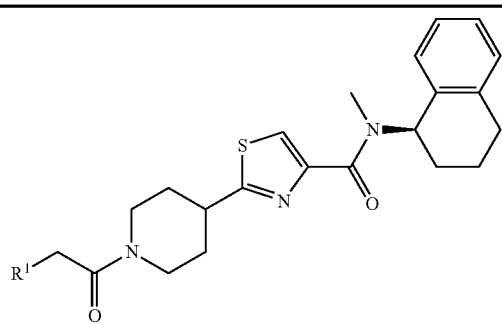

R¹

3,5-dimethylpyrazol-1-yl
3-chloro-5-methylpyrazol-1-yl
3-bromo-5-methylpyrazol-1-yl
3-iodo-5-methylpyrazol-1-yl
3-ethyl-5-methylpyrazol-1-yl
5-methyl-3-propylpyrazol-1-yl
3-isopropyl-5-methylpyrazol-1-yl
5-methyl-3-(trifluoromethyl)pyrazol-1-yl
5-methyl-3-(2,2,2-trifluoroethyl)pyrazol-1-yl
5-methyl-3-(pentafluoroethyl)pyrazol-1-yl
3-cyano-5-methylpyrazol-1-yl
5-methyl-3-nitropyrazol-1-yl
5-chloro-3-methylpyrazol-1-yl
3,5-dichloropyrazol-1-yl
5-chloro-3-bromopyrazol-1-yl
5-chloro-3-iodopyrazol-1-yl
5-chloro-3-ethylpyrazol-1-yl
5-chloro-3-propylpyrazol-1-yl
5-chloro-3-isopropylpyrazol-1-yl
5-chloro-3-(trifluoromethyl)pyrazol-1-yl
5-chloro-3-(2,2,2-trifluoroethyl)pyrazol-1-yl
5-chloro-3-(pentafluoroethyl)pyrazol-1-yl
5-chloro-3-cyanopyrazol-1-yl
5-chloro-3-nitropyrazol-1-yl
5-bromo-3-methylpyrazol-1-yl
5-bromo-3-chloropyrazol-1-yl
3,5-dibromopyrazol-1-yl
5-bromo-3-iodopyrazol-1-yl
5-bromo-3-ethylpyrazol-1-yl
5-bromo-3-propylpyrazol-1-yl
5-bromo-3-isopropylpyrazol-1-yl
5-bromo-3-(trifluoromethyl)pyrazol-1-yl
5-bromo-3-(2,2,2-trifluoroethyl)pyrazol-1-yl
5-bromo-3-(pentafluoroethyl)pyrazol-1-yl
5-bromo-3-cyanopyrazol-1-yl
5-bromo-3-nitropyrazol-1-yl
5-methoxy-3-methylpyrazol-1-yl
3-chloro-5-methoxypyrazol-1-yl
5-ethyl-3-methylpyrazol-1-yl
3-chloro-5-ethylpyrazol-1-yl
3-bromo-5-ethylpyrazol-1-yl
5-ethyl-3-iodopyrazol-1-yl
3,5-diethylpyrazol-1-yl
5-ethyl-3-propylpyrazol-1-yl
5-ethyl-3-isopropylpyrazol-1-yl
5-ethyl-3-(trifluoromethyl)pyrazol-1-yl
5-ethyl-3-(2,2,2-trifluoroethyl)pyrazol-1-yl
5-ethyl-3-(pentafluoroethyl)pyrazol-1-yl
3-cyano-5-ethylpyrazol-1-yl
5-ethyl-3-nitropyrazol-1-yl
5-butyl-2-methylphenyl
5-hexyl-2-methylphenyl
5-allyl-2-methylphenyl
2-methyl-5-(4-methyl-3-pentenyl)phenyl
2-methyl-5-propargylphenyl
2-methyl-5-(3-methylpropargyl)phenyl
5-cyclopropyl-2-methylphenyl
5-cyclohexyl-2-methylphenyl
2-methyl-5-(pentafluoroisopropyl)phenyl
5-(3,3-dichloro-2-propen-1-yl)-2-methylphenyl
2-methyl-5-(4,4,4-trifluoro-2-butyn-1-yl)phenyl
5-(2,2-dichlorocyclopropan-1-yl)-2-methylphenyl TABLE 1A-continued

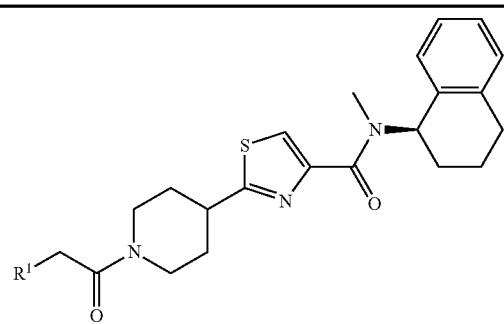

R¹

2-methyl-5-(trifluoromethoxy)phenyl
2-chloro-5-(isobutylthio)phenyl
2-chloro-5-(ethylsulfonyl)phenyl
2-chloro-5-(trifluoromethylthio)phenyl
2-chloro-5-(trifluoromethylsulfonyl)phenyl
2-chloro-5-(methylamino)phenyl
2-chloro-5-(tert-butylamino)phenyl
2-chloro-5-(dimethylamino)phenyl
2-chloro-5-9diethylamino)phenyl
2-chloro-5-(cyclopropylamino)phenyl
3-(methoxymethyl)phenyl
2-chloro-5-(ethoxymethyl)phenyl
2-chloro-5-(hyroxymethyl)phenyl
2-chloro-5-(methoxycarbonyl)phenyl
2-chloro-5-(ethylcarbonyl)phenyl
2-chloro-5-(methylcarbonyloxy)phenyl
2-chloro-5-(metylaminocarbonyl)phenyl
2-chloro-5-(dimethylaminocarbonyl)phenyl
2-methyl-5-(trimethylsilyl)phenyl
3,5-dimethyl-2-thienyl
3,5-dichloro-2-thienyl
3,5-dimethyl-2-furyl
1-methyl-2-pyrrolyl
4-methyl-2-trifluoromethyl-5-thiazolyl
4-trifluoromethyl-2-thiazolyl
4-trifluoromethyl-2-oxazolyl
4-methyl-2-trifluoromethyl-5-oxazolyl
4-bromo-5-isothiazolyl
4-bromo-5-isoxazolyl
1-methyl-5-pyrazolyl
1-methyl-5-imidazolyl
1-methyl-4-trifluoromethyl-2-imidazolyl
4-methyl-3-(1,3,4-triazolyl)
2-methyl-3-(1,2,4-triazolyl)
5-trifluoromethyl-2-(1,3,4-thiadiazolyl)
5-trifluoromethyl-2-(1,3,4-oxadiazolyl)
3-trifluoromethyl-5-(1,2,4-thiadiazolyl)
3-trifluoromethyl-5-(1,2,4-oxadiazolyl)
3-trifluoromethyl-1-(1,2,4-triazolyl)
2,5-dimethyl-1-pyrrolyl
2,5-dimethyl-3-furyl
2,5-dimethyl-3-thienyl
2,5-dichloro-3-thienyl
1,4-dimethyl-3-pyrrolyl
1,4-dimethyl-3-pyrazolyl
1,3-dimethyl-4-pyrazolyl
2,5-dimethyl-4-oxazolyl
2,5-dimethyl-4-thiazolyl
3-bromo-4-isothiazolyl
3-bromo-4-isooxazolyl
1-methyl-4-imidazolyl
5-trifluoromethyl-3-(1,2,4-oxadiazolyl)
5-trifluoromethyl-3-(1,2,4-thiadiazolyl)
2-bromo-1-(1,3,4-triazolyl)
5-trifluoromethyl-3-(1,2,4-triazolyl)
2-bromo-1-imidazolyl
3,6-dimethyl-2-pyridyl
2,5-dimethyl-3-pyridyl
2,5-dimethyl-4-pyridyl
3,6-dichloro-2-pyridyl
2,5-dichloro-3-pyridyl
2,5-dichloro-4-pyridyl

TABLE 1A-continued

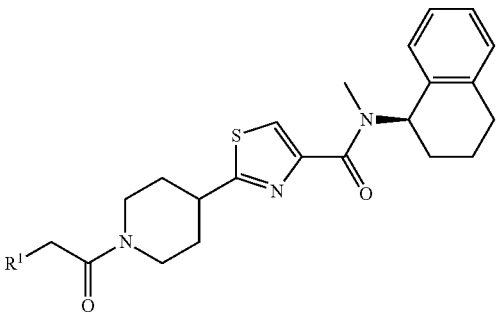

R[1]

4-bromo-3-pyridazinyl
4-trifluoromethyl-2-pyrimidinyl
3,6-dimethyl-2-pyrazinyl
2,5-dimethyl-4-pyrimidinyl
4-methoxy-5-pyrimidinyl
3,6-dimethyl-4-pyridazinyl
5-trifluoromethyl-3-(1,2,4-triazinyl)
5-methoxy-6-(1,2,4-triazinyl)
4-trifluoromethyl-2-(1,3,5-triazinyl)
3,6-dimethyl-5-(1,2,4-triazinyl)
3,5-bis-(trifluoromethyl)pyrazol-1-yl
1-methyl-3-(trifluoromethyl)pyrazol-5-yl
1-methyl-4-(trifluoromethylbiraidazol-2-yl

TABLE 1B

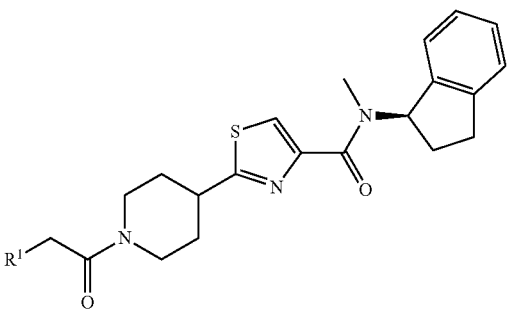

R[1]

2-methoxyphenyl
3-bromophenyl
3-iodophenyl
3-(trifluoromethyl)phenyl
3-(2,2,2-trifluoroethyl)phenyl
3-(pentafluoroethyl)phenyl
3-cyanophenyl
3-nitrophenyl
2,5-dichlorophenyl
5-bromo-2-chlorophenyl
2-chloro-5-iodophenyl
2-chloro-5-methylphenyl
2-chloro-5-ethylphenyl
2-chloro-5-(trifluoromethyl)phenyl
2-chloro-5-(2,2,2-trifluoroethyl)phenyl
2-chloro-5-(pentafluoroethyl)phenyl
2-chloro-5-cyanophenyl
2-chloro-5-nitrophenyl
2-bromo-5-chlorophenyl
2,5-dibromophenyl
2-bromo-5-iodophenyl
2-bromo-5-methylphenyl
2-bromo-5-ethylphenyl
2-bromo-5-propylphenyl
2-bromo-5-(trifluoromethyl)phenyl
2-bromo-5-(2,2,2-trifluoroethyl)phenyl

TABLE 1B-continued

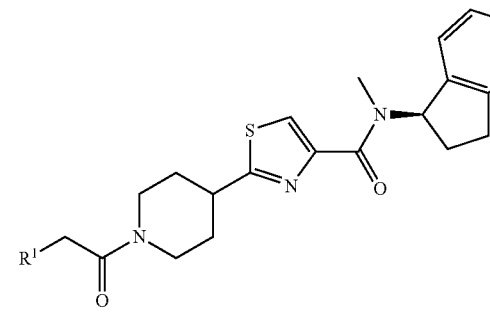

R[1]

2-bromo-5-(pentafluoroethyl)phenyl
2-bromo-5-cyanophenyl
2-bromo-5-nitrophenyl
5-chloro-2-methylphenyl
5-bromo-2-methylphenyl
5-iodo-2-methylphenyl
2,5-dimethylphenyl
5-ethyl-2-methylphenyl
2-methyl-5-propylphenyl
5-isopropyl-2-methylphenyl
2-methyl-5-(trifluoromethyl)phenyl
2-methyl-5-(2,2,2-trifluoroethyl)phenyl
2-methyl-5-(pentafluoroethyl)phenyl
5-cyano-2-methylphenyl
2-methyl-5-nitrophenyl
5-chloro-2-methoxyphenyl
5-bromo-2-methoxyphenyl
5-iodo-2-methoxyphenyl
2-methoxy-5-methylphenyl
5-ethyl-2-methoxyphenyl
2-methoxy-5-propylphenyl
2-methoxy-5-(trifluoromethyl)phenyl
2-methoxy-5-(2,2,2-trifluoroethyl)phenyl
2-methoxy-5-(pentafluoroethyl)phenyl
5-cyano-2-methoxyphenyl
2-methoxy-5-nitrophenyl
5-chloro-2-ethylphenyl
5-bromo-2-ethylphenyl
2-ethyl-5-iodophenyl
2-ethyl-5-methylpbenyl
2,5-diethylphenyl
2-ethyl-5-propylphenyl
2-ethyl-5-((trifluoromethyl))phenyl
2-ethyl-5-(2,2,2-trifluoroethyl)phenyl
2-ethyl-5-(pentafluoroethyl)phenyl
5-cyano-2-ethylphenyl
2-ethyl-5-nitrophenyl
3-chloropyrazol-1-yl
3-bromopyrazol-1-yl
3-(trifluoromethyl)pyrazol-1-yl
3-(2,2,2-trifluoroethyl)pyrazol-1-yl
3-(pentafluoroethyl)pyrazol-1-yl
3-cyanopyrazol-1-yl
3-nitropyrazol-1-yl
3,5-dimethylpyrazol-1-yl
3-chloro-5-methylpyrazol-1-yl
3-bromo-5-methylpyrazol-1-yl
3-iodo-5-methylpyrazol-1-yl
3-ethyl-5-methylpyrazol-1-yl
5-methyl-3-propylpyrazol-1-yl
5-methyl-3-(trifluoromethyl)pyrazol-1-yl
5-methyl-3-(2,2,2-trifluoroethyl)pyrazol-1-yl
5-methyl-3-(pentafluoroethyl)pyrazol-1-yl
3-cyano-5-methylpyrazol-1-yl
5-methyl-3-nitropyrazol-1-yl
5-chloro-3-methylpyrazol-1-yl
3,5-dichloropyrazol-1-yl
5-chloro-3-bromopyrazol-1-yl
5-chloro-3-iodopyrazol-1-yl
5-chloro-3-ethylpyrazol-1-yl
5-chloro-3-propylpyrazol-1-yl
5-chloro-3-(trifluoromethyl)pyrazol-1-yl

TABLE 1B-continued

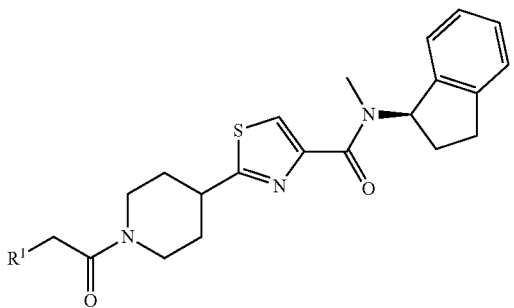

| R¹ |
|---|
| 5-chloro-3-(2,2,2-trifluoroethyl)pyrazol-1-yl |
| 5-chloro-3-(pentafluoroethyl)pyrazol-1-yl |
| 5-chloro-3-cyanopyrazol-1-yl |
| 5-chloro-3-nitropyrazol-1-yl |
| 5-bromo-3-methylpyrazol-1-yl |
| 5-bromo-3-chloropyrazol-1-yl |
| 3,5-dibromopyrazol-1-yl |
| 5-bromo-3-iodopyrazol-1-yl |
| 5-bromo-3-ethylpyrazol-1-yl |
| 5-bromo-3-propylpyrazol-1-yl |
| 5-bromo-3-(trifluoromethyl)pyrazol-1-yl |
| 5-bromo-3-(2,2,2-trifluoroethyl)pyrazol-1-yl |
| 5-bromo-3-(pentafluoroethyl)pyrazol-1-yl |
| 5-ethyl-3-methylpyrazol-1-yl |
| 3-chloro-5-ethylpyrazol-1-yl |
| 3-bromo-5-ethylpyrazol-1-yl |
| 5-ethyl-3-iodopyrazol-1-yl |
| 3,5-diethylpyrazol-1-yl |
| 5-ethyl-3-propylpyrazol-1-yl |
| 5-ethyl-3-(trifluoromethyl)pyrazol-1-yl |
| 5-ethyl-3-(2,2,2-trifluoroethyl)pyrazol-1-yl |
| 5-ethyl-3-(pentafluoroethyl)pyrazol-1-yl |
| 3,5-dimethyl-2-thienyl |
| 3,5-dichloro-2-thienyl |
| 2,5-dimethyl-3-thienyl |
| 2,5-dichloro-3-thienyl |
| 3,6-dimethyl-2-pyridyl |
| 2,5-dimethyl-3-pyridyl |
| 2,5-dimethyl-4-pyridyl |
| 3,6-dichloro-2-pyridyl |
| 2,5-dichloro-3-pyridyl |
| 2,5-dichloro-4-pyridyl |
| 3,5-bis-(trifluoromethyl)pyrazol-1-yl |
| 1-methyl-3-(trifluoromethyl)pyrazol-5-yl |
| 1-methyl-4-(trifluoromethyl)imidazol-2-yl |

TABLE 1C

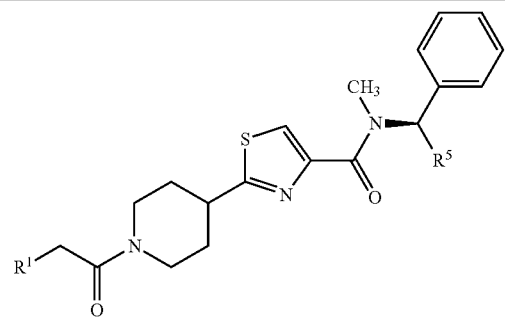

| R¹ | R⁵ |
|---|---|
| 2-methoxyphenyl | Et |
| 3-bromophenyl | Et |
| 3-iodophenyl | Et |
| 3-(trifluoromethyl)phenyl | Et |

TABLE 1C-continued

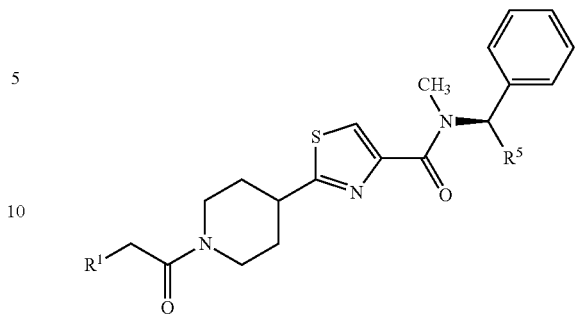

| R¹ | R⁵ |
|---|---|
| 3-(2,2,2-trifluoroethyl)phenyl | Et |
| 3-(pentafluoroethyl)phenyl | Et |
| 3-cyanophenyl | Et |
| 3-nitrophenyl | Et |
| 2,5-dichlorophenyl | Et |
| 5-bromo-2-chlorophenyl | Et |
| 2-chloro-5-iodophenyl | Et |
| 2-chloro-5-methylphenyl | Et |
| 2-chloro-5-ethylphenyl | Et |
| 2-chloro-5-(trifluoromethyl)phenyl | Et |
| 2-chloro-5-(2,2,2-trifluoroethyl)phenyl | Et |
| 2-chloro-5-(pentafluoroethyl)phenyl | Et |
| 2-chloro-5-cyanophenyl | Et |
| 2-chloro-5-nitrophenyl | Et |
| 2-bromo-5-chlorophenyl | Et |
| 2,5-dibromophenyl | Et |
| 2-bromo-5-iodophenyl | Et |
| 2-bromo-5-methylphenyl | Et |
| 2-bromo-5-ethylphenyl | Et |
| 2-bromo-5-propylphenyl | Et |
| 2-bromo-5-(trifluoromethyl)phenyl | Et |
| 2-bromo-5-(2,2,2-trifluoroethyl)phenyl | Et |
| 2-bromo-5-(pentafluoroethyl)phenyl | Et |
| 2-bromo-5-cyanophenyl | Et |
| 2-bromo-5-nitrophenyl | Et |
| 5-chloro-2-methylphenyl | Et |
| 5-bromo-2-methylphenyl | Et |
| 5-iodo-2-methylphenyl | Et |
| 2,5-dimethylphenyl | Et |
| 5-ethyl-2-methylphenyl | Et |
| 2-methyl-5-propylphenyl | Et |
| 5-isopropyl-2-methylphenyl | Et |
| 2-methyl-5-(trifluoromethyl)phenyl | Et |
| 2-methyl-5-(2,2,2-trifluoroethyl)phenyl | Et |
| 2-methyl-5-(pentafluoroethyl)phenyl | Et |
| 5-cyano-2-methylphenyl | Et |
| 2-methyl-5-nitrophenyl | Et |
| 5-chloro-2-methoxyphenyl | Et |
| 5-bromo-2-methoxyphenyl | Et |
| 5-iodo-2-methoxyphenyl | Et |
| 2-methoxy-5-methylphenyl | Et |
| 5-ethyl-2-methoxyphenyl | Et |
| 2-methoxy-5-propylphenyl | Et |
| 2-methoxy-5-(bifluoromethyl)phenyl | Et |
| 2-methoxy-5-(2,2,2-trifluoroethyl)phenyl | Et |
| 2-methoxy-5-(pentafluoroethyl)phenyl | Et |
| 5-cyano-2-methoxyphenyl | Et |
| 2-methoxy-5-nitrophenyl | Et |
| 5-chloro-2-ethylphenyl | Et |
| 5-bromo-2-ethylphenyl | Et |
| 2-ethyl-5-iodophenyl | Et |
| 2-ethyl-5-methylphenyl | Et |
| 2,5-diethylphenyl | Et |
| 2-ethyl-5-propylphenyl | Et |
| 2-ethyl-5-(trifluoromethyl)phenyl | Et |
| 2-ethyl-5-(2,2,2-trifluoroethyl)phenyl | Et |
| 2-ethyl-5-(pentafluoroethyl)phenyl | Et |
| 5-cyano-2-ethylphenyl | Et |
| 2-ethyl-5-nitrophenyl | Et |
| 3-chloropyrazol-1-yl | Et |
| 3-bromopyrazol-1-yl | Et |
| 3-(trifluoromethyl)pyrazol-1-yl | Et |

TABLE 1C-continued

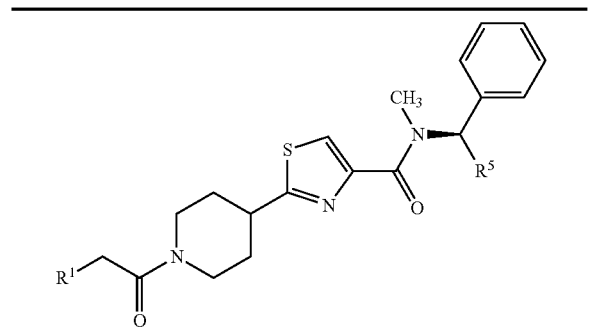

| R¹ | R⁵ |
|---|---|
| 3-(2,2,2-trifluoroethyl)pyrazol-1-yl | Et |
| 3-(pentafluoroethyl)pyrazol-1-yl | Et |
| 3-cyanopyrazol-1-yl | Et |
| 3-nitropyrazol-1-yl | Et |
| 3,5-dimethylpyrazol-1-yl | Et |
| 3-chloro-5-methylpyrazol-1-yl | Et |
| 3-bromo-5-methylpyrazol-1-yl | Et |
| 3-iodo-5-methylpyrazol-1-yl | Et |
| 3-ethyl-5-methylpyrazol-1-yl | Et |
| 5-methyl-3-propylpyrazol-1-yl | Et |
| 5-methyl-3-(trifluoromethyl)pyrazol-1-yl | Et |
| 5-methyl-3-(2,2,2-trifluoroethyl)pyrazol-1-yl | Et |
| 5-methyl-3-(pentafluoroethyl)pyrazol-1-yl | Et |
| 3-cyano-5-methylpyrazol-1-yl | Et |
| 5-methyl-3-nitropyrazol-1-yl | Et |
| 5-chloro-3-methylpyrazol-1-yl | Et |
| 3,5-dichloropyrazol-1-yl | Et |
| 5-chloro-3-bromopyrazol-1-yl | Et |
| 5-chloro-3-iodopyrazol-1-yl | Et |
| 5-chloro-3-ethylpyrazol-1-yl | Et |
| 5-chloro-3-propylpyrazol-1-yl | Et |
| 5-chloro-3-(trifluoromethyl)pyrazol-1-yl | Et |
| 5-chloro-3-(2,2,2-trifluoroethyl)pyrazol-1-yl | Et |
| 5-chloro-3-(pentafluoroethyl)pyrazol-1-yl | Et |
| 5-chloro-3-cyanopyrazol-1-yl | Et |
| 5-chloro-3-nitropyrazol-1-yl | Et |
| 5-bromo-3-methylpyrazol-1-yl | Et |
| 5-bromo-3-chloropyrazol-1-yl | Et |
| 3,5-dibromopyrazol-1-yl | Et |
| 5-bromo-3-iodopyrazol-1-yl | Et |
| 5-bromo-3-ethylpyrazol-1-yl | Et |
| 5-bromo-3-propylpyrazol-1-yl | Et |
| 5-bromo-3-(trifluoromethyl)pyrazol-1-yl | Et |
| 5-bromo-3-(2,2,2-trifluoroethyl)pyrazol-1-yl | Et |
| 5-bromo-3-(pentafluoroethyl)pyrazol-1-yl | Et |
| 5-ethyl-3-methylpyrazol-1-yl | Et |
| 3-chloro-5-ethylpyrazol-1-yl | Et |
| 3-bromo-5-ethylpyrazol-1-yl | Et |
| 5-ethyl-3-iodopyrazol-1-yl | Et |
| 3,5-diethylpyrazol-1-yl | Et |
| 5-ethyl-3-propylpyrazol-1-yl | Et |
| 5-ethyl-3-(trifluoromethyl)pyrazol-1-yl | Et |
| 5-ethyl-3-(2,2,2-trifluoroethyl)pyrazol-1-yl | Et |
| 5-ethyl-3-(pentafluoroethyl)pyrazol-1-yl | Et |
| 3,5-dimethyl-2-thienyl | Et |
| 3,5-dichloro-2-thienyl | Et |
| 2,5-dimethyl-3-thienyl | Et |
| 2,5-dichloro-3-thienyl | Et |
| 3,6-dimethyl-2-pyridyl | Et |
| 2,5-dimethyl-3-pyridyl | Et |
| 2,5-dimethyl-4-pyridyl | Et |
| 3,6-dichloro-2-pyridyl | Et |
| 2,5-dichloro-3-pyridyl | Et |
| 2,5-dichloro-4-pyridyl | Et |
| 2-methoxyphenyl | Me |
| 2,5-dichlorophenyl | Me |
| 5-bromo-2-chlorophenyl | Me |
| 2-chloro-5-methylphenyl | Me |
| 2-chloro-5-(trifluoromethyl)phenyl | Me |
| 2,5-dibromophenyl | Me |
| 2-bromo-5-methylphenyl | Me |
| 2-bromo-5-(trifluoromethyl)phenyl | Me |

TABLE 1C-continued

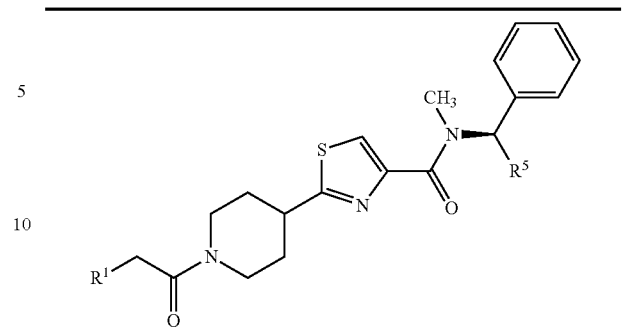

| R¹ | R⁵ |
|---|---|
| 5-chloro-2-methylphenyl | Me |
| 5-bromo-2-methylphenyl | Me |
| 2,5-dimethylphenyl | Me |
| 5-ethyl-2-methylphenyl | Me |
| 2-methyl-5-(trifluoromethyl)phenyl | Me |
| 5-bromo-2-methoxyphenyl | Me |
| 2-methoxy-5-methylphenyl | Me |
| 2-methoxy-5-(trifluoromethyl)phenyl | Me |
| 3-(trifluoromethyl)pyrazol-1-yl | Me |
| 3,5-dimethylpyrazol-1-yl | Me |
| 3-ethyl-5-methylpyrazol-1-yl | Me |
| 5-methyl-3-(trifluoromethyl)pyrazol-1-yl | Me |
| 3,5-dichloropyrazol-1-yl | Me |
| 5-chloro-3-(trifluoromethyl)pyrazol-1-yl | Me |
| 3,5-dibromopyrazol-1-yl | Me |
| 5-bromo-3-(trifluoromethyl)pyrazol-1-yl | Me |
| 3,5-diethylpyrazol-1-yl | Me |
| 5-ethyl-3-(trifluoromethyl)pyrazol-1-yl | Me |
| 2-methoxyphenyl | n-Pr |
| 2,5-dichlorophenyl | n-Pr |
| 5-bromo-2-chlorophenyl | n-Pr |
| 2-chloro-5-methylphenyl | n-Pr |
| 2-chloro-5-(trifluoromethyl)phenyl | n-Pr |
| 2,5-dibromophenyl | n-Pr |
| 2-bromo-5-methylphenyl | n-Pr |
| 2-bromo-5-(trifluoromethyl)phenyl | n-Pr |
| 5-chloro-2-methylphenyl | n-Pr |
| 5-bromo-2-methylphenyl | n-Pr |
| 2,5-dimethylphenyl | n-Pr |
| 5-ethyl-2-methylphenyl | n-Pr |
| 2-methyl-5-(trifluoromethyl)phenyl | n-Pr |
| 5-bromo-2-methoxyphenyl | n-Pr |
| 2-methoxy-5-methylphenyl | n-Pr |
| 2-methoxy-5-(trifluoromethyl)phenyl | n-Pr |
| 3-(trifluoromethyl)pyrazol-1-yl | n-Pr |
| 3,5-dimethylpyrazol-1-yl | n-Pr |
| 3-ethyl-5-methylpyrazol-1-yl | n-Pr |
| 5-methyl-3-(trifluoromethyl)pyrazol-1-yl | n-Pr |
| 3,5-dichloropyrazol-1-yl | n-Pr |
| 5-chloro-3-(trifluoromethyl)pyrazol-1-yl | n-Pr |
| 3,5-dibromopyrazol-1-yl | n-Pr |
| 5-bromo-3-(trifluoromethyl)pyrazol-1-yl | n-Pr |
| 3,5-diethylpyrazol-1-yl | n-Pr |
| 5-ethyl-3-(trifluoromethyl)pyrazol-1-yl | n-Pr |
| 2-methoxyphenyl | CN |
| 2,5-dichlorophenyl | CN |
| 5-bromo-2-chlorophenyl | CN |
| 2-chloro-5-methylphenyl | CN |
| 2-chloro-5-(trifluoromethyl)phenyl | CN |
| 2,5-dibromophenyl | CN |
| 2-bromo-5-methylphenyl | CN |
| 2-bromo-5-(trifluoromethyl)phenyl | CN |
| 5-chloro-2-methylphenyl | CN |
| 5-bromo-2-methylphenyl | CN |
| 2,5-dimethylphenyl | CN |
| 5-ethyl-2-methylphenyl | CN |
| 2-methyl-5-(trifluoromethyl)phenyl | CN |
| 5-bromo-2-methoxyphenyl | CN |
| 2-methoxy-5-methylphenyl | CN |
| 2-methoxy-5-(trifluoromethyl)phenyl | CN |
| 3-(trifluoromethyl)pyrazol-1-yl | CN |
| 3,5-dimethylpyrazol-1-yl | CN |

TABLE 1C-continued

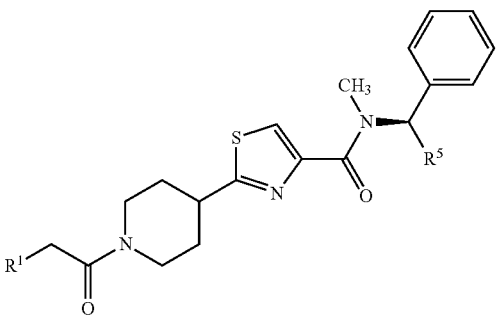

| R¹ | R⁵ |
|---|---|
| 3-ethyl-5-methylpyrazol-1-yl | CN |
| 5-methyl-3-(trifluoromethyl)pyrazol-1-yl | CN |
| 3,5-dichloropyrazol-1-yl | CN |
| 5-chloro-3-(trifluoromethyl)pyrazol-1-yl | CN |
| 3,5-dibromopyrazol-1-yl | CN |
| 5-bromo-3-(trifluoromethyl)pyrazol-1-yl | CN |
| 3,5-diethylpyrazol-1-yl | CN |
| 5-ethyl-3-(trifluoromethyl)pyrazol-1-yl | CN |
| 5-methyl-3-(trifluoromethyl)pyrazol-1-yl | i-Pr |
| 5-methyl-3-(trifluoromethyl)pyrazol-1-yl | n-Bu |
| 5-methyl-3-(trifluoromethyl)pyrazol-1-yl | i-Bu |
| 5-methyl-3-(trifluoromethyl)pyrazol-1-yl | n-Pen |
| 5-methyl-3-(trifluoromethyl)pyrazol-1-yl | n-Hex |
| 5-methyl-3-(trifluoromethyl)pyrazol-1-yl | ethenyl |
| 5-methyl-3-(trifluoromethyl)pyrazol-1-yl | ethynyl |
| 5-methyl-3-(trifluoromethyl)pyrazol-1-yl | 4-methyl-3-penten-1-yl |
| 5-methyl-3-(trifluoromethyl)pyrazol-1-yl | c-Pr |
| 5-methyl-3-(trifluoromethyl)pyrazol-1-yl | c-Bu |
| 5-methyl-3-(trifluoromethyl)pyrazol-1-yl | c-Pen |
| 5-methyl-3-(trifluoromethyl)pyrazol-1-yl | c-Hex |
| 5-methyl-3-(trifluoromethyl)pyrazol-1-yl | trifluoromethyl |
| 5-methyl-3-(trifluoromethyl)pyrazol-1-yl | 2,2,2-trifluoroethyl |
| 5-methyl-3-(trifluoromethyl)pyrazol-1-yl | 3,3-dichloro-2-propen-1-yl |
| 5-methyl-3-(trifluoromethyl)pyrazol-1-yl | ethynyl |
| 5-methyl-3-(trifluoromethyl)pyrazol-1-yl | propynyl |
| 5-methyl-3-(trifluoromethyl)pyrazol-1-yl | methylethynyl |
| 5-methyl-3-(trifluoromethyl)pyrazol-1-yl | trifluoromethylethynyl |
| 5-methyl-3-(trifluoromethyl)pyrazol-1-yl | 2,2-dichlorocycloprop-1-yl |
| 5-methyl-3-(trifluoromethyl)pyrazol-1-yl | nitro |
| 5-methyl-3-(trifluoromethyl)pyrazol-1-yl | methoxymethyl |
| 5-methyl-3-(trifluoromethyl)pyrazol-1-yl | methoxyethyl |
| 5-methyl-3-(trifluoromethyl)pyrazol-1-yl | 1-methoxyethyl |
| 5-methyl-3-(trifluoromethyl)pyrazol-1-yl | 2-methoxyethyl |
| 5-methyl-3-(trifluoromethyl)pyrazol-1-yl | hydroxymethyl |
| 5-methyl-3-(trifluoromethyl)pyrazol-1-yl | acetyl |
| 5-methyl-3-(trifluoromethyl)pyrazol-1-yl | isobutyryl |
| 5-methyl-3-(trifluoromethyl)pyrazol-1-yl | methoxycarbonyl |
| 5-methyl-3-(trifluoromethyl)pyrazol-1-yl | ethoxycarbonyl |
| 5-methyl-3-(trifluoromethyl)pyrazol-1-yl | methylaminocarbonyl |
| 5-methyl-3-(trifluoromethyl)pyrazol-1-yl | dimethylaminocarbonyl |
| 5-methyl-3-(trifluoromethyl)pyrazol-1-yl | trimethylsilyl |
| 3,5-bis-(trifluoromethyl)pyrazol-1-yl | Et |
| 1-methyl-3-(trifluoromethyl)pyrazol-5-yl | Et |
| 1-methyl-4-(trifluoromethyl)imidazol-2-yl | Et |

TABLE 1D

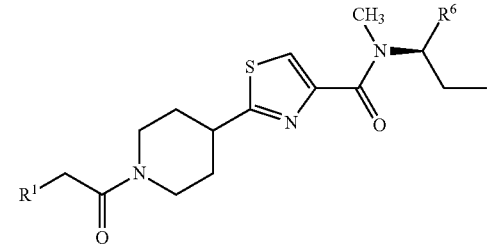

| R¹ | R⁶ |
|---|---|
| 2-methoxyphenyl | 2-methylphenyl |
| 2,5-dichlorophenyl | 2-methylphenyl |
| 5-bromo-2-chlorophenyl | 2-methylphenyl |
| 2-chloro-5-methylphenyl | 2-methylphenyl |
| 2-chloro-5-(trifluoromethyl)phenyl | 2-methylphenyl |
| 2,5-dibromophenyl | 2-methylphenyl |
| 2-bromo-5-methylphenyl | 2-methylphenyl |
| 2-bromo-5-(trifluoromethyl)phenyl | 2-methylphenyl |
| 5-chloro-2-methylphenyl | 2-methylphenyl |
| 5-bromo-2-methylphenyl | 2-methylphenyl |
| 2,5-dimethylphenyl | 2-methylphenyl |
| 5-ethyl-2-methylphenyl | 2-methylphenyl |
| 2-methyl-5-(trifluoromethyl)phenyl | 2-methylphenyl |
| 5-bromo-2-methoxyphenyl | 2-methylphenyl |
| 2-methoxy-5-methylphenyl | 2-methylphenyl |
| 2-methoxy-5-(trifluoromethyl)phenyl | 2-methylphenyl |
| 3-(trifluoromethyl)pyrazol-1-yl | 2-methylphenyl |
| 3,5-dimethylpyrazol-1-yl | 2-methylphenyl |
| 3-ethyl-5-methylpyrazol-1-yl | 2-methylphenyl |
| 5-methyl-3-(trifluoromethyl)pyrazol-1-yl | 2-methylphenyl |
| 3,5-dichloropyrazol-1-yl | 2-methylphenyl |
| 5-chloro-3-(trifluoromethyl)pyrazol-1-yl | 2-methylphenyl |
| 3,5-dibromopyrazol-1-yl | 2-methylphenyl |
| 5-bromo-3-(trifluoromethyl)pyrazol-1-yl | 2-methylphenyl |
| 3,5-diethylpyrazol-1-yl | 2-methylphenyl |
| 5-ethyl-3-(trifluoromethyl)pyrazol-1-yl | 2-methylphenyl |
| 2-methoxyphenyl | 4-methylphenyl |
| 2,5-dichlorophenyl | 4-methylphenyl |
| 5-bromo-2-chlorophenyl | 4-methylphenyl |
| 2-chloro-5-methylphenyl | 4-methylphenyl |
| 2-chloro-5-(trifluoromethyl)phenyl | 4-methylphenyl |
| 2,5-dibromophenyl | 4-methylphenyl |
| 2-bromo-5-methylphenyl | 4-methylphenyl |
| 2-bromo-5-(trifluoromethyl)phenyl | 4-methylphenyl |
| 5-chloro-2-methylphenyl | 4-methylphenyl |
| 5-bromo-2-methylphenyl | 4-methylphenyl |
| 2,5-dimethylphenyl | 4-methylphenyl |
| 5-ethyl-2-methylphenyl | 4-methylphenyl |
| 2-methyl-5-(trifluoromethyl)phenyl | 4-methylphenyl |
| 5-bromo-2-methoxyphenyl | 4-methylphenyl |
| 2-methoxy-5-methylphenyl | 4-methylphenyl |
| 2-methoxy-5-(trifluoromethyl)phenyl | 4-methylphenyl |
| 3-(trifluoromethyl)pyrazol-1-yl | 4-methylphenyl |
| 3,5-dimethylpyrazol-1-yl | 4-methylphenyl |
| 3-ethyl-5-methylpyrazol-1-yl | 4-methylphenyl |
| 5-methyl-3-(triflubromethyl)pyrazol-1-yl | 4-methylphenyl |
| 3,5-dichloropyrazol-1-yl | 4-methylphenyl |
| 5-chloro-3-(trifluoromethyl)pyrazol-1-yl | 4-methylphenyl |
| 3,5-dibromopyrazol-1-yl | 4-methylphenyl |
| 5-bromo-3-(trifluoromethyl)pyrazol-1-yl | 4-methylphenyl |
| 3,5-diethylpyrazol-1-yl | 4-methylphenyl |
| 5-ethyl-3-(trifluoromethyl)pyrazol-1-yl | 4-methylphenyl |
| 2-methoxyphenyl | 4-chlorophenyl |
| 2,5-dichlorophenyl | 4-chlorophenyl |
| 5-bromo-2-chlorophenyl | 4-chlorophenyl |
| 2-chloro-5-methylphenyl | 4-chlorophenyl |
| 2-chloro-5-(trifluoromethyl)phenyl | 4-chlorophenyl |
| 2,5-dibromophenyl | 4-chlorophenyl |
| 2-bromo-5-methylphenyl | 4-chlorophenyl |
| 2-bromo-5-(trifluoromethyl)phenyl | 4-chlorophenyl |
| 5-chloro-2-methylphenyl | 4-chlorophenyl |
| 5-bromo-2-methylphenyl | 4-chlorophenyl |
| 2,5-dimethylphenyl | 4-chlorophenyl |
| 5-ethyl-2-methylphenyl | 4-chlorophenyl |
| 2-methyl-5-(trifluoromethyl)phenyl | 4-chlorophenyl |

TABLE 1D-continued

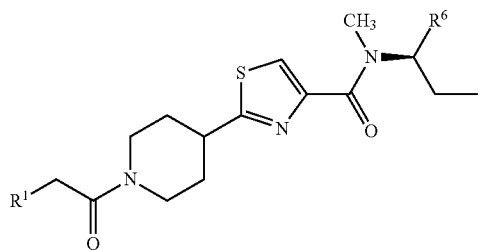

| R¹ | R⁶ |
|---|---|
| 5-bromo-2-methoxyphenyl | 4-chlorophenyl |
| 2-methoxy-5-methylphenyl | 4-chlorophenyl |
| 2-methoxy-5-(trifluoromethyl)phenyl | 4-chlorophenyl |
| 3-(trifluoromethyl)pyrazol-1-yl | 4-chlorophenyl |
| 3,5-dimethylpyrazol-1-yl | 4-chlorophenyl |
| 3-ethyl-5-methylpyrazol-1-yl | 4-chlorophenyl |
| 5-methyl-3-(trifluoromethyl)pyrazol-1-yl | 4-chlorophenyl |
| 3,5-dichloropyrazol-1-yl | 4-chlorophenyl |
| 5-chloro-3-(trifluoromethyl)pyrazol-1-yl | 4-chlorophenyl |
| 3,5-dibromopyrazol-1-yl | 4-chlorophenyl |
| 5-bromo-3-(trifluoromethyl)pyrazol-1-yl | 4-chlorophenyl |
| 3,5-diethylpyrazol-1-yl | 4-chlorophenyl |
| 5-ethyl-3-(trifluoromethyl)pyrazol-1-yl | 4-chlorophenyl |
| 5-methyl-3-(trifluoromethyl)pyrazol-1-yl | 2-ethylphenyl |
| 5-methyl-3-(trifluoromethyl)pyrazol-1-yl | 4-t-butylphenyl |
| 5-methyl-3-(trifluoromethyl)pyrazol-1-yl | 4-allylphenyl |
| 5-methyl-3-(trifluoromethyl)pyrazol-1-yl | 4-ethynylphenyl |
| 5-methyl-3-(trifluoromethyl)pyrazol-1-yl | 4-cyclopropylphenyl |
| 5-methyl-3-(trifluoromethyl)pyrazol-1-yl | 4-(trifluoromethyl)phenyl |
| 5-methyl-3-(trifluoromethyl)pyrazol-1-yl | 4-(2-chloroethenyl)phenyl |
| 5-methyl-3-(trifluoromethyl)pyrazol-1-yl | 4-bromoethynylphenyl |
| 5-methyl-3-(trifluoromethyl)pyrazol-1-yl | 4-(2,2-dichlorocycloprop-1-yl)phenyl |
| 5-methyl-3-(trifluoromethyl)pyrazol-1-yl | 2-fluorophenyl |
| 5-methyl-3-(trifluoromethyl)pyrazol-1-yl- | 3-fluorophenyl |
| 5-methyl-3-(trifluoromethyl)pyrazol-1-yl | 4-fluorophenyl |
| 5-methyl-3-(trifluoromethyl)pyrazol-1-yl | 2-chlorophenyl |
| 5-methyl-3-(trifluoromethyl)pyrazol-1-yl | 4-bromophenyl |
| 5-methyl-3-(trifluoromethyl)pyrazol-1-yl | 4-hydroxyphenyl |
| 5-methyl-3-(trifluoromethyl)pyrazol-1-yl | 4-aminophenyl |
| 5-methyl-3-(trifluoromethyl)pyrazol-1-yl | 4-cyanophenyl |
| 5-methyl-3-(trifluoromethyl)pyrazol-1-yl | 4-nitrophenyl |
| 5-methyl-3-(trifluoromethyl)pyrazol-1-yl | 4-methoxyphenyl |
| 5-methyl-3-(trifluoromethyl)pyrazol-1-yl | 4-(trifluoromethoxy)phenyl |
| 5-methyl-3-(trifluoromethyl)pyrazol-1-yl | 4-(methylthio)phenyl |
| 5-methyl-3-(trifluoromethyl)pyrazole-1-yl | 4-(methylsulfonyl)phenyl |
| (5-methyl-3-(trifluoromethyl)pyrazol-1-yl | 4-(methylsulfonyl)phenyl |
| 5-methyl-3-(trifluoromethyl)pyrazol-1-yl | 4-(trifluoromethylthio)phenyl |
| 5-methyl-3-(trifluoromethyl)pyrazol-1-yl | 4-(trifluoromethylsulfonyl)phenyl |
| 5-methyl-3-(trifluoromethyl)pyrazol-1-yl | 4-(methylamino)phenyl |
| 5-methyl-3-(trifluoromethyl)pyrazol-1-yl | 4-(dimethylamino)phenyl |
| 5-methyl-3-(trifluoromethyl)pyrazol-1-yl | 4-(cyclopropylamino)phenyl |
| 5-methyl-3-(trifluoromethyl)pyrazol-1-yl | 2-(methoxymethyl)phenyl |
| 5-methyl-3-(trifluoromethyl)pyrazol-1-yl | 3,4-(dimethoxy)phenyl |
| 5-methyl-3-(trifluoromethyl)pyrazol-1-yl | 4-acetylphenyl |
| 5-methyl-3-(trifluoromethyl)pyrazol-1-yl | 4-(methoxycarbonyl)phenyl |
| 5-methyl-3-(trifluoromethyl)pyrazol-1-yl | 4-(acetyloxy)phenyl |
| 5-methyl-3-(trifluoromethyl)pyrazol-1-yl | 4-(methylaminocarbonyl)phenyl |
| 5-methyl-3-(trifluoromethyl)pyrazol-1-yl | 4-(dimethylaminocarbonyl)phenyl |
| 5-methyl-3-(trifluoromethyl)pyrazol-1-yl | 4-(trimethylsilyl)phenyl |
| 5-methyl-3-(trifluoromethyl)pyrazol-1-yl | 2,6-difluorophenyl |
| 5-methyl-3-(trifluoromethyl)pyrazol-1-yl | 2,4,6-trifluorophenyl |
| 5-methyl-3-(trifluoromethyl)pyrazol-1-yl | 2,3-dimethylphenyl |
| 5-methyl-3-(trifluoromethyl)pyrazol-1-yl | 2,3-dichlorophenyl |
| 5-methyl-3-(trifluoromethyl)pyrazol-1-yl | 1-naphthalenyl |
| 5-methyl-3-(trifluoromethyl)pyrazol-1-yl | 2-thienyl |
| 5-methyl-3-(trifluoromethyl)pyrazol-1-yl | 2-furyl |
| 5-methyl-3-(trifluoromethyl)pyrazol-1-yl | 1-methyl-2-pyrrolyl |
| 5-methyl-3-(trifluoromethyl)pyrazol-1-yl | 5-thiazolyl |
| 5-methyl-3-(trifluoromethyl)pyrazol-1-yl | 2-oxazolyl |
| 5-methyl-3-(trifluoromethyl)pyrazol-1-yl | 2-thiazolyl |
| 5-methyl-3-(trifluoromethyl)pyrazol-1-yl | 5-oxazolyl |

TABLE 1D-continued

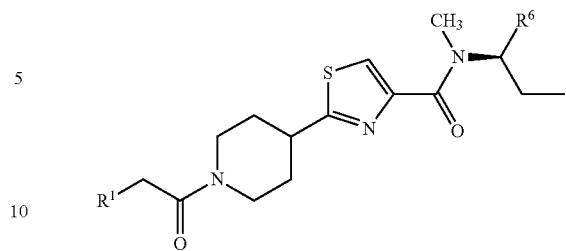

| R¹ | R⁶ |
|---|---|
| 5-methyl-3-(trifluoromethyl)pyrazol-1-yl | 5-isothiazolyl |
| 5-methyl-3-(trifluoromethyl)pyrazol-1-yl | 5-isoxazolyl |
| 5-methyl-3-(trifluoromethyl)pyrazol-1-yl | 1-methyl-5-pyrazolyl |
| 5-methyl-3-(trifluoromethyl)pyrazol-1-yl | 1-methyl-5-imidazolyl |
| 5-methyl-3-(trifluoromethyl)pyrazol-1-yl | 1-methyl-2-imidazolyl |
| 5-methyl-3-(trifluoromethyl)pyrazol-1-yl | 4-methyl-1,2,4-triazolyl-3-yl |
| 5-methyl-3-(trifluoromethyl)pyrazol-1-yl | 1-methyl-1,2,4-triazolyl-5-yl |
| 5-methyl-3-(trifluoromethyl)pyrazol-1-yl | 1,3,4-oxadiazol-2-yl |
| 5-methyl-3-(trifluoromethyl)pyrazol-1-yl | 1,3,4-thiadiazol-2-yl |
| 5-methyl-3-(trifluoromethyl)pyrazol-1-yl | 1,2,4-oxadiazol-2-yl |
| 5-methyl-3-(trifluoromethyl)pyrazol-1-yl | 1,2,4-thiadiazol-2-yl |
| 5-methyl-3-(trifluoromethyl)pyrazol-1-yl | 3-thienyl |
| 5-methyl-3-(trifluoromethyl)pyrazol-1-yl | 3-furyl |
| 5-methyl-3-(trifluoromethyl)pyrazol-1-yl | 1-methyl-3-pyrrolyl |
| 5-methyl-3-(trifluoromethyl)pyrazol-1-yl | 1-methyl-3-pyrazolyl |
| 5-methyl-3-(trifluoromethyl)pyrazol-1-yl | 1-methyl-4-pyrazolyl |
| 5-methyl-3-(trifluoromethyl)pyrazol-1-yl | 4-oxazolyl |
| 5-methyl-3-(trifluoromethyl)pyrazol-1-yl | 4-thiazolyl |
| 5-methyl-3-(trifluoromethyl)pyrazol-1-yl | 4-isothiazolyl |
| 5-methyl-3-(trifluoromethyl)pyrazol-1-yl | 4-isoxazolyl |
| 5-methyl-3-(trifluoromethyl)pyrazol-1-yl | 1-methyl-4-imidazolyl |
| 5-methyl-3-(trifluoromethyl)pyrazol-1-yl | 1,2,4-oxadiazol-3-yl |
| 5-methyl-3-(trifluoromethyl)pyrazol-1-yl | 1,2,4-thiadiazol-3-yl |
| 5-methyl-3-(trifluoromethyl)pyrazol-1-yl | 1-methyl-1,2,4-triazolyl-3-yl |
| 5-methyl-3-(trifluoromethyl)pyrazol-1-yl | 2-pyridyl |
| 5-methyl-3-(trifluoromethyl)pyrazol-1-yl | 3,5-dichloro-2-pyridyl |
| 5-methyl-3-(trifluoromethyl)pyrazol-1-yl | 3-pyridyl |
| 5-methyl-3-(trifluoromethyl)pyrazol-1-yl | 4-pyridyl |
| 5-methyl-3-(trifluoromethyl)pyrazol-1-yl | 3-pyrazinyl |
| 5-methyl-3-(trifluoromethyl)pyrazol-1-yl | 2-pyrimidinyl |
| 5-methyl-3-(trifluoromethyl)pyrazol-1-yl | 2-pyridazinyl |
| 5-methyl-3-(trifluoromethyl)pyrazol-1-yl | 4-pyrimidinyl |
| 5-methyl-3-(trifluoromethyl)pyrazol-1-yl | 5-pyrimidinyl |
| 5-methyl-3-(trifluoromethyl)pyrazol-1-yl | 4-pyrazinyl |
| 5-methyl-3-(trifluoromethyl)pyrazol-1-yl | 1,2,4-triazin-6-yl |
| 5-methyl-3-(trifluoromethyl)pyrazol-1-yl | 1,2,4-triazin-3-yl |
| 5-methyl-3-(trifluoromethyl)pyrazol-1-yl | 1,3,5-triazin-2-yl |
| 5-methyl-3-(trifluoromethyl)pyrazol-1-yl | 1,2,4-triazin-5-yl |

TABLE 2A

| R¹ |
|---|
| 2-methoxyphenyl |
| 3-bromophenyl |
| 3-iodophenyl |
| 3-(trifluoromethyl)phenyl |

TABLE 2A-continued

[Structure: oxazole-4-carboxamide with N-methyl-N-(1,2,3,4-tetrahydronaphthalen-1-yl) group, 2-(1-acyl-piperidin-4-yl) substituent, where the acyl group is -C(=O)-CH2-R1]

R1

3-(2,2,2-trifluoroethyl)phenyl
3-(pentafluoroethyl)phenyl
3-cyanophenyl
3-nitrophenyl
2,5-dichlorophenyl
5-bromo-2-chlorophenyl
2-chloro-5-iodophenyl
2-chloro-5-methylphenyl
2-chloro-5-ethylphenyl
2-chloro-5-(trifluoromethyl)phenyl
2-chloro-5-(2,2,2-trifluoroethyl)phenyl
2-chloro-5-(pentafluoroethyl)phenyl
2-chloro-5-cyanophenyl
2-chloro-5-nitrophenyl
2-bromo-5-chlorophenyl
2,5-dibromophenyl
2-bromo-5-iodophenyl
2-bromo-5-methylphenyl
2-bromo-5-ethylphenyl
2-bromo-5-propylphenyl
2-bromo-5-(trifluoromethyl)phenyl
2-bromo-5-(2,2,2-trifluoroethyl)phenyl
2-bromo-5-(pentafluoroethyl)phenyl
2-bromo-5-cyanophenyl
2-bromo-5-nitrophenyl
5-chloro-2-methylphenyl
5-bromo-2-methylphenyl
5-iodo-2-methylphenyl
2,5-dimethylphenyl
5-ethyl-2-methylphenyl
2-methyl-5-propylphenyl
5-isopropyl-2-methylphenyl
2-methyl-5-(trifluoromethyl)phenyl
2-methyl-5-(2,2,2-trifluoroethyl)phenyl
2-methyl-5-(pentafluoroethyl)phenyl
5-cyano-2-methylphenyl
2-methyl-5-nitrophenyl
5-chloro-2-methoxyphenyl
5-bromo-2-methoxyphenyl
5-iodo-2-methoxyphenyl
2-methoxy-5-methylphenyl
5-ethyl-2-methoxyphenyl
2-methoxy-5-propylphenyl
2-methoxy-5-(trifluoromethyl)phenyl
2-methoxy-5-(2,2,2-trifluoroethyl)phenyl
2-methoxy-5-(pentafluoroethyl)phenyl
5-cyano-2-methoxyphenyl
2-methoxy-5-nitrophenyl
5-chloro-2-ethylphenyl
5-bromo-2-ethylphenyl
2-ethyl-5-iodophenyl
2-ethyl-5-methylphenyl
2,5-diethylphenyl
2-ethyl-5-propylphenyl
2-ethyl-5-(trifluoromethyl)phenyl
2-ethyl-5-(2,2,2-trifluoroethyl)phenyl
2-ethyl-5-(pentafluoroethyl)phenyl
5-cyano-2-ethylphenyl
2-ethyl-5-nitrophenyl
3-chloropyrazol-1-yl
3-bromopyrazol-1-yl
3-(trifluoromethyl)pyrazol-1-yl

TABLE 2A-continued

[Structure: oxazole-4-carboxamide with N-methyl-N-(1,2,3,4-tetrahydronaphthalen-1-yl) group, 2-(1-acyl-piperidin-4-yl) substituent, where the acyl group is -C(=O)-CH2-R1]

R1

3-(2,2,2-trifluoroethyl)pyrazol-1-yl
3-(pentafluoroethyl)pyrazol-1-yl
3-cyanopyrazol-1-yl
3-nitropyrazol-1-yl
3,5-dimethylpyrazol-1-yl
3-chloro-5-methylpyrazol-1-yl
3-bromo-5-methylpyrazol-1-yl
3-iodo-5-methylpyrazol-1-yl
3-ethyl-5-methylpyrazol-1-yl
5-methyl-3-propylpyrazol-1-yl
5-methyl-3-(trifluoromethyl)pyrazol-1-yl
5-methyl-3-(2,2,2-trifluoroethyl)pyrazol-1-yl
5-methyl-3-(pentafluoroethyl)pyrazol-1-yl
3-cyano-5-methylpyrazol-1-yl
5-methyl-3-nitropyrazol-1-yl
5-chloro-3-methylpyrazol-1-yl
3,5-dichloropyrazol-1-yl
5-chloro-3-bromopyrazol-1-yl
5-chloro-3-iodopyrazol-1-yl
5-chloro-3-ethylpyrazol-1-yl
5-chloro-3-propylpyrazol-1-yl
5-chloro-3-(trifluoromethyl)pyrazol-1-yl
5-chloro-3(2,2,2-trifluoroethyl)pyrazol-1-yl
5-chloro-3-(pentafluoroethyl)pyrazol-1-yl
5-chloro-3-cyanopyrazol-1-yl
5-chloro-3-nitropyrazol-1-yl
5-bromo-3-methylpyrazol-1-yl
5-bromo-3-chloropyrazol-1-yl
3,5-dibromopyrazol-1-yl
5-bromo-3-iodopyrazol-1-yl
5-bromo-3-ethylpyrazol-1-yl
5-bromo-3-propylpyrazol-1-yl
5-bromo-3-(trifluoromethyl)pyrazol-1-yl
5-bromo-3-(2,2,2-trifluoroethyl)pyrazol-1-yl
5-bromo-3-(pentafluoroethyl)pyrazol-1-yl
5-ethyl-3-methylpyrazol-1-yl
3-chloro-5-ethylpyrazol-1-yl
3-bromo-5-ethylpyrazol-1-yl
5-ethyl-3-iodopyrazol-1-yl
3,5-diethylpyrazol-1-yl
5-ethyl-3-propylpyrazol-1-yl
5-ethyl-3-(trifluoromethyl)pyrazol-1-yl
5-ethyl-3-(2,2,2-trifluoroethyl)pyrazol-1-yl
5-ethyl-3-(pentafluoroethyl)pyrazol-1-yl
3,5-dimethyl-2-thienyl
3,5-dichloro-2-thienyl
2,5-dimethyl-3-thienyl
2,5-dichloro-3-thienyl
3,6-dimethyl-2-pyridyl
2,5-dimethyl-3-pyridyl
2,5-dimethyl-4-pyridyl
3,6-dichloro-2-pyridyl
2,5-dichloro-3-pyridyl
2,5-dichloro-4-pyridyl
3,5-bis-(trifluoromethyl)pyrazol-1-yl
1-methyl-3-(trifluoromethyl)pyrazol-5-yl
1-methyl-4-(trifluoromethyl)imidazol-2-yl

TABLE 2B

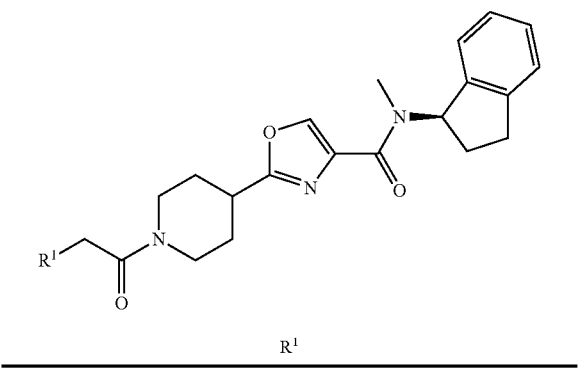

R¹

2-methoxyphenyl
3-bromophenyl
3-iodophenyl
3-(trifluoromethyl)phenyl
3-(2,2,2-trifluoroethyl)phenyl
3-(pentafluoroethyl)phenyl
3-cyanophenyl
3-nitrophenyl
2,5-dichlorophenyl
5-bromo-2-chlorophenyl
2-chloro-5-iodophenyl
2-chloro-5-methylphenyl
2-chloro-5-ethylphenyl
2-chloro-5-(trifluoromethyl)phenyl
2-chloro-5-(2,2,2-trifluoroethyl)phenyl
2-chloro-5-(pentafluoroethyl)phenyl
2-chloro-5-cyanophenyl
2-chloro-5-nitrophenyl
2-bromo-5-chlorophenyl
2,5-dibromophenyl
2-bromo-5-iodophenyl
2-bromo-5-methylphenyl
2-bromo-5-ethylphenyl
2-bromo-5-propylphenyl
2-bromo-5-(trifluoromethyl)phenyl
2-bromo-5-(2,2,2-trifluoroethyl)phenyl
2-bromo-5-(pentafluoroethyl)phenyl
2-bromo-5-cyanophenyl
2-bromo-5-nitrophenyl
5-chloro-2-methylphenyl
5-bromo-2-methylphenyl
5-iodo-2-methylphenyl
2,5-dimethylphenyl
5-ethyl-2-methylphenyl
2-methyl-5-propylphenyl
5-isopropyl-2-methylphenyl
2-methyl-5-(trifluoromethyl)phenyl
2-methyl-5-(2,2,2-trifluoroethyl)phenyl
2-methyl-5-(pentafluoroethyl)phenyl
5-cyano-2-methylphenyl
2-methyl-5-nitrophenyl
5-chloro-2-methoxyphenyl
5-bromo-2-methoxyphenyl
5-iodo-2-methoxyphenyl
2-methoxy-5-methylphenyl
5-ethyl-2-methoxyphenyl
2-methoxy-5-propylphenyl
2-methoxy-5-(trifluoromethyl)phenyl
2-methoxy-5-(2,2,2-trifluoroethyl)phenyl
2-methoxy-5-(pentafluoroethyl)phenyl
5-cyano-2-methoxyphenyl
2-methoxy-5-nitrophenyl
5-chloro-2-ethylphenyl
5-bromo-2-ethylphenyl
2-ethyl-5-iodophenyl
2-ethyl-5-methylphenyl
2,5-diethylphenyl
2-ethyl-5-propylphenyl
2-ethyl-5-(trifluoromethyl)phenyl
2-ethyl-5-(2,2,2-trifluoroethyl)phenyl
2-ethyl-5-(pentafluoroethyl)phenyl
5-cyano-2-ethylphenyl TABLE 2B-continued

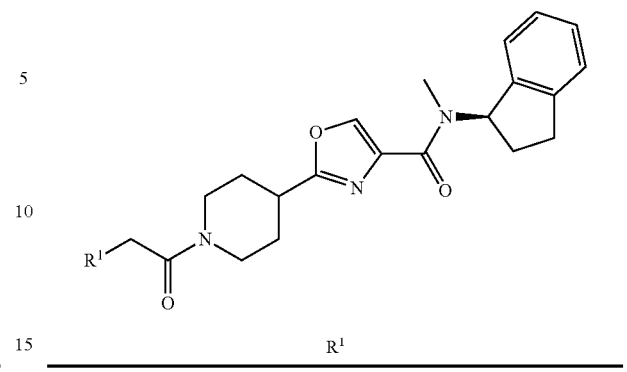

R¹

2-ethyl-5-nitrophenyl
3-chloropyrazol-1-yl
3-bromopyrazol-1-yl
3-(trifluoromethyl)pyrazol-1-yl
3-(2,2,2-trifluoroethyl)pyrazol-1-yl
3-(pentafluoroethyl)pyrazol-1-yl
3-cyanopyrazol-1-yl
3-nitropyrazol-1-yl
3,5-dimethylpyrazol-1-yl
3-chloro-5-methylpyrazol-1-yl
3-bromo-5-methylpyrazol-1-yl
3-iodo-5-methylpyrazol-1-yl
3-ethyl-5-methylpyrazol-1-yl
5-methyl-3-propylpyrazol-1-yl
5-methyl-3-(trifluoromethyl)pyrazol-1-yl
5-methyl-3-(2,2,2-trifluoroethyl)pyrazol-1-yl
5-methyl-3-(pentafluoroethyl)pyrazol-1-yl
3-cyano-5-methylpyrazol-1-yl
5-methyl-3-nitropyrazol-1-yl
5-chloro-3-methylpyrazol-1-yl
3,5-dichloropyrazol-1-yl
5-chloro-3-bromopyrazol-1-yl
5-chloro-3-iodopyrazol-1-yl
5-chloro-3-ethylpyrazol-1-yl
5-chloro-3-propylpyrazol-1-yl
5-chloro-3-(trifluoromethyl)pyrazol-1-yl
5-chloro-3-(2,2,2-trifluoroethyl)pyrazol-1-yl
5-chloro-3-(pentafluoroethyl)pyrazol-1-yl
5-chloro-3-cyanopyrazol-1-yl
5-chloro-3-nitropyrazol-1-yl
5-bromo-3-methylpyrazol-1-yl
5-bromo-3-chloropyrazol-1-yl
3,5-dibromopyrazol-1-yl
5-bromo-3-iodopyrazol-1-yl
5-bromo-3-ethylpyrazol-1-yl
5-bromo-3-propylpyrazol-1-yl
5-bromo-3-(trifluoromethyl)pyrazol-1-yl
5-bromo-3-(2,2,2-trifluoroethyl)pyrazol-1-yl
5-bromo-3-(pentafluoroethyl)pyrazol-1-yl
5-ethyl-3-methylpyrazol-1-yl
3-chloro-5-ethylpyrazol-1-yl
3-bromo-5-ethylpyrazol-1-yl
5-ethyl-3-iodopyrazol-1-yl
3,5-diethylpyrazol-1-yl
5-ethyl-3-propylpyrazol-1-yl
5-ethyl-3-(trifluoromethyl)pyrazol-1-yl
5-ethyl-3-(2,2,2-trifluoroethyl)pyrazol-1-yl
5-ethyl-3-(pentafluoroethyl)pyrazol-1-yl
3,5-dimethyl-2-thienyl
3,5-dichloro-2-thienyl
2,5-dimethyl-3-thienyl
2,5-dichloro-3-thienyl
3,6-dimethyl-2-pyridinyl
2,5-dimethyl-3-pyridinyl
2,5-dimethyl-4-pyridinyl
3,6-dichloro-2-pyridinyl
2,5-dichloro-3-pyridinyl
2,5-dichloro-4-pyridinyl
3,5-bis-(trifluoromethyl)pyrazol-1-yl
1-methyl-3-(trifluoromethyl)pyrazol-5-yl
1-methyl-4-(trifluoromethyl)imidazol-2-yl

TABLE 2C

[Structure: piperidine N-acylated with R¹-CH2-C(=O)-, 4-position attached to oxazole-2-yl; oxazole-4-carboxamide with N-methyl-N-[(1S)-1-phenylpropyl]]

R¹

2-methoxyphenyl
3-bromophenyl
3-iodophenyl
3-(trifluoromethyl)phenyl
3-(2,2,2-trifluoroethyl)phenyl
3-(pentafluoroethyl)phenyl
3-cyanophenyl
3-nitrophenyl
2,5-dichlorophenyl
5-bromo-2-chlorophenyl
2-chloro-5-iodophenyl
2-chloro-5-methylphenyl
2-chloro-5-ethylphenyl
2,5-dimethylphenyl
5-ethyl-2-methylphenyl
2-methyl-5-propylphenyl
5-isopropyl-2-methylphenyl
2-methyl-5-(trifluoromethyl)phenyl
2-methyl-5-(2,2,2-trifluoroethyl)phenyl
2-methyl-5-(pentafluoroethyl)phenyl
5-cyano-2-methylphenyl
2-methyl-5-nitrophenyl
5-chloro-2-methoxyphenyl
5-bromo-2-methoxyphenyl
5-iodo-2-methoxyphenyl
2-methoxy-5-methylphenyl
2-chloro-5-(trifluoromethyl)phenyl
2-chloro-5-(2,2,2-trifluoroethyl)phenyl
2-chloro-5-(pentafluoroethyl)phenyl
2-chloro-5-cyanophenyl
2-chloro-5-nitrophenyl
2-bromo-5-chlorophenyl
2,5-dibromophenyl
2-bromo-5-iodophenyl
2-bromo-5-methylphenyl
2-bromo-5-ethylphenyl
2-bromo-5-propylphenyl
2-bromo-5-(trifluoromethyl)phenyl
2-bromo-5-(2,2,2-trifluoroethyl)phenyl
2-bromo-5-(pentafluoroethyl)phenyl
2-bromo-5-cyanophenyl
2-bromo-5-nitrophenyl
5-chloro-2-methylphenyl
5-bromo-2-methylphenyl
5-iodo-2-methylphenyl
3-(trifluoromethyl)pyrazol-1-yl
3-(2,2,2-trifluoroethyl)pyrazol-1-yl
3-(pentafluoroethyl)pyrazol-1-yl
3-cyanopyrazol-1-yl
3-nitropyrazol-1-yl
3,5-dimethylpyrazol-1-yl
3-chloro-5-methylpyrazol-1-yl
3-bromo-5-methylpyrazol-1-yl
3-iodo-5-methylpyrazol-1-yl
3-ethyl-5-methylpyrazol-1-yl
5-methyl-3-propylpyrazol-1-yl
5-methyl-3-(trifluoromethyl)pyrazol-1-yl
5-methyl-3-(2,2,2-trifluoroethyl)pyrazol-1-yl
5-methyl-3-(pentafluoroethyl)pyrazol-1-yl
3-cyano-5-methylpyrazol-1-yl
5-methyl-3-nitropyrazol-1-yl
5-chloro-3-methylpyrazol-1-yl

TABLE 2C-continued

R¹

3,5-dichloropyrazol-1-yl
5-ethyl-2-methoxyphenyl
2-methoxy-5-propylphenyl
2-methoxy-5-(trifluoromethyl)phenyl
2-methoxy-5-(2,2,2-trifluoroethyl)phenyl
2-methoxy-5-(pentafluoroethyl)phenyl
5-cyano-2-methoxyphenyl
2-methoxy-5-nitrophenyl
5-chloro-2-ethylphenyl
5-bromo-2-ethylphenyl
2-ethyl-5-iodophenyl
2-ethyl-5-methylphenyl
2,5-diethylphenyl
2-ethyl-5-propylphenyl
2-ethyl-5-(trifluoromethyl)phenyl
2-ethyl-5-(2,2,2-trifluoroethyl)phenyl
2-ethyl-5-(pentafluoroethyl)phenyl
5-cyano-2-ethylphenyl
2-ethyl-5-nitrophenyl
3-chloropyrazol-1-yl
3-bromopyrazol-1-yl
5-bromo-3-iodopyrazol-1-yl
5-bromo-3-ethylpyrazol-1-yl
5-bromo-3-propylpyrazol-1-yl
5-bromo-3-(trifluoromethyl)pyrazol-1-yl
5-bromo-3-(2,2,2-trifluoroethyl)pyrazol-1-yl
5-bromo-3-(pentafluoroethyl)pyrazol-1-yl
5-ethyl-3-methylpyrazol-1-yl
3-chloro-5-ethylpyrazol-1-yl
3-bromo-5-ethylpyrazol-1-yl
5-ethyl-3-iodopyrazol-1-yl
3,5-diethylpyrazol-1-yl
5-ethyl-3-propylpyrazol-1-yl
5-ethyl-3-(trifluoromethyl)pyrazol-1-yl
5-ethyl-3-(2,2,2-trifluoroethyl)pyrazol-1-yl
5-ethyl-3-(pentafluoroethyl)pyrazol-1-yl
3,5-dimethyl-2-thienyl
3,5-dichloro-2-thienyl
5-chloro-3-bromopyrazol-1-yl
5-chloro-3-iodopyrazol-1-yl
5-chloro-3-ethylpyrazol-1-yl
5-chloro-3-propylpyrazol-1-yl
5-chloro-3-(trifluoromethyl)pyrazol-1-yl
5-chloro-3-(2,2,2-trifluoroethyl)pyrazol-1-yl
5-chloro-3-(pentafluoroethyl)pyrazol-1-yl
5-chloro-3-cyanopyrazol-1-yl
5-chloro-3-nitropyrazol-1-yl
5-bromo-3-methylpyrazol-1-yl
5-bromo-3-chloropyrazol-1-yl
3,5-dibromopyrazol-1-yl
2,5-dimethyl-3-thienyl
2,5-dichloro-3-thienyl
3,6-dimethyl-2-pyridinyl
2,5-dimethyl-3-pyridinyl
2,5-dimethyl-4-pyridinyl
3,6-dichloro-2-pyridinyl
2,5-dichloro-3-pyridinyl
2,5-dichloro-4-pyridinyl
3,5-bis-(trifluoromethyl)pyrazol-1-yl
1-methyl-3-(trifluoromethyl)pyrazol-5-yl
1-methyl-4-(trifluoromethyl)imidazol-2-yl

TABLE 3A

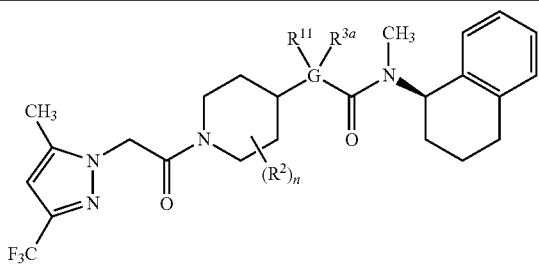

| (R²)ₙ | G | R³ᵃ | R¹¹ |
|---|---|---|---|
| H | G-1 | H | — |
| H | G-2 | H | — |
| H | G-3 | H | H |
| H | G-4 | H | — |
| H | G-5 | H | — |
| H | G-6 | H | H |
| H | G-7 | H | — |
| H | G-8 | H | — |
| H | G-9 | H | H |
| H | G-10 | H | — |
| H | G-11 | H | — |
| H | G-12 | H | H |
| H | G-13 | H | H |
| H | G-14 | H | — |
| H | G-15 | H | — |
| H | G-16 | H | H |
| H | G-17 | H | — |
| H | G-18 | H | — |
| H | G-19 | H | H |
| H | G-20 | H | — |
| H | G-21 | H | — |
| H | G-22 | H | H |
| H | G-23 | H | — |
| H | G-24 | H | — |
| H | G-25 | H | — |
| H | G-26 | H | — |
| H | G-27 | H | — |
| H | G-28 | H | — |
| H | G-29 | H | — |
| H | G-30 | H | — |
| H | G-31 | H | — |
| H | G-32 | H | — |
| H | G-33 | H | — |
| H | G-34 | H | — |
| H | G-35 | H | — |
| H | G-36 | H | — |
| H | G-37 | H | — |
| H | G-38 | H | — |
| H | G-39 | H | H |
| If | G-40 | H | — |
| H | G-41 | H | — |
| H | G-42 | H | H |
| H | G-43 | H | H |
| H | G-44 | H | — |
| H | G-45 | H | — |
| H | G-46 | H | — |
| H | G-47 | H | — |
| H | G-48 | H | H |
| H | G-49 | H | — |
| H | G-50 | H | — |
| H | G-51 | H | H |
| H | G-52 | H | — |
| H | G-53 | H | — |
| H | G-54 | H | H |
| H | G-55 | H | — |
| H | G-2 | Me | — |
| H | G-2 | Cl | — |
| H | G-2 | F | — |
| H | G-2 | CF₃ | — |
| H | G-14 | n-Pr | — |
| H | G-3 | H | Me |
| H | G-3 | H | n-Pr |
| H | G-26 | 5-Me | — |
| 2-Me | G-1 | H | — |

TABLE 3A-continued

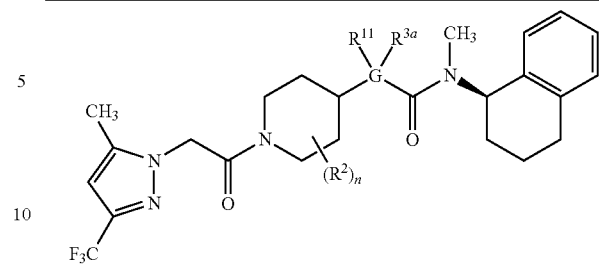

| (R²)ₙ | G | R³ᵃ | R¹¹ |
|---|---|---|---|
| 3-Me | G-1 | H | — |
| 2,6-di-Me | G-1 | H | — |
| 3,5-di-Me | G-1 | H | — |
| 3-n-Bu | G-1 | H | — |
| 4-MeO | G-1 | H | — |
| 4-OH | G-1 | H | — |
| 4-Cl | G-1 | H | — |
| 4-Br | G-1 | H | — |
| 4-CN | G-1 | H | — |

TABLE 3B

| (R²)ₙ | G | R³ᵃ | R¹¹ |
|---|---|---|---|
| H | G-1 | H | — |
| H | G-2 | H | — |
| H | G-3 | H | H |
| H | G-4 | H | — |
| H | G-5 | H | — |
| H | G-6 | H | H |
| H | G-7 | H | — |
| H | G-8 | H | — |
| H | G-9 | H | H |
| H | G-10 | H | — |
| H | G-11 | H | — |
| H | G-12 | H | H |
| H | G-13 | H | H |
| H | G-14 | H | — |
| H | G-15 | H | — |
| H | G-16 | H | H |
| H | G-17 | H | — |
| H | G-18 | H | — |
| H | G-19 | H | H |
| H | G-20 | H | — |
| H | G-21 | H | — |
| H | G-22 | H | H |
| H | G-23 | H | — |
| H | G-24 | H | — |
| H | G-31 | H | — |
| H | G-32 | H | — |
| H | G-33 | H | — |
| H | G-34 | H | — |
| H | G-35 | H | — |
| H | G-37 | H | — |
| H | G-38 | H | — |
| H | G-39 | H | H |
| H | G-40 | H | — |
| H | G-41 | H | — |
| H | G-42 | H | H |

TABLE 3B-continued

| (R²)ₙ | G | R³ᵃ | R¹¹ |
|---|---|---|---|
| H | G-43 | H | H |
| H | G-44 | H | — |
| H | G-45 | H | — |
| H | G-46 | H | — |
| H | G-47 | H | — |
| H | G-48 | H | H |
| H | G-49 | H | — |
| H | G-50 | H | — |
| H | G-51 | H | H |
| H | G-52 | H | — |
| H | G-53 | H | — |
| H | G-54 | H | H |
| H | G-2 | Me | — |
| H | G-2 | Cl | — |
| H | G-2 | F | — |
| H | G-2 | CF₃ | — |
| H | G-14 | n-Pr | — |
| H | G-3 | H | Me |
| H | G-3 | H | n-Pr |
| 2-Me | G-1 | H | — |
| 3-Me | G-1 | H | — |
| 2,6-di-Me | G-1 | H | — |
| 3,5-di-Me | G-1 | H | — |
| 3-n-Bu | G-1 | H | — |

TABLE 3C

| (R²)ₙ | G | R³ᵃ | R¹¹ |
|---|---|---|---|
| H | G-1 | H | — |
| H | G-2 | H | — |
| H | G-3 | H | H |
| H | G-4 | H | — |
| H | G-5 | H | — |
| H | G-6 | H | H |
| H | G-7 | H | — |
| H | G-8 | H | — |
| H | G-9 | H | H |
| H | G-10 | H | — |
| H | G-11 | H | — |
| H | G-12 | H | H |
| H | G-13 | H | H |
| H | G-14 | H | — |
| H | G-15 | H | — |
| H | G-16 | H | H |
| H | G-17 | H | — |
| H | G-18 | H | — |
| H | G-19 | H | H |
| H | G-20 | H | — |

TABLE 3C-continued

| (R²)ₙ | G | R³ᵃ | R¹¹ |
|---|---|---|---|
| H | G-21 | H | — |
| H | G-22 | H | H |
| H | G-23 | H | — |
| H | G-24 | H | — |
| H | G-31 | H | — |
| H | G-32 | H | — |
| H | G-33 | H | — |
| H | G-34 | H | — |
| H | G-35 | H | — |
| H | G-37 | H | — |
| H | G-38 | H | — |
| H | G-39 | H | H |
| H | G-40 | H | — |
| H | G-41 | H | — |
| H | G-42 | H | H |
| H | G-43 | H | H |
| H | G-44 | H | — |
| H | G-45 | H | — |
| H | G-46 | H | — |
| H | G-47 | H | — |
| H | G-48 | H | H |
| H | G-49 | H | — |
| H | G-50 | H | — |
| H | G-51 | H | H |
| H | G-52 | H | — |
| H | G-53 | H | — |
| H | G-54 | H | H |
| H | G-2 | Me | — |
| H | G-2 | Cl | — |
| H | G-2 | F | — |
| H | G-2 | CF₃ | — |
| H | G-14 | n-Pr | — |
| H | G-3 | H | Me |
| H | G-3 | H | n-Pr |
| 2-Me | G-1 | H | — |
| 3-Me | G-1 | H | — |
| 2,6-di-Me | G-1 | H | — |
| 3,5-di-Me | G-1 | H | — |
| 3-n-Bu | G-1 | H | — |
| 5-Me | G-1 | H | — |
| 6-Me | G-1 | H | — |

TABLE 4*

| Q | Qᵃ | R⁵ | (R⁸)ₘ | (R⁹)ⱼ | R¹⁰ | R¹⁵ | (R¹⁶)ₘ/R¹⁶ᵃ |
|---|---|---|---|---|---|---|---|
| Q-2 | Me | — | H | H | — | H | — |
| Q-3 | Me | — | H | H | — | H | — |
| Q-4 | Me | — | H | H | — | H | — |

TABLE 4*-continued

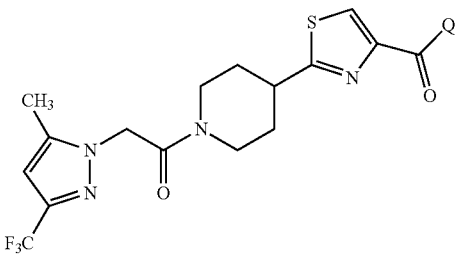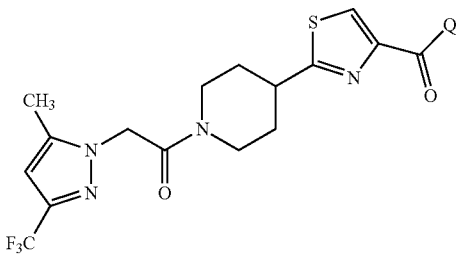

| Q | Qª | R⁵ | (R⁸)ₘ | (R⁹)ⱼ | R¹⁰ | R¹⁵ | (R¹⁶)ₘ/R¹⁶ª |
|---|---|---|---|---|---|---|---|
| Q-5 | Me | — | H | H | H | H | — |
| Q-6 | Me | — | H | H | — | H | — |
| Q-7 | Me | — | H | H | — | H | — |
| Q-8 | Me | — | H | H | — | H | — |
| Q-9 | Me | — | H | H | — | H | — |
| Q-10 | Me | — | H | H | — | H | — |
| Q-11 | Me | — | H | H | H | H | — |
| Q-12 | Me | — | H | H | — | H | — |
| Q-13 | Me | — | H | H | — | H | — |
| Q-14 | Me | — | H | H | — | H | — |
| Q-15 | Me | — | H | H | H | H | — |
| Q-2 | Me | — | 2-Me | H | — | H | — |
| Q-2 | Me | — | 2,2-di-Me | H | — | H | — |
| Q-2 | Me | — | 2-Et | H | — | H | — |
| Q-2 | Me | — | H | 6-Me | — | H | — |
| Q-2 | Me | — | H | 6-Cl | — | H | — |
| Q-2 | Me | — | H | 6-OMe | — | H | — |
| Q-2 | Me | — | H | 6-Br | — | H | — |
| Q-2 | Me | — | H | 6-F | — | H | — |
| Q-2 | Me | — | H | 5-OMe | — | H | — |
| Q-2 | Me | — | H | 7-OMe | — | H | — |
| Q-3 | Me | — | 3-Me | H | — | H | — |
| Q-4 | Me | — | 3-Me | H | — | H | — |
| Q-5 | Me | — | H | H | Me | H | — |
| Q-5 | Me | — | H | H | n-Pr | H | — |
| Q-6 | Me | — | H | 3-Cl | — | H | — |
| Q-7 | Me | — | H | 2-Cl | — | H | — |
| Q-8 | Me | — | 2-Me | H | — | H | — |
| Q-8 | Me | — | 2,2-di-Me | H | — | H | — |
| Q-8 | Me | — | 2-Et | H | — | H | — |
| Q-8 | Me | — | 2-n-Pr | H | — | H | — |
| Q-8 | Me | — | 3,3-di-Me | H | — | H | — |
| Q-8 | Me | — | H | 5-Me | — | H | — |
| Q-8 | Me | — | H | 5-Cl | — | H | — |
| Q-8 | Me | — | H | 5-OMe | — | H | — |
| Q-8 | Me | — | H | 5-Br | — | H | — |
| Q-9 | Me | — | 2-Me | H | — | H | — |
| Q-10 | Me | — | 2-Me | H | — | H | — |
| Q-11 | Me | — | H | H | Me | H | — |
| Q-13 | Me | — | H | 2-Me | — | H | — |
| Q-14 | Me | — | H | 2-Me | — | H | — |
| Q-14 | Me | — | H | 2-Cl | — | H | — |
| Q-15 | Me | — | H | H | Me | H | — |
| Q-16 | Me | — | H | H | — | H | — |
| Q-17 | Me | — | H | H | — | H | — |
| Q-18 | Me | — | H | H | Me | H | — |
| Q-19 | Me | — | H | H | — | H | — |
| Q-20 | Me | — | H | H | — | H | — |
| Q-21 | Me | — | H | H | Me | H | — |
| Q-22 | Me | — | H | H | — | H | — |
| Q-23 | Me | — | H | H | — | H | — |
| Q-24 | Me | — | H | H | — | H | — |
| Q-25 | Me | — | H | H | — | H | — |
| Q-26 | Me | — | H | H | — | H | — |
| Q-27 | Me | — | H | H | — | H | — |
| Q-28 | Me | — | H | H | — | H | — |
| Q-29 | Me | — | H | H | — | H | — |
| Q-30 | Me | — | H | H | — | H | — |
| Q-31 | Me | — | H | H | — | H | — |
| Q-32 | Me | — | H | H | — | H | — |
| Q-33 | Me | — | H | H | Me | H | — |
| Q-34 | Me | — | H | H | — | H | — |
| Q-35 | Me | — | H | H | — | H | — |
| Q-36 | Me | — | H | H | Me | H | — |
| Q-37 | Me | — | H | H | — | H | — |
| Q-38 | Me | — | H | H | — | H | — |
| Q-39 | Me | — | H | H | Me | H | — |
| Q-40 | Me | — | H | H | — | H | — |
| Q-41 | Me | — | H | H | — | H | — |
| Q-42 | Me | — | H | H | — | H | — |
| Q-43 | Me | — | H | H | — | H | — |
| Q-44 | Me | — | H | H | — | H | — |
| Q-45 | Me | — | H | H | — | H | — |
| Q-46 | Me | — | H | H | — | H | — |
| Q-47 | Me | — | H | H | — | H | — |
| Q-48 | Me | — | H | H | — | H | — |
| Q-49 | Me | — | H | H | — | H | — |
| Q-50 | Me | — | H | H | — | H | — |
| Q-51 | Me | — | H | H | — | H | — |
| Q-52 | Me | — | H | H | — | H | — |
| Q-53 | Me | — | H | H | — | H | — |
| Q-54 | Me | — | H | H | — | H | — |
| Q-55 | Me | — | H | H | — | H | — |
| Q-56 | Me | — | H | H | — | H | — |
| Q-57 | Me | — | H | H | — | H | — |
| Q-58 | — | — | H | H | — | H | — |
| Q-59 | — | — | H | H | — | H | — |
| Q-60 | — | — | H | H | — | H | — |
| Q-61 | — | — | H | H | — | H | — |
| Q-62 | — | — | H | H | — | H | — |
| Q-63 | — | — | H | H | — | H | — |
| Q-64 | — | — | H | H | — | H | — |
| Q-65 | — | — | H | H | — | H | — |
| Q-66 | — | — | H | H | — | H | — |
| Q-67 | — | — | H | H | — | H | — |
| Q-68 | — | — | H | H | — | H | — |
| Q-69 | — | — | H | H | — | H | — |
| Q-70 | — | Et | — | H | — | H | — |
| Q-71 | — | Et | — | H | — | H | — |
| Q-72 | — | Et | — | H | — | H | — |
| Q-73 | Me | — | — | H | — | H | — |
| Q-74 | Me | — | — | H | — | H | — |
| Q-75 | Me | Me | — | H | — | Me | — |
| Q-76 | — | — | — | — | — | — | 3-Ph |
| Q-77 | — | — | — | — | — | — | 4-Ph |
| Q-78 | — | — | — | — | — | — | 4-Ph |
| Q-79 | — | — | — | — | — | — | H |
| Q-80 | — | — | — | — | — | — | 4-Ph |
| Q-81 | — | — | — | — | — | — | 2-Me |
| Q-82 | — | — | — | — | — | — | H |
| Q-83 | Me | — | — | — | — | H | 2-Ph |
| Q-84 | Me | — | — | — | — | H | 2-Ph |
| Q-85 | Me | — | — | — | — | H | 2-Ph |
| Q-2 | Me | — | 4-Me | H | — | H | — |
| Q-2 | Me | — | 4,4-di-Me | H | — | H | — |
| Q-2 | Me | — | 4-Et | H | — | H | — |
| Q-2 | Me | — | 2-OH | H | — | H | — |
| Q-2 | Me | — | 4-OH | H | — | H | — |
| Q-2 | Me | — | 4-OMe | H | — | H | — |
| Q-2 | Me | — | 4-SMe | H | — | H | — |
| Q-2 | Me | — | 4-SOMe | H | — | H | — |
| Q-2 | Me | — | 4-SO₂Me | H | — | H | — |
| Q-2 | Me | — | 4-OCF₃ | H | — | H | — |
| Q-2 | Me | — | 2-CF₃ | H | — | H | — |
| Q-2 | Me | — | 4-NH₂ | H | — | H | — |
| Q-2 | Me | — | 2-n-Bu | H | — | H | — |
| Q-2 | Me | — | 2-propenyl | H | — | H | — |
| Q-2 | Me | — | 2-propynyl | H | — | H | — |
| Q-2 | Me | — | 4-Cl | H | — | H | — |
| Q-2 | Me | — | 2-CN | H | — | H | — |

TABLE 4*-continued

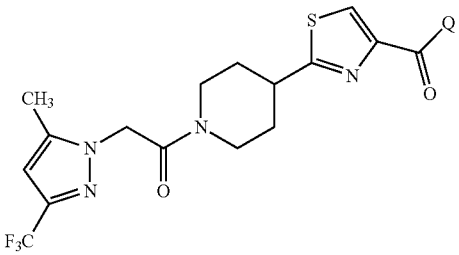

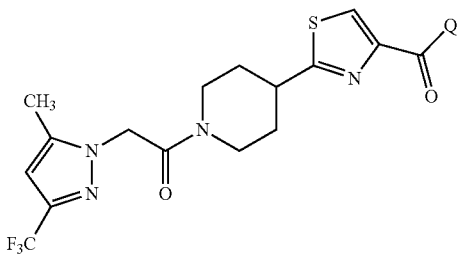

| Q | Qa | R5 | (R8)m | (R9)j | R10 | R15 | (R16)m/R16a |
|---|---|---|---|---|---|---|---|
| Q-2 | Me | — | 4-CN | H | — | H | — |
| Q-2 | Me | — | 4-O-t-Bu | H | — | H | — |
| Q-2 | Me | — | 4-NHMe | H | — | H | — |
| Q-2 | Me | — | 4-N(Me)Me | H | — | H | — |
| Q-2 | Me | — | 2-MeOMe | H | — | H | — |
| Q-2 | Me | — | 4-CH2OH | H | — | H | — |
| Q-2 | Me | — | 4-Ac | H | — | H | — |
| Q-2 | Me | — | 4-COOMe | H | — | H | — |
| Q-2 | Me | — | 4-OAc | H | — | H | — |
| Q-2 | Me | — | 4-O(C=O)-n-Bu | H | — | H | — |
| Q-2 | Me | — | 4-OEt | H | — | H | — |
| Q-2 | Me | — | 4-O(C=O)Et | H | — | H | — |
| Q-2 | Me | — | 4-SAc | H | — | H | — |
| Q-2 | Me | — | 4-CONHMe | H | — | H | — |
| Q-2 | Me | — | 4-CONMe2 | H | — | H | — |
| Q-2 | H | — | 2-Me | H | — | H | — |
| Q-2 | H | — | 2,2-di-Me | H | — | H | — |
| Q-2 | H | — | 4-Me | H | — | H | — |
| Q-2 | H | — | 4,4-di-Me | H | — | H | — |
| Q-2 | H | — | 4-OH | H | — | H | — |
| Q-2 | H | — | 4-OMe | H | — | H | — |
| Q-2 | H | — | 4-OAc | H | — | H | — |
| Q-2 | Me | — | 2-Me | H | — | Me | — |
| Q-2 | Me | — | 2,2-di-Me | H | — | Me | — |
| Q-2 | Me | — | 4-Me | H | — | Me | — |
| Q-2 | Me | — | 4,4-di-Me | H | — | Me | — |
| Q-2 | Me | — | 4-OH | H | — | Me | — |
| Q-2 | Me | — | 4-OMe | H | — | Me | — |
| Q-2 | Me | — | 4-OAc | H | — | Me | — |
| Q-2 | Et | — | H | H | — | H | — |
| Q-2 | Pr | — | H | H | — | H | — |
| Q-2 | 2-propenyl | — | H | H | — | H | — |
| Q-2 | 2-propynyl | — | H | H | — | H | — |
| Q-2 | c-propyl | — | H | H | — | H | — |
| Q-2 | CF3 | — | H | H | — | H | — |
| Q-2 | CN | — | H | H | — | H | — |
| Q-2 | OH | — | H | H | — | H | — |
| Q-2 | OMe | — | H | H | — | H | — |
| Q-2 | CH2OMe | — | H | H | — | H | — |
| Q-2 | CH2OH | — | H | H | — | H | — |
| Q-2 | Ac | — | H | H | — | H | — |
| Q-2 | COEt | — | H | H | — | H | — |
| Q-2 | CO2Me | — | H | H | — | H | — |
| Q-2 | CONHMe | — | H | H | — | H | — |
| Q-2 | CON(Me)2 | — | H | H | — | H | — |
| Q-8 | Me | — | 3-Me | H | — | H | — |
| Q-8 | Me | — | 3,3-di-Me | H | — | H | — |
| Q-8 | Me | — | 3-OH | H | — | H | — |
| Q-8 | Me | — | 3-OMe | H | — | H | — |
| Q-8 | Me | — | 3-OAc | H | — | H | — |
| Q-8 | Me | — | 2-Et | H | — | H | — |
| Q-8 | H | — | H | H | — | H | — |
| Q-14 | Me | — | 2-Me | H | — | H | — |
| Q-14 | Me | — | 2,2-di-Me | H | — | H | — |
| Q-14 | Me | — | 3-Me | H | — | H | — |
| Q-14 | Me | — | 3,3-di-Me | H | — | H | — |
| Q-14 | Me | — | 3-OH | H | — | H | — |
| Q-14 | Me | — | 3-OMe | H | — | H | — |
| Q-14 | Me | — | 3-OAc | H | — | H | — |
| Q-14 | Me | — | 2-Et | H | — | H | — |
| Q-14 | Me | — | H | H | — | H | — |
| Q-23 | Me | — | 2-Me | H | — | H | — |
| Q-23 | Me | — | 2,2-di-Me | H | — | H | — |
| Q-23 | Me | — | 3-Me | H | — | H | — |
| Q-23 | Me | — | 3,3-di-Me | H | — | H | — |
| Q-23 | H | — | H | H | — | H | — |
| Q-41 | Me | — | 2-Me | H | — | H | — |
| Q-41 | Me | — | 2,2-di-Me | H | — | H | — |
| Q-41 | H | — | H | H | — | H | — |
| Q-70 | — | Me | — | H | — | Me | — |
| Q-71 | — | Me | — | H | — | Me | — |
| Q-78 | — | — | — | — | — | — | H |
| Q-78 | — | — | — | — | — | — | 4-Me |
| Q-78 | — | — | — | — | — | — | 4-Et |
| Q-78 | — | — | — | — | — | — | 4-i-Pr |
| Q-78 | — | — | — | — | — | — | 4-t-Bu |
| Q-78 | — | — | — | — | — | — | 4-propen-2-yl |
| Q-78 | — | — | — | — | — | — | 4-propyn-2-yl |
| Q-78 | — | — | — | — | — | — | 4-c-propyl |
| Q-78 | — | — | — | — | — | — | 4-c-hexyl |
| Q-78 | — | — | — | — | — | — | 4-CF3 |
| Q-78 | — | — | — | — | — | — | 4-CH2CF3 |
| Q-78 | — | — | — | — | — | — | 4-SO2Me |
| Q-78 | — | — | — | — | — | — | 4-CH2OH |
| Q-78 | — | — | — | — | — | — | 4-Ac |
| Q-78 | — | — | — | — | — | — | 4-COEt |
| Q-78 | — | — | — | — | — | — | 4-COO-t-Bu |
| Q-78 | — | — | — | — | — | — | 4-benzyl |
| Q-78 | — | — | — | — | — | — | 4-(4-Cl—Ph) |
| Q-77 | — | — | — | — | — | — | H |
| Q-77 | — | — | — | — | — | — | 4-Me |
| Q-77 | — | — | — | — | — | — | 4-t-Bu |
| Q-77 | — | — | — | — | — | — | 4-OH |
| Q-77 | — | — | — | — | — | — | 4-OMe |
| Q-77 | — | — | — | — | — | — | 4-OPr |
| Q-77 | — | — | — | — | — | — | 4-Br |
| Q-77 | — | — | — | — | — | — | 4-Cl |
| Q-77 | — | — | — | — | — | — | 4-NH2 |
| Q-77 | — | — | — | — | — | — | 4-NHMe |
| Q-77 | — | — | — | — | — | — | 4-N(Et)2 |
| Q-77 | — | — | — | — | — | — | 4-CN |
| Q-77 | — | — | — | — | — | — | 4-NO2 |
| Q-77 | — | — | — | — | — | — | 4-OCF3 |
| Q-77 | — | — | — | — | — | — | 4-SMe |
| Q-77 | — | — | — | — | — | — | 4-SO-n-Bu |
| Q-77 | — | — | — | — | — | — | 4-SCHF2 |
| Q-77 | — | — | — | — | — | — | 4-NHMe |
| Q-77 | — | — | — | — | — | — | 4-N(Me)2 |
| Q-77 | — | — | — | — | — | — | 4-MeOMe |
| Q-77 | — | — | — | — | — | — | 4-CO2Me |
| Q-77 | — | — | — | — | — | — | 4-OAc |
| Q-77 | — | — | — | — | — | — | 4-CONHMe |
| Q-77 | — | — | — | — | — | — | 4-trimethyl-silyl |
| Q-77 | — | — | — | — | — | — | 3-Ph |
| Q-77 | — | — | — | — | — | — | 3-Me |
| Q-77 | — | — | — | — | — | — | 2-Ph |
| Q-75 | Me | Et | — | H | — | Et | — |
| Q-75 | Me | Et | — | H | — | Me | — |
| Q-75 | Me | Me | — | H | — | i-Pr | — |

Notes:
*The definitions of R5, R10, R15, (R16)m, R16a, Qa, (R8)m and (R9)j in the compounds of Table 4 are shown in Embodiment 50 unless otherwise noted.

TABLE 5

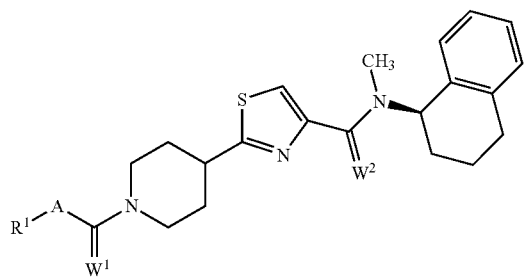

| R¹ | A | W¹ | W² |
|---|---|---|---|
| 2-methoxyphenyl | NH | O | O |
| 2,5-dichlorophenyl | NH | O | O |
| 5-bromo-2-chlorophenyl | NH | O | O |
| 2-chloro-5-methylphenyl | NH | O | O |
| 2-chloro-5-(trifluoromethyl)phenyl | NH | O | O |
| 2,5-dibromophenyl | NH | O | O |
| 2-bromo-5-methylphenyl | NH | O | O |
| 2-bromo-5-(trifluoromethyl)phenyl | NH | O | O |
| 5-chloro-2-methylphenyl | NH | O | O |
| 5-bromo-2-methylphenyl | NH | O | O |
| 2,5-dimethylphenyl | NH | O | O |
| 5-ethyl-2-methylphenyl | NH | O | O |
| 2-methyl-5-(trifluoromethyl)phenyl | NH | O | O |
| 5-bromo-2-methoxyphenyl | NH | O | O |
| 2-methoxy-5-methylphenyl | NH | O | O |
| 2-methoxy-5-(trifluoromethyl)phenyl | NH | O | O |
| 3-(trifluoromethyl)pyrazol-1-yl | NH | O | O |
| 3,5-dimethylpyrazol-1-yl | NH | O | O |
| 3-ethyl-5-methylpyrazol-1-yl | NH | O | O |
| 5-methyl-3-(trifluoromethyl)pyrazol-1-yl | NH | O | O |
| 3,5-dichloropyrazol-1-yl | NH | O | O |
| 5-chloro-3-(trifluoromethyl)pyrazol-1-yl | NH | O | O |
| 3,5-dibromopyrazol-1-yl | NH | O | O |
| 5-bromo-3-(trifluoromethyl)pyrazol-1-yl | NH | O | O |
| 3,5-diethylpyrazol-1-yl | NH | O | O |
| 5-ethyl-3-(trifluoromethyl)pyrazol-1-yl | NH | O | O |
| 2-methoxyphenyl | NH | S | O |
| 2,5-dichlorophenyl | NH | S | O |
| 5-bromo-2-chlorophenyl | NH | S | O |
| 2-chloro-5-methylphenyl | NH | S | O |
| 2-chloro-5-(trifluoromethyl)phenyl | NH | S | O |
| 2,5-dibromophenyl | NH | S | O |
| 2-bromo-5-methylphenyl | NH | S | O |
| 2-bromo-5-(trifluoromethyl)phenyl | NH | S | O |
| 5-chloro-2-methylphenyl | NH | S | O |
| 5-bromo-2-methylphenyl | NH | S | O |
| 2,5-dimethylphenyl | NH | S | O |
| 5-ethyl-2-methylphenyl | NH | S | O |
| 2-methyl-5-(trifluoromethyl)phenyl | NH | S | O |
| 5-bromo-2-methoxyphenyl | NH | S | O |
| 2-methoxy-5-methylphenyl | NH | S | O |
| 2-methoxy-5-(trifluoromethyl)phenyl | NH | S | O |
| 3-(trifluoromethyl)pyrazol-1-yl | NH | S | O |
| 3,5-dimethylpyrazol-1-yl | NH | S | O |
| 3-ethyl-5-methylpyrazol-1-yl | NH | S | O |
| 5-methyl-3-(trifluoromethyl)pyrazol-1-yl | NH | S | O |
| 3,5-dichloropyrazol-1-yl | NH | S | O |
| 5-chloro-3-(trifluoromethyl)pyrazol-1-yl | NH | S | O |
| 3,5-dibromopyrazol-1-yl | NH | S | O |
| 5-bromo-3-(trifluoromethyl)pyrazol-1-yl | NH | S | O |
| 3,5-diethylpyrazol-1-yl | NH | S | O |
| 5-ethyl-3-(trifluoromethyl)pyrazol-1-yl | NH | S | O |
| 5-methyl-3-(trifluoromethyl)pyrazol-1-yl | CH₂ | S | S |
| 5-methyl-3-(trifluoromethyl)pyrazol-1-yl | CH₂ | O | S |
| 3,5-dichloropyrazol-1-yl | CH₂ | O | S |
| 5-chloro-3-(trifluoromethyl)pyrazol-1-yl | CH₂ | O | S |
| 3,5-diethylpyrazol-1-yl | CH₂ | O | S |
| 5-ethyl-3-(trifluoromethyl)pyrazol-1-yl | CH₂ | O | S |
| 3,5-bis-(trifluoromethyl)pyrazol-1-yl | CH₂ | O | S |
| 1-methyl-3-(trifluoromethyl)pyrazol-5-yl | CH₂ | O | S |
| 1-methyl-4-(trifluoromethyl)imidazol-2-yl | CH₂ | O | S |

TABLE 6A

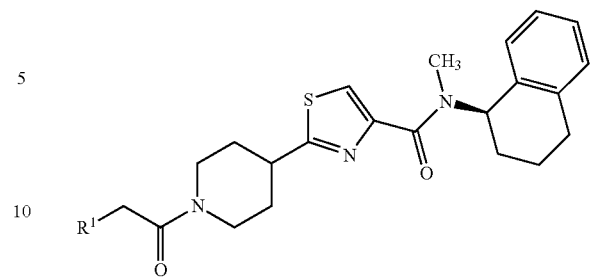

| R¹ |
|---|
| 2-methoxyphenyl |
| 3-bromophenyl |
| 3-iodophenyl |
| 3-(trifluoromethyl)phenyl |
| 3-(2,2,2-trifluoroethyl)phenyl |
| 3-(pentafluoroethyl)phenyl |
| 3-cyanophenyl |
| 3-nitrophenyl |
| 2,5-dichlorophenyl |
| 5-bromo-2-chlorophenyl |
| 2-chloro-5-iodophenyl |
| 2-chloro-5-methylphenyl |
| 2-chloro-5-ethylphenyl |
| 2-chloro-5-(trifluoromethyl)phenyl |
| 2-chloro-5-(2,2,2-trifluoroethyl)phenyl |
| 2-chloro-5-(pentafluoroethyl)phenyl |
| 2-chloro-5-cyanophenyl |
| 2-chloro-5-nitrophenyl |
| 2-bromo-5-chlorophenyl |
| 2,5-dibromophenyl |
| 2-bromo-5-iodophenyl |
| 2-bromo-5-methylphenyl |
| 2-bromo-5-ethylphenyl |
| 2-bromo-5-propylphenyl |
| 2-bromo-5-(trifluoromethyl)phenyl |
| 2-bromo-5-(2,2,2-trifluoroethyl)phenyl |
| 2-bromo-5-(pentafluoroethyl)phenyl |
| 2-bromo-5-cyanophenyl |
| 2-bromo-5-nitrophenyl |
| 5-chloro-2-methylphenyl |
| 5-bromo-2-methylphenyl |
| 5-iodo-2-methylphenyl |
| 2,5-dimethylphenyl |
| 5-ethyl-2-methylphenyl |
| 2-methyl-5-propylphenyl |
| 5-isopropyl-2-methylphenyl |
| 2-methyl-5-(trifluoromethyl)phenyl |
| 2-methyl-5-(2,2,2-trifluoroethyl)phenyl |
| 2-methyl-5-(pentafluoroethyl)phenyl |
| 5-cyano-2-methylphenyl |
| 2-methyl-5-nitrophenyl |
| 5-chloro-2-methoxyphenyl |
| 5-bromo-2-methoxyphenyl |
| 5-iodo-2-methoxyphenyl |
| 2-methoxy-5-methylphenyl |
| 5-ethyl-2-methoxyphenyl |
| 2-methoxy-5-propylphenyl |
| 2-methoxy-5-(trifluoromethyl)phenyl |
| 2-methoxy-5-(2,2,2-trifluoroethyl)phenyl |
| 2-methoxy-5-(pentafluoroethyl)phenyl |
| 5-cyano-2-methoxyphenyl |
| 2-methoxy-5-nitrophenyl |
| 5-chloro-2-ethylphenyl |
| 5-bromo-2-ethylphenyl |
| 2-ethyl-5-iodophenyl |
| 2-ethyl-5-methylphenyl |
| 2,5-diethylphenyl |
| 2-ethyl-5-propylphenyl |
| 2-ethyl-5-(trifluoromethyl)phenyl |
| 2-ethyl-5-(2,2,2-trifluoroethyl)phenyl |
| 2-ethyl-5-(pentafluoroethyl)phenyl |
| 5-cyano-2-ethylphenyl |
| 2-ethyl-5-nitrophenyl |
| 3-chloropyrazol-1-yl |

TABLE 6A-continued

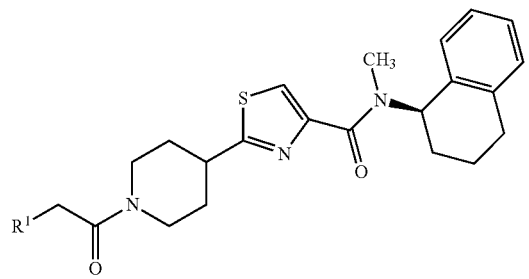

R¹

3-bromopyrazol-1-yl
3-(trifluoromethyl)pyrazol-1-yl
3-(2,2,2-trifluoroethyl)pyrazol-1-yl
3-(pentafluoroethyl)pyrazol-1-yl
3-cyanopyrazol-1-yl
3-nitropyrazol-1-yl
3,5-dimethylpyrazol-1-yl
3-chloro-5-methylpyrazol-1-yl
3-bromo-5-methylpyrazol-1-yl
3-iodo-5-methylpyrazol-1-yl
3-ethyl-5-methylpyrazol-1-yl
5-methyl-3-propylpyrazol-1-yl
5-methyl-3-(trifluoromethyl)pyrazol-1-yl
5-methyl-3-(2,2,2-trifluoroethyl)pyrazol-1-yl
5-methyl-3-(pentafluoroethyl)pyrazol-1-yl
3-cyano-5-methylpyrazol-1-yl
5-methyl-3-nitropyrazol-1-yl
5-chloro-3-methylpyrazol-1-yl
3,5-dichloropyrazol-1-yl
5-chloro-3-bromopyrazol-1-yl
5-chloro-3-iodopyrazol-1-yl
5-chloro-3-ethylpyrazol-1-yl
5-chloro-3-propylpyrazol-1-yl
5-chloro-3-(trifluoromethyl)pyrazol-1-yl
5-chloro-3-(2,2,2-trifluoroethyl)pyrazol-1-yl
5-chloro-3-(pentafluoroethyl)pyrazol-1-yl
5-chloro-3-cyanopyrazol-1-yl
5-chloro-3-nitropyrazol-1-yl
5-bromo-3-methylpyrazol-1-yl
5-bromo-3-chloropyrazol-1-yl
3,5-dibromopyrazol-1-yl
5-bromo-3-iodopyrazol-1-yl
5-bromo-3-ethylpyrazol-1-yl
5-bromo-3-propylpyrazol-1-yl
5-bromo-3-(trifluoromethyl)pyrazol-1-yl
5-bromo-3-(2,2,2-trifluoroethyl)pyrazol-1-yl
5-bromo-3-(pentafluoroethyl)pyrazol-1-yl
5-ethyl-3-methylpyrazol-1-yl
3-chloro-5-ethylpyrazol-1-yl
3-bromo-5-ethylpyrazol-1-yl
5-ethyl-3-iodopyrazol-1-yl
3,5-diethylpyrazol-1-yl
5-ethyl-3-propylpyrazol-1-yl
5-ethyl-3-(trifluoromethyl)pyrazol-1-yl
5-ethyl-3-(2,2,2-trifluoroethyl)pyrazol-1-yl
5-ethyl-3-(pentafluoroethyl)pyrazol-1-yl
3,5-dimethyl-2-thienyl
3,5-dichloro-2-thienyl
2,5-dimethyl-3-thienyl
2,5-dichloro-3-thienyl
3,6-dimethyl-2-pyridyl
2,5-dimethyl-3-pyridyl
2,5-dimethyl-4-pyridyl
3,6-dichloro-2-pyridyl
2,5-dichloro-3-pyridyl
2,5-dichloro-4-pyridyl
3,5-bis-(trifluoromethyl)pyrazol-1-yl
1-methyl-3-(trifluoromethyl)pyrazol-5-yl
1-methyl-4-(trifluoromethyl)imidazol-2-yl

TABLE 6B

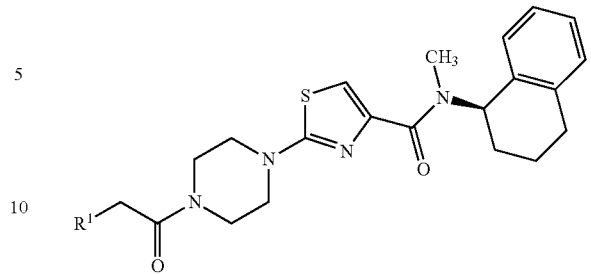

R¹

2-methoxyphenyl
3-bromophenyl
3-iodophenyl
3-(trifluoromethyl)phenyl
3-(2,2,2-trifluoroethyl)phenyl
3-(pentafluoroethyl)phenyl
3-cyanophenyl
3-nitrophenyl
2,5-dichlorophenyl
5-bromo-2-chlorophenyl
2-chloro-5-iodophenyl
2-chloro-5-methylphenyl
2-chloro-5-ethylphenyl
2-chloro-5-(trifluoromethyl)phenyl
2-chloro-5-(2,2,2-trifluoroethyl)phenyl
2-chloro-5-(pentafluoroethyl)phenyl
2-chloro-5-cyanophenyl
2-chloro-5-nitrophenyl
2-bromo-5-chlorophenyl
2,5-dibromophenyl
2-bromo-5-iodophenyl
2-bromo-5-methylphenyl
2-bromo-5-ethylphenyl
2-bromo-5-propylphenyl
2-bromo-5-(trifluoromethyl)phenyl
2-bromo-5-(2,2,2-trifluoroethyl)phenyl
2-bromo-5-(pentafluoroethyl)phenyl
2-bromo-5-cyanophenyl
2-bromo-5-nitrophenyl
5-chloro-2-methylphenyl
5-bromo-2-methylphenyl
5-iodo-2-methylphenyl
2,5-dimethylphenyl
5-ethyl-2-methylphenyl
2-methyl-5-propylphenyl
5-isopropyl-2-methylphenyl
2-methyl-5-(trifluoromethyl)phenyl
2-methyl-5-(2,2,2-trifluoroethyl)phenyl
2-methyl-5-(pentafluoroethyl)phenyl
5-cyano-2-methylphenyl
2-methyl-5-nitrophenyl
5-chloro-2-methoxyphenyl
5-bromo-2-methoxyphenyl
5-iodo-2-methoxyphenyl
2-methoxy-5-methylphenyl
5-ethyl-2-methoxyphenyl
2-methoxy-5-propylphenyl
2-methoxy-5-(trifluoromethyl)phenyl
2-methoxy-5-(2,2,2-trifluoroethyl)phenyl
2-methoxy-5-(pentafluoroethyl)phenyl
5-cyano-2-methoxyphenyl
2-methoxy-5-nitrophenyl
5-chloro-2-ethylphenyl
5-bromo-2-ethylphenyl
2-ethyl-5-iodophenyl
2-ethyl-5-methylphenyl
2,5-diethylphenyl
2-ethyl-5-propylphenyl
2-ethyl-5-(trifluoromethyl)phenyl
2-ethyl-5-(2,2,2-trifluoroethyl)phenyl
2-ethyl-5-(pentafluoroethyl)phenyl
5-cyano-2-ethylphenyl
2-ethyl-5-nitrophenyl
3-chloropyrazol-1-yl

TABLE 6B-continued

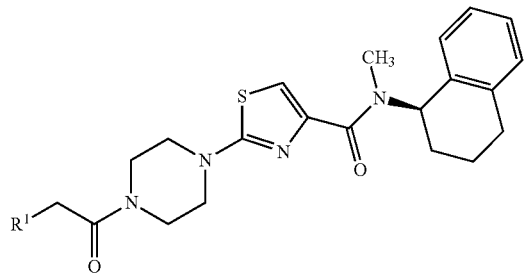

R[1]

3-bromopyrazol-1-yl
3-(trifluoromethyl)pyrazol-1-yl
3-(2,2,2-trifluoroethyl)pyrazol-1-yl
3-(pentafluoroethyl)pyrazol-1-yl
3-cyanopyrazol-1-yl
3-nitropyrazol-1-yl
3,5-dimethylpyrazol-1-yl
3-chloro-5-methylpyrazol-1-yl
3-bromo-5-methylpyrazol-1-yl
3-iodo-5-methylpyrazol-1-yl
3-ethyl-5-methylpyrazol-1-yl
5-methyl-3-propylpyrazol-1-yl
5-methyl-3-(trifluoromethyl)pyrazol-1-yl
5-methyl-3-(2,2,2-trifluoroethyl)pyrazol-1-yl
5-methyl-3-(pentafluoroethyl)pyrazol-1-yl
3-cyano-5-methylpyrazol-1-yl
5-methyl-3-nitropyrazol-1-yl
5-chloro-3-methylpyrazol-1-yl
3,5-dichloropyrazol-1-yl
5-chloro-3-bromopyrazol-1-yl
5-chloro-3-iodopyrazol-1-yl
5-chloro-3-ethylpyrazol-1-yl
5-chloro-3-propylpyrazol-1-yl
5-chloro-3-(trifluoromethyl)pyrazol-1-yl
5-chloro-3-(2,2,2-trifluoroethyl)pyrazol-1-yl
5-chloro-3-(pentafluoroethyl)pyrazol-1-yl
5-chloro-3-cyanopyrazol-1-yl
5-chloro-3-nitropyrazol-1-yl
5-bromo-3-methylpyrazol-1-yl
5-bromo-3-chloropyrazol-1-yl
3,5-dibromopyrazol-1-yl
5-bromo-3-iodopyrazol-1-yl
5-bromo-3-ethylpyrazol-1-yl
5-bromo-3-propylpyrazol-1-yl
5-bromo-3-(trifluoromethyl)pyrazol-1-yl
5-bromo-3-(2,2,2-trifluoroethyl)pyrazol-1-yl
5-bromo-3-(pentafluoroethyl)pyrazol-1-yl
5-ethyl-3-methylpyrazol-1-yl
3-chloro-5-ethylpyrazol-1-yl
3-bromo-5-ethylpyrazol-1-yl
5-ethyl-3-iodopyrazol-1-yl
3,5-diethylpyrazol-1-yl
5-ethyl-3-propylpyrazol-1-yl
5-ethyl-3-(trifluoromethyl)pyrazol-1-yl
5-ethyl-3-(2,2,2-trifluoroethyl)pyrazol-1-yl
5-ethyl-3-(pentafluoroethyl)pyrazol-1-yl
3,5-dimethyl-2-thienyl
3,5-dichloro-2-thienyl
2,5-dimethyl-3-thienyl
2,5-dichloro-3-thienyl
3,6-dimethyl-2-pyridyl
2,5-dimethyl-3-pyridyl
2,5-dimethyl-4-pyridyl
3,6-dichloro-2-pyridyl
2,5-dichloro-3-pyridyl
2,5-dichloro-4-pyridyl
3,5-bis-(trifluoromethyl)pyrazol-1-yl
1-methyl-3-(trifluoromethyl)pyrazol-5-yl
1-methyl-4-(trifluoromethyl)imidazol-2-yl

TABLE 6C

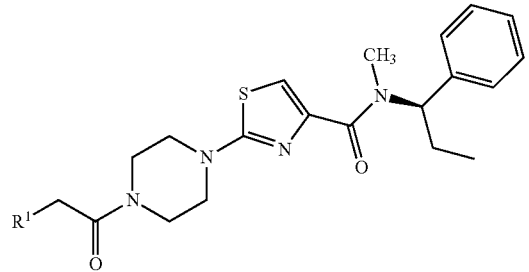

R[1]

2-methoxyphenyl
3-bromophenyl
3-iodophenyl
3-(trifluoromethyl)phenyl
3-(2,2,2-trifluoroethyl)phenyl
3-(pentafluoroethyl)phenyl
3-cyanophenyl
3-nitrophenyl
2,5-dichlorophenyl
5-bromo-2-chlorophenyl
2-chloro-5-iodophenyl
2-chloro-5-methylphenyl
2-chloro-5-ethylphenyl
2-chloro-5-(trifluoromethyl)phenyl
2-chloro-5-(2,2,2-trifluoroethyl)phenyl
2-chloro-5-(pentafluoroethyl)phenyl
2-chloro-5-cyanophenyl
2-chloro-5-nitrophenyl
2-bromo-5-chlorophenyl
2,5-dibromophenyl
2-bromo-5-iodophenyl
2-bromo-5-methylphenyl
2-bromo-5-ethylphenyl
2-bromo-5-propylphenyl
2-bromo-5-(trifluoromethyl)phenyl
2-bromo-5-(2,2,2-trifluoroethyl)phenyl
2-bromo-5-(pentafluoroethyl)phenyl
2-bromo-5-cyanophenyl
2-bromo-5-nitrophenyl
5-chloro-2-methylphenyl
5-bromo-2-methylphenyl
5-iodo-2-methylphenyl
2,5-dimethylphenyl
5-ethyl-2-methylphenyl
2-methyl-5-propylphenyl
5-isopropyl-2-methylphenyl
2-methyl-5-(trifluoromethyl)phenyl
2-methyl-5-(2,2,2-trifluoroethyl)phenyl
2-methyl-5-(pentafluoroethyl)phenyl
5-cyano-2-methylphenyl
2-methyl-5-nitrophenyl
5-chloro-2-methoxyphenyl
5-bromo-2-methoxyphenyl
5-iodo-2-methoxyphenyl
2-methoxy-5-methylphenyl
5-ethyl-2-methoxyphenyl
2-methoxy-5-propylphenyl
2-methoxy-5-(trifluoromethyl)phenyl
2-methoxy-5-(2,2,2-trifluoroethyl)phenyl
2-methoxy-5-(pentafluoroethyl)phenyl
5-cyano-2-methoxyphenyl
2-methoxy-5-nitrophenyl
5-chloro-2-ethylphenyl
5-bromo-2-ethylphenyl
2-ethyl-5-iodophenyl
2-ethyl-5-methylphenyl
2,5-diethylphenyl
2-ethyl-5-propylphenyl
2-ethyl-5-(trifluoromethyl)phenyl
2-ethyl-5-(2,2,2-trifluoroethyl)phenyl
2-ethyl-5-(pentafluoroethyl)phenyl
5-cyano-2-ethylphenyl
2-ethyl-5-nitrophenyl
3-chloropyrazol-1-yl

TABLE 6C-continued

[Structure: thiazole with N-methyl-N-(1-phenylpropyl)carboxamide and piperazine-N-C(O)-R¹]

R¹

3-bromopyrazol-1-yl
3-(trifluoromethyl)pyrazol-1-yl
3-(2,2,2-trifluoroethyl)pyrazol-1-yl
3-(pentafluoroethyl)pyrazol-1-yl
3-cyanopyrazol-1-yl
3-nitropyrazol-1-yl
3,5-dimethylpyrazol-1-yl
3-chloro-5-methylpyrazol-1-yl
3-bromo-5-methylpyrazol-1-yl
3-iodo-5-methylpyrazol-1-yl
3-ethyl-5-methylpyrazol-1-yl
5-methyl-3-propylpyrazol-1-yl
5-methyl-3-(trifluoromethyl)pyrazol-1-yl
5-methyl-3-(2,2,2-trifluoroethyl)pyrazol-1-yl
5-methyl-3-(pentafluoroethyl)pyrazol-1-yl
3-cyano-5-methylpyrazol-1-yl
5-methyl-3-nitropyrazol-1-yl
5-chloro-3-methylpyrazol-1-yl
3,5-dichloropyrazol-1-yl
5-chloro-3-bromopyrazol-1-yl
5-chloro-3-iodopyrazol-1-yl
5-chloro-3-ethylpyrazol-1-yl
5-chloro-3-propylpyrazol-1-yl
5-chloro-3-(trifluoromethyl)pyrazol-1-yl
5-chloro-3-(2,2,2-trifluoroethyl)pyrazol-1-yl
5-chloro-3-(pentafluoroethyl)pyrazol-1-yl
5-chloro-3-cyanopyrazol-1-yl
5-chloro-3-nitropyrazol-1-yl
5-bromo-3-methylpyrazol-1-yl
5-bromo-3-chloropyrazol-1-yl
3,5-dibromopyrazol-1-yl
5-bromo-3-iodopyrazol-1-yl
5-bromo-3-ethylpyrazol-1-yl
5-bromo-3-propylpyrazol-1-yl
5-bromo-3-(trifluoromethyl)pyrazol-1-yl
5-bromo-3-(2,2,2-trifluoroethyl)pyrazol-1-yl
5-bromo-3-(pentafluoroethyl)pyrazol-1-yl
5-ethyl-3-methylpyrazol-1-yl
3-chloro-5-ethylpyrazol-1-yl
3-bromo-5-ethylpyrazol-1-yl
5-ethyl-3-iodopyrazol-1-yl
3,5-diethylpyrazol-1-yl
5-ethyl-3-propylpyrazol-1-yl
5-ethyl-3-(trifluoromethyl)pyrazol-1-yl
5-ethyl-3-(2,2,2-trifluoroethyl)pyrazol-1-yl
5-ethyl-3-(pentafluoroethyl)pyrazol-1-yl
3,5-dimethyl-2-thienyl
3,5-dichloro-2-thienyl
2,5-dimethyl-3-thienyl
2,5-dichloro-3-thienyl
3,6-dimethyl-2-pyridyl
2,5-dimethyl-3-pyridyl
2,5-dimethyl-4-pyridyl
3,6-dichloro-2-pyridyl
2,5-dichloro-3-pyridyl
2,5-dichloro-4-pyridyl
3,5-bis-(trifluoromethyl)pyrazol-1-yl
1-methyl-3-(trifluoromethyl)pyrazol-5-yl
1-methyl-4-(trifluoromethyl)imidazol-2-yl

TABLE 7A

[Structure: thiazole with N-methyl-N-(1,2,3,4-tetrahydronaphthalen-1-yl)carboxamide and tetrahydropyridine-N-C(O)-R¹]

R¹

2-methoxyphenyl
3-bromophenyl
3-iodophenyl
3-(trifluoromethyl)phenyl
3-(2,2,2-trifluoroethyl)phenyl
3-(pentafluoroethyl)phenyl
3-cyanophenyl
3-nitrophenyl
2,5-dichlorophenyl
5-bromo-2-chlorophenyl
2-chloro-5-iodophenyl
2-chloro-5-methylphenyl
2-chloro-5-ethylphenyl
2-chloro-5-(trifluoromethyl)phenyl
2-chloro-5-(2,2,2-trifluoroethyl)phenyl
2-chloro-5-(pentafluoroethyl)phenyl
2-chloro-5-cyanophenyl
2-chloro-5-nitrophenyl
2-bromo-5-chlorophenyl
2,5-dibromophenyl
2-bromo-5-iodophenyl
2-bromo-5-methylphenyl
2-bromo-5-ethylphenyl
2-bromo-5-propylphenyl
2-bromo-5-(trifluoromethyl)phenyl
2-bromo-5-(2,2,2-trifluoroethyl)phenyl
2-bromo-5-(pentafluoroethyl)phenyl
2-bromo-5-cyanophenyl
2-bromo-5-nitrophenyl
5-chloro-2-methylphenyl
5-bromo-2-methylphenyl
5-iodo-2-methylphenyl
2,5-dimethylphenyl
5-ethyl-2-methylphenyl
2-methyl-5-propylphenyl
5-isopropyl-2-methylphenyl
2-methyl-5-(trifluoromethyl)phenyl
2-methyl-5-(2,2,2-trifluoroethyl)phenyl
2-methyl-5-(pentafluoroethyl)phenyl
5-cyano-2-methylphenyl
2-methyl-5-nitrophenyl
5-chloro-2-methoxyphenyl
5-bromo-2-methoxyphenyl
5-iodo-2-methoxyphenyl
2-methoxy-5-methylphenyl
5-ethyl-2-methoxyphenyl
2-methoxy-5-propylphenyl
2-methoxy-5-(trifluoromethyl)phenyl
2-methoxy-5-(2,2,2-trifluoroethyl)phenyl
2-methoxy-5-(pentafluoroethyl)phenyl
5-cyano-2-methoxyphenyl
2-methoxy-5-nitrophenyl
5-chloro-2-ethylphenyl
5-bromo-2-ethylphenyl
2-ethyl-5-iodophenyl
2-ethyl-5-methylphenyl
2,5-diethylphenyl
2-ethyl-5-propylphenyl
2-ethyl-5-(trifluoromethyl)phenyl
2-ethyl-5-(2,2,2-trifluoroethyl)phenyl
2-ethyl-5-(pentafluoroethyl)phenyl
5-cyano-2-ethylphenyl
2-ethyl-5-nitrophenyl
3-chloropyrazol-1-yl

TABLE 7A-continued

[Structure: thiazole-carboxamide with N-methyl-tetrahydronaphthalenyl group and tetrahydropyridine bearing R¹-C(O)-]

R¹

3-bromopyrazol-1-yl
3-(trifluoromethyl)pyrazol-1-yl
3-(2,2,2-trifluoroethyl)pyrazol-1-yl
3-(pentafluoroethyl)pyrazol-1-yl
3-cyanopyrazol-1-yl
3-nitropyrazol-1-yl
3,5-dimethylpyrazol-1-yl
3-chloro-5-methylpyrazol-1-yl
3-bromo-5-methylpyrazol-1-yl
3-iodo-5-methylpyrazol-1-yl
3-ethyl-5-methylpyrazol-1-yl
5-methyl-3-propylpyrazol-1-yl
5-methyl-3-(trifluoromethyl)pyrazol-1-yl
5-methyl-3-(2,2,2-trifluoroethyl)pyrazol-1-yl
5-methyl-3-(pentafluoroethyl)pyrazol-1-yl
3-cyano-5-methylpyrazol-1-yl
5-methyl-3-nitropyrazol-1-yl
5-chloro-3-methylpyrazol-1-yl
3,5-dichloropyrazol-1-yl
5-chloro-3-bromopyrazol-1-yl
5-chloro-3-iodopyrazol-1-yl
5-chloro-3-ethylpyrazol-1-yl
5-chloro-3-propylpyrazol-1-yl
5-chloro-3-(trifluoromethyl)pyrazol-1-yl
5-chloro-3-(2,2,2-trifluoroethyl)pyrazol-1-yl
5-chloro-3-(pentafluoroethyl)pyrazol-1-yl
5-chloro-3-cyanopyrazol-1-yl
5-chloro-3-nitropyrazol-1-yl
5-bromo-3-methylpyrazol-1-yl
5-bromo-3-chloropyrazol-1-yl
3,5-dibromopyrazol-1-yl
5-bromo-3-iodopyrazol-1-yl
5-bromo-3-ethylpyrazol-1-yl
5-bromo-3-propylpyrazol-1-yl
5-bromo-3-(trifluoromethyl)pyrazol-1-yl
5-bromo-3-(2,2,2-trifluoroethyl)pyrazol-1-yl
5-bromo-3-(pentafluoroethyl)pyrazol-1-yl
5-ethyl-3-methylpyrazol-1-yl
3-chloro-5-ethylpyrazol-1-yl
3-bromo-5-ethylpyrazol-1-yl
5-ethyl-3-iodopyrazol-1-yl
3,5-diethylpyrazol-1-yl
5-ethyl-3-propylpyrazol-1-yl
5-ethyl-3-(trifluoromethyl)pyrazol-1-yl
5-ethyl-3-(2,2,2-trifluoroethyl)pyrazol-1-yl
5-ethyl-3-(pentafluoroethyl)pyrazol-1-yl
3,5-dimethyl-2-thienyl
3,5-dichloro-2-thienyl
2,5-dimethyl-3-thienyl
2,5-dichloro-3-thienyl
3,6-dimethyl-2-pyridyl
2,5-dimethyl-3-pyridyl
2,5-dimethyl-4-pyridyl
3,6-dichloro-2-pyridyl
2,5-dichloro-3-pyridyl
2,5-dichloro-4-pyridyl
3,5-bis-(trifluoromethyl)pyrazol-1-yl
1-methyl-3-(trifluoromethyl)pyrazol-5-yl
1-methyl-4-(trifluoromethyl)imidazol-2-yl

TABLE 7B

[Structure: thiazole-carboxamide with N-methyl-indanyl group and tetrahydropyridine bearing R¹-C(O)-]

R¹

2-methoxyphenyl
3-bromophenyl
3-iodophenyl
3-(trifluoromethyl)phenyl
3-(2,2,2-trifluoroethyl)phenyl
3-(pentafluoroethyl)phenyl
3-cyanophenyl
3-nitrophenyl
2,5-dichlorophenyl
5-bromo-2-chlorophenyl
2-chloro-5-iodophenyl
2-chloro-5-methylphenyl
2-bromo-5-(trifluoromethyl)phenyl
2-bromo-5-(2,2,2-trifluoroethyl)phenyl
2-bromo-5-(pentafluoroethyl)phenyl
2-bromo-5-cyanophenyl
2-bromo-5-nitrophenyl
5-chloro-2-methylphenyl
5-bromo-2-methylphenyl
5-iodo-2-methylphenyl
2,5-dimethylphenyl
5-ethyl-2-methylphenyl
2-methyl-5-propylphenyl
5-isopropyl-2-methylphenyl
2-methyl-5-(trifluoromethyl)phenyl
2-methyl-5-(2,2,2-trifluoroethyl)phenyl
2-methyl-5-(pentafluoroethyl)phenyl
5-cyano-2-methylphenyl
2-methyl-5-nitrophenyl
5-chloro-2-methoxyphenyl
5-bromo-2-methoxyphenyl
5-iodo-2-methoxyphenyl
2-methoxy-5-methylphenyl
5-ethyl-2-methoxyphenyl
2-methoxy-5-propylphenyl
2-methoxy-5-(trifluoromethyl)phenyl
2-methoxy-5-(2,2,2-trifluoroethyl)phenyl
2-methoxy-5-(pentafluoroethyl)phenyl
5-cyano-2-methoxyphenyl
2-methoxy-5-nitrophenyl
5-chloro-2-ethylphenyl
5-bromo-2-ethylphenyl
2-ethyl-5-iodophenyl
2-ethyl-5-methylphenyl
2,5-diethylphenyl
5-chloro-3-cyanopyrazol-1-yl
5-chloro-3-nitropyrazol-1-yl
5-bromo-3-methylpyrazol-1-yl
5-bromo-3-chloropyrazol-1-yl
3,5-dibromopyrazol-1-yl
5-bromo-3-iodopyrazol-1-yl
5-bromo-3-ethylpyrazol-1-yl
5-bromo-3-propylpyrazol-1-yl
5-bromo-3-(trifluoromethyl)pyrazol-1-yl
5-bromo-3-(2,2,2-trifluoroethyl)pyrazol-1-yl
5-bromo-3-(pentafluoroethyl)pyrazol-1-yl
5-ethyl-3-methylpyrazol-1-yl
3-chloro-5-ethylpyrazol-1-yl
3-bromo-5-ethylpyrazol-1-yl
5-ethyl-3-iodopyrazol-1-yl
3,5-diethylpyrazol-1-yl
5-ethyl-3-propylpyrazol-1-yl
2-chloro-5-ethylphenyl
2-chloro-5-(trifluoromethyl)phenyl

TABLE 7B-continued

[Structure: thiazole-4-carboxamide with N-methyl-N-[(1S)-indan-1-yl] group, 2-(1-acyl-1,2,3,6-tetrahydropyridin-4-yl) substituent, where acyl = R¹-CH₂-C(O)-]

R¹

2-chloro-5-(2,2,2-trifluoroethyl)phenyl
2-chloro-5-(pentafluoroethyl)phenyl
2-chloro-5-cyanophenyl
2-chloro-5-nitrophenyl
2-bromo-5-chlorophenyl
2,5-dibromophenyl
2-bromo-5-iodophenyl
2-bromo-5-methylphenyl
2-bromo-5-ethylphenyl
2-bromo-5-propylphenyl
2-ethyl-5-propylphenyl
2-ethyl-5-(trifluoromethyl)phenyl
2-ethyl-5-(2,2,2-trifluoroethyl)phenyl
2-ethyl-5-(pentafluoroethyl)phenyl
5-cyano-2-ethylphenyl
2-ethyl-5-nitrophenyl
3-chloropyrazol-1-yl
3-bromopyrazol-1-yl
3-(trifluoromethyl)pyrazol-1-yl
3-(2,2,2-trifluoroethyl)pyrazol-1-yl
3-(pentafluoroethyl)pyrazol-1-yl
3-cyanopyrazol-1-yl
3-nitropyrazol-1-yl
3,5-dimethylpyrazol-1-yl
3-chloro-5-methylpyrazol-1-yl
3-bromo-5-methylpyrazol-1-yl
3-iodo-5-methylpyrazol-1-yl
3-ethyl-5-methylpyrazol-1-yl
5-methyl-3-propylpyrazol-1-yl
5-methyl-3-(trifluoromethyl)pyrazol-1-yl
5-methyl-3-(2,2,2-trifluoroethyl)pyrazol-1-yl
5-methyl-3-(pentafluoroethyl)pyrazol-1-yl
3-cyano-5-methylpyrazol-1-yl
5-methyl-3-nitropyrazol-1-yl
5-chloro-3-methylpyrazol-1-yl
3,5-dichloropyrazol-1-yl
5-chloro-3-bromopyrazol-1-yl
5-chloro-3-iodopyrazol-1-yl
5-chloro-3-ethylpyrazol-1-yl
5-chloro-3-propylpyrazol-1-yl
5-chloro-3-(trifluoromethyl)pyrazol-1-yl
5-chloro-3-(2,2,2-trifluoroethyl)pyrazol-1-yl
5-chloro-3-(pentafluoroethyl)pyrazol-1-yl
5-ethyl-3-(trifluoromethyl)pyrazol-1-yl
5-ethyl-3-(2,2,2-trifluoroethyl)pyrazol-1-yl
5-ethyl-3-(pentafluoroethyl)pyrazol-1-yl
3,5-dimethyl-2-thienyl
3,5-dichloro-2-thienyl
2,5-dimethyl-3-thienyl
2,5-dichloro-3-thienyl
3,6-dimethyl-2-pyridyl
2,5-dimethyl-3-pyridyl
2,5-dimethyl-4-pyridyl
3,6-dichloro-2-pyridyl
2,5-dichloro-3-pyridyl
2,5-dichloro-4-pyridyl
3,5-bis-(trifluoromethyl)pyrazol-1-yl
1-methyl-3-(trifluoromethyl)pyrazol-5-yl
1-methyl-4-(trifluoromethyl)imidazol-2-yl

TABLE 7C

[Structure: thiazole-4-carboxamide with N-methyl-N-[(1S)-1-phenylpropyl] group, 2-(1-acyl-1,2,3,6-tetrahydropyridin-4-yl) substituent, where acyl = R¹-CH₂-C(O)-]

R¹

2-methoxyphenyl
3-bromophenyl
3-iodophenyl
3-(trifluoromethyl)phenyl
3-(2,2,2-trifluoroethyl)phenyl
3-(pentafluoroethyl)phenyl
2-chloro-5-ethylphenyl
2-chloro-5-(trifluoromethyl)phenyl
2-chloro-5-(2,2,2-trifluoroethyl)phenyl
2-chloro-5-(pentafluoroethyl)phenyl
2-chloro-5-cyanophenyl
2-chloro-5-nitrophenyl
2-bromo-5-chlorophenyl
2,5-dibromophenyl
2-bromo-5-iodophenyl
2-bromo-5-methylphenyl
2-bromo-5-ethylphenyl
2-bromo-5-propylphenyl
2-bromo-5-(trifluoromethyl)phenyl
2-bromo-5-(2,2,2-trifluoroethyl)phenyl
2-bromo-5-(pentafluoroethyl)phenyl
2-bromo-5-cyanophenyl
2-bromo-5-nitrophenyl
5-chloro-2-methylphenyl
5-bromo-2-methylphenyl
5-iodo-2-methylphenyl
2,5-dimethylphenyl
5-ethyl-2-methylphenyl
2-methyl-5-propylphenyl
5-isopropyl-2-methylphenyl
2-methyl-5-(trifluoromethyl)phenyl
2-methyl-5-(2,2,2-trifluoroethyl)phenyl
2-methyl-5-(pentafluoroethyl)phenyl
5-cyano-2-methylphenyl
2-methyl-5-nitrophenyl
5-chloro-2-methoxyphenyl
5-bromo-2-methoxyphenyl
5-iodo-2-methoxyphenyl
2-methoxy-5-methylphenyl
5-methyl-3-(pentafluoroethyl)pyrazol-1-yl
3-cyano-5-methylpyrazol-1-yl
5-methyl-3-nitropyrazol-1-yl
5-chloro-3-methylpyrazol-1-yl
3,5-dichloropyrazol-1-yl
5-chloro-3-bromopyrazol-1-yl
5-chloro-3-iodopyrazol-1-yl
5-chloro-3-ethylpyrazol-1-yl
5-chloro-3-propylpyrazol-1-yl
5-chloro-3-(trifluoromethyl)pyrazol-1-yl
5-chloro-3-(2,2,2-trifluoroethyl)pyrazol-1-yl
5-chloro-3-(pentafluoroethyl)pyrazol-1-yl
5-chloro-3-cyanopyrazol-1-yl
5-chloro-3-nitropyrazol-1-yl
5-bromo-3-methylpyrazol-1-yl
5-bromo-3-chloropyrazol-1-yl
3,5-dibromopyrazol-1-yl
5-bromo-3-iodopyrazol-1-yl
5-bromo-3-ethylpyrazol-1-yl
5-bromo-3-propylpyrazol-1-yl
5-bromo-3-(trifluoromethyl)pyrazol-1-yl
5-bromo-3-(2,2,2-trifluoroethyl)pyrazol-1-yl
5-bromo-3-(pentafluoroethyl)pyrazol-1-yl
3-cyanophenyl
3-nitrophenyl

TABLE 7C-continued

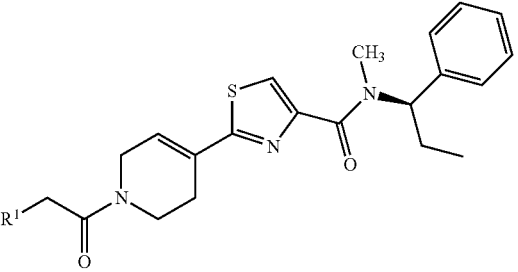

R[1]

2,5-dichlorophenyl
5-bromo-2-chlorophenyl
2-chloro-5-iodophenyl
2-chloro-5-methylphenyl
5-ethyl-2-methoxyphenyl
2-methoxy-5-propylphenyl
2-methoxy-5-(trifluoromethyl)phenyl
2-methoxy-5-(2,2,2-trifluoroethyl)phenyl
2-methoxy-5-(pentafluoroethyl)phenyl
5-cyano-2-methoxyphenyl
2-methoxy-5-nitrophenyl
5-chloro-2-ethylphenyl
5-bromo-2-ethylphenyl
2-ethyl-5-iodophenyl
2-ethyl-5-methylphenyl
2,5-diethylphenyl
2-ethyl-5-propylphenyl
2-ethyl-5-(trifluoromethyl)phenyl
2-ethyl-5-(2,2,2-trifluoroethyl)phenyl
2-ethyl-5-(pentafluoroethyl)phenyl
5-cyano-2-ethylphenyl
2-ethyl-5-nitrophenyl
3-chloropyrazol-1-yl
3-bromopyrazol-1-yl
3-(trifluoromethyl)pyrazol-1-yl
3-(2,2,2-trifluoroethyl)pyrazol-1-yl
3-(pentafluoroethyl)pyrazol-1-yl
3-cyanopyrazol-1-yl
3-nitropyrazol-1-yl
3,5-dimethylpyrazol-1-yl
3-chloro-5-methylpyrazol-1-yl
3-bromo-5-methylpyrazol-1-yl
3-iodo-5-methylpyrazol-1-yl
3-ethyl-5-methylpyrazol-1-yl
5-methyl-3-propylpyrazol-1-yl
5-methyl-3-(trifluoromethyl)pyrazol-1-yl
5-methyl-3-(2,2,2-trifluoroethyl)pyrazol-1-yl
5-ethyl-3-methylpyrazol-1-yl
3-chloro-5-ethylpyrazol-1-yl
3-bromo-5-ethylpyrazol-1-yl
5-ethyl-3-iodopyrazol-1-yl
3,5-diethylpyrazol-1-yl
5-ethyl-3-propylpyrazol-1-yl
5-ethyl-3-(trifluoromethyl)pyrazol-1-yl
5-ethyl-3-(2,2,2-trifluoroethyl)pyrazol-1-yl
5-ethyl-3-(pentafluoroethyl)pyrazol-1-yl
3,5-dimethyl-2-thienyl
3,5-dichloro-2-thienyl
2,5-dimethyl-3-thienyl
2,5-dichloro-3-thienyl
3,6-dimethyl-2-pyridyl
2,5-dimethyl-3-pyridyl
2,5-dimethyl-4-pyridyl
3,6-dichloro-2-pyridyl
2,5-dichloro-3-pyridyl
2,5-dichloro-4-pyridyl
3,5-bis-(trifluoromethyl)pyrazol-1-yl
1-methyl-3-(trifluoromethyl)pyrazol-5-yl
1-methyl-4-(trifluoromethyl)imidazol-2-yl

TABLE 8A

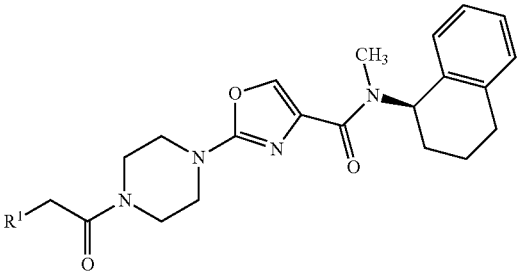

R[1]

2-methoxyphenyl
3-bromophenyl
3-iodophenyl
3-(trifluoromethyl)phenyl
3-(2,2,2-trifluoroethyl)phenyl
3-(pentafluoroethyl)phenyl
3-cyanophenyl
3-nitrophenyl
2,5-dichlorophenyl
5-bromo-2-chlorophenyl
2-chloro-5-iodophenyl
2-chloro-5-methylphenyl
2-chloro-5-ethylphenyl
2-chloro-5-(trifluoromethyl)phenyl
2-chloro-5-(2,2,2-trifluoroethyl)phenyl
2-chloro-5-(pentafluoroethyl)phenyl
2-chloro-5-cyanophenyl
2-chloro-5-nitrophenyl
2-bromo-5-chlorophenyl
2,5-dibromophenyl
2-bromo-5-iodophenyl
2-bromo-5-methylphenyl
2-bromo-5-ethylphenyl
2-bromo-5-propylphenyl
2-bromo-5-(trifluoromethyl)phenyl
2-bromo-5-(2,2,2-trifluoroethyl)phenyl
2-bromo-5-(pentafluoroethyl)phenyl
2-bromo-5-cyanophenyl
2-bromo-5-nitrophenyl
5-chloro-2-methylphenyl
5-bromo-2-methylphenyl
5-iodo-2-methylphenyl
2,5-dimethylphenyl
3-(2,2,2-trifluoroethyl)pyrazol-1-yl
3-(pentafluoroethyl)pyrazol-1-yl
3-cyanopyrazol-1-yl
3-nitropyrazol-1-yl
3,5-dimethylpyrazol-1-yl
3-chloro-5-methylpyrazol-1-yl
3-bromo-5-methylpyrazol-1-yl
3-iodo-5-methylpyrazol-1-yl
3-ethyl-5-methylpyrazol-1-yl
5-methyl-3-propylpyrazol-1-yl
5-methyl-3-(trifluoromethyl)pyrazol-1-yl
5-methyl-3-(2,2,2-trifluoroethyl)pyrazol-1-yl
5-methyl-3-(pentafluoroethyl)pyrazol-1-yl
3-cyano-5-methylpyrazol-1-yl
5-methyl-3-nitropyrazol-1-yl
5-chloro-3-methylpyrazol-1-yl
3,5-dichloropyrazol-1-yl
5-chloro-3-bromopyrazol-1-yl
5-chloro-3-iodopyrazol-1-yl
5-chloro-3-ethylpyrazol-1-yl
5-chloro-3-propylpyrazol-1-yl
5-chloro-3-(trifluoromethyl)pyrazol-1-yl
5-chloro-3-(2,2,2-trifluoroethyl)pyrazol-1-yl
5-chloro-3-(pentafluoroethyl)pyrazol-1-yl
5-chloro-3-cyanopyrazol-1-yl
5-chloro-3-nitropyrazol-1-yl
5-bromo-3-methylpyrazol-1-yl
5-bromo-3-chloropyrazol-1-yl
3,5-dibromopyrazol-1-yl
5-ethyl-2-methylphenyl
2-methyl-5-propylphenyl

TABLE 8A-continued

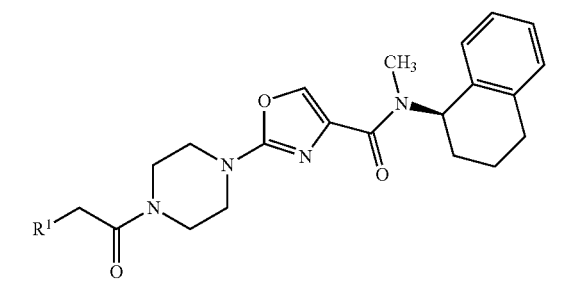

R[1]

5-isopropyl-2-methylphenyl
2-methyl-5-(trifluoromethyl)phenyl
2-methyl-5-(2,2,2-trifluoroethyl)phenyl
2-methyl-5-(pentafluoroethyl)phenyl
5-cyano-2-methylphenyl
2-methyl-5-nitrophenyl
5-chloro-2-methoxyphenyl
5-bromo-2-methoxyphenyl
5-iodo-2-methoxyphenyl
2-methoxy-5-methylphenyl
5-ethyl-2-methoxyphenyl
2-methoxy-5-propylphenyl
2-methoxy-5-(trifluoromethyl)phenyl
2-methoxy-5-(2,2,2-trifluoroethyl)phenyl
2-methoxy-5-(pentafluoroethyl)phenyl
5-cyano-2-methoxyphenyl
2-methoxy-5-nitrophenyl
5-chloro-2-ethylphenyl
5-bromo-2-ethylphenyl
2-ethyl-5-iodophenyl
2-ethyl-5-methylphenyl
2,5-diethylphenyl
2-ethyl-5-propylphenyl
2-ethyl-5-(trifluoromethyl)phenyl
2-ethyl-5-(2,2,2-trifluoroethyl)phenyl
2-ethyl-5-(pentafluoroethyl)phenyl
5-cyano-2-ethylphenyl
2-ethyl-5-nitrophenyl
3-chloropyrazol-1-yl
3-bromopyrazol-1-yl
3-(trifluoromethyl)pyrazol-1-yl
5-bromo-3-iodopyrazol-1-yl
5-bromo-3-ethylpyrazol-1-yl
5-bromo-3-propylpyrazol-1-yl
5-bromo-3-(trifluoromethyl)pyrazol-1-yl
5-bromo-3-(2,2,2-trifluoroethyl)pyrazol-1-yl
5-bromo-3-(pentafluoroethyl)pyrazol-1-yl
5-ethyl-3-methylpyrazol-1-yl
3-chloro-5-ethylpyrazol-1-yl
3-bromo-5-ethylpyrazol-1-yl
5-ethyl-3-iodopyrazol-1-yl
3,5-diethylpyrazol-1-yl
5-ethyl-3-propylpyrazol-1-yl
5-ethyl-3-(trifluoromethyl)pyrazol-1-yl
5-ethyl-3-(2,2,2-trifluoroethyl)pyrazol-1-yl
5-ethyl-3-(pentafluoroethyl)pyrazol-1-yl
3,5-dimethyl-2-thienyl
3,5-dichloro-2-thienyl
2,5-dimethyl-3-thienyl
2,5-dichloro-3-thienyl
3,6-dimethyl-2-pyridyl
2,5-dimethyl-3-pyridyl
2,5-dimethyl-4-pyridyl
3,6-dichloro-2-pyridyl
2,5-dichloro-3-pyridyl
2,5-dichloro-4-pyridyl
3,5-bis-(trifluoromethyl)pyrazol-1-yl
1-methyl-3-(trifluoromethyl)pyrazol-5-yl
1-methyl-4-(trifluoromethyl)imidazol-2-yl

TABLE 8B

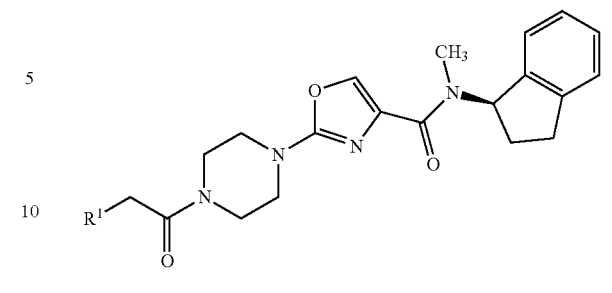

R[1]

2-methoxyphenyl
3-bromophenyl
3-iodophenyl
3-(trifluoromethyl)phenyl
3-(2,2,2-trifluoroethyl)phenyl
3-(pentafluoroethyl)phenyl
3-cyanophenyl
3-nitrophenyl
2,5-dichlorophenyl
5-bromo-2-chlorophenyl
2-chloro-5-iodophenyl
2-chloro-5-methylphenyl
2-chloro-5-ethylphenyl
2-chloro-5-(trifluoromethyl)phenyl
2-chloro-5-(2,2,2-trifluoroethyl)phenyl
2-chloro-5-(pentafluoroethyl)phenyl
2-chloro-5-cyanophenyl
2-chloro-5-nitrophenyl
2-bromo-5-chlorophenyl
2,5-dibromophenyl
2-bromo-5-iodophenyl
2-bromo-5-methylphenyl
2-bromo-5-ethylphenyl
2-bromo-5-propylphenyl
2-methoxy-5-(2,2,2-trifluoroethyl)phenyl
2-methoxy-5-(pentafluoroethyl)phenyl
5-cyano-2-methoxyphenyl
2-methoxy-5-nitrophenyl
5-chloro-2-ethylphenyl
5-bromo-2-ethylphenyl
2-ethyl-5-iodophenyl
2-ethyl-5-methylphenyl
2,5-diethylphenyl
2-ethyl-5-propylphenyl
2-ethyl-5-(trifluoromethyl)phenyl
2-ethyl-5-(2,2,2-trifluoroethyl)phenyl
2-ethyl-5-(pentafluoroethyl)phenyl
5-cyano-2-ethylphenyl
2-ethyl-5-nitrophenyl
3-chloropyrazol-1-yl
3-bromopyrazol-1-yl
3-(trifluoromethyl)pyrazol-1-yl
3-(2,2,2-trifluoroethyl)pyrazol-1-yl
3-(pentafluoroethyl)pyrazol-1-yl
3-cyanopyrazol-1-yl
3-nitopyrazol-1-yl
3,5-dimethylpyrazol-1-yl
3-chloro-5-methylpyrazol-1-yl
3-bromo-5-methylpyrazol-1-yl
3-iodo-5-methylpyrazol-1-yl
3-ethyl-5-methylpyrazol-1-yl
5-methyl-3-propylpyrazol-1-yl
5-methyl-3-(trifluoromethyl)pyrazol-1-yl
5-methyl-3-(2,2,2-trifluoroethyl)pyrazol-1-yl
5-methyl-3-(pentafluoroethyl)pyrazol-1-yl
3-cyano-5-methylpyrazol-1-yl
5-methyl-3-nitropyrazol-1-yl
3,6-dimethyl-2-pyridyl
2,5-dimethyl-3-pyridyl
2,5-dimethyl-4-pyridyl
3,6-dichloro-2-pyridyl
2,5-dichloro-3-pyridyl
2-bromo-5-(trifluoromethyl)phenyl
2-bromo-5-(2,2,2-trifluoroethyl)phenyl

TABLE 8B-continued

[Structure: oxazole with N-methyl-N-(indan-1-yl) carboxamide, piperazine acylated with R¹CH₂C(O)-]

R¹

2-bromo-5-(pentafluoroethyl)phenyl
2-bromo-5-cyanophenyl
2-bromo-5-nitrophenyl
5-chloro-2-methylphenyl
5-bromo-2-methylphenyl
5-iodo-2-methylphenyl
2,5-dimethylphenyl
5-ethyl-2-methylphenyl
2-methyl-5-propylphenyl
5-isopropyl-2-methylphenyl
2-methyl-5-(trifluoromethyl)phenyl
2-methyl-5-(2,2,2-trifluoroethyl)phenyl
2-methyl-5-(pentafluoroethyl)phenyl
5-cyano-2-methylphenyl
2-methyl-5-nitrophenyl
5-chloro-2-methoxyphenyl
5-bromo-2-methoxyphenyl
5-iodo-2-methoxyphenyl
2-methoxy-5-methylphenyl
5-ethyl-2-methoxyphenyl
2-methoxy-5-propylphenyl
2-methoxy-5-(trifluoromethyl)phenyl
5-chloro-3-methylpyrazol-1-yl
3,5-dichloropyrazol-1-yl
5-chloro-3-bromopyrazol-1-yl
5-chloro-3-iodopyrazol-1-yl
5-chloro-3-ethylpyrazol-1-yl
5-chloro-3-propylpyrazol-1-yl
5-chloro-3-(trifluoromethyl)pyrazol-1-yl
5-chloro-3-(2,2,2-trifluoroethyl)pyrazol-1-yl
5-chloro-3-(pentafluoroethyl)pyrazol-1-yl
5-chloro-3-cyanopyrazol-1-yl
5-chloro-3-nitropyrazol-1-yl
5-bromo-3-methylpyrazol-1-yl
5-bromo-3-chloropyrazol-1-yl
3,5-dibromopyrazol-1-yl
5-bromo-3-iodopyrazol-1-yl
5-bromo-3-ethylpyrazol-1-yl
5-bromo-3-propylpyrazol-1-yl
5-bromo-3-(trifluoromethyl)pyrazol-1-yl
5-bromo-3-(2,2,2-trifluoroethyl)pyrazol-1-yl
5-bromo-3-(pentafluoroethyl)pyrazol-1-yl
5-ethyl-3-methylpyrazol-1-yl
3-chloro-5-ethylpyrazol-1-yl
3-bromo-5-ethylpyrazol-1-yl
5-ethyl-3-iodopyrazol-1-yl
3,5-diethylpyrazol-1-yl
5-ethyl-3-propylpyrazol-1-yl
5-ethyl-3-(trifluoromethyl)pyrazol-1-yl
5-ethyl-3-(2,2,2-trifluoroethyl)pyrazol-1-yl
5-ethyl-3-(pentafluoroethyl)pyrazol-1-yl
3,5-dimethyl-2-thienyl
3,5-dichloro-2-thienyl
2,5-dimethyl-3-thienyl
2,5-dichloro-3-thienyl
2,5-dichloro-4-pyridyl
3,5-bis-(trifluoromethyl)pyrazol-1-yl
1-methyl-3-(trifluoromethyl)pyrazol-5-yl
1-methyl-4-(trifluoromethyl)imidazol-2-yl

TABLE 8C

[Structure: oxazole with N-methyl-N-(1-phenylpropyl) carboxamide, piperazine acylated with R¹CH₂C(O)-]

R¹

2-methoxyphenyl
3-bromophenyl
3-iodophenyl
3-(trifluoromethyl)phenyl
3-(2,2,2-trifluoroethyl)phenyl
3-(pentafluoroethyl)phenyl
3-cyanophenyl
3-nitrophenyl
2,5-dichlorophenyl
5-bromo-2-chlorophenyl
2-chloro-5-iodophenyl
2-chloro-5-methylphenyl
2-chloro-5-ethylphenyl
2-chloro-5-(trifluoromethyl)phenyl
2-chloro-5-(2,2,2-trifluoroethyl)phenyl
2-chloro-5-(pentafluoroethyl)phenyl
2-chloro-5-cyanophenyl
2-chloro-5-nitrophenyl
2-methyl-5-(trifluoromethyl)phenyl
2-methyl-5-(2,2,2-trifluoroethyl)phenyl
2-methyl-5-(pentafluoroethyl)phenyl
5-cyano-2-methylphenyl
2-methyl-5-nitrophenyl
5-chloro-2-methoxyphenyl
5-bromo-2-methoxyphenyl
5-iodo-2-methoxyphenyl
2-methoxy-5-methylphenyl
5-ethyl-2-methoxyphenyl
2-methoxy-5-propylphenyl
2-methoxy-5-(trifluoromethyl)phenyl
2-methoxy-5-(2,2,2-trifluoroethyl)phenyl
2-methoxy-5-(pentafluoroethyl)phenyl
5-cyano-2-methoxyphenyl
2-methoxy-5-nitrophenyl
5-chloro-2-ethylphenyl
5-bromo-2-ethylphenyl
2-ethyl-5-iodophenyl
2-ethyl-5-methylphenyl
2,5-diethylphenyl
2-ethyl-5-propylphenyl
2-ethyl-5-(trifluoromethyl)phenyl
2-ethyl-5-(2,2,2-trifluoroethyl)phenyl
2-ethyl-5-(pentafluoroethyl)phenyl
5-cyano-2-ethylphenyl
2-ethyl-5-nitrophenyl
3-chloropyrazol-1-yl
3-bromopyrazol-1-yl
3-(trifluoromethyl)pyrazol-1-yl
3-(2,2,2-trifluoroethyl)pyrazol-1-yl
3-(pentafluoroethyl)pyrazol-1-yl
3-cyanopyrazol-1-yl
3-chloro-5-ethylpyrazol-1-yl
3-bromo-5-ethylpyrazol-1-yl
5-ethyl-3-iodopyrazol-1-yl
3,5-diethylpyrazol-1-yl
5-ethyl-3-propylpyrazol-1-yl
5-ethyl-3-(trifluoromethyl)pyrazol-1-yl
5-ethyl-3-(2,2,2-trifluoroethyl)pyrazol-1-yl
5-ethyl-3-(pentafluoroethyl)pyrazol-1-yl
3,5-dimethyl-2-thienyl
3,5-dichloro-2-thienyl
2,5-dimethyl-3-thienyl
2-bromo-5-chlorophenyl
2,5-dibromophenyl

TABLE 8C-continued

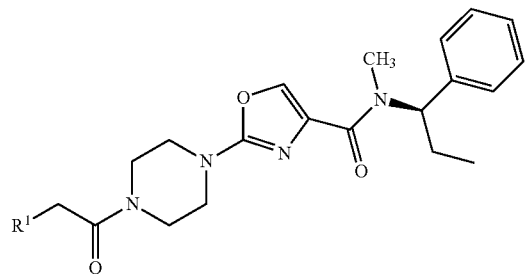

R[1]

2-bromo-5-iodophenyl
2-bromo-5-methylphenyl
2-bromo-5-ethylphenyl
2-bromo-5-propylphenyl
2-bromo-5-(trifluoromethyl)phenyl
2-bromo-5-(2,2,2-trifluoroethyl)phenyl
2-bromo-5-(pentafluoroethyl)phenyl
2-bromo-5-cyanophenyl
2-bromo-5-nitrophenyl
5-chloro-2-methylphenyl
5-bromo-2-methylphenyl
5-iodo-2-methylphenyl
2,5-dimethylphenyl
5-ethyl-2-methylphenyl
2-methyl-5-propylphenyl
5-isopropyl-2-methylphenyl
3-nitropyrazol-1-yl
3,5-dimethylpyrazol-1-yl
3-chloro-5-methylpyrazol-1-yl
3-bromo-5-methylpyrazol-1-yl
3-iodo-5-methylpyrazol-1-yl
3-ethyl-5-methylpyrazol-1-yl
5-methyl-3-propylpyrazol-1-yl
5-methyl-3-(trifluoromethyl)pyrazol-1-yl
5-methyl-3-(2,2,2-trifluoroethyl)pyrazol-1-yl
5-methyl-3-(pentafluoroethyl)pyrazol-1-yl
3-cyano-5-methylpyrazol-1-yl
5-methyl-3-nitropyrazol-1-yl
5-chloro-3-methylpyrazol-1-yl
3,5-dichloropyrazol-1-yl
5-chloro-3-bromopyrazol-1-yl
5-chloro-3-iodopyrazol-1-yl
5-chloro-3-ethylpyrazol-1-yl
5-chloro-3-propylpyrazol-1-yl
5-chloro-3-(trifluoromethyl)pyrazol-1-yl
5-chloro-3-(2,2,2-trifluoroethyl)pyrazol-1-yl
5-chloro-3-(pentafluoroethyl)pyrazol-1-yl
5-chloro-3-cyanopyrazol-1-yl
5-chloro-3-nitropyrazol-1-yl
5-bromo-3-methylpyrazol-1-yl
5-bromo-3-chloropyrazol-1-yl
3,5-dibromopyrazol-1-yl
5-bromo-3-iodopyrazol-1-yl
5-bromo-3-ethylpyrazol-1-yl
5-bromo-3-propylpyrazol-1-yl
5-bromo-3-(trifluoromethyl)pyrazol-1-yl
5-bromo-3-(2,2,2-trifluoroethyl)pyrazol-1-yl
5-bromo-3-(pentafluoroethyl)pyrazol-1-yl
5-ethyl-3-methylpyrazol-1-yl
2,5-dichloro-3-thienyl
3,6-dimethyl-2-pyridyl
2,5-dimethyl-3-pyridyl
2,5-dimethyl-4-pyridyl
3,6-dichloro-2-pyridyl
2,5-dichloro-3-pyridyl
2,5-dichloro-4-pyridyl
3,5-bis-(trifluoromethyl)pyrazol-1-yl
1-methyl-3-(trifluoromethyl)pyrazol-5-yl
1-methyl-4-(trifluoromethyl)imidazol-2-yl

TABLE 9A

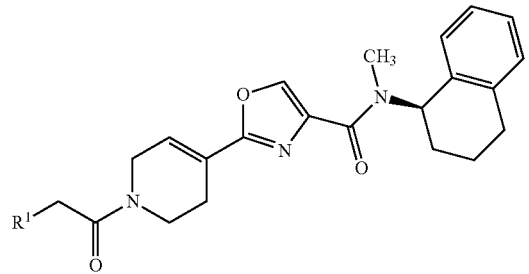

R[1]

2-methoxyphenyl
3-bromophenyl
3-iodophenyl
3-(trifluoromethyl)phenyl
3-(2,2,2-trifluoroethyl)phenyl
3-(pentafluoroethyl)phenyl
3-cyanophenyl
3-nitrophenyl
2,5-dichlorophenyl
5-bromo-2-chlorophenyl
2-chloro-5-iodophenyl
2-chloro-5-methylphenyl
2-bromo-5-(trifluoromethyl)phenyl
2-bromo-5-(2,2,2-trifluoroethyl)phenyl
2-bromo-5-(pentafluoroethyl)phenyl
2-bromo-5-cyanophenyl
2-bromo-5-nitrophenyl
5-chloro-2-methylphenyl
5-bromo-2-methylphenyl
5-iodo-2-methylphenyl
2,5-dimethylphenyl
5-ethyl-2-methylphenyl
2-methyl-5-propylphenyl
5-isopropyl-2-methylphenyl
2-methyl-5-(trifluoromethyl)phenyl
2-methyl-5-(2,2,2-trifluoroethyl)phenyl
2-methyl-5-(pentafluoroethyl)phenyl
5-cyano-2-methylphenyl
2-methyl-5-nitrophenyl
5-chloro-2-methoxyphenyl
5-bromo-2-methoxyphenyl
5-iodo-2-methoxyphenyl
2-methoxy-5-methylphenyl
5-ethyl-2-methoxyphenyl
2-methoxy-5-propylphenyl
2-methoxy-5-(trifluoromethyl)phenyl
2-methoxy-5-(2,2,2-trifluoroethyl)phenyl
2-methoxy-5-(pentafluoroethyl)phenyl
5-cyano-2-methoxyphenyl
2-methoxy-5-nitrophenyl
5-chloro-2-ethylphenyl
5-bromo-2-ethylphenyl
2-ethyl-5-iodophenyl
2-ethyl-5-methylphenyl
2,5-diethylphenyl
5-chloro-3-cyanopyrazol-1-yl
5-chloro-3-nitropyrazol-1-yl
5-bromo-3-methylpyrazol-1-yl
5-bromo-3-chloropyrazol-1-yl
3,5-dibromopyrazol-1-yl
5-bromo-3-iodopyrazol-1-yl
5-bromo-3-ethylpyrazol-1-yl
5-bromo-3-propylpyrazol-1-yl
5-bromo-3-(trifluoromethyl)pyrazol-1-yl
5-bromo-3-(2,2,2-trifluoroethyl)pyrazol-1-yl
5-bromo-3-(pentafluoroethyl)pyrazol-1-yl
5-ethyl-3-methylpyrazol-1-yl
3-chloro-5-ethylpyrazol-1-yl
3-bromo-5-ethylpyrazol-1-yl
5-ethyl-3-iodopyrazol-1-yl
3,5-diethylpyrazol-1-yl
5-ethyl-3-propylpyrazol-1-yl
2-chloro-5-ethylphenyl
2-chloro-5-(trifluoromethyl)phenyl

TABLE 9A-continued

[Structure: N-methyl-N-(tetrahydronaphthalenyl) oxazole carboxamide with piperidine-R¹C(O) substituent]

R¹

2-chloro-5-(2,2,2-trifluoroethyl)phenyl
2-chloro-5-(pentafluoroethyl)phenyl
2-chloro-5-cyanophenyl
2-chloro-5-nitrophenyl
2-bromo-5-chlorophenyl
2,5-dibromophenyl
2-bromo-5-iodophenyl
2-bromo-5-methylphenyl
2-bromo-5-ethylphenyl
2-bromo-5-propylphenyl
2-ethyl-5-propylphenyl
2-ethyl-5-(trifluoromethyl)phenyl
2-ethyl-5-(2,2,2-trifluoroethyl)phenyl
2-ethyl-5-(pentafluoroethyl)phenyl
5-cyano-2-ethylphenyl
2-ethyl-5-nitrophenyl
3-chloropyrazol-1-yl
3-bromopyrazol-1-yl
3-(trifluoromethyl)pyrazol-1-yl
3-(2,2,2-trifluoroethyl)pyrazol-1-yl
3-(pentafluoroethyl)pyrazol-1-yl
3-cyanopyrazol-1-yl
3-nitropyrazol-1-yl
3,5-dimethylpyrazol-1-yl
3-chloro-5-methylpyrazol-1-yl
3-bromo-5-methylpyrazol-1-yl
3-iodo-5-methylpyrazol-1-yl
3-ethyl-5-methylpyrazol-1-yl
5-methyl-3-propylpyrazol-1-yl
5-methyl-3-(trifluoromethyl)pyrazol-1-yl
5-methyl-3-(2,2,2-trifluoroethyl)pyrazol-1-yl
5-methyl-3-(pentafluoroethyl)pyrazol-1-yl
3-cyano-5-methylpyrazol-1-yl
5-methyl-3-nitropyrazol-1-yl
5-chloro-3-methylpyrazol-1-yl
3,5-dichloropyrazol-1-yl
5-chloro-3-bromopyrazol-1-yl
5-chloro-3-iodopyrazol-1-yl
5-chloro-3-ethylpyrazol-1-yl
5-chloro-3-propylpyrazol-1-yl
5-chloro-3-(trifluoromethyl)pyrazol-1-yl
5-chloro-3-(2,2,2-trifluoroethyl)pyrazol-1-yl
5-chloro-3-(pentafluoroethyl)pyrazol-1-yl
5-ethyl-3-(trifluoromethyl)pyrazol-1-yl
5-ethyl-3-(2,2,2-trifluoroethyl)pyrazol-1-yl
5-ethyl-3-(pentafluoroethyl)pyrazol-1-yl
3,5-dimethyl-2-thienyl
3,5-dichloro-2-thienyl
2,5-dimethyl-3-thienyl
2,5-dichloro-3-thienyl
3,6-dimethyl-2-pyridyl
2,5-dimethyl-3-pyridyl
2,5-dimethyl-4-pyridyl
3,6-dichloro-2-pyridyl
2,5-dichloro-3-pyridyl
2,5-dichloro-4-pyridyl
3,5-bis-(trifluoromethyl)pyrazol-1-yl
1-methyl-3-(trifluoromethyl)pyrazol-5-yl
1-methyl-4-(trifluoromethyl)imidazol-2-yl

TABLE 9B

[Structure: N-methyl-N-(indanyl) oxazole carboxamide with piperidine-R¹C(O) substituent]

R¹

2-methoxyphenyl
3-bromophenyl
3-iodophenyl
3-(trifluoromethyl)phenyl
3-(2,2,2-trifluoroethyl)phenyl
3-(pentafluoroethyl)phenyl
2-chloro-5-ethylphenyl
2-chloro-5-(trifluoromethyl)phenyl
2-chloro-5-(2,2,2-trifluoroethyl)phenyl
2-chloro-5-(pentafluoroethyl)phenyl
2-chloro-5-cyanophenyl
2-chloro-5-nitrophenyl
2-bromo-5-chlorophenyl
2,5-dibromophenyl
2-bromo-5-iodophenyl
2-bromo-5-methylphenyl
2-bromo-5-ethylphenyl
2-bromo-5-propylphenyl
2-bromo-5-(trifluoromethyl)phenyl
2-bromo-5-(2,2,2-trifluoroethyl)phenyl
2-bromo-5-(pentafluoroethyl)phenyl
2-bromo-5-cyanophenyl
2-bromo-5-nitrophenyl
5-chloro-2-methylphenyl
5-bromo-2-methylphenyl
5-iodo-2-methylphenyl
2,5-dimethylphenyl
5-ethyl-2-methylphenyl
2-methyl-5-propylphenyl
5-isopropyl-2-methylphenyl
2-methyl-5-(trifluoromethyl)phenyl
2-methyl-5-(2,2,2-trifluoroethyl)phenyl
2-methyl-5-(pentafluoroethyl)phenyl
5-cyano-2-methylphenyl
2-methyl-5-nitrophenyl
5-chloro-2-methoxyphenyl
5-bromo-2-methoxyphenyl
5-iodo-2-methoxyphenyl
2-methoxy-5-methylphenyl
5-methyl-3-(pentafluoroethyl)pyrazol-1-yl
3-cyano-5-methylpyrazol-1-yl
5-methyl-3-nitropyrazol-1-yl
5-chloro-3-methylpyrazol-1-yl
3,5-dichloropyrazol-1-yl
5-chloro-3-bromopyrazol-1-yl
5-chloro-3-iodopyrazol-1-yl
5-chloro-3-ethylpyrazol-1-yl
5-chloro-3-propylpyrazol-1-yl
5-chloro-3-(trifluoromethyl)pyrazol-1-yl
5-chloro-3-(2,2,2-trifluoroethyl)pyrazol-1-yl
5-chloro-3-(pentafluoroethyl)pyrazol-1-yl
5-chloro-3-cyanopyrazol-1-yl
5-chloro-3-nitropyrazol-1-yl
5-bromo-3-methylpyrazol-1-yl
5-bromo-3-chloropyrazol-1-yl
3,5-dibromopyrazol-1-yl
5-bromo-3-iodopyrazol-1-yl
5-bromo-3-ethylpyrazol-1-yl
5-bromo-3-propylpyrazol-1-yl
5-bromo-3-(trifluoromethyl)pyrazol-1-yl
5-bromo-3-(2,2,2-trifluoroethyl)pyrazol-1-yl
5-bromo-3-(pentafluoroethyl)pyrazol-1-yl
3-cyanophenyl
3-nitrophenyl

TABLE 9B-continued

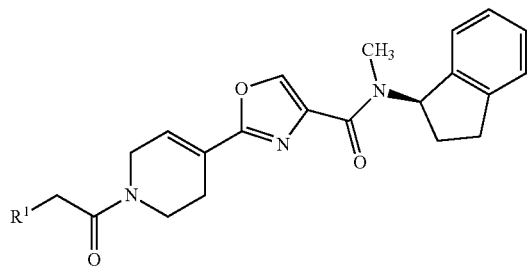

R¹

2,5-dichlorophenyl
5-bromo-2-chlorophenyl
2-chloro-5-iodophenyl
2-chloro-5-methylphenyl
5-ethyl-2-methoxyphenyl
2-methoxy-5-propylphenyl
2-methoxy-5-(trifluoromethyl)phenyl
2-methoxy-5-(2,2,2-trifluoroethyl)phenyl
2-methoxy-5-(pentafluoroethyl)phenyl
5-cyano-2-methoxyphenyl
2-methoxy-5-nitrophenyl
5-chloro-2-ethylphenyl
5-bromo-2-ethylphenyl
2-ethyl-5-iodophenyl
2-ethyl-5-methylphenyl
2,5-diethylphenyl
2-ethyl-5-propylphenyl
2-ethyl-5-(trifluoromethyl)phenyl
2-ethyl-5-(2,2,2-trifluoroethyl)phenyl
2-ethyl-5-(pentafluoroethyl)phenyl
5-cyano-2-ethylphenyl
2-ethyl-5-nitrophenyl
3-chloropyrazol-1-yl
3-bromopyrazol-1-yl
3-(trifluoromethyl)pyrazol-1-yl
3-(2,2,2-trifluoroethyl)pyrazol-1-yl
3-(pentafluoroethyl)pyrazol-1-yl
3-cyanopyrazol-1-yl
3-nitropyrazol-1-yl
3,5-dimethylpyrazol-1-yl
3-chloro-5-methylpyrazol-1-yl
3-bromo-5-methylpyrazol-1-yl
3-iodo-5-methylpyrazol-1-yl
3-ethyl-5-methylpyrazol-1-yl
5-methyl-3-propylpyrazol-1-yl
5-methyl-3-(trifluoromethyl)pyrazol-1-yl
5-methyl-3-(2,2,2-trifluoroethyl)pyrazol-1-yl
5-ethyl-3-methylpyrazol-1-yl
3-chloro-5-ethylpyrazol-1-yl
3-bromo-5-ethylpyrazol-1-yl
5-ethyl-3-iodopyrazol-1-yl
3,5-diethylpyrazol-1-yl
5-ethyl-3-propylpyrazol-1-yl
5-ethyl-3-(trifluoromethyl)pyrazol-1-yl
5-ethyl-3-(2,2,2-trifluoroethyl)pyrazol-1-yl
5-ethyl-3-(pentafluoroethyl)pyrazol-1-yl
3,5-dimethyl-2-thienyl
3,5-dichloro-2-thienyl
2,5-dimethyl-3-thienyl
2,5-dichloro-3-thienyl
3,6-dimethyl-2-pyridyl
2,5-dimethyl-3-pyridyl
2,5-dimethyl-4-pyridyl
3,6-dichloro-2-pyridyl
2,5-dichloro-3-pyridyl
2,5-dichloro-4-pyridyl
3,5-bis-(trifluoromethyl)pyrazol-1-yl
1-methyl-3-(trifluoromethyl)pyrazol-5-yl
1-methyl-4-(trifluoromethyl)imidazol-2-yl

TABLE 9C

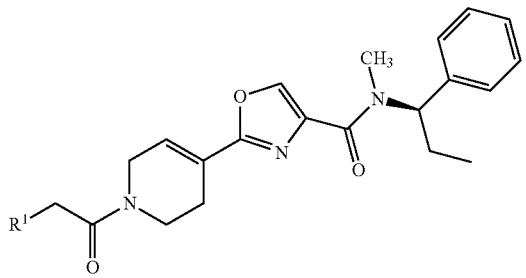

R¹

2-methoxyphenyl
3-bromophenyl
3-iodophenyl
3-(trifluoromethyl)phenyl
3-(2,2,2-trifluoroethyl)phenyl
3-(pentafluoroethyl)phenyl
3-cyanophenyl
3-nitrophenyl
2,5-dichlorophenyl
5-bromo-2-chlorophenyl
2-chloro-5-iodophenyl
2-chloro-5-methylphenyl
2-chloro-5-ethylphenyl
2-chloro-5-(tifloromethyl)phenyl
2-chloro-5-(2,2,2-trifluoroethyl)phenyl
2-chloro-5-(pentafluoroethyl)phenyl
2-chloro-5-cyanophenyl
2-chloro-5-nitrophenyl
2-bromo-5-chlorophenyl
2,5-dibromophenyl
2-bromo-5-iodophenyl
2-bromo-5-methylphenyl
2-bromo-5-ethylphenyl
2-bromo-5-propylphenyl
2-bromo-5-(trifluoromethyl)phenyl
2-bromo-5-(2,2,2-trifluoroethyl)phenyl
2-bromo-5-(pentafluoroethyl)phenyl
2-bromo-5-cyanophenyl
2-bromo-5-nitrophenyl
5-chloro-2-methylphenyl
5-bromo-2-methylphenyl
5-iodo-2-methylphenyl
2,5-dimethylphenyl
3-(2,2,2-trifluoroethyl)pyrazol-1-yl
3-(pentafluoroethyl)pyrazol-1-yl
3-cyanopyrazol-1-yl
3-nitropyrazol-1-yl
3,5-dimethylpyrazol-1-yl
3-chloro-5-methylpyrazol-1-yl
3-bromo-5-methylpyrazol-1-yl
3-iodo-5-methylpyrazol-1-yl
3-ethyl-5-methylpyrazol-1-yl
5-methyl-3-propylpyrazol-1-yl
5-methyl-3-(trifluoromethyl)pyrazol-1-yl
5-methyl-3-(2,2,2-trifluoroethyl)pyrazol-1-yl
5-methyl-3-(pentafluoroethyl)pyrazol-1-yl
3-cyano-5-methylpyrazol-1-yl
5-methyl-3-nitropyrazol-1-yl
5-chloro-3-methylpyrazol-1-yl
3,5-dichloropyrazol-1-yl
5-chloro-3-bromopyrazol-1-yl
5-chloro-3-iodopyrazol-1-yl
5-chloro-3-ethylpyrazol-1-yl
5-chloro-3-propylpyrazol-1-yl
5-chloro-3-(trifluoromethyl)pyrazol-1-yl
5-chloro-3-(2,2,2-trifluoroethyl)pyrazol-1-yl
5-chloro-3-(pentafluoroethyl)pyrazol-1-yl
5-chloro-3-cyanopyrazol-1-yl
5-chloro-3-nitropyrazol-1-yl
5-bromo-3-methylpyrazol-1-yl
5-bromo-3-chloropyrazol-1-yl
3,5-dibromopyrazol-1-yl
5-ethyl-2-methylphenyl
2-methyl-5-propylphenyl TABLE 9C-continued

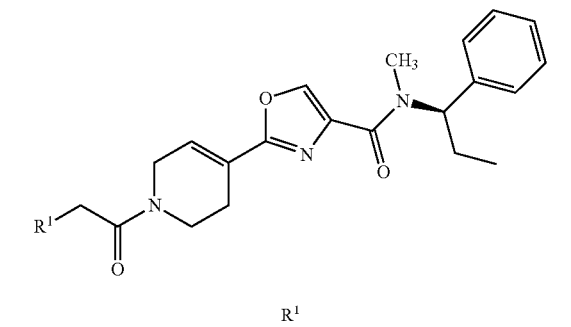

R¹

5-isopropyl-2-methylphenyl
2-methyl-5-(trifluoromethyl)phenyl
2-methyl-5-(2,2,2-trifluoroethyl)phenyl
2-methyl-5-(pentafluoroethyl)phenyl
5-cyano-2-methylphenyl
2-methyl-5-nitrophenyl
5-chloro-2-methoxyphenyl
5-bromo-2-methoxyphenyl
5-iodo-2-methoxyphenyl
2-methoxy-5-methylphenyl
5-ethyl-2-methoxyphenyl
2-methoxy-5-propylphenyl
2-methoxy-5-(trifluoromethyl)phenyl
2-methoxy-5-(2,2,2-trifluoroethyl)phenyl
2-methoxy-5-(pentafluoroethyl)phenyl
5-cyano-2-methoxyphenyl
2-methoxy-5-nitrophenyl
5-chloro-2-ethylphenyl
5-bromo-2-ethylphenyl
2-ethyl-5-iodophenyl
2-ethyl-5-methylphenyl
2,5-diethylphenyl
2-ethyl-5-propylphenyl
2-ethyl-5-(trifluoromethyl)phenyl
2-ethyl-5-(2,2,2-trifluoroethyl)phenyl
2-ethyl-5-(pentafluoroethyl)phenyl
5-cyano-2-ethylphenyl
2-ethyl-5-nitrophenyl
3-chloropyrazol-1-yl
3-bromopyrazol-1-yl TABLE 9C-continued

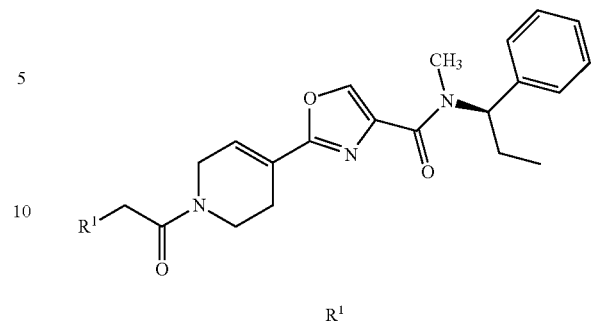

R¹

3-(trifluoromethyl)pyrazol-1-yl
5-bromo-3-iodopyrazol-1-yl
5-bromo-3-ethylpyrazol-1-yl
5-bromo-3-propylpyrazol-1-yl
5-bromo-3-(trifluoromethyl)pyrazol-1-yl
5-bromo-3-(2,2,2-trifluoroethyl)pyrazol-1-yl
5-bromo-3-(pentafluoroethyl)pyrazol-1-yl
5-ethyl-3-methylpyrazol-1-yl
3-chloro-5-ethylpyrazol-1-yl
3-bromo-5-ethylpyrazol-1-yl
5-ethyl-3-iodopyrazol-1-yl
3,5-diethylpyrazol-1-yl
5-ethyl-3-propylpyrazol-1-yl
5-ethyl-3-(trifluoromethyl)pyrazol-1-yl
5-ethyl-3-(2,2,2-trifluoroethyl)pyrazol-1-yl
5-ethyl-3-(pentafluoroethyl)pyrazol-1-yl
3,5-dimethyl-2-thienyl
3,5-dichloro-2-thienyl
2,5-dimethyl-3-thienyl
2,5-dichloro-3-thienyl
3,6-dimethyl-2-pyridyl
2,5-dimethyl-3-pyridyl
2,5-dimethyl-4-pyridyl
3,6-dichloro-2-pyridyl
2,5-dichloro-3-pyridyl
2,5-dichloro-4-pyridyl
3,5-bis-(trifluoromethyl)pyrazol-1-yl
1-methyl-3-(trifluoromethyl)pyrazol-5-yl
1-methyl-4-(trifluoromethyl)imidazol-2-yl

TABLE 10

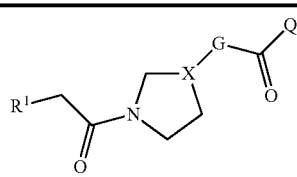

| R¹ | X* | G** | Q |
|---|---|---|---|
| 2,5-dichlorophenyl | X¹ | G-26 | (1R)-N-methyl-1-phenylpropylamino |
| 2-chloro-5-(trifluoromethyl)phenyl | X¹ | G-26 | (1R)-N-methyl-1-phenylpropylamino |
| 2,5-dimethylphenyl | X¹ | G-26 | (1R)-N-methyl-1-phenylpropylamino |
| 2-methyl-5-(trifluoromethyl)phenyl | X¹ | G-26 | (1R)-N-methyl-1-phenylpropylamino |
| 3,5-dimethylpyrazol-1-yl | X¹ | G-26 | (1R)-N-methyl-1-phenylpropylamino |
| 5-methyl-3-(trifluoromethyl)pyrazol-1-yl | X¹ | G-26 | (1R)-N-methyl-1-phenylpropylamino |
| 3,5-dichloropyrazol-1-yl | X¹ | G-26 | (1R)-N-methyl-1-phenylpropylamino |
| 5-chloro-3-(trifluoromethyl)pyrazol-1-yl | X¹ | G-26 | (1R)-N-methyl-1-phenylpropylamino |
| 3,5-dibromopyrazol-1-yl | X¹ | G-26 | (1R)-N-methyl-1-phenylpropylamino |
| 5-bromo-3-(trifluoromethyl)pyrazol-1-yl | X¹ | G-26 | (1R)-N-methyl-1-phenylpropylamino |
| 3,5-diethylpyrazol-1-yl | X¹ | G-26 | (1R)-N-methyl-1-phenylpropylamino |
| 5-ethyl-3-(trifluoromethyl)pyrazol-1-yl | X¹ | G-26 | (1R)-N-methyl-1-phenylpropylamino |
| 3,5-bis-(trifluoromethyl)pyrazol-1-yl | X¹ | G-26 | (1R)-N-methyl-1-phenylpropylamino |
| 1-methyl-3-(trifluoromethyl)pyrazol-5-yl | X¹ | G-26 | (1R)-N-methyl-1-phenylpropylamino |
| 1-methyl-4-(trifluoromethyl)imidazol-2-yl | X¹ | G-26 | (1R)-N-methyl-1-phenylpropylamino |
| 2,5-dichlorophenyl | X¹ | G-26 | (1R)-N-methyl-1,2,3,4-tetrahydro-1-naphthalenylamino |
| 2-chloro-5-(trifluoromethyl)phenyl | X¹ | G-26 | (1R)-N-methyl-1,2,3,4-tetrahydro-1-naphthalenylamino |

TABLE 10-continued

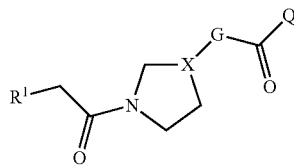

| R¹ | X* | G** | Q |
|---|---|---|---|
| 2,5-dimethylphenyl | X¹ | G-26 | (1R)-N-methyl-1,2,3,4-tetrahydro-1-naphthalenylamino |
| 2-methyl-5-(trifluoromethyl)phenyl | X¹ | G-26 | (1R)-N-methyl-1,2,3,4-tetrahydro-1-naphthalenylamino |
| 3,5-dimethylpyrazol-1-yl | X¹ | G-26 | (1R)-N-methyl-1,2,3,4-tetrahydro-1-naphthalenylamino |
| 5-methyl-3-(trifluoromethyl)pyrazol-1-yl | X¹ | G-26 | (1R)-N-methyl-1,2,3,4-tetrahydro-1-naphthalenylamino |
| 3,5-dichloropyrazol-1-yl | X¹ | G-26 | (1R)-N-methyl-1,2,3,4-tetrahydro-1-naphthalenylamino |
| 5-chloro-3-(trifluoromethyl)pyrazol-1-yl | X¹ | G-26 | (1R)-N-methyl-1,2,3,4-tetrahydro-1-naphthalenylamino |
| 3,5-dibromopyrazol-1-yl | X¹ | G-26 | (1R)-N-methyl-1,2,3,4-tetrahydro-1-naphthalenylamino |
| 5-bromo-3-(trifluoromethyl)pyrazol-1-yl | X¹ | G-26 | (1R)-N-methyl-1,2,3,4-tetrahydro-1-naphthalenylamino |
| 3,5-diethylpyrazol-1-yl | X¹ | G-26 | (1R)-N-methyl-1,2,3,4-tetrahydro-1-naphthalenylamino |
| 5-ethyl-3-(trifluoromethyl)pyrazol-1-yl | X¹ | G-26 | (1R)-N-methyl-1,2,3,4-tetrahydro-1-naphthalenylamino |
| 3,5-bis-(trifluoromethyl)pyrazol-1-yl | X¹ | G-26 | (1R)-N-methyl-1,2,3,4-tetrahydro-1-naphthalenylamino |
| 1-methyl-3-(trifluoromethyl)pyrazol-5-yl | X¹ | G-26 | (1R)-N-methyl-1,2,3,4-tetrahydro-1-naphthalenylamino |
| 1-methyl-4-(trifluoromethyl)imidazol-2-yl | X¹ | G-26 | (1R)-N-methyl-1,2,3,4-tetrahydro-1-naphthalenylamino |
| 2,5-dichlorophenyl | X¹ | G-26 | N-methyl-4-hydroxy-1,2,3,4-tetrahydro-1-naphthalenylamino |
| 2-chloro-5-(trifluoromethyl)phenyl | X¹ | G-26 | N-methyl-4-hydroxy-1,2,3,4-tetrahydro-1-naphthalenylamino |
| 2,5-dimethylphenyl | X¹ | G-26 | N-methyl-4-hydroxy-1,2,3,4-tetrahydro-1-naphthalenylamino |
| 2-methyl-5-(trifluoromethyl)phenyl | X¹ | G-26 | N-methyl-4-hydroxy-1,2,3,4-tetrahydro-1-naphthalenylamino |
| 3,5-dimethylpyrazol-1-yl | X¹ | G-26 | N-methyl-4-hydroxy-1,2,3,4-tetrahydro-1-naphthalenylamino |
| 5-methyl-3-(trifluoromethyl)pyrazol-1-yl | X¹ | G-26 | N-methyl-4-hydroxy-1,2,3,4-tetrahydro-1-naphthalenylamino |
| 3,5-dichloropyrazol-1-yl | X¹ | G-26 | N-methyl-4-hydroxy-1,2,3,4-tetrahydro-1-naphthalenylamino |
| 5-chloro-3-(trifluoromethyl)pyrazol-1-yl | X¹ | G-26 | N-methyl-4-hydroxy-1,2,3,4-tetrahydro-1-naphthalenylamino |
| 3,5-dibromopyrazol-1-yl | X¹ | G-26 | N-methyl-4-hydroxy-1,2,3,4-tetrahydro-1-naphthalenylamino |
| 5-bromo-3-(trifluoromethyl)pyrazol-1-yl | X¹ | G-26 | N-methyl-4-hydroxy-1,2,3,4-tetrahydro-1-naphthalenylamino |
| 3,5-diethylpyrazol-1-yl | X¹ | G-26 | N-methyl-4-hydroxy-1,2,3,4-tetrahydro-1-naphthalenylamino |
| 5-ethyl-3-(trifluoromethyl)pyrazol-1-yl | X¹ | G-26 | N-methyl-4-hydroxy-1,2,3,4-tetrahydro-1-naphthalenylamino |
| 3,5-bis-(trifluoromethyl)pyrazol-1-yl | X¹ | G-26 | N-methyl-4-hydroxy-1,2,3,4-tetrahydro-1-naphthalenylamino |
| 1-methyl-3-(trifluoromethyl)pyrazol-5-yl | X¹ | G-26 | N-methyl-4-hydroxy-1,2,3,4-tetrahydro-1-naphthalenylamino |
| 1-methyl-4-(trifluoromethyl)imidazol-2-yl | X¹ | G-26 | N-methyl-4-hydroxy-1,2,3,4-tetrahydro-1-naphthalenylamino |
| 2,5-dichlorophenyl | X¹ | G-26 | N,2-dimethyl-1,2,3,4-tetrahydro-1-naphthalenylamino |
| 2-chloro-5-(trifluoromethyl)phenyl | X¹ | G-26 | N,2-dimethyl-1,2,3,4-tetrahydro-1-naphthalenylamino |
| 2,5-dimethylphenyl | X¹ | G-26 | N,2-dimethyl-1,2,3,4-tetrahydro-1-naphthalenylamino |
| 2-methyl-5-(trifluoromethyl)phenyl | X¹ | G-26 | N,2-dimethyl-1,2,3,4-tetrahydro-1-naphthalenylamino |
| 3,5-dimethylpyrazol-1-yl | X¹ | G-26 | N,2-dimethyl-1,2,3,4-tetrahydro-1-naphthalenylamino |
| 5-methyl-3-(trifluoromethyl)pyrazol-1-yl | X¹ | G-26 | N,2-dimethyl-1,2,3,4-tetrahydro-1-naphthalenylamino |

TABLE 10-continued

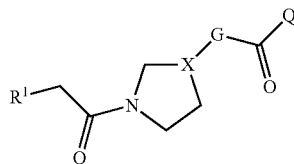

| R¹ | X* | G** | Q |
|---|---|---|---|
| 3,5-dichloropyrazol-1-yl | X¹ | G-26 | N,2-dimethyl-1,2,3,4-tetrahydro-1-naphthalenylamino |
| 5-chloro-3-(trifluoromethyl)pyrazol-1-yl | X¹ | G-26 | N,2-dimethyl-1,2,3,4-tetrahydro-1-naphthalenylamino |
| 3,5-dibromopyrazol-1-yl | X¹ | G-26 | N,2-dimethyl-1,2,3,4-tetrahydro-1-naphthalenylamino |
| 5-bromo-3-(trifluoromethyl)pyrazol-1-yl | X¹ | G-26 | N,2-dimethyl-1,2,3,4-tetrahydro-1-naphthalenylamino |
| 3,5-diethylpyrazol-1-yl | X¹ | G-26 | N,2-dimethyl-1,2,3,4-tetrahydro-1-naphthalenylamino |
| 5-ethyl-3-(trifluoromethyl)pyrazol-1-yl | X¹ | G-26 | N,2-dimethyl-1,2,3,4-tetrahydro-1-naphthalenylamino |
| 3,5-bis-(trifluoromethyl)pyrazol-1-yl | X¹ | G-26 | N,2-dimethyl-1,2,3,4-tetrahydro-1-naphthalenylamino |
| 1-methyl-3-(trifluoromethyl)pyrazol-5-yl | X¹ | G-26 | N,2-dimethyl-1,2,3,4-tetrahydro-1-naphthalenylamino |
| 1-methyl-4-(trifluoromethyl)imidazol-2-yl | X¹ | G-26 | N,2-dimethyl-1,2,3,4-tetrahydro-1-naphthalenylamino |
| 2,5-dichlorophenyl | X¹ | G-26 | N,2,2-trimethyl-1,2,3,4-tetrahydro-1-naphthalenylamino |
| 2-chloro-5-(trifluoromethyl)phenyl | X¹ | G-26 | N,2,2-trimethyl-1,2,3,4-tetrahydro-1-naphthalenylamino |
| 2,5-dimethylphenyl | X¹ | G-26 | N,2,2-trimethyl-1,2,3,4-tetrahydro-1-naphthalenylamino |
| 2-methyl-5-(trifluoromethyl)phenyl | X¹ | G-26 | N,2,2-trimethyl-1,2,3,4-tetrahydro-1-naphthalenylamino |
| 3,5-dimethylpyrazol-1-yl | X¹ | G-26 | N,2,2-trimethyl-1,2,3,4-tetrahydro-1-naphthalenylamino |
| 5-methyl-3-(trifluoromethyl)pyrazol-1-yl | X¹ | G-26 | N,2,2-trimethyl-1,2,3,4-tetrahydro-1-naphthalenylamino |
| 3,5-dichloropyrazol-1-yl | X¹ | G-26 | N,2,2-trimethyl-1,2,3,4-tetrahydro-1-naphthalenylamino |
| 5-chloro-3-(trifluoromethyl)pyrazol-1-yl | X¹ | G-26 | N,2,2-trimethyl-1,2,3,4-tetrahydro-1-naphthalenylamino |
| 3,5-dibromopyrazol-1-yl | X¹ | G-26 | N,2,2-trimethyl-1,2,3,4-tetrahydro-1-naphthalenylamino |
| 5-bromo-3-(trifluoromethyl)pyrazol-1-yl | X¹ | G-26 | N,2,2-trimethyl-1,2,3,4-tetrahydro-1-naphthalenylamino |
| 3,5-diethylpyrazol-1-yl | X¹ | G-26 | N,2,2-trimethyl-1,2,3,4-tetrahydro-1-naphthalenylamino |
| 5-ethyl-3-(trifluoromethyl)pyrazol-1-yl | X¹ | G-26 | N,2,2-trimethyl-1,2,3,4-tetrahydro-1-naphthalenylamino |
| 3,5-bis-(trifluoromethyl)pyrazol-1-yl | X¹ | G-26 | N,2,2-trimethyl-1,2,3,4-tetrahydro-1-naphthalenylamino |
| 1-methyl-3-(trifluoromethyl)pyrazol-5-yl | X¹ | G-26 | N,2,2-trimethyl-1,2,3,4-tetrahydro-1-naphthalenylamino |
| 1-methyl-4-(trifluoromethyl)imidazol-2-yl | X¹ | G-26 | N,2,2-trimethyl-1,2,3,4-tetrahydro-1-naphthalenylamino |
| 2,5-dichlorophenyl | X¹ | G-26 | N-methyl-4-oxo-1,2,3,4-tetrahydro-1-naphthalenylamino |
| 2-chloro-5-(trifluoromethyl)phenyl | X¹ | G-26 | N-methyl-4-oxo-1,2,3,4-tetrahydro-1-naphthalenylamino |
| 2,5-dimethylphenyl | X¹ | G-26 | N-methyl-4-oxo-1,2,3,4-tetrahydro-1-naphthalenylamino |
| 2-methyl-5-(trifluoromethyl)phenyl | X¹ | G-26 | N-methyl-4-oxo-1,2,3,4-tetrahydro-1-naphthalenylamino |
| 3,5-dimethylpyrazol-1-yl | X¹ | G-26 | N-methyl-4-oxo-1,2,3,4-tetrahydro-1-naphthalenylamino |
| 5-methyl-3-(trifluoromethyl)pyrazol-1-yl | X¹ | G-26 | N-methyl-4-oxo-1,2,3,4-tetrahydro-1-naphthalenylamino |
| 3,5-dichloropyrazol-1-yl | X¹ | G-26 | N-methyl-4-oxo-1,2,3,4-tetrahydro-1-naphthalenylamino |
| 5-chloro-3-(trifluoromethyl)pyrazol-1-yl | X¹ | G-26 | N-methyl-4-oxo-1,2,3,4-tetrahydro-1-naphthalenylamino |
| 3,5-dibromopyrazol-1-yl | X¹ | G-26 | N-methyl-4-oxo-1,2,3,4-tetrahydro-1-naphthalenylamino |
| 5-bromo-3-(trifluoromethyl)pyrazol-1-yl | X¹ | G-26 | N-methyl-4-oxo-1,2,3,4-tetrahydro-1-naphthalenylamino |

TABLE 10-continued

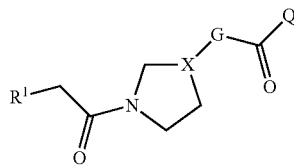

| R[1] | X* | G** | Q |
|---|---|---|---|
| 3,5-diethylpyrazol-1-yl | X[1] | G-26 | N-methyl-4-oxo-1,2,3,4-tetrahydro-1-naphthalenylamino |
| 5-ethyl-3-(trifluoromethyl)pyrazol-1-yl | X[1] | G-26 | N-methyl-4-oxo-1,2,3,4-tetrahydro-1-naphthalenylamino |
| 3,5-bis-(trifluoromethyl)pyrazol-1-yl | X[1] | G-26 | N-methyl-4-oxo-1,2,3,4-tetrahydro-1-naphthalenylamino |
| 1-methyl-3-(trifluoromethyl)pyrazol-5-yl | X[1] | G-26 | N-methyl-4-oxo-1,2,3,4-tetrahydro-1-naphthalenylamino |
| 1-methyl-4-(trifluoromethyl)imidazol-2-yl | X[1] | G-26 | N-methyl-4-oxo-1,2,3,4-tetrahydro-1-naphthalenylamino |
| 2,5-dichlorophenyl | X[1] | G-26 | (1R)-N-methyl-1-indanylamino |
| 2-chloro-5-(trifluoromethyl)phenyl | X[1] | G-26 | (1R)-N-methyl-1-indanylamino |
| 2,5-dimethylphenyl | X[1] | G-26 | (1R)-N-methyl-1-indanylamino |
| 2-methyl-5-(trifluoromethyl)phenyl | X[1] | G-26 | (1R)-N-methyl-1-indanylamino |
| 3,5-dimethylpyrazol-1-yl | X[1] | G-26 | (1R)-N-methyl-1-indanylamino |
| 5-methyl-3-(trifluoromethyl)pyrazol-1-yl | X[1] | G-26 | (1R)-N-methyl-1-indanylamino |
| 3,5-dichloropyrazol-1-yl | X[1] | G-26 | (1R)-N-methyl-1-indanylamino |
| 5-chloro-3-(trifluoromethyl)pyrazol-1-yl | X[1] | G-26 | (1R)-N-methyl-1-indanylamino |
| 3,5-dibromopyrazol-1-yl | X[1] | G-26 | (1R)-N-methyl-1-indanylamino |
| 5-bromo-3-(trifluoromethyl)pyrazol-1-yl | X[1] | G-26 | (1R)-N-methyl-1-indanylamino |
| 3,5-diethylpyrazol-1-yl | X[1] | G-26 | (1R)-N-methyl-1-indanylamino |
| 5-ethyl-3-(trifluoromethyl)pyrazol-1-yl | X[1] | G-26 | (1R)-N-methyl-1-indanylamino |
| 3,5-bis-(trifluoromethyl)pyrazol-1-yl | X[1] | G-26 | (1R)-N-methyl-1-indanylamino |
| 1-methyl-3-(trifluoromethyl)pyrazol-5-yl | X[1] | G-26 | (1R)-N-methyl-1-indanylamino |
| 1-methyl-4-(trifluoromethyl)imidazol-2-yl | X[1] | G-26 | (1R)-N-methyl-1-indanylamino |
| 2,5-dichlorophenyl | X[1] | G-26 | N,2-dimethyl-1-indanylamino |
| 2-chloro-5-(trifluoromethyl)phenyl | X[1] | G-26 | N,2-dimethyl-1-indanylamino |
| 2,5-dimethylphenyl | X[1] | G-26 | N,2-dimethyl-1-indanylamino |
| 2-methyl-5-(trifluoromethyl)phenyl | X[1] | G-26 | N,2-dimethyl-1-indanylamino |
| 3,5-dimethylpyrazol-1-yl | X[1] | G-26 | N,2-dimethyl-1-indanylamino |
| 5-methyl-3-(trifluoromethyl)pyrazol-1-yl | X[1] | G-26 | N,2-dimethyl-1-indanylamino |
| 3,5-dichloropyrazol-1-yl | X[1] | G-26 | N,2-dimethyl-1-indanylamino |
| 5-chloro-3-(trifluoromethyl)pyrazol-1-yl | X[1] | G-26 | N,2-dimethyl-1-indanylamino |
| 3,5-dibromopyrazol-1-yl | X[1] | G-26 | N,2-dimethyl-1-indanylamino |
| 5-bromo-3-(trifluoromethyl)pyrazol-1-yl | X[1] | G-26 | N,2-dimethyl-1-indanylamino |
| 3,5-diethylpyrazol-1-yl | X[1] | G-26 | N,2-dimethyl-1-indanylamino |
| 5-ethyl-3-(trifluoromethyl)pyrazol-1-yl | X[1] | G-26 | N,2-dimethyl-1-indanylamino |
| 3,5-bis-(trifluoromethyl)pyrazol-1-yl | X[1] | G-26 | N,2-dimethyl-1-indanylamino |
| 1-methyl-3-(trifluoromethyl)pyrazol-5-yl | X[1] | G-26 | N,2-dimethyl-1-indanylamino |
| 1-methyl-4-(trifluoromethyl)imidazol-2-yl | X[1] | G-26 | N,2-dimethyl-1-indanylamino |
| 2,5-dichlorophenyl | X[1] | G-26 | N,2,2-trimethyl-1-indanylamino |
| 2-chloro-5-(trifluoromethyl)phenyl | X[1] | G-26 | N,2,2-trimethyl-1-indanylamino |
| 2,5-dimethylphenyl | X[1] | G-26 | N,2,2-trimethyl-1-indanylamino |
| 2-methyl-5-(trifluoromethyl)phenyl | X[1] | G-26 | N,2,2-trimethyl-1-indanylamino |
| 3,5-dimethylpyrazol-1-yl | X[1] | G-26 | N,2,2-trimethyl-1-indanylamino |
| 5-methyl-3-(trifluoromethyl)pyrazol-1-yl | X[1] | G-26 | N,2,2-trimethyl-1-indanylamino |
| 3,5-dichloropyrazol-1-yl | X[1] | G-26 | N,2,2-trimethyl-1-indanylamino |
| 5-chloro-3-(trifluoromethyl)pyrazol-1-yl | X[1] | G-26 | N,2,2-trimethyl-1-indanylamino |
| 3,5-dibromopyrazol-1-yl | X[1] | G-26 | N,2,2-trimethyl-1-indanylamino |
| 5-bromo-3-(trifluoromethyl)pyrazol-1-yl | X[1] | G-26 | N,2,2-trimethyl-1-indanylamino |
| 3,5-diethylpyrazol-1-yl | X[1] | G-26 | N,2,2-trimethyl-1-indanylamino |
| 5-ethyl-3-(trifluoromethyl)pyrazol-1-yl | X[1] | G-26 | N,2,2-trimethyl-1-indanylamino |
| 3,5-bis-(trifluoromethyl)pyrazol-1-yl | X[1] | G-26 | N,2,2-trimethyl-1-indanylamino |
| 1-methyl-3-(trifluoromethyl)pyrazol-5-yl | X[1] | G-26 | N,2,2-trimethyl-1-indanylamino |
| 1-methyl-4-(trifluoromethyl)imidazol-2-yl | X[1] | G-26 | N,2,2-trimethyl-1-indanylamino |
| 2,5-dichlorophenyl | X[1] | G-26 | N-methyl-3-hydroxy-1-indanylamino |
| 2-chloro-5-(trifluoromethyl)phenyl | X[1] | G-26 | N-methyl-3-hydroxy-1-indanylamino |
| 2,5-dimethylphenyl | X[1] | G-26 | N-methyl-3-hydroxy-1-indanylamino |
| 2-methyl-5-(trifluoromethyl)phenyl | X[1] | G-26 | N-methyl-3-hydroxy-1-indanylamino |
| 3,5-dimethylpyrazol-1-yl | X[1] | G-26 | N-methyl-3-hydroxy-1-indanylamino |
| 5-methyl-3-(trifluoromethyl)pyrazol-1-yl | X[1] | G-26 | N-methyl-3-hydroxy-1-indanylamino |
| 3,5-dichloropyrazol-1-yl | X[1] | G-26 | N-methyl-3-hydroxy-1-indanylamino |
| 5-chloro-3-(trifluoromethyl)pyrazol-1-yl | X[1] | G-26 | N-methyl-3-hydroxy-1-indanylamino |
| 3,5-dibromopyrazol-1-yl | X[1] | G-26 | N-methyl-3-hydroxy-1-indanylamino |
| 5-bromo-3-(trifluoromethyl)pyrazol-1-yl | X[1] | G-26 | N-methyl-3-hydroxy-1-indanylamino |
| 3,5-diethylpyrazol-1-yl | X[1] | G-26 | N-methyl-3-hydroxy-1-indanylamino |
| 5-ethyl-3-(trifluoromethyl)pyrazol-1-yl | X[1] | G-26 | N-methyl-3-hydroxy-1-indanylamino |
| 3,5-bis-(trifluoromethyl)pyrazol-1-yl | X[1] | G-26 | N-methyl-3-hydroxy-1-indanylamino |
| 1-methyl-3-(trifluoromethyl)pyrazol-5-yl | X[1] | G-26 | N-methyl-3-hydroxy-1-indanylamino |

TABLE 10-continued

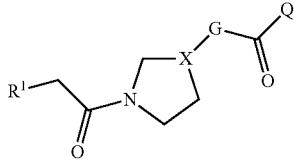

| R¹ | X* | G** | Q |
|---|---|---|---|
| 1-methyl-4-(trifluoromethyl)imidazol-2-yl | X¹ | G-26 | N-methyl-3-hydroxy-1-indanylamino |
| 2,5-dichlorophenyl | X¹ | G-26 | N-methyl-3-oxo-1-indanylamino |
| 2-chloro-5-(trifluoromethyl)phenyl | X¹ | G-26 | N-methyl-3-oxo-1-indanylamino |
| 2,5-dimethylphenyl | X¹ | G-26 | N-methyl-3-oxo-1-indanylamino |
| 2-methyl-5-(trifluoromethyl)phenyl | X¹ | G-26 | N-methyl-3-oxo-1-indanylamino |
| 3,5-dimethylpyrazol-1-yl | X¹ | G-26 | N-methyl-3-oxo-1-indanylamino |
| 5-methyl-3-(trifluoromethyl)pyrazol-1-yl | X¹ | G-26 | N-methyl-3-oxo-1-indanylamino |
| 3,5-dichloropyrazol-1-yl | X¹ | G-26 | N-methyl-3-oxo-1-indanylamino |
| 5-chloro-3-(trifluoromethyl)pyrazol-1-yl | X¹ | G-26 | N-methyl-3-oxo-1-indanylamino |
| 3,5-dibromopyrazol-1-yl | X¹ | G-26 | N-methyl-3-oxo-1-indanylamino |
| 5-bromo-3-(trifluoromethyl)pyrazol-1-yl | X¹ | G-26 | N-methyl-3-oxo-1-indanylamino |
| 3,5-diethylpyrazol-1-yl | X¹ | G-26 | N-methyl-3-oxo-1-indanylamino |
| 5-ethyl-3-(trifluoromethyl)pyrazol-1-yl | X¹ | G-26 | N-methyl-3-oxo-1-indanylamino |
| 3,5-bis-(trifluoromethyl)pyrazol-1-yl | X¹ | G-26 | N-methyl-3-oxo-1-indanylamino |
| 1-methyl-3-(trifluoromethyl)pyrazol-5-yl | X¹ | G-26 | N-methyl-3-oxo-1-indanylamino |
| 1-methyl-4-(trifluoromethyl)imidazol-2-yl | X¹ | G-26 | N-methyl-3-oxo-1-indanylamino |
| 2,5-dichlorophenyl | X¹ | G-27 | (1R)-N-methyl-1-phenylpropylamino |
| 2-chloro-5-(trifluoromethyl)phenyl | X¹ | G-27 | (1R)-N-methyl-1-phenylpropylamino |
| 2,5-dimethylphenyl | X¹ | G-27 | (1R)-N-methyl-1-phenylpropylamino |
| 2-methyl-5-(trifluoromethyl)phenyl | X¹ | G-27 | (1R)-N-methyl-1-phenylpropylamino |
| 3,5-dimethylpyrazol-1-yl | X¹ | G-27 | (1R)-N-methyl-1-phenylpropylamino |
| 5-methyl-3-(trifluoromethyl)pyrazol-1-yl | X¹ | G-27 | (1R)-N-methyl-1-phenylpropylamino |
| 3,5-dichloropyrazol-1-yl | X¹ | G-27 | (1R)-N-methyl-1-phenylpropylamino |
| 5-chloro-3-(trifluoromethyl)pyrazol-1-yl | X¹ | G-27 | (1R)-N-methyl-1-phenylpropylamino |
| 3,5-dibromopyrazol-1-yl | X¹ | G-27 | (1R)-N-methyl-1-phenylpropylamino |
| 5-bromo-3-(trifluoromethyl)pyrazol-1-yl | X¹ | G-27 | (1R)-N-methyl-1-phenylpropylamino |
| 3,5-diethylpyrazol-1-yl | X¹ | G-27 | (1R)-N-methyl-1-phenylpropylamino |
| 5-ethyl-3-(trifluoromethyl)pyrazol-1-yl | X¹ | G-27 | (1R)-N-methyl-1-phenylpropylamino |
| 3,5-bis-(trifluoromethyl)pyrazol-1-yl | X¹ | G-27 | (1R)-N-methyl-1-phenylpropylamino |
| 1-methyl-3-(trifluoromethyl)pyrazol-5-yl | X¹ | G-27 | (1R)-N-methyl-1-phenylpropylamino |
| 1-methyl-4-(trifluoromethyl)imidazol-2-yl | X¹ | G-27 | (1R)-N-methyl-1-phenylpropylamino |
| 2,5-dichlorophenyl | X¹ | G-27 | (1R)-N-methyl-1,2,3,4-tetahydro-1-naphthalenylamino |
| 2-chloro-5-(trifluoromethyl)phenyl | X¹ | G-27 | (1R)-N-methyl-1,2,3,4-tetahydro-1-naphthalenylamino |
| 2,5-dimethylphenyl | X¹ | G-27 | (1R)-N-methyl-1,2,3,4-tetahydro-1-naphthalenylamino |
| 2-methyl-5-(trifluoromethyl)phenyl | X¹ | G-27 | (1R)-N-methyl-1,2,3,4-tetahydro-1-naphthalenylamino |
| 3,5-dimethylpyrazol-1-yl | X¹ | G-27 | (1R)-N-methyl-1,2,3,4-tetahydro-1-naphthalenylamino |
| 5-methyl-3-(trifluoromethyl)pyrazol-1-yl | X¹ | G-27 | (1R)-N-methyl-1,2,3,4-tetahydro-1-naphthalenylamino |
| 3,5-dichloropyrazol-1-yl | X¹ | G-27 | (1R)-N-methyl-1,2,3,4-tetahydro-1-naphthalenylamino |
| 5-chloro-3-(trifluoromethyl)pyrazol-1-yl | X¹ | G-27 | (1R)-N-methyl-1,2,3,4-tetahydro-1-naphthalenylamino |
| 3,5-dibromopyrazol-1-yl | X¹ | G-27 | (1R)-N-methyl-1,2,3,4-tetahydro-1-naphthalenylamino |
| 5-bromo-3-(trifluoromethyl)pyrazol-1-yl | X¹ | G-27 | (1R)-N-methyl-1,2,3,4-tetahydro-1-naphthalenylamino |
| 3,5-diethylpyrazol-1-yl | X¹ | G-27 | (1R)-N-methyl-1,2,3,4-tetahydro-1-naphthalenylamino |
| 5-ethyl-3-(trifluoromethyl)pyrazol-1-yl | X¹ | G-27 | (1R)-N-methyl-1,2,3,4-tetahydro-1-naphthalenylamino |
| 3,5-bis-(trifluoromethyl)pyrazol-1-yl | X¹ | G-27 | (1R)-N-methyl-1,2,3,4-tetahydro-1-naphthalenylamino |
| 1-methyl-3-(trifluoromethyl)pyrazol-5-yl | X¹ | G-27 | (1R)-N-methyl-1,2,3,4-tetahydro-1-naphthalenylamino |
| 1-methyl-4-(trifluoromethyl)imidazol-2-yl | X¹ | G-27 | (1R)-N-methyl-1,2,3,4-tetahydro-1-naphthalenylamino |
| 2,5-dichlorophenyl | X¹ | G-27 | N-methyl-4-hydroxy-1,2,3,4-tetrahydro-1-naphthalenylamino |
| 2-chloro-5-(trifluoromethyl)phenyl | X¹ | G-27 | N-methyl-4-hydroxy-1,2,3,4-tetrahydro-1-naphthalenylamino |
| 2,5-dimethylphenyl | X¹ | G-27 | N-methyl-4-hydroxy-1,2,3,4-tetrahydro-1-naphthalenylamino |
| 2-methyl-5-(trifluoromethyl)phenyl | X¹ | G-27 | N-methyl-4-hydroxy-1,2,3,4-tetrahydro-1-naphthalenylamino |

TABLE 10-continued

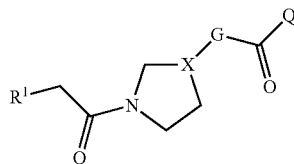

| R¹ | X* | G** | Q |
|---|---|---|---|
| 3,5-dimethylpyrazol-1-yl | X¹ | G-27 | N-methyl-4-hydroxy-1,2,3,4-tetrahydro-1-naphthalenylamino |
| 5-methyl-3-(trifluoromethyl)pyrazol-1-yl | X¹ | G-27 | N-methyl-4-hydroxy-1,2,3,4-tetrahydro-1-naphthalenylamino |
| 3,5-dichloropyrazol-1-yl | X¹ | G-27 | N-methyl-4-hydroxy-1,2,3,4-tetrahydro-1-naphthalenylamino |
| 5-chloro-3-(trifluoromethyl)pyrazol-1-yl | X¹ | G-27 | N-methyl-4-hydroxy-1,2,3,4-tetrahydro-1-naphthalenylamino |
| 3,5-dibromopyrazol-1-yl | X¹ | G-27 | N-methyl-4-hydroxy-1,2,3,4-tetrahydro-1-naphthalenylamino |
| 5-bromo-3-(trifluoromethyl)pyrazol-1-yl | X¹ | G-27 | N-methyl-4-hydroxy-1,2,3,4-tetrahydro-1-naphthalenylamino |
| 3,5-diethylpyrazol-1-yl | X¹ | G-27 | N-methyl-4-hydroxy-1,2,3,4-tetrahydro-1-naphthalenylamino |
| 5-ethyl-3-(trifluoromethyl)pyrazol-1-yl | X¹ | G-27 | N-methyl-4-hydroxy-1,2,3,4-tetrahydro-1-naphthalenylamino |
| 3,5-bis-(trifluoromethyl)pyrazol-1-yl | X¹ | G-27 | N-methyl-4-hydroxy-1,2,3,4-tetrahydro-1-naphthalenylamino |
| 1-methyl-3-(trifluoromethyl)pyrazol-5-yl | X¹ | G-27 | N-methyl-4-hydroxy-1,2,3,4-tetrahydro-1-naphthalenylamino |
| 1-methyl-4-(trifluoromethyl)imidazol-2-yl | X¹ | G-27 | N-methyl-4-hydroxy-1,2,3,4-tetrahydro-1-naphthalenylamino |
| 2,5-dichlorophenyl | X¹ | G-27 | N,2-dimethyl-1,2,3,4-tetrahydro-1-naphthalenylamino |
| 2-chloro-5-(trifluoromethyl)phenyl | X¹ | G-27 | N,2-dimethyl-1,2,3,4-tetrahydro-1-naphthalenylamino |
| 2,5-dimethylphenyl | X¹ | G-27 | N,2-dimethyl-1,2,3,4-tetrahydro-1-naphthalenylamino |
| 2-methyl-5-(trifluoromethyl)phenyl | X¹ | G-27 | N,2-dimethyl-1,2,3,4-tetrahydro-1-naphthalenylamino |
| 3,5-dimethylpyrazol-1-yl | X¹ | G-27 | N,2-dimethyl-1,2,3,4-tetrahydro-1-naphthalenylamino |
| 5-methyl-3-(trifluoromethyl)pyrazol-1-yl | X¹ | G-27 | N,2-dimethyl-1,2,3,4-tetrahydro-1-naphthalenylamino |
| 3,5-dichloropyrazol-1-yl | X¹ | G-27 | N,2-dimethyl-1,2,3,4-tetrahydro-1-naphthalenylamino |
| 5-chloro-3-(trifluoromethyl)pyrazol-1-yl | X¹ | G-27 | N,2-dimethyl-1,2,3,4-tetrahydro-1-naphthalenylamino |
| 3,5-dibromopyrazol-1-yl | X¹ | G-27 | N,2-dimethyl-1,2,3,4-tetrahydro-1-naphthalenylamino |
| 5-bromo-3-(trifluoromethyl)pyrazol-1-yl | X¹ | G-27 | N,2-dimethyl-1,2,3,4-tetrahydro-1-naphthalenylamino |
| 3,5-diethylpyrazol-1-yl | X¹ | G-27 | N,2-dimethyl-1,2,3,4-tetrahydro-1-naphthalenylamino |
| 5-ethyl-3-(trifluoromethyl)pyrazol-1-yl | X¹ | G-27 | N,2-dimethyl-1,2,3,4-tetrahydro-1-naphthalenylamino |
| 3,5-bis-(trifluoromethyl)pyrazol-1-yl | X¹ | G-27 | N,2-dimethyl-1,2,3,4-tetrahydro-1-naphthalenylamino |
| 1-methyl-3-(trifluoromethyl)pyrazol-5-yl | X¹ | G-27 | N,2-dimethyl-1,2,3,4-tetrahydro-1-naphthalenylamino |
| 1-methyl-4-(trifluoromethyl)imidazol-2-yl | X¹ | G-27 | N,2-dimethyl-1,2,3,4-tetrahydro-1-naphthalenylamino |
| 2,5-dichlorophenyl | X¹ | G-27 | N,2,2-trimethyl-1,2,3,4-tetrahydro-1-naphthalenylamino |
| 2-chloro-5-(trifluoromethyl)phenyl | X¹ | G-27 | N,2,2-trimethyl-1,2,3,4-tetrahydro-1-naphthalenylamino |
| 2,5-dimethylphenyl | X¹ | G-27 | N,2,2-trimethyl-1,2,3,4-tetrahydro-1-naphthalenylamino |
| 2-methyl-5-(trifluoromethyl)phenyl | X¹ | G-27 | N,2,2-trimethyl-1,2,3,4-tetrahydro-1-naphthalenylamino |
| 3,5-dimethylpyrazol-1-yl | X¹ | G-27 | N,2,2-trimethyl-1,2,3,4-tetrahydro-1-naphthalenylamino |
| 5-methyl-3-(trifluoromethyl)pyrazol-1-yl | X¹ | G-27 | N,2,2-trimethyl-1,2,3,4-tetrahydro-1-naphthalenylamino |
| 3,5-dichloropyrazol-1-yl | X¹ | G-27 | N,2,2-trimethyl-1,2,3,4-tetrahydro-1-naphthalenylamino |
| 5-chloro-3-(trifluoromethyl)pyrazol-1-yl | X¹ | G-27 | N,2,2-trimethyl-1,2,3,4-tetrahydro-1-naphthalenylamino |

TABLE 10-continued

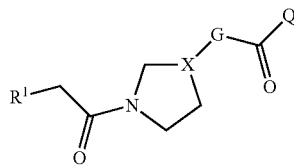

| R¹ | X* | G** | Q |
|---|---|---|---|
| 3,5-dibromopyrazol-1-yl | X¹ | G-27 | N,2,2-trimethyl-1,2,3,4-tetrahydro-1-naphthalenylamino |
| 5-bromo-3-(trifluoromethyl)pyrazol-1-yl | X¹ | G-27 | N,2,2-trimethyl-1,2,3,4-tetrahydro-1-naphthalenylamino |
| 3,5-diethylpyrazol-1-yl | X¹ | G-27 | N,2,2-trimethyl-1,2,3,4-tetrahydro-1-naphthalenylamino |
| 5-ethyl-3-(trifluoromethyl)pyrazol-1-yl | X¹ | G-27 | N,2,2-trimethyl-1,2,3,4-tetrahydro-1-naphthalenylamino |
| 3,5-bis-(trifluoromethyl)pyrazol-1-yl | X¹ | G-27 | N,2,2-trimethyl-1,2,3,4-tetrahydro-1-naphthalenylamino |
| 1-methyl-3-(trifluoromethyl)pyrazol-5-yl | X¹ | G-27 | N,2,2-trimethyl-1,2,3,4-tetrahydro-1-naphthalenylamino |
| 1-methyl-4-(trifluoromethyl)imidazol-2-yl | X¹ | G-27 | N,2,2-trimethyl-1,2,3,4-tetrahydro-1-naphthalenylamino |
| 2,5-dichlorophenyl | X¹ | G-27 | N-methyl-4-oxo-1,2,3,4-tetrahydro-1-naphthalenylamino |
| 2-chloro-5-(trifluoromethyl)phenyl | X¹ | G-27 | N-methyl-4-oxo-1,2,3,4-tetrahydro-1-naphthalenylamino |
| 2,5-dimethylphenyl | X¹ | G-27 | N-methyl-4-oxo-1,2,3,4-tetrahydro-1-naphthalenylamino |
| 2-methyl-5-(trifluoromethyl)phenyl | X¹ | G-27 | N-methyl-4-oxo-1,2,3,4-tetrahydro-1-naphthalenylamino |
| 3,5-dimethylpyrazol-1-yl | X¹ | G-27 | N-methyl-4-oxo-1,2,3,4-tetrahydro-1-naphthalenylamino |
| 5-methyl-3-(trifluoromethyl)pyrazol-1-yl | X¹ | G-27 | N-methyl-4-oxo-1,2,3,4-tetrahydro-1-naphthalenylamino |
| 3,5-dichloropyrazol-1-yl | X¹ | G-27 | N-methyl-4-oxo-1,2,3,4-tetrahydro-1-naphthalenylamino |
| 5-chloro-3-(trifluoromethyl)pyrazol-1-yl | X¹ | G-27 | N-methyl-4-oxo-1,2,3,4-tetrahydro-1-naphthalenylamino |
| 3,5-dibromopyrazol-1-yl | X¹ | G-27 | N-methyl-4-oxo-1,2,3,4-tetrahydro-1-naphthalenylamino |
| 5-bromo-3-(trifluoromethyl)pyrazol-1-yl | X¹ | G-27 | N-methyl-4-oxo-1,2,3,4-tetrahydro-1-naphthalenylamino |
| 3,5-diethylpyrazol-1-yl | X¹ | G-27 | N-methyl-4-oxo-1,2,3,4-tetrahydro-1-naphthalenylamino |
| 5-ethyl-3-(trifluoromethyl)pyrazol-1-yl | X¹ | G-27 | N-methyl-4-oxo-1,2,3,4-tetrahydro-1-naphthalenylamino |
| 3,5-bis-(trifluoromethyl)pyrazol-1-yl | X¹ | G-27 | N-methyl-4-oxo-1,2,3,4-tetrahydro-1-naphthalenylamino |
| 1-methyl-3-(trifluoromethyl)pyrazol-5-yl | X¹ | G-27 | N-methyl-4-oxo-1,2,3,4-tetrahydro-1-naphthalenylamino |
| 1-methyl-4-(trifluoromethyl)imidazol-2-yl | X¹ | G-27 | N-methyl-4-oxo-1,2,3,4-tetrahydro-1-naphthalenylamino |
| 2,5-dichlorophenyl | X¹ | G-27 | (1R)-N-methyl-1-indanylamino |
| 2-chloro-5-(trifluoromethyl)phenyl | X¹ | G-27 | (1R)-N-methyl-1-indanylamino |
| 2,5-dimethylphenyl | X¹ | G-27 | (1R)-N-methyl-1-indanylamino |
| 2-methyl-5-(trifluoromethyl)phenyl | X¹ | G-27 | (1R)-N-methyl-1-indanylamino |
| 3,5-dimethylpyrazol-1-yl | X¹ | G-27 | (1R)-N-methyl-1-indanylamino |
| 5-methyl-3-(trifluoromethyl)pyrazol-1-yl | X¹ | G-27 | (1R)-N-methyl-1-indanylamino |
| 3,5-dichloropyrazol-1-yl | X¹ | G-27 | (1R)-N-methyl-1-indanylamino |
| 5-chloro-3-(trifluoromethyl)pyrazol-1-yl | X¹ | G-27 | (1R)-N-methyl-1-indanylamino |
| 3,5-dibromopyrazol-1-yl | X¹ | G-27 | (1R)-N-methyl-1-indanylamino |
| 5-bromo-3-(trifluoromethyl)pyrazol-1-yl | X¹ | G-27 | (1R)-N-methyl-1-indanylamino |
| 3,5-diethylpyrazol-1-yl | X¹ | G-27 | (1R)-N-methyl-1-indanylamino |
| 5-ethyl-3-(trifluoromethyl)pyrazol-1-yl | X¹ | G-27 | (1R)-N-methyl-1-indanylamino |
| 3,5-bis-(trifluoromethyl)pyrazol-1-yl | X¹ | G-27 | (1R)-N-methyl-1-indanylamino |
| 1-methyl-3-(trifluoromethyl)pyrazol-5-yl | X¹ | G-27 | (1R)-N-methyl-1-indanylamino |
| 1-methyl-4-(trifluoromethyl)imidazol-2-yl | X¹ | G-27 | (1R)-N-methyl-1-indanylamino |
| 2,5-dichlorophenyl | X¹ | G-27 | N,2-dimethyl-1-indanylamino |
| 2-chloro-5-(trifluoromethyl)phenyl | X¹ | G-27 | N,2-dimethyl-1-indanylamino |
| 2,5-dimethylphenyl | X¹ | G-27 | N,2-dimethyl-1-indanylamino |
| 2-methyl-5-(trifluoromethyl)phenyl | X¹ | G-27 | N,2-dimethyl-1-indanylamino |
| 3,5-dimethylpyrazol-1-yl | X¹ | G-27 | N,2-dimethyl-1-indanylamino |
| 5-methyl-3-(trifluoromethyl)pyrazol-1-yl | X¹ | G-27 | N,2-dimethyl-1-indanylamino |
| 3,5-dichloropyrazol-1-yl | X¹ | G-27 | N,2-dimethyl-1-indanylamino |
| 5-chloro-3-(trifluoromethyl)pyrazol-1-yl | X¹ | G-27 | N,2-dimethyl-1-indanylamino |
| 3,5-dibromopyrazol-1-yl | X¹ | G-27 | N,2-dimethyl-1-indanylamino |
| 5-bromo-3-(trifluoromethyl)pyrazol-1-yl | X¹ | G-27 | N,2-dimethyl-1-indanylamino |

TABLE 10-continued

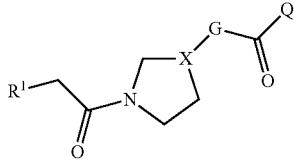

| R¹ | X* | G** | Q |
|---|---|---|---|
| 3,5-diethylpyrazol-1-yl | X¹ | G-27 | N,2-dimethyl-1-indanylamino |
| 5-ethyl-3-(trifluoromethyl)pyrazol-1-yl | X¹ | G-27 | N,2-dimethyl-1-indanylamino |
| 3,5-bis-(trifluoromethyl)pyrazol-1-yl | X¹ | G-27 | N,2-dimethyl-1-indanylamino |
| 1-methyl-3-(trifluoromethyl)pyrazol-5-yl | X¹ | G-27 | N,2-dimethyl-1-indanylamino |
| 1-methyl-4-(trifluoromethyl)imidazol-2-yl | X¹ | G-27 | N,2-dimethyl-1-indanylamino |
| 2,5-dichlorophenyl | X¹ | G-27 | N,2,2-trimethyl-1-indanylamino |
| 2-chloro-5-(trifluoromethyl)phenyl | X¹ | G-27 | N,2,2-trimethyl-1-indanylamino |
| 2,5-dimethylphenyl | X¹ | G-27 | N,2,2-trimethyl-1-indanylamino |
| 2-methyl-5-(trifluoromethyl)phenyl | X¹ | G-27 | N,2,2-trimethyl-1-indanylamino |
| 3,5-dimethylpyrazol-1-yl | X¹ | G-27 | N,2,2-trimethyl-1-indanylamino |
| 5-methyl-3-(trifluoromethyl)pyrazol-1-yl | X¹ | G-27 | N,2,2-trimethyl-1-indanylamino |
| 3,5-dichloropyrazol-1-yl | X¹ | G-27 | N,2,2-trimethyl-1-indanylamino |
| 5-chloro-3-(trifluoromethyl)pyrazol-1-yl | X¹ | G-27 | N,2,2-trimethyl-1-indanylamino |
| 3,5-dibromopyrazol-1-yl | X¹ | G-27 | N,2,2-trimethyl-1-indanylamino |
| 5-bromo-3-(trifluoromethyl)pyrazol-1-yl | X¹ | G-27 | N,2,2-trimethyl-1-indanylamino |
| 3,5-diethylpyrazol-1-yl | X¹ | G-27 | N,2,2-trimethyl-1-indanylamino |
| 5-ethyl-3-(trifluoromethyl)pyrazol-1-yl | X¹ | G-27 | N,2,2-trimethyl-1-indanylamino |
| 3,5-bis-(trifluoromethyl)pyrazol-1-yl | X¹ | G-27 | N,2,2-trimethyl-1-indanylamino |
| 1-methyl-3-(trifluoromethyl)pyrazol-5-yl | X¹ | G-27 | N,2,2-trimethyl-1-indanylamino |
| 1-methyl-4-(trifluoromethyl)imidazol-2-yl | X¹ | G-27 | N,2,2-trimethyl-1-indanylamino |
| 2,5-dichlorophenyl | X¹ | G-27 | N-methyl-3-hydroxy-1-indanylamino |
| 2-chloro-5-(trifluoromethyl)phenyl | X¹ | G-27 | N-methyl-3-hydroxy-1-indanylamino |
| 2,5-dimethylphenyl | X¹ | G-27 | N-methyl-3-hydroxy-1-indanylamino |
| 2-methyl-5-(trifluoromethyl)phenyl | X¹ | G-27 | N-methyl-3-hydroxy-1-indanylamino |
| 3,5-dimethylpyrazol-1-yl | X¹ | G-27 | N-methyl-3-hydroxy-1-indanylamino |
| 5-methyl-3-(trifluoromethyl)pyrazol-1-yl | X¹ | G-27 | N-methyl-3-hydroxy-1-indanylamino |
| 3,5-dichloropyrazol-1-yl | X¹ | G-27 | N-methyl-3-hydroxy-1-indanylamino |
| 5-chloro-3-(trifluoromethyl)pyrazol-1-yl | X¹ | G-27 | N-methyl-3-hydroxy-1-indanylamino |
| 3,5-dibromopyrazol-1-yl | X¹ | G-27 | N-methyl-3-hydroxy-1-indanylamino |
| 5-bromo-3-(trifluoromethyl)pyrazol-1-yl | X¹ | G-27 | N-methyl-3-hydroxy-1-indanylamino |
| 3,5-diethylpyrazol-1-yl | X¹ | G-27 | N-methyl-3-hydroxy-1-indanylamino |
| 5-ethyl-3-(trifluoromethyl)pyrazol-1-yl | X¹ | G-27 | N-methyl-3-hydroxy-1-indanylamino |
| 3,5-bis-(trifluoromethyl)pyrazol-1-yl | X¹ | G-27 | N-methyl-3-hydroxy-1-indanylamino |
| 1-methyl-3-(trifluoromethyl)pyrazol-5-yl | X¹ | G-27 | N-methyl-3-hydroxy-1-indanylamino |
| 1-methyl-4-(trifluoromethyl)imidazol-2-yl | X¹ | G-27 | N-methyl-3-hydroxy-1-indanylamino |
| 2,5-dichlorophenyl | X¹ | G-27 | N-methyl-3-oxo-1-indanylamino |
| 2-chloro-5-(trifluoromethyl)phenyl | X¹ | G-27 | N-methyl-3-oxo-1-indanylamino |
| 2,5-dimethylphenyl | X¹ | G-27 | N-methyl-3-oxo-1-indanylamino |
| 2-methyl-5-(trifluoromethyl)phenyl | X¹ | G-27 | N-methyl-3-oxo-1-indanylamino |
| 3,5-dimethylpyrazol-1-yl | X¹ | G-27 | N-methyl-3-oxo-1-indanylamino |
| 5-methyl-3-(trifluoromethyl)pyrazol-1-yl | X¹ | G-27 | N-methyl-3-oxo-1-indanylamino |
| 3,5-dichloropyrazol-1-yl | X¹ | G-27 | N-methyl-3-oxo-1-indanylamino |
| 5-chloro-3-(trifluoromethyl)pyrazol-1-yl | X¹ | G-27 | N-methyl-3-oxo-1-indanylamino |
| 3,5-dibromopyrazol-1-yl | X¹ | G-27 | N-methyl-3-oxo-1-indanylamino |
| 5-bromo-3-(trifluoromethyl)pyrazol-1-yl | X¹ | G-27 | N-methyl-3-oxo-1-indanylamino |
| 3,5-diethylpyrazol-1-yl | X¹ | G-27 | N-methyl-3-oxo-1-indanylamino |
| 5-ethyl-3-(trifluoromethyl)pyrazol-1-yl | X¹ | G-27 | N-methyl-3-oxo-1-indanylamino |
| 3,5-bis-(trifluoromethyl)pyrazol-1-yl | X¹ | G-27 | N-methyl-3-oxo-1-indanylamino |
| 1-methyl-3-(trifluoromethyl)pyrazol-5-yl | X¹ | G-27 | N-methyl-3-oxo-1-indanylamino |
| 1-methyl-4-(trifluoromethyl)imidazol-2-yl | X¹ | G-27 | N-methyl-3-oxo-1-indanylamino |
| 2,5-dichlorophenyl | X¹ | G-36 | (1R)-N-methyl-1-phenylpropylamino |
| 2-chloro-5-(trifluoromethyl)phenyl | X¹ | G-36 | (1R)-N-methyl-1-phenylpropylamino |
| 2,5-dimethylphenyl | X¹ | G-36 | (1R)-N-methyl-1-phenylpropylamino |
| 2-methyl-5-(trifluoromethyl)phenyl | X¹ | G-36 | (1R)-N-methyl-1-phenylpropylamino |
| 3,5-dimethylpyrazol-1-yl | X¹ | G-36 | (1R)-N-methyl-1-phenylpropylamino |
| 5-methyl-3-(trifluoromethyl)pyrazol-1-yl | X¹ | G-36 | (1R)-N-methyl-1-phenylpropylamino |
| 3,5-dichloropyrazol-1-yl | X¹ | G-36 | (1R)-N-methyl-1-phenylpropylamino |
| 5-chloro-3-(trifluoromethyl)pyrazol-1-yl | X¹ | G-36 | (1R)-N-methyl-1-phenylpropylamino |
| 3,5-dibromopyrazol-1-yl | X¹ | G-36 | (1R)-N-methyl-1-phenylpropylamino |
| 5-bromo-3-(trifluoromethyl)pyrazol-1-yl | X¹ | G-36 | (1R)-N-methyl-1-phenylpiopylamino |
| 3,5-diethylpyrazol-1-yl | X¹ | G-36 | (1R)-N-methyl-1-phenylpropylamino |
| 5-ethyl-3-(trifluoromethyl)pyrazol-1-yl | X¹ | G-36 | (1R)-N-methyl-1-phenylpropylamino |
| 3,5-bis-(trifluoromethyl)pyrazol-1-yl | X¹ | G-36 | (1R)-N-methyl-1-phenylpropylamino |
| 1-methyl-3-(trifluoromethyl)pyrazol-5-yl | X¹ | G-36 | (1R)-N-methyl-1-phenylpropylamino |
| 1-methyl-4-(trifluoromethyl)imidazol-2-yl | X¹ | G-36 | (1R)-N-methyl-1-phenylpropylamino |
| 2,5-dichlorophenyl | X¹ | G-36 | (1R)-N-methyl-1,2,3,4-tetrahydro-1-naphthalenylamino |
| 2-chloro-5-(trifluoromethyl)phenyl | X¹ | G-36 | (1R)-N-methyl-1,2,3,4-tetrahydro-1-naphthalenylamino |

TABLE 10-continued

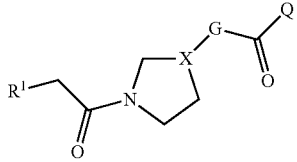

| R¹ | X* | G** | Q |
|---|---|---|---|
| 2,5-dimethylphenyl | X¹ | G-36 | (1R)-N-methyl-1,2,3,4-tetrahydro-1-naphthalenylamino |
| 2-methyl-5-(trifluoromethyl)phenyl | X¹ | G-36 | (1R)-N-methyl-1,2,3,4-tetrahydro-1-naphthalenylamino |
| 3,5-dimethylpyrazol-1-yl | X¹ | G-36 | (1R)-N-methyl-1,2,3,4-tetrahydro-1-naphthalenylamino |
| 5-methyl-3-(trifluoromethyl)pyrazol-1-yl | X¹ | G-36 | (1R)-N-methyl-1,2,3,4-tetrahydro-1-naphthalenylamino |
| 3,5-dichloropyrazol-1-yl | X¹ | G-36 | (1R)-N-methyl-1,2,3,4-tetrahydro-1-naphthalenylamino |
| 5-chloro-3-(trifluoromethyl)pyrazol-1-yl | X¹ | G-36 | (1R)-N-methyl-1,2,3,4-tetrahydro-1-naphthalenylamino |
| 3,5-dibromopyrazol-1-yl | X¹ | G-36 | (1R)-N-methyl-1,2,3,4-tetrahydro-1-naphthalenylamino |
| 5-bromo-3-(trifluoromethyl)pyrazol-1-yl | X¹ | G-36 | (1R)-N-methyl-1,2,3,4-tetrahydro-1-naphthalenylamino |
| 3,5-diethylpyrazol-1-yl | X¹ | G-36 | (1R)-N-methyl-1,2,3,4-tetrahydro-1-naphthalenylamino |
| 5-ethyl-3-(trifluoromethyl)pyrazol-1-yl | X¹ | G-36 | (1R)-N-methyl-1,2,3,4-tetrahydro-1-naphthalenylamino |
| 3,5-bis-(trifluoromethyl)pyrazol-1-yl | X¹ | G-36 | (1R)-N-methyl-1,2,3,4-tetrahydro-1-naphthalenylamino |
| 1-methyl-3-(trifluoromethyl)pyrazol-5-yl | X¹ | G-36 | (1R)-N-methyl-1,2,3,4-tetrahydro-1-naphthalenylamino |
| 1-methyl-4-(trifluoromethyl)imidazol-2-yl | X¹ | G-36 | (1R)-N-methyl-1,2,3,4-tetrahydro-1-naphthalenylamino |
| 2,5-dichlorophenyl | X¹ | G-36 | N-methyl-4-hydroxy-1,2,3,4-tetrahydro-1-naphthalenylamino |
| 2-chloro-5-(trifluoromethyl)phenyl | X¹ | G-36 | N-methyl-4-hydroxy-1,2,3,4-tetrahydro-1-naphthalenylamino |
| 2,5-dimethylphenyl | X¹ | G-36 | N-methyl-4-hydroxy-1,2,3,4-tetrahydro-1-naphthalenylamino |
| 2-methyl-5-(trifluoromethyl)phenyl | X¹ | G-36 | N-methyl-4-hydroxy-1,2,3,4-tetrahydro-1-naphthalenylamino |
| 3,5-dimethylpyrazol-1-yl | X¹ | G-36 | N-methyl-4-hydroxy-1,2,3,4-tetrahydro-1-naphthalenylamino |
| 5-methyl-3-(trifluoromethyl)pyrazol-1-yl | X¹ | G-36 | N-methyl-4-hydroxy-1,2,3,4-tetrahydro-1-naphthalenylamino |
| 3,5-dichloropyrazol-1-yl | X¹ | G-36 | N-methyl-4-hydroxy-1,2,3,4-tetrahydro-1-naphthalenylamino |
| 5-chloro-3-(trifluoromethyl)pyrazol-1-yl | X¹ | G-36 | N-methyl-4-hydroxy-1,2,3,4-tetrahydro-1-naphthalenylamino |
| 3,5-dibromopyrazol-1-yl | X¹ | G-36 | N-methyl-4-hydroxy-1,2,3,4-tetrahydro-1-naphthalenylamino |
| 5-bromo-3-(trifluoromethyl)pyrazol-1-yl | X¹ | G-36 | N-methyl-4-hydroxy-1,2,3,4-tetrahydro-1-naphthalenylamino |
| 3,5-diethylpyrazol-1-yl | X¹ | G-36 | N-methyl-4-hydroxy-1,2,3,4-tetrahydro-1-naphthalenylamino |
| 5-ethyl-3-(trifluoromethyl)pyrazol-1-yl | X¹ | G-36 | N-methyl-4-hydroxy-1,2,3,4-tetrahydro-1-naphthalenylamino |
| 3,5-bis-(trifluoromethyl)pyrazol-1-yl | X¹ | G-36 | N-methyl-4-hydroxy-1,2,3,4-tetrahydro-1-naphthalenylamino |
| 1-methyl-3-(trifluoromethyl)pyrazol-5-yl | X¹ | G-36 | N-methyl-4-hydroxy-1,2,3,4-tetrahydro-1-naphthalenylamino |
| 1-methyl-4-(trifluoromethyl)imidazol-2-yl | X¹ | G-36 | N-methyl-4-hydroxy-1,2,3,4-tetrahydro-1-naphthalenylamino |
| 2,5-dichlorophenyl | X¹ | G-36 | N,2-dimethyl-1,2,3,4-tetrahydro-1-naphthalenylamino |
| 2-chloro-5-(trifluoromethyl)phenyl | X¹ | G-36 | N,2-dimethyl-1,2,3,4-tetrahydro-1-naphthalenylamino |
| 2,5-dimethylphenyl | X¹ | G-36 | N,2-dimethyl-1,2,3,4-tetrahydro-1-naphthalenylamino |
| 2-methyl-5-(trifluoromethyl)phenyl | X¹ | G-36 | N,2-dimethyl-1,2,3,4-tetrahydro-1-naphthalenylamino |
| 3,5-dimethylpyrazol-1-yl | X¹ | G-36 | N,2-dimethyl-1,2,3,4-tetrahydro-1-naphthalenylamino |
| 5-methyl-3-(trifluoromethyl)pyrazol-1-yl | X¹ | G-36 | N,2-dimethyl-1,2,3,4-tetrahydro-1-naphthalenylamino |

TABLE 10-continued

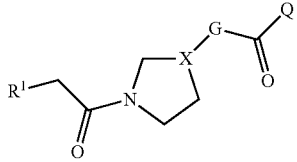

| R¹ | X* | G** | Q |
|---|---|---|---|
| 3,5-dichloropyrazol-1-yl | X¹ | G-36 | N,2-dimethyl-1,2,3,4-tetrahydro-1-naphthalenylamino |
| 5-chloro-3-(trifluoromethyl)pyrazol-1-yl | X¹ | G-36 | N,2-dimethyl-1,2,3,4-tetrahydro-1-naphthalenylamino |
| 3,5-dibromopyrazol-1-yl | X¹ | G-36 | N,2-dimethyl-1,2,3,4-tetrahydro-1-naphthalenylamino |
| 5-bromo-3-(trifluoromethyl)pyrazol-1-yl | X¹ | G-36 | N,2-dimethyl-1,2,3,4-tetrahydro-1-naphthalenylamino |
| 3,5-diethylpyrazol-1-yl | X¹ | G-36 | N,2-dimethyl-1,2,3,4-tetrahydro-1-naphthalenylamino |
| 5-ethyl-3-(trifluoromethyl)pyrazol-1-yl | X¹ | G-36 | N,2-dimethyl-1,2,3,4-tetrahydro-1-naphthalenylamino |
| 3,5-bis-(trifluoromethyl)pyrazol-1-yl | X¹ | G-36 | N,2-dimethyl-1,2,3,4-tetrahydro-1-naphthalenylamino |
| 1-methyl-3-(trifluoromethyl)pyrazol-5-yl | X¹ | G-36 | N,2-dimethyl-1,2,3,4-tetrahydro-1-naphthalenylamino |
| 1-methyl-4-(trifluoromethyl)imidazol-2-yl | X¹ | G-36 | N,2-dimethyl-1,2,3,4-tetrahydro-1-naphthalenylamino |
| 2,5-dichlorophenyl | X¹ | G-36 | N,2,2-trimethyl-1,2,3,4-tetrahydro-1-naphthalenylamino |
| 2-chloro-5-(trifluoromethyl)phenyl | X¹ | G-36 | N,2,2-trimethyl-1,2,3,4-tetrahydro-1-naphthalenylamino |
| 2,5-dimethylphenyl | X¹ | G-36 | N,2,2-trimethyl-1,2,3,4-tetrahydro-1-naphthalenylamino |
| 2-methyl-5-(trifluoromethyl)phenyl | X¹ | G-36 | N,2,2-trimethyl-1,2,3,4-tetrahydro-1-naphthalenylamino |
| 3,5-dimethylpyrazol-1-yl | X¹ | G-36 | N,2,2-trimethyl-1,2,3,4-tetrahydro-1-naphthalenylamino |
| 5-methyl-3-(trifluoromethyl)pyrazol-1-yl | X¹ | G-36 | N,2,2-trimethyl-1,2,3,4-tetrahydro-1-naphthalenylamino |
| 3,5-dichloropyrazol-1-yl | X¹ | G-36 | N,2,2-trimethyl-1,2,3,4-tetrahydro-1-naphthalenylamino |
| 5-chloro-3-(trifluoromethyl)pyrazol-1-yl | X¹ | G-36 | N,2,2-trimethyl-1,2,3,4-tetrahydro-1-naphthalenylamino |
| 3,5-dibromopyrazol-1-yl | X¹ | G-36 | N,2,2-trimethyl-1,2,3,4-tetrahydro-1-naphthalenylamino |
| 5-bromo-3-(trifluoromethyl)pyrazol-1-yl | X¹ | G-36 | N,2,2-trimethyl-1,2,3,4-tetrahydro-1-naphthalenylamino |
| 3,5-diethylpyrazol-1-yl | X¹ | G-36 | N,2,2-trimethyl-1,2,3,4-tetrahydro-1-naphthalenylamino |
| 5-ethyl-3-(trifluoromethyl)pyrazol-1-yl | X¹ | G-36 | N,2,2-trimethyl-1,2,3,4-tetrahydro-1-naphthalenylamino |
| 3,5-bis-(trifluoromethyl)pyrazol-1-yl | X¹ | G-36 | N,2,2-trimethyl-1,2,3,4-tetrahydro-1-naphthalenylamino |
| 1-methyl-3-(trifluoromethyl)pyrazol-5-yl | X¹ | G-36 | N,2,2-trimethyl-1,2,3,4-tetrahydro-1-naphthalenylamino |
| 1-methyl-4-(trifluoromethyl)imidazol-2-yl | X¹ | G-36 | N,2,2-trimethyl-1,2,3,4-tetrahydro-1-naphthalenylamino |
| 2,5-dichlorophenyl | X¹ | G-36 | N-methyl-4-oxo-1,2,3,4-tetrahydro-1-naphthalenylamino |
| 2-chloro-5-(trifluoromethyl)phenyl | X¹ | G-36 | N-methyl-4-oxo-1,2,3,4-tetrahydro-1-naphthalenylamino |
| 2,5-dimethylphenyl | X¹ | G-36 | N-methyl-4-oxo-1,2,3,4-tetrahydro-1-naphthalenylamino |
| 2-methyl-5-(trifluoromethyl)phenyl | X¹ | G-36 | N-methyl-4-oxo-1,2,3,4-tetrahydro-1-naphthalenylamino |
| 3,5-dimethylpyrazol-1-yl | X¹ | G-36 | N-methyl-4-oxo-1,2,3,4-tetrahydro-1-naphthalenylamino |
| 5-methyl-3-(trifluoromethyl)pyrazol-1-yl | X¹ | G-36 | N-methyl-4-oxo-1,2,3,4-tetrahydro-1-naphthalenylamino |
| 3,5-dichloropyrazol-1-yl | X¹ | G-36 | N-methyl-4-oxo-1,2,3,4-tetrahydro-1-naphthalenylamino |
| 5-chloro-3-(trifluoromethyl)pyrazol-1-yl | X¹ | G-36 | N-methyl-4-oxo-1,2,3,4-tetrahydro-1-naphthalenylamino |
| 3,5-dibromopyrazol-1-yl | X¹ | G-36 | N-methyl-4-oxo-1,2,3,4-tetrahydro-1-naphthalenylamino |
| 5-bromo-3-(trifluoromethyl)pyrazol-1-yl | X¹ | G-36 | N-methyl-4-oxo-1,2,3,4-tetrahydro-1-naphthalenylamino |

TABLE 10-continued

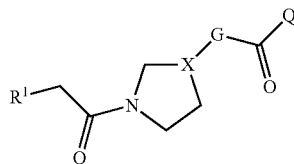

| R¹ | X* | G** | Q |
|---|---|---|---|
| 3,5-diethylpyrazol-1-yl | X¹ | G-36 | N-methyl-4-oxo-1,2,3,4-tetrahydro-1-naphthalenylamino |
| 5-ethyl-3-(trifluoromethyl)pyrazol-1-yl | X¹ | G-36 | N-methyl-4-oxo-1,2,3,4-tetrahydro-1-naphthalenylamino |
| 3,5-bis-(trifluoromethyl)pyrazol-1-yl | X¹ | G-36 | N-methyl-4-oxo-1,2,3,4-tetrahydro-1-naphthalenylamino |
| 1-methyl-3-(trifluoromethyl)pyrazol-5-yl | X¹ | G-36 | N-methyl-4-oxo-1,2,3,4-tetrahydro-1-naphthalenylamino |
| 1-methyl-4-(trifluoromethyl)imidazol-2-yl | X¹ | G-36 | N-methyl-4-oxo-1,2,3,4-tetrahydro-1-naphthalenylamino |
| 2,5-dichlorophenyl | X¹ | G-36 | (1R)-N-methyl-1-indanylamino |
| 2-chloro-5-(trifluoromethyl)phenyl | X¹ | G-36 | (1R)-N-methyl-1-indanylamino |
| 2,5-dimethylphenyl | X¹ | G-36 | (1R)-N-methyl-1-indanylamino |
| 2-methyl-5-(trifluoromethyl)phenyl | X¹ | G-36 | (1R)-N-methyl-1-indanylamino |
| 3,5-dimethylpyrazol-1-yl | X¹ | G-36 | (1R)-N-methyl-1-indanylamino |
| 5-methyl-3-(trifluoromethyl)pyrazol-1-yl | X¹ | G-36 | (1R)-N-methyl-1-indanylamino |
| 3,5-dichloropyrazol-1-yl | X¹ | G-36 | (1R)-N-methyl-1-indanylamino |
| 5-chloro-3-(trifluoromethyl)pyrazol-1-yl | X¹ | G-36 | (1R)-N-methyl-1-indanylamino |
| 3,5-dibromopyrazol-1-yl | X¹ | G-36 | (1R)-N-methyl-1-indanylamino |
| 5-bromo-3-(trifluoromethyl)pyrazol-1-yl | X¹ | G-36 | (1R)-N-methyl-1-indanylamino |
| 3,5-diethylpyrazol-1-yl | X¹ | G-36 | (1R)-N-methyl-1-indanylamino |
| 5-ethyl-3-(trifluoromethyl)pyrazol-1-yl | X¹ | G-36 | (1R)-N-methyl-1-indanylamino |
| 3,5-bis-(trifluoromethyl)pyrazol-1-yl | X¹ | G-36 | (1R)-N-methyl-1-indanylamino |
| 1-methyl-3-(trifluoromethyl)pyrazol-5-yl | X¹ | G-36 | (1R)-N-methyl-1-indanylamino |
| 1-methyl-4-(trifluoromethyl)imidazol-2-yl | X¹ | G-36 | (1R)-N-methyl-1-indanylamino |
| 2,5-dichlorophenyl | X¹ | G-36 | N,2-dimethyl-1-indanylamino |
| 2-chloro-5-(trifluoromethyl)phenyl | X¹ | G-36 | N,2-dimethyl-1-indanylamino |
| 2,5-dimethylphenyl | X¹ | G-36 | N,2-dimethyl-1-indanylamino |
| 2-methyl-5-(trifluoromethyl)phenyl | X¹ | G-36 | N,2-dimethyl-1-indanylamino |
| 3,5-dimethylpyrazol-1-yl | X¹ | G-36 | N,2-dimethyl-1-indanylamino |
| 5-methyl-3-(trifluoromethyl)pyrazol-1-yl | X¹ | G-36 | N,2-dimethyl-1-indanylamino |
| 3,5-dichloropyrazol-1-yl | X¹ | G-36 | N,2-dimethyl-1-indanylamino |
| 5-chloro-3-(trifluoromethyl)pyrazol-1-yl | X¹ | G-36 | N,2-dimethyl-1-indanylamino |
| 3,5-dibromopyrazol-1-yl | X¹ | G-36 | N,2-dimethyl-1-indanylamino |
| 5-bromo-3-(trifluoromethyl)pyrazol-1-yl | X¹ | G-36 | N,2-dimethyl-1-indanylamino |
| 3,5-diethylpyrazol-1-yl | X¹ | G-36 | N,2-dimethyl-1-indanylamino |
| 5-ethyl-3-(trifluoromethyl)pyrazol-1-yl | X¹ | G-36 | N,2-dimethyl-1-indanylamino |
| 3,5-bis-(trifluoromethyl)pyrazol-1-yl | X¹ | G-36 | N,2-dimethyl-1-indanylamino |
| 1-methyl-3-(trifluoromethyl)pyrazol-5-yl | X¹ | G-36 | N,2-dimethyl-1-indanylamino |
| 1-methyl-4-(trifluoromethyl)imidazol-2-yl | X¹ | G-36 | N,2-dimethyl-1-indanylamino |
| 2,5-dichlorophenyl | X¹ | G-36 | N,2,2-dimethyl-1-indanylamino |
| 2-chloro-5-(trifluoromethyl)phenyl | X¹ | G-36 | N,2,2-trimethyl-1-indanylamino |
| 2,5-dimethylphenyl | X¹ | G-36 | N,2,2-trimethyl-1-indanylamino |
| 2-methyl-5-(trifluoromethyl)phenyl | X¹ | G-36 | N,2,2-trimethyl-1-indanylamino |
| 3,5-dimethylpyrazol-1-yl | X¹ | G-36 | N,2,2-dimethyl-1-indanylamino |
| 5-methyl-3-(trifluoromethyl)pyrazol-1-yl | X¹ | G-36 | N,2,2-trimethyl-1-indanylamino |
| 3,5-dichloropyrazol-1-yl | X¹ | G-36 | N,2,2-dimethyl-1-indanylamino |
| 5-chloro-3-(trifluoromethyl)pyrazol-1-yl | X¹ | G-36 | N,2,2-trimethyl-1-indanylamino |
| 3,5-dibromopyrazol-1-yl | X¹ | G-36 | N,2,2-trimethyl-1-indanylamino |
| 5-bromo-3-(trifluoromethyl)pyrazol-1-yl | X¹ | G-36 | N,2,2-trimethyl-1-indanylamino |
| 3,5-diethylpyrazol-1-yl | X¹ | G-36 | N,2,2-trimethyl-1-indanylamino |
| 5-ethyl-3-(trifluoromethyl)pyrazol-1-yl | X¹ | G-36 | N,2,2-trimethyl-1-indanylamino |
| 3,5-bis-(trifluoromethyl)pyrazol-1-yl | X¹ | G-36 | N,2,2-trimethyl-1-indanylamino |
| 1-methyl-3-(trifluoromethyl)pyrazol-5-yl | X¹ | G-36 | N,2,2-trimethyl-1-indanylamino |
| 1-methyl-4-(trifluoromethyl)imidazol-2-yl | X¹ | G-36 | N,2,2-trimethyl-1-indanylamino |
| 2,5-dichlorophenyl | X¹ | G-36 | N-methyl-3-hydroxy-1-indanylamino |
| 2-chloro-5-(trifluoromethyl)phenyl | X¹ | G-36 | N-methyl-3-hydroxy-1-indanylamino |
| 2,5-dimethylphenyl | X¹ | G-36 | N-methyl-3-hydroxy-1-indanylamino |
| 2-methyl-5-(trifluoromethyl)phenyl | X¹ | G-36 | N-methyl-3-hydroxy-1-incianylamino |
| 3,5-dimethylpyrazol-1-yl | X¹ | G-36 | N-methyl-3-hydroxy-1-indanylamino |
| 5-methyl-3-(trifluoromethyl)pyrazol-1-yl | X¹ | G-36 | N-methyl-3-hydroxy-1-indanylamino |
| 3,5-dichloropyrazol-1-yl | X¹ | G-36 | N-methyl-3-hydroxy-1-indanylamino |
| 5-chloro-3-(trifluoromethyl)pyrazol-1-yl | X¹ | G-36 | N-methyl-3-hydroxy-1-indanylamino |
| 3,5-dibromopyrazol-1-yl | X¹ | G-36 | N-methyl-3-hydroxy-1-indanylamino |
| 5-bromo-3-(trifluoromethyl)pyrazol-1-yl | X¹ | G-36 | N-methyl-3-hydroxy-1-indanylamino |
| 3,5-diethylpyrazol-1-yl | X¹ | G-36 | N-methyl-3-hydroxy-1-indanylamino |
| 5-ethyl-3-(trifluoromethyl)pyrazol-1-yl | X¹ | G-36 | N-methyl-3-hydroxy-1-indanylamino |
| 3,5-bis-(trifluoromethyl)pyrazol-1-yl | X¹ | G-36 | N-methyl-3-hydroxy-1-indanylamino |
| 1-methyl-3-(trifluoromethyl)pyrazol-5-yl | X¹ | G-36 | N-methyl-3-hydroxy-1-indanylamino |

TABLE 10-continued

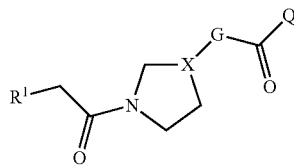

| R¹ | X* | G** | Q |
|---|---|---|---|
| 1-methyl-4-(trifluoromethyl)imidazol-2-yl | X¹ | G-36 | N-methyl-3-hydroxy-1-indanylamino |
| 2,5-dichlorophenyl | X¹ | G-36 | N-methyl-3-oxo-1-indanylamino |
| 2-chloro-5-(trifluoromethyl)phenyl | X¹ | G-36 | N-methyl-3-oxo-1-indanylamino |
| 2,5-dimethylphenyl | X¹ | G-36 | N-methyl-3-oxo-1-indanylamino |
| 2-methyl-5-(trifluoromethyl)phenyl | X¹ | G-36 | N-methyl-3-oxo-1-indanylamino |
| 3,5-dimethylpyrazol-1-yl | X¹ | G-36 | N-methyl-3-oxo-1-indanylamino |
| 5-methyl-3-(trifluoromethyl)pyrazol-1-yl | X¹ | G-36 | N-methyl-3-oxo-1-indanylamino |
| 3,5-dichloropyrazol-1-yl | X¹ | G-36 | N-methyl-3-oxo-1-indanylamino |
| 5-chloro-3-(trifluoromethyl)pyrazol-1-yl | X¹ | G-36 | N-methyl-3-oxo-1-indanylamino |
| 3,5-dibromopyrazol-1-yl | X¹ | G-36 | N-methyl-3-oxo-1-indanylamino |
| 5-bromo-3-(trifluoromethyl)pyrazol-1-yl | X¹ | G-36 | N-methyl-3-oxo-1-indanylamino |
| 3,5-diethylpyrazol-1-yl | X¹ | G-36 | N-methyl-3-oxo-1-indanylamino |
| 5-ethyl-3-(trifluoromethyl)pyrazol-1-yl | X¹ | G-36 | N-methyl-3-oxo-1-indanylamino |
| 3,5-bis-(trifluoromethyl)pyrazol-1-yl | X¹ | G-36 | N-methyl-3-oxo-1-indanylamino |
| 1-methyl-3-(trifluoromethyl)pyrazol-5-yl | X¹ | G-36 | N-methyl-3-oxo-1-indanylamino |
| 1-methyl-4-(trifluoromethyl)imidazol-2-yl | X¹ | G-36 | N-methyl-3-oxo-1-indanylamino |
| 2,5-dichlorophenyl | X¹ | G-1 | N-methyl-4-hydroxy-1,2,3,4-tetrahydro-1-naphthalenylamino |
| 2-chloro-5-(trifluoromethyl)phenyl | X¹ | G-1 | N-methyl-4-hydroxy-1,2,3,4-tetrahydro-1-naphthalenylamino |
| 2,5-dimethylphenyl | X¹ | G-1 | N-methyl-4-hydroxy-1,2,3,4-tetrahydro-1-naphthalenylamino |
| 2-methyl-5-(trifluoromethyl)phenyl | X¹ | G-1 | N-methyl-4-hydroxy-1,2,3,4-tetrahydro-1-naphthalenylamino |
| 3,5-dimethylpyrazol-1-yl | X¹ | G-1 | N-methyl-4-hydroxy-1,2,3,4-tetrahydro-1-naphthalenylamino |
| 5-methyl-3-(trifluoromethyl)pyrazol-1-yl | X¹ | G-1 | N-methyl-4-hydroxy-1,2,3,4-tetrahydro-1-naphthalenylamino |
| 3,5-dichloropyrazol-1-yl | X¹ | G-1 | N-methyl-4-hydroxy-1,2,3,4-tetrahydro-1-naphthalenylamino |
| 5-chloro-3-(trifluoromethyl)pyrazol-1-yl | X¹ | G-1 | N-methyl-4-hydroxy-1,2,3,4-tetrahydro-1-naphthalenylamino |
| 3,5-dibromopyrazol-1-yl | X¹ | G-1 | N-methyl-4-hydroxy-1,2,3,4-tetrahydro-1-naphthalenylamino |
| 5-bromo-3-(trifluoromethyl)pyrazol-1-yl | X¹ | G-1 | N-methyl-4-hydroxy-1,2,3,4-tetrahydro-1-naphthalenylamino |
| 3,5-diethylpyrazol-1-yl | X¹ | G-1 | N-methyl-4-hydroxy-1,2,3,4-tetrahydro-1-naphthalenylamino |
| 5-ethyl-3-(trifluoromethyl)pyrazol-1-yl | X¹ | G-1 | N-methyl-4-hydroxy-1,2,3,4-tetrahydro-1-naphthalenylamino |
| 3,5-bis-(trifluoromethyl)pyrazol-1-yl | X¹ | G-1 | N-methyl-4-hydroxy-1,2,3,4-tetrahydro-1-naphthalenylamino |
| 1-methyl-3-(trifluoromethyl)pyrazol-5-yl | X¹ | G-1 | N-methyl-4-hydroxy-1,2,3,4-tetrahydro-1-naphthalenylamino |
| 1-methyl-4-(trifluoromethyl)imidazol-2-yl | X¹ | G-1 | N-methyl-4-hydroxy-1,2,3,4-tetrahydro-1-naphthalenylamino |
| 2,5-dichlorophenyl | X¹ | G-1 | N,2-dimethyl-1,2,3,4-tetrahydro-1-naphthalenylamino |
| 2-chloro-5-(trifluoromethyl)phenyl | X¹ | G-1 | N,2-dimethyl-1,2,3,4-tetrahydro-1-naphthalenylamino |
| 2,5-dimethylphenyl | X¹ | G-1 | N,2-dimethyl-1,2,3,4-tetrahydro-1-naphthalenylamino |
| 2-methyl-5-(trifluoromethyl)phenyl | X¹ | G-1 | N,2-dimethyl-1,2,3,4-tetrahydro-1-naphthalenylamino |
| 3,5-dimethylpyrazol-1-yl | X¹ | G-1 | N,2-dimethyl-1,2,3,4-tetrahydro-1-naphthalenylamino |
| 5-methyl-3-(trifluoromethyl)pyrazol-1-yl | X¹ | G-1 | N,2-dimethyl-1,2,3,4-tetrahydro-1-naphthalenylamino |
| 3,5-dichloropyrazol-1-yl | X¹ | G-1 | N,2-dimethyl-1,2,3,4-tetrahydro-1-naphthalenylamino |
| 5-chloro-3-(trifluoromethyl)pyrazol-1-yl | X¹ | G-1 | N,2-dimethyl-1,2,3,4-tetrahydro-1-naphthalenylamino |
| 3,5-dibromopyrazol-1-yl | X¹ | G-1 | N,2-dimethyl-1,2,3,4-tetrahydro-1-naphthalenylamino |
| 5-bromo-3-(trifluoromethyl)pyrazol-1-yl | X¹ | G-1 | N,2-dimethyl-1,2,3,4-tetrahydro-1-naphthalenylamino |
| 3,5-diethylpyrazol-1-yl | X¹ | G-1 | N,2-dimethyl-1,2,3,4-tetrahydro-1-naphthalenylamino |

TABLE 10-continued

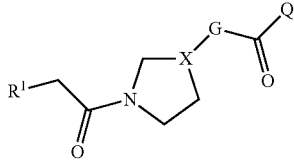

| R¹ | X* | G** | Q |
|---|---|---|---|
| 5-ethyl-3-(trifluoromethyl)pyrazol-1-yl | X¹ | G-1 | N,2-dimethyl-1,2,3,4-tetrahydro-1-naphthalenylamino |
| 3,5-bis-(trifluoromethyl)pyrazol-1-yl | X¹ | G-1 | N,2-dimethyl-1,2,3,4-tetrahydro-1-naphthalenylamino |
| 1-methyl-3-(trifluoromethyl)pyrazol-5-yl | X¹ | G-1 | N,2-dimethyl-1,2,3,4-tetrahydro-1-naphthalenylamino |
| 1-methyl-4-(trifluoromethyl)imidazol-2-yl | X¹ | G-1 | N,2-dimethyl-1,2,3,4-tetrahydro-1-naphthalenylamino |
| 2,5-dichlorophenyl | X¹ | G-1 | N,2,2-trimethyl-1,2,3,4-tetrahydro-1-naphthalenylamino |
| 2-chloro-5-(trifluoromethyl)phenyl | X¹ | G-1 | N,2,2-trimethyl-1,2,3,4-tetrahydro-1-naphthalenylamino |
| 2,5-dimethylphenyl | X¹ | G-1 | N,2,2-trimethyl-1,2,3,4-tetrahydro-1-naphthalenylamino |
| 2-methyl-5-(trifluoromethyl)phenyl | X¹ | G-1 | N,2,2-trimethyl-1,2,3,4-tetrahydro-1-naphthalenylamino |
| 3,5-dimethylpyrazol-1-yl | X¹ | G-1 | N,2,2-trimethyl-1,2,3,4-tetrahydro-1-naphthalenylamino |
| 5-methyl-3-(trifluoromethyl)pyrazol-1-yl | X¹ | G-1 | N,2,2-trimethyl-1,2,3,4-tetrahydro-1-naphthalenylamino |
| 3,5-dichloropyrazol-1-yl | X¹ | G-1 | N,2,2-trimethyl-1,2,3,4-tetrahydro-1-naphthalenylamino |
| 5-chloro-3-(trifluoromethyl)pyrazol-1-yl | X¹ | G-1 | N,2,2-trimethyl-1,2,3,4-tetrahydro-1-naphthalenylamino |
| 3,5-dibromopyrazol-1-yl | X¹ | G-1 | N,2,2-trimethyl-1,2,3,4-tetrahydro-1-naphthalenylamino |
| 5-bromo-3-(trifluoromethyl)pyrazol-1-yl | X¹ | G-1 | N,2,2-trimethyl-1,2,3,4-tetrahydro-1-naphthalenylamino |
| 3,5-diethylpyrazol-1-yl | X¹ | G-1 | N,2,2-trimethyl-1,2,3,4-tetrahydro-1-naphthalenylamino |
| 5-ethyl-3-(trifluoromethyl)pyrazol-1-yl | X¹ | G-1 | N,2,2-trimethyl-1,2,3,4-tetrahydro-1-naphthalenylamino |
| 3,5-bis-(trifluoromethyl)pyrazol-1-yl | X¹ | G-1 | N,2,2-trimethyl-1,2,3,4-tetrahydro-1-naphthalenylamino |
| 1-methyl-3-(trifluoromethyl)pyrazol-5-yl | X¹ | G-1 | N,2,2-trimethyl-1,2,3,4-tetrahydro-1-naphthalenylamino |
| 1-methyl-4-(trifluoromethyl)imidazol-2-yl | X¹ | G-1 | N,2,2-trimethyl-1,2,3,4-tetrahydro-1-naphthalenylamino |
| 2,5-dichlorophenyl | X¹ | G-1 | N-methyl-4-oxo-1,2,3,4-tetrahydro-1-naphthalenylamino |
| 2-chloro-5-(trifluoromethyl)phenyl | X¹ | G-1 | N-methyl-4-oxo-1,2,3,4-tetrahydro-1-naphthalenylamino |
| 2,5-dimethylphenyl | X¹ | G-1 | N-methyl-4-oxo-1,2,3,4-tetrahydro-1-naphthalenylamino |
| 2-methyl-5-(trifluoromethyl)phenyl | X¹ | G-1 | N-methyl-4-oxo-1,2,3,4-tetrahydro-1-naphthalenylamino |
| 3,5-dimethylpyrazol-1-yl | X¹ | G-1 | N-methyl-4-oxo-1,2,3,4-tetrahydro-1-naphthalenylamino |
| 5-methyl-3-(trifluoromethyl)pyrazol-1-yl | X¹ | G-1 | N-methyl-4-oxo-1,2,3,4-tetrahydro-1-naphthalenylamino |
| 3,5-dichloropyrazol-1-yl | X¹ | G-1 | N-methyl-4-oxo-1,2,3,4-tetrahydro-1-naphthalenylamino |
| 5-chloro-3-(trifluoromethyl)pyrazol-1-yl | X¹ | G-1 | N-methyl-4-oxo-1,2,3,4-tetrahydro-1-naphthalenylamino |
| 3,5-dibromopyrazol-1-yl | X¹ | G-1 | N-methyl-4-oxo-1,2,3,4-tetrahydro-1-naphthalenylamino |
| 5-bromo-3-(trifluoromethyl)pyrazol-1-yl | X¹ | G-1 | N-methyl-4-oxo-1,2,3,4-tetrahydro-1-naphthalenylamino |
| 3,5-diethylpyrazol-1-yl | X¹ | G-1 | N-methyl-4-oxo-1,2,3,4-tetrahydro-1-naphthalenylamino |
| 5-ethyl-3-(trifluoromethyl)pyrazol-1-yl | X¹ | G-1 | N-methyl-4-oxo-1,2,3,4-tetrahydro-1-naphthalenylamino |
| 3,5-bis-(trifluoromethyl)pyrazol-1-yl | X¹ | G-1 | N-methyl-4-oxo-1,2,3,4-tetrahydro-1-naphthalenylamino |
| 1-methyl-3-(trifluoromethyl)pyrazol-5-yl | X¹ | G-1 | N-methyl-4-oxo-1,2,3,4-tetrahydro-1-naphthalenylamino |
| 1-methyl-4-(trifluoromethyl)imidazol-2-yl | X¹ | G-1 | N-methyl-4-oxo-1,2,3,4-tetrahydro-1-naphthalenylamino |

TABLE 10-continued

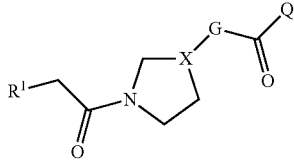

| R¹ | X* | G** | Q |
|---|---|---|---|
| 2,5-dichlorophenyl | X¹ | G-1 | N,2-dimethyl-1-indanylamino |
| 2-chloro-5-(trifluoromethyl)phenyl | X¹ | G-1 | N,2-dimethyl-1-indanylamino |
| 2,5-dimethylphenyl | X¹ | G-1 | N,2-dimethyl-1-indanylamino |
| 2-methyl-5-(trifluoromethyl)phenyl | X¹ | G-1 | N,2-dimethyl-1-indanylamino |
| 3,5-dimethylpyrazol-1-yl | X¹ | G-1 | N,2-dimethyl-1-indanylamino |
| 5-methyl-3-(trifluoromethyl)pyrazol-1-yl | X¹ | G-1 | N,2-dimethyl-1-indanylamino |
| 3,5-dichloropyrazol-1-yl | X¹ | G-1 | N,2-dimethyl-1-indanylamino |
| 5-chloro-3-(trifluoromethyl)pyrazol-1-yl | X¹ | G-1 | N,2-dimethyl-1-indanylamino |
| 3,5-dibromopyrazol-1-yl | X¹ | G-1 | N,2-dimethyl-1-indanylamino |
| 5-bromo-3-(trifluoromethyl)pyrazol-1-yl | X¹ | G-1 | N,2-dimethyl-1-indanylamino |
| 3,5-diethylpyrazol-1-yl | X¹ | G-1 | N,2-dimethyl-1-indanylamino |
| 5-ethyl-3-(trifluoromethyl)pyrazol-1-yl | X¹ | G-1 | N,2-dimethyl-1-indanylamino |
| 3,5-bis-(trifluoromethyl)pyrazol-1-yl | X¹ | G-1 | N,2-dimethyl-1-indanylamino |
| 1-methyl-3-(trifluoromethyl)pyrazol-5-yl | X¹ | G-1 | N,2-dimethyl-1-indanylamino |
| 1-methyl-4-(trifluoromethyl)imidazol-2-yl | X¹ | G-1 | N,2-dimethyl-1-indanylamino |
| 2,5-dichlorophenyl | X¹ | G-1 | N,2,2-trimethyl-1-indanylamino |
| 2-chloro-5-(trifluoromethyl)phenyl | X¹ | G-1 | N,2,2-trimethyl-1-indanylamino |
| 2,5-dimethylphenyl | X¹ | G-1 | N,2,2-trimethyl-1-indanylamino |
| 2-methyl-5-(trifluoromethyl)phenyl | X¹ | G-1 | N,2,2-trimethyl-1-indanylaraino |
| 3,5-dimethylpyrazol-1-yl | X¹ | G-1 | N,2,2-trimethyl-1-indanylamino |
| 5-methyl-3-(trifluoromethyl)pyrazol-1-yl | X¹ | G-1 | N,2,2-trimethyl-1-indanylamino |
| 3,5-dichloropyrazol-1-yl | X¹ | G-1 | N,2,2-trimethyl-1-indanylamino |
| 5-chloro-3-(trifluoromethyl)pyrazol-1-yl | X¹ | G-1 | N,2,2-trimethyl-1-indanylamino |
| 3,5-dibromopyrazol-1-yl | X¹ | G-1 | N,2,2-trimethyl-1-indanylamino |
| 5-bromo-3-(trifluoromethyl)pyrazol-1-yl | X¹ | G-1 | N,2,2-trimethyl-1-indanylamino |
| 3,5-diethylpyrazol-1-yl | X¹ | G-1 | N,2,2-trimethyl-1-indanylamino |
| 5-ethyl-3-(trifluoromethyl)pyrazol-1-yl | X¹ | G-1 | N,2,2-trimethyl-1-indanylamino |
| 3,5-bis-(trifluoromethyl)pyrazol-1-yl | X¹ | G-1 | N,2,2-trimethyl-1-indanylamino |
| 1-methyl-3-(trifluoromethyl)pyrazol-5-yl | X¹ | G-1 | N,2,2-trimethyl-1-indanylamino |
| 1-methyl-4-(trifluoromethyl)imidazol-2-yl | X¹ | G-1 | N,2,2-trimethyl-1-indanylamino |
| 2,5-dichlorophenyl | X¹ | G-1 | N-methyl-3-hydroxy-1-indanylamino |
| 2-chloro-5-(trifluoromethyl)phenyl | X¹ | G-1 | N-methyl-3-hydroxy-1-indanylamino |
| 2,5-dimethylphenyl | X¹ | G-1 | N-methyl-3-hydroxy-1-indanylamino |
| 2-methyl-5-(trifluoromethyl)phenyl | X¹ | G-1 | N-methyl-3-hydroxy-1-indanylamino |
| 3,5-dimethylpyrazol-1-yl | X¹ | G-1 | N-methyl-3-hydroxy-1-indanylamino |
| 5-methyl-3-(trifluoromethyl)pyrazol-1-yl | X¹ | G-1 | N-methyl-3-hydroxy-1-indanylamino |
| 3,5-dichloropyrazol-1-yl | X¹ | G-1 | N-methyl-3-hydroxy-1-indanylamino |
| 5-chloro-3-(trifluoromethyl)pyrazol-1-yl | X¹ | G-1 | N-methyl-3-hydroxy-1-indanylamino |
| 3,5-dibromopyrazol-1-yl | X¹ | G-1 | N-methyl-3-hydroxy-1-indanylamino |
| 5-bromo-3-(trifluoromethyl)pyrazol-1-yl | X¹ | G-1 | N-methyl-3-hydroxy-1-indanylamino |
| 3,5-diethylpyrazol-1-yl | X¹ | G-1 | N-methyl-3-hydroxy-1-indanylamino |
| 5-ethyl-3-(trifluoromethyl)pyrazol-1-yl | X¹ | G-1 | N-methyl-3-hydroxy-1-indanylamino |
| 3,5-bis-(trifluoromethyl)pyrazol-1-yl | X¹ | G-1 | N-methyl-3-hydroxy-1-indanylamino |
| 1-methyl-3-(trifluoromethyl)pyrazol-5-yl | X¹ | G-1 | N-methyl-3-hydroxy-1-indanylamino |
| 1-methyl-4-(trifluoromethyl)imidazol-2-yl | X¹ | G-1 | N-methyl-3-hydroxy-1-indanylamino |
| 2,5-dichlorophenyl | X¹ | G-1 | N-methyl-3-oxo-1-indanylamino |
| 2-chloro-5-(trifluoromethyl)phenyl | X¹ | G-1 | N-methyl-3-oxo-1-indanylamino |
| 2,5-dimethylphenyl | X¹ | G-1 | N-methyl-3-oxo-1-indanylamino |
| 2-methyl-5-(trifluoromethyl)phenyl | X¹ | G-1 | N-methyl-3-oxo-1-indanylamino |
| 3,5-dimethylpyrazol-1-yl | X¹ | G-1 | N-methyl-3-oxo-1-indanylamino |
| 5-methyl-3-(trifluoromethyl)pyrazol-1-yl | X¹ | G-1 | N-methyl-3-oxo-1-indanylamino |
| 3,5-dichloropyrazol-1-yl | X¹ | G-1 | N-methyl-3-oxo-1-indanylamino |
| 5-chloro-3-(trifluoromethyl)pyrazol-1-yl | X¹ | G-1 | N-methyl-3-oxo-1-indanylamino |
| 3,5-dibromopyrazol-1-yl | X¹ | G-1 | N-methyl-3-oxo-1-indanylamino |
| 5-bromo-3-(trifluoromethyl)pyrazol-1-yl | X¹ | G-1 | N-methyl-3-oxo-1-indanylamino |
| 3,5-diethylpyrazol-1-yl | X¹ | G-1 | N-methyl-3-oxo-1-indanylamino |
| 5-ethyl-3-(trifluoromethyl)pyrazol-1-yl | X¹ | G-1 | N-methyl-3-oxo-1-indanylamino |
| 3,5-bis-(trifluoromethyl)pyrazol-1-yl | X¹ | G-1 | N-methyl-3-oxo-1-indanylamino |
| 1-methyl-3-(trifluoromethyl)pyrazol-5-yl | X¹ | G-1 | N-methyl-3-oxo-1-indanylamino |
| 1-methyl-4-(trifluoromethyl)imidazol-2-yl | X¹ | G-1 | N-methyl-3-oxo-1-indanylamino |
| 2,5-dichlorophenyl | X¹ | G-2 | N-methyl-4-hydroxy-1,2,3,4-tetrahydro-1-naphthalenylamino |
| 2-chloro-5-(trifluoromethyl)phenyl | X¹ | G-2 | N-methyl-4-hydroxy-1,2,3,4-tetrahydro-1-naphthalenylamino |
| 2,5-dimethylphenyl | X¹ | G-2 | N-methyl-4-hydroxy-1,2,3,4-tetrahydro-1-naphthalenylamino |
| 2-methyl-5-(trifluoromethyl)phenyl | X¹ | G-2 | N-methyl-4-hydroxy-1,2,3,4-tetrahydro-1-naphthalenylamino |

TABLE 10-continued

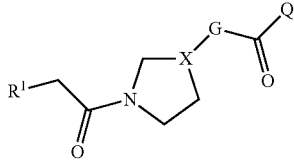

| R¹ | X* | G** | Q |
|---|---|---|---|
| 3,5-dimethylpyrazol-1-yl | X¹ | G-2 | N-methyl-4-hydroxy-1,2,3,4-tetrahydro-1-naphthalenylamino |
| 5-methyl-3-(trifluoromethyl)pyrazol-1-yl | X¹ | G-2 | N-methyl-4-hydroxy-1,2,3,4-tetrahydro-1-naphthalenylamino |
| 3,5-dichloropyrazol-1-yl | X¹ | G-2 | N-methyl-4-hydroxy-1,2,3,4-tetrahydro-1-naphthalenylamino |
| 5-chloro-3-(trifluoromethyl)pyrazol-1-yl | X¹ | G-2 | N-methyl-4-hydroxy-1,2,3,4-tetrahydro-1-naphthalenylamino |
| 3,5-dibromopyrazol-1-yl | X¹ | G-2 | N-methyl-4-hydroxy-1,2,3,4-tetrahydro-1-naphthalenylamino |
| 5-bromo-3-(trifluoromethyl)pyrazol-1-yl | X¹ | G-2 | N-methyl-4-hydroxy-1,2,3,4-tetrahydro-1-naphthalenylamino |
| 3,5-diethylpyrazol-1-yl | X¹ | G-2 | N-methyl-4-hydroxy-1,2,3,4-tetrahydro-1-naphthalenylamino |
| 5-ethyl-3-(trifluoromethyl)pyrazol-1-yl | X¹ | G-2 | N-methyl-4-hydroxy-1,2,3,4-tetrahydro-1-naphthalenylamino |
| 3,5-bis-(trifluoromethyl)pyrazol-1-yl | X¹ | G-2 | N-methyl-4-hydroxy-1,2,3,4-tetrahydro-1-naphthalenylamino |
| 1-methyl-3-(trifluoromethyl)pyrazol-5-yl | X¹ | G-2 | N-methyl-4-hydroxy-1,2,3,4-tetrahydro-1-naphthalenylamino |
| 1-methyl-4-(trifluoromethyl)imidazol-2-yl | X¹ | G-2 | N-methyl-4-hydroxy-1,2,3,4-tetrahydro-1-naphthalenylamino |
| 2,5-dichlorophenyl | X¹ | G-2 | N,2-dimethyl-1,2,3,4-tetrahydro-1-naphthalenylamino |
| 2-chloro-5-(trifluoromethyl)phenyl | X¹ | G-2 | N,2-dimethyl-1,2,3,4-tetrahydro-1-naphthalenylamino |
| 2,5-dimethylphenyl | X¹ | G-2 | N,2-dimethyl-1,2,3,4-tetrahydro-1-naphthalenylamino |
| 2-methyl-5-(trifluoromethyl)phenyl | X¹ | G-2 | N,2-dimethyl-1,2,3,4-tetrahydro-1-naphthalenylamino |
| 3,5-dimethylpyrazol-1-yl | X¹ | G-2 | N,2-dimethyl-1,2,3,4-tetrahydro-1-naphthalenylamino |
| 5-methyl-3-(trifluoromethyl)pyrazol-1-yl | X¹ | G-2 | N,2-dimethyl-1,2,3,4-tetrahydro-1-naphthalenylamino |
| 3,5-dichloropyrazol-1-yl | X¹ | G-2 | N,2-dimethyl-1,2,3,4-tetrahydro-1-naphthalenylamino |
| 5-chloro-3-(trifluoromethyl)pyrazol-1-yl | X¹ | G-2 | N,2-dimethyl-1,2,3,4-tetrahydro-1-naphthalenylamino |
| 3,5-dibromopyrazol-1-yl | X¹ | G-2 | N,2-dimethyl-1,2,3,4-tetrahydro-1-naphthalenylamino |
| 5-bromo-3-(trifluoromethyl)pyrazol-1-yl | X¹ | G-2 | N,2-dimethyl-1,2,3,4-tetrahydro-1-naphthalenylamino |
| 3,5-diethylpyrazol-1-yl | X¹ | G-2 | N,2-dimethyl-1,2,3,4-tetrahydro-1-naphthalenylamino |
| 5-ethyl-3-(trifluoromethyl)pyrazol-1-yl | X¹ | G-2 | N,2-dimethyl-1,2,3,4-tetrahydro-1-naphthalenylamino |
| 3,5-bis-(trifluoromethyl)pyrazol-1-yl | X¹ | G-2 | N,2-dimethyl-1,2,3,4-tetrahydro-1-naphthalenylamino |
| 1-methyl-3-(trifluoromethyl)pyrazol-5-yl | X¹ | G-2 | N,2-dimethyl-1,2,3,4-tetrahydro-1-naphthalenylamino |
| 1-methyl-4-(trifluoromethyl)imidazol-2-yl | X¹ | G-2 | N,2-dimethyl-1,2,3,4-tetrahydro-1-naphthalenylamino |
| 2,5-dichlorophenyl | X¹ | G-2 | N,2,2-trimethyl-1,2,3,4-tetrahydro-1-naphthalenylamino |
| 2-chloro-5-(trifluoromethyl)phenyl | X¹ | G-2 | N,2,2-trimethyl-1,2,3,4-tetrahydro-1-naphthalenylamino |
| 2,5-dimethylphenyl | X¹ | G-2 | N,2,2-trimethyl-1,2,3,4-tetrahydro-1-naphthalenylamino |
| 2-methyl-5-(trifluoromethyl)phenyl | X¹ | G-2 | N,2,2-trimethyl-1,2,3,4-tetrahydro-1-naphthalenylamino |
| 3,5-dimethylpyrazol-1-yl | X¹ | G-2 | N,2,2-trimethyl-1,2,3,4-tetrahydro-1-naphthalenylamino |
| 5-methyl-3-(trifluoromethyl)pyrazol-1-yl | X¹ | G-2 | N,2,2-trimethyl-1,2,3,4-tetrahydro-1-naphthalenylamino |
| 3,5-dichloropyrazol-1-yl | X¹ | G-2 | N,2,2-trimethyl-1,2,3,4-tetrahydro-1-naphthalenylamino |
| 5-chloro-3-(trifluoromethyl)pyrazol-1-yl | X¹ | G-2 | N,2,2-trimethyl-1,2,3,4-tetrahydro-1-naphthalenylamino |

TABLE 10-continued

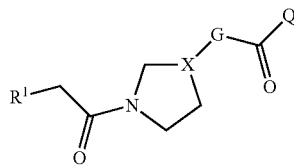

| R¹ | X* | G** | Q |
|---|---|---|---|
| 3,5-dibromopyrazol-1-yl | X¹ | G-2 | N,2,2-trimethyl-1,2,3,4-tetrahydro-1-naphthalenylamino |
| 5-bromo-3-(trifluoromethyl)pyrazol-1-yl | X¹ | G-2 | N,2,2-trimethyl-1,2,3,4-tetrahydro-1-naphthalenylamino |
| 3,5-diethylpyrazol-1-yl | X¹ | G-2 | N,2,2-trimethyl-1,2,3,4-tetrahydro-1-naphthalenylamino |
| 5-ethyl-3-(trifluoromethyl)pyrazol-1-yl | X¹ | G-2 | N,2,2-trimethyl-1,2,3,4-tetrahydro-1-naphthalenylamino |
| 3,5-bis-(trifluoromethyl)pyrazol-1-yl | X¹ | G-2 | N,2,2-trimethyl-1,2,3,4-tetrahydro-1-naphthalenylamino |
| 1-methyl-3-(trifluoromethyl)pyrazol-5-yl | X¹ | G-2 | N,2,2-trimethyl-1,2,3,4-tetrahydro-1-naphthalenylamino |
| 1-methyl-4-(trifluoromethyl)imidazol-2-yl | X¹ | G-2 | N,2,2-trimethyl-1,2,3,4-tetrahydro-1-naphthalenylamino |
| 2,5-dichlorophenyl | X¹ | G-2 | N-methyl-4-oxo-1,2,3,4-tetrahydro-1-naphthalenylamino |
| 2-chloro-5-(trifluoromethyl)phenyl | X¹ | G-2 | N-methyl-4-oxo-1,2,3,4-tetrahydro-1-naphthalenylamino |
| 2,5-dimethylphenyl | X¹ | G-2 | N-methyl-4-oxo-1,2,3,4-tetrahydro-1-naphthalenylamino |
| 2-methyl-5-(trifluoromethyl)phenyl | X¹ | G-2 | N-methyl-4-oxo-1,2,3,4-tetrahydro-1-naphthalenylamino |
| 3,5-dimethylpyrazol-1-yl | X¹ | G-2 | N-methyl-4-oxo-1,2,3,4-tetrahydro-1-naphthalenylamino |
| 5-methyl-3-(trifluoromethyl)pyrazol-1-yl | X¹ | G-2 | N-methyl-4-oxo-1,2,3,4-tetrahydro-1-naphthalenylamino |
| 3,5-dichloropyrazol-1-yl | X¹ | G-2 | N-methyl-4-oxo-1,2,3,4-tetrahydro-1-naphthalenylamino |
| 5-chloro-3-(trifluoromethyl)pyrazol-1-yl | X¹ | G-2 | N-methyl-4-oxo-1,2,3,4-tetrahydro-1-naphthalenylamino |
| 3,5-dibromopyrazol-1-yl | X¹ | G-2 | N-methyl-4-oxo-1,2,3,4-tetrahydro-1-naphthalenylamino |
| 5-bromo-3-(trifluoromethyl)pyrazol-1-yl | X¹ | G-2 | N-methyl-4-oxo-1,2,3,4-tetrahydro-1-naphthalenylamino |
| 3,5-diethylpyrazol-1-yl | X¹ | G-2 | N-methyl-4-oxo-1,2,3,4-tetrahydro-1-naphthalenylamino |
| 5-ethyl-3-(trifluoromethyl)pyrazol-1-yl | X¹ | G-2 | N-methyl-4-oxo-1,2,3,4-tetrahydro-1-naphthalenylamino |
| 3,5-bis-(trifluoromethyl)pyrazol-1-yl | X¹ | G-2 | N-methyl-4-oxo-1,2,3,4-tetrahydro-1-naphthalenylamino |
| 1-methyl-3-(trifluoromethyl)pyrazol-5-yl | X¹ | G-2 | N-methyl-4-oxo-1,2,3,4-tetrahydro-1-naphthalenylamino |
| 1-methyl-4-(trifluoromethyl)imidazol-2-yl | X¹ | G-2 | N-methyl-4-oxo-1,2,3,4-tetrahydro-1-naphthalenylamino |
| 2,5-dichlorophenyl | X¹ | G-2 | N,2-dimethyl-1-indanylamino |
| 2-chloro-5-(trifluoromethyl)phenyl | X¹ | G-2 | N,2-dimethyl-1-indanylamino |
| 2,5-dimethylphenyl | X¹ | G-2 | N,2-dimethyl-1-indanylamino |
| 2-methyl-5-(trifluoromethyl)phenyl | X¹ | G-2 | N,2-dimethyl-1-indanylamino |
| 3,5-dimethylpyrazol-1-yl | X¹ | G-2 | N,2-dimethyl-1-indanylamino |
| 5-methyl-3-(trifluoromethyl)pyrazol-1-yl | X¹ | G-2 | N,2-dimethyl-1-indanylamino |
| 3,5-dichloropyrazol-1-yl | X¹ | G-2 | N,2-dimethyl-1-indanylamino |
| 5-chloro-3-(trifluoromethyl)pyrazol-1-yl | X¹ | G-2 | N,2-dimethyl-1-indanylamino |
| 3,5-dibromopyrazol-1-yl | X¹ | G-2 | N,2-dimethyl-1-indanylamino |
| 5-bromo-3-(trifluoromethyl)pyrazol-1-yl | X¹ | G-2 | N,2-dimethyl-1-indanylamino |
| 3,5-diethylpyrazol-1-yl | X¹ | G-2 | N,2-dimethyl-1-indanylamino |
| 5-ethyl-3-(trifluoromethyl)pyrazol-1-yl | X¹ | G-2 | N,2-dimethyl-1-indanylamino |
| 3,5-bis-(trifluoromethyl)pyrazol-1-yl | X¹ | G-2 | N,2-dimethyl-1-indanylamino |
| 1-methyl-3-(trifluoromethyl)pyrazol-5-yl | X¹ | G-2 | N,2-dimethyl-1-indanylamino |
| 1-methyl-4-(trifluoromethyl)imidazol-2-yl | X¹ | G-2 | N,2-dimethyl-1-indanylamino |
| 2,5-dichlorophenyl | X¹ | G-2 | N,2,2-trimethyl-1-indanylamino |
| 2-chloro-5-(trifluoromethyl)phenyl | X¹ | G-2 | N,2,2-trimethyl-1-indanylamino |
| 2,5-dimethylphenyl | X¹ | G-2 | N,2,2-trimethyl-1-indanylamino |
| 2-methyl-5-(trifluoromethyl)phenyl | X¹ | G-2 | N,2,2-trimethyl-1-indanylamino |
| 3,5-dimethylpyrazol-1-yl | X¹ | G-2 | N,2,2-trimethyl-1-indanylamino |
| 5-methyl-3-(trifluoromethyl)pyrazol-1-yl | X¹ | G-2 | N,2,2-trimethyl-1-indanylamino |
| 3,5-dichloropyrazol-1-yl | X¹ | G-2 | N,2,2-trimethyl-1-indanylamino |
| 5-chloro-3-(trifluoromethyl)pyrazol-1-yl | X¹ | G-2 | N,2,2-trimethyl-1-indanylamino |
| 3,5-dibromopyrazol-1-yl | X¹ | G-2 | N,2,2-trimethyl-1-indanylamino |
| 5-bromo-3-(trifluoromethyl)pyrazol-1-yl | X¹ | G-2 | N,2,2-trimethyl-1-indanylamino |

TABLE 10-continued

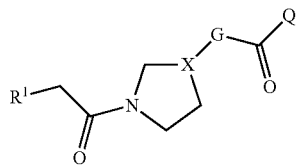

| R¹ | X* | G** | Q |
|---|---|---|---|
| 3,5-diethylpyrazol-1-yl | X¹ | G-2 | N,2,2-trimethyl-1-indanylamino |
| 5-ethyl-3-(trifluoromethyl)pyrazol-1-yl | X¹ | G-2 | N,2,2-trimethyl-1-indanylamino |
| 3,5-bis-(trifluoromethyl)pyrazol-1-yl | X¹ | G-2 | N,2,2-trimethyl-1-indanylamino |
| 1-methyl-3-(trifluoromethyl)pyrazol-5-yl | X¹ | G-2 | N,2,2-trimethyl-1-indanylamino |
| 1-methyl-4-(trifluoromethyl)imidazol-2-yl | X¹ | G-2 | N,2,2-trimethyl-1-indanylamino |
| 2,5-dichlorophenyl | X¹ | G-2 | N-methyl-3-hydroxy-1-indanylamino |
| 2-chloro-5-(trifluoromethyl)phenyl | X¹ | G-2 | N-methyl-3-hydroxy-1-indanylamino |
| 2,5-dimethylphenyl | X¹ | G-2 | N-methyl-3-hydroxy-1-indanylamino |
| 2-methyl-5-(trifluoromethyl)phenyl | X¹ | G-2 | N-methyl-3-hydroxy-1-indanylamino |
| 3,5-dimethylpyrazol-1-yl | X¹ | G-2 | N-methyl-3-hydroxy-1-indanylamino |
| 5-methyl-3-(trifluoromethyl)pyrazol-1-yl | X¹ | G-2 | N-methyl-3-hydroxy-1-indanylamino |
| 3,5-dichloropyrazol-1-yl | X¹ | G-2 | N-methyl-3-hydroxy-1-indanylamino |
| 5-chloro-3-(trifluoromethyl)pyrazol-1-yl | X¹ | G-2 | N-methyl-3-hydroxy-1-indanylamino |
| 3,5-dibromopyrazol-1-yl | X¹ | G-2 | N-methyl-3-hydroxy-1-indanylamino |
| 5-bromo-3-(trifluoromethyl)pyrazol-1-yl | X¹ | G-2 | N-methyl-3-hydroxy-1-indanylamino |
| 3,5-diethylpyrazol-1-yl | X¹ | G-2 | N-methyl-3-hydroxy-1-indanylamino |
| 5-ethyl-3-(trifluoromethyl)pyrazol-1-yl | X¹ | G-2 | N-methyl-3-hydroxy-1-indanylamino |
| 3,5-bis-(trifluoromethyl)pyrazol-1-yl | X¹ | G-2 | N-methyl-3-hydroxy-1-indanylamino |
| 1-methyl-3-(trifluoromethyl)pyrazol-5-yl | X¹ | G-2 | N-methyl-3-hydroxy-1-indanylamino |
| 1-methyl-4-(trifluoromethyl)imidazol-2-yl | X¹ | G-2 | N-methyl-3-hydroxy-1-indanylamino |
| 2,5-dichlorophenyl | X¹ | G-2 | N-methyl-3-oxo-1-indanylamino |
| 2-chloro-5-(trifluoromethyl)phenyl | X¹ | G-2 | N-methyl-3-oxo-1-indanylamino |
| 2,5-dimethylphenyl | X¹ | G-2 | N-methyl-3-oxo-1-indanylamino |
| 2-methyl-5-(trifluoromethyl)phenyl | X¹ | G-2 | N-methyl-3-oxo-1-indanylamino |
| 3,5-dimethylpyrazol-1-yl | X¹ | G-2 | N-methyl-3-oxo-1-indanylamino |
| 5-methyl-3-(trifluoromethyl)pyrazol-1-yl | X¹ | G-2 | N-methyl-3-oxo-1-indanylamino |
| 3,5-dichloropyrazol-1-yl | X¹ | G-2 | N-methyl-3-oxo-1-indanylamino |
| 5-chloro-3-(trifluoromethyl)pyrazol-1-yl | X¹ | G-2 | N-methyl-3-oxo-1-indanylamino |
| 3,5-dibromopyrazol-1-yl | X¹ | G-2 | N-methyl-3-oxo-1-indanylamino |
| 5-bromo-3-(trifluoromethyl)pyrazol-1-yl | X¹ | G-2 | N-methyl-3-oxo-1-indanylamino |
| 3,5-diethylpyrazol-1-yl | X¹ | G-2 | N-methyl-3-oxo-1-indanylamino |
| 5-ethyl-3-(trifluoromethyl)pyrazol-1-yl | X¹ | G-2 | N-methyl-3-oxo-1-indanylamino |
| 3,5-bis-(trifluoromethyl)pyrazol-1-yl | X¹ | G-2 | N-methyl-3-oxo-1-indanylamino |
| 1-methyl-3-(trifluoromethyl)pyrazol-5-yl | X¹ | G-2 | N-methyl-3-oxo-1-indanylamino |
| 1-methyl-4-(trifluoromethyl)imidazol-2-yl | X¹ | G-2 | N-methyl-3-oxo-1-indanylamino |
| 2,5-dichlorophenyl | X² | G-1 | N-methyl-4-hydroxy-1,2,3,4-tetrahydro-1-naphthalenylamino |
| 2-chloro-5-(trifluoromethyl)phenyl | X² | G-1 | N-methyl-4-hydroxy-1,2,3,4-tetrahydro-1-naphthalenylamino |
| 2,5-dimethylphenyl | X² | G-1 | N-methyl-4-hydroxy-1,2,3,4-tetrahydro-1-naphthalenylamino |
| 2-methyl-5-(trifluoromethyl)phenyl | X² | G-1 | N-methyl-4-hydroxy-1,2,3,4-tetrahydro-1-naphthalenylamino |
| 3,5-dimethylpyrazol-1-yl | X² | G-1 | N-methyl-4-hydroxy-1,2,3,4-tetrahydro-1-naphthalenylamino |
| 5-methyl-3-(trifluoromethyl)pyrazol-1-yl | X² | G-1 | N-methyl-4-hydroxy-1,2,3,4-tetrahydro-1-naphthalenylamino |
| 3,5-dichloropyrazol-1-yl | X² | G-1 | N-methyl-4-hydroxy-1,2,3,4-tetrahydro-1-naphthalenylamino |
| 5-chloro-3-(trifluoromethyl)pyrazol-1-yl | X² | G-1 | N-methyl-4-hydroxy-1,2,3,4-tetrahydro-1-naphthalenylamino |
| 3,5-dibromopyrazol-1-yl | X² | G-1 | N-methyl-4-hydroxy-1,2,3,4-tetrahydro-1-naphthalenylamino |
| 5-bromo-3-(trifluoromethyl)pyrazol-1-yl | X² | G-1 | N-methyl-4-hydroxy-1,2,3,4-tetrahydro-1-naphthalenylamino |
| 3,5-diethylpyrazol-1-yl | X² | G-1 | N-methyl-4-hydroxy-1,2,3,4-tetrahydro-1-naphthalenylamino |
| 5-ethyl-3-(trifluoromethyl)pyrazol-1-yl | X² | G-1 | N-methyl-4-hydroxy-1,2,3,4-tetrahydro-1-naphthalenylamino |
| 3,5-bis-(trifluoromethyl)pyrazol-1-yl | X² | G-1 | N-methyl-4-hydroxy-1,2,3,4-tetrahydro-1-naphthalenylamino |
| 1-methyl-3-(trifluoromethyl)pyrazol-5-yl | X² | G-1 | N-methyl-4-hydroxy-1,2,3,4-tetrahydro-1-naphthalenylamino |
| 1-methyl-4-(trifluoromethyl)imidazol-2-yl | X² | G-1 | N-methyl-4-hydroxy-1,2,3,4-tetrahydro-1-naphthalenylamino |
| 2,5-dichlorophenyl | X² | G-1 | N,2-dimethyl-1,2,3,4-tetrahydro-1-naphthalenylamino |
| 2-chloro-5-(trifluoromethyl)phenyl | X² | G-1 | N,2-dimethyl-1,2,3,4-tetrahydro-1-naphthalenylamino |

TABLE 10-continued

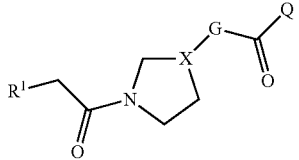

| R[1] | X* | G** | Q |
|---|---|---|---|
| 2,5-dimethylphenyl | X[2] | G-1 | N,2-dimethyl-1,2,3,4-tetrahydro-1-naphthalenylamino |
| 2-methyl-5-(trifluoromethyl)phenyl | X[2] | G-1 | N,2-dimethyl-1,2,3,4-tetrahydro-1-naphthalenylamino |
| 3,5-dimethylpyrazol-1-yl | X[2] | G-1 | N,2-dimethyl-1,2,3,4-tetrahydro-1-naphthalenylamino |
| 5-methyl-3-(trifluoromethyl)pyrazol-1-yl | X[2] | G-1 | N,2-dimethyl-1,2,3,4-tetrahydro-1-naphthalenylamino |
| 3,5-dichloropyrazol-1-yl | X[2] | G-1 | N,2-dimethyl-1,2,3,4-tetrahydro-1-naphthalenylamino |
| 5-chloro-3-(trifluoromethyl)pyrazol-1-yl | X[2] | G-1 | N,2-dimethyl-1,2,3,4-tetrahydro-1-naphthalenylamino |
| 3,5-dibromopyrazol-1-yl | X[2] | G-1 | N,2-dimethyl-1,2,3,4-tetrahydro-1-naphthalenylamino |
| 5-bromo-3-(trifluoromethyl)pyrazol-1-yl | X[2] | G-1 | N,2-dimethyl-1,2,3,4-tetrahydro-1-naphthalenylamino |
| 3,5-diethylpyrazol-1-yl | X[2] | G-1 | N,2-dimethyl-1,2,3,4-tetrahydro-1-naphthalenylamino |
| 5-ethyl-3-(trifluoromethyl)pyrazol-1-yl | X[2] | G-1 | N,2-dimethyl-1,2,3,4-tetrahydro-1-naphthalenylamino |
| 3,5-bis-(trifluoromethyl)pyrazol-1-yl | X[2] | G-1 | N,2-dimethyl-1,2,3,4-tetrahydro-1-naphthalenylamino |
| 1-methyl-3-(trifluoromethyl)pyrazol-5-yl | X[2] | G-1 | N,2-dimethyl-1,2,3,4-tetrahydro-1-naphthalenylamino |
| 1-methyl-4-(trifluoromethyl)imidazol-2-yl | X[2] | G-1 | N,2-dimethyl-1,2,3,4-tetrahydro-1-naphthalenylamino |
| 2,5-dichlorophenyl | X[2] | G-1 | N,2,2-trimethyl-1,2,3,4-tetrahydro-1-naphthalenylamino |
| 2-chloro-5-(trifluoromethyl)phenyl | X[2] | G-1 | N,2,2-trimethyl-1,2,3,4-tetrahydro-1-naphthalenylamino |
| 2,5-dimethylphenyl | X[2] | G-1 | N,2,2-trimethyl-1,2,3,4-tetrahydro-1-naphthalenylamino |
| 2-methyl-5-(trifluoromethyl)phenyl | X[2] | G-1 | N,2,2-trimethyl-1,2,3,4-tetrahydro-1-naphthalenylamino |
| 3,5-dimethylpyrazol-1-yl | X[2] | G-1 | N,2,2-trimethyl-1,2,3,4-tetrahydro-1-naphthalenylamino |
| 5-methyl-3-(trifluoromethyl)pyrazol-1-yl | X[2] | G-1 | N,2,2-trimethyl-1,2,3,4-tetrahydro-1-naphthalenylamino |
| 3,5-dichloropyrazol-1-yl | X[2] | G-1 | N,2,2-trimethyl-1,2,3,4-tetrahydro-1-naphthalenylamino |
| 5-chloro-3-(trifluoromethyl)pyrazol-1-yl | X[2] | G-1 | N,2,2-trimethyl-1,2,3,4-tetrahydro-1-naphthalenylamino |
| 3,5-dibromopyrazol-1-yl | X[2] | G-1 | N,2,2-trimethyl-1,2,3,4-tetrahydro-1-naphthalenylamino |
| 5-bromo-3-(trifluoromethyl)pyrazol-1-yl | X[2] | G-1 | N,2,2-trimethyl-1,2,3,4-tetrahydro-1-naphthalenylamino |
| 3,5-diethylpyrazol-1-yl | X[2] | G-1 | N,2,2-trimethyl-1,2,3,4-tetrahydro-1-naphthalenylamino |
| 5-ethyl-3-(trifluoromethyl)pyrazol-1-yl | X[2] | G-1 | N,2,2-trimethyl-1,2,3,4-tetrahydro-1-naphthalenylamino |
| 3,5-bis-(trifluoromethyl)pyrazol-1-yl | X[2] | G-1 | N,2,2-trimethyl-1,2,3,4-tetrahydro-1-naphthalenylamino |
| 1-methyl-3-(trifluoromethyl)pyrazol-5-yl | X[2] | G-1 | N,2,2-trimethyl-1,2,3,4-tetrahydro-1-naphthalenylamino |
| 1-methyl-4-(trifluoromethyl)imidazol-2-yl | X[2] | G-1 | N,2,2-trimethyl-1,2,3,4-tetrahydro-1-naphthalenylamino |
| 2,5-dichlorophenyl | X[2] | G-1 | N-methyl-4-oxo-1,2,3,4-tetrahydro-1-naphthalenylamino |
| 2-chloro-5-(trifluoromethyl)phenyl | X[2] | G-1 | N-methyl-4-oxo-1,2,3,4-tetrahydro-1-naphthalenylamino |
| 2,5-dimethylphenyl | X[2] | G-1 | N-methyl-4-oxo-1,2,3,4-tetrahydro-1-naphthalenylamino |
| 2-methyl-5-(trifluoromethyl)phenyl | X[2] | G-1 | N-methyl-4-oxo-1,2,3,4-tetrahydro-1-naphthalenylamino |
| 3,5-dimethylpyrazol-1-yl | X[2] | G-1 | N-methyl-4-oxo-1,2,3,4-tetrahydro-1-naphthalenylamino |
| 5-methyl-3-(trifluoromethyl)pyrazol-1-yl | X[2] | G-1 | N-methyl-4-oxo-1,2,3,4-tetrahydro-1-naphthalenylamino |

TABLE 10-continued

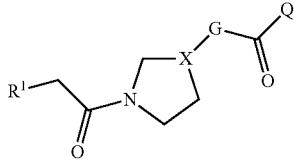

| R¹ | X* | G** | Q |
|---|---|---|---|
| 3,5-dichloropyrazol-1-yl | X² | G-1 | N-methyl-4-oxo-1,2,3,4-tetrahydro-1-naphthalenylamino |
| 5-chloro-3-(trifluoromethyl)pyrazol-1-yl | X² | G-1 | N-methyl-4-oxo-1,2,3,4-tetrahydro-1-naphthalenylamino |
| 3,5-dibromopyrazol-1-yl | X² | G-1 | N-methyl-4-oxo-1,2,3,4-tetrahydro-1-naphthalenylamino |
| 5-bromo-3-(trifluoromethyl)pyrazol-1-yl | X² | G-1 | N-methyl-4-oxo-1,2,3,4-tetrahydro-1-naphthalenylamino |
| 3,5-diethylpyrazol-1-yl | X² | G-1 | N-methyl-4-oxo-1,2,3,4-tetrahydro-1-naphthalenylamino |
| 5-ethyl-3-(trifluoromethyl)pyrazol-1-yl | X² | G-1 | N-methyl-4-oxo-1,2,3,4-tetrahydro-1-naphthalenylamino |
| 3,5-bis-(trifluoromethyl)pyrazol-1-yl | X² | G-1 | N-methyl-4-oxo-1,2,3,4-tetrahydro-1-naphthalenylamino |
| 1-methyl-3-(trifluoromethyl)pyrazol-5-yl | X² | G-1 | N-methyl-4-oxo-1,2,3,4-tetrahydro-1-naphthalenylamino |
| 1-methyl-4-(trifluoromethyl)imidazol-2-yl | X² | G-1 | N-methyl-4-oxo-1,2,3,4-tetrahydro-1-naphthalenylamino |
| 2,5-dichlorophenyl | X² | G-1 | N,2-dimethyl-1-indanylamino |
| 2-chloro-5-(trifluoromethyl)phenyl | X² | G-1 | N,2-dimethyl-1-indanylamino |
| 2,5-dimethylphenyl | X² | G-1 | N,2-dimethyl-1-indanylamino |
| 2-methyl-5-(trifluoromethyl)phenyl | X² | G-1 | N,2-dimethyl-1-indanylamino |
| 3,5-dimethylpyrazol-1-yl | X² | G-1 | N,2-dimethyl-1-indanylamino |
| 5-methyl-3-(trifluoromethyl)pyrazol-1-yl | X² | G-1 | N,2-dimethyl-1-indanylamino |
| 3,5-dichloropyrazol-1-yl | X² | G-1 | N,2-dimethyl-1-indanylamino |
| 5-chloro-3-(trifluoromethyl)pyrazol-1-yl | X² | G-1 | N,2-dimethyl-1-indanylamino |
| 3,5-dibromopyrazol-1-yl | X² | G-1 | N,2-dimethyl-1-indanylamino |
| 5-bromo-3-(trifluoromethyl)pyrazol-1-yl | X² | G-1 | N,2-dimethyl-1-indanylamino |
| 3,5-diethylpyrazol-1-yl | X² | G-1 | N,2-dimethyl-1-indanylamino |
| 5-ethyl-3-(trifluoromethyl)pyrazol-1-yl | X² | G-1 | N,2-dimethyl-1-indanylamino |
| 3,5-bis-(trifluoromethyl)pyrazol-1-yl | X² | G-1 | N,2-dimethyl-1-indanylamino |
| 1-methyl-3-(trifluoromethyl)pyrazol-5-yl | X² | G-1 | N,2-dimethyl-1-indanylamino |
| 1-methyl-4-(trifluoromethyl)imidazol-2-yl | X² | G-1 | N,2-dimethyl-1-indanylamino |
| 2,5-dichlorophenyl | X² | G-1 | N,2,2-trimethyl-1-indanylamino |
| 2-chloro-5-(trifluoromethyl)phenyl | X² | G-1 | N,2,2-trimethyl-1-indanylamino |
| 2,5-dimethylphenyl | X² | G-1 | N,2,2-trimethyl-1-indanylamino |
| 2-methyl-5-(trifluoromethyl)phenyl | X² | G-1 | N,2,2-trimethyl-1-indanylamino |
| 3,5-dimethylpyrazol-1-yl | X² | G-1 | N,2,2-trimethyl-1-indanylamino |
| 5-methyl-3-(trifluoromethyl)pyrazol-1-yl | X² | G-1 | N,2,2-trimethyl-1-indanylamino |
| 3,5-dichloropyrazol-1-yl | X² | G-1 | N,2,2-trimethyl-1-indanylamino |
| 5-chloro-3-(trifluoromethyl)pyrazol-1-yl | X² | G-1 | N,2,2-trimethyl-1-indanylamino |
| 3,5-dibromopyrazol-1-yl | X² | G-1 | N,2,2-trimethyl-1-indanylamino |
| 5-bromo-3-(trifluoromethyl)pyrazol-1-yl | X² | G-1 | N,2,2-trimethyl-1-indanylamino |
| 3,5-diethylpyrazol-1-yl | X² | G-1 | N,2,2-trimethyl-1-indanylamino |
| 5-ethyl-3-(trifluoromethyl)pyrazol-1-yl | X² | G-1 | N,2,2-trimethyl-1-indanylamino |
| 3,5-bis-(trifluoromethyl)pyrazol-1-yl | X² | G-1 | N,2,2-trimethyl-1-indanylamino |
| 1-methyl-3-(trifluoromethyl)pyrazol-5-yl | X² | G-1 | N,2,2-trimethyl-1-indanylamino |
| 1-methyl-4-(trifluoromethyl)imidazol-2-yl | X² | G-1 | N,2,2-trimethyl-1-indanylamino |
| 2,5-dichlorophenyl | X² | G-1 | N-methyl-3-hydroxy-1-indanylamino |
| 2-chloro-5-(trifluoromethyl)phenyl | X² | G-1 | N-methyl-3-hydroxy-1-indanylamino |
| 2,5-dimethylphenyl | X² | G-1 | N-methyl-3-hydroxy-1-indanylamino |
| 2-methyl-5-(trifluoromethyl)phenyl | X² | G-1 | N-methyl-3-hydroxy-1-indanylamino |
| 3,5-dimethylpyrazol-1-yl | X² | G-1 | N-methyl-3-hydroxy-1-indanylamino |
| 5-methyl-3-(trifluoromethyl)pyrazol-1-yl | X² | G-1 | N-methyl-3-hydroxy-1-indanylamino |
| 3,5-dichloropyrazol-1-yl | X² | G-1 | N-methyl-3-hydroxy-1-indanylamino |
| 5-chloro-3-(trifluoromethyl)pyrazol-1-yl | X² | G-1 | N-methyl-3-hydroxy-1-indanylamino |
| 3,5-dibromopyrazol-1-yl | X² | G-1 | N-methyl-3-hydroxy-1-indanylamino |
| 5-bromo-3-(trifluoromethyl)pyrazol-1-yl | X² | G-1 | N-methyl-3-hydroxy-1-indanylamino |
| 3,5-diethylpyrazol-1-yl | X² | G-1 | N-methyl-3-hydroxy-1-indanylamino |
| 5-ethyl-3-(trifluoromethyl)pyrazol-1-yl | X² | G-1 | N-methyl-3-hydroxy-1-indanylamino |
| 3,5-bis-(trifluoromethyl)pyrazol-1-yl | X² | G-1 | N-methyl-3-hydroxy-1-indanylamino |
| 1-methyl-3-(trifluoromethyl)pyrazol-5-yl | X² | G-1 | N-methyl-3-hydroxy-1-indanylamino |
| 1-methyl-4-(trifluoromethyl)imidazol-2-yl | X² | G-1 | N-methyl-3-hydroxy-1-indanylamino |
| 2,5-dichlorophenyl | X² | G-1 | N-methyl-3-oxo-1-indanylamino |
| 2-chloro-5-(trifluoromethyl)phenyl | X² | G-1 | N-methyl-3-oxo-1-indanylamino |
| 2,5-dimethylphenyl | X² | G-1 | N-methyl-3-oxo-1-indanylamino |
| 2-methyl-5-(trifluoromethyl)phenyl | X² | G-1 | N-methyl-3-oxo-1-indanylamino |
| 3,5-dimethylpyrazol-1-yl | X² | G-1 | N-methyl-3-oxo-1-indanylamino |
| 5-methyl-3-(trifluoromethyl)pyrazol-1-yl | X² | G-1 | N-methyl-3-oxo-1-indanylamino |

TABLE 10-continued

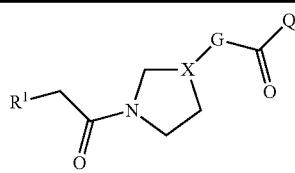

| R¹ | X* | G** | Q |
|---|---|---|---|
| 3,5-dichloropyrazol-1-yl | X² | G-1 | N-methyl-3-oxo-1-indanylamino |
| 5-chloro-3-(trifluoromethyl)pyrazol-1-yl | X² | G-1 | N-methyl-3-oxo-1-indanylamino |
| 3,5-dibromopyrazol-1-yl | X² | G-1 | N-methyl-3-oxo-1-indanylamino |
| 5-bromo-3-(trifluoromethyl)pyrazol-1-yl | X² | G-1 | N-methyl-3-oxo-1-indanylamino |
| 3,5-diethylpyrazol-1-yl | X² | G-1 | N-methyl-3-oxo-1-indanylamino |
| 5-ethyl-3-(trifluoromethyl)pyrazol-1-yl | X² | G-1 | N-methyl-3-oxo-1-indanylamino |
| 3,5-bis-(trifluoromethyl)pyrazol-1-yl | X² | G-1 | N-methyl-3-oxo-1-indanylamino |
| 1-methyl-3-(trifluoromethyl)pyrazol-5-yl | X² | G-1 | N-methyl-3-oxo-1-indanylamino |
| 1-methyl-4-(trifluoromethyl)imidazol-2-yl | X² | G-1 | N-methyl-3-oxo-1-indanylamino |
| 2,5-dichlorophenyl | X² | G-2 | N-methyl-4-hydroxy-1,2,3,4-tetrahydro-1-naphthalenylamino |
| 2-chloro-5-(trifluoromethyl)phenyl | X² | G-2 | N-methyl-4-hydroxy-1,2,3,4-tetrahydro-1-naphthalenylamino |
| 2,5-dimethylphenyl | X² | G-2 | N-methyl-4-hydroxy-1,2,3,4-tetrahydro-1-naphthalenylamino |
| 2-methyl-5-(trifluoromethyl)phenyl | X² | G-2 | N-methyl-4-hydroxy-1,2,3,4-tetrahydro-1-naphthalenylamino |
| 3,5-dimethylpyrazol-1-yl | X² | G-2 | N-methyl-4-hydroxy-1,2,3,4-tetrahydro-1-naphthalenylamino |
| 5-methyl-3-(trifluoromethyl)pyrazol-1-yl | X² | G-2 | N-methyl-4-hydroxy-1,2,3,4-tetrahydro-1-naphthalenylamino |
| 3,5-dichloropyrazol-1-yl | X² | G-2 | N-methyl-4-hydroxy-1,2,3,4-tetrahydro-1-naphthalenylamino |
| 5-chloro-3-(trifluoromethyl)pyrazol-1-yl | X² | G-2 | N-methyl-4-hydroxy-1,2,3,4-tetrahydro-1-naphthalenylamino |
| 3,5-dibromopyrazol-1-yl | X² | G-2 | N-methyl-4-hydroxy-1,2,3,4-tetrahydro-1-naphthalenylamino |
| 5-bromo-3-(trifluoromethyl)pyrazol-1-yl | X² | G-2 | N-methyl-4-hydroxy-1,2,3,4-tetrahydro-1-naphthalenylamino |
| 3,5-diethylpyrazol-1-yl | X² | G-2 | N-methyl-4-hydroxy-1,2,3,4-tetrahydro-1-naphthalenylamino |
| 5-ethyl-3-(trifluoromethyl)pyrazol-1-yl | X² | G-2 | N-methyl-4-hydroxy-1,2,3,4-tetrahydro-1-naphthalenylamino |
| 3,5-bis-(trifluoromethyl)pyrazol-1-yl | X² | G-2 | N-methyl-4-hydroxy-1,2,3,4-tetrahydro-1-naphthalenylamino |
| 1-methyl-3-(trifluoromethyl)pyrazol-5-yl | X² | G-2 | N-methyl-4-hydroxy-1,2,3,4-tetrahydro-1-naphthalenylamino |
| 1-methyl-4-(trifluoromethyl)imidazol-2-yl | X² | G-2 | N-methyl-4-hydroxy-1,2,3,4-tetrahydro-1-naphthalenylamino |
| 2,5-dichlorophenyl | X² | G-2 | N,2-dimethyl-1,2,3,4-tetrahydro-1-naphthalenylamino |
| 2-chloro-5-(trifluoromethyl)phenyl | X² | G-2 | N,2-dimethyl-1,2,3,4-tetrahydro-1-naphthalenylamino |
| 2,5-dimethylphenyl | X² | G-2 | N,2-dimethyl-1,2,3,4-tetrahydro-1-naphthalenylamino |
| 2-methyl-5-(trifluoromethyl)phenyl | X² | G-2 | N,2-dimethyl-1,2,3,4-tetrahydro-1-naphthalenylamino |
| 3,5-dimethylpyrazol-1-yl | X² | G-2 | N,2-dimethyl-1,2,3,4-tetrahydro-1-naphthalenylamino |
| 5-methyl-3-(trifluoromethyl)pyrazol-1-yl | X² | G-2 | N,2-dimethyl-1,2,3,4-tetrahydro-1-naphthalenylamino |
| 3,5-dichloropyrazol-1-yl | X² | G-2 | N,2-dimethyl-1,2,3,4-tetrahydro-1-naphthalenylamino |
| 5-chloro-3-(trifluoromethyl)pyrazol-1-yl | X² | G-2 | N,2-dimethyl-1,2,3,4-tetrahydro-1-naphthalenylamino |
| 3,5-dibromopyrazol-1-yl | X² | G-2 | N,2-dimethyl-1,2,3,4-tetrahydro-1-naphthalenylamino |
| 5-bromo-3-(trifluoromethyl)pyrazol-1-yl | X² | G-2 | N,2-dimethyl-1,2,3,4-tetrahydro-1-naphthalenylamino |
| 3,5-diethylpyrazol-1-yl | X² | G-2 | N,2-dimethyl-1,2,3,4-tetrahydro-1-naphthalenylamino |
| 5-ethyl-3-(trifluoromethyl)pyrazol-1-yl | X² | G-2 | N,2-dimethyl-1,2,3,4-tetrahydro-1-naphthalenylamino |
| 3,5-bis-(trifluoromethyl)pyrazol-1-yl | X² | G-2 | N,2-dimethyl-1,2,3,4-tetrahydro-1-naphthalenylamino |
| 1-methyl-3-(trifluoromethyl)pyrazol-5-yl | X² | G-2 | N,2-dimethyl-1,2,3,4-tetrahydro-1-naphthalenylamino |
| 1-methyl-4-(trifluoromethyl)imidazol-2-yl | X² | G-2 | N,2-dimethyl-1,2,3,4-tetrahydro-1-naphthalenylamino |

TABLE 10-continued

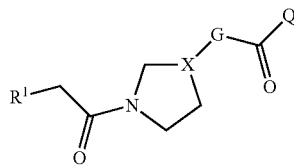

| R¹ | X* | G** | Q |
|---|---|---|---|
| 2,5-dichlorophenyl | X² | G-2 | N,2,2-trimethyl-1,2,3,4-tetrahydro-1-naphthalenylamino |
| 2-chloro-5-(trifluoromethyl)phenyl | X² | G-2 | N,2,2-trimethyl-1,2,3,4-tetrahydro-1-naphthalenylamino |
| 2,5-dimethylphenyl | X² | G-2 | N,2,2-trimethyl-1,2,3,4-tetrahydro-1-naphthalenylamino |
| 2-methyl-5-(trifluoromethyl)phenyl | X² | G-2 | N,2,2-trimethyl-1,2,3,4-tetrahydro-1-naphthalenylamino |
| 3,5-dimethylpyrazol-1-yl | X² | G-2 | N,2,2-trimethyl-1,2,3,4-tetrahydro-1-naphthalenylamino |
| 5-methyl-3-(trifluoromethyl)pyrazol-1-yl | X² | G-2 | N,2,2-trimethyl-1,2,3,4-tetrahydro-1-naphthalenylamino |
| 3,5-dichloropyrazol-1-yl | X² | G-2 | N,2,2-trimethyl-1,2,3,4-tetrahydro-1-naphthalenylamino |
| 5-chloro-3-(trifluoromethyl)pyrazol-1-yl | X² | G-2 | N,2,2-trimethyl-1,2,3,4-tetrahydro-1-naphthalenylamino |
| 3,5-dibromopyrazol-1-yl | X² | G-2 | N,2,2-trimethyl-1,2,3,4-tetrahydro-1-naphthalenylamino |
| 5-bromo-3-(trifluoromethyl)pyrazol-1-yl | X² | G-2 | N,2,2-trimethyl-1,2,3,4-tetrahydro-1-naphthalenylamino |
| 3,5-diethylpyrazol-1-yl | X² | G-2 | N,2,2-trimethyl-1,2,3,4-tetrahydro-1-naphthalenylamino |
| 5-ethyl-3-(trifluoromethyl)pyrazol-1-yl | X² | G-2 | N,2,2-trimethyl-1,2,3,4-tetrahydro-1-naphthalenylamino |
| 3,5-bis-(trifluoromethyl)pyrazol-1-yl | X² | G-2 | N,2,2-trimethyl-1,2,3,4-tetrahydro-1-naphthalenylamino |
| 1-methyl-3-(trifluoromethyl)pyrazol-5-yl | X² | G-2 | N,2,2-trimethyl-1,2,3,4-tetrahydro-1-naphthalenylamino |
| 1-methyl-4-(trifluoromethyl)imidazol-2-yl | X² | G-2 | N,2,2-trimethyl-1,2,3,4-tetrahydro-1-naphthalenylamino |
| 2,5-dichlorophenyl | X² | G-2 | N-methyl-4-oxo-1,2,3,4-tetrahydro-1-naphthalenylamino |
| 2-chloro-5-(trifluoromethyl)phenyl | X² | G-2 | N-methyl-4-oxo-1,2,3,4-tetrahydro-1-naphthalenylamino |
| 2,5-dimethylphenyl | X² | G-2 | N-methyl-4-oxo-1,2,3,4-tetrahydro-1-naphthalenylamino |
| 2-methyl-5-(trifluoromethyl)phenyl | X² | G-2 | N-methyl-4-oxo-1,2,3,4-tetrahydro-1-naphthalenylamino |
| 3,5-dimethylpyrazol-1-yl | X² | G-2 | N-methyl-4-oxo-1,2,3,4-tetrahydro-1-naphthalenylamino |
| 5-methyl-3-(trifluoromethyl)pyrazol-1-yl | X² | G-2 | N-methyl-4-oxo-1,2,3,4-tetrahydro-1-naphthalenylamino |
| 3,5-dichloropyrazol-1-yl | X² | G-2 | N-methyl-4-oxo-1,2,3,4-tetrahydro-1-naphthalenylamino |
| 5-chloro-3-(trifluoromethyl)pyrazol-1-yl | X² | G-2 | N-methyl-4-oxo-1,2,3,4-tetrahydro-1-naphthalenylamino |
| 3,5-dibromopyrazol-1-yl | X² | G-2 | N-methyl-4-oxo-1,2,3,4-tetrahydro-1-naphthalenylamino |
| 5-bromo-3-(trifluoromethyl)pyrazol-1-yl | X² | G-2 | N-methyl-4-oxo-1,2,3,4-tetrahydro-1-naphthalenylamino |
| 3,5-diethylpyrazol-1-yl | X² | G-2 | N-methyl-4-oxo-1,2,3,4-tetrahydro-1-naphthalenylamino |
| 5-ethyl-3-(trifluoromethyl)pyrazol-1-yl | X² | G-2 | N-methyl-4-oxo-1,2,3,4-tetrahydro-1-naphthalenylamino |
| 3,5-bis-(trifluoromethyl)pyrazol-1-yl | X² | G-2 | N-methyl-4-oxo-1,2,3,4-tetrahydro-1-naphthalenylamino |
| 1-methyl-3-(trifluoromethyl)pyrazol-5-yl | X² | G-2 | N-methyl-4-oxo-1,2,3,4-tetrahydro-1-naphthalenylamino |
| 1-methyl-4-(trifluoromethyl)imidazol-2-yl | X² | G-2 | N-methyl-4-oxo-1,2,3,4-tetrahydro-1-naphthalenylamino |
| 2,5-dichlorophenyl | X² | G-2 | N,2-dimethyl-1-indanylamino |
| 2-chloro-5-(trifluoromethyl)phenyl | X² | G-2 | N,2-dimethyl-1-indanylamino |
| 2,5-dimethylphenyl | X² | G-2 | N,2-dimethyl-1-indanylamino |
| 2-methyl-5-(trifluoromethyl)phenyl | X² | G-2 | N,2-dimethyl-1-indanylamino |
| 3,5-dimethylpyrazol-1-yl | X² | G-2 | N,2-dimethyl-1-indanylamino |
| 5-methyl-3-(trifluoromethyl)pyrazol-1-yl | X² | G-2 | N,2-dimethyl-1-indanylamino |
| 3,5-dichloropyrazol-1-yl | X² | G-2 | N,2-dimethyl-1-indanylamino |
| 5-chloro-3-(trifluoromethyl)pyrazol-1-yl | X² | G-2 | N,2-dimethyl-1-indanylamino |
| 3,5-dibromopyrazol-1-yl | X² | G-2 | N,2-dimethyl-1-indanylamino |

TABLE 10-continued

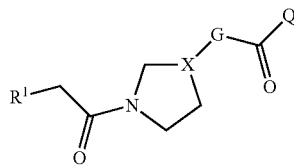

| R¹ | X* | G** | Q |
|---|---|---|---|
| 5-bromo-3-(trifluoromethyl)pyrazol-1-yl | X² | G-2 | N,2-dimethyl-1-indanylamino |
| 3,5-diethylpyrazol-1-yl | X² | G-2 | N,2-dimethyl-1-indanylamino |
| 5-ethyl-3-(trifluoromethyl)pyrazol-1-yl | X² | G-2 | N,2-dimethyl-1-indanylamino |
| 3,5-bis-(trifluoromethyl)pyrazol-1-yl | X² | G-2 | N,2-dimethyl-1-indanylamino |
| 1-methyl-3-(trifluoromethyl)pyrazol-5-yl | X² | G-2 | N,2-dimethyl-1-indanylamino |
| 1-methyl-4-(trifluoromethyl)imidazol-2-yl | X² | G-2 | N,2-dimethyl-1-indanylamino |
| 2,5-dichlorophenyl | X² | G-2 | N,2,2-trimethyl-1-indanylamino |
| 2-chloro-5-(trifluoromethyl)phenyl | X² | G-2 | N,2,2-trimethyl-1-indanylamino |
| 2,5-dimethylphenyl | X² | G-2 | N,2,2-trimethyl-1-indanylamino |
| 2-methyl-5-(trifluoromethyl)phenyl | X² | G-2 | N,2,2-trimethyl-1-indanylamino |
| 3,5-dimethylpyrazol-1-yl | X² | G-2 | N,2,2-trimethyl-1-indanylamino |
| 5-methyl-3-(trifluoromethyl)pyrazol-1-yl | X² | G-2 | N,2,2-trimethyl-1-indanylamino |
| 3,5-dichloropyrazol-1-yl | X² | G-2 | N,2,2-trimethyl-1-indanylamino |
| 5-chloro-3-(trifluoromethyl)pyrazol-1-yl | X² | G-2 | N,2,2-trimethyl-1-indanylamino |
| 3,5-dibromopyrazol-1-yl | X² | G-2 | N,2,2-trimethyl-1-indanylamino |
| 5-bromo-3-(trifluoromethyl)pyrazol-1-yl | X² | G-2 | N,2,2-trimethyl-1-indanylamino |
| 3,5-diethylpyrazol-1-yl | X² | G-2 | N,2,2-trimethyl-1-indanylamino |
| 5-ethyl-3-(trifluoromethyl)pyrazol-1-yl | X² | G-2 | N,2,2-trimethyl-1-indanylamino |
| 3,5-bis-(trifluoromethyl)pyrazol-1-yl | X² | G-2 | N,2,2-trimethyl-1-indanylamino |
| 1-methyl-3-(trifluoromethyl)pyrazol-5-yl | X² | G-2 | N,2,2-trimethyl-1-indanylamino |
| 1-methyl-4-(trifluoromethyl)imidazol-2-yl | X² | G-2 | N,2,2-trimethyl-1-indanylamino |
| 2,5-dichlorophenyl | X² | G-2 | N-methyl-3-hydroxy-1-indanylamino |
| 2-chloro-5-(trifluoromethyl)phenyl | X² | G-2 | N-methyl-3-hydroxy-1-indanylamino |
| 2,5-dimethylphenyl | X² | G-2 | N-methyl-3-hydroxy-1-indanylamino |
| 2-methyl-5-(trifluoromethyl)phenyl | X² | G-2 | N-methyl-3-hydroxy-1-indanylamino |
| 3,5-dimethylpyrazol-1-yl | X² | G-2 | N-methyl-3-hydroxy-1-indanylamino |
| 5-methyl-3-(trifluoromethyl)pyrazol-1-yl | X² | G-2 | N-methyl-3-hydroxy-1-indanylamino |
| 3,5-dichloropyrazol-1-yl | X² | G-2 | N-methyl-3-hydroxy-1-indanylamino |
| 5-chloro-3-(trifluoromethyl)pyrazol-1-yl | X² | G-2 | N-methyl-3-hydroxy-1-indanylamino |
| 3,5-dibromopyrazol-1-yl | X² | G-2 | N-methyl-3-hydroxy-1-indanylamino |
| 5-bromo-3-(trifluoromethyl)pyrazol-1-yl | X² | G-2 | N-methyl-3-hydroxy-1-indanylamino |
| 3,5-diethylpyrazol-1-yl | X² | G-2 | N-methyl-3-hydroxy-1-indanylamino |
| 5-ethyl-3-(trifluoromethyl)pyrazol-1-yl | X² | G-2 | N-methyl-3-hydroxy-1-indanylamino |
| 3,5-bis-(trifluoromethyl)pyrazol-1-yl | X² | G-2 | N-methyl-3-hydroxy-1-indanylamino |
| 1-methyl-3-(trifluoromethyl)pyrazol-5-yl | X² | G-2 | N-methyl-3-hydroxy-1-indanylamino |
| 1-methyl-4-(trifluoromethyl)imidazol-2-yl | X² | G-2 | N-methyl-3-hydroxy-1-indanylamino |
| 2,5-dichlorophenyl | X² | G-2 | N-methyl-3-oxo-1-indanylamino |
| 2-chloro-5-(trifluoromethyl)phenyl | X² | G-2 | N-methyl-3-oxo-1-indanylamino |
| 2,5-dimethylphenyl | X² | G-2 | N-methyl-3-oxo-1-indanylamino |
| 2-methyl-5-(trifluoromethyl)phenyl | X² | G-2 | N-methyl-3-oxo-1-indanylamino |
| 3,5-dimethylpyrazol-1-yl | X² | G-2 | N-methyl-3-oxo-1-indanylamino |
| 5-methyl-3-(trifluoromethyl)pyrazol-1-yl | X² | G-2 | N-methyl-3-oxo-1-indanylamino |
| 3,5-dichloropyrazol-1-yl | X² | G-2 | N-methyl-3-oxo-1-indanylamino |
| 5-chloro-3-(trifluoromethyl)pyrazol-1-yl | X² | G-2 | N-methyl-3-oxo-1-indanylamino |
| 3,5-dibromopyrazol-1-yl | X² | G-2 | N-methyl-3-oxo-1-indanylamino |
| 5-bromo-3-(trifluoromethyl)pyrazol-1-yl | X² | G-2 | N-methyl-3-oxo-1-indanylamino |
| 3,5-diethylpyrazol-1-yl | X² | G-2 | N-methyl-3-oxo-1-indanylamino |
| 5-ethyl-3-(trifluoromethyl)pyrazol-1-yl | X² | G-2 | N-methyl-3-oxo-1-indanylamino |
| 3,5-bis-(trifluoromethyl)pyrazol-1-yl | X² | G-2 | N-methyl-3-oxo-1-indanylamino |
| 1-methyl-3-(trifluoromethyl)pyrazol-5-yl | X² | G-2 | N-methyl-3-oxo-1-indanylamino |
| 1-methyl-4-(trifluoromethyl)imidazol-2-yl | X² | G-2 | N-methyl-3-oxo-1-indanylamino |
| 2,5-dichlorophenyl | X³ | G-1 | N-methyl-4-hydroxy-1,2,3,4-tetrahydro-1-naphthalenylamino |
| 2-chloro-5-(trifluoromethyl)phenyl | X³ | G-1 | N-methyl-4-hydroxy-1,2,3,4-tetrahydro-1-naphthalenylamino |
| 2,5-dimethylphenyl | X³ | G-1 | N-methyl-4-hydroxy-1,2,3,4-tetrahydro-1-naphthalenylamino |
| 2-methyl-5-(trifluoromethyl)phenyl | X³ | G-1 | N-methyl-4-hydroxy-1,2,3,4-tetrahydro-1-naphthalenylamino |
| 3,5-dimethylpyrazol-1-yl | X³ | G-1 | N-methyl-4-hydroxy-1,2,3,4-tetrahydro-1-naphthalenylamino |
| 5-methyl-3-(trifluoromethyl)pyrazol-1-yl | X³ | G-1 | N-methyl-4-hydroxy-1,2,3,4-tetrahydro-1-naphthalenylamino |
| 3,5-dichloropyrazol-1-yl | X³ | G-1 | N-methyl-4-hydroxy-1,2,3,4-tetrahydro-1-naphthalenylamino |
| 5-chloro-3-(trifluoromethyl)pyrazol-1-yl | X³ | G-1 | N-methyl-4-hydroxy-1,2,3,4-tetrahydro-1-naphthalenylamino |
| 3,5-dibromopyrazol-1-yl | X³ | G-1 | N-methyl-4-hydroxy-1,2,3,4-tetrahydro-1-naphthalenylamino |

TABLE 10-continued

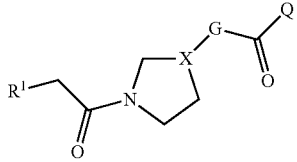

| R¹ | X* | G** | Q |
|---|---|---|---|
| 5-bromo-3-(trifluoromethyl)pyrazol-1-yl | X³ | G-1 | N-methyl-4-hydroxy-1,2,3,4-tetrahydro-1-naphthalenylamino |
| 3,5-diethylpyrazol-1-yl | X³ | G-1 | N-methyl-4-hydroxy-1,2,3,4-tetrahydro-1-naphthalenylamino |
| 5-ethyl-3-(trifluoromethyl)pyrazol-1-yl | X³ | G-1 | N-methyl-4-hydroxy-1,2,3,4-tetrahydro-1-naphthalenylamino |
| 3,5-bis-(trifluoromethyl)pyrazol-1-yl | X³ | G-1 | N-methyl-4-hydroxy-1,2,3,4-tetrahydro-1-naphthalenylamino |
| 1-methyl-3-(trifluoromethyl)pyrazol-5-yl | X³ | G-1 | N-methyl-4-hydroxy-1,2,3,4-tetrahydro-1-naphthalenylamino |
| 1-methyl-4-(trifluoromethyl)imidazol-2-yl | X³ | G-1 | N-methyl-4-hydroxy-1,2,3,4-tetrahydro-1-naphthalenylamino |
| 2,5-dichlorophenyl | X³ | G-1 | N,2-dimethyl-1,2,3,4-tetrahydro-1-naphthalenylamino |
| 2-chloro-5-(trifluoromethyl)phenyl | X³ | G-1 | N,2-dimethyl-1,2,3,4-tetrahydro-1-naphthalenylamino |
| 2,5-dimethylphenyl | X³ | G-1 | N,2-dimethyl-1,2,3,4-tetrahydro-1-naphthalenylamino |
| 2-methyl-5-(trifluoromethyl)phenyl | X³ | G-1 | N,2-dimethyl-1,2,3,4-tetrahydro-1-naphthalenylamino |
| 3,5-dimethylpyrazol-1-yl | X³ | G-1 | N,2-dimethyl-1,2,3,4-tetrahydro-1-naphthalenylamino |
| 5-methyl-3-(trifluoromethyl)pyrazol-1-yl | X³ | G-1 | N,2-dimethyl-1,2,3,4-tetrahydro-1-naphthalenylamino |
| 3,5-dichloropyrazol-1-yl | X³ | G-1 | N,2-dimethyl-1,2,3,4-tetrahydro-1-naphthalenylamino |
| 5-chloro-3-(trifluoromethyl)pyrazol-1-yl | X³ | G-1 | N,2-dimethyl-1,2,3,4-tetrahydro-1-naphthalenylamino |
| 3,5-dibromopyrazol-1-yl | X³ | G-1 | N,2-dimethyl-1,2,3,4-tetrahydro-1-naphthalenylamino |
| 5-bromo-3-(trifluoromethyl)pyrazol-1-yl | X³ | G-1 | N,2-dimethyl-1,2,3,4-tetrahydro-1-naphthalenylamino |
| 3,5-diethylpyrazol-1-yl | X³ | G-1 | N,2-dimethyl-1,2,3,4-tetrahydro-1-naphthalenylamino |
| 5-ethyl-3-(trifluoromethyl)pyrazol-1-yl | X³ | G-1 | N,2-dimethyl-1,2,3,4-tetrahydro-1-naphthalenylamino |
| 3,5-bis-(trifluoromethyl)pyrazol-1-yl | X³ | G-1 | N,2-dimethyl-1,2,3,4-tetrahydro-1-naphthalenylamino |
| 1-methyl-3-(trifluoromethyl)pyrazol-5-yl | X³ | G-1 | N,2-dimethyl-1,2,3,4-tetrahydro-1-naphthalenylamino |
| 1-methyl-4-(trifluoromethyl)imidazol-2-yl | X³ | G-1 | N,2-dimethyl-1,2,3,4-tetrahydro-1-naphthalenylamino |
| 2,5-dichlorophenyl | X³ | G-1 | N,2,2-trimethyl-1,2,3,4-tetrahydro-1-naphthalenylamino |
| 2-chloro-5-(trifluoromethyl)phenyl | X³ | G-1 | N,2,2-trimethyl-1,2,3,4-tetrahydro-1-naphthalenylamino |
| 2,5-dimethylphenyl | X³ | G-1 | N,2,2-trimethyl-1,2,3,4-tetrahydro-1-naphthalenylamino |
| 2-methyl-5-(trifluoromethyl)phenyl | X³ | G-1 | N,2,2-trimethyl-1,2,3,4-tetrahydro-1-naphthalenylamino |
| 3,5-dimethylpyrazol-1-yl | X³ | G-1 | N,2,2-trimethyl-1,2,3,4-tetrahydro-1-naphthalenylamino |
| 5-methyl-3-(trifluoromethyl)pyrazol-1-yl | X³ | G-1 | N,2,2-trimethyl-1,2,3,4-tetrahydro-1-naphthalenylamino |
| 3,5-dichloropyrazol-1-yl | X³ | G-1 | N,2,2-trimethyl-1,2,3,4-tetrahydro-1-naphthalenylamino |
| 5-chloro-3-(trifluoromethyl)pyrazol-1-yl | X³ | G-1 | N,2,2-trimethyl-1,2,3,4-tetrahydro-1-naphthalenylamino |
| 3,5-dibromopyrazol-1-yl | X³ | G-1 | N,2,2-trimethyl-1,2,3,4-tetrahydro-1-naphthalenylamino |
| 5-bromo-3-(trifluoromethyl)pyrazol-1-yl | X³ | G-1 | N,2,2-trimethyl-1,2,3,4-tetrahydro-1-naphthalenylamino |
| 3,5-diethylpyrazol-1-yl | X³ | G-1 | N,2,2-trimethyl-1,2,3,4-tetrahydro-1-naphthalenylamino |
| 5-ethyl-3-(trifluoromethyl)pyrazol-1-yl | X³ | G-1 | N,2,2-trimethyl-1,2,3,4-tetrahydro-1-naphthalenylamino |
| 3,5-bis-(trifluoromethyl)pyrazol-1-yl | X³ | G-1 | N,2,2-trimethyl-1,2,3,4-tetrahydro-1-naphthalenylamino |

TABLE 10-continued

| R¹ | X* | G** | Q |
|---|---|---|---|
| 1-methyl-3-(trifluoromethyl)pyrazol-5-yl | X³ | G-1 | N,2,2-trimethyl-1,2,3,4-tetrahydro-1-naphthalenylamino |
| 1-methyl-4-(trifluoromethyl)imidazol-2-yl | X³ | G-1 | N,2,2-trimethyl-1,2,3,4-tetrahydro-1-naphthalenylamino |
| 2,5-dichlorophenyl | X³ | G-1 | N-methyl-4-oxo-1,2,3,4-tetrahydro-1-naphthalenylamino |
| 2-chloro-5-(trifluoromethyl)phenyl | X³ | G-1 | N-methyl-4-oxo-1,2,3,4-tetrahydro-1-naphthalenylamino |
| 2,5-dimethylphenyl | X³ | G-1 | N-methyl-4-oxo-1,2,3,4-tetrahydro-1-naphthalenylamino |
| 2-methyl-5-(trifluoromethyl)phenyl | X³ | G-1 | N-methyl-4-oxo-1,2,3,4-tetrahydro-1-naphthalenylamino |
| 3,5-dimethylpyrazol-1-yl | X³ | G-1 | N-methyl-4-oxo-1,2,3,4-tetrahydro-1-naphthalenylamino |
| 5-methyl-3-(trifluoromethyl)pyrazol-1-yl | X³ | G-1 | N-methyl-4-oxo-1,2,3,4-tetrahydro-1-naphthalenylamino |
| 3,5-dichloropyrazol-1-yl | X³ | G-1 | N-methyl-4-oxo-1,2,3,4-tetrahydro-1-naphthalenylamino |
| 5-chloro-3-(trifluoromethyl)pyrazol-1-yl | X³ | G-1 | N-methyl-4-oxo-1,2,3,4-tetrahydro-1-naphthalenylamino |
| 3,5-dibromopyrazol-1-yl | X³ | G-1 | N-methyl-4-oxo-1,2,3,4-tetrahydro-1-naphthalenylamino |
| 5-bromo-3-(trifluoromethyl)pyrazol-1-yl | X³ | G-1 | N-methyl-4-oxo-1,2,3,4-tetrahydro-1-naphthalenylamino |
| 3,5-diethylpyrazol-1-yl | X³ | G-1 | N-methyl-4-oxo-1,2,3,4-tetrahydro-1-naphthalenylamino |
| 5-ethyl-3-(trifluoromethyl)pyrazol-1-yl | X³ | G-1 | N-methyl-4-oxo-1,2,3,4-tetrahydro-1-naphthalenylamino |
| 3,5-bis-(trifluoromethyl)pyrazol-1-yl | X³ | G-1 | N-methyl-4-oxo-1,2,3,4-tetrahydro-1-naphthalenylamino |
| 1-methyl-3-(trifluoromethyl)pyrazol-5-yl | X³ | G-1 | N-methyl-4-oxo-1,2,3,4-tetrahydro-1-naphthalenylamino |
| 1-methyl-4-(trifluoromethyl)imidazol-2-yl | X³ | G-1 | N-methyl-4-oxo-1,2,3,4-tetrahydro-1-naphthalenylamino |
| 2,5-dichlorophenyl | X³ | G-1 | N,2-dimethyl-1-indanylamino |
| 2-chloro-5-(trifluoromethyl)phenyl | X³ | G-1 | N,2-dimethyl-1-indanylamino |
| 2,5-dimethylphenyl | X³ | G-1 | N,2-dimethyl-1-indanylamino |
| 2-methyl-5-(trifluoromethyl)phenyl | X³ | G-1 | N,2-dimethyl-1-indanylamino |
| 3,5-dimethylpyrazol-1-yl | X³ | G-1 | N,2-dimethyl-1-indanylamino |
| 5-methyl-3-(trifluoromethyl)pyrazol-1-yl | X³ | G-1 | N,2-dimethyl-1-indanylamino |
| 3,5-dichloropyrazol-1-yl | X³ | G-1 | N,2-dimethyl-1-indanylamino |
| 5-chloro-3-(trifluoromethyl)pyrazol-1-yl | X³ | G-1 | N,2-dimethyl-1-indanylamino |
| 3,5-dibromopyrazol-1-yl | X³ | G-1 | N,2-dimethyl-1-indanylamino |
| 5-bromo-3-(trifluoromethyl)pyrazol-1-yl | X³ | G-1 | N,2-dimethyl-1-indanylamino |
| 3,5-diethylpyrazol-1-yl | X³ | G-1 | N,2-dimethyl-1-indanylamino |
| 5-ethyl-3-(trifluoromethyl)pyrazol-1-yl | X³ | G-1 | N,2-dimethyl-1-indanylamino |
| 3,5-bis-(trifluoromethyl)pyrazol-1-yl | X³ | G-1 | N,2-dimethyl-1-indanylamino |
| 1-methyl-3-(trifluoromethyl)pyrazol-5-yl | X³ | G-1 | N,2-dimethyl-1-indanylamino |
| 1-methyl-4-(trifluoromethyl)imidazol-2-yl | X³ | G-1 | N,2-dimethyl-1-indanylamino |
| 2,5-dichlorophenyl | X³ | G-1 | N,2,2-trimethyl-1-indanylamino |
| 2-chloro-5-(trifluoromethyl)phenyl | X³ | G-1 | N,2,2-trimethyl-1-indanylamino |
| 2,5-dimethylphenyl | X³ | G-1 | N,2,2-trimethyl-1-indanylamino |
| 2-methyl-5-(trifluoromethyl)phenyl | X³ | G-1 | N,2,2-trimethyl-1-indanylamino |
| 3,5-dimethylpyrazol-1-yl | X³ | G-1 | N,2,2-trimethyl-1-indanylamino |
| 5-methyl-3-(trifluoromethyl)pyrazol-1-yl | X³ | G-1 | N,2,2-trimethyl-1-indanylamino |
| 3,5-dichloropyrazol-1-yl | X³ | G-1 | N,2,2-trimethyl-1-indanylamino |
| 5-chloro-3-(trifluoromethyl)pyrazol-1-yl | X³ | G-1 | N,2,2-trimethyl-1-indanylamino |
| 3,5-dibromopyrazol-1-yl | X³ | G-1 | N,2,2-trimethyl-1-indanylamino |
| 5-bromo-3-(trifluoromethyl)pyrazol-1-yl | X³ | G-1 | N,2,2-trimethyl-1-indanylamino |
| 3,5-diethylpyrazol-1-yl | X³ | G-1 | N,2,2-trimethyl-1-indanylamino |
| 5-ethyl-3-(trifluoromethyl)pyrazol-1-yl | X³ | G-1 | N,2,2-trimethyl-1-indanylamino |
| 3,5-bis-(trifluoromethyl)pyrazol-1-yl | X³ | G-1 | N,2,2-trimethyl-1-indanylamino |
| 1-methyl-3-(trifluoromethyl)pyrazol-5-yl | X³ | G-1 | N,2,2-trimethyl-1-indanylamino |
| 1-methyl-4-(trifluoromethyl)imidazol-2-yl | X³ | G-1 | N,2,2-trimethyl-1-indanylamino |
| 2,5-dichlorophenyl | X³ | G-1 | N-methyl-3-hydroxy-1-indanylamino |
| 2-chloro-5-(trifluoromethyl)phenyl | X³ | G-1 | N-methyl-3-hydroxy-1-indanylamino |
| 2,5-dimethylphenyl | X³ | G-1 | N-methyl-3-hydroxy-1-indanylamino |
| 2-methyl-5-(trifluoromethyl)phenyl | X³ | G-1 | N-methyl-3-hydroxy-1-indanylamino |
| 3,5-dimethylpyrazol-1-yl | X³ | G-1 | N-methyl-3-hydroxy-1-indanylamino |

TABLE 10-continued

| R¹ | X* | G** | Q |
|---|---|---|---|
| 5-methyl-3-(trifluoromethyl)pyrazol-1-yl | X³ | G-1 | N-methyl-3-hydroxy-1-indanylamino |
| 3,5-dichloropyrazol-1-yl | X³ | G-1 | N-methyl-3-hydroxy-1-indanylamino |
| 5-chloro-3-(trifluoromethyl)pyrazol-1-yl | X³ | G-1 | N-methyl-3-hydroxy-1-indanylamino |
| 3,5-dibromopyrazol-1-yl | X³ | G-1 | N-methyl-3-hydroxy-1-indanylamino |
| 5-bromo-3-(trifluoromethyl)pyrazol-1-yl | X³ | G-1 | N-methyl-3-hydroxy-1-indanylamino |
| 3,5-diethylpyrazol-1-yl | X³ | G-1 | N-methyl-3-hydroxy-1-indanylamino |
| 5-ethyl-3-(trifluoromethyl)pyrazol-1-yl | X³ | G-1 | N-methyl-3-hydroxy-1-indanylamino |
| 3,5-bis-(trifluoromethyl)pyrazol-1-yl | X³ | G-1 | N-methyl-3-hydroxy-1-indanylamino |
| 1-methyl-3-(trifluoromethyl)pyrazol-5-yl | X³ | G-1 | N-methyl-3-hydroxy-1-indanylamino |
| 1-methyl-4-(trifluoromethyl)imidazol-2-yl | X³ | G-1 | N-methyl-3-hydroxy-1-indanylamino |
| 2,5-dichlorophenyl | X³ | G-1 | N-methyl-3-oxo-1-indanylamino |
| 2-chloro-5-(trifluoromethyl)phenyl | X³ | G-1 | N-methyl-3-oxo-1-indanylamino |
| 2,5-dimethylphenyl | X³ | G-1 | N-methyl-3-oxo-1-indanylamino |
| 2-methyl-5-(trifluoromethyl)phenyl | X³ | G-1 | N-methyl-3-oxo-1-indanylamino |
| 3,5-dimethylpyrazol-1-yl | X³ | G-1 | N-methyl-3-oxo-1-indanylamino |
| 5-methyl-3-(trifluoromethyl)pyrazol-1-yl | X³ | G-1 | N-methyl-3-oxo-1-indanylamino |
| 3,5-dichloropyrazol-1-yl | X³ | G-1 | N-methyl-3-oxo-1-indanylamino |
| 5-chloro-3-(trifluoromethyl)pyrazol-1-yl | X³ | G-1 | N-methyl-3-oxo-1-indanylamino |
| 3,5-dibromopyrazol-1-yl | X³ | G-1 | N-methyl-3-oxo-1-indanylamino |
| 5-bromo-3-(trifluoromethyl)pyrazol-1-yl | X³ | G-1 | N-methyl-3-oxo-1-indanylamino |
| 3,5-diethylpyrazol-1-yl | X³ | G-1 | N-methyl-3-oxo-1-indanylamino |
| 5-ethyl-3-(trifluoromethyl)pyrazol-1-yl | X³ | G-1 | N-methyl-3-oxo-1-indanylamino |
| 3,5-bis-(trifluoromethyl)pyrazol-1-yl | X³ | G-1 | N-methyl-3-oxo-1-indanylamino |
| 1-methyl-3-(trifluoromethyl)pyrazol-5-yl | X³ | G-1 | N-methyl-3-oxo-1-indanylamino |
| 1-methyl-4-(trifluoromethyl)imidazol-2-yl | X³ | G-1 | N-methyl-3-oxo-1-indanylamino |
| 5-methyl-3-(trifluoromethyl)pyrazol-1-yl | X⁴ | G-1 | (1R)-N-methyl-1,2,3,4-tetrahydro-1-naphthalenylamino |
| 5-methyl-3-(trifluoromethyl)pyrazol-1-yl | X⁵ | G-1 | (1R)-N-methyl-1,2,3,4-tetrahydro-1-naphthalenylamino |
| 5-methyl-3-(trifluoromethyl)pyrazol-1-yl | X⁶ | G-1 | (1R)-N-methyl-1,2,3,4-tetrahydro-1-naphthalenylamino |
| 5-methyl-3-(trifluoromethyl)pyrazol-1-yl | X⁷ | G-1 | (1R)-N-methyl-1,2,3,4-tetrahydro-1-naphthalenylamino |
| 5-methyl-3-(trifluoromethyl)pyrazol-1-yl | X⁸ | G-1 | (1R)-N-methyl-1,2,3,4-tetrahydro-1-naphthalenylamino |
| 5-methyl-3-(trifluoromethyl)pyrazol-1-yl | X⁴ | G-2 | (1R)-N-methyl-1,2,3,4-tetrahydro-1-naphthalenylamino |
| 5-methyl-3-(trifluoromethyl)pyrazol-1-yl | X⁵ | G-2 | (1R)-N-methyl-1,2,3,4-tetrahydro-1-naphthalenylamino |
| 5-methyl-3-(trifluoromethyl)pyrazol-1-yl | X⁶ | G-2 | (1R)-N-methyl-1,2,3,4-tetrahydro-1-naphthalenylamino |
| 5-methyl-3-(trifluoromethyl)pyrazol-1-yl | X⁷ | G-2 | (1R)-N-methyl-1,2,3,4-tetrahydro-1-naphthalenylamino |
| 5-methyl-3-(trifluoromethyl)pyrazol-1-yl | X⁸ | G-2 | (1R)-N-methyl-1,2,3,4-tetrahydro-1-naphthalenylamino |
| 5-methyl-3-(trifluoromethyl)pyrazol-1-yl | X¹ | G-1 | N-methyl-1-phenylcycloprop-1-ylamino |
| 5-methyl-3-(trifluoromethyl)pyrazol-1-yl | X¹ | G-1 | N-methyl-1-phenylcycloprop-1-ylamino |

Notes:
*$R^2$ is H.
**$R^{3a}$ is H.

Formulation/Utility

A compound of this invention will generally be used as a fungicidal active ingredient in a composition, i.e. formulation, with at least one additional component selected from the group consisting of surfactants, solid diluents and liquid diluents, which serves as a carrier. The formulation or composition ingredients are selected to be consistent with the physical properties of the active ingredient, mode of application and environmental factors such as soil type, moisture and temperature.

Useful formulations include both liquid and solid compositions. Liquid compositions include solutions (including emulsifiable concentrates), suspensions, emulsions (including microemulsions and/or suspoemulsions) and the like, which optionally can be thickened into gels. The general types of aqueous liquid compositions are soluble concentrate, suspension concentrate, capsule suspension, concentrated emulsion, microemulsion and suspo-emulsion. The general types of nonaqueous liquid compositions are emulsifiable concentrate, microemulsifiable concentrate, dispersible concentrate and oil dispersion.

The general types of solid compositions are dusts, powders, granules, pellets, pills, pastilles, tablets, filled films (including seed coatings) and the like, which can be water-dispersible ("wettable") or water-soluble. Films and coatings formed from film-forming solutions or flowable suspensions are particularly useful for seed treatment. Active ingredient can be (micro)encapsulated and further formed into a suspension or solid formulation; alternatively the entire formulation of active ingredient can be encapsulated (or "overcoated"). Encapsulation can control or delay release of the active ingredient. An emulsifiable granule combines the advantages of both an emulsifiable concentrate formulation and a dry granular formulation. High-strength compositions are primarily used as intermediates for further formulation.

Sprayable formulations are typically extended in a suitable medium before spraying. Such liquid and solid formulations are formulated to be readily diluted in the spray medium, usually water. Spray volumes can range from about from about one to several thousand liters per hectare, but more typically are in the range from about ten to several hundred liters per hectare. Sprayable formulations can be tank mixed with water or another suitable medium for foliar treatment by aerial or ground application, or for application to the growing medium of the plant. Liquid and dry formulations can be metered directly into drip irrigation systemi or metered into the furrow during planting. Liquid and solid formulations can be applied onto vegetable seeds as seed treatments before planting to protect developing roots and other subterranean plant parts and/or foliage through systemic uptake.

The formulations will typically contain effective amounts of active ingredient, diluent and surfactant within the following approximate ranges which add up to 100 percent by weight.

| | Weight Percent | | |
|---|---|---|---|
| | Active Ingredient | Diluent | Surfactant |
| Water-Dispersible and Water-soluble Granules, Tablets and Powders. | 0.001-90 | 0-99.999 | 0-15 |
| Oil Dispersions, Suspensions, Emulsions, Solutions (including Emulsifiable Concentrates) | 1-50 | 40-99 | 0-50 |
| Dusts | 1-25 | 70-99 | 0-5 |
| Granules and Pellets | 0.001-99 | 5-99.999 | 0-15 |
| High Strength Compositions | 90-99 | 0-10 | 0-2 |

Solid diluents include, for example, clays such as bentonite, montmorillonite, attapulgite and kaolin, gypsum, cellulose, titanium dioxide, zinc oxide, starch, dextrin, sugars (e.g., lactose, sucrose), silica, talc, mica, diatomaceous earth, urea, calcium carbonate, sodium carbonate and bicarbonate, and sodium sulfate. Typical solid diluents are described in Watkins et al., *Handbook of Insecticide Dust Diluents and Carriers*, 2nd Ed., Dorland Books, Caldwell, N.J.

Liquid diluents include, for example, water, N,N-dimethylalkanamides (e.g., N,N-dimethylformamide), limonene, dimethyl sulfoxide, N-alkylpyrrolidones (e.g., N-methylpyrrolidinone), ethylene glycol, triethylene glycol, propylene glycol, dipropylene glycol, polypropylene glycol, propylene carbonate, butylene carbonate, paraffins (e.g., white mineral oils, normal paraffins, isoparaffins), alkylbenzenes, alkylnaphthalenes, glycerine, glycerol triacetate, sorbitol, triacetin, aromatic hydrocarbons, dearomatized aliphatics, alkylbenzenes, alkylnaphthalenes, ketones such as cyclohexanone, 2-heptanone, isophorone and 4-hydroxy-4-methyl-2-pentanone, acetates such as isoamyl acetate, hexyl acetate, heptyl acetate, octyl acetate, nonyl acetate, tridecyl acetate and isobornyl acetate, other esters such as alkylated lactate esters, dibasic esters and γ-butyrolactone, and alcohols, which can be linear, branched, saturated or unsaturated, such as methanol, ethanol, n-propanol, isopropyl alcohol, n-butanol, isobutyl alcohol, n-hexanol, 2-ethylhexanol, n-octanol, decanol, isodecyl alcohol, isooctadecanol, cetyl alcohol, lauryl alcohol, tridecyl alcohol, oleyl alcohol, cyclohexanol, tetrahydrofurfuryl alcohol, diacetone alcohol and benzyl alcohol. Liquid diluents also include glycerol esters of saturated and unsaturated fatty acids (typically $C_6$-$C_{22}$), such as plant seed and fruit oils (e.g., oils of olive, castor, linseed, sesame, corn (maize), peanut, sunflower, grapeseed, safflower, cottonseed, soybean, rapeseed, coconut and palm kernel), animal-sourced fats (e.g., beef tallow, pork tallow, lard, cod liver oil, fish oil), and mixtures thereof. Liquid diluents also include alkylated fatty acids (e.g., methylated, ethylated, butylated) wherein the fatty acids may be obtained by hydrolysis of glycerol esters from plant and animal sources, and can be purified by distillation. Typical liquid diluents are described in Marsden, *Solvents Guide*, 2nd Ed., Interscience, New York, 1950.

The solid and liquid compositions of the present invention often include one or more surfactants. Surfactants can be classified as nonionic, anionic or cationic. Nonionic surfactants useful for the present compositions include, but are not limited to: alcohol alkoxylates such as alcohol alkoxylates based on natural and synthetic alcohols (which may be branched or linear) and prepared from the alcohols and ethylene oxide, propylene oxide, butylene oxide or mixtures thereof; amine ethoxylates, alkanolamides and ethoxylated alkanolamides; alkoxylated triglycerides such as ethoxylated soybean, castor and rapeseed oils; alkylphenol alkoxylates such as octylphenol ethoxylates, nonylphenol ethoxylates, dinonyl phenol ethoxylates and dodecyl phenol ethoxylates (prepared from the phenols and ethylene oxide, propylene oxide, butylene oxide or mixtures thereof); block polymers prepared from ethylene oxide or propylene oxide and reverse block polymers where the terminal blocks are prepared from propylene oxide; ethoxylated fatty acids; ethoxylated fatty esters and oils; ethoxylated methyl esters; ethoxylated tristyrylphenol (including those prepared from ethylene oxide, propylene oxide, butylene oxide or mixtures thereof); fatty acid esters, glycerol esters, lanolin-based derivatives, polyethoxylate esters such as polyethoxylated sorbitan fatty acid esters, polyethoxylated sorbitol fatty acid esters and polyethoxylated glycerol fatty acid esters; other sorbitan derivatives such as sorbitan esters; polymeric surfactants such as random copolymers, block copolymers, alkyd peg (polyethylene glycol) resins, graft or comb polymers and star polymers; polyethylene glycols (pegs); polyethylene glycol fatty acid esters; silicone-based surfactants; and sugar-derivatives such as sucrose esters, alkyl polyglycosides and alkyl polysaccharides.

Useful anionic surfactants include, but are not limited to: alkylaryl sulfonic acids and their salts; carboxylated alcohol or alkylphenol ethoxylates; diphenyl sulfonate derivatives; lignin and lignin derivatives such as lignosulfonates; maleic or succinic acids or their anhydrides; olefin sulfonates; phosphate esters such as phosphate esters of alcohol alkoxylates, phosphate esters of alkylphenol alkoxylates and phosphate esters of styryl phenol ethoxylates; protein-based surfactants; sarcosine derivatives; styryl phenol ether sulfate; sulfates and sulfonates of oils and fatty acids; sulfates and sulfonates of ethoxylated alkylphenols; sulfates of alcohols; sulfates of ethoxylated alcohols; sulfonates of amines and amides such as N,N-alkyltaurates; sulfonates of benzene, cumene, toluene, xylene, and dodecyl and tridecylbenzenes; sulfonates of condensed naphthalenes; sulfonates of naphthalene and alkyl naphthalene; sulfonates of fractionated petroleum; sulfosuccinamates; and sulfosuccinates and their derivatives such as dialkyl sulfosuccinate salts.

Useful cationic surfactants include, but are not limited to: amides and ethoxylated amides; amines such as N-alkyl propanediamines, tripropylenetriamines and dipropylenetetramines, and ethoxylated amines, ethoxylated diamines and propoxylated amines (prepared from the amines and ethylene oxide, propylene oxide, butylene oxide or mixtures thereof); amine salts such as amine acetates and diamine salts; quaternary ammonium salts such as quaternary salts, ethoxylated quaternary salts and diquaternary salts; and amine oxides such as alkyldimethylamine oxides and bis-(2-hydroxyethyl)-alkylamine oxides.

Also useful for the present compositions are mixtures of nonionic and anionic surfactants or mixtures of nonionic and cationic surfactants. Nonionic, anionic and cationic surfactants and their recommended uses are disclosed in a variety of published references including *McCutcheon's Emulsifiers and Detergents*, annual American and International Editions published by McCutcheon's Division, The Manufacturing Confectioner Publishing Co.; Sisely and Wood, *Encyclopedia of Surface Active Agents*, Chemical Publ. Co., Inc., New York, 1964; and A. S. Davidson and B. Milwidsky, *Synthetic Detergents*, Seventh Edition, John Wiley and Sons, New York, 1987.

Compositions of this invention may also contain formulation auxiliaries and additives, known to those skilled in the art as formulation aids. Such formulation auxiliaries and additives may control: pH (buffers), foaming during processing (antifoams such polyorganosiloxanes (e.g., Rhodorsil® 416)), sedimentation of active ingredients (suspending agents), viscosity (thixotropic thickeners), in-container microbial growth (antimicrobials), product freezing (antifreezes), color (dyes/pigment dispersions (e.g., Pro-Ized® Colorant Red)), wash-off (film formers or stickers), evaporation (evaporation retardants), and other formulation attributes. Film formers include, for example, polyvinyl acetates, polyvinyl acetate copolymers, polyvinylpyrrolidone-vinyl acetate copolymer, polyvinyl alcohols, polyvinyl alcohol copolymers and waxes. Examples of formulation auxiliaries and additives include those listed in *McCutcheon's Volume 2: Functional Materials*, annual International and North American editions published by McCutcheon's Division, The Manufacturing Confectioner Publishing Co.; and PCT Publication WO 03/024222.

It will be evident that scope of compositions of this invention relating to Formula 1 compounds together with the scope of compositions of this invention relating to compounds having a formula corresponding to Formula 1 except that $R^1$ is 4-fluorophenyl and the scope of compositions of this invention relating to the compound of 2-[1-[(2-chlorophenyl)acetyl]-4-piperidinyl]-N-methyl-N-[(1R)-1-phenylethyl]-4-thiazolecarboxamide, corresponds to a scope of compositions of compounds having a formula corresponding to Formula 1 as described above where proviso (a) and proviso (c) are both omitted (i.e., only proviso (b) is in effect).

The compound of Formula 1 (or the compound having a formula corresponding to Formula 1 except that $R^1$ is 4-fluorophenyl or the compound of 2-[1-[(2-chlorophenyl)acetyl]-4-piperidinyl]-N-methyl-N-[(1R)-1-phenylethyl]-4-thiazolecarboxamide, as the case may be) and any other active ingredients are typically incorporated into the present compositions by dissolving the active ingredient in a solvent or by grinding in a liquid or dry diluent. Solutions, including emulsifiable concentrates, can be prepared by simply mixing the ingredients. If the solvent of a liquid composition intended for use as an emulsifiable concentrate is water-immiscible, an emulsifier is typically added to emulsify the active-containing solvent upon dilution with water. Active ingredient slurries, with particle diameters of up to 2,000 μm can be wet milled using media mills to obtain particles with average diameters below 3 μm. Aqueous slurries can be made into finished suspension concentrates (see, for example, U.S. Pat. No. 3,060,084) or further processed by spray drying to form water-dispersible granules. Dry formulations usually require dry milling processes, which produce average particle diameters in the 2 to 10 μm range. Dusts and powders can be prepared by blending and, usually, grinding as in a hammer mill or fluid-energy mill. Granules and pellets can be prepared by spraying the active material upon preformed granular carriers or by agglomeration techniques. See Browning, "Agglomeration", *Chemical Engineering*, Dec. 4, 1967, pp 147-48, *Perry's Chemical Engineer's Handbook*, 4th Ed., McGraw-Hill, New York, 1963, pages 8-57 and following, and WO 91/13546. Pellets can be prepared as described in U.S. Pat. No. 4,172,714. Water-dispersible and water-soluble granules can be prepared as taught in U.S. Pat. Nos. 4,144,050, 3,920,442 and DE 3,246,493. Tablets can be prepared as taught in U.S. Pat. Nos. 5,180,587, 5,232,701 and 5,208,030. Films can be prepared as taught in GB 2,095,558 and U.S. Pat. No. 3,299,566.

For further information regarding the art of formulation, see T. S. Woods, "The Formulator's Toolbox—Product Forms for Modern Agriculture" in *Pesticide Chemistry and Bioscience, The Food-Environment Challenge*, T. Brooks and T. R. Roberts, Eds., Proceedings of the 9th International Congress on Pesticide Chemistry, The Royal Society of Chemistry, Cambridge, 1999, pp. 120-133. See also U.S. Pat. No. 3,235,361, Col. 6, line 16 through Col. 7, line 19 and Examples 10-41; U.S. Pat. No. 3,309,192, Col. 5, line 43 through Col. 7, line 62 and Examples 8, 12, 15, 39, 41, 52, 53, 58, 132, 138-140, 162-164, 166, 167 and 169-182; U.S. Pat. No. 2,891,855, Col. 3, line 66 through Col. 5, line 17 and Examples 1-4; Klingman, *Weed Control as a Science*, John Wiley and Sons, Inc., New York, 1961, pp 81-96; Hance et al., *Weed Control Handbook*, 8th Ed., Blackwell Scientific Publications, Oxford, 1989; and *Developments in formulation technology*, PJB Publications, Richmond, UK, 2000.

In the following Examples, all percentages are by weight and all formulations are prepared in conventional ways. Compound numbers refer to compounds in Index Tables A.

EXAMPLE A

High Strength Concentrate

| | |
|---|---|
| Compound 1 | 98.5% |
| silica aerogel | 0.5% |
| synthetic amorphous fine silica | 1.0%. |

EXAMPLE B

Wettable Powder

| | |
|---|---|
| Compound 1 | 65.0% |
| dodecylphenol polyethylene glycol ether | 2.0% |
| sodium ligninsulfonate | 4.0% |
| sodium silicoaluminate | 6.0% |
| montmorillonite (calcined) | 23.0%. |

EXAMPLE C

Granule

| | |
|---|---|
| Compound 1 | 10.0% |
| attapulgite granules (low volatile matter, 0.71/0.30 mm; U.S.S. No. 25-50 sieves) | 90.0%. |

EXAMPLE D

Aqueous Suspension

| | |
|---|---|
| Compound 1 | 25.0% |
| hydrated attapulgite | 3.0% |
| crude calcium ligninsulfonate | 10.0% |
| sodium dihydrogen phosphate | 0.5% |
| water | 61.5%. |

EXAMPLE E

Extruded Pellet

| | |
|---|---|
| Compound 1 | 25.0% |
| anhydrous sodium sulfate | 10.0% |
| crude calcium ligninsulfonate | 5.0% |
| sodium alkylnaphthalenesulfonate | 1.0% |
| calcium/magnesium bentonite | 59.0%. |

EXAMPLE F

Microemulsion

| | |
|---|---|
| Compound 1 | 1.0% |
| triacetine | 30.0% |
| $C_8$-$C_{10}$ alkylpolyglycoside | 30.0% |
| glyceryl monooleate | 19.0% |
| water | 20.0%. |

EXAMPLE G

Emulsifiable Concentrate

| | |
|---|---|
| Compound 1 | 10.0% |
| $C_8$-$C_{10}$ fatty acid methyl ester | 70.0% |
| polyoxyethylene sorbitol hexoleate | 20.0%. |

Emulsifiable concentrate formulations are particularly suitable compositions for compounds of the present invention that are amorphous solids softening only a few degree above ambient temperature (e.g., Compound 149). While a wide variety of water-immiscible solvents and surfactants can be used in such emulsifiable concentrate formulations, glycerol esters such as caprylic/capric triglyceride as the solvent and mixtures of polyethylene glycol (peg) alkyd resin and sorbitol ethoxylate ester as the surfactant work especially well. Using these ingredients, the emulsifiable concentrate can be simply prepared by adding the sorbitol ethoxylate ester to the caprylic/capric triglyceride solvent, and then warming the mechanically stirred mixture to about 50° C. The compound of Formula 1 is added to the mixture, which is stirred vigorously until the Formula 1 compound completely dissolves. Heating is discontinued, the alkyd peg resin is added, and the mixture is stirred until the liquid cools to ambient temperature. Example H illustrates such a formulated composition. This formulation is highly efficacious in curing grape downy mildew and potato late blight disease.

EXAMPLE H

Emulsifiable Concentrate

| | |
|---|---|
| Compound 149 | 10.0% |
| caprylic/capric triglyceride | 70.0% |
| sorbitol ethoxylate ester | 12.0% |
| alkyd peg resin | 8.0%. |

The compounds of this invention are useful as plant disease control agents. The present invention therefore further comprises a method for controlling plant diseases caused by fungal plant pathogens comprising applying to the plant or portion thereof to be protected, or to the plant seed or seedling to be protected, an effective amount of a compound of the invention or a fungicidal composition containing said compound. The compounds and/or compositions of this invention provide control of diseases caused by a broad spectrum of fungal plant pathogens in the Basidiomycete, Ascomycete, Oomycete and Deuteromycete classes. They are effective in controlling a broad spectrum of plant diseases, particularly foliar pathogens of ornamental, turf, vegetable, field, cereal, and fruit crops. These pathogens include: Oomycetes, including *Phytophthora* diseases such as *Phytophthora infestans, Phytophthora megasperma, Phytophthora parasitica, Phytophthora cinnamoni, Phytophthora capsici; Pythium* diseases such as *Pythium aphanidermatum*; and diseases in the Peronosporaceae family, such as *Plasmopara viticola, Peronospora* spp. (including *Peronospora tabacina* and *Peronospora parasitica*), *Pseudoperonospora* spp. (including *Pseudoperonospora cubensis*), and *Bremia lactucae*; Ascomycetes, including *Alternaria* diseases such as *Alternaria solani* and *Alternaria brassicae; Guignardia* diseases such as *Guignardia bidwell; Venturia* diseases such as *Venturia inaequalis; Septoria* diseases such as *Septoria nodorum* and *Septoria tritici*; powdery mildew diseases such as *Erysiphe* spp. (including *Erysiphe graminis* and *Erysiphe polygoni*), *Uncinula necatur, Sphaerotheca fuligena*, and *Podosphaera leucotricha; Pseudocercosporella herpotrichoides; Botrytis* diseases such as *Botytis cinerea; Monilinia fructicola; Sclerotinia* diseases such as *Sclerotinia sclerotiorum; Magnaporthe grisea; Phomopsis viticola; Helminthosporium* diseases such as *Helminthosporium tritici repentis; Pyrenophora teres*; anthracnose diseases such as *Glomerella* or *Colletotrichum* spp. (such as *Colletotrichum graminicola* and *Colletotrichum orbiculare*); and *Gaeumannomyces graminis*; Basidiomycetes, including rust diseases caused by *Puccinia* spp. (such as *Puccinia recondita, Puccinia striiformis, Puccinia hordei, Puccinia graminis*, and *Puccinia arachidis*); *Hemileia vastatrix*; and *Phakopsora pachyrhizi*; other pathogens including *Rhizoctonia* spp (such as *Rhizoctonia solani*); *Fusarium* diseases such as *Fusarium roseum, Fusarium graminearum, Fusarium oxysporum; Verticillium dahliae; Sclerotiwn rolfsii; Rynchosporium secalis; Cer-* cosporidium personatum, Cercospora arachidicola* and *Cercospora beticola*; and other genera and species closely related to these pathogens. In addition to their fungicidal activity, the compositions or combinations also have activity against bacteria such as *Erwinia arnylovora; Xanthomonas campestris; Pseudomonas syringae*; and other related species. Of note is control provided to disease caused by the Ascomycete and Oomycete classes. Of particular note is control provided to disease caused by the Oomycete class.

Plant disease control is ordinarily accomplished by applying an effective amount of a compound of this invention either pre- or post-infection, to the portion of the plant to be protected such as the roots, stems, foliage, fruit, seeds, tubers or bulbs, or to the media (soil or sand) in which the plants to be protected are growing. The compounds can also be applied to the seed to protect the seed and seedling. The compounds can also be applied through irrigation water to treat plants.

Rates of application for these compounds can be influenced by many factors of the environment and should be determined under actual use conditions. Foliage can normally be protected when treated at a rate of from less than about 1 g/ha to about 5,000 g/ha of active ingredient. Seed and seedlings can normally be protected when seed is treated at a rate of from about 0.1 to about 10 g per kilogram of seed.

Compounds of this invention can also be mixed with one or more other insecticides, fungicides, nematocides, bactericides, acaricides, growth regulators, chemosterilants, seraiochemicals, repellents, attractants, pheromones, feeding stimulants or other biologically active compounds to form a multi-component pesticide giving an even broader spectrum of agricultural protection. Examples of such agricultural protectants with which compounds of this invention can be formulated are: insecticides such as abamectin, acephate, azinphos-methyl, bifenthrin, buprofezin, carbofuran, chlorfenapyr, chlorpyrifos, chlorpyrifos-methyl, cyflumetofen, cyfluthrin, beta-cyfluthrin, cyhalothrin, lambda-cyhalothrin, deltamethrin, diafenthiuron, diazinon, diflubenzuron, dimefluthrin, dimethoate, dinotefuran, esfenvalerate, fenoxycarb, fenpropathrin, fenvalerate, fipronil, flonicamid, flubendiamide, flucythrinate, tau-fluvalinate, fonophos, imidacloprid, indoxacarb, isofenphos, malathion, metaflumizone, metaldehyde, methamidophos, methidathion, methomyl, methoprene, methoxychlor, metofluthrin, monocrotophos, noviflumuron, oxamyl, parathion, parathion-methyl, permethrin, phorate, phosalone, phosmet, phosphamidon, pirimicarb, profenofos, profluthrin, pyrafluprole, pyridalyl, pyriprole, rotenone, spirodiclofen, spiromesifen, spirotetramat, sulprofos, tebufenozide, tefluthrin, terbufos, tetrachlorvinphos, thiamethoxam, thiodicarb, tralomethrin, trichlorfon and triflumuron; fungicides such as acibenzolar, aldimorph, amisulbrom, azaconazole, azoxystrobin, benalaxyl, benomyl, benthiavalicarb, benthiavalicarb-isopropyl, binomial, biphenyl, bitertanol, blasticidin-S, Bordeaux mixture (Tribasic copper sulfate), boscalid/nicobifen, bromuconazole, bupirimate, buthiobate, carboxin, carpropamid, captafol, captan, carbendazim, chloroneb, chlorothalonil, chlozolinate, clotrimazole, copper oxychloride, copper salts such as copper sulfate and copper hydroxide, cyazofamid, cyflunamid, cymoxanil, cyproconazole, cyprodinil, dichlofluanid, diclocymet, diclomezine, dicloran, diethofencarb, difenoconazole, dimethomorph, dimoxystrobin, diniconazole, diniconazole-M, dinocap, discostrobin, dithianon, dodemorph, dodine, econazole, etaconazole, edifenphos, epoxiconazole, ethaboxam, ethirimol, ethridiazole, famoxadone, fenamidone, fenarimol, fenbuconazole, fencaramid, fenfuram, fenhexamide, fenoxanil, fenpiclonil, fenpropidin, fenpropimorph, fentin acetate, fentin hydroxide, ferbam, ferfurazoate, ferimzone, fluazinam, fludioxonil, flumetover, fluopicolide, fluoxastrobin, fluquinconazole, fluquinconazole, flusilazole, flusulfamide, flutolanil, flutriafol, folpet, fosetyl-aluminum, fuberidazole, furalaxyl, furametapyr, hexaconazole, hymexazole, guazatine, imazalil, imibenconazole, iminoctadine, iodicarb, ipconazole, iprobenfos, iprodione, iprovalicarb, isoconazole, isoprothiolane, kasugamycin, kresoxim-methyl, mancozeb, mandipropamid, maneb, mapanipyrin, mefenoxam, mepronil, metalaxyl, metconazole, methasulfocarb, metiram, metominostrobin, mepanipyrim, metiram, metrafenone, miconazole, myclobutanil, neo-asozin (ferric methanearsonate), nuarimol, octhilinone, ofurace, orysastrobin, oxadixyl, oxolinic acid, oxpoconazole, oxycarboxin, paclobutrazol, penconazole, pencycuron, penthiopyrad, perfurazoate, phosphonic acid, phthalide, picobenzanaid, picoxystrobin, polyoxin, probenazole, prochloraz, procymidone, propamocarb, propamocarb-hydrochloride, propiconazole, propineb, proquinazid, prothioconazole, pyraclostrobin, pryazophos, pyrifenox, pyrimethanil, pyrifenox, pyrolnitrine, pyroquilon, quinconazole, quinoxyfen, quintozene, silthiofam, simeconazole, spiroxamine, streptomycin, sulfur, tebuconazole, techrazene, tecloftalam, tecnazene, tetraconazole, thiabendazole, thifluzamide, thiophanate, thiophanate-methyl, thiram, tiadinil, tolclofos-methyl, tolyfluanid, triadimefon, triadimenol, triarimol, triazoxide, tridemorph, trimoprhamide tricyclazole, trifloxystrobin, triforine, triticonazole, uniconazole, validamycin, vinclozolin, zineb, ziram, and zoxamide, nematocides such as aldoxycarb and fenamiphos; bactericides such as streptomycin; acaricides such as amitraz, chinomethionat, chlorobenzilate, cyhexatin, dicofol, dienochlor, etoxazole, fenazaquin, fenbutatin oxide, fenpropathrin, fenpyroximate, hexythiazox, propargite, pyridaben and tebufenpyrad; and biological agents such as *Bacillus thuringiensis, Bacillus thuringiensis* delta endotoxin, baculovirus, and entomopathogenic bacteria, virus and fungi. Descriptions of various commercially available compounds listed above may be found in *The Pesticide Manual, Twelfth Edition*, C. D. S. Thomlin, ed., British Crop Protection Council, 2000. For embodiments where one or more of these various mixing partners are used, the weight ratio of these various mixing partners (in total) to the compound of Formula 1 is typically between about 1:100 and about 3000:1. Of note are weight ratios between about 1:30 and about 300:1 (for example ratios between about 1:1 and about 30:1). It will be evident that including these additional components may expand the spectrum of diseases controlled beyond the spectrum controlled by the compound of Formula 1 alone.

Of note are combinations of a compound of Formula 1, a compound having a formula corresponding to Formula 1 except that $R^1$ is 4-fluorophenyl and/or the compound of 2-[1-[(2-chlorophenyl)acetyl]-4-piperidinyl]-N-methyl-N-[(1R)-1-phenylethyl]-4-thiazolecarboxamide with at least one other fungicide. Of particular note are such compositions where the other fungicide has different site of action with at least one other fungicide. Of particular note are compositions which in addition to compound of Formula 1 (or the compound having a formula corresponding to Formula 1 except that $R^1$ is 4-fluorophenyl or the compound of 2-[1-[(2-chlorophenyl)acetyl]-4-piperidinyl]-N-methyl-N-[(1R)-1-phenylethyl]-4-thiazolecarboxamide, as the case may be) include at least one compound selected from the group consisting of
(1) alkylenebis(dithiocarbamate) fungicides;
(2) cymoxanil;
(3) phenylamide fungicides;
(4) pyrimidinone fungicides;
(5) chlorothalonil;

(6) carboxamides acting at complex II of the fungal mitochondrial respiratory electron transfer site;
(7) quinoxyfen;
(8) metrafenone;
(9) cyflufenamid;
(10) cyprodinil;
(11) copper compounds;
(12) phthalimide fungicides;
(13) fosetyl-aluminum;
(14) benzimidazole fungicides;
(15) cyazofamid;
(16) fluazinam;
(17) iprovalicarb;
(18) propamocarb;
(19) validomycin;
(20) dichlorophenyl dicarboximide fungicides;
(21) zoxamide;
(22) fluopicolide;
(23) mandipropamid;
(24) carboxylic acid amides acting on phospholipid biosynthesis and cell wall deposition;
(25) dimethomorph;
(26) non-DMI sterol biosynthesis inhibitors;
(27) inhibitors of demethylase in sterol biosynthesis;
(28) bc$_1$ complex fungicides; and agriculturally suitable salts of compounds of (1) through (285).

Pyrimidinone Fungicides (Group (4))

Pyrimidinone fungicides include compounds of Formula 47

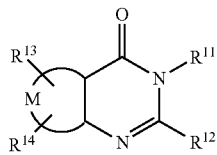

47 wherein
M forms a fused phenyl, thiophene or pyridine ring;
R$^{11}$ is C$_1$-C$_6$ alkyl;
R$^{12}$ is C$_1$-C$_6$ alkyl or C$_1$-C$_5$ alkoxy;
R$^{13}$ is halogen; and
R$^{14}$ is hydrogen or halogen.

Pyrimidinone fungicides are described in World Patent Application Publication WO 94/26722, U.S. Pat. Nos. 6,066,638, 6,245,770, 6,262,058 and 6,277,858.

Of note are pyrimidinone fungicides selected from the group:
6-bromo-3-propyl-2-propyloxy-4(3H)-quinazolinone,
6,8-diiodo-3-propyl-2-propyloxy-4(3H)-quinazolinone,
6-iodo-3-propyl-2-propyloxy-4(3H)-quinazolinone (proquinazid),
6-chloro-2-propoxy-3-propylthieno[2,3-d]pyrimidin-4(3H)-one,
6-bromo-2-propoxy-3-propylthieno[2,3-d]pyrimidin-4(3H)-one,
7-bromo-2-propoxy-3-propylthieno[3,2-d]pyrimidin-4(3H)-one,
6-bromo-2-propoxy-3-propylpyrido[2,3-d]pyrimidin-4(3H)-one,
6,7-dibromo-2-propoxy-3-propylthieno[3,2-d]pyrimidin-4(3H)-one, and
3-(cyclopropylmethyl)-6-iodo-2-(propylthio)pyrido[2,3-d]pyrimidin-4(3H)-one.

Inhibitors of Demethylase in Sterol Biosynthesis (27)

Sterol biosynthesis inhibitors control fungi by inhibiting enzymes in the sterol biosynthesis pathway. Demethylase-inhibiting fungicides have a common site of action within the fungal sterol biosynthesis pathway; that is inhibition of demethylation at position 14 of lanosterol or 24-methylene dihydrolanosterol, which are precursors to sterols in fungi. Compounds acting at this site are often referred to as demethylase inhibitors, DMI fungicides, or DMIs. The demethylase enzyme is sometimes referred to by other names in the biochemical literature, including cytochrome P450 (14DM). The demethylase enzyme is described in, for example, *J. Biol. Chem.* 1992, 267, 13175-79 and references cited therein. DMI fungicides fall into several chemical classes: azoles (including triazoles and imidazoles), pyrimidines, piperazines and pyridines. The triazoles include azaconazole, bromuconazole, cyproconazole, difenoconazole, diniconazole (including diniconazole-M), epoxiconazole, etaconazole, fenbuconazole, fluquinconazole, flusilazole, flutriafol, hexaconazole, imibenconazole, ipconazole, metconazole, myclobutanil, penconazole, propiconazole, prothioconazole, quincothiazole, simeconazole, tebuconazole, tetraconazole, triadimefon, triadimenol, triticonazole and uniconazole. The imidazoles include clotrimazole, econazole, imazalil, isoconazole, miconazole, oxpoconazole, prochloraz and triflumizole. The pyrimidines include fenarimol, nuarimol and triarimol. The piperazines include triforine. The pyridines include buthiobate and pyrifenox. Biochemical investigations have shown that all of the above mentioned fungicides are DMI fungicides as described by K. H. Kuck, et al. in *Modern Selective Fungicides—Properties, Applications and Mechanisms of Action*, H. Lyr (Ed.), Gustav Fischer Verlag: New York, 1995, 205-258.

bc$_1$ Complex Fungicides (28)

Strobilurin fungicides such as fluoxastrobin, orysastrobin, picoxystrobin, pyraclostrobin and trifloxystrobin are known to have a fungicidal mode of action which inhibits the bc$_1$ complex in the mitochondrial respiration chain (*Angew. Chem. Int. Ed.* 1999, 38, 1328-1349). Other strobilurin fungicides include (2E)-2-(2-[[6-(3-chloro-2-methylphenoxy)-5-fluor-4-pyrimidinyl]oxy]phenyl)-2-(methoxyimino)-N-methyl-ethanamide, (2E)-2-(methoxyimino)-N-methyl-2-(2-[[([(1E)-1-[3-(trifluoromethyl)phenyl]ethyliden]amino)oxy]methyl]phenyl)ethanamide, (2E)-2-methoxyimino)-N-methyl-2-[2-[(E)-([1-[3-(trifluoromethyl)phenyl]ethoxy]imino)methyl]phenyl)ethanamide. Other compounds that inhibit the bc$_1$ complex in the mitochondrial respiration chain include famoxadone and fenamidone. The bc$_1$ complex is sometimes referred to by other names in the biochemical literature, including complex III of the electron transfer chain, and ubihydroquinone:cytochrome c oxidoreductase. It is uniquely identified by the Enzyme Commission number EC1.10.2.2. The bc$_1$ complex is described in, for example, *J. Biol. Chem.* 1989, 264, 14543-48; *Methods Enzymol.* 1986, 126, 253-71; and references cited therein.

Other Fungicide Groups

Alkylenebis(dithiocarbamate)s (1) include compounds such as mancozeb, maneb, propineb and zineb.

Phenylamides (3) include compounds such as metalaxyl, benalaxyl, furalaxyl and oxadixyl.

Carboxamides (6) include compounds such as boscalid, carboxin, fenfuram, flutolanil, furametpyr, mepronil, oxycarboxin, thifluzamide, penthiopyrad, and N-(2-(1,3-dimethylbutyl)phenyl)-5-fluoro-1,3-dimethyl-1H-pyrazole-4-carboxamide (PCT Patent Application Publication WO 2003/010149) are known to inhibit mitochondrial function by disrupting complex II (succinate dehydrogenase) in the respiratory electron transport chain.

Copper compounds (II) include compounds such as copper oxychloride, copper sulfate and copper hydroxide, including compositions such as Bordeaux mixture (tribasic copper sulfate).

Phthalimides (12) include compounds such as folpet and captan.

Benzimidazole fungicides (14) include benomyl and carbendazim.

Dichlorophenyl dicarboximide fungicides (20) include chlozolinate, dichlozoline, iprodione, isovaledione, myclozolin, procymidone and vinclozolin.

Non-DMI sterol biosynthesis inhibitors (26) include morpholine and piperidine fungicides. The morpholines and piperidines are sterol biosynthesis inhibitors that have been shown to inhibit steps in the sterol biosynthesis pathway at a point later than the inhibitions achieved by the DMI sterol biosynthesis (27). The morpholines include aldimorph, dodemorph, fenpropimorph, tridemorph and trimorphamide. The piperidines include fenpropidin.

It will be evident that scope of methods of controlling plant disease of this invention relating to Formula 1 compounds together with the scope of methods of controlling plant disease of this invention relating to compounds haying a formula corresponding to Formula 1 except that $R^1$ is 4-fluorophenyl and the scope of methods of controlling plant disease of this invention relating to the compound of 2-[1-[(2-chlorophenyl)acetyl]-4-piperidinyl]-N-methyl-N-[(1R)-1-phenylethyl]-4-thiazolecarboxamide, corresponds to a scope of methods of controlling plant disease with compounds having a formula corresponding to Formula 1 as described above where proviso (a) and proviso (c) are both omitted (i.e., only proviso (b) is in effect). Of note are these methods where plant disease cause by Oomycete fungal plant pathogens are controlled.

Plant disease control is ordinarily accomplished by applying an effective amount of a compound of this invention either, pre- or post-infection, to the portion of the plant to be protected such as the roots, stems, foliage, fruit, seeds, tubers or bulbs, or to the media (soil or sand) in which the plants to be protected are growing. The compounds can also be applied to the seed to protect the seed and seedling.

Rates of application for these compounds can be influenced by many factors of the environment and should be determined under actual use conditions. Foliage can normally be protected when treated at a rate of from less than about 1 g/ha to about 5,000 g/ha of active ingredient. Seed and seedlings can normally be protected when seed is treated at a rate of from about 0.1 to about 10 g per kilogram of seed.

The following Tests demonstrate the control efficacy of compounds of this invention on specific pathogens. The pathogen control protection afforded by the compounds is not limited, however, to these species. See Index Tables A and B for compound descriptions. The following abbreviations are used in the Index Tables which follow: t means tertiary, means secondary, Ph means phenyl. The stereocenters are labeled as R (rectus) and S (sinister) based on Cahn-Ingold-Prelog system. The abbreviation "Ex." stands for "Example" and is followed by a number indicating in which example the compound is prepared. Index Tables A and B list the molecular weight of the highest isotopic abundance parent ion (M+1) formed by addition of $H^+$ (molecular weight of 1) to the molecule, observed by mass spectrometry using atmospheric pressure chemical ionization ($AP^+$).

INDEX TABLE A

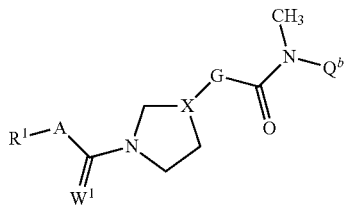

| Cmpd | $R^1$ | A | $W^1$ | X | G (*) | $Q^b$ | $AP^+$ (M + 1) |
|---|---|---|---|---|---|---|---|
| 1 | 2-chlorophenyl | $CH_2$ | O | $X^1$ | G-1 | (1S)-1-phenylethyl | 482 |
| 2 | 2-chlorophenyl | $CH_2$ | O | $X^1$ | G-1 | (1R)-1-phenylethyl | 482 |
| 3 | phenyl | $CH_2$ | O | $X^1$ | G-1 | (1R)-1-phenylethyl | 448 |
| 4 | 4-methoxyphenyl | $CH_2$ | O | $X^1$ | G-1 | (1R)-1-phenylethyl | 478 |
| 5 | 3-methoxyphenyl | $CH_2$ | O | $X^1$ | G-1 | (1R)-1-phenylethyl | 478 |
| 6 | 2,4-dichlorophenyl | $CH_2$ | O | $X^1$ | G-1 | (1R)-1-phenylethyl | 516 |
| 7 | 2,6-dichlorophenyl | $CH_2$ | O | $X^1$ | G-1 | (1R)-1-phenylethyl | 516 |
| 8 | 2-bromophenyl | $CH_2$ | O | $X^1$ | G-1 | (1R)-1-phenylethyl | 526 |
| 9 | 2-fluorophenyl | $CH_2$ | O | $X^1$ | G-1 | (1R)-1-phenylethyl | 466 |
| 10 | 2-trifluoromethylphenyl | $CH_2$ | O | $X^1$ | G-1 | (1R)-1-phenylethyl | 516 |
| 11 | 2-methylphenyl | $CH_2$ | O | $X^1$ | G-1 | (1R)-1-phenylethyl | 462 |
| 12 | 4-methylphenyl | $CH_2$ | O | $X^1$ | G-1 | (1R)-1-phenylethyl | 462 |
| 13 | 4-chlorophenyl | $CH_2$ | O | $X^1$ | G-1 | (1R)-1-phenylethyl | 482 |
| 14 | 4-trifluoromethylphenyl | $CH_2$ | O | $X^1$ | G-1 | (1R)-1-phenylethyl | 516 |
| 15 | 3-chlorophenyl | $CH_2$ | O | $X^1$ | G-1 | (1R)-1-phenylethyl | 482 |
| 16 | 3-trifluoromethylphenyl | $CH_2$ | O | $X^1$ | G-1 | (1R)-1-phenylethyl | 516 |
| 17 | 2,3-dichlorophenyl | $CH_2$ | O | $X^1$ | G-1 | (1R)-1-phenylethyl | 516 |
| 18 | 3-trifluoromethylphenyl | $CH_2$ | O | $X^1$ | G-1 | (1R)-1-phenylethyl | 517 |
| 19 | 3-bromophenyl | $CH_2$ | O | $X^1$ | G-1 | (1R)-1-phenylethyl | 526 |
| 20 | 3-nitrophenyl | $CH_2$ | O | $X^1$ | G-1 | (1R)-1-phenylethyl | 493 |
| 21 | 3-iodophenyl | $CH_2$ | O | $X^1$ | G-1 | (1R)-1-phenylethyl | 574 |
| 22 | 3,5-di-$CF_3$—Ph | $CH_2$ | O | $X^1$ | G-1 | (1R)-1-phenylethyl | 584 |
| 23 | 3-fluorophenyl | $CH_2$ | O | $X^1$ | G-1 | (1R)-1-phenylethyl | 466 |
| 24 | 3-trifluoromethyl-pyrazol-1-yl | $CH_2$ | O | $X^1$ | G-1 | (1R)-1-phenylethyl | 505 |
| 25 | 2-chlorophenyl | $CH_2$ | O | $X^2$ | G-1 | (1R)-1-phenylethyl | 483 |
| 26 | 3-chlorophenyl | $CH_2$ | O | $X^2$ | G-1 | (1R)-1-phenylethyl | 483 |

INDEX TABLE A-continued

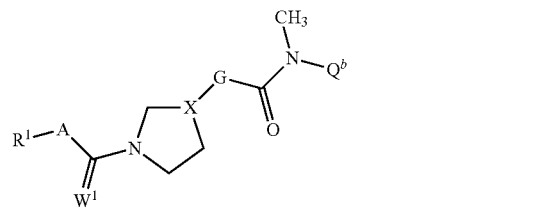

| Cmpd | R¹ | A | W¹ | X | G (*) | Q^b | AP⁺ (M + 1) |
|---|---|---|---|---|---|---|---|
| 27 | 3-bromophenyl | $CH_2$ | O | $X^2$ | G-1 | (1R)-1-phenylethyl | 527 |
| 28 | 3-nitrophenyl | $CH_2$ | O | $X^2$ | G-1 | (1R)-1-phenylethyl | 494 |
| 29 | 3-iodophenyl | $CH_2$ | O | $X^2$ | G-1 | (1R)-1-phenylethyl | 575 |
| 30 | 3-trifluorophenyl | $CH_2$ | O | $X^1$ | G-1^a | (1R)-1-phenylethyl | 550 |
| 31 | 3-methylsulfonylphenyl | $CH_2$ | O | $X^1$ | G-1 | (1R)-1-phenylethyl | 526 |
| 32 | 3-bromophenyl | $CH_2$ | O | $X^2$ | G-37 | (1R)-1-phenylethyl | 527 |
| 33 | 2-fluoro-3-chlorophenyl | $CH_2$ | O | $X^1$ | G-1 | (1R)-1-phenylethyl | 500 |
| 34 | 4-fluoro-3-trifluorophenyl | $CH_2$ | O | $X^1$ | G-1 | (1R)-1-phenylethyl | 534 |
| 35 | 4-fluoro-3-chlorophenyl | $CH_2$ | O | $X^1$ | G-1 | (1R)-1-phenylethyl | 500 |
| 36 | 3-methylphenyl | $CH_2$ | O | $X^1$ | G-1 | (1R)-1-phenylethyl | 462 |
| 37 | 3,5-difluorophenyl | $CH_2$ | O | $X^1$ | G-1 | (1R)-1-phenylethyl | 484 |
| 38 | 3,4-difluorophenyl | $CH_2$ | O | $X^1$ | G-1 | (1R)-1-phenylethyl | 484 |
| 39 | 2-chloro-5-trifluoromethylphenyl | $CH_2$ | O | $X^1$ | G-1 | (1R)-1-phenylethyl | 550 |
| 40 | 3-fluoro-5-trifluoromethylphenyl | $CH_2$ | O | $X^1$ | G-1 | (1R)-1-phenylethyl | 534 |
| 41 | 2-methoxyphenyl | $CH_2$ | O | $X^1$ | G-1 | (1R)-1-phenylethyl | 478 |
| 42 | 2-fluoro-3-trifluoromethylphenyl | $CH_2$ | O | $X^1$ | G-1 | (1R)-1-phenylethyl | 534 |
| 43 | 3,5-dimethylphenyl | $CH_2$ | O | $X^1$ | G-1 | (1R)-1-phenylethyl | 476 |
| 44 | 2,5-difluorophenyl | $CH_2$ | O | $X^1$ | G-1 | (1R)-1-phenylethyl | 484 |
| 45 | 2-trifluoromethoxyphenyl | $CH_2$ | O | $X^1$ | G-1 | (1R)-1-phenylethyl | 532 |
| 46 | 2,3-difluorophenyl | $CH_2$ | O | $X^1$ | G-1 | (1R)-1-phenylethyl | 484 |
| 47 | 2,5-dimethylphenyl | $CH_2$ | O | $X^1$ | G-1 | (1R)-1-phenylethyl | 476 |
| 48 | 3-methylthienyl | $CH_2$ | O | $X^1$ | G-1 | (1R)-1-phenylethyl | 494 |
| 49 | 3-trifluoromethoxyphenyl | $CH_2$ | O | $X^1$ | G-1 | (1R)-1-phenylethyl | 532 |
| 50 | 2,5-dimethylphenyl | $CH_2$ | O | $X^2$ | G-2 | (1R)-1-phenylethyl | 461 |
| 51 | 2-chloro-5-trifluoromethylphenyl | $CH_2$ | O | $X^2$ | G-2 | (1R)-1-phenylethyl | 535 |
| 52 | 3-methylphenyl | $CH_2$ | O | $X^2$ | G-2 | (1R)-1-phenylethyl | 447 |
| 53 | 2-methoxyphenyl | $CH_2$ | O | $X^2$ | G-2 | (1R)-1-phenylethyl | 463 |
| 54 | 3-bromophenyl | $CH_2$ | O | $X^2$ | G-2 | (1R)-1-phenylethyl | 511 |
| 55 | 3-trifluoromethylphenyl | $CH_2$ | O | $X^2$ | G-2 | (1R)-1-phenylethyl | 501 |
| 56 | 2,5-dimethylphenyl | $CH_2$ | O | $X^1$ | G-1 | (1R)-1-(3-trifluoromethylphenyl)-ethyl | 544 |
| 57 | 2,5-dimethylphenyl | $CH_2$ | O | $X^1$ | G-1 | (1R)-1-(2-fluorophenyl)ethyl | 494 |
| 58 (Ex. 1) | 2,5-dimethylphenyl | $CH_2$ | O | $X^1$ | G-1 | (1R)-1-phenylpropyl | 490 |
| 59 | 2,5-dimethylphenyl | $CH_2$ | O | $X^1$ | G-1 | (1R)-1-(4-methoxyphenyl)ethyl | 506 |
| 60 | 2,5-dimethylphenyl | $CH_2$ | O | $X^1$ | G-1 | (1R)-1-(4-chlorophenyl)ethyl | 510 |
| 61 | 3-methylphenyl | $CH_2$ | O | $X^1$ | G-1 | 1-(3,5-dichloro-2-pyridinyl)ethyl | 531 |
| 62 | 2,5-dimethylphenyl | $CH_2$ | O | $X^1$ | G-1 | (1R)-1-(4-methylphenyl)-ethyl | 490 |
| 63 | 2,5-dimethylphenyl | $CH_2$ | O | $X^1$ | G-1 | (1R)-1-(4-bromophenyl)-ethyl | 554 |
| 64 | 2,5-dimethylphenyl | $CH_2$ | O | $X^1$ | G-1 | (1R)-1-(4-fluorophenyl)ethyl | 494 |
| 65 | 3,5-dimethylpyrazol-1-yl | $CH_2$ | O | $X^1$ | G-1 | (1R)-1-phenylethyl | 466 |
| 66 | 3-trifluoromethylphenyl | $CH_2$ | O | $X^1$ | G-1 | 1-(3-pyridinyl)ethyl | 517 |
| 67 | 2,5-dimethylphenyl | $CH_2$ | O | $X^1$ | G-1 | (1R)-1-(3-trifluoromethylphenyl)-ethyl | 544 |
| 68 | 2,5-dimethylphenyl | $CH_2$ | O | $X^1$ | G-1 | (1S)-1-phenylethyl | 476 |
| 69 | 2,5-dimethylphenyl | $CH_2$ | O | $X^1$ | G-1 | (1R)-1-(3-methoxyphenyl)ethyl | 506 |
| 70 (Ex. 5) | 3-trifluoromethyl-5-methylpyrazol-1-yl | $CH_2$ | O | $X^1$ | G-1 | (1R)-1-phenylethyl | 520 |

INDEX TABLE A-continued

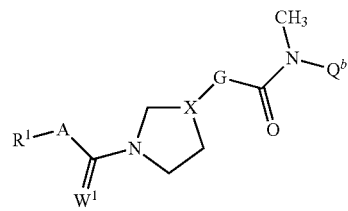

| Cmpd | R¹ | A | W¹ | X | G (*) | Q$^b$ | AP⁺ (M + 1) |
|---|---|---|---|---|---|---|---|
| 71 | 4-bromopyrazol-1-yl | CH$_2$ | O | X$^1$ | G-1 | (1R)-1-phenylethyl | 516 |
| 72 | 3-methylpyrazol-1-yl | CH$_2$ | O | X$^1$ | G-1 | (1R)-1-phenylethyl | 452 |
| 73 | 4-methylpyrazol-1-yl | CH$_2$ | O | X$^1$ | G-1 | (1R)-1-phenylethyl | 452 |
| 74 (Ex. 4) | 2,5-dimethylphenyl | CH$_2$ | O | X$^2$ | G-37 | (1R)-1-phenylethyl | 477 |
| 75 | 3-trifluoromethylphenyl | CH$_2$ | O | X$^1$ | G-1 | 1-(2-pyridinyl)ethyl | 517 |
| 76 | 3-trifluoromethylphenyl | CH$_2$ | O | X$^1$ | G-1 | 1-(4-pyridinyl)ethyl | 517 |
| 77 | 2,5-dichlorophenyl | CH$_2$ | O | X$^1$ | G-1 | (1R)-1-phenylethyl | 516 |
| 78 | 2-ethoxyphenyl | CH$_2$ | O | X$^1$ | G-1 | (1R)-1-phenylethyl | 492 |
| 79 | 3-ethoxyphenyl | CH$_2$ | O | X$^1$ | G-1 | (1R)-1-phenylethyl | 492 |
| 80 | 2-methyl-5-fluorophenyl | CH$_2$ | O | X$^1$ | G-1 | (1R)-1-phenylethyl | 481 |
| 81 | 2-methoxy-5-bromophenyl | CH$_2$ | O | X$^1$ | G-1 | (1R)-1-phenylethyl | 556 |
| 82 | 2,5-dimethylphenyl | CH$_2$ | O | X$^1$ | G-1 | 1-phenylbutyl | 504 |
| 83 | pyridin-3-yl | CH$_2$ | O | X$^1$ | G-1 | (1R)-1-phenylethyl | 449 |
| 84 | pyridin-4-yl | CH$_2$ | O | X$^1$ | G-1 | (1R)-1-phenylethyl | 449 |
| 85 | 2,5-dimethylphenyl | CH$_2$ | O | X$^1$ | G-1 | 1-phenylpentyl | 518 |
| 86 | 2-bromo-5-chlorophenyl | CH$_2$ | O | X$^1$ | G-1 | (1R)-1-phenylethyl | 560 |
| 87 | 2,5-bis-trifluoromethylphenyl | CH$_2$ | O | X$^1$ | G-1 | (1R)-1-phenylethyl | 584 |
| 88 | 2-thienyl | CH$_2$ | O | X$^1$ | G-1 | (1R)-1-phenylethyl | 454 |
| 89 | 2,5-dimethylphenyl | CH$_2$ | O | X$^1$ | G-1 | 1-(2-thienyl)ethyl | 482 |
| 90 | 2-methoxycarbonyl-methylphenyl | CH$_2$ | O | X$^1$ | G-1 | (1R)-1-phenylethyl | 521 |
| 91 | 2-methylthiazol-4-yl | CH$_2$ | O | X$^1$ | G-1 | (1R)-1-phenylethyl | 469 |
| 92 | 2,5-dimethylthiazol-4-yl | CH$_2$ | O | X$^1$ | G-1 | (1R)-1-phenylethyl | 483 |
| 93 | 3-t-butylisoxazol-5-yl | CH$_2$ | O | X$^1$ | G-1 | (1R)-1-phenylethyl | 495 |
| 94 | 2,5-dimethylphenyl | CH$_2$ | O | X$^1$ | G-1 | 1-(2-pyridinyl)ethyl | 477 |
| 95 | 2,5-dimethylphenyl | CH$_2$ | O | X$^1$ | G-1 | 1-(3-pyridinyl)ethyl | 477 |
| 96 | 2,5-dimethylphenyl | CH$_2$ | O | X$^1$ | G-1 | 1-phenyl-2-methylpropan-1-yl | 504 |
| 97 | 2,5-dimethylphenyl | CH$_2$ | O | X$^1$ | G-1 | 1-phenyl-3-methylbutan-1-yl | 518 |
| 98 | 2,5-dimethylphenyl | CH$_2$ | O | X$^1$ | G-1 | 1,2,3,4-tetrahydro-2-naphthalenyl | 502 |
| 99 | 2,5-dimethylphenyl | CH$_2$ | O | X$^1$ | G-1 | 1,2,3,4-tetrahydro-1-naphthalenyl | 502 |
| 100 | 2,5-dimethylphenyl | CH$_2$ | O | X$^1$ | G-1 | indan-1-yl | 488 |
| 101 | 2,4-dimethylpyrrol-1-yl | CH$_2$ | O | X$^1$ | G-1 | (1R)-1-phenylethyl | 465 |
| 102 | 2,5-dimethylphenyl | CH$_2$ | O | X$^1$ | G-1 | phenyl-cyanomethyl | 487 |
| 103 | 2,5-dimethylphenyl | CH$_2$ | O | X$^1$ | G-1 | 1-phenyl-2-propen-1-yl | 488 |
| 104 | 2,5-dimethylphenyl | CH$_2$ | O | X$^1$ | G-1 | 1-phenyl-3-buten-1-yl | 502 |
| 105 | 2,5-dimethylphenyl | CH$_2$ | O | X$^1$ | G-1 | (1R)-1-naphthalenylethyl | 526 |
| 106 | 2,5-dimethylphenyl | CH$_2$ | O | X$^1$ | G-1 | (1R)-2-naphthalenylethyl | 526 |
| 107 | 3-bromophenyl | CH$_2$ | O | X$^1$ | G-1 | (1R)-1-phenylpropyl | 540 |
| 108 | 3-trifluoromethylphenyl | CH$_2$ | O | X$^1$ | G-1 | (1R)-1-phenylpropyl | 531 |
| 109 | 2,5-dimethylphenyl | CH$_2$ | O | X$^1$ | G-1 | 1-phenyl-2-methoxyethyl | 506 |
| 110 (Ex. 3) | 2,5-dichlorophenyl | CH$_2$ | O | X$^1$ | G-1 | (1R)-1-phenylpropyl | 530 |
| 111 (Ex. 11) | 2,5-dimethylphenyl | CH$_2$ | O | X$^1$ | G-1 | (1R)-1-(3,5-dichloro-2-pyridinyl)ethyl | 545 |
| 112 | 2,5-dimethylphenyl | CH$_2$ | O | X$^1$ | G-1 | 1-(2,5-dimethyl-3-thienyl)ethyl | 510 |
| 113 | 2,5-dimethylphenyl | CH$_2$ | O | X$^1$ | G-1 | 1-(2,5-dimethyl-3-furyl)ethyl | 494 |
| 114 | 2-chloro-5-trifluoromethylphenyl | CH$_2$ | O | X$^1$ | G-1 | (1R)-1-phenylpropyl | 564 |
| 115 | 2-methoxyphenyl | CH$_2$ | O | X$^1$ | G-1 | (1R)-1-phenylpropyl | 492 |
| 116 | 3-methylphenyl | CH$_2$ | O | X$^1$ | G-1 | (1R)-1-phenylpropyl | 476 |
| 117 (Ex. 2) | 3-trifluoromethyl-5-methylpyrazol-1-yl | CH$_2$ | O | X$^1$ | G-1 | (1R)-1-phenylpropyl | 534 |
| 118 | 3,5-dimethylpyrazol-1-yl | CH$_2$ | O | X$^1$ | G-1 | (1R)-1-phenylpropyl | 480 |
| 119 | 3-ethylphenyl | CH$_2$ | O | X$^1$ | G-1 | (1R)-1-phenylethyl | 476 |
| 120 | 3,5-dimethyltriazol-1-yl | CH$_2$ | O | X$^1$ | G-1 | (1R)-1-phenylethyl | 467 |

INDEX TABLE A-continued

[Structure: R¹–A–C(=W¹)–N(pyrrolidine with X)–G–C(=O)–N(CH₃)–Q^b]

| Cmpd | R¹ | A | W¹ | X | G (*) | Q^b | AP⁺ (M + 1) |
|---|---|---|---|---|---|---|---|
| 121 | 2,4-dimethylimidazol-1-yl | CH₂ | O | X¹ | G-1 | (1R)-1-phenylethyl | 466 |
| 122 | 3-trifluoromethyltriazol-1-yl | CH₂ | O | X¹ | G-1 | (1R)-1-phenylethyl | 507 |
| 123 | 2-propyl-4-trifluoromethylimidazol-1-yl | CH₂ | O | X¹ | G-1 | (1R)-1-phenylethyl | 548 |
| 124 | 2-methyl-5-trifluoromethylphenyl | CH₂ | O | X¹ | G-1 | (1R)-1-phenylethyl | 530 |
| 125 | 2-methoxy-5-methylphenyl | CH₂ | O | X¹ | G-1 | (1R)-1-phenylethyl | 492 |
| 126 | 2,5-dimethylphenyl | CH₂ | O | X¹ | G-2 | (1R)-1-phenylethyl | 460 |
| 127 | 3-isopropyl-5-methylpyrazol-1-yl | CH₂ | O | X¹ | G-1 | (1R)-1-phenylethyl | 494 |
| 128 | 2-ethyl-4-methylimidazol-1-yl | CH₂ | O | X¹ | G-1 | (1R)-1-phenylethyl | 480 |
| 129 | 2,5-dimethylphenyl | CH₂ | O | X¹ | G-1 | 6,7,8,9-tetrahydro-5H-benzocyclohepten-5-yl | 516 |
| 130 | 2,5-dimethylphenyl | CH₂ | O | X¹ | G-1 | (R)-indan-1-yl | 488 |
| 131 | 2,5-dimethylphenyl | CH₂ | O | X¹ | G-1 | (S)-indan-1-yl | 488 |
| 132 (Ex. 6) | 2,5-dimethylphenyl | CH₂ | O | X¹ | G-1 | (1R)-1,2,3,4-tetrahydro-1-naphthalenyl | 502 |
| 133 | 2,5-dimethylphenyl | CH₂ | O | X¹ | G-1 | (1S)-1,2,3,4-tetrahydro-1-naphthalenyl | 502 |
| 134 | 2,5-dimethylphenyl | CH₂ | O | X¹ | G-1 | 4,5,6,7-tetrahydro-benzo[b]thien-4-yl | 508 |
| 135 | 2,5-dimethylphenyl | CH₂ | O | X¹ | G-1 | 4,5,6,7-tetrahydro-benzo[b]furan-4-yl | 492 |
| 136 | 2,5-dimethylphenyl | CH₂ | O | X¹ | G-1 | thiochroman-4-yl | 520 |
| 137 | 2,5-dimethylphenyl | CH₂ | O | X¹ | G-1 | chroman-4-yl | 504 |
| 138 | 2,5-dimethylphenyl | CH₂ | O | X¹ | G-1 | 2,3-dihydro-benzofuran-3-yl | 490 |
| 139 | 2-isopropylimidazol-1-yl | CH₂ | O | X¹ | G-1 | (1R)-1-phenylethyl | 480 |
| 140 | 3-cyclohexyltriazol-1-yl | CH₂ | O | X¹ | G-1 | (1R)-1-phenylethyl | 521 |
| 141 | 4-t-butylimidazol-1-yl | CH₂ | O | X¹ | G-1 | (1R)-1-phenylethyl | 494 |
| 142 | 3-s-butyl-5-methylpyrazol-1-yl | CH₂ | O | X¹ | G-1 | (1R)-1-phenylethyl | 508 |
| 143 | 3-trifluoromethyl-5-methylpyrazol-1-yl | CH₂ | O | X¹ | G-1 | (R)-1-(3,5-dichloro-2-pyridinyl)ethyl | 589 |
| 144 (Ex. 6) | 2,5-dichlorophenyl | CH₂ | O | X¹ | G-1 | (1R)-1,2,3,4-tetrahydro-1-naphthalenyl | 542 |
| 145 (Ex. 6) | 2-methoxyphenyl | CH₂ | O | X¹ | G-1 | (1R)-1,2,3,4-tetrahydro-1-naphthalenyl | 504 |
| 146 (Ex. 6) | 2-methoxy-5-methylphenyl | CH₂ | O | X¹ | G-1 | (1R)-1,2,3,4-tetrahydro-1-naphthalenyl | 518 |
| 147 (Ex. 6) | 2-chloro-5-trifluoromethylphenyl | CH₂ | O | X¹ | G-1 | (1R)-1,2,3,4-tetrahydro-1-naphthalenyl | 576 |
| 148 (Ex. 6) | 2-methoxy-5-bromophenyl | CH₂ | O | X¹ | G-1 | (1R)-1,2,3,4-tetrahydro-1-naphthalenyl | 582 |
| 149 (Ex. 6) | 3-trifluoromethyl-5-methylpyrazol-1-yl | CH₂ | O | X¹ | G-1 | (1R)-1,2,3,4-tetrahydro-1-naphthalenyl | 546 |
| 150 (Ex. 6) | 3,5-dimethylpyrazol-1-yl | CH₂ | O | X¹ | G-1 | (1R)-1,2,3,4-tetrahydro-1-naphthalenyl | 492 |
| 151 (Ex. 8) | 3-trifluoromethyl-5-methylpyrazol-1-yl | CH₂ | O | X¹ | G-2 | (1R)-1,2,3,4-tetrahydro-1-naphthalenyl | 530 |
| 152 (Ex. 7) | 3-trifluoromethyl-5-methylpyrazol-1-yl | CH₂ | O | X¹ | G-2 | (1R)-1-phenylpropyl | 518 |
| 153 (Ex. 9) | 2,5-dimethylphenyl | CH₂ | O | X¹ | G-2 | (1R)-1,2,3,4-tetrahydro-1-naphthalenyl | 486 |
| 154 (Ex. 10) | 2,5-dimethylphenyl | CH₂ | O | X¹ | G-2 | (1R)-1-phenylpropyl | 474 |
| 155 | 3-trifluoromethylphenyl | NH | O | X¹ | G-1 | (1R)-1-phenylethyl | 518 |
| 156 | 3-trifluoromethylphenyl | NH | O | X¹ | G-1 | (1R)-1-phenylethyl | 517 |
| 157 | 2-methoxyphenyl | NH | O | X¹ | G-2 | (1R)-1-phenylethyl | 464 |
| 158 | 3-trifluoromethylphenyl | NH | O | X¹ | G-2 | (1R)-1-phenylethyl | 502 |

INDEX TABLE A-continued

| Cmpd | R¹ | A | W¹ | X | G (*) | Qᵇ | AP⁺ (M + 1) |
|---|---|---|---|---|---|---|---|
| 159 | 2-methoxy-5-methylphenyl | NH | S | X¹ | G-1 | (1R)-1-phenylethyl | 509 |
| 160 | 3-trifluoromethylphenyl | NH | S | X¹ | G-1 | (1R)-1-phenylethyl | 533 |
| 161 | 2-chlorophenyl | $CH_2$ | O | X¹ | G-1 | benzyl | 468 |
| 162 | 2-chlorophenyl | $CH_2$ | O | X¹ | G-1 | 2-phenylethyl | 482 |
| 163 | 3-trifluromethylphenyl | $CH_2$ | O | X¹ | G-1 | 3-pyridinylmethyl | 503 |
| 164 | 3-methylphenyl | $CH_2$ | O | X¹ | G-1 | 3-pyridylmethyl | 449 |
| 165 | 3-methylphenyl | $CH_2$ | O | X¹ | G-1 | 2-pyridylmethyl | 449 |
| 166 | 2,5-dimethylphenyl | $CH_2$ | O | X¹ | G-1 | (1R)-1-cyclohexylethyl | 483 |
| 167 | 2,5-dimethylphenyl | $CH_2$ | O | X¹ | G-1 | benzyl | 463 |
| 168 | 3-trifluoromethylphenyl | $CH_2$ | O | X¹ | G-1 | 2-pyridylmethyl | 503 |
| 169 | 3-trifluoromethylphenyl | $CH_2$ | O | X¹ | G-1 | 4-pyridylmethyl | 503 |
| 170 | 3-methylphenyl | $CH_2$ | O | X¹ | G-1 | 4-pyridylmethyl | 449 |
| 171 | 2,5-dimethylphenyl | $CH_2$ | O | X¹ | G-1 | 3,4-dimethoxy-2-phenylethyl | 536 |
| 172 | 2,5-dimethylphenyl | $CH_2$ | O | X¹ | G-1 | isothiochroman-4-yl | 520 |
| 173 | 2,5-dimethylphenyl | $CH_2$ | O | X¹ | G-1 | 1,2,3,4-tetrahydrophenanthren-1-yl | 552 |
| 174 | 2,5-dimethylphenyl | $CH_2$ | O | X¹ | G-1 | cyclohexyl | 454 |
| 175 | 2,5-dimethylphenyl | $CH_2$ | O | X¹ | G-1 | 1,1-dimethyl-2-(4-fluorophenyl)ethyl | 522 |
| 176 | 2,5-dimethylphenyl | $CH_2$ | O | X¹ | G-1 | 3-methylcyclohex-1-yl | 468 |
| 177 | 2,5-dimethylphenyl | $CH_2$ | O | X¹ | G-1 | 2,3-dimethylcyclohex-1-yl | 482 |
| 178 (Ex. 19) | 3-trifluoromethyl-5-methylpyrazol-1-yl | $CH_2$ | O | X¹ | G-1 | (R)-1-indan-1-yl | 533 |
| 179 | 3-trifluoromethyl-5-methylpyrazol-1-yl | $CH_2$ | O | X¹ | G-1 | chroman-4-yl | 548 |
| 180 | 3-trifluoromethyl-5-methylpyrazol-1-yl | $CH_2$ | O | X¹ | G-1 | thiochroman-4-yl | 564 |
| 181 | 3-trifluoromethyl-5-methylpyrazol-1-yl | $CH_2$ | O | X¹ | G-1 | 6,7,8,9-tetrahydro-5H-benzocyclohepten-5-yl | 560 |
| 182 | 3-trifluoromethyl-5-methylpyrazol-1-yl | $CH_2$ | O | X¹ | G-1 | 4,5,6,7-tetrahydrobenzo[b]thien-4-yl | 552 |
| 183 | 3-trifluoromethyl-5-methylpyrazol-1-yl | $CH_2$ | O | X¹ | G-1 | 4,5,6,7-benzo[b]furan-4-yl | 536 |
| 184 | 3-trifluoromethyl-5-methylpyrazol-1-yl | $CH_2$ | O | X¹ | G-1 | 2,3-dihydro-benzofuran-3-yl | 534 |
| 185 | 3-trifluoromethyl-5-methylpyrazol-1-yl | $CH_2$ | O | X¹ | G-1 | isothiochroman-4-yl | 564 |
| 186 | 3-trifluoromethyl-5-methylpyrazol-1-yl | $CH_2$ | O | X¹ | G-1 | 2-phenylcyclohex-1-yl | 574 |
| 187 | 3-trifluoromethyl-5-methylpyrazol-1-yl | $CH_2$ | O | X¹ | G-1 | (1S)-1,2,3,4-tetrahydro-1-naphthalenyl | 546 |
| 188 (Ex. 23) | 3-trifluoromethyl-5-methylpyrazol-1-yl | $CH_2$ | O | X¹ | G-1 | 1,2,3,4-tetrahydro-1-naphthalenyl | 546 |
| 189 | 3-trifluoromethyl-5-methylpyrazol-1-yl | $CH_2$ | O | X¹ | G-1 | 5-hydroxy-1,2,3,4-tetrahydro-1-naphthalenyl | 562 |
| 190 | 3-trifluoromethyl-5-methylpyrazol-1-yl | $CH_2$ | O | X¹ | G-1 | 6-hydroxy-1,2,3,4-tetrahydro-1-naphthalenyl | 562 |
| 191 [h] (Ex. 26) | 3-trifluoromethyl-5-methylpyrazol-1-yl | $CH_2$ | O | X¹ | G-1 | (1R,4S)-1,2,3,4-tetrahydro-4-hydroxy-1-naphthalenyl | 562 |
| 192 [b] | 3-trifluoromethyl-5-methylpyrazol-1-yl | $CH_2$ | O | X¹ | G-1 | 4-methyl-1,2,3,4-tetrahydro-1-naphthalenyl | 560 |
| 193 [c] (Ex. 22) | 3-trifluoromethyl-5-methylpyrazol-1-yl | $CH_2$ | O | X¹ | G-1 | 2-methyl-1,2,3,4-tetrahydro-1-naphthalenyl | 560 |
| 194 | 3-trifluoromethyl-5-methylpyrazol-1-yl | $CH_2$ | O | X¹ | G-1 | trans-2-hydroxy-1,2,3,4-tetrahydro-1-naphthalenyl | 562 |

INDEX TABLE A-continued

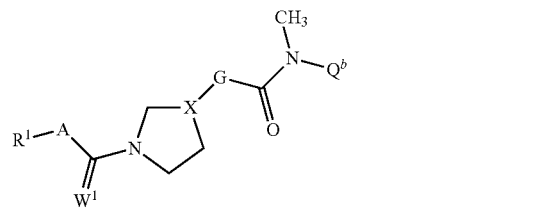

| Cmpd | R¹ | A | W¹ | X | G (*) | Q^b | AP⁺ (M + 1) |
|---|---|---|---|---|---|---|---|
| 195 | 3-trifluoromethyl-5-methylpyrazol-1-yl | $CH_2$ | O | $X^1$ | G-1 | trans-2-acetoxy-1,2,3,4-tetrahydro-1-naphthalenyl | 604 |
| 196 | 3-trifluoromethyl-5-methylpyrazol-1-yl | $CH_2$ | O | $X^1$ | G-1 | 5-methoxy-1,2,3,4-tetrahydro-1-naphthalenyl | 576 |
| 197 | 3-trifluoromethyl-5-methylpyrazol-1-yl | $CH_2$ | O | $X^1$ | G-1 | 6-methoxy-1,2,3,4-tetrahydro-1-naphthalenyl | 576 |
| 198 | 3-trifluoromethyl-5-methylpyrazol-1-yl | $CH_2$ | O | $X^1$ | G-1 | 7-methoxy-1,2,3,4-tetrahydro-1-naphthalenyl | 576 |
| 199 | 3-trifluoromethyl-5-methylpyrazol-1-yl | $CH_2$ | O | $X^1$ | G-1 | 4,4-dimethyl-1,2,3,4-tetrahydro-1-naphthalenyl | 574 |
| 200 [h] | 3-trifluoromethyl-5-methylpyrazol-1-yl | $CH_2$ | O | $X^1$ | G-1 | (1S,2R)-2-hydroxyindan-1-yl | 548 |
| 201 | 3-trifluoromethyl-5-methylpyrazol-1-yl | $CH_2$ | O | $X^1$ | G-1 | 6-chloro-1,2,3,4-tetrahydro-1-naphthalenyl | 580 |
| 202 | 3-trifluoromethyl-5-methylpyrazol-1-yl | $CH_2$ | O | $X^1$ | G-11 | (1R)-1,2,3,4-tetrahydro-1-naphthalenyl | 530 |
| 203 | 3-trifluoromethyl-5-methylpyrazol-1-yl | $CH_2$ | O | $X^1$ | G-23 | (1R)-1,2,3,4-tetrahydro-1-naphthalenyl | 530 |
| 204 | 3-methyl-2-pyridyl | $CH_2$ | O | $X^1$ | G-1 | (1R)-1,2,3,4-tetrahydro-1-naphthalenyl | 489 |
| 205 | 2-pyridinyl | $CH_2$ | O | $X^1$ | G-1 | (1R)-1,2,3,4-tetrahydro-1-naphthalenyl | 475 |
| 206 [h] (Ex. 28) | 3-trifluoromethyl-5-methylpyrazol-1-yl | $CH_2$ | O | $X^1$ | G-1 | (1R,4R)-1,2,3,4-tetrahydro-4-hydroxy-1-naphthalenyl | 562 |
| 207 | 3-trifluoromethyl-5-methylpyrazol-1-yl | $CH_2$ | O | $X^1$ | G-1 | trans-2-hydroxy-indan-1-yl | 548 |
| 208 (Ex. 16) | 3-trifluoromethyl-5-ethylpyrazol-1-yl | $CH_2$ | O | $X^1$ | G-1 | (1R)-1,2,3,4-tetrahydro-1-naphthalenyl | 560 |
| 209 (Ex. 15) | 3,5-diethylpyrazol-1-yl | $CH_2$ | O | $X^1$ | G-1 | (1R)-1,2,3,4-tetrahydro-1-naphthalenyl | 520 |
| 210 (Ex. 14) | 3,5-bis-trifluoromethyl-pyrazol-1-yl | $CH_2$ | O | $X^1$ | G-1 | (1R)-1,2,3,4-tetrahydro-1-naphthalenyl | 600 |
| 211 (Ex. 27) | 3-trifluoromethyl-5-methylpyrazol-1-yl | $CH_2$ | O | $X^1$ | G-1 | 4-oxo-1,2,3,4-tetrahydro-1-naphthalenyl | 560 |
| 212 | 3-trifluoromethyl-5-methylpyrazol-1-yl | $CH_2$ | O | $X^1$ | G-1 | cis-4-acetoxy-1,2,3,4-tetrahydro-1-naphthalenyl | 604 |
| 213 | 3-trifluoromethyl-5-methylpyrazol-1-yl | $CH_2$ | O | $X^1$ | G-1 | cis-4-methoxy-1,2,3,4-tetrahydro-1-naphthalenyl | 576 |
| 214 | 6-chloro-2-pyridyl | $CH_2$ | O | $X^1$ | G-1 | (1R)-1,2,3,4-tetrahydro-1-naphthalenyl | 509 |
| 215 | 4,6-dimethyl-2-pyridyl | $CH_2$ | O | $X^1$ | G-1 | (1R)-1,2,3,4-tetrahydro-1-naphthalenyl | 503 |
| 216 | 3-trifluoromethyl-5-methylpyrazol-1-yl | $CH_2$ | O | $X^1$ | G-20 | (1R)-1-phenylethyl | 505 |
| 217 | 3-trifluoromethyl-5-methylpyrazol-1-yl | $CH_2$ | O | $X^1$ | G-30 | (1R)-1,2,3,4-tetrahydro-1-naphthalenyl | 530 |
| 218 (Ex. 31) | 3-trifluoromethyl-5-methylpyrazol-1-yl | $CH_2$ | O | $X^3$ | G-1 | (1R)-1,2,3,4-tetrahydro-1-naphthalenyl | 544 |
| 219 | 3-trifluoromethyl-5-methylpyrazol-1-yl | $CH_2$ | O | $X^1$ | G-1 | 1,2,3,4-tetrahydro-4-naphthalenol-1-yl methylcarbamate [aa] | 619 |
| 220 (Ex. 30) | 3-trifluoromethyl-5-methylpyrazol-1-yl | $CH_2$ | O | $X^2$ | G-1 | (1R)-1,2,3,4-tetrahydro-1-naphthalenyl | 547 |
| 221 | 3-trifluoromethyl-5-methylpyrazol-1-yl | $CH_2$ | O | $X^1$ | G-1 | 5-chloroindan-1-yl | 566 |
| 222 (Ex. 21) | 3-trifluoromethyl-5-methylpyrazol-1-yl | $CH_2$ | O | $X^1$ | G-1 | 2,2-dimethylindan-1-yl | 560 |

INDEX TABLE A-continued

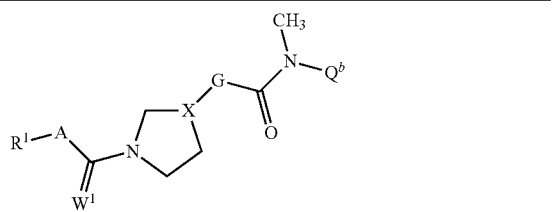

| Cmpd | R¹ | A | W¹ | X | G (*) | Q$^b$ | AP$^+$ (M + 1) |
|---|---|---|---|---|---|---|---|
| 223 | 3-trifluoromethyl-5-methylpyrazol-1-yl | CH$_2$ | O | X¹ | G-15 | (1R)-1,2,3,4-tetrahydro-1-naphthalenyl | 546 |
| 224 | 3-trifluoromethyl-5-methylpyrazol-1-yl | CH$_2$ | O | X² | G-7 | (1R)-1,2,3,4-tetrahydro-1-naphthalenyl | 548 |
| 225 | 3-trifluoromethyl-5-methylpyrazol-1-yl | CH$_2$ | O | X¹ | G-8 | (1R)-1,2,3,4-tetrahydro-1-naphthalenyl | 531 |
| 226 (Ex. 20) | 3-trifluoromethyl-5-methylpyrazol-1-yl | CH$_2$ | O | X¹ | G-1 | 2-methylindan-1-yl | 546 |
| 227 | 3-trifluoromethyl-5-methylpyrazol-1-yl | CH$_2$ | O | X¹ | G-37 (d) | (1R)-1,2,3,4-tetrahydro-1-naphthalenyl | 560 |
| 228 | 3-trifluoromethyl-5-methylpyrazol-1-yl | CH$_2$ | O | X¹ | G-1 | trans-2-ethyl-1,2-dihydro-1-naphthalenyl | 572 |
| 229 | 3-trifluoromethyl-5-methylpyrazol-1-yl | CH$_2$ | O | X¹ | G-1 | 3-carbomethoxy-indan-1-yl | 590 |
| 230 | 3-trifluoromethyl-5-methylpyrazol-1-yl | CH$_2$ | O | X¹ | G-1 | trans-2-methyl-1,2-dihydro-1-naphthalenyl | 558 |
| 231 (Ex. 18) | 3-trifluoromethyl-5-methylpyrazol-1-yl | CH$_2$ | O | X¹ | G-26 | (1R)-1,2,3,4-tetrahydro-1-naphthalenyl | 529 |
| 232 (Ex. 32) | 3-trifluoromethyl-5-methylpyrazol-1-yl | CH$_2$ | O | X¹ | G-36 | (1R)-1,2,3,4-tetrahydro-1-naphthalenyl | 530 |
| 233 (Ex. 33) | 3-trifluoromethyl-5-methylpyrazol-1-yl | CH$_2$ | O | X¹ | G-27 | (1R)-1,2,3,4-tetrahydro-1-naphthalenyl | 529 |
| 234 [h] (Ex. 24) | 3-trifluoromethyl-5-methylpyrazol-1-yl | CH$_2$ | O | X¹ | G-1 | (1R,2S)-1,2,3,4-tetrahydro-2-methyl-1-naphthalenyl | 560 |
| 235 | 3-trifluoromethyl-5-methylpyrazol-1-yl | CH$_2$ | O | X¹ | G-1 | 3-hydroxymethylindan-1-yl | 562 |
| 236 (Ex. 25) | 3-trifluoromethyl-5-methylpyrazol-1-yl | CH$_2$ | O | X¹ | G-1 | 2,2-dimethyl-1,2,3,4-tetrahydro-1-naphthalenyl | 574 |
| 237 | 3-trifluoromethyl-5-methylpyrazol-1-yl | CH$_2$ | O | X¹ | G-1 | 1-methyl-1-phenylethyl | 534 |
| 238 (Ex. 12) | 3,5-dichloro-pyrazol-1-yl | CH$_2$ | O | X¹ | G-1 | (1R)-1,2,3,4-tetrahydro-1-naphthalenyl | 532 |
| 239 [e] | 3-trifluoromethyl-5-t-butylpyrazol-1-yl | CH$_2$ | O | X¹ | G-1 | (1R)-1,2,3,4-tetrahydro-1-naphthalenyl | 588 |
| 240 | 3-trifluoromethyl-5-isopropylpyrazol-1-yl | CH$_2$ | O | X¹ | G-1 | (1R)-1,2,3,4-tetrahydro-1-naphthalenyl | 574 |
| 241 | 3-trifluoromethyl-5-methylpyrazol-1-yl | CH$_2$ | O | X⁸ | G-1 | (1R)-1,2,3,4-tetrahydro-1-naphthalenyl | 561 |
| 242 [f] | 3-trifluoromethyl-5-methylpyrazol-1-yl | CH$_2$ | O | X⁸ | G-1 | (1R)-1,2,3,4-tetrahydro-1-naphthalenyl | 597 |
| 243 | 3-trifluoromethyl-5-methylpyrazol-1-yl | CH$_2$ | O | X¹ | G-1 | 1-(2-methylphenyl)ethyl | 534 |
| 244 | 3-trifluoromethyl-5-methylpyrazol-1-yl | CH$_2$ | O | X¹ | G-1 | (αS)-α-phenylacetic acid methyl ester | 564 |
| 245 | 3-trifluoromethyl-5-methylpyrazol-1-yl | CH$_2$ | O | X¹ | G-1 | (αS)-α-phenylacetic acid | 550 |
| 246 (Ex. 17) | 3-trifluoromethyl-5-methylpyrazol-1-yl | CH$_2$ | O | X¹ | G-49 | (1R)-1,2,3,4-tetrahydro-1-naphthalenyl | 532 |
| 247 | 3-trifluoromethyl-5-methylpyrazol-1-yl | CH$_2$ | O | X¹ | G-1 | (αS)-α-phenylacetamide | 549 |
| 248 | 3-trifluoromethyl-5-methylpyrazol-1-yl | CH$_2$ | O | X¹ | G-1 | benzyl | 506 |
| 249 (Ex. 13) | 3-trifluoromethyl-5-chloropyrazol-1-yl | CH$_2$ | O | X¹ | G-1 | (1R)-1,2,3,4-tetrahydro-1-naphthalenyl | 566 |
| 250 | 3-trifluoromethyl-5-methylpyrazol-1-yl | CH$_2$ | O | X¹ | G-1 | 1-(2-fluorophenyl)ethyl | 538 |
| 251 | 3-trifluoromethyl-5-methylpyrazol-1-yl | CH$_2$ | O | X¹ | G-1 | 1-(2-chlorophenyl)ethyl | 554 |
| 252 | 3-trifluoromethyl-5-methylpyrazol-1-yl | CH$_2$ | O | X¹ | G-1 | 1-(2-bromophenyl)ethyl | 598 |
| 253 | 3-trifluoromethyl-5-methylpyrazol-1-yl | CH$_2$ | O | X¹ | G-1 | 1-(4-chlorophenyl)-2,2,2-trifluoroethyl | 608 |
| 254 [g] | 3-trifluoromethyl-5-methylpyrazol-1-yl | CH$_2$ | O | X¹ | G-1 | perhydronaphthalen-1-yl | 552 |

INDEX TABLE A-continued

![Structure A]

| Cmpd | R¹ | A | W¹ | X | G (*) | Qᵇ | AP⁺ (M + 1) |
|------|----|----|----|----|-------|----|------------|
| 255 | 3-trifluoromethyl-5-methylpyrazol-1-yl | $CH_2$ | O | $X^1$ | G-1 | 1-(2-methoxyphenyl)ethyl | 550 |
| 256 | 3-trifluoromethyl-5-methylpyrazol-1-yl | $CH_2$ | O | $X^1$ | G-55 | (1R)-1,2,3,4-tetrahydro-1-naphthalenyl | 531 |
| 257 | 3-chloro-5-methylpyrazol-1-yl | $CH_2$ | O | $X^1$ | G-1 | (1R)-1,2,3,4-tetrahydro-1-naphthalenyl | 512 |
| 258 | 3-bromo-5-methylpyrazol-1-yl | $CH_2$ | O | $X^1$ | G-1 | (1R)-1,2,3,4-tetrahydro-1-naphthalenyl | 556 |
| 259 | 3-trifluoromethyl-5-methylpyrazol-1-yl | $CH_2$ | O | $X^1$ | G-1 | 2-phenylethyl | 520 |

Notes:
(*) $R^{3a}$ is H unless otherwise indicated.
ᵃ wherein $R^{3a}$ is 5-CL
ᵇ mixture of cis and trans.
ᶜ mixture of cis and trans.
(d) $R^{3a}$ is $CH_3$.
ᵉ contains 40 % of 3-t-butyl-5-trifluoromethyl-pyrazol-1-yl isomer.
⁽ᶠ⁾ HCl salt.
⁽ᵍ⁾ mixture of cis and trans.
⁽ʰ⁾ racemic mixture with its enantiomer.
⁽ᵃᵃ⁾ 1,2,3,4-tetrahydro-4-naphthalenol-1-yl methylcarbamate means

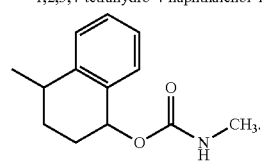

INDEX TABLE B

![Structure B]

| Cmpd | R¹ | X | W¹ | Q | AP⁺ (M + 1) |
|------|----|----|----|----|------------|
| 260 | 2-chlorophenyl | $X^1$ | O | (1S)-1-phenylethylamino | 468 |
| 261 | 2-chlorophenyl | $X^1$ | O | (1R)-1-phenylethylamino | 468 |
| 262 | 2-chlorophenyl | $X^1$ | O | benzylamino | 454 |
| 263 | 2-chlorophenyl | $X^1$ | O | 1-methyl-1-phenylethylamino | 482 |
| 264 | 2-chlorophenyl | $X^1$ | O | 2-phenylethylamino | 468 |
| 265 | 2-chlorophenyl | $X^1$ | O | 2-indanylamino | 480 |
| 266 | 2-chlorophenyl | $X^1$ | O | 1,2,3,4-tetrahydro-1-naphthalenylamino | 494 |
| 267 | 2-chlorophenyl | $X^1$ | O | 1,2,3,4-tetrahydroisoquinolino | 481 |
| 268 | 2-chlorophenyl | $X^1$ | O | 4-methylpiperidino | 446 |
| 269 | 2-chlorophenyl | $X^1$ | O | 2-(3-pyridinyl)pyrrolidino | 495 |
| 270 | 3-trifluoromethylphenyl | $X^1$ | O | (1R)-1-(4-bromophenyl)ethylamino | 580 |
| 271 | 3-bromophenyl | $X^1$ | O | (1R)-1-(4-fluorophenyl)ethylamino | 530 |
| 272 | 3-bromophenyl | $X^1$ | O | (1R)-1-cyclohexylethylamino | 518 |
| 273 | 3-bromophenyl | $X^1$ | O | (1R)-1-(4-nitrophenyl)ethylamino | 557 |
| 274 | 3-bromophenyl | $X^1$ | O | (1R)-1-(4-methylphenyl)ethylamino | 526 |
| 275 | 3-bromophenyl | $X^1$ | O | (1R)-1-(2-trifluoromethylphenyl)ethylamino | 580 |

INDEX TABLE B-continued

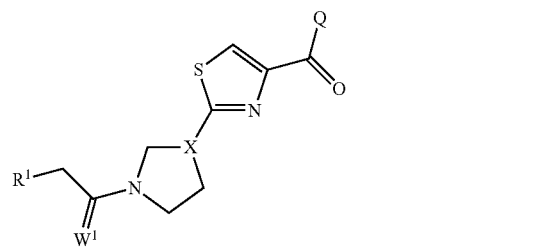

| Cmpd | R¹ | X | W¹ | Q | AP⁺ (M + 1) |
|---|---|---|---|---|---|
| 276 | 3-bromophenyl | $X^1$ | O | (1R)-1-(2-fluorophenyl)ethylamino | 530 |
| 277 | 3-bromophenyl | $X^1$ | O | (1R)-1-(3-trifluoromethylphenyl)ethylamino | 580 |
| 278 | 3-bromophenyl | $X^1$ | O | (1R)-1-phenylpropylamino | 526 |
| 279 | 3-bromophenyl | $X^1$ | O | (1R)-1-(4-methoxyphenyl)ethylamino | 542 |
| 280 | 3-bromophenyl | $X^1$ | O | (1R)-1-(4-chlorophenyl)ethylamino | 546 |
| 281 | 3-bromophenyl | $X^1$ | O | (1R)-1-(3-methoxyphenyl)ethylamino | 542 |
| 282 | 3-bromophenyl | $X^1$ | O | α-cyanobenzylamino | 523 |
| 283 | 2,5-dimethylphenyl | $X^1$ | O | (1R)-1-phenylethylamino | 463 |
| 284 | 2,5-dimethylphenyl | $X^1$ | O | (1R)-N-allyl-1-phenylethylamino | 502 |
| 285 | 2,5-dimethylphenyl | $X^1$ | O | (1R)-N-isopropyl-1-phenylethylamino | 504 |
| 286 | 2,5-dimethylphenyl | $X^1$ | O | (1R)-N-ethyl-1-phenylethylamino | 490 |
| 287 | 2,5-dimethylphenyl | $X^1$ | O | (1R)-N-propyl-1-phenylethylamino | 504 |
| 288 | 2,5-dimethylphenyl | $X^1$ | O | 2-(3,4-dimethoxyphenyl)ethylamino | 522 |
| 289 (Ex. 29) | 3-trifluoromethyl-5-methylpyrazol-1-yl | $X^1$ | S | (1R)-N-methyl-1,2,3,4-tetrahydro-1-naphthalenylamino | 562 |
| 290 | 3-trifluoromethyl-5-methylpyrazol-1-yl | $X^1$ | O | 2-(4-chlorophenyl)pyrrolidino | 566 |
| 291 | 3-trifluoromethyl-5-methylpyrazol-1-yl | $X^1$ | O | 7(1H)-oxo-2,3,8,8a-tetrahydrocyclopent[ij]isoquinolino | 558 |
| 292 (i) | 3-trifluoromethyl-5-methylpyrazol-1-yl | $X^2$ | O | (1R)-N-methyl-1,2,3,4-tetrahydro-1-naphthalenylamino | 575 |
| 293 (j) | 3-trifluoromethyl-5-methylpyrazol-1-yl | $X^2$ | O | (1R)-N-methyl-1,2,3,4-tetrahydro-1-naphthalenylamino | 561 |
| 294 | 3-trifluoromethyl-5-methylpyrazol-1-yl | $X^1$ | O | 1,2,3,4-tetrahydro-1-naphthalenylamino | 532 |
| 295 | 3-trifluoromethyl-5-methylpyrazol-1-yl | $X^1$ | O | 2,3-dihydro-1H-isoindolo | 504 |
| 296 | 3-trifluoromethyl-5-methylpyrazol-1-yl | $X^1$ | O | 1,2,3,4-tetrahydroisoquinolino | 518 |
| 297 | 3-trifluoromethyl-5-methylpyrazol-1-yl | $X^1$ | O | 6,7-dimethoxy-1,2,3,4-tetrahydroisoquinolino | 578 |
| 298 | 3-trifluoromethyl-5-methylpyrazol-1-yl | $X^1$ | O | 1-methyl-2,3-dihydro-1H-isoindolo | 518 |
| 299 | 3-trifluoromethyl-5-methylpyrazol-1-yl | $X^1$ | O | perhydroisoquinolino | 524 |
| 300 | 3-trifluoromethyl-5-methylpyrazol-1-yl | $X^1$ | O | perhydroquinolino | 524 |
| 301 | 3-trifluoromethyl-5-methylpyrazol-1-yl | $X^1$ | O | (1R)-1-phenylethylamino | 506 |
| 302 | 3-trifluoromethyl-5-methylpyrazol-1-yl | $X^1$ | O | (1R)-N-ethyl-1-phenylethylamino | 534 |
| 303 | 3-trifluoromethyl-5-methylpyrazol-1-yl | $X^1$ | O | (1R)-N-propyl-1-phenylethylamino | 548 |
| 304 | 3-trifluoromethyl-5-methylpyrazol-1-yl | $X^1$ | O | (1R)-N-allyl-1-phenylethylamino | 546 |
| 305 | 3-trifluoromethyl-5-methylpyrazol-1-yl | $X^1$ | O | (1R)-1,2,3,4-tetrahydro-1-naphthalenylamino | 532 |
| 306 | 3-trifluoromethyl-5-methylpyrazol-1-yl | $X^1$ | O | (1R)-N-ethyl-1,2,3,4-tetrahydro-1-naphthalenylamino | 560 |
| 307 | 3-trifluoromethyl-5-methylpyrazol-1-yl | $X^1$ | O | piperidino | 470 |
| 308 | 3-trifluoromethyl-5-methylpyrazol-1-yl | $X^1$ | O | 4-methylpiperidino | 484 |
| 309 | 3-trifluoromethyl-5-methylpyrazol-1-yl | $X^1$ | O | 4,4-dimethylpiperidino | 498 |
| 310 | 3-trifluoromethyl-5-methylpyrazol-1-yl | $X^1$ | O | 1,2,3,6-tetrahydropyridino | 468 |
| 311 | 3-trifluoromethyl-5-methylpyrazol-1-yl | $X^1$ | O | 4-phenyl-1,2,3,6-tetrahydropyridino | 544 |
| 312 | 3-trifluoromethyl-5-methylpyrazol-1-yl | $X^1$ | O | 3-methylpiperidino | 484 |
| 313 | 3-trifluoromethyl-5-methylpyrazol-1-yl | $X^1$ | O | 3,3-dimethylpiperidino | 498 |

INDEX TABLE B-continued

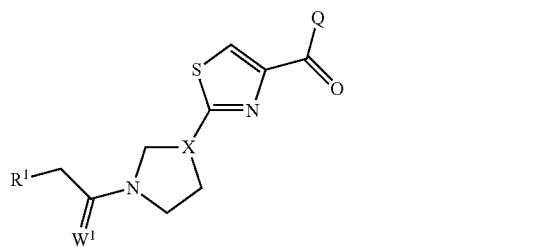

| Cmpd | R¹ | X | W¹ | Q | AP+ (M + 1) |
|---|---|---|---|---|---|
| 314 | 3-trifluoromethyl-5-methylpyrazol-1-yl | X¹ | O | 2-phenylethylamino | 506 |
| 315 (k) (Ex. 31) | 3-trifluoromethyl-5-methylpyrazol-1-yl | X¹ | O | (1R)-N-methyl-1,2,3,4-tetrahydro-1-naphthalenylamino | 544 |
| 316 (l) | 3-trifluoromethyl-5-methylpyrazol-1-yl | X¹ | O | (1R)-N-methyl-1,2,3,4-tetrahydro-1-naphthalenylamino | 572 |

Notes:
(i) Has 2,6-dimethyl substitution on the carbon atoms adjacent to the nitrogen atom bonded to C(=W¹) of the piperazine ring comprising X.
(j) Has 2-methyl substitution on one of the carbon atoms adjacent to the nitrogen atom bonded to C(=W¹) of the piperazine ring comprising X.
(k) Ring comprising X contains one carbon-carbon double bond and thus is a 1,2,3,4-tetrahydropyridine ring.
(l) Has ethylene bridge between the 2 and 6 positions (on carbon atoms adjacent to the nitrogen atom) of the piperidine ring comprising x (to form and 8-azabicyclo[3.2.1]octane ring system).

BIOLOGICAL EXAMPLES OF THE INVENTION

General Protocol for Preparing Test Suspensions for Test A-E:

The test compounds were first dissolved in acetone in an amount equal to 3% of the final volume and then suspended at the desired concentration (in ppm) in acetone and purified water (50/50 mix by volume) containing 250 ppm of the surfactant Trem® 014 (polyhydric alcohol esters). The resulting test suspensions were then used in tests A-E. Spraying a 200 ppm test suspension to the point of run-off on the test plants was the equivalent of a rate of 500 g/ha.

Test A

The test suspension was sprayed to the point of run-off on cucumber seedlings. The following day the seedlings were inoculated with a spore suspension of *Pseudoperonospora cubensis* (the causal agent of cucumber downy mildew) and incubated in a saturated atmosphere at 20° C. for 24 h, and then moved to a growth chamber at 20° C. for 6 days, after which disease ratings were made.

Test B

Grape seedlings were inoculated with a spore suspension of *Plasmopara viticola* (the causal agent of grape downy mildew) and incubated in a saturated atmosphere at 20° C. for 24 h. After a short drying period, the test suspension was sprayed to the point of run-off on the grape seedlings and then moved to a growth chamber at 20° C. for 5 days, after which the test units were placed back into a saturated atmosphere at 20° C. for 24 h. Upon removal, disease ratings were made.

Test C

The test suspension was sprayed to the point of run-off on tomato seedlings. The following day the seedlings were inoculated with a spore suspension of *Phytophthora infestans* (the causal agent of tomato late blight) and incubated in a saturated atmosphere at 20° C. for 24 h, and then moved to a growth chamber at 20° C. for 5 days, after which disease ratings were made.

Test D

Tomato seedlings were inoculated with a spore suspension of *Phytophthora infestans* (the causal agent of tomato late blight) and incubated in a saturated atmosphere at 20° C. for 17 h. After a short drying period, the test suspension was sprayed to the point of run-off on the tomato seedlings and then moved to a growth chamber at 20° C. for 4 days, after which disease ratings were made.

Test E

The test suspension was sprayed to the point of run-off on wheat seedlings. The following day the seedlings were inoculated with a spore dust of *Erysiphe graminis* f. sp. *tritici*, (the causal agent of wheat powdery mildew) and incubated in a growth chamber at 20° C. for 7 days, after which disease ratings were made.

In addition to tests A-E, the compounds were also sprayed on tomato plants inoculated with *Botrytis cinerea* 24 h after treatment and two separate sets of wheat plants inoculated with *Puccinia recondita* or *Septoria nodorum* 24 h after treatment. The compounds tested were not effective against these pathogens under the condition of these tests.

General Protocol for Preparing Test Suspensions for Test F:

The test compounds were first dissolved in dimethyl sulfoxide (DMSO) in an amount equal to 4% of the final volume and then suspended at the desired concentration (in ppm) in acetone and purified water (30/70 mix by volume). The resulting test suspensions were then used in test F. Spraying a 250 ppm test suspension on the test plants was the equivalent of a rate of 250 g/ha.

Test F

The test suspension was sprayed on cucumber seedlings. The following day the seedlings were inoculated with a spore suspension of *Pseudoperonospora cubensis* (the causal agent of cucumber downy mildew) and incubated in a saturated atmosphere at 20° C. for 24 h, and then moved to a growth chamber at 20° C. for 6 days, after which disease ratings were made.

Results for Tests A-F are given in Table A. In the table, a rating of 100 indicates 100% disease control and a rating of 0 indicates no disease control (relative to the controls). A dash (-) indicates no test results.

TABLE A

| Cmpd No | Test A | Test B | Test C | Test D | Test E | Test F |
|---|---|---|---|---|---|---|
| 1 | 0 | 20 | 56 | — | 0 | — |
| 2 | 100 | 67 | 96 | — | 50 | 86 |
| 3 | 0 | 53 | 0 | — | 21 | — |
| 4 | 0 | 14 | 0 | — | 21 | — |
| 5 | 0 | 0 | 33 | — | 0 | — |
| 6 | 0 | 28 | 0 | — | 41 | — |
| 7 | 0 | 0 | 0 | — | 0 | — |
| 8 | 99 | 31 | 29 | — | 0 | 93 |
| 9 | 82 | 28 | 0 | — | 0 | — |
| 10 | 0 | 20 | 0 | — | 0 | 95 |
| 11 | 0 | 31 | 91 | — | 0 | 97 |
| 12 | 0 | 6 | 0 | — | 0 | — |
| 13 | 0 | 0 | 0 | — | 0 | — |
| 14 | 0 | 6 | 0 | — | 0 | — |
| 15 | 100 | 76 | 98 | — | 0 | 99 |
| 16 | 100 | 95 | 100 | — | 0 | 99 |
| 17 | 0 | 4 | 0 | — | 79 | — |
| 18 | 100 | 80 | 100 | — | 0 | 96 |
| 19 | 100 | 99 | 100 | — | 0 | — |
| 20 | 100 | 0 | 93 | — | 0 | 99 |
| 21 | 100 | 99 | 99 | — | 21 | 100 |
| 22 | 93 | 20 | 31 | — | 21 | — |
| 23 | 90 | 6 | 29 | — | 86 | — |
| 24 | 100 | 100 | 100 | — | 21 | — |
| 25 | 97 | 61 | 62 | — | 0 | — |
| 26 | 97 | 17 | 90 | — | 0 | — |
| 27 | 100 | 8 | 99 | — | 0 | 92 |
| 28 | 99 | 5 | 31 | — | 0 | — |
| 29 | 100 | 33 | 98 | — | 0 | 47 |
| 30 | 0 | 0 | 0 | — | 0 | — |
| 31 | 0 | 0 | 0 | — | 0 | — |
| 32 | 87 | 0 | 95 | — | 0 | 93 |
| 33 | 96 | 51 | 91 | — | 29 | — |
| 34 | 85 | 48 | 31 | — | 0 | — |
| 35 | 88 | 66 | 93 | — | 0 | 97 |
| 36 | 100 | 99 | 100 | — | 91 | 95 |
| 37 | 85 | 23 | 80 | — | 87 | — |
| 38 | 0 | 45 | 0 | — | 55 | 43 |
| 39 | 100 | 100 | 100 | — | 85 | 100 |
| 40 | 98 | 76 | 60 | — | 0 | — |
| 41 | 100 | 94 | 100 | — | 0 | 82 |
| 42 | 99 | 31 | 100 | — | 21 | — |
| 43 | 100 | 83 | 100 | — | 21 | — |
| 44 | 97 | 57 | 98 | — | 21 | 0 |
| 45 | 95 | 70 | 98 | — | 0 | — |
| 46* | — | 0 | 0 | 0 | 0 | — |
| 47 | 100 | 100 | 100 | — | 96 | 100 |
| 48 | 0 | 6 | 29 | — | 49 | 39 |
| 49 | 97 | 83 | 67 | — | 85 | — |
| 50 | — | 55 | 100 | 99 | 0 | 100 |
| 51 | — | 20 | 100 | 96 | 0 | 100 |
| 52 | — | 20 | 100 | 74 | 0 | 96 |
| 53 | — | 20 | 100 | 89 | 0 | — |
| 54 | — | 11 | 100 | 69 | 0 | 50 |
| 55 | — | 7 | 100 | 92 | 0 | 47 |
| 56 | — | 31 | 93 | 0 | 0 | — |
| 57 | — | 100 | 100 | 94 | 50 | 99 |
| 58 | — | 100 | 100 | 94 | 0 | 100 |
| 59 | — | 84 | 98 | 63 | 21 | 93 |
| 60 | — | 95 | 93 | 42 | 67 | 47 |
| 61 | — | 2 | 69 | 0 | 0 | — |
| 62 | — | 92 | 92 | 24 | 29 | 43 |
| 63 | — | 100 | 100 | 93 | 0 | 99 |
| 64 | — | 100 | 100 | 95 | 92 | 93 |
| 65 | — | 92 | 100 | 100 | 0 | 100 |
| 66 | — | 2 | 54 | 42 | 0 | — |
| 67 | — | 10 | 68 | 0 | 0 | 99 |
| 68 | — | 47 | 100 | 16 | 0 | 95 |
| 69 | — | 88 | 100 | 0 | 29 | 100 |
| 70 | — | 100 | 100 | 100 | 0 | — |
| 71 | — | 34 | 74 | 0 | 0 | — |
| 72 | — | 1 | 91 | 66 | 0 | — |
| 73 | — | 2 | 75 | 9 | 0 | — |
| 74 | — | 27 | 99 | 92 | 0 | — |
| 75 | — | 16 | 100 | 72 | 0 | 0 |
| 76 | — | 0 | 79 | 0 | 0 | — |
| 77 | — | 100 | 100 | 100 | 88 | 50 |
| 78 | — | 100 | 78 | 46 | 0 | — |
| 79 | — | 82 | 77 | 0 | 0 | — |
| 80 | — | 99 | 100 | 70 | 29 | 49 |
| 81 | — | 100 | 100 | 100 | 0 | 50 |
| 82 | — | 100 | 97 | 53 | 55 | 93 |
| 83 | — | 14 | 31 | 0 | 0 | — |
| 84 | — | 41 | 44 | 0 | 0 | — |
| 85 | — | 99 | 99 | 9 | 32 | — |
| 86 | — | 99 | 99 | 100 | 0 | 86 |
| 87 | — | 79 | 88 | 8 | 0 | 100 |
| 88 | — | 43 | 33 | 0 | 0 | — |
| 89 | — | 100 | 99 | 99 | 43 | 93 |
| 90 | — | 17 | 26 | 9 | 0 | — |
| 91 | — | 16 | 99 | 79 | 0 | — |
| 92 | — | 83 | 100 | 100 | 0 | 100 |
| 93 | — | 9 | 26 | 0 | 0 | — |
| 94 | — | 0 | 100 | 100 | 0 | 93 |
| 95 | — | 0 | 100 | 83 | 0 | 97 |
| 96 | — | 98 | 100 | 49 | 0 | — |
| 97 | — | 53 | 86 | 0 | 0 | — |
| 98 | — | 0 | 84 | 0 | 0 | — |
| 99 | — | 97 | 100 | 99 | 0 | — |
| 100 | — | 94 | 100 | 99 | 0 | — |
| 101 | — | 0 | 70 | 8 | 0 | — |
| 102 | — | 100 | 99 | — | 0 | — |
| 103 | — | 100 | 71 | — | 79 | — |
| 104 | — | 100 | 87 | — | 0 | — |
| 105 | — | 96 | 100 | — | 0 | — |
| 106 | — | 0 | 24 | — | 0 | — |
| 107 | — | 99 | 100 | — | 0 | — |
| 108 | — | 99 | 100 | — | 0 | — |
| 109 | — | 99 | 99 | — | 94 | — |
| 110 | — | 100 | 100 | — | 50 | — |
| 111 | — | 96 | 99 | 37 | 98 | — |
| 112 | — | 93 | 100 | 99 | 95 | — |
| 113 | — | 0 | 97 | 31 | 0 | — |
| 114 | — | 99 | 100 | 99 | 0 | — |
| 115 | — | 100 | 100 | 99 | 0 | — |
| 116 | — | 100 | 49 | 87 | 0 | — |
| 117 | — | 100 | 100 | 100 | 0 | — |
| 118 | — | 99 | 100 | 99 | 0 | — |
| 119 | — | 95 | 99 | 33 | 89 | 100 |
| 120 | — | 7 | 51 | 100 | 0 | — |
| 121 | — | 0 | 47 | 0 | 0 | — |
| 122 | — | 28 | 53 | 96 | 17 | — |
| 123 | — | 13 | 100 | 47 | 7 | — |
| 124 | — | 100 | 100 | 0 | 71 | 90 |
| 125 | — | 100 | 100 | 99 | 94 | 100 |
| 126 | — | — | — | — | — | — |
| 127 | — | 0 | 92 | 0 | 0 | — |
| 128 | — | 0 | 0 | 0 | 0 | — |
| 129 | — | 0 | 50 | 57 | 0 | — |
| 130 | — | 99 | 54 | 100 | 0 | — |
| 131 | — | 77 | 55 | 62 | 0 | — |
| 132 | — | 100 | 100 | 100 | 0 | 100 |
| 133 | — | 77 | 53 | 79 | 0 | — |
| 134 | — | 97 | 51 | 100 | 0 | — |
| 135 | — | 16 | 51 | 47 | 0 | — |
| 136 | — | 77 | 100 | 80 | 0 | — |
| 137 | — | 100 | 51 | 93 | 0 | — |
| 138 | — | 91 | 100 | 37 | 44 | — |
| 139 | — | 0 | 0 | 0 | 0 | — |
| 140 | — | 0 | 0 | 0 | 0 | — |
| 141 | — | 0 | 0 | 0 | 0 | — |
| 142 | — | 0 | 0 | 0 | 87 | — |
| 143 | — | 69 | 100 | 99 | 0 | 50 |

TABLE A-continued

| Cmpd No | Test A | Test B | Test C | Test D | Test E | Test F |
|---|---|---|---|---|---|---|
| 144 | — | 100 | 100 | 100 | 0 | 99 |
| 145 | — | 96 | 100 | 100 | 0 | 93 |
| 146 | — | 100 | 100 | 100 | 0 | 99 |
| 147 | — | 98 | 100 | 100 | 0 | 100 |
| 148 | — | 98 | 100 | 100 | 0 | 92 |
| 149 | — | 100 | 100 | 100 | 0 | 100 |
| 150 | — | 83 | 100 | 100 | 0 | 100 |
| 151* | — | 99 | 100 | 99 | 0 | — |
| 152* | — | 99 | 100 | 99 | 0 | — |
| 153* | — | 99 | 100 | 98 | 0 | — |
| 154* | — | 99 | 100 | 68 | 0 | — |
| 155 | 100 | 41 | 31 | — | 0 | — |
| 156 | 100 | — | 62 | — | 21 | 100 |
| 157 | — | 63 | 100 | 91 | 0 | — |
| 158 | — | 9 | 95 | 0 | 0 | 90 |
| 159 | — | 95 | 99 | 91 | 73 | 93 |
| 160 | — | 47 | 40 | 0 | 0 | 50 |
| 161 | 0 | 14 | 15 | | 42 | — |
| 162 | 0 | 14 | 15 | | 42 | 43 |
| 163 | — | 24 | 55 | 0 | 0 | — |
| 164 | — | 1 | 60 | 0 | 0 | — |
| 165 | — | 11 | 14 | 0 | 0 | — |
| 166 | — | 34 | 68 | 16 | 0 | — |
| 167 | — | 27 | 97 | 0 | 0 | 99 |
| 168 | — | 15 | 8 | 0 | 0 | — |
| 169 | — | 8 | 68 | 0 | 0 | — |
| 170 | — | 7 | 29 | 0 | 0 | — |
| 171 | — | 0 | | 24 | 0 | — |
| 172 | — | 43 | 100 | 100 | 0 | 99 |
| 173 | — | 0 | 0 | 0 | 0 | 95 |
| 174 | — | 68 | 100 | 63 | 0 | 90 |
| 175 | — | 93 | 95 | 0 | 0 | 43 |
| 176 | — | 15 | 95 | 24 | 0 | 49 |
| 177 | — | 86 | 100 | 79 | 0 | 43 |
| 178 | — | 100 | 100 | 99 | 0 | — |
| 179** | — | 96 | 100 | 87 | 0 | — |
| 180** | — | 47 | 100 | 92 | 0 | — |
| 181** | — | 73 | 100 | 98 | 0 | — |
| 182* | — | 99 | 100 | 98 | 0 | — |
| 183** | — | 0 | 40 | 16 | 0 | — |
| 184** | — | 77 | 99 | 76 | 0 | — |
| 185** | — | 99 | 100 | 98 | 0 | — |
| 186** | — | 0 | 97 | 58 | 0 | — |
| 187 | — | 98 | 100 | 99 | 0 | 93 |
| 188** | — | 99 | 100 | 99 | 84 | 99 |
| 189 | — | 93 | 100 | 99 | 0 | — |
| 190 | — | 8 | 100 | 99 | 0 | 93 |
| 191 | — | 79 | 100 | 99 | 0 | — |
| 192 | — | 97 | 100 | 99 | 0 | — |
| 193 | — | 100 | 100 | 99 | 0 | — |
| 194* | — | 0 | 98 | 74 | 0 | — |
| 195 | — | 47 | 99 | 88 | 0 | — |
| 196* | — | 97 | 100 | 99 | 0 | — |
| 197* | — | 98 | 100 | 99 | 0 | — |
| 198* | — | 99 | 100 | 99 | 0 | — |
| 199* | — | 99 | 100 | 99 | 0 | — |
| 200* | — | 39 | 98 | 98 | 0 | — |
| 201* | — | 98 | 100 | 99 | 0 | — |
| 202 | — | 97 | 100 | 99 | 0 | — |
| 203 | — | 94 | 100 | 99 | 0 | — |
| 204 | — | 16 | 99 | 98 | 0 | — |
| 205 | — | 0 | 75 | 17 | 0 | — |
| 206* | — | 99 | 100 | 99 | 0 | — |
| 207 | — | 36 | 99 | 99 | 0 | — |
| 208 | — | 100 | 100 | 99 | 0 | — |
| 209 | — | 98 | 100 | 99 | 0 | — |
| 210 | — | 100 | 100 | 99 | 0 | — |
| 211* | — | 99 | 100 | 99 | 0 | — |
| 212* | — | 97 | 100 | 99 | 0 | — |
| 213* | — | 99 | 100 | 99 | 0 | — |
| 214 | — | 98 | 99 | 99 | 0 | — |
| 215 | — | 0 | 100 | 99 | 0 | — |
| 216 | — | 72 | 95 | 16 | 0 | — |
| 217 | — | 52 | 99 | 40 | 0 | — |
| 218* | — | 91 | 100 | 99 | 0 | — |
| 219 | — | 69 | 99 | 99 | 0 | — |
| 220* | — | 95 | 100 | 98 | 0 | — |
| 221** | — | 77 | 99 | 98 | 0 | — |
| 222* | — | 100 | 100 | 99 | 0 | — |
| 223* | — | 99 | 100 | 99 | 0 | — |
| 224* | — | 93 | 100 | 99 | 0 | — |
| 225 | — | 83 | 100 | 99 | 0 | — |
| 226* | — | 100 | 100 | 99 | 0 | — |
| 227 | — | 44 | 63 | 0 | 0 | — |
| 228 | — | 88 | 100 | 99 | 0 | — |
| 229 | — | 97 | 100 | 90 | 0 | — |
| 230 | — | 87 | 100 | 94 | 0 | — |
| 231 | — | 100 | 100 | 99 | 0 | — |
| 232 | — | 100 | 100 | 99 | 0 | — |
| 233* | — | 99 | 100 | 99 | 0 | — |
| 234* | — | 100 | 100 | 99 | 0 | — |
| 235 | — | 94 | 100 | 99 | 0 | — |
| 236* | — | 100 | 100 | 99 | 0 | — |
| 237 | — | 81 | 99 | 99 | 62 | — |
| 238** | — | 100 | 100 | 99 | 0 | — |
| 239* | — | 63 | 57 | 0 | 0 | — |
| 240** | — | 99 | 100 | 99 | 0 | — |
| 241 | — | 17 | 99 | 68 | 47 | — |
| 242 | — | 16 | 100 | 73 | 0 | — |
| 243* | — | 91 | 86 | 82 | 0 | — |
| 244 | — | 100 | 99 | 93 | 0 | — |
| 245 | — | 0 | 47 | 0 | 0 | — |
| 246 | — | 16 | 100 | 96 | 0 | — |
| 247 | — | 0 | 90 | 17 | 0 | — |
| 248 | — | 88 | 100 | 80 | 53 | — |
| 249* | — | 100 | 100 | 99 | 0 | — |
| 250** | — | 97 | 97 | 71 | 0 | — |
| 251** | — | 100 | 100 | 97 | 0 | — |
| 252** | — | 99 | 99 | 85 | 19 | — |
| 253* | — | 96 | 90 | 67 | 0 | — |
| 254 | — | 95 | 99 | 99 | 0 | — |
| 255** | — | 25 | 9 | 0 | 0 | — |
| 256* | — | 99 | 100 | 86 | — | — |
| 257** | — | 99 | 100 | 99 | — | — |
| 258** | — | 100 | 100 | 99 | — | — |
| 259 | — | — | — | — | — | — |
| 260 | — | | 14 | 0 | — | 0 |
| 261 | 93 | 0 | 31 | — | 21 | — |
| 262 | 94 | 6 | 52 | — | 0 | — |
| 263 | 92 | 0 | 15 | — | 0 | 0 |
| 264 | 96 | 20 | 0 | — | 68 | 93 |
| 265 | 0 | 34 | 0 | — | 47 | — |
| 266 | 100 | 6 | 57 | — | 42 | 86 |
| 267 | 95 | 6 | 21 | — | 0 | — |
| 268 | 0 | 6 | 36 | — | 0 | — |
| 269 | 0 | 40 | 0 | — | 0 | — |
| 270 | 0 | 0 | 0 | — | 0 | — |
| 271 | — | 7 | 67 | 0 | 0 | — |
| 272 | — | 14 | 50 | 0 | 0 | — |
| 273 | — | 44 | 0 | 0 | 0 | — |
| 274 | — | 29 | 37 | 0 | 0 | — |
| 275 | — | 30 | 9 | 0 | 0 | 0 |
| 276 | — | 30 | 17 | 0 | 0 | — |
| 277 | — | 15 | 9 | 0 | 0 | — |
| 278 | — | 0 | 33 | 0 | 0 | 93 |
| 279 | — | 0 | 0 | 0 | 0 | 0 |
| 280 | — | 0 | 24 | 0 | 0 | — |
| 281 | — | 15 | 0 | 0 | 0 | — |
| 282 | 55 | 8 | 0 | | 0 | 39 |
| 283 | — | 48 | 84 | 0 | 0 | 99 |
| 284 | — | 10 | 21 | 0 | 0 | — |
| 285 | — | 10 | 25 | 0 | 0 | — |
| 286 | — | 39 | 23 | 0 | 52 | — |
| 287 | — | 0 | 50 | 0 | 0 | — |
| 288 | — | 73 | | 76 | 0 | 95 |
| 289* | — | 100 | 100 | 99 | 65 | — |
| 290 | — | 0 | 90 | 26 | 0 | — |
| 291 | — | 95 | 100 | 99 | 0 | — |
| 292 | — | 71 | 100 | 93 | 0 | — |
| 293 | — | 100 | 100 | 99 | 0 | — |
| 294 | — | 99 | 100 | 96 | 0 | — |
| 295 | — | 39 | 95 | 39 | 0 | — |
| 296 | — | 82 | 100 | 93 | 0 | — |
| 297 | — | 39 | 63 | 33 | 0 | — |
| 298** | — | 57 | 80 | 0 | 0 | — |
| 299 | — | 83 | 99 | 96 | 0 | — |

TABLE A-continued

| Cmpd No | Test A | Test B | Test C | Test D | Test E | Test F |
|---------|--------|--------|--------|--------|--------|--------|
| 300 | — | 62 | 97 | 58 | 0 | — |
| 301 | — | 99 | 99 | 80 | — | — |
| 302 | — | 86 | 95 | 26 | — | — |
| 303 | — | 45 | 95 | 26 | — | — |
| 304 | — | 72 | 57 | 26 | — | — |
| 305 | — | 100 | 100 | 99 | — | — |
| 306 | — | 96 | 100 | 83 | — | — |
| 307 | — | 79 | 100 | 26 | 0 | — |
| 308 | — | 98 | 100 | 93 | 0 | — |
| 309 | — | 96 | 100 | 83 | 0 | — |
| 310 | — | 47 | 73 | 9 | 0 | — |
| 311 | — | 31 | 83 | 0 | 28 | — |
| 312 | — | 91 | 100 | 80 | 0 | — |
| 313 | — | 98 | 99 | 92 | 0 | — |
| 314 | — | 98 | 100 | 99 | 0 | — |
| 315** | — | 72 | 100 | 88 | 0 | — |
| 316 | — | 97 | 100 | 97 | 0 | — |

*indicates compounds tested at 40 ppm.
**indicates compounds tested at 10 ppm.

What is claimed is:

1. A compound selected from Formula 1, an N-oxide or an agriculturally suitable salt thereof,

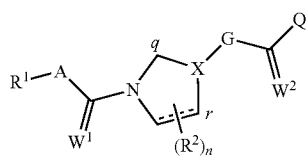

wherein
R$^1$ is

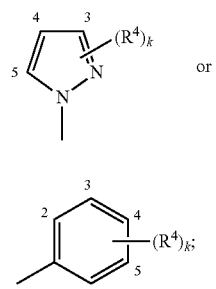

k is 1 or 2;
each R$^4$ is independently halogen, C$_1$-C$_3$ alkyl, C$_1$-C$_3$ haloalkyl or C$_1$-C$_2$ alkoxy;
A is CH$_2$;
W$^1$ is O;
X is a radical selected from

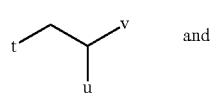

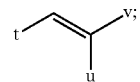

wherein the bond of X which is identified with "t" is connected to the carbon atom identified with "q" of Formula 1, the bond which is identified with "u" is connected to the carbon atom identified with "r" of Formula 1, and the bond which is identified with "v" is connected to G;
n is 0;
G is

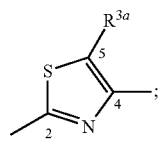

R$^{3a}$ is H;
W$^2$ is O;
Q is

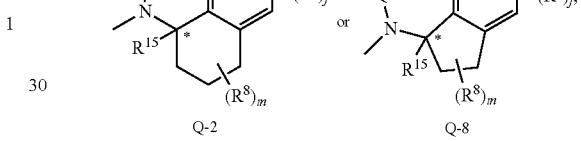

wherein carbon atom identified with the asterisk (*) contains a stereocenter; each R$^8$ is independently attached to the carbon atoms of the nonaromatic carbocyclic ring or heterocyclic ring of the Q group, and each R$^9$ is independently attached to the carbon atoms of phenyl or heteroaromatic ring of the Q group;
Q$^a$ is CH$_3$;
R$^{15}$ is H;
m and j are each independently 0 or 1;
each R$^8$ is independently C$_1$-C$_2$ alkyl, C$_1$-C$_2$ alkoxy or hydroxy; and
each R$^9$ is independently F, Cl, Br, hydroxy, OCH$_3$ or CH$_3$;
provided that:
(a) when X is X$^3$, then G is not linked to X via a heteroatom of the G ring; and
(b) R$^1$ is other than 4-fluorophenyl.

2. The compound of claim 1 selected from the group consisting of:
2-[1-[(2,5-dimethylphenyl)acetyl]-4-piperidinyl]-N-methyl-N-[(1R)-1,2,3,4-tetrahydro-1-naphthalenyl]-4-thiazolecarboxamide,
2-[1-[(2,5-dichlorophenyl)acetyl]-4-piperidinyl]-N-methyl-N-[(1R)-1,2,3,4-tetrahydro-1-naphthalenyl]-4-thiazolecarboxamide,
N-methyl-2-[1-[[5-methyl-3-(trifluoromethyl)-1H-pyrazol-1-yl]acetyl]-4-piperidinyl]-N-[(1R)-1,2,3,4-tetrahydro-1-naphthalenyl]-4-thiazolecarboxamide,
N-[(1R)-2,3-dihydro-1H-inden-1-yl]-N-methyl-2-[1-[[5-methyl-3-(trifluoromethyl)-1H-pyrazol-1-yl]acetyl]-4-piperidinyl]-4-thiazolecarboxamide,
N-methyl-2-[1-[[5-methyl-3-(trifluoromethyl)-1H-pyrazol-1-yl]acetyl]-4-piperidinyl]-N-[(1R)-1,2,3,4-tetrahydro-1-naphthalenyl]-4-thiazolecarbothioamide, N-methyl-2-[1-[[5-methyl-3-(trifluoromethyl)-1H-pyrazol-1-yl]acetyl]-4-piperidinyl]-N-[(1R,4S)-1,2,3,4-tetrahydro-4-hydroxy-1-naphthalenyl]-4-thiazolecarboxamide and its enantiomer, N-methyl-2-[1-[[5-methyl-3-(trifluoromethyl)-1H-pyrazol-1-yl]acetyl]-4-piperidinyl]-N-(1,2,3,4-tetrahydro-2-methyl-1-naphthalenyl)-4-thiazolecarboxamide, N-methyl-2-[1-[[5-methyl-3-(trifluoromethyl)-1H-pyrazol-1-yl]acetyl]-4-piperidinyl]-N-[(1R,4R)-1,2,3,4-tetrahydro-4-hydroxy-1-naphthalenyl]-4-thiazolecarboxamide and its enantiomer, 2-[1-[[5-ethyl-3-(trifluoromethyl)-1H-pyrazol-1-yl]acetyl]-4-piperidinyl]-N-methyl-N-[(1R)-1,2,3,4-tetrahydro-1-naphthalenyl]-4-thiazolecarboxamide, 2-[1-[[3,5-bis(trifluoromethyl)-1H-pyrazol-1-yl]acetyl]-4-piperidinyl]-N-methyl-N-[(1R)-1,2,3,4-tetrahydro-1-naphthalenyl]-4-thiazolecarboxamide, N-(2,3-dihydro-2,2-dimethyl-1H-inden-1-yl)-N-methyl-2-[1-[[5-methyl-3-(trifluoromethyl)-1H-pyrazol-1-yl]acetyl]-4-piperidinyl]-4-thiazolecarboxamide, N-(2,3-dihydro-2-methyl-1H-inden-1-yl)-N-methyl-2-[1-[[5-methyl-3-(trifluoromethyl)-1H-pyrazol-1-yl]acetyl]-4-piperidinyl]-4-thiazolecarboxamide, N-methyl-1-[1-[[5-methyl-3-(trifluoromethyl)-1H-pyrazol-1-yl]acetyl]-4-piperidinyl]-N-[(1R)-1,2,3,4-tetrahydro-1-naphthalenyl]-1H-pyrazole-3-carboxamide, N-methyl-2-[1-[[5-methyl-3-(trifluoromethyl)-1H-pyrazol-1-yl]acetyl]-4-piperidinyl]-N-[(1R)-1,2,3,4-tetrahydro-1-naphthalenyl]-2H-1,2,3-triazole-4-carboxamide, N-methyl-1-[1-[[5-methyl-3-(trifluoromethyl)-1H-pyrazol-1-yl]acetyl]-4-piperidinyl]-N-[(1R)-1,2,3,4-tetrahydro-1-naphthalenyl]-1H-pyrazole-4-carboxamide, N-methyl-2-[1-[[5-methyl-3-(trifluoromethyl)-1H-pyrazol-1-yl]acetyl]-4-piperidinyl]-N-[(1R,2S)-1,2,3,4-tetrahydro-2-methyl-1-naphthalenyl]-4-thiazolecarboxamide, N-methyl-2-[1-[[5-methyl-3-(trifluoromethyl)-1H-pyrazol-1-yl]acetyl]-4-piperidinyl]-N-(1,2,3,4-tetrahydro-2,2-dimethyl-1-naphthalenyl)-4-thiazolecarboxamide and its enantiomer, 2-[1-[(3,5-dichloro-1H-pyrazol-1-yl)acetyl]-4-piperidinyl]-N-methyl-N-[(1R)-1,2,3,4-tetrahydro-1-naphthalenyl]-4-thiazolecarboxamide, 2-[1-[[5-chloro-3-(trifluoromethyl)-1H-pyrazol-1-yl]acetyl]-4-piperidinyl]-N-methyl-N-[(1R)-1,2,3,4-tetrahydro-1-naphthalenyl]-4-thiazolecarboxamide, and N-methyl-2-[1-[[5-methyl-3-(trifluoromethyl)-1H-pyrazol-1-yl]acetyl]-4-piperidinyl]-N-(1,2,3,4-tetrahydro-1-naphthalenyl)-4-thiazolecarboxamide.

3. A method for controlling plant diseases caused by Oomycete fungal plant pathogens comprising applying to the plant or portion thereof, or to the plant seed or seedling, a fungicidally effective amount of a compound having a formula corresponding to of Formula 1 of claim 1 where proviso (a) and proviso (b) are both omitted.

4. A fungicidal composition comprising (1) a fungicidally effective amount of a compound having a formula corresponding to of Formula 1 of claim 1 where proviso (a) and proviso (b) are both omitted; and (2) at least one additional component selected from the group consisting of surfactants, solid diluents and liquid diluents.

* * * * *